United States Patent
Wang et al.

(10) Patent No.: US 12,421,253 B2
(45) Date of Patent: Sep. 23, 2025

(54) TETRAHYDROPYRIDOPYRIMIDINE PAN-KRAS INHIBITORS

(71) Applicant: Mirati Therapeutics, Inc., San Diego, CA (US)

(72) Inventors: Xiaolun Wang, San Diego, CA (US); Anthony Ivetac, San Diego, CA (US); Svitlana Kulyk, San Diego, CA (US); John David Lawson, Carlsbad, CA (US); Matthew Arnold Marx, San Diego, CA (US); Christopher Ronald Smith, San Diego, CA (US)

(73) Assignee: Mirati Therapeutics, Inc., Princeton, NJ (US)

( * ) Notice: Subject to any disclaimer, the term of this patent is extended or adjusted under 35 U.S.C. 154(b) by 0 days.

(21) Appl. No.: 18/644,945

(22) Filed: Apr. 24, 2024

(65) Prior Publication Data
US 2024/0376127 A1 Nov. 14, 2024

Related U.S. Application Data

(62) Division of application No. 17/553,224, filed on Dec. 16, 2021, now Pat. No. 11,999,753.

(60) Provisional application No. 63/126,350, filed on Dec. 16, 2020, provisional application No. 63/158,119, filed on Mar. 8, 2021, provisional application No. 63/164,345, filed on Mar. 22, 2021.

(51) Int. Cl.
*A61K 31/519* (2006.01)
*A61P 35/00* (2006.01)
*C07D 471/04* (2006.01)
*C07D 519/00* (2006.01)
*C12Q 1/00* (2006.01)

(52) U.S. Cl.
CPC ............ *C07D 519/00* (2013.01); *A61P 35/00* (2018.01); *C07D 471/04* (2013.01)

(58) Field of Classification Search
CPC .......... A61K 31/519; A61P 35/00; C12Q 1/25
USPC ....................................... 514/264.1; 435/184
See application file for complete search history.

(56) References Cited

U.S. PATENT DOCUMENTS

| | | | |
|---|---|---|---|
| 6,924,284 | B2 | 8/2005 | Beaton et al. |
| 8,163,763 | B2 | 4/2012 | Bergeron et al. |
| 8,426,401 | B2 | 4/2013 | Bian et al. |
| 9,562,019 | B2 | 2/2017 | Djaballah et al. |
| 9,840,516 | B2 | 12/2017 | Li et al. |
| 10,125,134 | B2 | 11/2018 | Blake et al. |
| 2003/0191143 | A1 | 10/2003 | Pitts et al. |
| 2006/0229307 | A1 | 10/2006 | Blurton et al. |
| 2007/0021445 | A1 | 1/2007 | Berthel et al. |
| 2009/0253693 | A1 | 10/2009 | Koltun et al. |
| 2009/0312342 | A1 | 12/2009 | Wilson et al. |
| 2010/0081654 | A1 | 4/2010 | Stockwell et al. |
| 2011/0269244 | A1 | 11/2011 | Petter et al. |
| 2013/0029978 | A1 | 1/2013 | Kamino et al. |
| 2014/0288045 | A1 | 9/2014 | Ren et al. |
| 2015/0175558 | A1 | 6/2015 | Stockwell et al. |
| 2015/0239900 | A1 | 8/2015 | Li et al. |
| 2016/0031898 | A1 | 2/2016 | Ren et al. |
| 2016/0108019 | A1 | 4/2016 | Li et al. |
| 2016/0166571 | A1 | 6/2016 | Janes et al. |
| 2016/0229836 | A1 | 8/2016 | Stockwell et al. |
| 2016/0264627 | A1 | 9/2016 | Henning et al. |
| 2016/0297774 | A1 | 10/2016 | Li et al. |
| 2017/0022184 | A1 | 1/2017 | Li et al. |
| 2017/0115303 | A1 | 4/2017 | Cravatt et al. |
| 2017/0190672 | A1 | 7/2017 | Mani et al. |
| 2017/0197945 | A1 | 7/2017 | Li et al. |
| 2017/0275289 | A1 | 9/2017 | Albrecht et al. |
| 2018/0015087 | A1 | 1/2018 | Liu et al. |
| 2018/0072723 | A1 | 3/2018 | Blake et al. |
| 2018/0118757 | A1 | 5/2018 | Li et al. |
| 2018/0118761 | A1 | 5/2018 | Sebti et al. |
| 2018/0127396 | A1 | 5/2018 | Li et al. |
| 2018/0141927 | A1 | 5/2018 | Li et al. |
| 2018/0155348 | A1 | 6/2018 | Li et al. |
| 2018/0162812 | A1 | 6/2018 | Ren et al. |
| 2018/0177767 | A1 | 6/2018 | Lanman et al. |
| 2018/0194748 | A1 | 7/2018 | Li et al. |
| 2018/0201610 | A1 | 7/2018 | Tao et al. |
| 2018/0273515 | A1 | 9/2018 | Li et al. |
| 2018/0273523 | A1 | 9/2018 | Li et al. |
| 2018/0273577 | A1 | 9/2018 | Revenko et al. |
| 2018/0282307 | A1 | 10/2018 | Li et al. |
| 2018/0282308 | A1 | 10/2018 | Li et al. |
| 2018/0289583 | A1 | 10/2018 | McCormick et al. |

(Continued)

FOREIGN PATENT DOCUMENTS

CN 113999226 A 2/2022
WO 02/053558 A1 7/2002

(Continued)

OTHER PUBLICATIONS

Rajitha et al., "Synthesis and pharmacological evaluations of novel 2H-benzo[b](1,4)oxazin3(4H)-one derivatives as a new class of anti-cancer agents", European Journal of Medicinal Chemistry, 2011, vol. 46, pp. 4887-4896, Table 1.

(Continued)

*Primary Examiner* — Charanjit Aulakh
(74) *Attorney, Agent, or Firm* — Sterne, Kessler, Goldstein &Fox P.L.L.C.

(57) ABSTRACT

The present invention relates to compounds that inhibit at least one of KRas wild type, KRas G12A, KRas G12C, KRas G12D, KRas G12R, KRas G12S, KRas G12V, KRas G13D and KRas Q61H, pharmaceutical compositions comprising the compounds and methods of use therefor.

29 Claims, No Drawings

(56) References Cited

U.S. PATENT DOCUMENTS

| | | |
|---|---|---|
| 2018/0289683 A1 | 10/2018 | Mccormick et al. |
| 2019/0144444 A1 | 5/2019 | Blake et al. |
| 2019/0284275 A1 | 9/2019 | Zhou et al. |
| 2019/0292182 A1 | 9/2019 | Kuramoto et al. |
| 2019/0374542 A1 | 12/2019 | Allen et al. |
| 2020/0069657 A1 | 3/2020 | Lanman et al. |
| 2020/0262837 A1 | 8/2020 | Marx et al. |
| 2020/0331911 A1 | 10/2020 | Marx et al. |
| 2020/0399297 A1 | 12/2020 | Campbell et al. |
| 2021/0024501 A1 | 1/2021 | Liansheng et al. |
| 2021/0139517 A1 | 5/2021 | Gill et al. |

FOREIGN PATENT DOCUMENTS

| | | |
|---|---|---|
| WO | 02/087513 A2 | 11/2002 |
| WO | 2007/146122 A2 | 12/2007 |
| WO | 2008/009078 A2 | 1/2008 |
| WO | 2009/047255 A1 | 4/2009 |
| WO | 2010/014939 A1 | 2/2010 |
| WO | 2010/120996 A1 | 10/2010 |
| WO | 2013/155223 A1 | 10/2013 |
| WO | 2014/143659 A1 | 9/2014 |
| WO | 2014/152588 A1 | 9/2014 |
| WO | 2016/049568 A1 | 3/2015 |
| WO | 2015/054572 A1 | 4/2015 |
| WO | 2016/025650 A1 | 2/2016 |
| WO | 2016/044772 A1 | 3/2016 |
| WO | 2016/049565 A1 | 3/2016 |
| WO | 2016130460 A2 | 8/2016 |
| WO | 2016/164675 A1 | 10/2016 |
| WO | 2016/168540 A1 | 10/2016 |
| WO | 2017/058728 A1 | 4/2017 |
| WO | 2017/058768 A1 | 4/2017 |
| WO | 2017/058792 A1 | 4/2017 |
| WO | 2017/058805 A1 | 4/2017 |
| WO | 2017/058807 A1 | 4/2017 |
| WO | 2017/058902 A1 | 4/2017 |
| WO | 2017/058915 A1 | 4/2017 |
| WO | 2017/070256 A2 | 4/2017 |
| WO | 2017/079864 A1 | 5/2017 |
| WO | 2017/080980 A1 | 5/2017 |
| WO | 2017/087528 A1 | 5/2017 |
| WO | 2017/100546 A1 | 6/2017 |
| WO | 2018/064510 A1 | 4/2018 |
| WO | 2018/068017 A1 | 4/2018 |
| WO | 2018/102452 A2 | 6/2018 |
| WO | 2018/102453 A1 | 6/2018 |
| WO | 2018/112420 A1 | 6/2018 |
| WO | 2018/115380 A1 | 6/2018 |
| WO | 2018/119183 A2 | 6/2018 |
| WO | 2018/140512 A1 | 8/2018 |
| WO | 2018/140513 A1 | 8/2018 |
| WO | 2018/140514 A1 | 8/2018 |
| WO | 2018/140598 A1 | 8/2018 |
| WO | 2018/140599 A1 | 8/2018 |
| WO | 2018/140600 A1 | 8/2018 |
| WO | 2018/143315 A1 | 8/2018 |
| WO | 2018/195439 A2 | 10/2018 |
| WO | 2018218070 A2 | 11/2018 |
| WO | 2019051291 A1 | 3/2019 |
| WO | 2019099524 A1 | 5/2019 |
| WO | 2019110751 A1 | 6/2019 |
| WO | 2019150305 A1 | 8/2019 |
| WO | 2019155399 A1 | 8/2019 |
| WO | 202063594 | 4/2020 |
| WO | 202098488 | 5/2020 |
| WO | 2020097537 A2 | 5/2020 |
| WO | 2020118066 A1 | 6/2020 |
| WO | 2020146613 A1 | 7/2020 |
| WO | 202027202 | 8/2020 |
| WO | 2020163598 | 8/2020 |
| WO | 2020165670 | 8/2020 |
| WO | 2020169838 | 8/2020 |
| WO | 2020171499 | 8/2020 |
| WO | 2020172332 | 8/2020 |
| WO | 2020123395 A1 | 9/2020 |
| WO | 2020176693 | 9/2020 |
| WO | 2020176963 | 9/2020 |
| WO | 2020177629 | 9/2020 |
| WO | 2020178282 | 9/2020 |
| WO | 2020181142 | 9/2020 |
| WO | 2020198125 | 10/2020 |
| WO | 2020204359 | 10/2020 |
| WO | 2020205473 | 10/2020 |
| WO | 2020205486 | 10/2020 |
| WO | 2020212895 | 10/2020 |
| WO | 2020214537 | 10/2020 |
| WO | 2020221239 | 11/2020 |
| WO | 2020230028 | 11/2020 |
| WO | 2020230091 | 11/2020 |
| WO | 2020231806 | 11/2020 |
| WO | 2020231808 | 11/2020 |
| WO | 2020232130 | 11/2020 |
| WO | 2020233592 | 11/2020 |
| WO | 2020234103 | 11/2020 |
| WO | 2020236940 | 11/2020 |
| WO | 2020236947 | 11/2020 |
| WO | 2020236948 | 11/2020 |
| WO | 2020247914 | 12/2020 |
| WO | 2020252336 | 12/2020 |
| WO | 2020252353 | 12/2020 |
| WO | WO-2020238791 A1 | 12/2020 |
| WO | 2021000885 | 1/2021 |
| WO | 2021023154 | 2/2021 |
| WO | 2021023247 | 2/2021 |
| WO | 2021027911 | 2/2021 |
| WO | 2021027943 | 2/2021 |
| WO | 2021031952 | 2/2021 |
| WO | 2021034992 | 2/2021 |
| WO | 2021037018 | 3/2021 |
| WO | 2021041671 | 3/2021 |
| WO | 2021043322 | 3/2021 |
| WO | 2021045279 | 3/2021 |
| WO | 2021050732 | 3/2021 |
| WO | 2021051034 | 3/2021 |
| WO | 2021052499 | 3/2021 |
| WO | 2021055728 | 3/2021 |
| WO | 2021057832 | 4/2021 |
| WO | 2021058018 | 4/2021 |
| WO | 2021061515 | 4/2021 |
| WO | 2021061749 | 4/2021 |
| WO | 2021063346 | 4/2021 |
| WO | 2021068898 | 4/2021 |
| WO | 2021075147 | 4/2021 |
| WO | 2021076655 | 4/2021 |
| WO | 2021078285 | 4/2021 |
| WO | 2021078312 | 4/2021 |
| WO | 2021080359 | 4/2021 |
| WO | 2021081212 | 4/2021 |
| WO | 2021083167 | 5/2021 |
| WO | 2021084765 | 5/2021 |
| WO | 2021085653 | 5/2021 |
| WO | 2021086833 | 5/2021 |
| WO | 2021088458 | 5/2021 |
| WO | 2021088938 | 5/2021 |
| WO | 2021091956 | 5/2021 |
| WO | 2021091967 | 5/2021 |
| WO | 2021091982 | 5/2021 |
| WO | 2021093758 A1 | 5/2021 |
| WO | 2021104431 A1 | 6/2021 |
| WO | 2021106230 A1 | 6/2021 |
| WO | 2021106231 A1 | 6/2021 |
| WO | 2021107160 A1 | 6/2021 |
| WO | 2021108683 A1 | 6/2021 |
| WO | 2021109737 A1 | 6/2021 |
| WO | 2021113595 A1 | 6/2021 |
| WO | 2021120045 A1 | 6/2021 |
| WO | 2021121330 A1 | 6/2021 |
| WO | 2021121367 A1 | 6/2021 |
| WO | 2021121371 A1 | 6/2021 |
| WO | 2021121397 A1 | 6/2021 |
| WO | 2021126120 A1 | 6/2021 |
| WO | 2021126799 A1 | 6/2021 |
| WO | 2021127404 A1 | 6/2021 |

(56) References Cited

FOREIGN PATENT DOCUMENTS

| | | |
|---|---|---|
| WO | 2021129820 A1 | 7/2021 |
| WO | 2021129824 A1 | 7/2021 |
| WO | 2021139678 A1 | 7/2021 |
| WO | 2021139748 A1 | 7/2021 |
| WO | 2021141628 A1 | 7/2021 |
| WO | 2021142252 A1 | 7/2021 |
| WO | 2021143693 A1 | 7/2021 |
| WO | 2021145520 A1 | 7/2021 |
| WO | 2021145521 A1 | 7/2021 |
| WO | 2021147965 A1 | 7/2021 |
| WO | 2021147967 A1 | 7/2021 |
| WO | 2021150613 A1 | 7/2021 |
| WO | 2021152149 A1 | 8/2021 |
| WO | 2021168193 A1 | 8/2021 |
| WO | 2021169963 A1 | 9/2021 |
| WO | 2021169990 A1 | 9/2021 |
| WO | 2021173923 A1 | 9/2021 |
| WO | 2021175199 A1 | 9/2021 |
| WO | 2021177721 A1 | 9/2021 |
| WO | 2021178740 A2 | 9/2021 |
| WO | 2021178741 A1 | 9/2021 |
| WO | 2021180181 A1 | 9/2021 |
| WO | 2021185233 A1 | 9/2021 |
| WO | 2021190467 A2 | 9/2021 |
| WO | 2021197499 A1 | 10/2021 |
| WO | 2021203768 A1 | 10/2021 |
| WO | 2021207172 A1 | 10/2021 |
| WO | 2021211864 A1 | 10/2021 |
| WO | 2021215544 A1 | 10/2021 |
| WO | 2021216770 A1 | 10/2021 |
| WO | 2021217019 A1 | 10/2021 |
| WO | 2021090855 A1 | 11/2021 |
| WO | 2021218110 A1 | 11/2021 |
| WO | 2021219072 A1 | 11/2021 |
| WO | 2021219090 A2 | 11/2021 |
| WO | 2021219091 A1 | 11/2021 |
| WO | 2021228161 A1 | 11/2021 |
| WO | 2021231526 A1 | 11/2021 |
| WO | 2021236475 A1 | 11/2021 |
| WO | 2021239058 A1 | 12/2021 |
| WO | 2021243280 A1 | 12/2021 |
| WO | 2021244603 A1 | 12/2021 |
| WO | 2021245051 A1 | 12/2021 |
| WO | 2021245055 A1 | 12/2021 |
| WO | 2021245499 A1 | 12/2021 |
| WO | 2021248079 A1 | 12/2021 |
| WO | 2021248082 A1 | 12/2021 |
| WO | 2021248083 A1 | 12/2021 |
| WO | 2021248090 A1 | 12/2021 |
| WO | 2021248095 A1 | 12/2021 |
| WO | 2021249563 A1 | 12/2021 |
| WO | 2021252339 A1 | 12/2021 |
| WO | 2021257828 A1 | 12/2021 |
| WO | 2021259331 A1 | 12/2021 |
| WO | 2022002102 A1 | 1/2022 |
| WO | 2022015375 A1 | 1/2022 |
| WO | 2022017339 A1 | 1/2022 |
| WO | 2022028346 A1 | 2/2022 |
| WO | 2022028492 A1 | 2/2022 |
| WO | 2022031678 A1 | 2/2022 |
| WO | 2022036176 A1 | 2/2022 |
| WO | WO-2022106897 A2 | 5/2022 |
| WO | 2022258974 A1 | 12/2022 |
| WO | 2023039240 A1 | 3/2023 |

OTHER PUBLICATIONS

PubChem-SID-132593111, Modify Date: May 31, 2019 (May 31, 2019), p. 2, figure, this is a purchasable chemical.

JP 2015-124211 A (Dainippon Sumitomo Pharma CO L TD) Jul. 6, 2015 (Jul. 6, 2015), especially: original document, p. 58, Table, formula 93.

Bakalova et al. "Electronic absorption and emission spectra and computational studies of some 2-aryl, 2-styryl, and 2-(40-aryl)butadienyl quinazolin-4-ones", Journal of Molecular Structure (Theochem). 2004. 710, 229-234, especially: p. 230, Scheme 2.

Orlov et al. "Rapid Improvement of the Performance Status and Reduction of the Tumor Size in KRAS-Mutated Colorectal Cancer Patient Receiving Binimetinib, Hydroxychloroquine, and Bevacizumab", Case Rep Oncol. 2020. 13: pp. 985-989, para 3; p. 988, para 4.

Canon et al. "The clinical KRAS(G12C) inhibitor AMG 510 drives anti-tumour immunity", Nature. 2019. vol. 575, pp. 217-223, especially: abstract; p. 218, Fig. 1a, formula AMG 510; p. 220, col. 2, para 2.

Lanman et al. "Discovery of a Covalent Inhibitor of KRASG12C (AMG 510) for the Treatment of Solid Tumors" Journal of Medicinal Chemistry. Dec. 10, 2019 (Dec. 10, 2019) vol. 63, p. 52-65; p. 52, abstract.

Abe, H et al. Discovery of a Highly Potent and Selective MEK Inhibitor: GSK1120212 (JTP-74057 DMSO Solvate). ACS Medicinal Chemistry Letters, vol. 2, No. 4, Feb. 28, 2011, doi: 10.1021/ml200004g, pp. 320-324; p. 321, figure 1.

Sunaga, N. et al., "Oncogenic KRAS-induced epiregulin overexpression contributes to aggressive phenotype and is a promising therapeutic target in non-small-cell lung cancer", Oncogene (2013) 32, 4034-4042& 2013 Macmillan Publishers Limited.

Blake et al., "Discovery of 5,6,7,8-tetrahydropyrido[3,4-d]pyrimidine inhibitors of Erk2" Bioorganic & Medicinal Chemistry Letters, Jun. 15, 2014, vol. 24, p. 2635-2639; p. 2635, Figure 1, p. 2637, right col. Para 2.

Ambrogio, C. et al., "Combined inhibition of DDR1 and Notch signaling is a therapeutic strategy for KRAS-driven lung adenocarcinoma", Nature Medicine, vol. 22, No. 3, pp. 270-279, Mar. 2016.

Araki, M. et al., "Solution Structure of the State 1 Conformer of GTP-bound H-Ras Protein and Distinct Dynamic Properties between the State 1 and State 2 Conformers" The Journal of Biological Chemistry vol. 286, No. 45, pp. 39644-39653, Nov. 11, 2011.

Broutin, S. et al., "Insights into significance of combined inhibition of MEK and m-TOR signalling output in KRAS mutant non-small-cell lung cancer", British Journal of Cancer (2016), 1-4 | doi: 10.1038/bjc.2016.220.

Burgess, M. et al., "KRAS Allelic Imbalance Enhances Fitness and Modulates MAP Kinase Dependence in Cancer", Cell 168, 817-829, Feb. 23, 2017, Elsevier Inc.

Cammarata, M. et al., "Impact of G12 Mutations on the Structure of K-Ras Probed by Ultraviolet Photodissociation Mass Spectrometry", . Am. Chem. Soc., 2016, 138 (40), pp. 13187-13196.

Costa-Cabral, S. et al., "CDK1 Is a Synthetic Lethal Target for KRAS Mutant Tumours", PLOS ONE | DOI: 10.1371/journal.pone.0149099 Feb. 16, 2016.

Cully, "Closing the door on KRAS-mutant lung cancer", Nature Reviews Drug Discovery | Published online Nov. 3, 2016; doi:10.1038/nrd.2016.216, MacMillan Publishers.

Dharmaiah, S. et al., "Structural basis of recognition of farnesylated and methylated KRAS4b by PDEδ", E6766-E6775, PNAS, Published online Oct. 17, 2016.

Fiala, O. et al., "The dominant role of G12C over other KRAS mutation types in the negative prediction of efficacy of epidermal growth factor tyrosine kinase inhibitors in nonesmall cell lung cancer", Cancer Genetics 206 (2013) 26-31.

Ford, B. et al., "Structure of the G60A Mutant of Ras Implications for the Dominant Negative Effect", J. Biol. Chem., vol. 280, No. 27, Issue of July 8, pp. 25697-25705, 2005.

Hall, B. et al., "The structural basis for the transition from Ras-GTP to Ras-GDP", PNAS, vol. 99, No. 19, pp. 12138-12142, Sep. 17, 2002.

Hunter, J. et al., "In situ selectivity profiling and crystal structure of SML-8-73-1, an active site inhibitor of oncogenic K-Ras G12C", PNAS, vol. 111, No. 24, pp. 8895-8900, Jun. 17, 2014.

Ihle, N. et al., "Effect of KRAS Oncogene Substitutions on Protein Behavior: Implications for Signaling and Clinical Outcome", JNCI, Oxford Journals, vol. 104, Issue 3, Feb. 8, 2012.

Jarvis, L., "Have drug hunters finally cracked KRas?", c&en, vol. 94, Issue 23, pp. 28-33, Jun. 6, 2016.

(56) References Cited

OTHER PUBLICATIONS

Kamerkar, S. et al., "Exosomes facilitate therapeutic targeting of oncogenic KRAS in pancreatic cancer", Nature 546, 498-503 (Jun. 22, 2017) doi:10.1038/nature22341.

Kaufman, J. et al., "Treatment of KRAS-Mutant Non-Small Cell Lung Cancer The End of the Beginning for Targeted Therapies", JAMA May 9, 2017 vol. 317, No. 18.

Kerr, E. et al., "Mutant Kras copy number defines metabolic reprogramming and therapeutic susceptibilities", Nature 531, 110-113, (Mar. 3, 2016) doi:10.1038/nature16967.

Kim, J. et al., "CPS1 maintains pyrimidine pools and DNA synthesis in KRAS/LKB1-mutant lung cancer cells", Nature 546, 168-172, (Jun. 1, 2017) doi:10.1038/nature22359.

Kim, J. et al., "XPO1-dependent nuclear export is a druggable vulnerability in KRAS-mutant lung cancer", Nature 538, 114-117 (Oct. 6, 2016) doi:10.1038/nature19771.

Kosloff, M. et al., "GTPase Catalysis by Ras and Other G-proteins: Insights from Substrate Directed SuperImposition", J. Mol. Biol. (2003) 331, 1157-1170, doi:10.1016/S0022-2836(03)00847-7.

Ledford, H., "Thirty years of pursuit have failed to yield a drug to take on one of the deadliest families of cancer-causing proteins. Now some researchers are taking another shot." The RAS Renaissance, Nature, vol. 520, 278-280, Apr. 16, 2015.

Lim, S. et all., "Therapeutic Targeting of Oncogenic K-Ras by a Covalent Catalytic Site Inhibitor", Angew. Chem. Int. Ed. 2014, 53, 199-204.

Loncle, C. et al., "The pancreatitis-associated protein VMP1, a key regulator of inducible autophagy, promotes KrasG12D-mediated pancreatic cancer initiation", Cell Death and Disease (2016) 7, e2295; doi:10.1038/cddis.2016.202 Official journal of the Cell Death Differentiation Association.

Manchado, E. et al., "A combinatorial strategy for treating KRAS-mutant lung cancer", Nature 534, 647-651 (Jun. 30, 2016) doi:10.1038/nature18600.

Maurer, T. et al., "Small-molecule ligands bind to a distinct pocket in Ras and inhibit SOS-mediated nucleotide exchange activity", PNAS, Apr. 3, 2012, vol. 109, No. 14, pp. 5299-5304.

Nadal, E. et al., "Abstract C141: KRAS G12C mutation is prognostic of poor outcome in resected lung adenocarcinomas and predictive of poor response to MEK inhibition in vitro", Mol Cancer Ther Nov. 12, 2013; C141, doi: 10.1158/1535-7163.TARG-13-C141.

Nussinov, R. et al., "Independent and core pathways in oncogenic KRAS signaling", Journal: Expert Review of Proteomics, DOI: 10.1080/14789450.2016.1209417, Published by Taylor & Francis.

Ostrem, J. et al., "Direct small-molecule inhibitors of KRAS: from structural insights to mechanism-based design", Nature Reviews Drug Discovery 15, 771-785 (2016) doi: 10.1038/nrd.2016.139.

Ostrem, J. et al., "K-Ras(G12C) inhibitors allosterically control GTP affinity and effector interactions", Nature, vol. 503: 548, Nov. 28, 2013.

Papke, B. et al., "Drugging RAS: Know the enemy", Science 355, 1158-1163 (2017) Mar. 17, 2017.

Park, K. et al., "The HSP90 inhibitor, NVP-AUY922, sensitizes KRAS-mutant non-small cell lung cancer with intrinsic resistance to MEK inhibitor, trametinib", Cancer Letters 372 (2016) 75-81.

Patricelli, M. et al., "Selective Inhibition of Oncogenic KRAS Output with Small Molecules Targeting the Inactive State", OnlineFirst on Jan. 6, 2016; DOI: 10.1158/2159-8290.CD-15-1105.

Renaud, S. et al., "KRAS in Non-Small-Cell Lung Cancer: Oncogenic Addiction and Epidermal Growth Factor Receptor Tyrosine Kinase Inhibitors", JAMA Oncology Published online Jul. 21, 2016.

Riquelme, E. et al., "Modulation of EZH2 expression by MEK-ERK or PI3K-AKT signaling in lung cancer is dictated by different KRAS oncogene mutations", Author Manuscript Published OnlineFirst on Dec. 16, 2015; DOI: 10.1158/0008-5472.CAN-15-1141, American Association for Cancer Research.

Ross, S. et al., "Targeting KRAS-dependent tumors with AZD4785, a high-affinity therapeutic antisense oligonucleotide inhibitor of KRAS", Sci. Transl. Med. 9, eaal5253 (2017) Jun. 14, 2017.

Rudoni, S. et al., "Role of guanine nucleotides in the regulation of the Ras/cAMP pathway in *Saccharomyces cerevisiae*", Biochimica et Biophysica Acta 1538 (2001) 181⁁189.

Samatar, A. et al., "Targeting RAS-ERK signalling in cancer: promises and challenges", Nature Reviews Drug Discovery, vol. 13, pp. 928-942, Dec. 2014.

Serresi, M. et al., "Polycomb Repressive Complex 2 Is a Barrier to KRAS-Driven Inflammation and Epithelial-Mesenchymal Transition in Non-Small-Cell Lung Cancer", Cancer Cell 29, 17-31, Jan. 11, 2016, 2016 Elsevier Inc. 17.

Shima, F. et al., "Structural Basis for Conformational Dynamics of GTP-bound Ras Protein", The Journal of Biological Chemistry, vol. 285, No. 29, pp. 22696 -22705, Jul. 16, 2010.

Shipman, L., "Putting the brakes on KRAS-G12C nucleotide cycling", Nature Reviews Cancer, Published online Feb. 19, 2016; doi:10.1038/nrc.2016.13.

Spoerner, M. et al., "Dynamic properties of the Ras switch I region and its importance for binding to effectors", PNAS, vol. 98, No. 9, pp. 4944-4949, Apr. 24, 2001.

Sun, Q. et al., "Discovery of Small Molecules that Bind to K-Ras and Inhibit Sos-Mediated Activation", Angew. Chem. Int. Ed. 2012, 51, 1-5, 2012 Wiley-VCH Verlag Gmbh & Co. KGaA, Weinheim.

Sun, Q., et al., "A method for the second-site screening of K-Ras in the presence of a covalently attached first-site ligand", J Biomol NMR (2014) 60:11-14 DOI 10.1007/s10858-014-9849-8.

Sung, Y. et al., "Mutagenesis of the H-ras p21 at Glycine-60 Residue Disrupts GTP-Induced Conformational Change", Biochemistry 1995, 34, 3470-3477, American Chemical Society.

Tape, C. et al., "Oncogenic KRAS Regulates Tumor Cell Signaling via Stromal Reciprocation", Cell 165, 1-11 May 5, 2016.

Thierry, A. et al., "Clinical validation of the detection of KRAS and BRAF mutations from circulating tumor DNA", Nature Medicine, vol. 20, No. 4, pp. 430-436 , Apr. 2014.

Tran, E. et al., "T-Cell Transfer Therapy Targeting Mutant KRAS in Cancer", N Engl J Med 2016;375:2255-62., Dec. 8, 2016; DOI: 10.1056/NEJMoa1609279.

Wang, Y. et al., "Targeting Mutant KRAS for Anticancer Therapeutics: A Review of Novel Small Molecule Modulators", J. Med. Chem. 2013, 56, 5219-5230, dx.doi.org/10.1021/jm3017706; 2013 American Chemical Society, ACS Publications.

Wang, Y. et al., "Ezh2 Acts as a Tumor Suppressor in Kras-driven Lung Adenocarcinoma", International Journal of Biological Sciences 2017; 13(5): 652-659. doi: 10.7150/ijbs.19108.

Welsch, M. et al., "Multivalent Small-Molecule Pan-RAS Inhibitors", Welsch et al., 2017, Cell 168, 878-889 Feb. 23, 2017; 2017 Elsevier Inc. http://dx.doi.org/10.1016/j.cell.2017.02.006.

Winter, J. et al., "Small Molecule Binding Sites on the Ras:SOS Complex Can Be Exploited for Inhibition of Ras Activation", J. Med. Chem. 2015, 58, 2265-2274; DOI: 10.1021/jm501660t; 2015 American Chemical Society, ACS Publications.

Wood, K. et al., "Reply" Comments & Response, Letters JAMA Oncology Published online Jul. 21, 2016, American Medical Association.

Xiong, Y. et al., "Development of covalent guanosine mimetic inhibitors of G12C KRAS", ACS Med. Chem. Lett., Just Accepted Manuscript . DOI: 10.1021/acsmedchemlett.6b00373 • Publication Date (Web): Nov. 30, 2016 Downloaded from http://pubs.acs.org on Dec. 1, 2016.

Xiong, Y. et al., "Covalent Guanosine Mimetic Inhibitors of G12C KRAS" ACS Med. Chem. Lett. 2017, 8, 61-66, DOI: 10.1021/acsmedchemlett.6b00373; 2016 American Chemical Society, ACS Publications.

Janes et al., "Targeting KRAS Mutant Cancers with a Covalent G12C-Specific Inhibitor", Cell 172, 578-589, Jan. 25, 2018.

Singh et al., A Gene Expression Signature Associated with "K-Ras Addiction" Reveals Regulators of EMT and Tumor Cell Survival, Cancer Cell 15, p. 489-500, Jun. 2, 2009.

Stephen et al., "Dragging Ras Back in the Ring", Cancer Cell 25, p. 272, Mar. 17, 2014.

Zhu et al., "Inhibition of KRAS-driven tumorigenicity by interruption of an autocrine cytokine circuit", doi:10.1158/2159-8290.CD-13-0646; Cancer Discovery Published OnlineFirst Jan. 20, 2014.

(56) References Cited

OTHER PUBLICATIONS

Simanshu et al., "RAS Proteins and Their Regulators in Human Disease", Cell 170, p. 17, Jun. 29, 2017.
Pacold et al., "Crystal Structure and Functional Analysis of Ras Binding to Its Effector Phosphoinositide 3-Kinase gamma", Cell, vol. 103, p. 931-943, Dec. 8, 2000.
Lech-Gustav et al., "The Renaissance of Ras", ACS Chem. Biol., 2014, 9, 2447-2458.
Karachaliou et al., "KRAS Mutations in Lung Cancer", Clinical Lung Cancer, vol. 14, No. 3, p. 2015-14, 2013.
Schwartz et al., "Covalent EGFR inhibitor analysis reveals importance of reversible interactions to potency and mechanisms of drug resistance", PNAS, vol. 111, No. 1, p. 173-178, Jan. 7, 2014.
Sun et al., "A method for the second-site screening of K-Ras in the presence of a covalently attached first-site ligand", J. Biomol. NMR (2014) vol. 60 p. 11-14.
Kyriakis, J., "Thinking Outside the Box about Ras", J. Biol. Chem. 2009, 284:10993-10994, published online Dec. 17, 2008.
Sunaga et al., "Knockdown of Oncogenic KRAS in Non-Small Cell Lung Cancers Suppresses Tumor Growth and Sensitizes Tumor Cells to Targeted Therapy", Mol. Cancer Ther. 2011; 10:336-346.
Walker et al., "Structural insights into phosphoinositide 3-kinase catalysis and signalling", Nature vol. 402, p. 18 Nov. 1999; www.nature.com.
Barbie et al., "Systematic RNA interference reveals that oncogenic KRAS-driven cancers require TBK1", Nature, vol. 462, p. 108, Nov. 5, 2009; doi:10.1038/nature08460.
Zimmermann et al., "Small molecule inhibition of the KRAS-PDEdelta interaction impairs oncogenic KRAS signalling", Nature, vol. 497, p. 638, May 30, 2013.
Karnoub et al., "Ras oncogenes: split personalities", Nature Reviews, molecular Cell Biology, vol. 9, Jul. 2008 p. 517.
Nassar et al., "Ras/Rap effector specificity determined by charge reversal", Nature Structural Biology, vol. 3, No. 8, Aug. 1996.
De Rooij et al., "Minimal Ras-binding domain of Raf1 can be used as an activation-specific probe for Ras", Oncogene (1997) 14, 623-625, 1997 Stockton Press.
Cox et al., "The dark side of RAs: regulation of apoptosis", Oncogene (2003) 22, 8999-9006, 2003 Nature Publishing Group.
Tanaka et al., "Interfering with RAS-effector protein interactions prevent RAS-dependent tumour initiation and causes stop-start control of cancer growth", Oncogene (2010) 29, 6064-6070, 2010 Macmillan Publishers Limited.
Grant et al., "Novel Allosteric Sites on Ras for Lead Generation", PLOS ONE, vol. 6, Issue 10, Oct. 2011.
Maegley et al., "Ras-catalyzed hydrolysis of GTP: A new perspective from model studies", Proc. Natl. Acad. Sci. USA, vol. 93, pp. 8160-8166, Aug. 1996.
Ahmadian et al., "Guanosine triphosphatase stimulation of oncogenic Ras mutants", Proc. Natl. Acad. Sci. USA, vol. 96, pp. 7065-7070, Jun. 1999.
Kiel et al., "Electrostatically optimized Ras-binding Ral guanine dissociation stimulator mutants increase the rate of association by stabilizing the encounter complex", PNAS, vol. 101, No. 25, p. 9223-9228, Jun. 22, 2004.
Kotting et al., "The GAP arginine finger movement into the catalytic site of Ras increases the activation entropy", PNAS, vol. 105, No. 17, p. 6260-6265, Apr. 29, 2008.
Shaw et al., "Selective killing of K-ras mutant cancer cells by small molecule inducers of oxidative stress", PNAS, vol. 108, No. 21, p. 8773-8778, May 24, 2011.
Ischenko et al., "Direct reprogramming by oncogenic Ras and Myc", PNAS early edition 1, 2013.
Smith et al., "NMR-based functional profiling of RASopathies and oncogenic RAS mutations", PNAS, vol. 110, No. 12, p. 4574-4579, Mar. 19, 2013.
Shima, et al., "In silico discovery of small-molecule Ras inhibitors that display antitumor activity by blocking the Ras-effector interaction", PNAS, vol. 110, No. 20, p. 8182-8187, May 14, 2013.
Burns et al., "Approach for targeting Ras with small molecules that activate SOS-mediated nucleotide exchange", PNAS, vol. 111, No. 9, p. 3401-3406, Mar. 4, 2014.
Zeng et al., "Design of inhibitors of Ras-Raf interaction using a computational combinatorial algorithm", Protein Engineering, vol. 14, No. 1, p. 39-45, 2001.
Scheffzek et al., "The Ras-RasGAP Complex: Structural Basis for GTPAse Activation and Its Loss in Oncogenic Ras Mutants", Science, vol. 277, Jul. 18, 1997.
Taylor et al., "Protein Kinases: Evolution of Synamic Regulatory Proteins", Trends Biochem Sci. Feb. 2011; 36 (2): 65-77. doi:10.1016/j.tibs.2010.09.006.
Fell et al. 'Discovery of Tetrahydropyridopyrimidines as Irreversible Covalent Inhibitors of Kras-G12C with In Vivo Activity', ACS Medicinal Chemistry Letters, Nov. 7, 2018 (Jul. 11, 2018), vol. 9, pp. 1230-1234.
International Search Report and Written Opinion for corresponding PCT application No. PCT/US18/61060 mailed Feb. 7, 2019.
Martin, James S. et al., "Characterising covalent warhead reactivity", Bioorganic & Medicinal Chemistry, 27 (2019) 2066-2074.
Palkowitz, Maximilian D. et al., "Synthesis of Diverse N-Acryloyl Azetidines and Evaluation of Their Enhanced Thiol Reactivities", ACS Publications Mar. 16, 2017, 9, 9, 2270-2273.
Figueras, A. et al., "The impact of KRAS mutations on VEGF-A production and tumour vascular network", BMC Cancer 2013, 13:125.
Janes, M. et al., "Targeting KRAS Mutant Cancers with a Covalent G12C-Specific Inhibitor", 2018, Cell 172, 578-589, Jan. 25, 2018, Elsevier Inc.
Matikas, A. et al., "Targeting KRAS mutated non-small cell lung cancer: A history of failures and a future of hope for a diverse entity", Cretical Reviews in Oncology/Hematology 110 (2017) 1-12, Elsevier Ireland Ltd.
McCormick, F., "Targeting KRAS Directly", Annual Review of Cancer Biology, 2018, 2:81, 81-90.
Misalee, S. et al., KRAS G12C NSCLC models are sensitive to direct targeting of KRAS in combination with PI3K inhibition, Downloaded from clincancerres.aacrjournals.org on Oct. 22, 2018. © 2018 American Association for Cancer Research.
O'Bryan, J., "Pharmacological Targeting of RAS: Recent Success with Direct Inhibitors", Pharmacological Research (2018), https://doi.org/10.1016/j.phrs.2018.10.021.
Simanshu, D. et al., "RAS Proteins and Their Regulators in Human Disease", Cell 170, 17-33, Jun. 29, 2017.
Suzawa, K., et al., "Activation of KRAS mediates resistance to targeted therapy in MET exon 14 mutant non-small cell lung cancer", Author Manuscript Published OnlineFirst on Oct. 23, 2018; DOI: 10.1158/1078-0432.CCR-18-1640, Downloaded from clincancerres.aacrjournals.org on Oct. 29, 2018. © 2018 American Association for Cancer Research.
Wijeratne, A. et al., "Chemical Proteomic Characterization of a covalent KRASG12C inhibitor", ACS Med. Chem. Ltter., DOI: 10.1021/acsmedchemlett.8b00110, May 21, 2018.
Wood, K. et al., "Prognostic and Predictive Value in KRAS in Non-Small-Cell Lung Cancer A Review", JAMA Oncol. 2016:2(6), 805-812, Apr. 21, 2016.
Yen, I. et al., "Pharmacological Induction of RAS-GTP Confers RAF Inhibitor Sensitivity in KRAS Mutant Tumors", Cancer Cell 34, 611-625, Oct. 8, 2018, Elsevier Inc.
Ziemke, E. et al., "Sensitivity of KRAS-Mutant Colorectal Cancers to Combination Therapy That Cotargets MEK and CDK4/6", Clin Cancer Res; 22(2) Jan. 15, 2016.
Ambrogio, C. et al., "KRAS Dimerization Impacts MEK Inhibitor Sensitivity and Oncogenic Activity of Mutant KRAS", Cell 172, 1-12, Feb. 8, 2018, Elsevier Inc.
Hansen, R. et al., "An Internally Controlled Quantitative Target Occupancy Assay for Covalent Inhibitors", Scientific Reports, 8:14312 (2018), DOI: 10.1038/s41598-018-32683-w.
Pantar, T. et al., "Assessment of mutation probabilities of Kras G12 missense mutants and their long-timescale dynamics by atomistic molecular simulations and Markov state modeling", PLOS Computational Biology, Sep. 10, 2018.

(56) References Cited

OTHER PUBLICATIONS

Skoulidis, F. et al., "STK11/LKB1 Mutations and PD-1 Inhibitor Resistance in KRAS-Mutant Lung Adenocarcinoma", Downloaded from cancerdiscovery.aacrjournals.org on May 21, 2018. © 2018 American Association for Cancer Research.

Yuan, T. et al., "Differential Effector Engagement by Oncogenic KRAS", Cell Reports 22, 1889-1902, Feb. 13, 2018, Cell Press.

TETRAHYDROPYRIDOPYRIMIDINE PAN-KRAS INHIBITORS

FIELD OF THE INVENTION

The present invention relates to compounds that inhibit multiple mutated forms of KRas, i.e., pan-KRas inhibitors. In particular, the present invention relates to pan-KRas compounds, pharmaceutical compositions comprising the compounds and methods of use therefor.

BACKGROUND OF THE INVENTION

Kirsten Rat Sarcoma 2 Viral Oncogene Homolog ("KRas") is a small GTPase and a member of the Ras family of oncogenes. KRas serves as a molecular switch cycling between inactive (GDP-bound) and active (GTP-bound) states to transduce upstream cellular signals received from multiple tyrosine kinases to downstream effectors to regulate a wide variety of processes, including cellular proliferation (e.g., see Alamgeer et al., (2013) Current Opin Pharmcol. 13:394-401).

The role of activated KRas in malignancy was observed over thirty years ago (e.g., see Santos et al., (1984) Science 223:661-664). Aberrant expression of KRas accounts for up to 20% of all cancers and oncogenic KRas mutations that stabilize GTP binding and lead to constitutive activation of KRas. KRas mutations at codons 12, 13, 61 and other positions of the KRas primary amino acid sequence are present in 88% of all pancreatic adenocarcinoma patients, 50% of all colon/rectal adenocarcinoma patients, and 32% lung adenocarcinoma patients (e.g., see Prior et all., (2020) Cancer Res 80:2969-74). A recent publication also suggested wild type Kras inhibition could be a viable therapeutic strategy to treat KRas$^{WT}$ dependent cancers (e.g., see Bery et al., (2020) Nat. Commun. 11: 3233).

The well-known role of KRas in malignancy and the discovery of these frequent mutations in KRas in various tumor types made KRas a highly attractive target of the pharmaceutical industry for cancer therapy. Notwithstanding thirty years of large-scale discovery efforts to develop inhibitors of KRas for treating cancer, no KRas inhibitor has yet demonstrated sufficient safety and/or efficacy to obtain regulatory approval (e.g., see McCormick (2015) Clin Cancer Res. 21 (8):1797-1801).

Compounds that inhibit KRas activity are still highly desirable and under investigation, including those that disrupt effectors such as guanine nucleotide exchange factors (e.g., see Sun et al., (2012) Agnew Chem Int Ed Engl. 51(25):6140-6143 doi: 10.1002/anie201201358) as well recent advances in the covalent targeting of an allosteric pocket of KRas G12C (e.g., see Ostrem et al., (2013) Nature 503:548-551 and Fell et al., (2018) ACS Med. Chem. Lett. 9:1230-1234). Clearly there remains a continued interest and effort to develop inhibitors of KRas, particularly inhibitors of activating KRas mutants.

Thus, there is a need to develop new pan-KRas inhibitors that demonstrate sufficient efficacy for treating KRas-mediated cancers.

SUMMARY OF THE INVENTION

In one aspect of the invention, compounds are provided that inhibit KRas activity.

In another aspect of the invention, compounds of Formula (I):

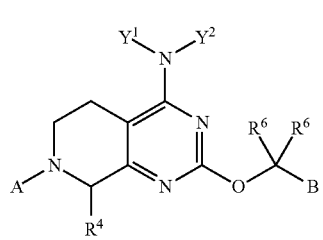

Formula (I)

or a pharmaceutically acceptable salt thereof are provided, wherein:
A is aryl or heteroaryl, wherein the aryl or the heteroaryl is optionally substituted with 1-4 $R^1$;
B is selected from:

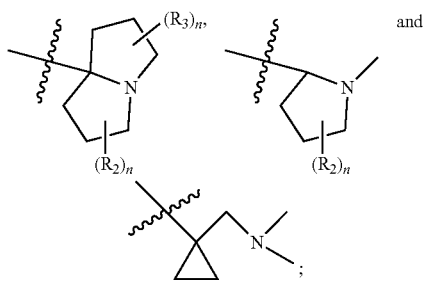

$Y^1$ is L-hydrogen, hydroxy, halogen, L-C3-C6 cycloalkyl optionally substituted with 1-4 $R^9$, L-S(O)$_2$NH$_2$ optionally substituted with 1-4 $R^9$, L-heteroaryl optionally substituted with 1-4 $R^8$, L-aryl optionally substituted with 1-4 $R^8$, and L-heterocycle substituted with 1-2 oxo (=O) or oxo-containing substituent and optionally further substituted with 1-2 heteroaryl-$R^8$ or $R^8$;
$Y^2$ is hydrogen or C1-C4 alkyl;
or $Y^1$ and $Y^2$ join to form:

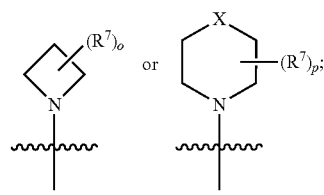

where X is selected from: a bond, —S—, —O—, —N<bound to a fused ring, —CH$_2$—, —CH$_2$—NH—, —CH$_2$—NH—CH$_2$—, —CH$_2$—CH$_2$—CH$_2$—, —CH$_2$—CH$_2$—, —O—CH$_2$— and —S—CH$_2$—;
each $R^1$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, —S—C1-C3 haloalkyl, C1-C3 alkoxy, hydroxyC1-C3 alkyl, —CH$_2$C(=O)N(R$^5$)$_2$, —C3-C4 alkynyl(NR$^5$)$_2$, —N(R$^5$)$_2$, deuteroC2-C4 alkynyl, (C1-C3 alkoxy)haloC1-C3 alkyl-, or C3-C6 cycloalkyl wherein said C3-C6 cycloalkyl is optionally substituted with halogen or C1-C3 alkyl;
each $R^2$ is independently hydrogen, hydroxy, halogen, C1-C3 alkyl, C1-C3 cyanoalkyl, C1-C3 hydroxyalkyl, HC(=O)—, —OC(O)N(R$^5$)$_2$, —CO$_2$R$^5$, or —CO$_2$N(R$^5$)$_2$;

each $R^3$ is independently hydrogen, hydroxy, halogen, C1-C3 alkyl, C1-C3 cyanoalkyl, C1-C3 hydroxyalkyl, HC(=O)—, —OC(O)N($R^5$)$_2$, —CO$_2$$R^5$, or —CO$_2$N($R^5$)$_2$;

$R^4$ is hydrogen, halogen or C1-C3 alkyl;

each $R^5$ is independently hydrogen or C1-C3 alkyl;

each $R^6$ is independently hydrogen, hydroxy, C1-C4 hydroxyalkyl or heteroaryl, or two $R^6$ join to form C3-C6 cycloalkyl or heterocycle;

each $R^7$ is independently hydrogen, C1-C3 alkyl, hydroxy, halogen, halo-C1-C3 alkyl, —NH$_2$, —NH(C1-C3 alkyl), —N(C1-C3 alkyl)$_2$, oxo (=O), —O—(C1-C3 alkyl), —(C1-C3 alkyl)-OH, —C(O)OH, —C(O)O(C1-C3 alkyl), —O—CH$_2$—C(O)NH$_2$, L-C(O)NH$_2$, —C(O)NH(C1-C3 alkyl), —NHC(O)(C1-C3 alkyl), —C(O)N(C1-C3 alkyl)$_2$, —CN, aryl, dialkylphosphine oxide, —S(O)$_2$NH(CH$_3$), sulfone, L-heterocycle optionally substituted with 1-2 substituents selected from oxo (=O), C1-C3 alkyl and C3 cycloalkyl, or L-heteroaryl optionally substituted with 1-2 substituents selected from NH$_2$, C1-C3 alkyl, C1-C3 haloalkyl, C3 cycloalkyl, —C(O)NH(C3-C4 cycloalkyl) and —NHC(O)(C1-C3 alkyl), two $R^7$ on the same atom optionally join to form a spirocyclic ring selected from C3-C6 cycloalkyl and heterocycle, where said spirocyclic ring is optionally substituted with 1-2 substituents selected from oxo (=O), halogen, hydroxy, C1-C3 alkyl and —O—(C1-C3 alkyl), two $R^7$ on adjacent atoms optionally join to form a bond or a fused ring selected from C3-C6 cycloalkyl optionally substituted with 1-4 $R^8$, heteroaryl optionally substituted with 1-4 $R^8$, aryl optionally substituted with 1-4 $R^8$, and heterocycle optionally substituted with 1-4 $R^8$, and two $R^7$ on non-adjacent atoms optionally join to form a 1-2 carbon bridge;

each $R^8$ is independently C1-C3 alkyl, hydroxy, halogen, —NH$_2$, —NH(C1-C3 alkyl), —N(C1-C3 alkyl)$_2$, oxo (=O), —O—(C1-C3 alkyl), —(C1-C3 alkyl)-OH, —C(O)OH, —C(O)O(C1-C3 alkyl), —C(O)NH$_2$, —(C1-C3 alkyl)C(O)NH$_2$, —C(O)NH(C1-C3 alkyl), —C(O)N(C1-C3 alkyl)$_2$, —C(O)N($R^{10}$)$_2$, —CN, heteroaryl optionally substituted with C1-C3 alkyl, C1-C3 haloalkyl, —CH$_2$—S—CH$_3$, —S(O)$_2$NH$_2$ or —S(O)$_2$(C1-C3 alkyl);

each $R^9$ is independently C1-C3 alkyl, hydroxy, halogen, oxo (=O), —O—(C1-C3 alkyl), —(C1-C3 alkyl)-OH, —C(O)OH, —C(O)O(C1-C3 alkyl), —C(O)NH$_2$, —C(O)NH(C1-C3 alkyl), —C(O)N(C1-C3 alkyl)$_2$ or —CN, or two $R^9$ join to form a bond or —S(O)(CH$_3$)$_2$;

each $R^{10}$ is independently hydrogen, C1-C3 alkyl, halogen, or joins with $R^7$ or another $R^{10}$ to form a heterocyclic ring;

L is a bond, —C1-C4 alkyl-, —NH—, —C(O)—, —N(C1-C3 alkyl)- or —(C1-C3 alkyl)NH—;

each n is 0-3;

is 1-6; and p is 1-8.

In another aspect of the invention, pharmaceutical compositions are provided comprising a therapeutically effective amount of a compound of the present invention or a pharmaceutically acceptable salt thereof and a pharmaceutically acceptable excipient.

In yet another aspect of the invention, methods for inhibiting the activity of cells containing wild type KRas or one or more KRas mutations, for instance the KRas mutations G12A, G12C, G12D, G12R, G12S, G12V, G13D or Q61H, in a in a cell, comprising contacting the cell with a compound of Formula (I), or a pharmaceutically acceptable salt thereof, or a pharmaceutical composition thereof as defined herein. In one embodiment, the contacting is in vitro. In one embodiment, the contacting is in vivo.

Also provided herein is a method of inhibiting cell proliferation, in vitro or in vivo, the method comprising contacting a cell with an effective amount of a compound of Formula (I), or a pharmaceutically acceptable salt thereof, or a pharmaceutical composition thereof as defined herein.

Also provided are methods for treating cancer in a patient comprising administering a therapeutically effective amount of a compound or pharmaceutical composition of the present invention or a pharmaceutically acceptable salt thereof to a patient in need thereof.

Also provided herein is a method of treating a KRas wild type-associated or KRas G12A, G12C, G12D, G12R, G12S, G12V, G13D and/or Q61H-associated disease or disorder in a patient in need of such treatment, the method comprising administering to the patient a therapeutically effective amount of a compound of Formula (I), or a pharmaceutically acceptable salt thereof, or a pharmaceutical composition thereof as defined herein.

Also provided herein is a compound of Formula (I), or a pharmaceutically acceptable salt thereof, or a pharmaceutical composition thereof as defined herein for use in therapy.

Also provided herein is a compound of Formula (I), or a pharmaceutically acceptable salt thereof or a pharmaceutical composition thereof as defined herein for use in the treatment of cancer.

Also provided herein is a compound of Formula (I), or a pharmaceutically acceptable salt thereof for use in the inhibition of wild type KRas or multiple types of KRas mutations, for instance KRas G12A, G12C, G12D, G12R, G12S, G12V, G13D and/or Q61H mutations.

Also provided herein is a compound of Formula (I), or a pharmaceutically acceptable salt thereof or a pharmaceutical composition thereof as defined herein, for use in the treatment of wild type KRas or a KRas mutation G12A, G12C, G12D, G12R, G12S, G12V, G13D and/or Q61H-associated disease or disorder.

Also provided herein is the use of a compound of Formula (I), or a pharmaceutically acceptable salt thereof, as defined herein in the manufacture of a medicament for the treatment of cancer.

Also provided herein is a use of a compound of Formula (I), or a pharmaceutically acceptable salt thereof, as defined herein in the manufacture of a medicament for the inhibition of activity of wild type KRas or mutated forms of KRas, including the mutations: G12A, G12C, G12D, G12R, G12S, G12V, G13D and/or Q61H.

Also provided herein is the use of a compound of Formula (I), or a pharmaceutically acceptable salt thereof, as defined herein, in the manufacture of a medicament for the treatment of a wild type KRas-associated or a KRas G12A, G12C, G12D, G12R, G12S, G12V, G13D and/or Q61H-associated disease or disorder.

Also provided herein is a method for treating cancer in a patient in need thereof, the method comprising (a) determining that the cancer is associated with wild type KRas or a KRas G12A, G12C, G12D, G12R, G12S, G12V, G13D and/or Q61H mutation (i.e., a wild type KRas-associated or a KRas G12A, G12C, G12D, G12R, G12S, G12V, G13D and/or Q61HG12X-associated cancer); and (b) administering to the patient a therapeutically effective amount of a compound of Formula (I), or a pharmaceutically acceptable salt thereof, or a pharmaceutical composition thereof.

One potential utility of the herein-described pan-KRas inhibitors, including pan-KRas inhibitors such as (R)-1-(7-(8-ethyl-7-fluoro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)-3-methylpiperidin-3-ol (Example 5 in 63/125,776), is for the treatment of cancers that develop resistance following long-term treatment with KRas G12C inhibitors. Thus, embodiments of the invention include those wherein a patient suffering from cancer is treated with a herein-described pan-KRas inhibitor after treatment with a G12C inhibitor becomes ineffective or less effective due to the emergence of resistance-imparting mutations.

Treatment of KRas G12C mutant cancers with covalent KRas G12C inhibitors such as adagrasib (MRTX849) or sotorasib (AMG510) may result in the incorporation of additional mutations that confer resistance to adagrasib. These mutations could confer resistance through numerous mechanisms.

Mutations that change the mutant cysteine at codon 12 to another amino acid would render the current covalent KRas G12C inhibitors ineffective since current inhibitors make a covalent bond with the mutant cysteine amino acid side chain. Likewise, in patients that have one wild type KRas allele in addition to the KRas G12C-mutant allele, mutations in the wild type codon 12 glycine to another codon would allow bypass signaling in these tumors through the novel mutant protein. The repertoire of codon 12 mutations that can occur with a single nucleotide substitution in the wild type gene (glycine codon) includes mutations commonly observed in cancer such as G12S, G12V, G12R, G12C. The repertoire of codon 12 mutations that can occur with single nucleotide base substitutions of the cysteine codon 12 include mutations not frequently observed in cancer, G12Y, G12F and G12W, in addition to G12S and G12R.

Second-site mutations may also occur in another location in the KRas G12C mutant gene that confers resistance to KRas G12C inhibitor treatment. These mutations may confer resistance through different mechanisms. RAS proteins are small GTPases that normally cycle between an active, GTP-bound state and an inactive, GDP-bound state. RAS proteins are loaded with GTP through guanine nucleotide exchange factors (GEFs; e.g., SOS1) which are activated by upstream receptor tyrosine kinases, triggering subsequent interaction with effector proteins that activate RAS-dependent signaling. RAS proteins hydrolyze GTP to GDP through their intrinsic GTPase activity which is dramatically enhanced by GTPase-activating proteins (GAPs). Mutations at codons 12 and 13 in RAS proteins impair GAP-stimulated GTP hydrolysis leaving RAS predominantly in the GTP-bound, active state. Covalent KRas G12C inhibitors in current clinical development only bind GDP-bound KRas G12C. Mutations such as Q61 codon mutations, which may or may not occur on the same allele as the G12C mutation, reduce the intrinsic GTPase activity of KRas and may represent a mechanism of resistance to KRas G12C inhibitor treatment by shifting KRas into the GTP-loaded state where it is not susceptible to covalent inhibition. Co-mutations such as R68, H95 and Y96 may be present along with the KRas G12C mutation and may diminish the binding affinity of KRas G12C inhibitors to the Switch II binding pocket.

The herein-described pan-KRas inhibitors may demonstrate activity against common as well as uncommon codon 12 mutations or mutations that occur in the KRas protein that diminish binding of KRas G12C inhibitors to the KRas protein.

Also provided herein is a process for preparing a compound of Formula (I), or a pharmaceutically acceptable salt thereof.

Also provided herein is a compound of Formula (I), or a pharmaceutically acceptable salt thereof obtained by a process of preparing the compound as defined herein.

DETAILED DESCRIPTION OF THE INVENTION

The present invention relates to inhibitors of wild type KRas or multiple mutated forms of KRas, for instance KRas G12A, G12C, G12D, G12R, G12S, G12V, G13D and/or Q61H mutations. In particular, the present invention relates to compounds that inhibit the activity of wild type KRas or KRas mutations such as G12A, G12C, G12D, G12R, G12S, G12V, G13D and/or Q61H, pharmaceutical compositions comprising a therapeutically effective amount of the compounds and methods of use therefor.

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "KRas G12A" refers to a mutant form of a mammalian KRas protein that contains an amino acid substitution of an alanine for a glycine at amino acid position 12. The assignment of amino acid codon and residue positions for human KRas is based on the amino acid sequence identified by UniProtKB/Swiss-Prot P01116: Variantp.Gly12Asp.s used herein, a "KRas G12A inhibitor" refers to compounds of the present invention that are represented by Formula (I), as described herein. These compounds are capable of negatively modulating or inhibiting all or a portion of the enzymatic activity of KRas G12A. A "KRas G12A-associated disease or disorder" as used herein refers to diseases or disorders associated with or mediated by or having a KRas G12A mutation. A non-limiting example of a KRas G12A-associated disease or disorder is a KRas G12A-associated cancer.

As used herein, "KRas G12C" refers to a mutant form of a mammalian KRas protein that contains an amino acid substitution of a cysteine for a glycine at amino acid position 12. The assignment of amino acid codon and residue positions for human KRas is based on the amino acid sequence identified by UniProtKB/Swiss-Prot P01116: Variantp.Gly12Asp.s used herein, a "KRas G12C inhibitor" refers to compounds of the present invention that are represented by Formula (I), as described herein. These compounds are capable of negatively modulating or inhibiting all or a portion of the enzymatic activity of KRas G12C. A "KRas G12C-associated disease or disorder" as used herein refers to diseases or disorders associated with or mediated by or having a KRas G12C mutation. A non-limiting example of a KRas G12C-associated disease or disorder is a KRas G12CD-associated cancer.

As used herein, "KRas G12D" refers to a mutant form of a mammalian KRas protein that contains an amino acid substitution of an aspartic acid for a glycine at amino acid position 12. The assignment of amino acid codon and residue positions for human KRas is based on the amino acid sequence identified by UniProtKB/Swiss-Prot P01116: Variantp.Gly12Asp.s used herein, a "KRas G12D inhibitor" refers to compounds of the present invention that are represented by Formula (I), as described herein. These compounds are capable of negatively modulating or inhibiting all or a portion of the enzymatic activity of KRas G12D. A "KRas G12D-associated disease or disorder" as used herein refers to diseases or disorders associated with or mediated by or having a KRas G12D mutation. A non-limiting example of a KRas G12D-associated disease or disorder is a KRas G12D-associated cancer.

As used herein, "KRas G12R" refers to a mutant form of a mammalian KRas protein that contains an amino acid substitution of an arginine for a glycine at amino acid position 12. The assignment of amino acid codon and residue positions for human KRas is based on the amino acid sequence identified by UniProtKB/Swiss-Prot P01116: Variantp.Gly12Asp.s used herein, a "KRas G12R inhibitor" refers to compounds of the present invention that are represented by Formula (I), as described herein. These compounds are capable of negatively modulating or inhibiting all or a portion of the enzymatic activity of KRas G12R. A "KRas G12R-associated disease or disorder" as used herein refers to diseases or disorders associated with or mediated by or having a KRas G12R mutation. A non-limiting example of a KRas G12R-associated disease or disorder is a KRas G12R-associated cancer.

As used herein, "KRas G12S" refers to a mutant form of a mammalian KRas protein that contains an amino acid substitution of a serine for a glycine at amino acid position 12. The assignment of amino acid codon and residue positions for human KRas is based on the amino acid sequence identified by UniProtKB/Swiss-Prot P01116: Variantp.Gly12Asp.s used herein, a "KRas G12S inhibitor" refers to compounds of the present invention that are represented by Formula (I), as described herein. These compounds are capable of negatively modulating or inhibiting all or a portion of the enzymatic activity of KRas G12S. A "KRas G12S-associated disease or disorder" as used herein refers to diseases or disorders associated with or mediated by or having a KRas G12S mutation. A non-limiting example of a KRas G12S-associated disease or disorder is a KRas G12S-associated cancer.

As used herein, "KRas G12V" refers to a mutant form of a mammalian KRas protein that contains an amino acid substitution of a valine for a glycine at amino acid position 12. The assignment of amino acid codon and residue positions for human KRas is based on the amino acid sequence identified by UniProtKB/Swiss-Prot P01116: Variantp.Gly12Asp.s used herein, a "KRas G12V inhibitor" refers to compounds of the present invention that are represented by Formula (I), as described herein. These compounds are capable of negatively modulating or inhibiting all or a portion of the enzymatic activity of KRas G12V. A "KRas G12V-associated disease or disorder" as used herein refers to diseases or disorders associated with or mediated by or having a KRas G12V mutation. A non-limiting example of a KRas G12V-associated disease or disorder is a KRas G12V-associated cancer.

As used herein, "KRas G13D" refers to a mutant form of a mammalian KRas protein that contains an amino acid substitution of an aspartic acid for a glycine at amino acid position 13. The assignment of amino acid codon and residue positions for human KRas is based on the amino acid sequence identified by UniProtKB/Swiss-Prot P01116: Variantp.Gly12Asp.s used herein, a "KRas G13D inhibitor" refers to compounds of the present invention that are represented by Formula (I), as described herein. These compounds are capable of negatively modulating or inhibiting all or a portion of the enzymatic activity of KRas G13D. A "KRas G13D-associated disease or disorder" as used herein refers to diseases or disorders associated with or mediated by or having a KRas G13D mutation. A non-limiting example of a KRas G13D-associated disease or disorder is a KRas G13D-associated cancer.

As used herein, "KRas Q61H" refers to a mutant form of a mammalian KRas protein that contains an amino acid substitution of a histidine for a glutamine at amino acid position 61. The assignment of amino acid codon and residue positions for human KRas is based on the amino acid sequence identified by UniProtKB/Swiss-Prot P01116: Variantp.Gly12Asp.s used herein, a "KRas Q61H inhibitor" refers to compounds of the present invention that are represented by Formula (I), as described herein. These compounds are capable of negatively modulating or inhibiting all or a portion of the enzymatic activity of KRas Q61H. A "KRas Q61H-associated disease or disorder" as used herein refers to diseases or disorders associated with or mediated by or having a KRas Q61H mutation. A non-limiting example of a KRas Q61H-associated disease or disorder is a KRas Q61H-associated cancer.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having wild type KRas or a KRas G12A, G12C, G12D, G12R, G12S, G12V, G13D and/or Q61H mutation (e.g., as determined using a regulatory agency-approved, e.g., FDA-approved, assay or kit). In some embodiments, the subject has a tumor that is positive for wild type KRas or a KRas G12A, G12C, G12D, G12R, G12S, G12V, G13D and/or Q61H mutation (e.g., as determined using a regulatory agency-approved assay or kit). The subject can be a subject with a tumor(s) that is positive for wild type KRas or a KRas G12A, G12C, G12D, G12R, G12S, G12V, G13D and/or Q61H mutation (e.g., identified as positive using a regulatory agency-approved, e.g., FDA-approved, assay or kit). The subject can be a subject whose tumors have wild type KRas or a KRas G12A, G12C, G12D, G12R, G12S, G12V, G13D and/or Q61H mutation (e.g., where the tumor is identified as such using a regulatory agency-approved, e.g., FDA-approved, kit or assay). In some embodiments, the subject is suspected of having wild type KRas-associated or a KRas G12A, KRas G12C, KRas G12D, KRas G12R, KRas G12S, KRas G12V, KRas G13D or KRas Q61H gene-associated cancer. In some embodiments, the subject has a clinical record indicating that the subject has a tumor that has wild type KRas or a KRas G12A, G12C, G12D, G12R, G12S, G12V, G13D and/or Q61H mutation (and optionally the clinical record indicates that the subject should be treated with any of the compositions provided herein).

In some embodiments of any of the methods or uses described herein, an assay is used to determine whether the patient has wild type KRas or a KRas G12A, G12C, G12D, G12R, G12S, G12V, G13D and/or Q61H mutation using a sample (e.g., a biological sample or a biopsy sample (e.g., a paraffin-embedded biopsy sample) from a patient (e.g., a patient suspected of having wild type KRas or a KRas G12A, G12C, G12D, G12R, G12S, G12V, G13D and/or Q61H-associated cancer, a patient having one or more symptoms of a wild type KRas-associated or a KRas G12A, G12C, G12D, G12R, G12S, G12V, G13D and/or Q61H-associated cancer, and/or a patient that has an increased risk of developing a wild type KRas-associated or a KRas G12A, G12C, G12D, G12R, G12S, G12V, G13D and/or Q61H-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof.

The term "regulatory agency" is a country's agency for the approval of the medical use of pharmaceutical agents with the country. For example, a non-limiting example of a regulatory agency is the U.S. Food and Drug Administration (FDA).

The term "acyl" refers to —C(O)CH$_3$.

The terms "C1-C6 alkyl", "C1-C4 alkyl" and "C1-C3 alkyl" as employed herein refers to straight and branched chain aliphatic groups having from 1-6 carbon atoms, or 1-4 carbon atoms, or 1-3 carbon atoms, respectively. Examples of alkyl groups include, without limitation, methyl, ethyl, propyl, isopropyl, butyl, isobutyl, sec-butyl, tert-butyl, pentyl, and hexyl.

The terms "C1-C3 haloalkyl" and "C1-C4 haloalkyl" refer to a C1-C3 alkyl chain or C1-C4 alkyl chain, respectively, as defined herein in which one or more hydrogen has been replaced by a halogen. Examples include trifluoromethyl, difluoromethyl and fluoromethyl.

An "C1-C4 alkylene," group is a C1-C4 alkyl group, as defined hereinabove, that is positioned between and serves to connect two other chemical groups. Exemplary alkylene groups include, without limitation, methylene, ethylene, propylene, and butylene.

The terms "C1-C3 alkoxy" and "C1-C4 alkoxy" refer to —OC1-C3 alkyl and —OC1-C4 alkyl, respectively, wherein the alkyl portion is as defined herein above.

The term "cycloalkyl" as employed herein includes saturated and partially unsaturated cyclic hydrocarbon groups having 3 to 12 carbons, for example 3 to 8 carbons, and as a further example 3 to 6 carbons, wherein the cycloalkyl group additionally is optionally substituted with one or more R$^8$ or R$^9$ groups as defined herein. Examples of cycloalkyl groups include, without limitation, cyclopropyl, cyclobutyl, cyclopentyl, cyclopentenyl, cyclohexyl, cyclohexenyl, cycloheptyl, and cyclooctyl. The term "cycloalkyl" also includes bridged cycloalkyls, such as bicyclo[1.1.1]pentanyl.

As used herein, the terms "C1-C3 hydroxyalkyl" and "C1-C4 hydroxyalkyl" refer to —C1-C3 alkylene-OH and —C1-C4 alkylene-OH, respectively.

As used herein, the term "C2-C4 hydroxyalkynyl" refers to —C2-C4 alkynylene-OH.

An "aryl" group is a C6-C14 aromatic moiety comprising one to three aromatic rings, which is optionally substituted with one or more substituents as defined herein and in Formula I. As one embodiment, the aryl group is a C6-C10 aryl group. Examples of aryl groups include, without limitation, phenyl, naphthyl, anthracenyl, fluorenyl, and dihydrobenzofuranyl. "Aryl" also refers to bicyclic or tricyclic ring systems in which one or two rings, respectively, of said aryl ring system may be saturated or partially saturated, and wherein if said ring system includes two saturated rings, said saturated rings may be fused or spirocyclic. An example of an aryl ring system comprising two saturated rings wherein the rings are spirocyclic includes the following ring system:

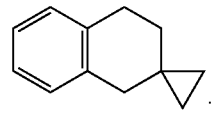 [SMILES: c1ccc2c(c1)CCC1(CC1)C2]

An "araC1-C6 alkyl" or "arylalkyl" group comprises an aryl group covalently linked to an alkyl group, either of which may independently be optionally substituted or unsubstituted. An example of an aralkyl group is (C$_6$-C$_{10}$) aryl(C$_1$-C$_6$)alkyl-, including, without limitation, benzyl, phenethyl, and naphthylmethyl. An example of a substituted araC1-C6 alkyl is wherein the alkyl group is substituted with hydroxyalkyl.

A "heterocyclyl" or "heterocyclic" group is a saturated or partially unsaturated ring structure having from 3 to 12 atoms, for example 4 to 8 atoms, wherein one or more atoms are selected from the group consisting of N, O, and S wherein the ring N atom may be oxidized to N—O, and the ring S atom may be oxidized to SO or SO$_2$, the remainder of the ring atoms being carbon. The heterocyclyl may be a monocyclic, a bicyclic, a spirocyclic or a bridged ring system. The heterocyclic group is optionally substituted on ring carbon or ring nitrogen at one or more positions as defined herein and in Formula I. The heterocyclic group is also independently optionally substituted on a ring nitrogen atom with alkyl, aralkyl, alkylcarbonyl, or on sulfur with lower alkyl. Examples of heterocyclic groups include, without limitation, epoxy, azetidinyl, aziridinyl, tetrahydrofuranyl, tetrahydropyranyl, pyrrolidinyl, pyrrolidinonyl, piperidinyl, piperazinyl, imidazolidinyl, imidazopyridinyl, thiazolidinyl, dithianyl, trithianyl, dioxolanyl, oxazolidinyl, oxazolidinonyl, decahydroquinolinyl, piperidonyl, 4-piperidinonyl, quinuclidinyl, thiomorpholinyl, thiomorpholinyl 1,1 dioxide, morpholinyl, azepanyl, oxazepanyl, azabicyclohexanyls, azabicycloheptanyl, azabicyclooctanyls, azabicyclononanyls (e.g., octahydroindolizinyl), azaspiroheptanyls, dihydro-1H,3H,5H-oxazolo[3,4-c]oxazolyl, tetrahydro-1'H, 3'H-spiro[cyclopropane-1,2'-pyrrolizine], hexahydro-1H-pyrrolizinyl, hexahydro-1H-pyrrolo[2,1-c][1,4]oxazinyl, octahydroindolizinyl, oxaazaspirononanyls, oxaazaspirooctanyls, diazaspirononanyls, oxaazabiocycloheptanyls, hexahydropyrrolizinyl 4(1H)-oxide, tetrahydro-2H-thiopyranyl 1-oxide and tetrahydro-2H-thiopyranyl 1,1-dioxide. Specifically excluded from the scope of this term are compounds having adjacent annular O and/or S atoms.

As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from one to three heteroatoms per ring, or from one to three heteroatoms in at least one ring, selected from the group consisting of N, O, and S. Examples of heteroaryl groups include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, 6,7-dihydro-5H-pyrrolo[1,2-a]imidazole, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. "Heteroaryl" also refers to bicyclic ring systems having, in addition to carbon atoms, from one to three heteroatoms per ring selected from the group consisting of N, O, and S in which one ring system may be saturated or partially saturated.

As used herein, "an effective amount" of a compound is an amount that is sufficient to negatively modulate or inhibit the activity of one or more of wild type KRas or a KRas G12A, KRas G12C, KRas G12D, KRas G12R, KRas G12S, KRas G12V, KRas G13D or KRas Q61H. Such amount may be administered as a single dosage or may be administered according to a regimen, whereby it is effective.

As used herein, a "therapeutically effective amount" of a compound is an amount that is sufficient to ameliorate, or in some manner reduce a symptom or stop or reverse progression of a condition, or negatively modulate or inhibit the activity of wild type KRas or one or more of KRas G12A, KRas G12C, KRas G12D, KRas G12R, KRas G12S, KRas G12V, KRas G13D or KRas Q61H. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

Compounds

In certain embodiments of the invention, compound of Formula (I):

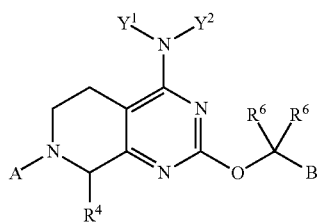

Formula (I)

or a pharmaceutically acceptable salt thereof are provided, wherein:

A is aryl or heteroaryl, wherein the aryl or the heteroaryl is optionally substituted with 1-4 $R^1$;

B is selected from:

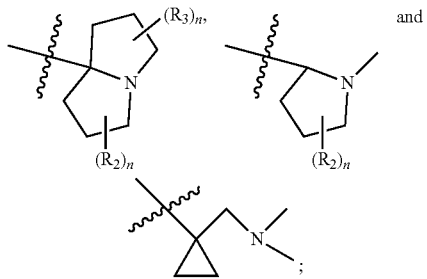

and

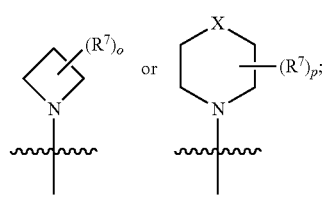

$Y^1$ is L-hydrogen, hydroxy, halogen, L-C3-C6 cycloalkyl optionally substituted with 1-4 $R^9$, L-S(O)$_2$NH$_2$ optionally substituted with 1-4 $R^9$, L-heteroaryl optionally substituted with 1-4 $R^8$, L-aryl optionally substituted with 1-4 $R^8$, and L-heterocycle substituted with 1-2 oxo (=O) or oxo-containing substituent and optionally further substituted with 1-2 heteroaryl-$R^8$ or $R^8$;

$Y^2$ is hydrogen or C1-C4 alkyl;

or $Y^1$ and $Y^2$ join to form:

where X is selected from: a bond, —S—, —O—, —N<bound to a fused ring, —CH$_2$—, —CH$_2$—NH—, —CH$_2$—NH—CH$_2$—, —CH$_2$—CH$_2$—CH$_2$—, —CH$_2$—CH$_2$—, —O—CH$_2$— and —S—CH$_2$—;

each $R^1$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, —S—C1-C3 haloalkyl, C1-C3 alkoxy, hydroxyC1-C3 alkyl, —CH$_2$C(=O)N(R$^5$)$_2$, —C3-C4 alkynyl(NR$^5$)$_2$, —N(R$^5$)$_2$, deuteroC2-C4 alkynyl, (C1-C3 alkoxy)haloC1-C3 alkyl-, or C3-C6 cycloalkyl wherein said C3-C6 cycloalkyl is optionally substituted with halogen or C1-C3 alkyl;

each $R^2$ is independently hydrogen, hydroxy, halogen, C1-C3 alkyl, C1-C3 cyanoalkyl, C1-C3 hydroxyalkyl, HC(=O)—, —OC(O)N(R')$_2$, —CO$_2$R$^5$, or —CO$_2$N(R$^5$)$_2$;

each $R^3$ is independently hydrogen, hydroxy, halogen, C1-C3 alkyl, C1-C3 cyanoalkyl, C1-C3 hydroxyalkyl, HC(=O)—, —OC(O)N(R')$_2$, —CO$_2$R$^5$, or —CO$_2$N(R$^5$)$_2$;

$R^4$ is hydrogen, halogen or C1-C3 alkyl;

each $R^5$ is independently hydrogen or C1-C3 alkyl;

each $R^6$ is independently hydrogen, hydroxy, C1-C4 hydroxyalkyl or heteroaryl, or two $R^6$ join to form C3-C6 cycloalkyl or heterocycle;

each $R^7$ is independently hydrogen, C1-C3 alkyl, hydroxy, halogen, halo-C1-C3 alkyl, —NH$_2$, —NH(C1-C3 alkyl), —N(C1-C3 alkyl)$_2$, oxo (=O), —O—

(C1-C3 alkyl), —(C1-C3 alkyl)-OH, —C(O)OH, —C(O)O(C1-C3 alkyl), —O—CH$_2$—C(O)NH$_2$, L-C(O)NH$_2$, —C(O)NH(C1-C3 alkyl), —NHC(O)(C1-C3 alkyl), —C(O)N(C1-C3 alkyl)$_2$, —CN, aryl, dialkylphosphine oxide, —S(O)$_2$NH(CH$_3$), sulfone, L-heterocycle optionally substituted with 1-2 substituents selected from oxo (=O), C1-C3 alkyl and C3 cycloalkyl, or L-heteroaryl optionally substituted with 1-2 substituents selected from NH$_2$, C1-C3 alkyl, C1-C3 haloalkyl, C3 cycloalkyl, —C(O)NH(C3-C4 cycloalkyl) and —NHC(O)(C1-C3 alkyl), two R$^7$ on the same atom optionally join to form a spirocyclic ring selected from C3-C6 cycloalkyl and heterocycle, where said spirocyclic ring is optionally substituted with 1-2 substituents selected from oxo (=O), halogen, hydroxy, C1-C3 alkyl and —O—(C1-C3 alkyl), two R$^7$ on adjacent atoms optionally join to form a bond or a fused ring selected from C3-C6 cycloalkyl optionally substituted with 1-4 R$^8$, heteroaryl optionally substituted with 1-4 R$^8$, aryl optionally substituted with 1-4 R$^8$, and heterocycle optionally substituted with 1-4 R$^8$, and two R$^7$ on non-adjacent atoms optionally join to form a 1-2 carbon bridge;

each R$^8$ is independently C1-C3 alkyl, hydroxy, halogen, —NH$_2$, —NH(C1-C3 alkyl), —N(C1-C3 alkyl)$_2$, oxo (=O), —O—(C1-C3 alkyl), —(C1-C3 alkyl)-OH, —C(O)OH, —C(O)O(C1-C3 alkyl), —C(O)NH$_2$, —(C1-C3 alkyl)C(O)NH$_2$, —C(O)NH(C1-C3 alkyl), —C(O)N(C1-C3 alkyl)$_2$, —C(O)N(R$^{10}$)$_2$, —CN, heteroaryl optionally substituted with C1-C3 alkyl, C1-C3 haloalkyl, —CH$_2$—S—CH$_3$, —S(O)$_2$NH$_2$ or —S(O)$_2$(C1-C3 alkyl);

each R$^9$ is independently C1-C3 alkyl, hydroxy, halogen, oxo (=O), —O—(C1-C3 alkyl), —(C1-C3 alkyl)-OH, —C(O)OH, —C(O)O(C1-C3 alkyl), —C(O)NH$_2$, —C(O)NH(C1-C3 alkyl), —C(O)N(C1-C3 alkyl)$_2$ or —CN, or two R$^9$ join to form a bond or —S(O)(CH$_3$)$_2$;

each R$^{10}$ is independently hydrogen, C1-C3 alkyl, halogen, or joins with R$^7$ or another R$^{10}$ to form a heterocyclic ring;

L is a bond, —C1-C4 alkyl-, —NH—, —C(O)—, —N(C1-C3 alkyl)- or —(C1-C3 alkyl)NH—;

each n is 0-3;

is 1-6; and p is 1-8.

In certain other embodiments of the invention, compounds of Formula (I):

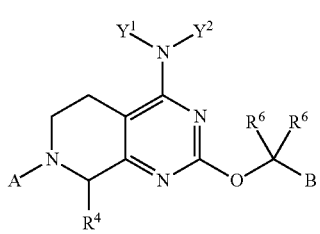

Formula (I)

or a pharmaceutically acceptable salt thereof are provided, wherein:

A is naphthyl, optionally substituted with 1-4 R$^1$;

B is:

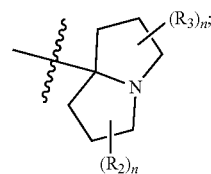

Y$^1$ is hydrogen, hydroxy, halogen or L-heteroaryl optionally substituted with 1-4 R$^8$ Y$^2$ is hydrogen or C1-C4 alkyl;

or Y$^1$ and Y$^2$ join to form:

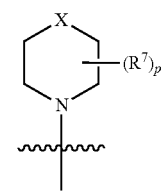

where X is selected from: a bond, —CH—, —CH$_2$—NH—, —CH$_2$—NH—CH$_2$—, —CH$_2$—CH$_2$—CH$_2$—, —CH$_2$—CH$_2$— and —O—CH$_2$—;

each R$^1$ is independently halogen, cyano, hydroxy;

each R$^2$ is independently hydrogen, hydroxy or, halogen;

each R$^3$ is independently hydrogen, hydroxy or halogen;

R$^4$ is hydrogen, halogen or C1-C3 alkyl;

each R$^5$ is independently hydrogen or C1-C3 alkyl;

each R$^6$ is independently hydrogen, hydroxy, C1-C4 hydroxyalkyl or heteroaryl, or two R$^6$ join to form C3-C6 cycloalkyl or heterocycle;

each R$^7$ is independently hydrogen, C1-C3 alkyl, halo-C1-C3 alkyl, hydroxy, —(C1-C3 alkyl)-OH, sulfone, or heteroaryl optionally substituted with NH$_2$;

two R$^7$ on the same atom optionally join to form a spirocyclic ring selected from C3-C6 cycloalkyl and heterocycle, where said spirocyclic ring is optionally substituted with oxo (=O), halogen, hydroxy, C1-C3 alkyl and —O—(C1-C3 alkyl), two R$^7$ on adjacent atoms optionally join to form a bond or a fused ring selected from heteroaryl optionally substituted with 1-4 R$^8$, and heterocycle optionally substituted with 1-4 R$^8$;

each R$^8$ is independently C1-C3 alkyl, hydroxy, halogen, —NH$_2$, —NH(C1-C3 alkyl), —N(C1-C3 alkyl)$_2$, oxo (=O), —O—(C1-C3 alkyl), —(C1-C3 alkyl)-OH, —C(O)OH, —C(O)O(C1-C3 alkyl), —C(O)NH$_2$, —C(O)NH(C1-C3 alkyl), —C(O)N(C1-C3 alkyl)$_2$ or —CN;

each R$^9$ is independently C1-C3 alkyl, hydroxy, halogen, oxo (=O), —O—(C1-C3 alkyl), —(C1-C3 alkyl)-OH, —C(O)OH, —C(O)O(C1-C3 alkyl), —C(O)NH$_2$, —C(O)NH(C1-C3 alkyl), —C(O)N(C1-C3 alkyl)$_2$ or —CN;

L is a bond, —C1-C4 alkyl-, —NH— or —N(C1-C3 alkyl)-;

each n is 0-3;

is 1-6; and p is 1-8.

In certain other embodiments of the invention, compounds or salts of Formula I are provided, wherein:

A is naphthyl;

B is:

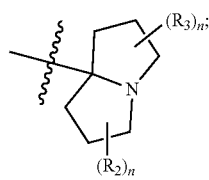

and Y¹ and Y² join to form:

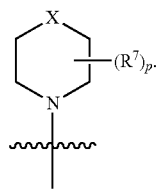

In certain other embodiments of the invention, compounds or salts of Formula I are provided, wherein Y¹ is hydrogen, hydroxy, halogen or L-heteroaryl optionally substituted with 1-4 $R^8$, and Y² is hydrogen or C1-C4 alkyl.

In certain other embodiments of the invention, compounds or salts of Formula I are provided, wherein Y¹ and Y² join to form:

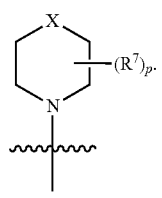

In some embodiments of the invention, compounds or salts of Formula I are provided, wherein X is —CH$_2$—NH—, and two $R^7$ join to form a fused heteroaryl ring substituted with 1-4 $R^8$ where one $R^8$ is —C(O)N($R^{10}$)$_2$.

In some of these embodiments, the fused heteroaryl ring is pyrazolyl, one $R^8$ is —C(O)N($R^{10}$)$_2$ and one $R^8$ is halogen or C1-C3 alkyl.

In specific embodiments, compounds or salts of Formula I are provided, wherein the compound has the formula:

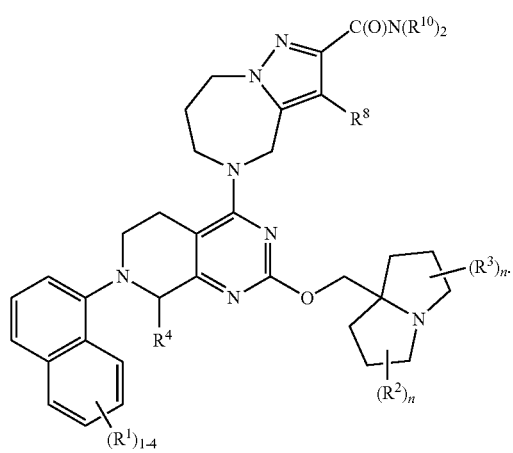

In some embodiments of the invention, compounds or salts of Formula I are provided, wherein X is a bond, and two $R^7$ join to form a fused heterocyclyl ring, optionally substituted with one or two oxo.

In specific embodiments, compounds or salts of Formula I are provided, wherein the compound have the formula:

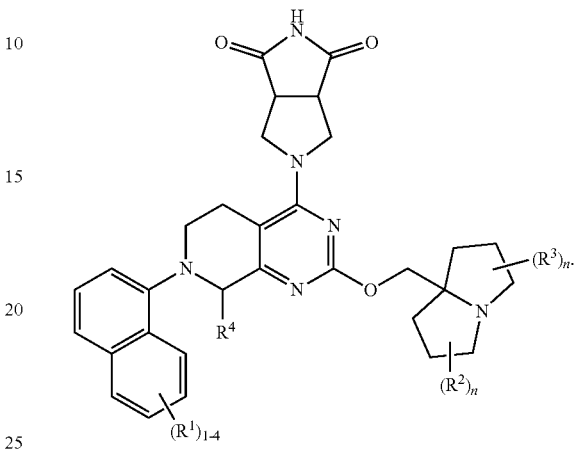

In some embodiments of the invention, compounds or salts of Formula I are provided, wherein X is —CH2—, and two $R^7$ join to form a spirocyclic heterocyclyl ring substituted with one or two oxo.

In specific embodiments, compound or salts of Formula I are provided, wherein the compound has the formula:

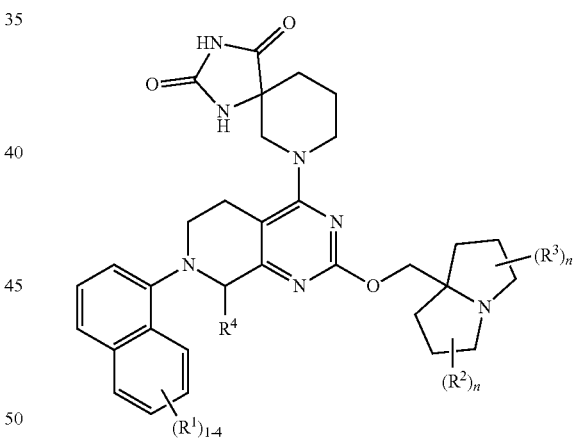

In some embodiments of the invention, compounds or salts of Formula I are provided, wherein at least one $R^1$ is C1-C4 alkyl.

In some embodiments of the invention, compounds or salts of Formula I are provided, wherein at least one $R^1$ is halogen.

In some embodiments of the invention, compounds or salts of Formula I are provided, wherein said $R^1$ halogen is a fluorine.

In some embodiments of the invention, compounds or salts of Formula I are provided, wherein at least one $R^1$ is hydroxy.

In some embodiments of the invention, compounds or salts of Formula I are provided, wherein one $R^2$ is C1-C4 alkyl.

In some embodiments of the invention, compounds or salts of Formula I are provided, wherein at least one $R^2$ is halogen.

In some embodiments of the invention, compounds or salts of Formula I are provided, wherein said $R^2$ halogen is a fluorine.

In some embodiments of the invention, compounds or salts of Formula I are provided, wherein at least one $R^2$ is hydroxy.

In some embodiments of the invention, compounds or salts of Formula I are provided, wherein at least one $R^3$ is C1-C4 alkyl.

In some embodiments of the invention, compounds or salts of Formula I are provided, wherein at least one $R^3$ is halogen.

In some embodiments of the invention, compounds or salts of Formula I are provided, wherein said $R^3$ halogen is fluorine.

In some embodiments of the invention, compounds or salts of Formula I are provided, wherein at least one $R^3$ is hydroxy.

In some embodiments of the invention, compounds or salts of Formula I are provided, wherein $R^4$ is halogen.

In some embodiments of the invention, compounds or salts of Formula I are provided, wherein the $R^4$ halogen is fluorine.

In some embodiments of the invention, compounds or salts of Formula I are provided, wherein at least one $R^5$ is C1-C4 alkyl.

In some embodiments of the invention, compounds or salts of Formula I are provided, wherein at least one $R^5$ is hydrogen.

In some embodiments of the invention, compounds or salts of Formula I are provided, wherein one or both $R^6$ are hydrogen or C1-C4 alkyl.

In some embodiments of the invention, compounds or salts of Formula I are provided, wherein two $R^6$ join to form C3-C6 cycloalkyl or heterocycle.

In some embodiments of the invention, compounds or salts of Formula I are provided, wherein $Y^1$ is L-C3-C6 cycloalkyl, L-heteroaryl, L-aryl, or L-heterocycle, where L is a bond, C1-C4 alkyl, NH or N(C1-C3) alkyl.

In some embodiments of the invention, compounds or salts of Formula I are provided, wherein $Y^1$ is L-heteroaryl.

In some such embodiments the heteroaryl is thietane dioxide, iso-thiazolidine dioxide, imidazopyrazine, pyridine or pyrimidine.

In some embodiments of the invention, compounds or salts of Formula I are provided, wherein $Y^1$ is L-C3-C6 cycloalkyl.

In some such embodiments, the cycloalkyl is cyclobutane, cyclopentane, cyclohexane or cycloheptane.

In some embodiments of the invention, compounds or salts of Formula I are provided, wherein $Y^1$ is L-heterocycle.

In some such embodiments the heterocycle is pyrrolidinone.

In some embodiments of the invention, compounds or salts of Formula I are provided, wherein $Y^2$ is hydrogen.

In some embodiments of the invention, compounds or salts of Formula I are provided, wherein $Y^2$ is C1-C4 alkyl;

In some embodiments of the invention, compounds or salts of Formula I are provided, wherein at least one $R^8$ is C1-C4 alkyl.

In some embodiments of the invention, compounds or salts of Formula I are provided, wherein at least one $R^8$ is hydroxy or C1-C3 alkyl-hydroxy.

In some embodiments of the invention, compounds or salts of Formula I are provided, wherein one or two $R^8$ are oxo (=O).

In some embodiments of the invention, compounds or salts of Formula I are provided, wherein at least one $R^8$ is aryl or heteroaryl.

In some embodiments of the invention, compounds or salts of Formula I are provided, wherein at least one $R^8$ is C(O)OH.

In some embodiments of the invention, compounds or salts of Formula I are provided, wherein at least one R is —C(O)NH$_2$, —C(O)NH(C1-C3 alkyl) or —C(O)N(C1-C3 alkyl)$_2$.

In some embodiments of the invention, compounds or salts of Formula I are provided, wherein at least one $R^8$ is —NH$_2$, —NH(C1-C3 alkyl); —N(C1-C3 alkyl)$_2$.

In some embodiments of the invention, compounds or salts of Formula I are provided, wherein at least one $R^9$ is C1-C4 alkyl.

In some embodiments of the invention, compounds or salts of Formula I are provided, wherein at least one $R^9$ is hydroxy or C1-C3 alkyl-hydroxy.

In some embodiments of the invention, compounds or salts of Formula I are provided, wherein one or two $R^9$ is oxo (=O).

In some embodiments of the invention, compounds or salts of Formula I are provided, wherein at least one $R^9$ is aryl or heteroaryl.

In some embodiments of the invention, compounds or salts of Formula I are provided, wherein at least one $R^9$ is C(O)OH.

In some embodiments of the invention, compounds or salts of Formula I are provided, wherein at least one $R^9$ is —C(O)NH$_2$, —C(O)NH(C1-C3 alkyl) or —C(O)N(C1-C3 alkyl)$_2$.

In some embodiments of the invention, compounds or salts of Formula I are provided, wherein $Y^1$ and $Y^2$ join to form piperidine, azepane, azocane, thiazepine, diazepane, oxazepane, azetidine, pyrrolidine, piperazine bound to a fused ring via nitrogen or thiomorpholine.

In some embodiments of the invention, compounds or salts of Formula I are provided, wherein two $R^7$ on the same atom join to form a spirocyclic ring selected from C3-C6 cycloalkyl and heterocycle, where said spirocyclic ring is optionally substituted with one or more substituents selected from oxo (=O), halogen, hydroxy, C1-C3 alkyl and —O—(C1-C3 alkyl).

In some embodiments of the invention, compounds or salts of Formula I are provided, wherein two $R^7$ on adjacent atoms join to form a bond or a fused ring selected from C3-C6 cycloalkyl optionally substituted with 1-4 $R^8$; heteroaryl optionally substituted with 1-4 $R^8$; aryl optionally substituted with 1-4 $R^1$, and heterocycle optionally substituted with 1-4 $R^8$.

In some embodiments of the invention, compounds or salts of Formula I are provided, wherein two $R^7$ on non-adjacent atoms join to form a 1-2 carbon bridge.

In some embodiments of the invention, compounds or salts of Formula I are provided, wherein one $R^{10}$ is hydrogen, C1-C3 alkyl or halogen, and another $R^{10}$ joins with $R^7$ to form a heterocyclic ring.

In some embodiments of the invention, compounds or salts of Formula I are provided, wherein two $R^{10}$ join to form a heterocyclic ring.

In some embodiments of the invention, compounds or salts of Formula I are provided, wherein each $R^{10}$ is independently hydrogen, C1-C3 alkyl or halogen.

Non-limiting examples of compounds of Formula (I) are selected from the group consisting of:
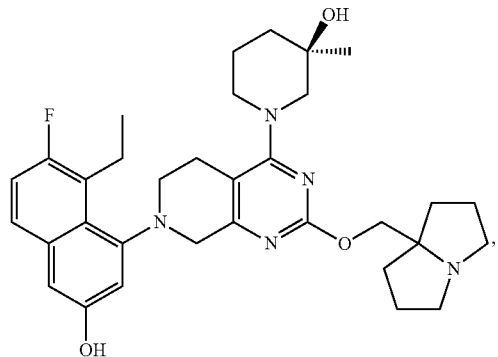
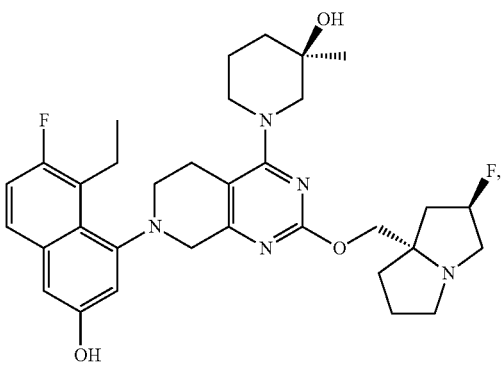
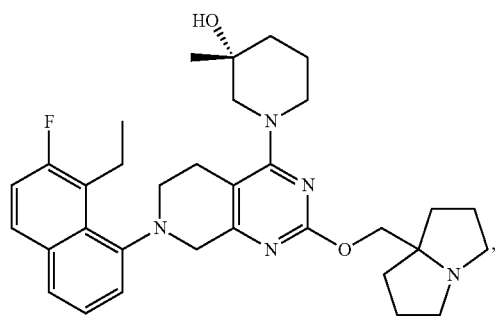
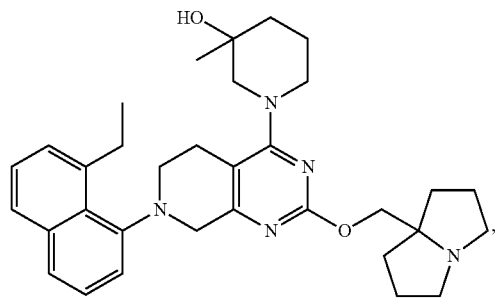
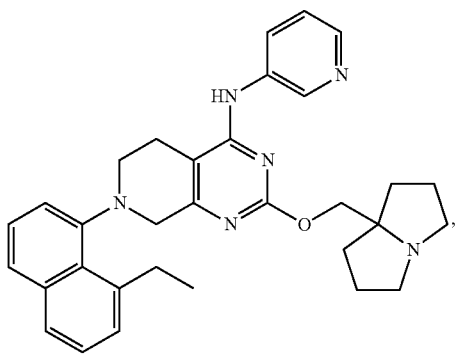
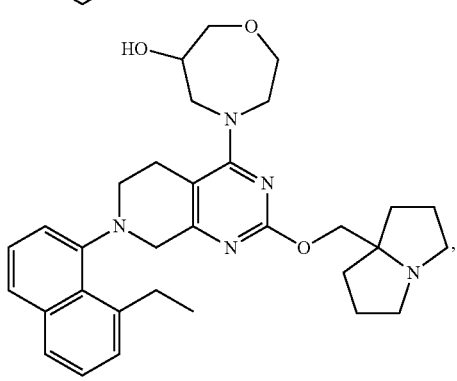
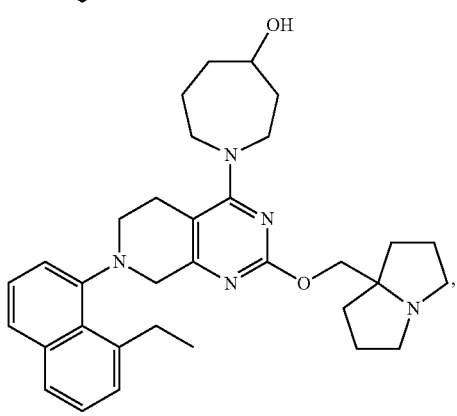
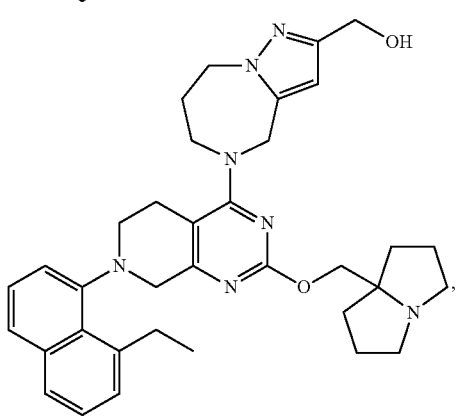

-continued
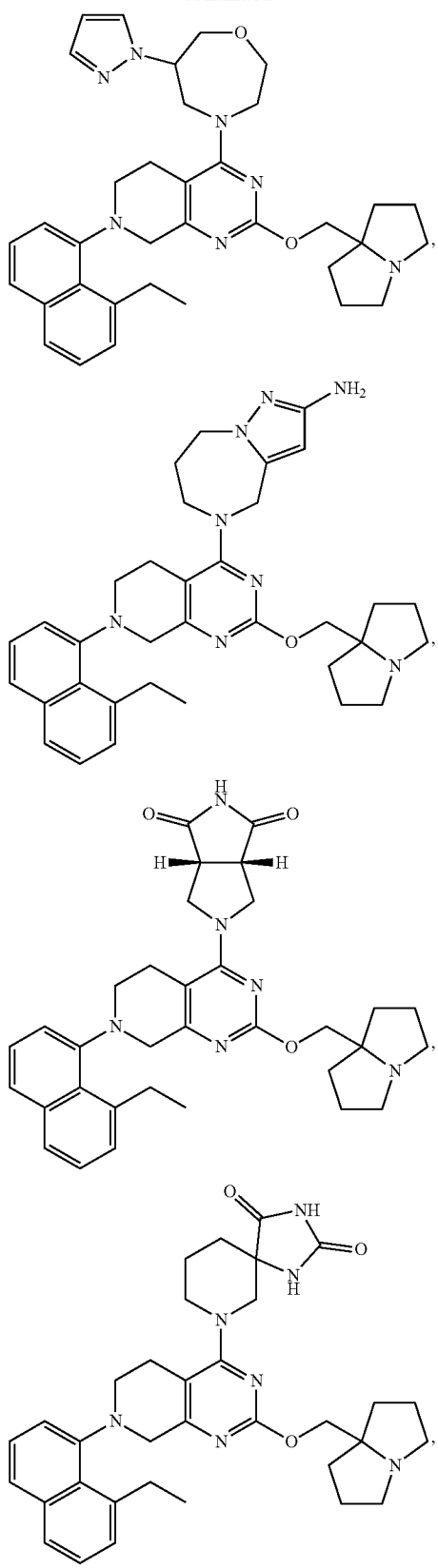
-continued
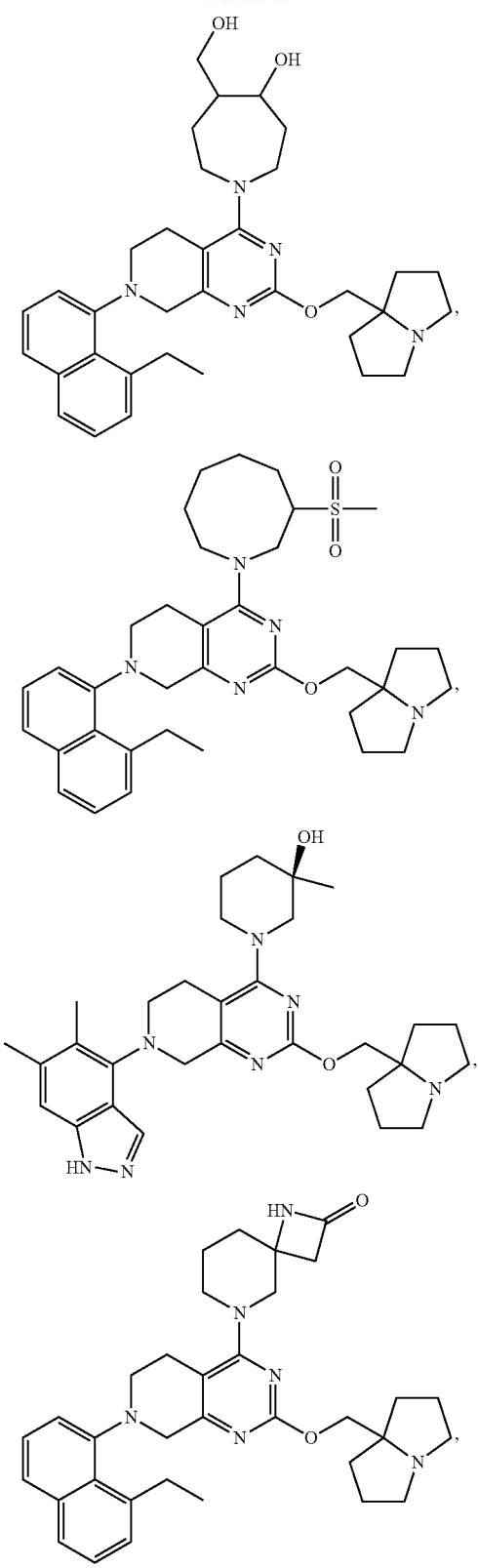

23
-continued
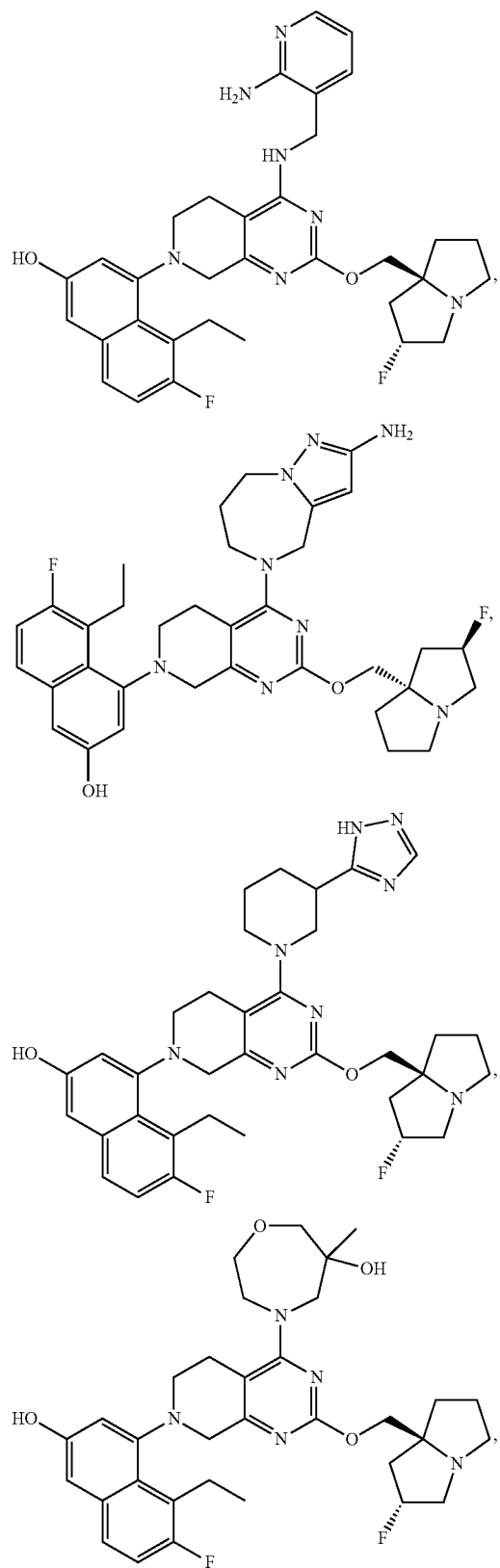
24
-continued
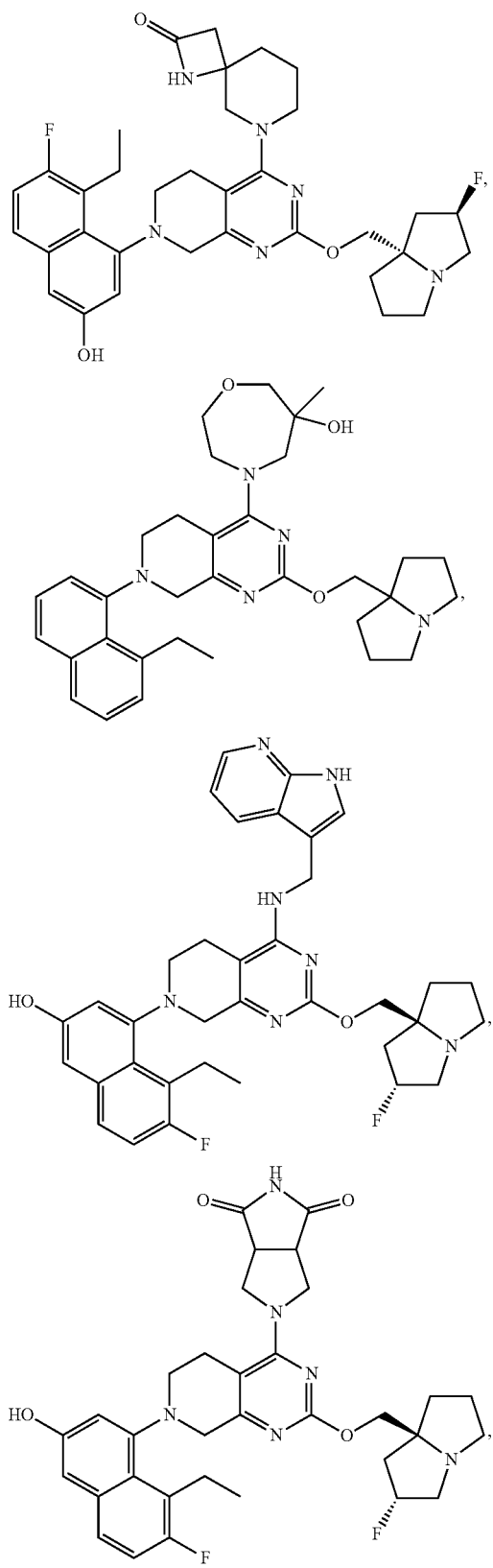

25
-continued
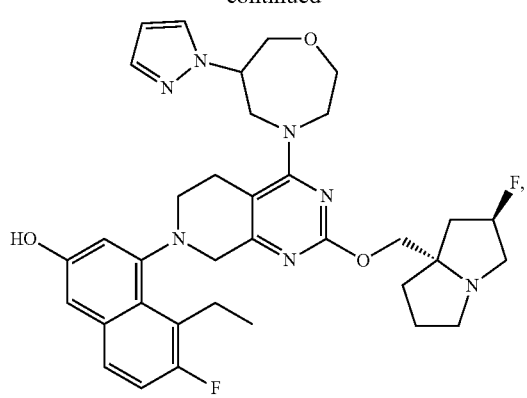
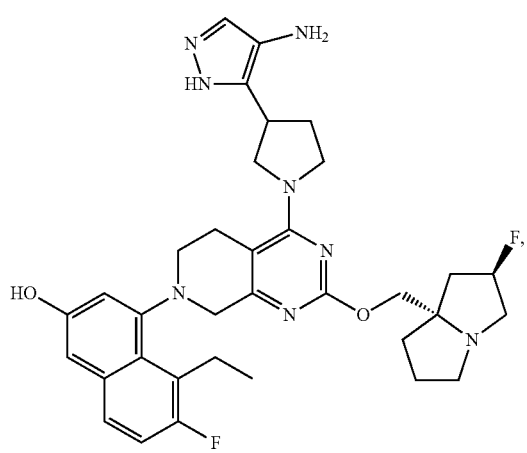
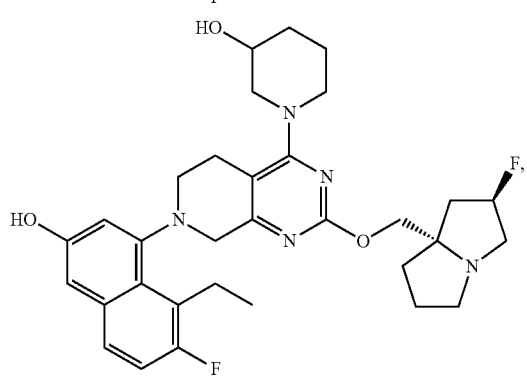
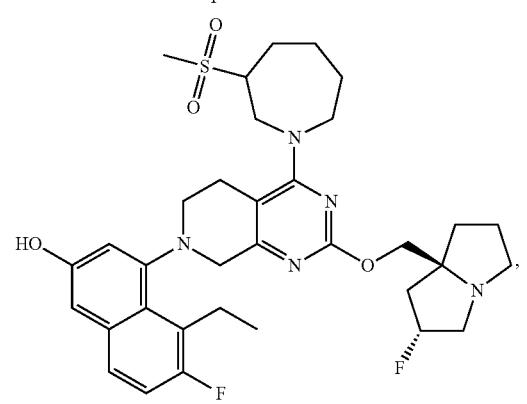
26
-continued
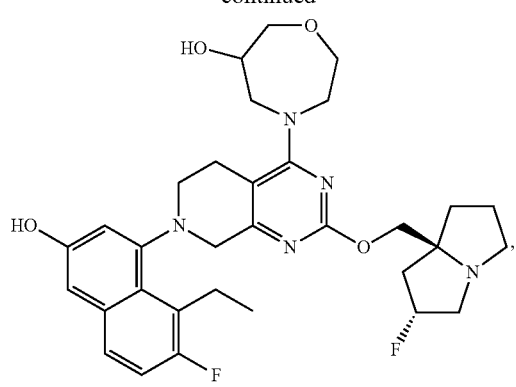
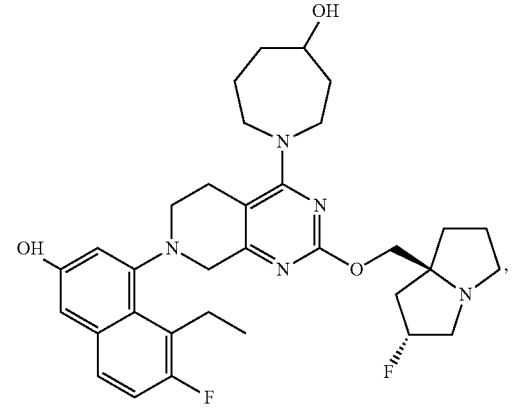
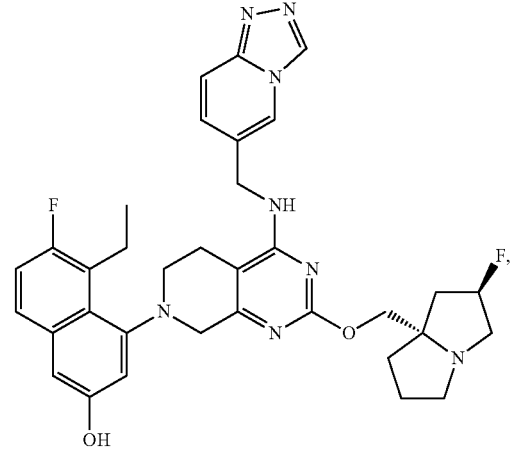
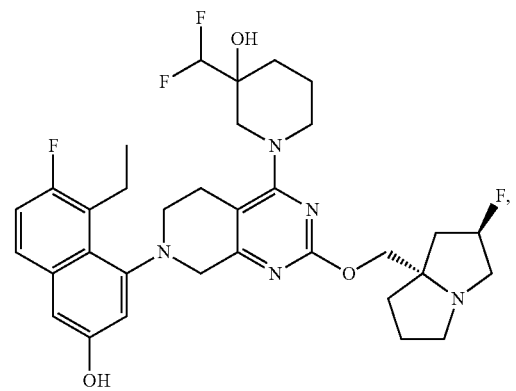

-continued
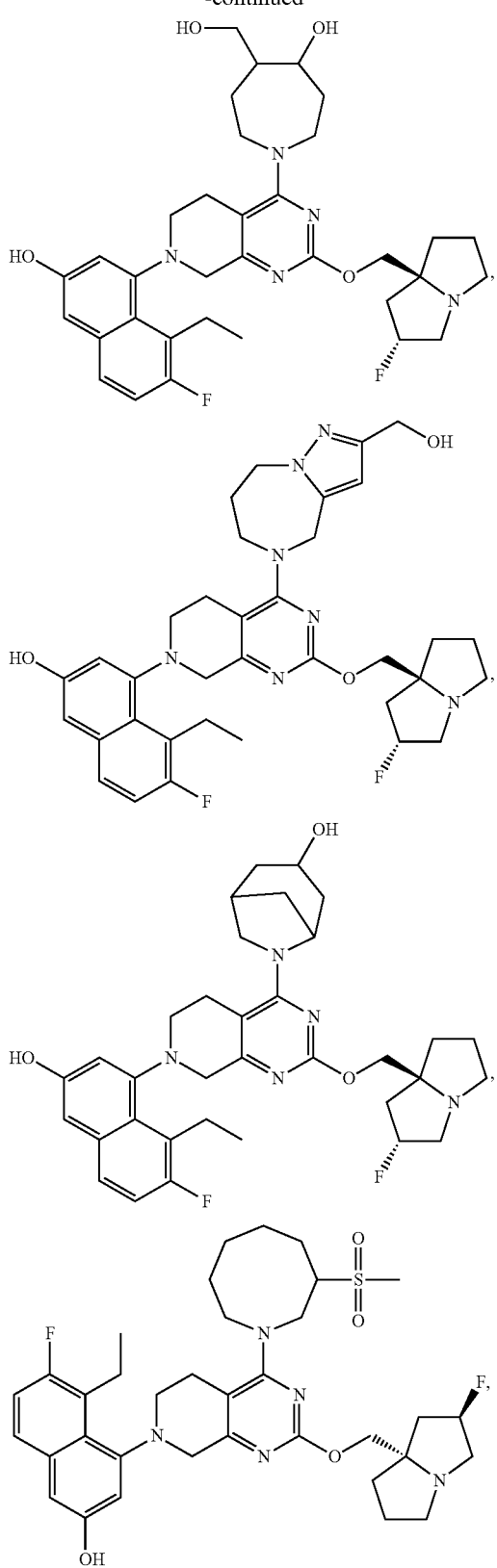
-continued
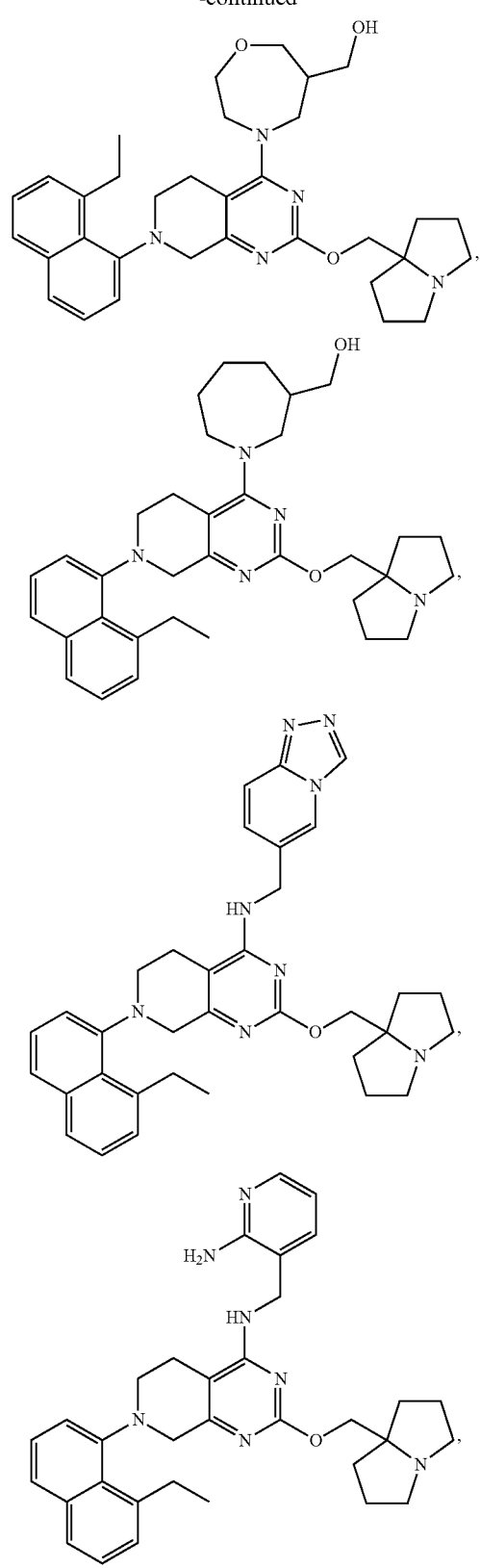

29
-continued
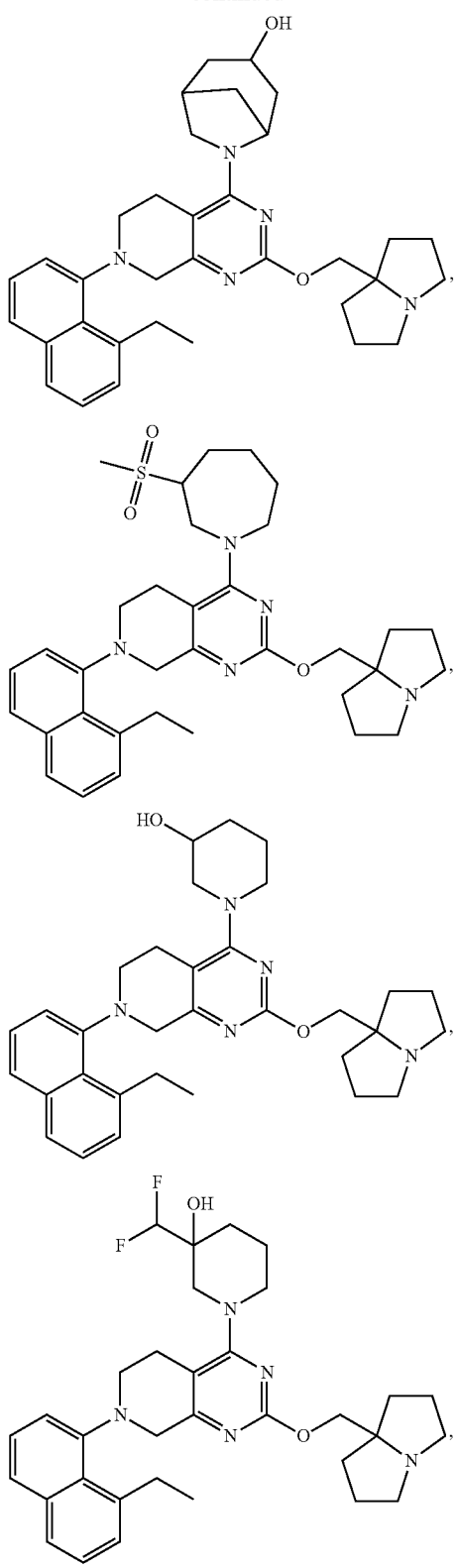
30
-continued
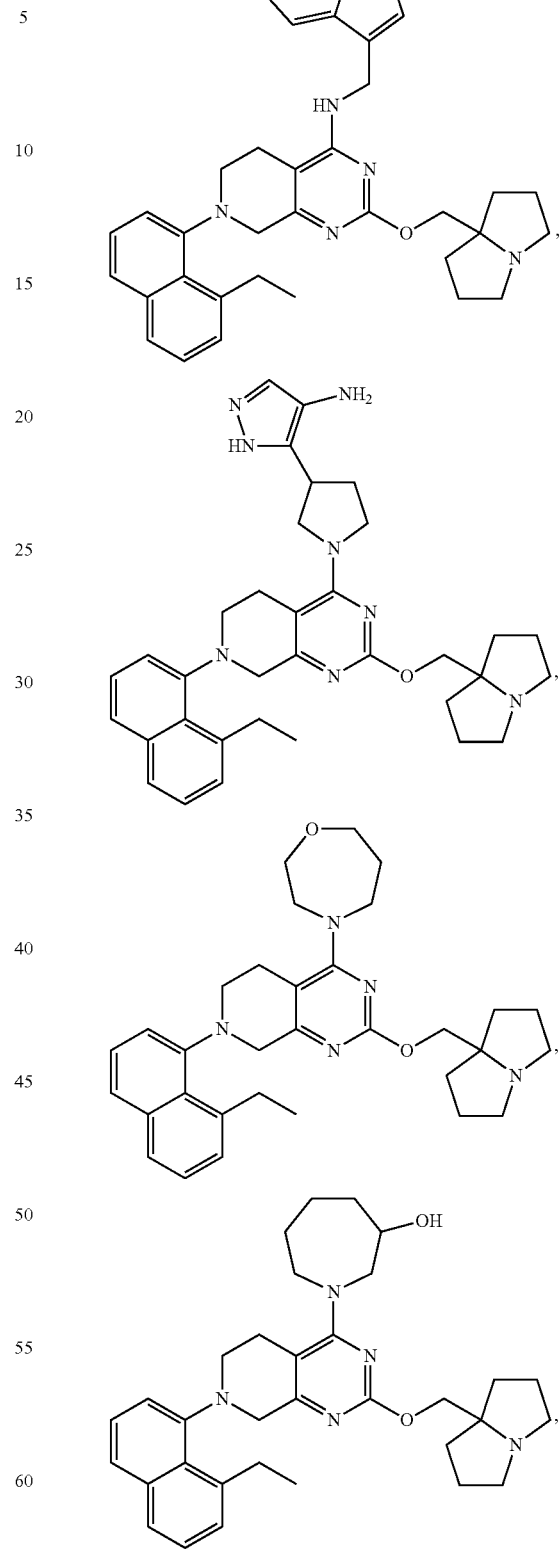

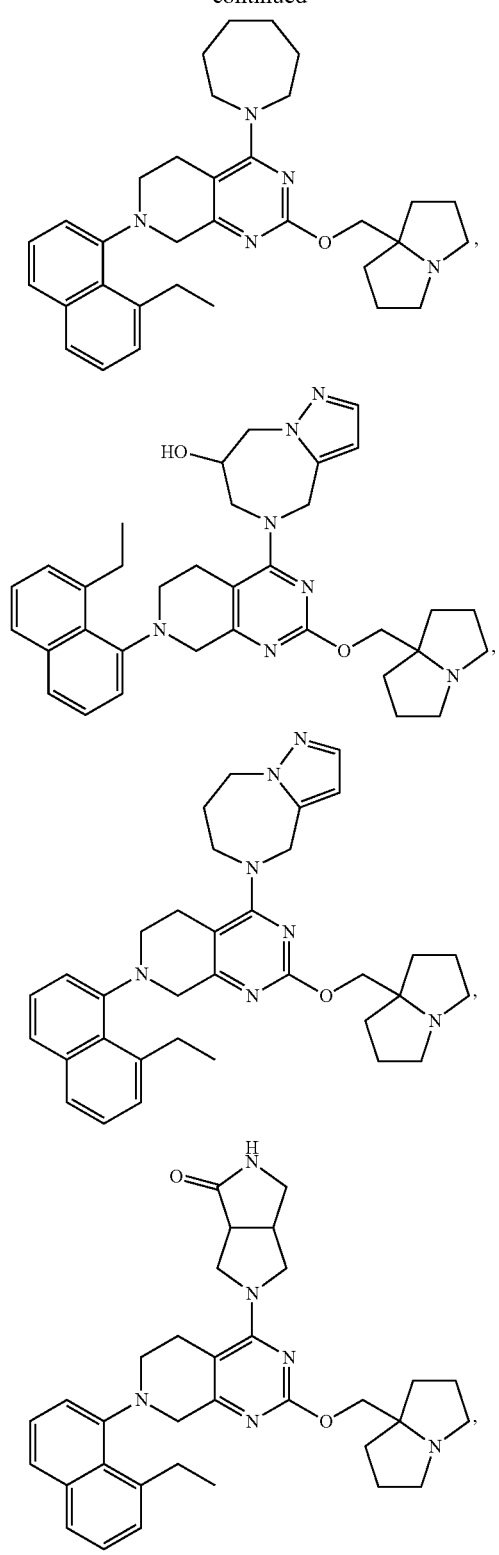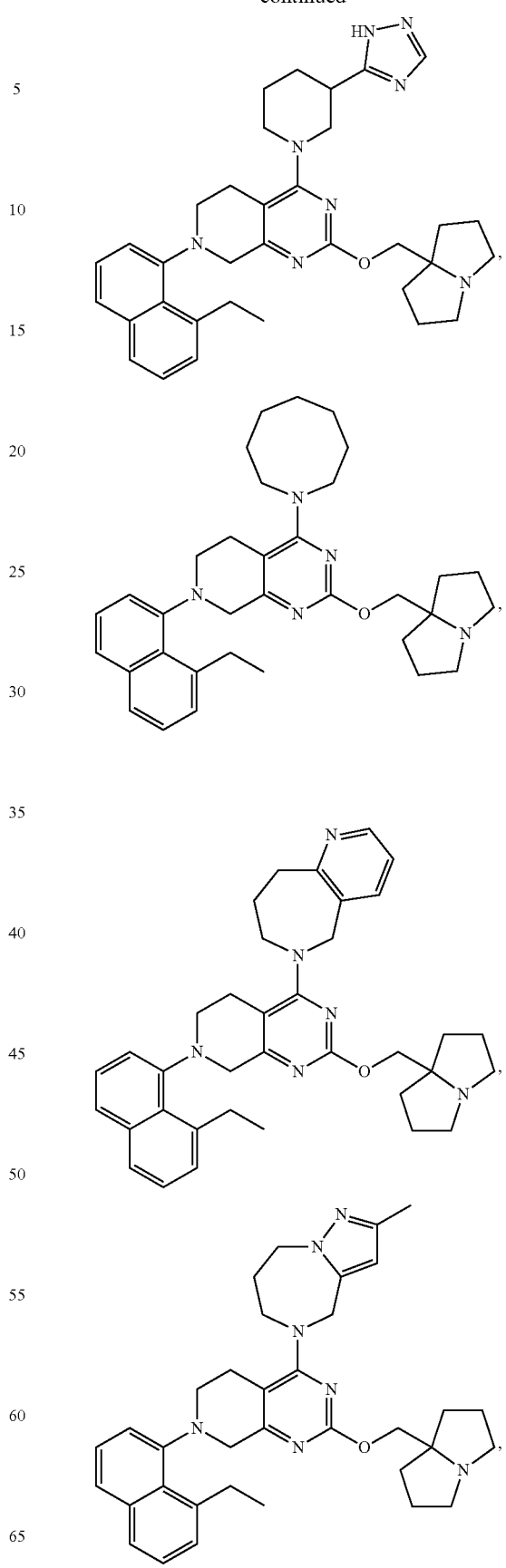

-continued
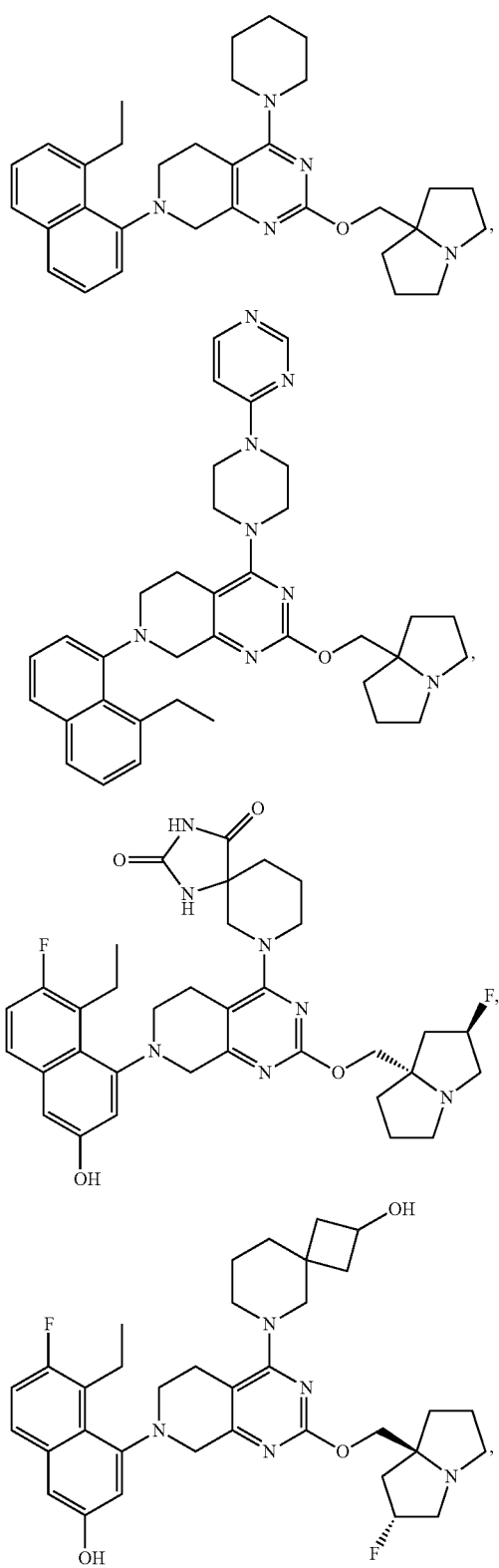
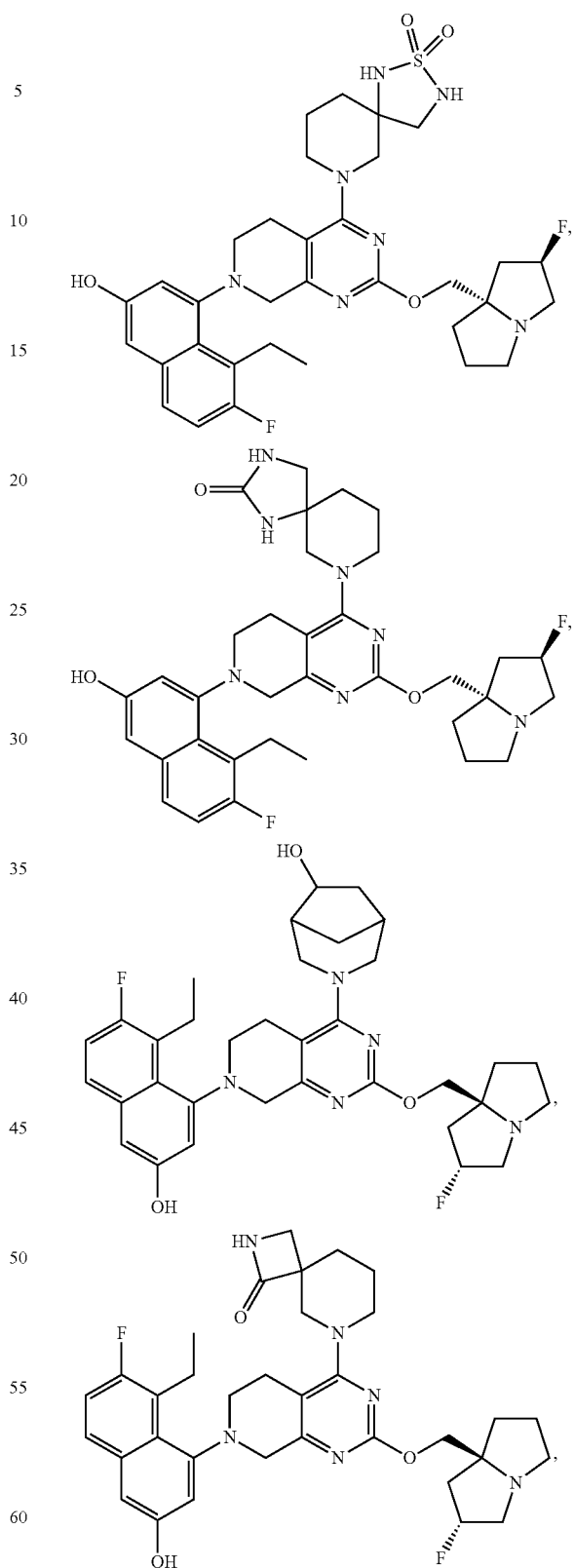

-continued
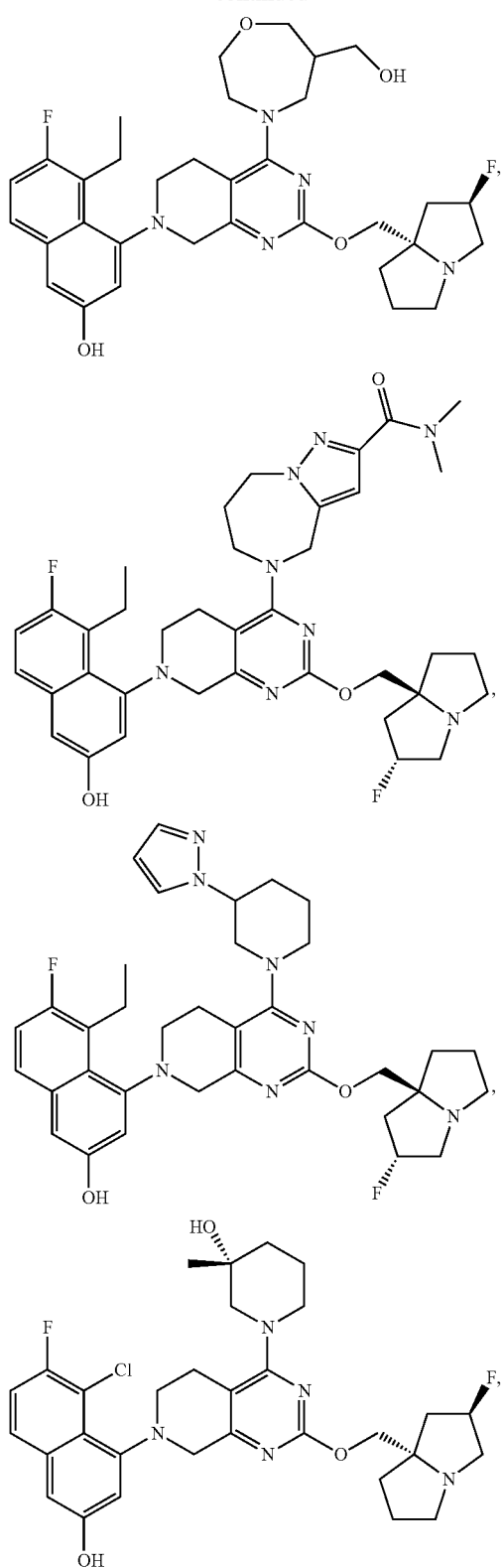
-continued
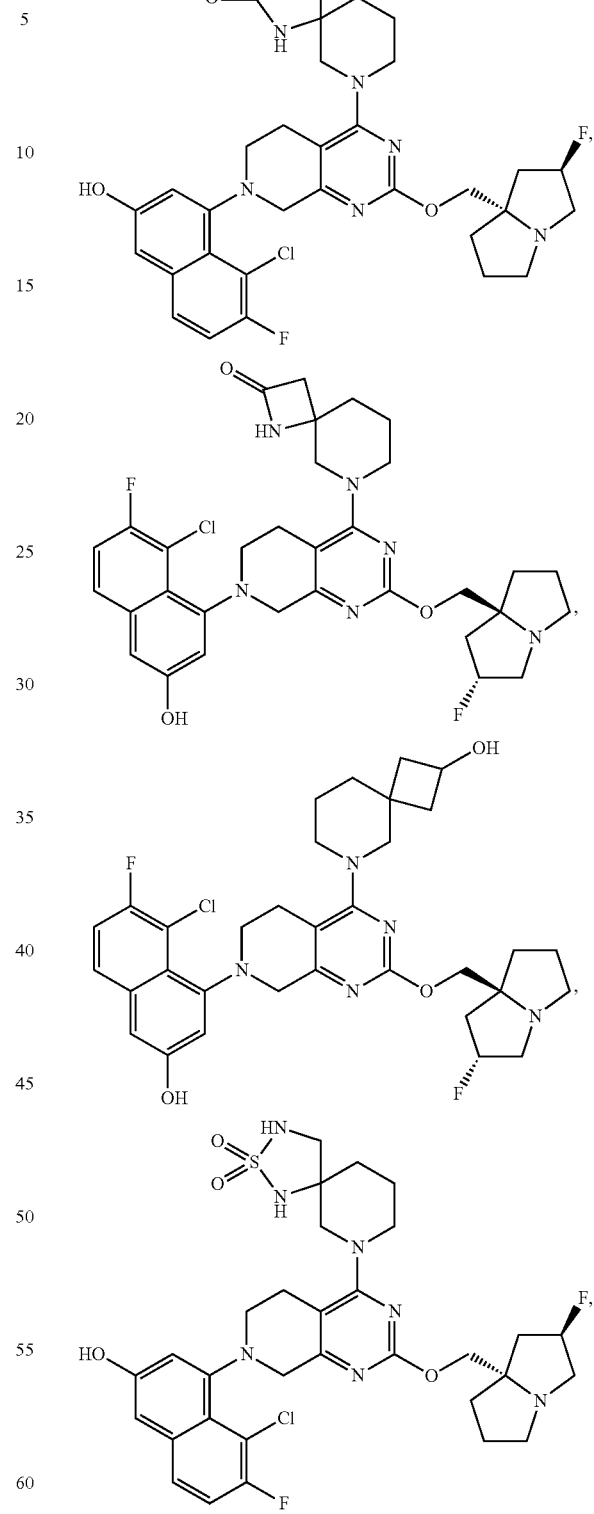

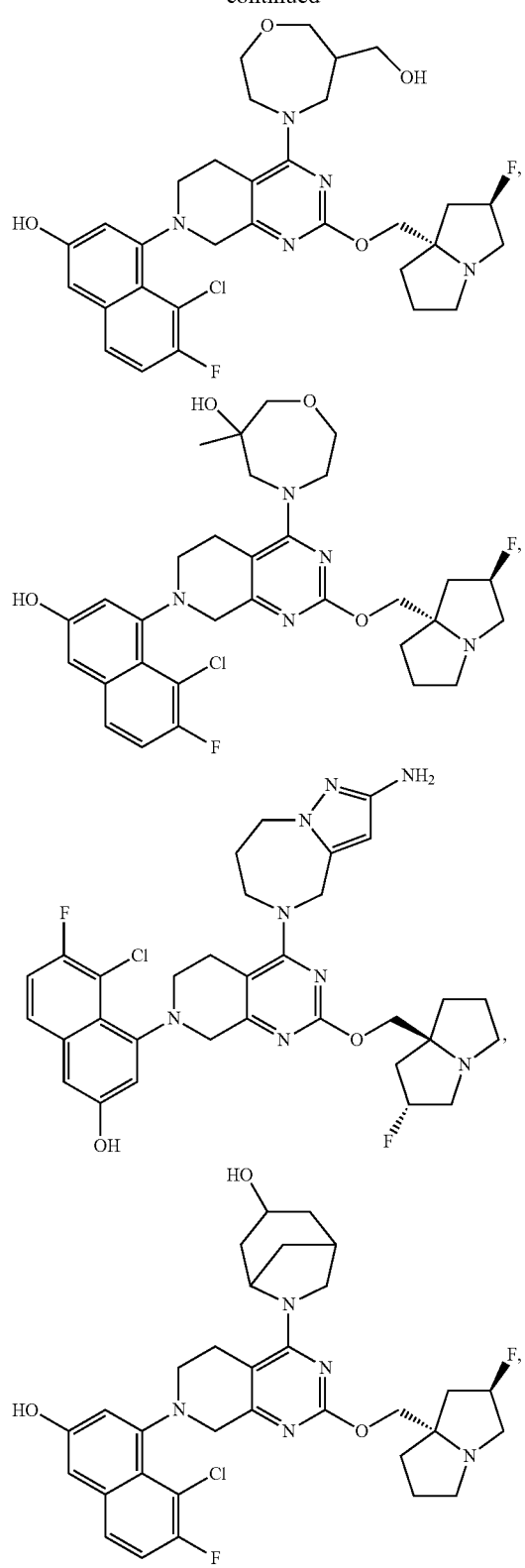
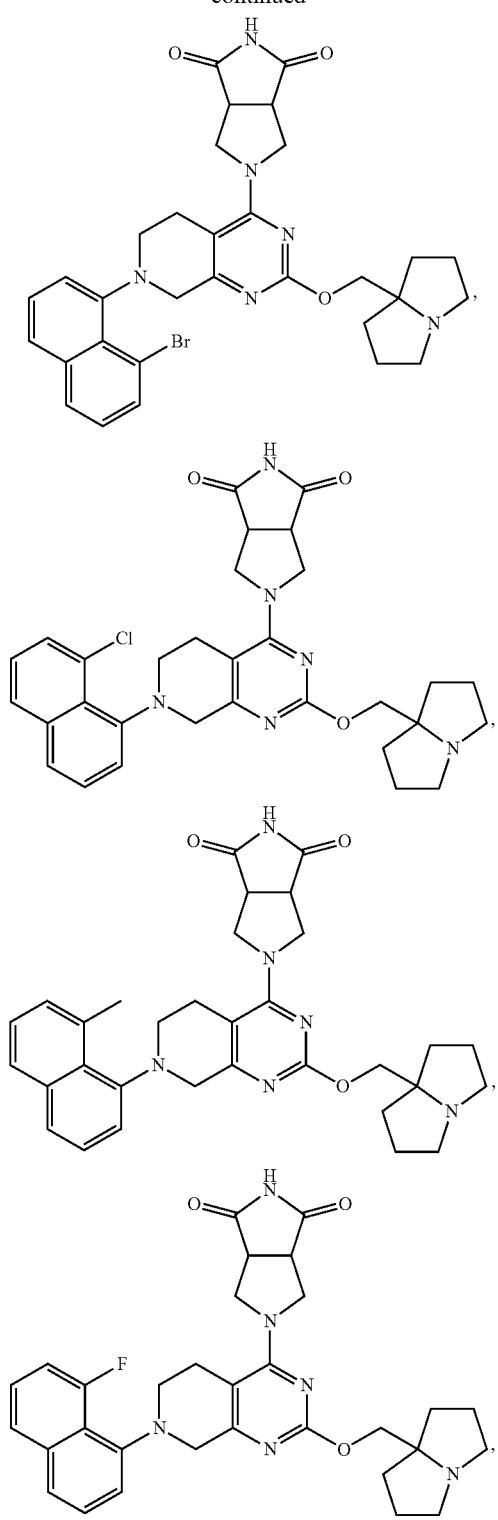

39
-continued
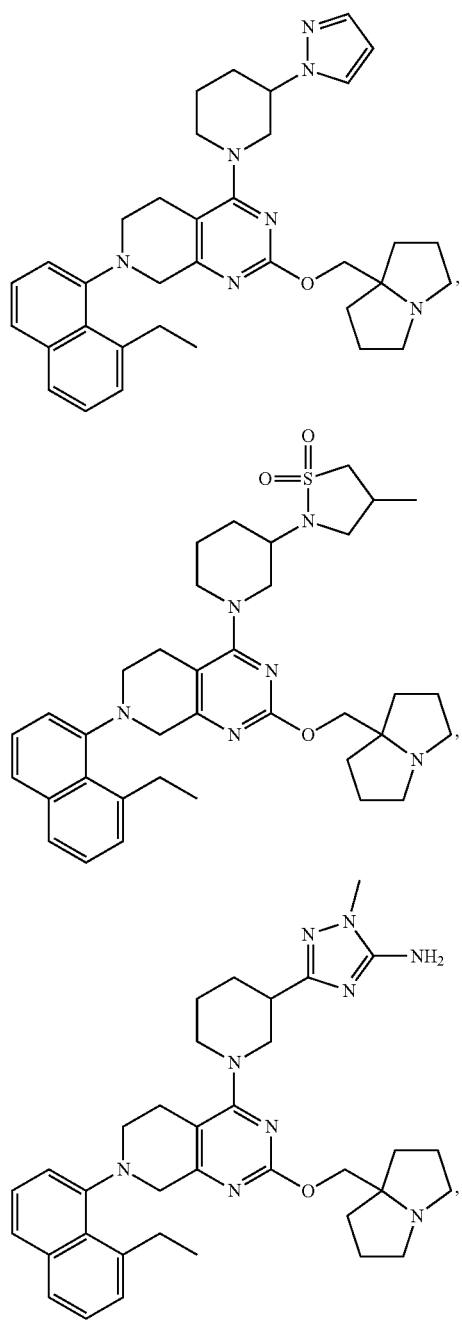
40
-continued
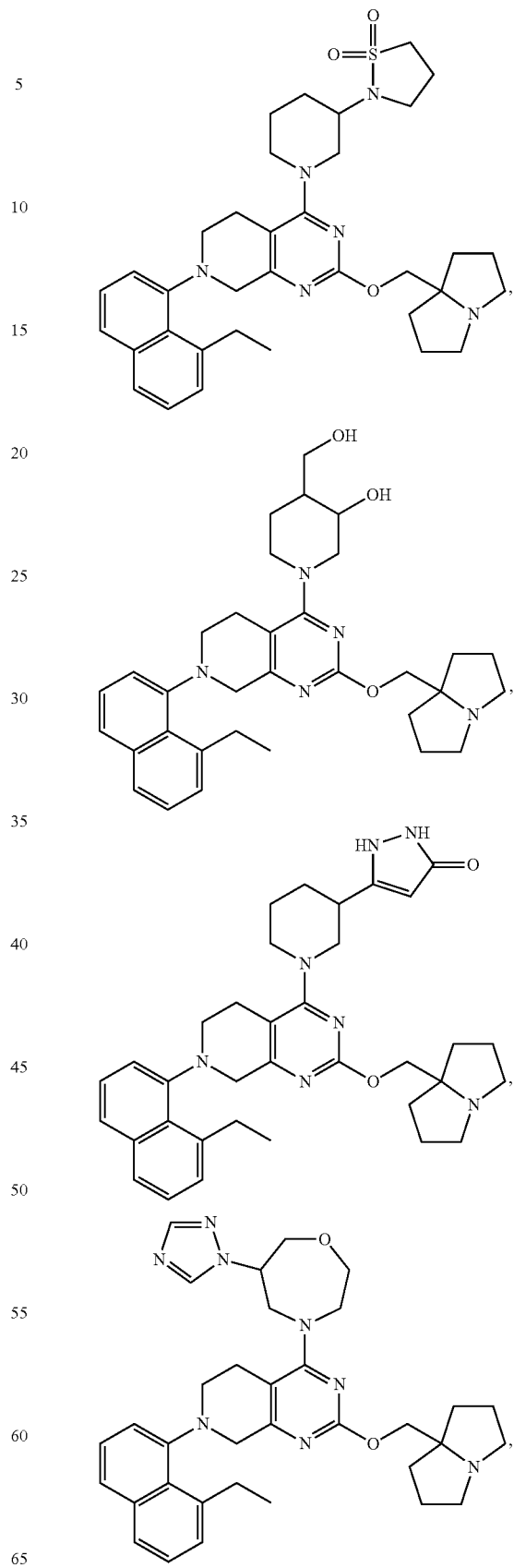

41
-continued
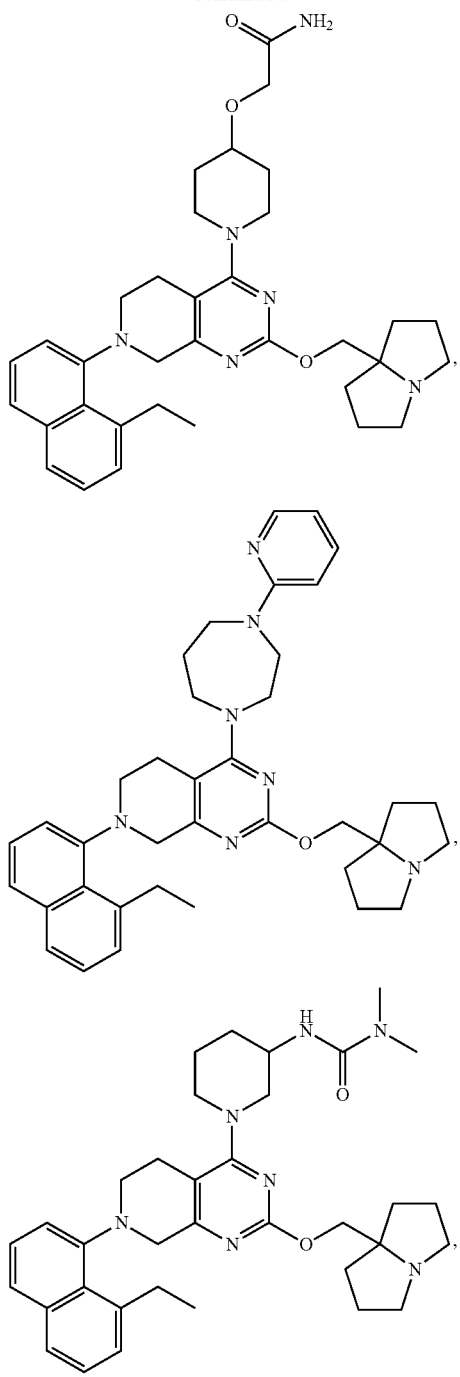
42
-continued
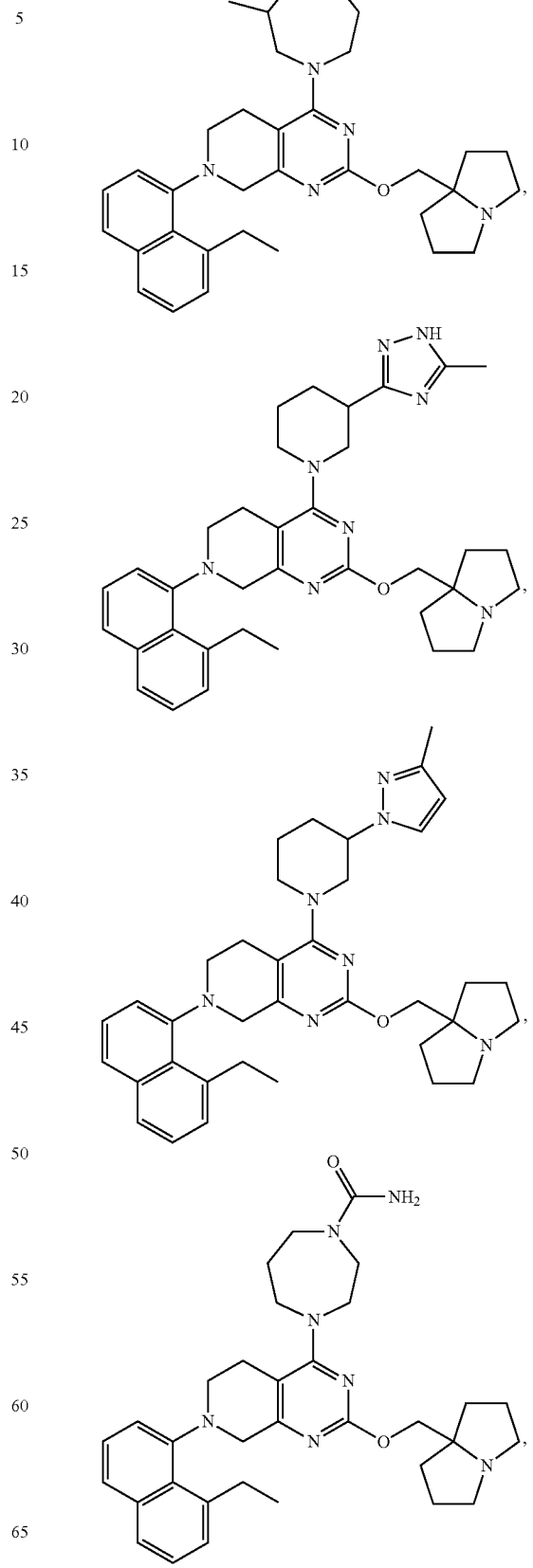

43
-continued
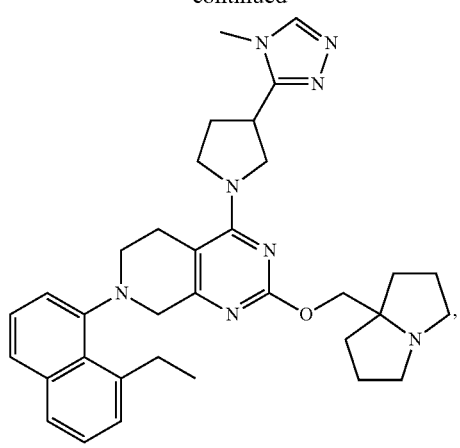
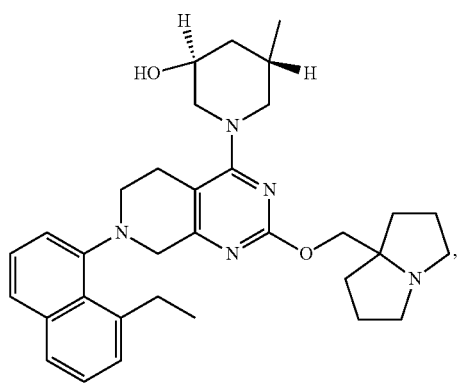
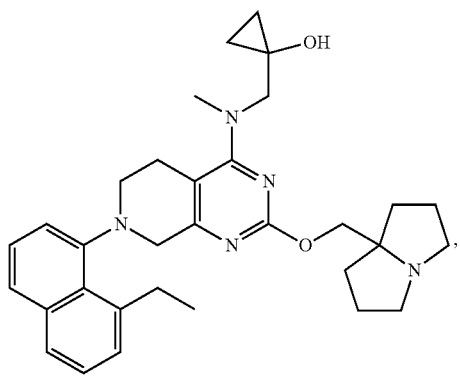
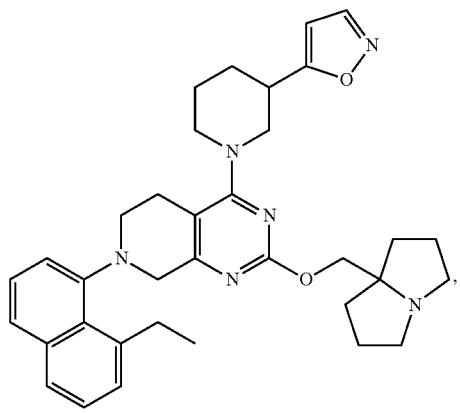
44
-continued
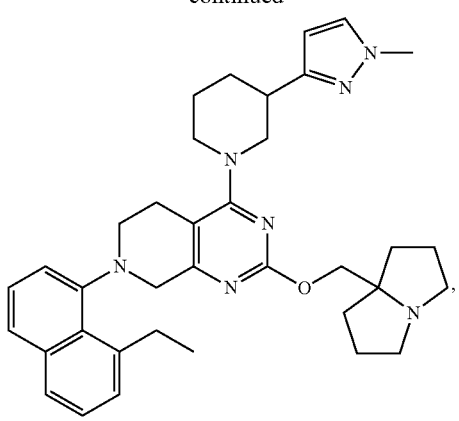
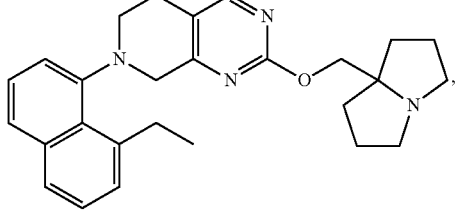
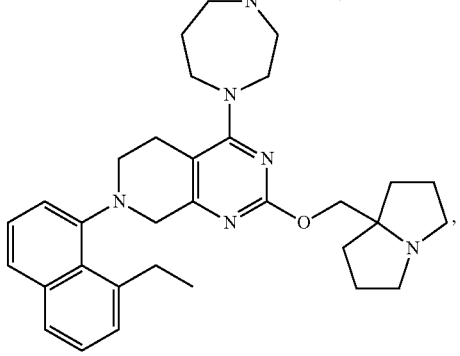

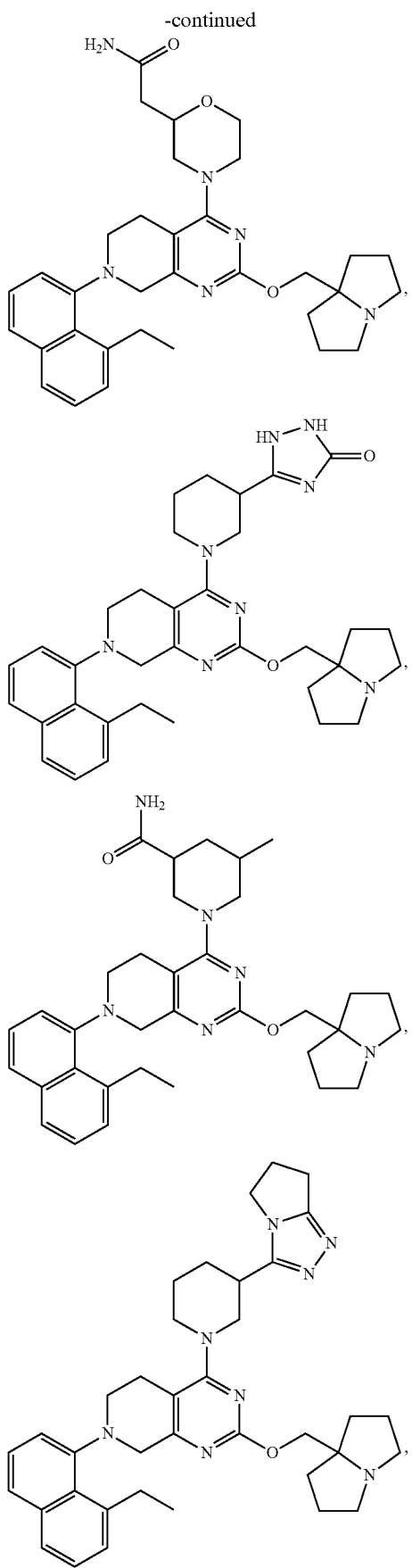

47
-continued
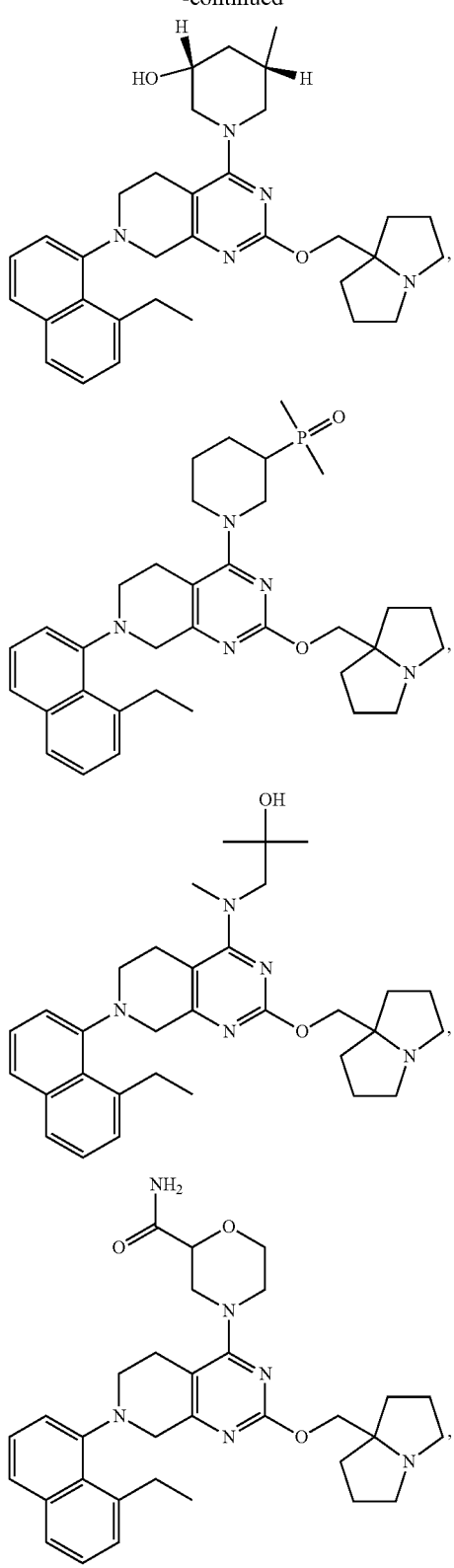
48
-continued
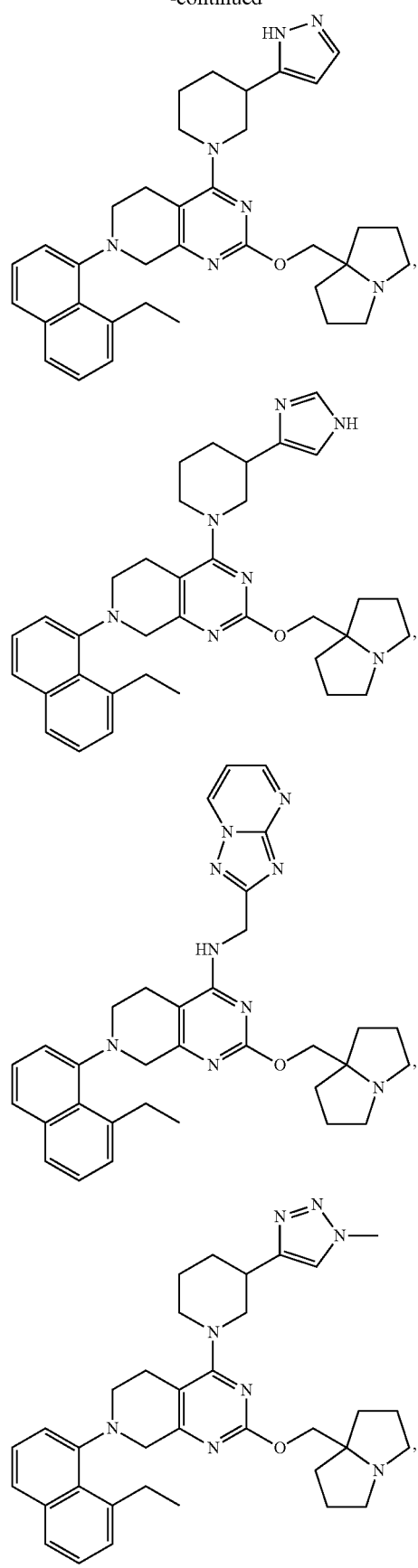

49
-continued
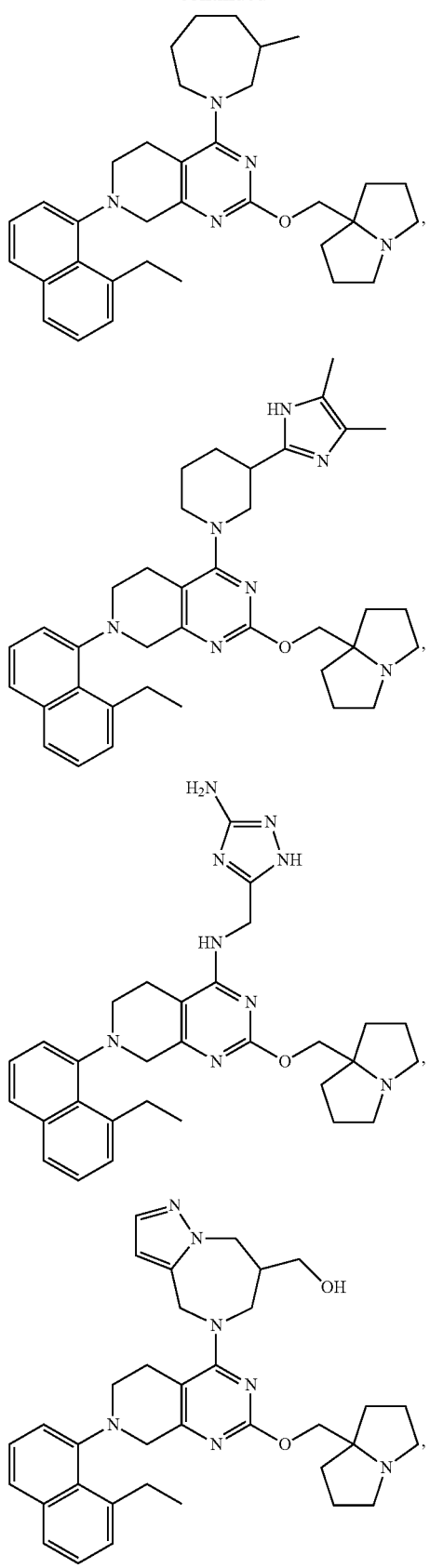
50
-continued
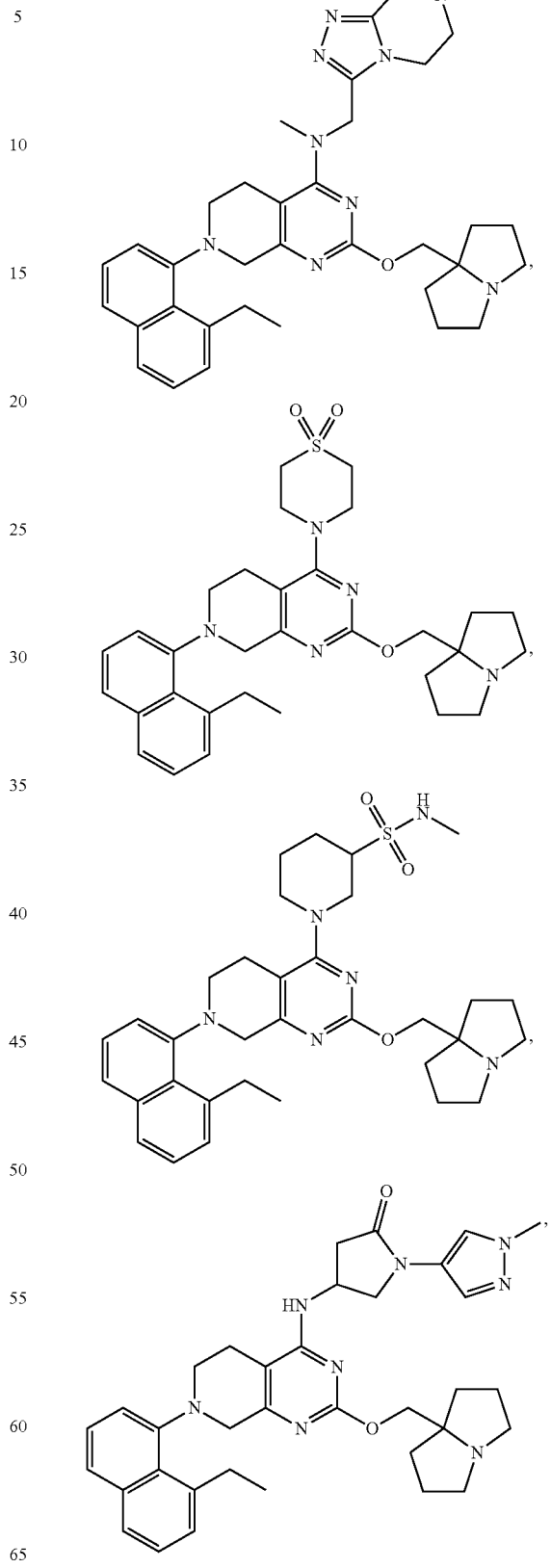

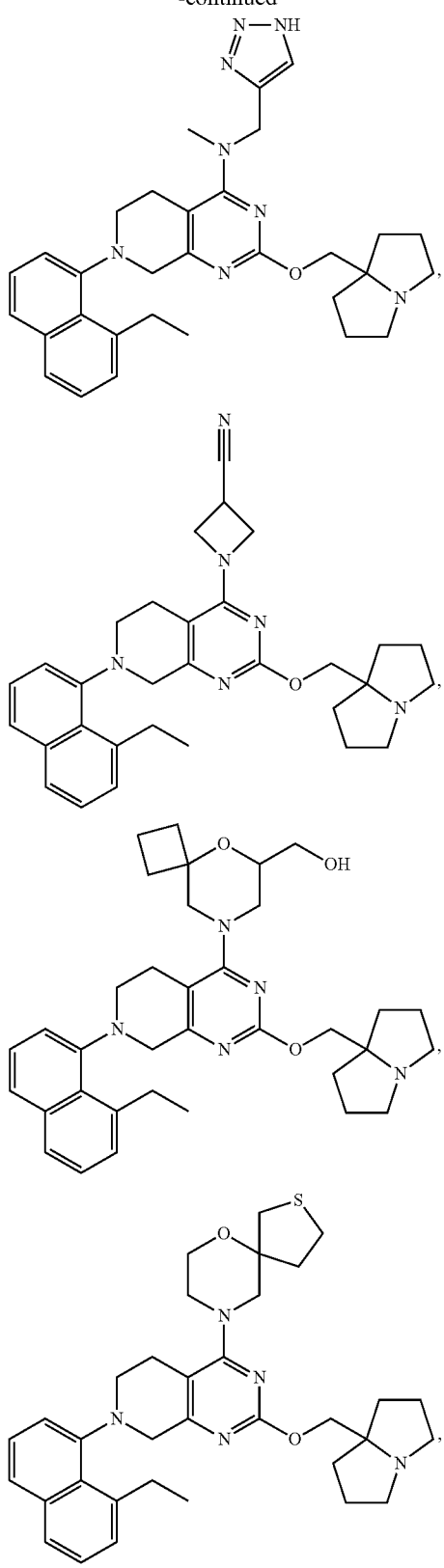
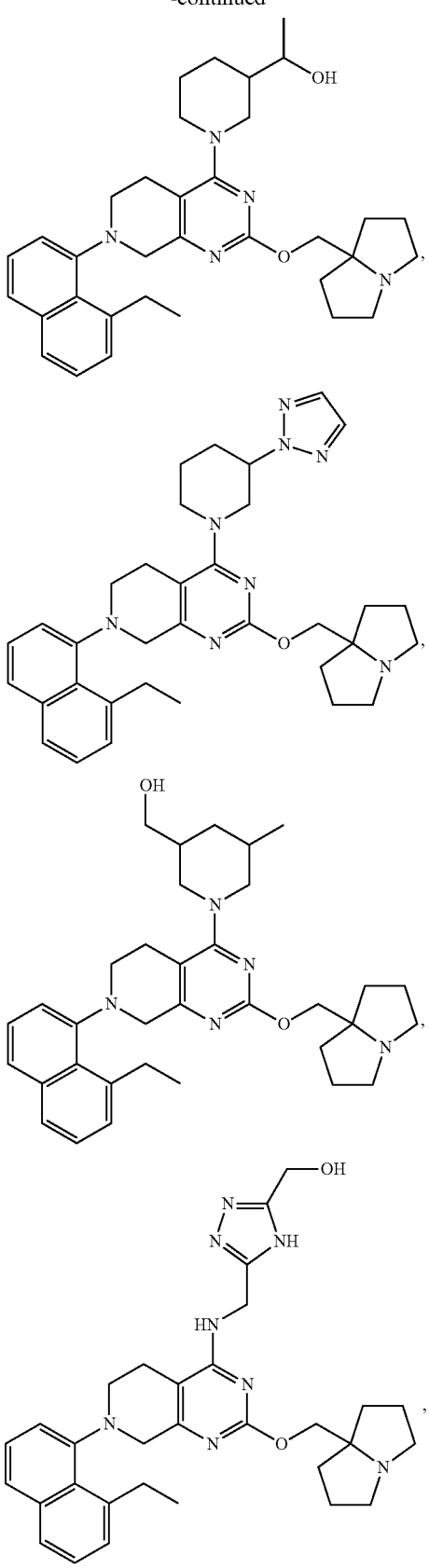

53
-continued
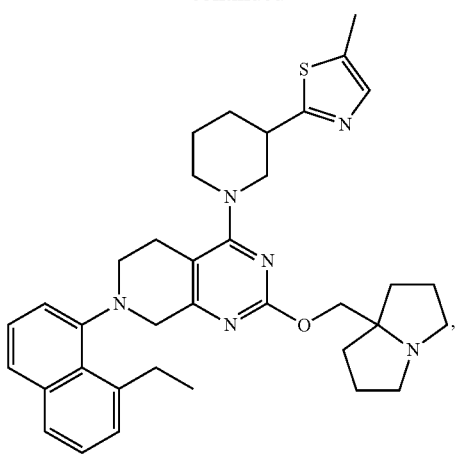
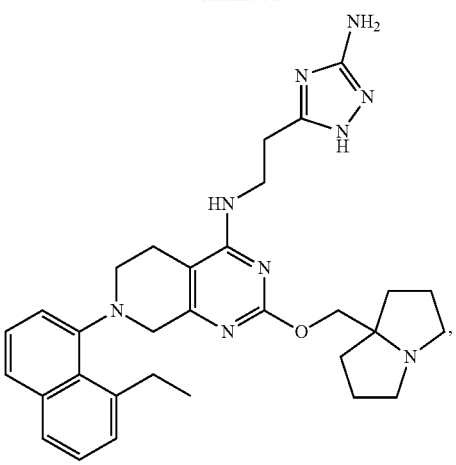
54
-continued
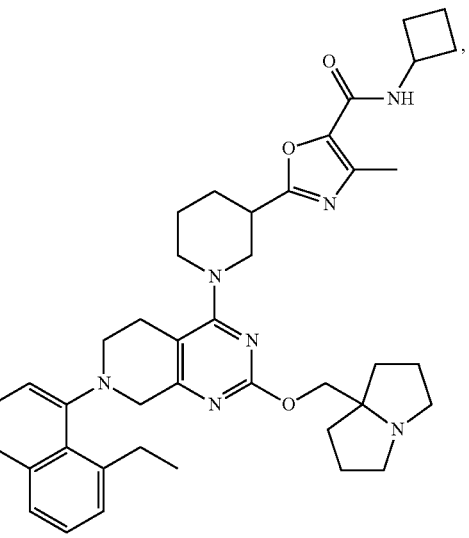

55
-continued
56
-continued
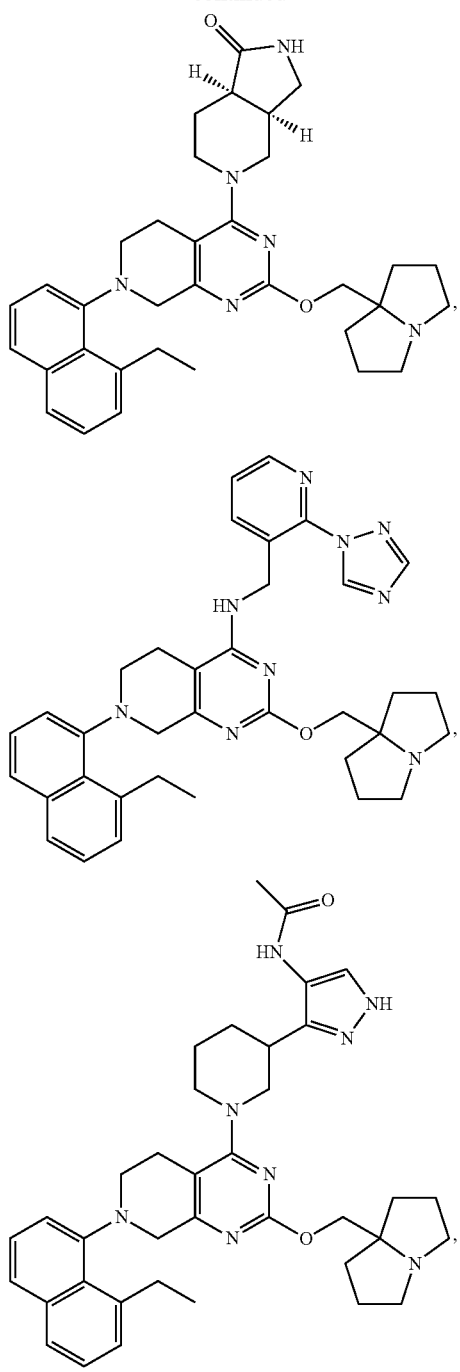
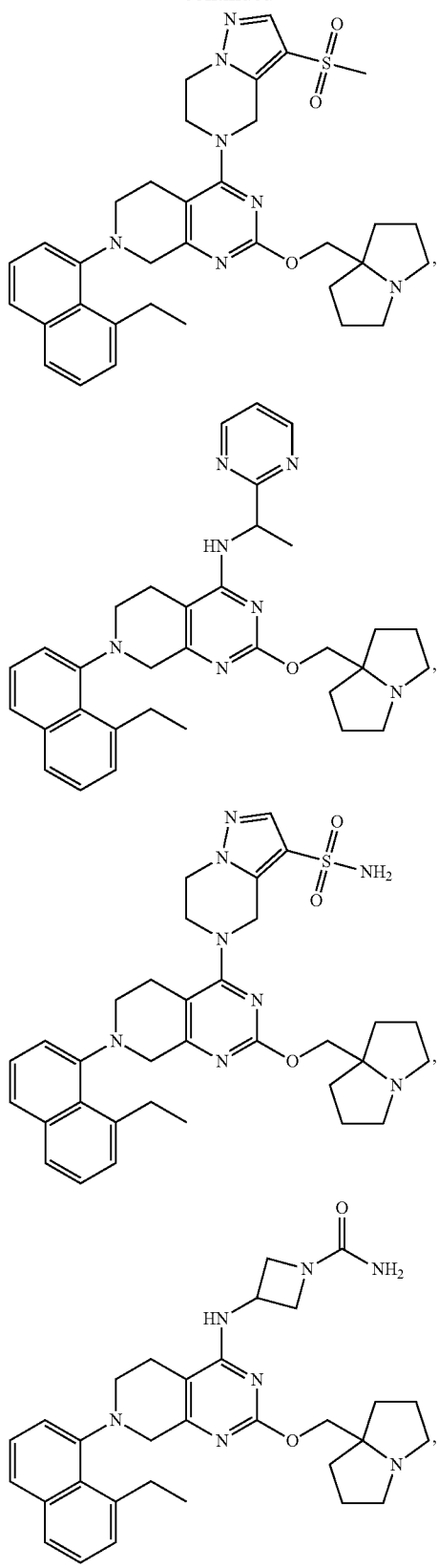

57
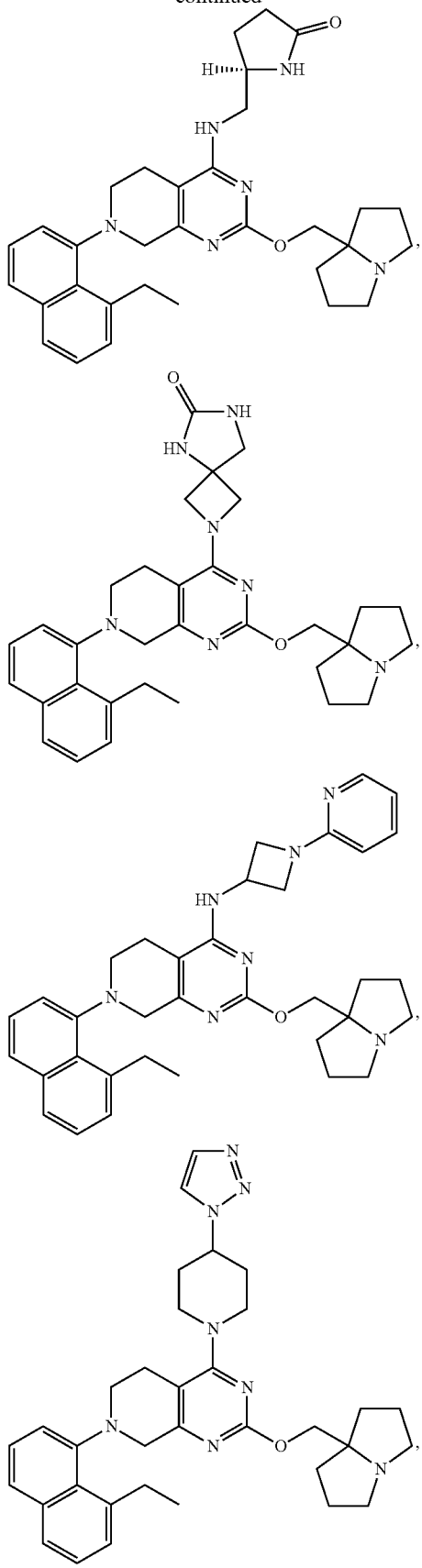
58
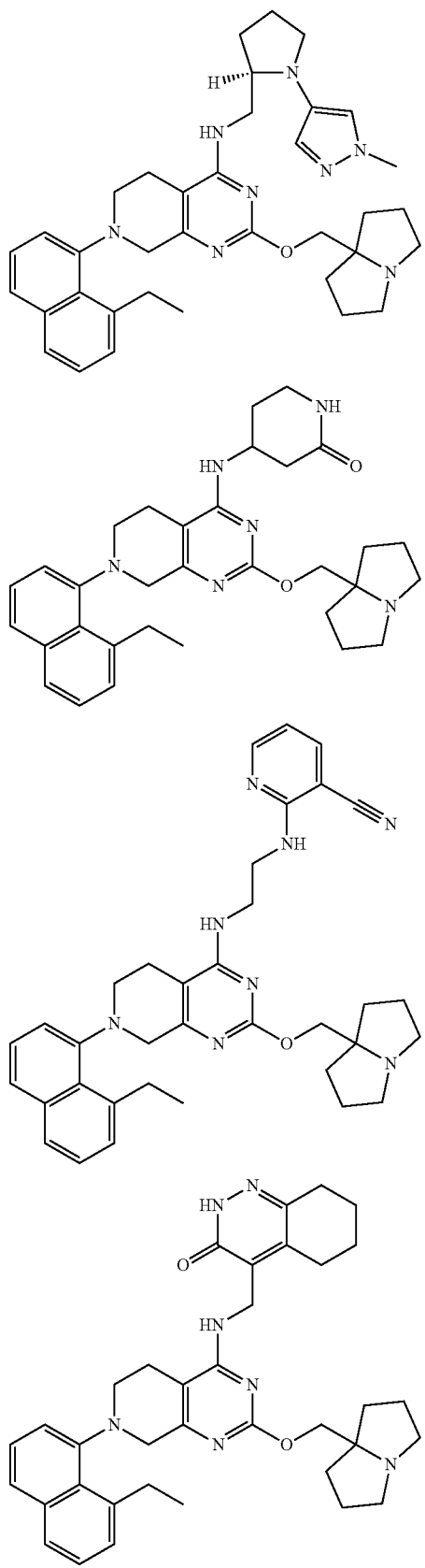

59
-continued
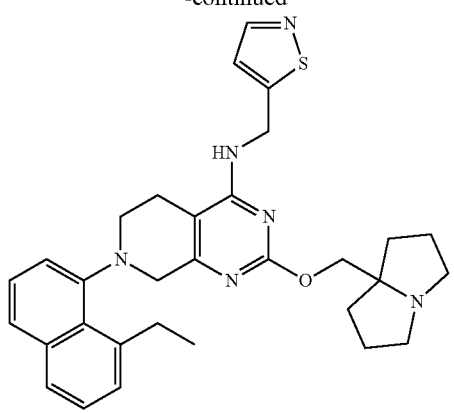
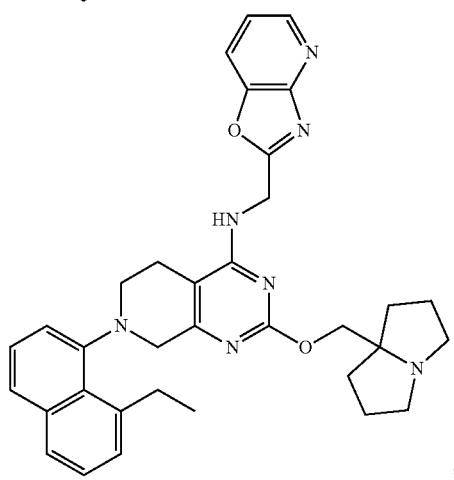
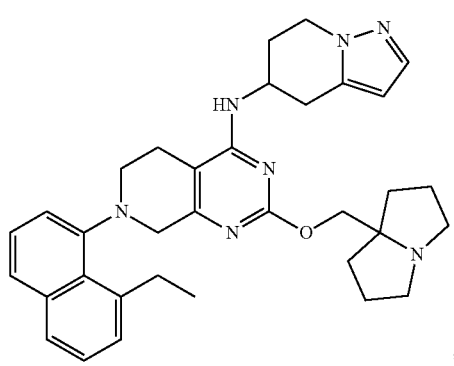
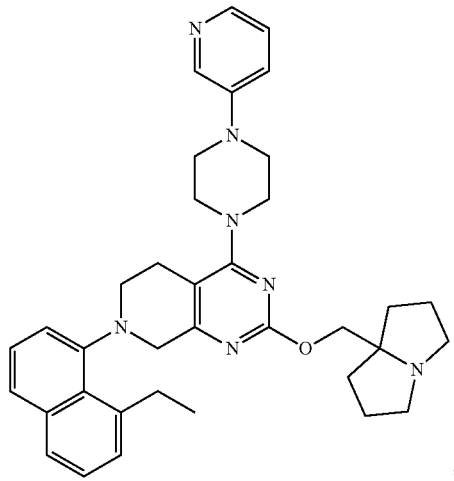
60
-continued
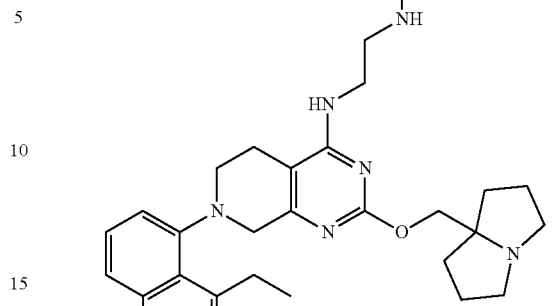
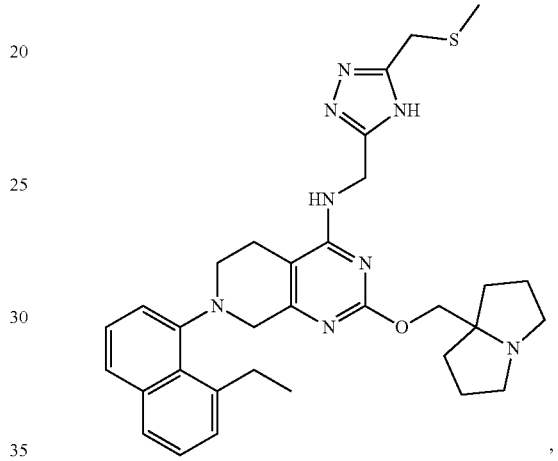
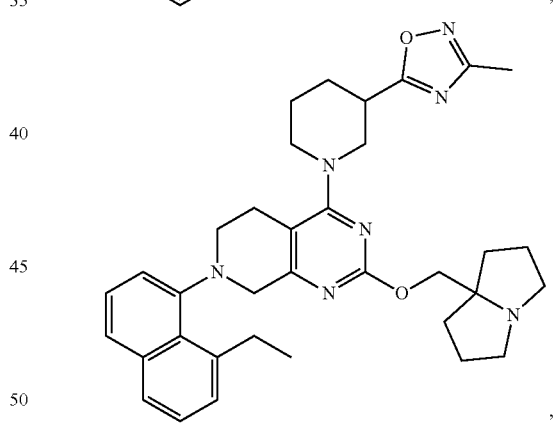
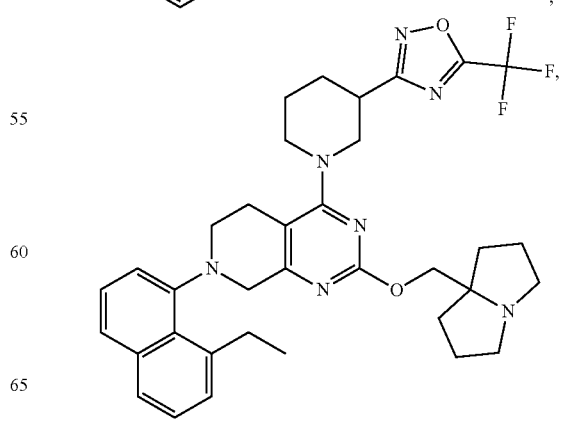

-continued
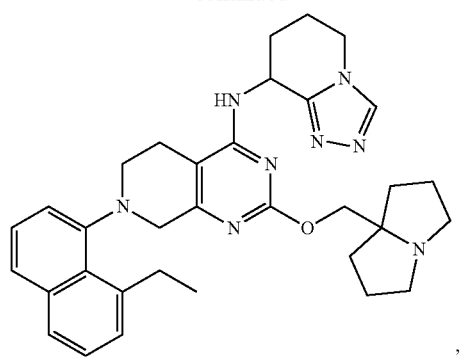
,
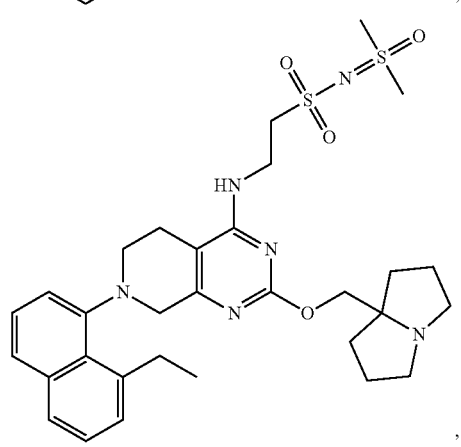
,
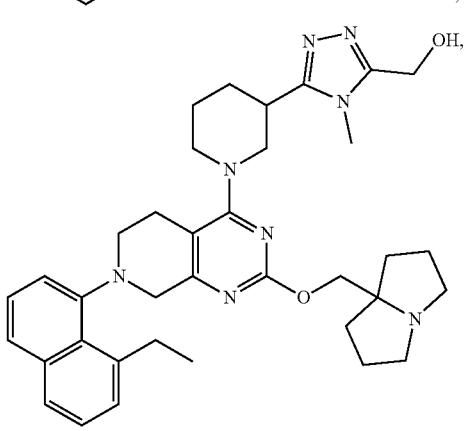
,
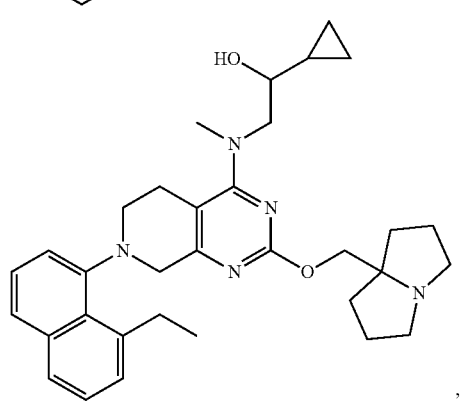
,
-continued
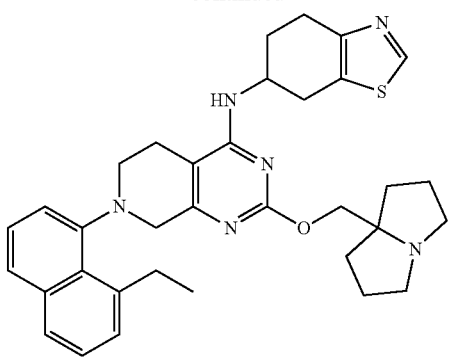
,
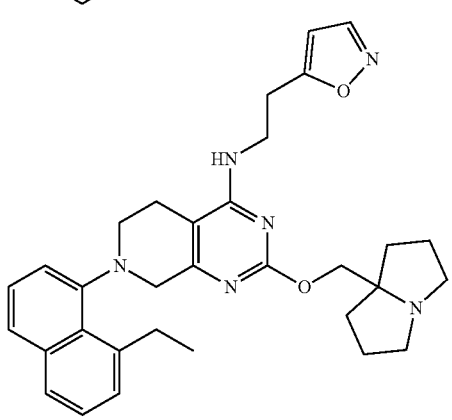
,
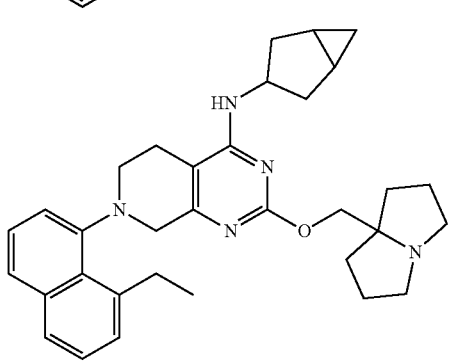
,
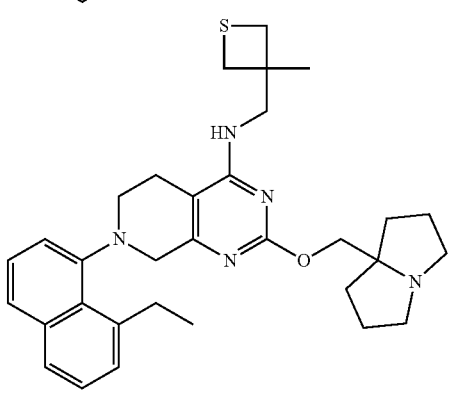
, 63
-continued
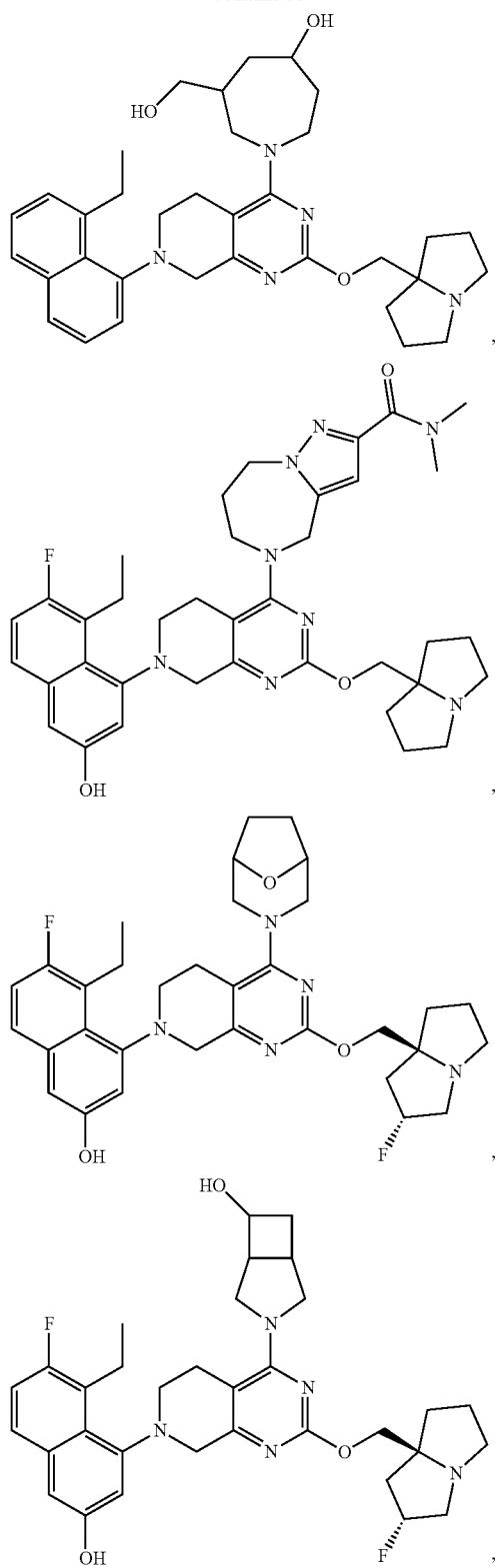
64
-continued
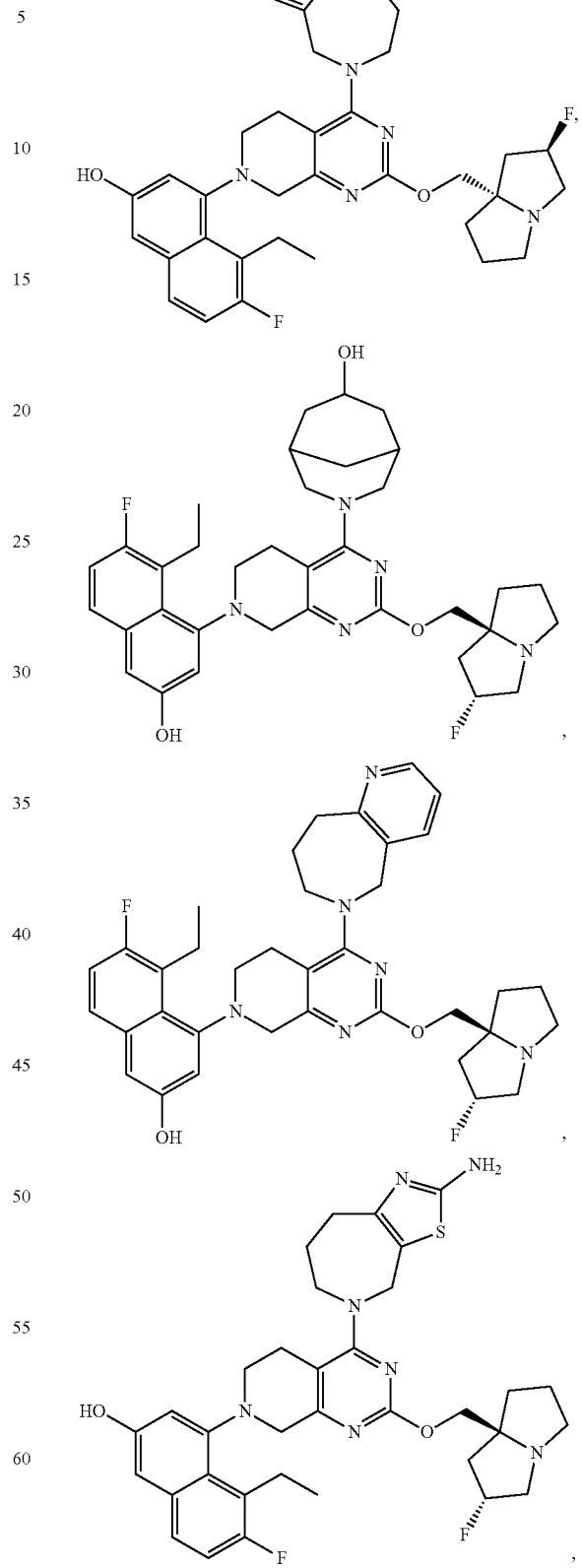

-continued
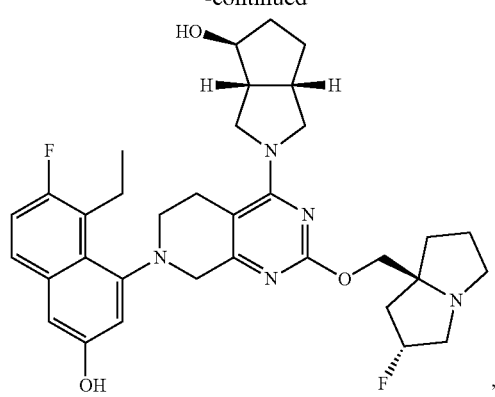
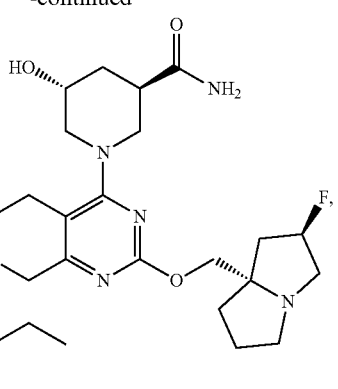

67
-continued
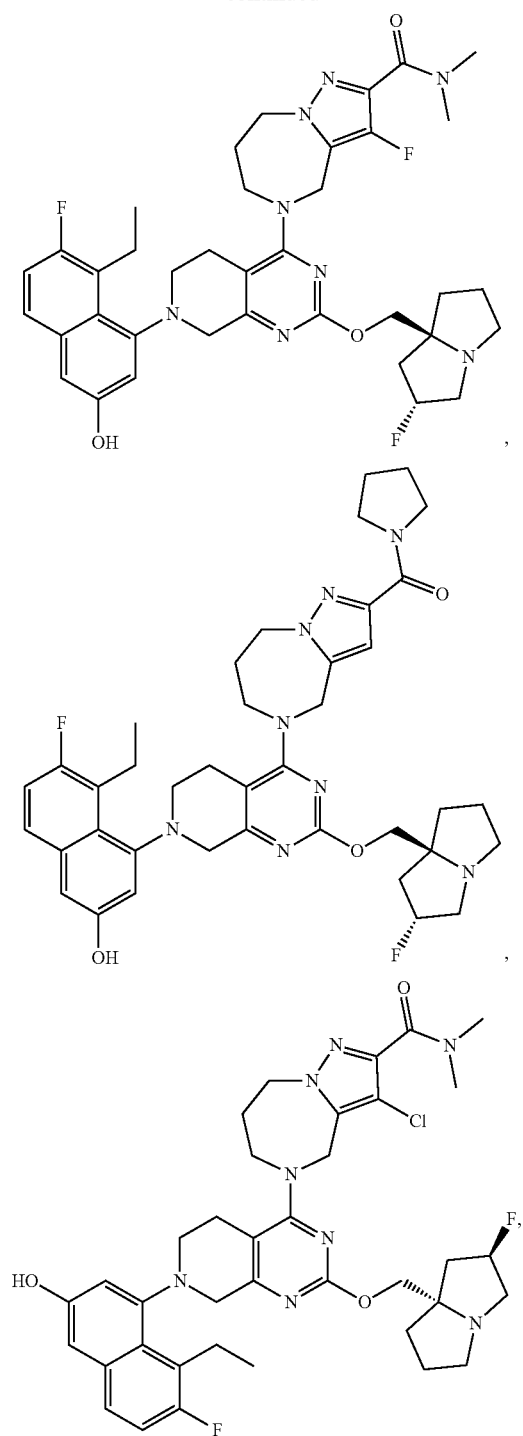
68
-continued
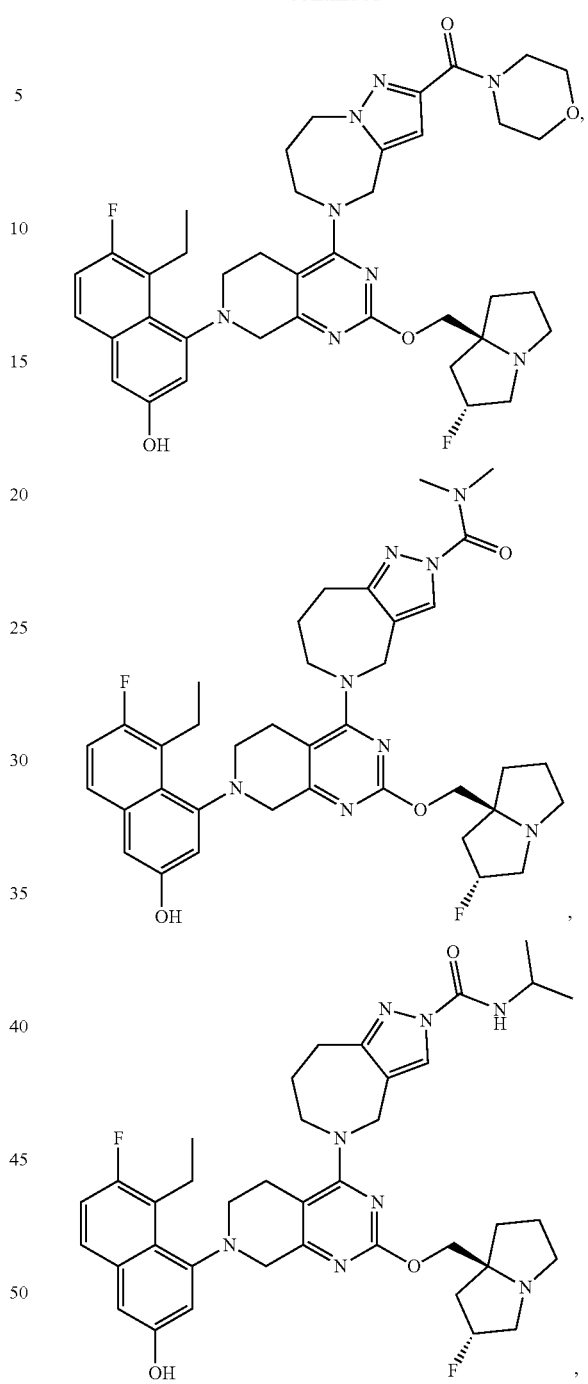

69
-continued
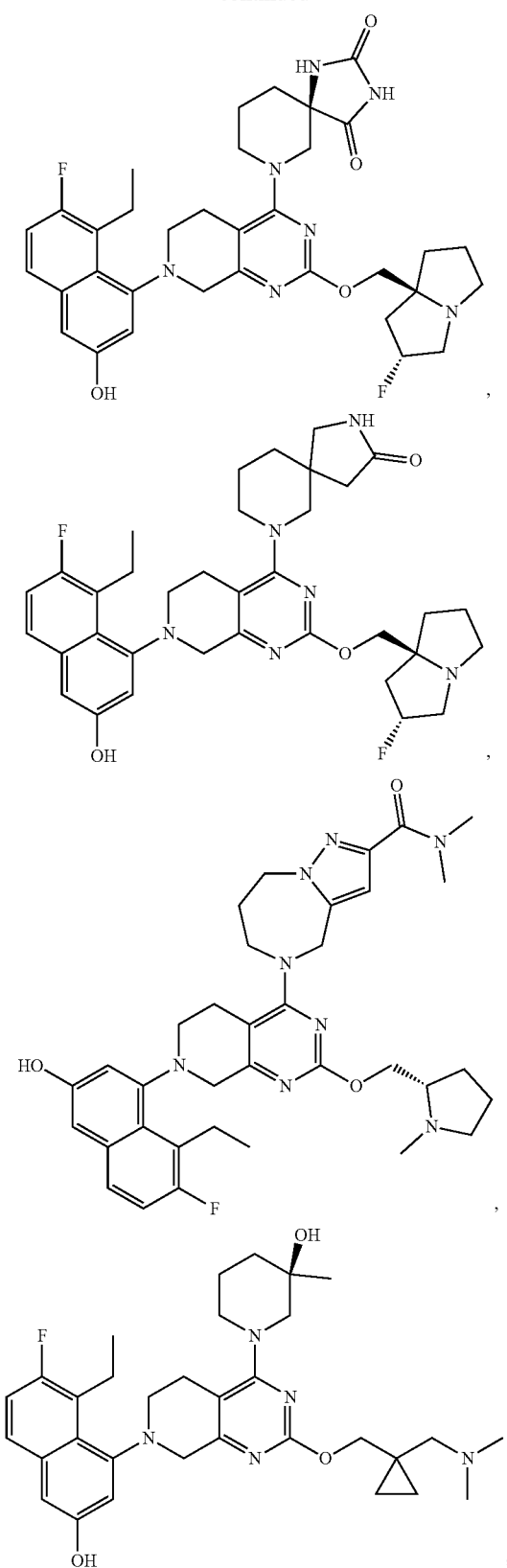
70
-continued
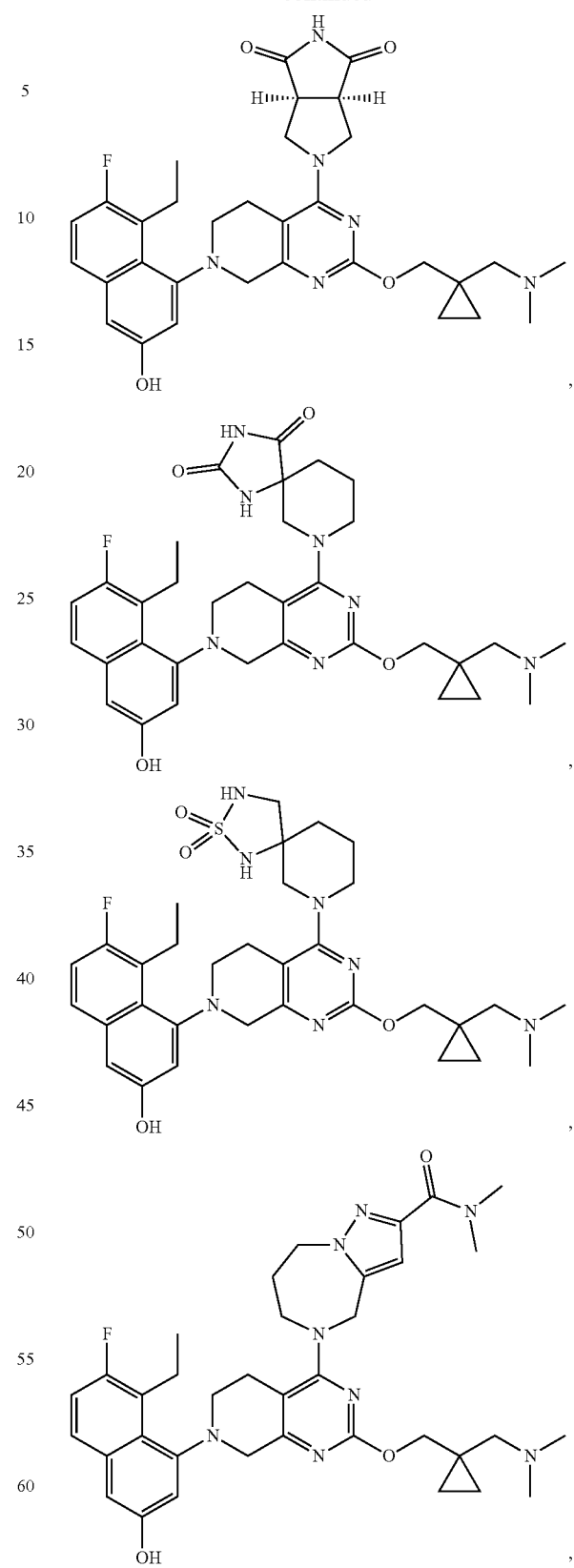

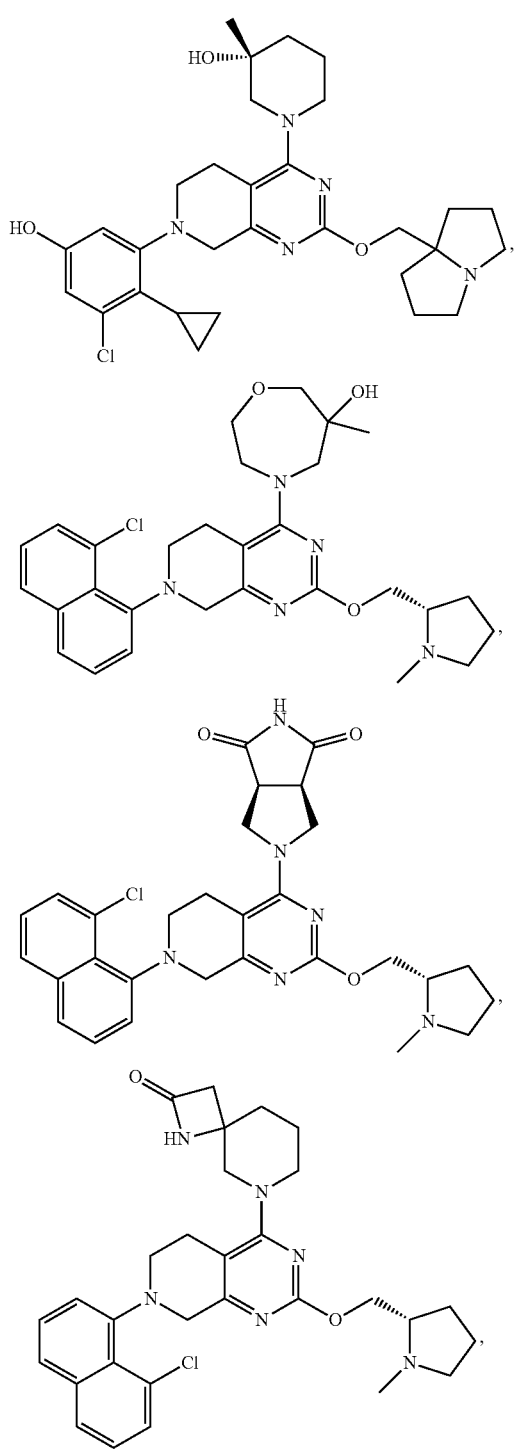
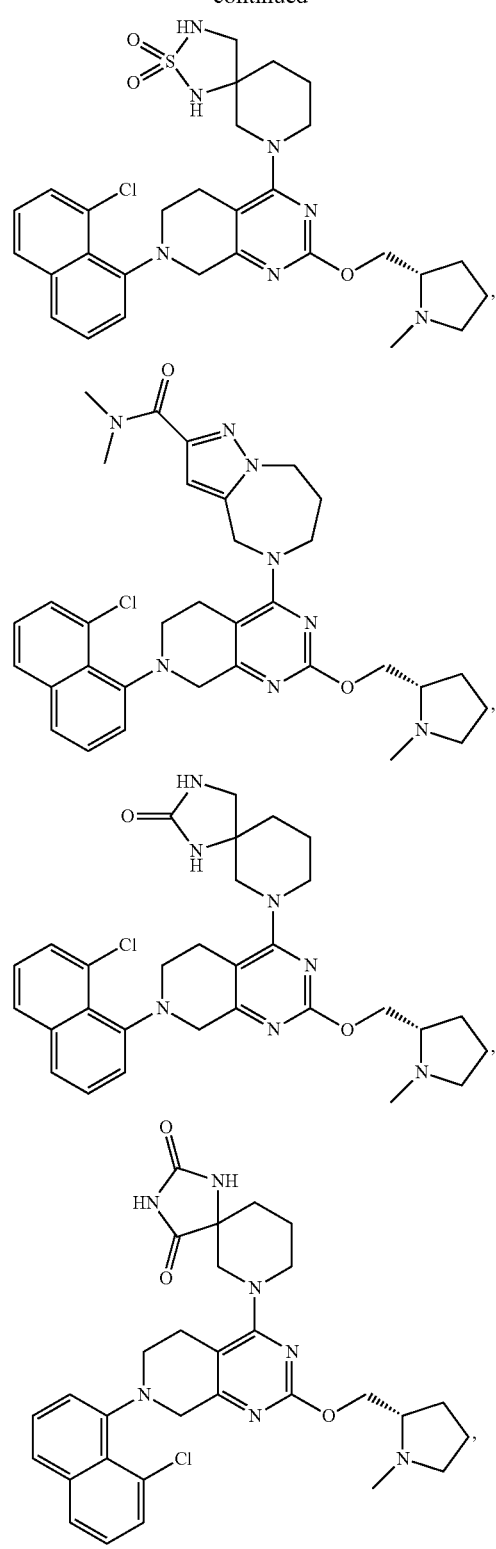

73
-continued
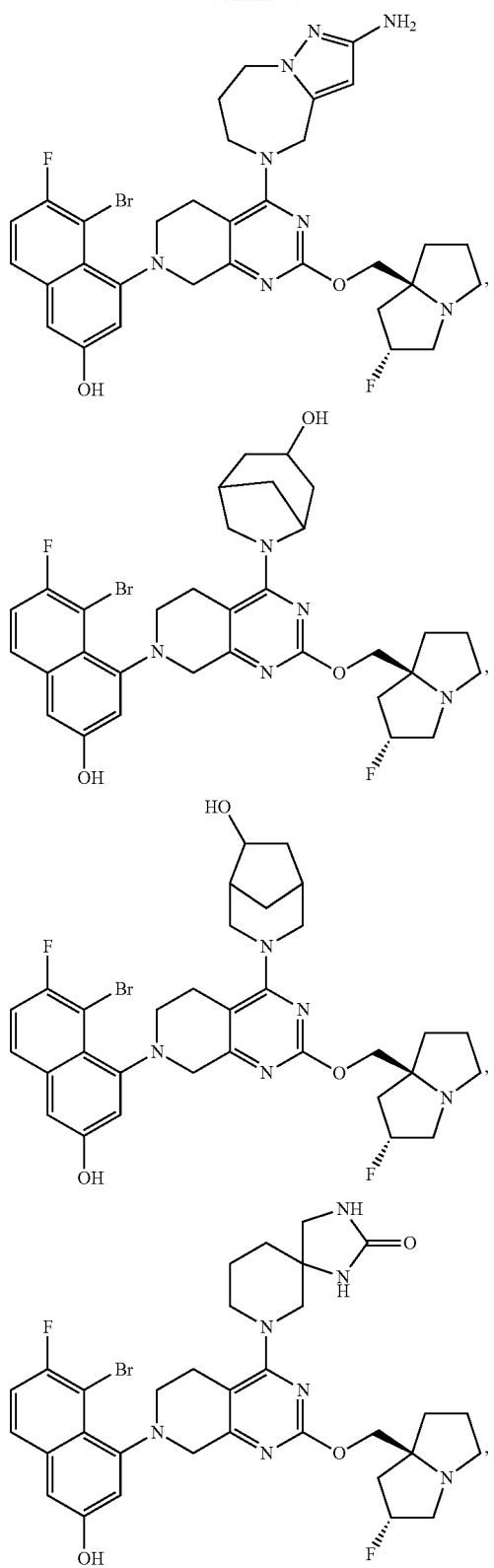
74
-continued
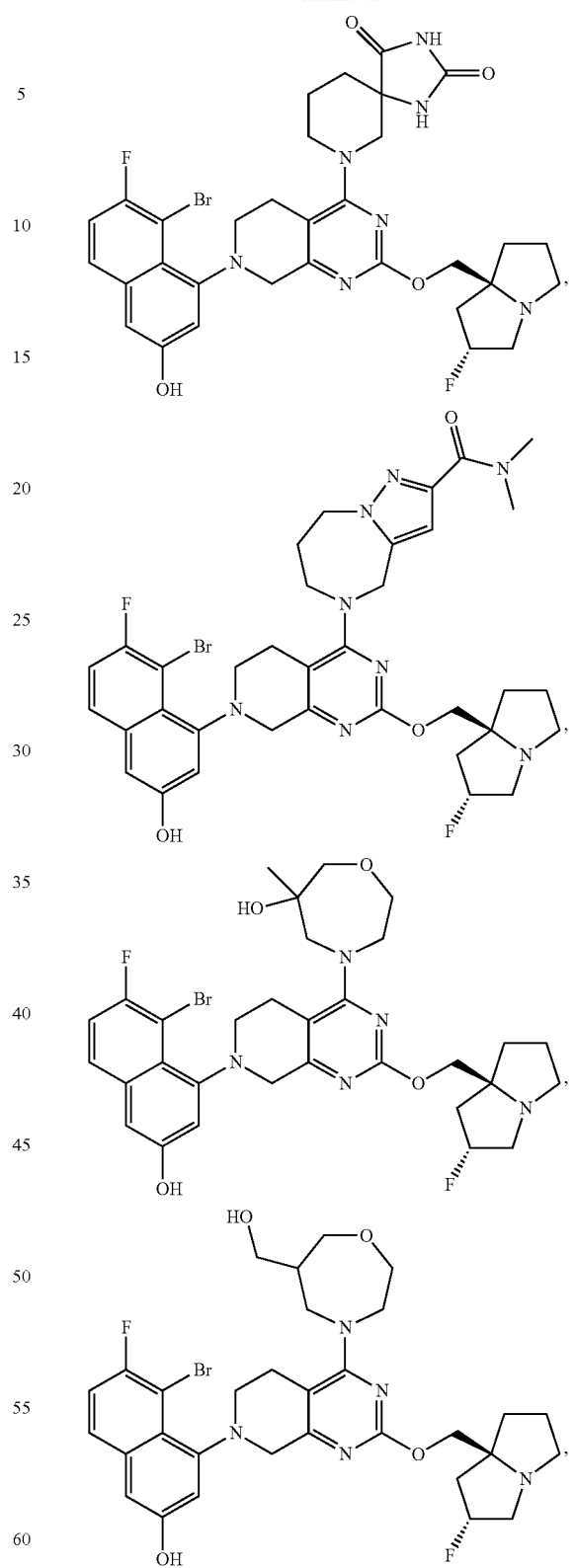

75
-continued
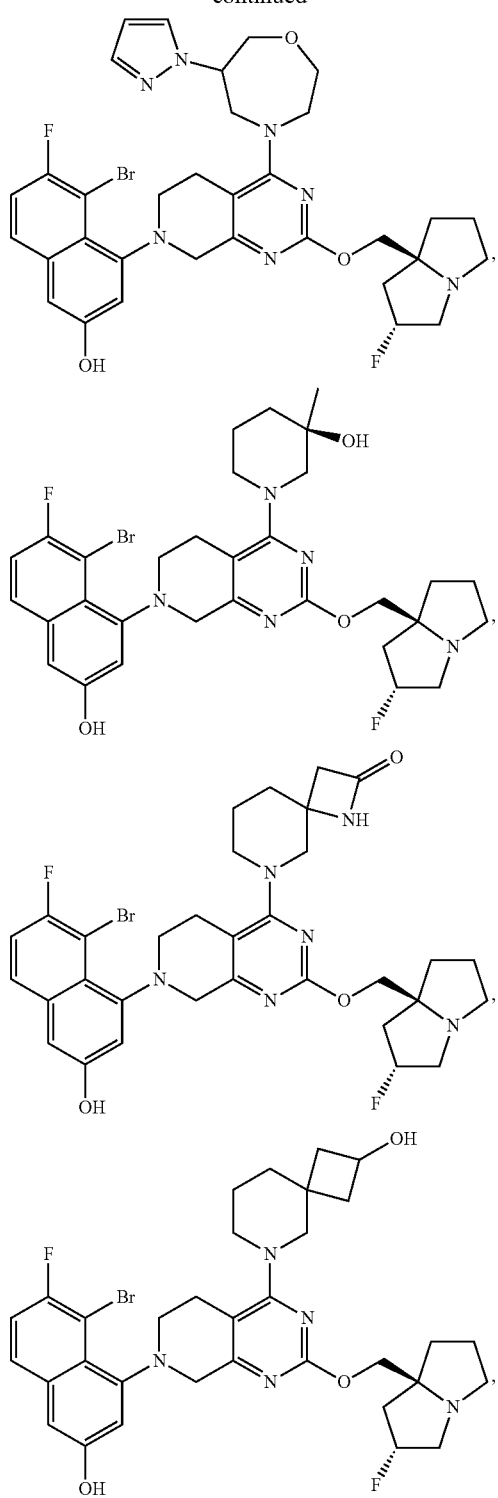
76
-continued
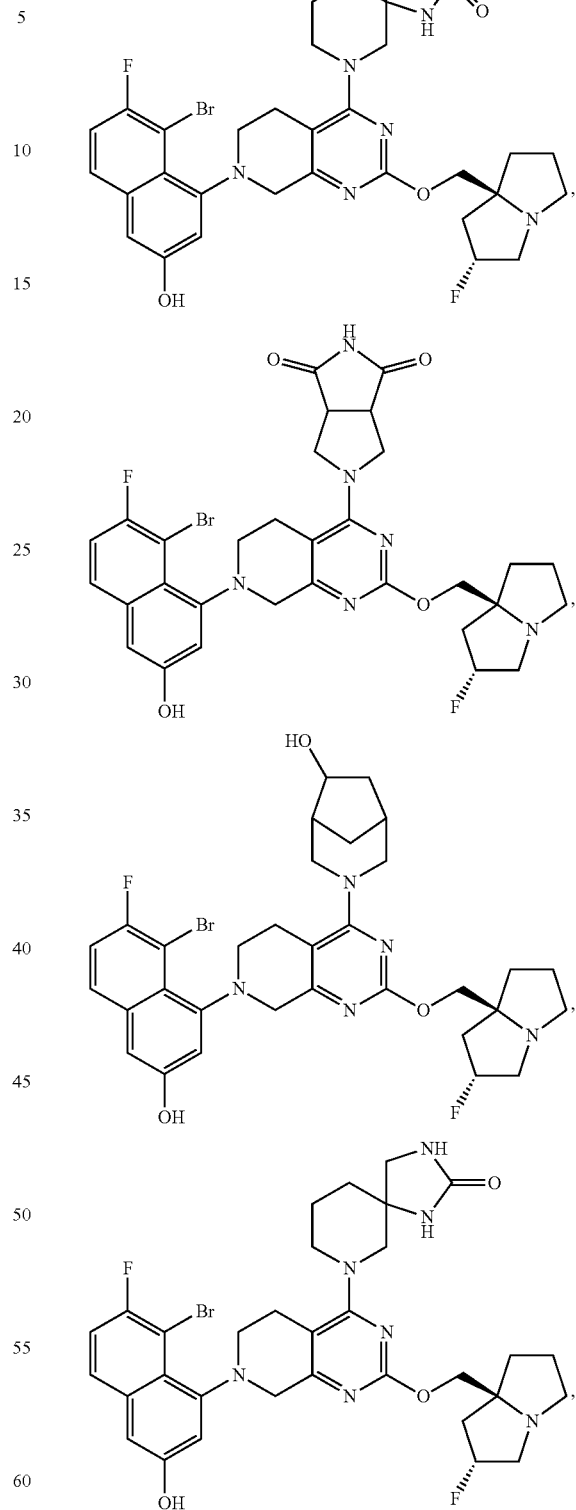

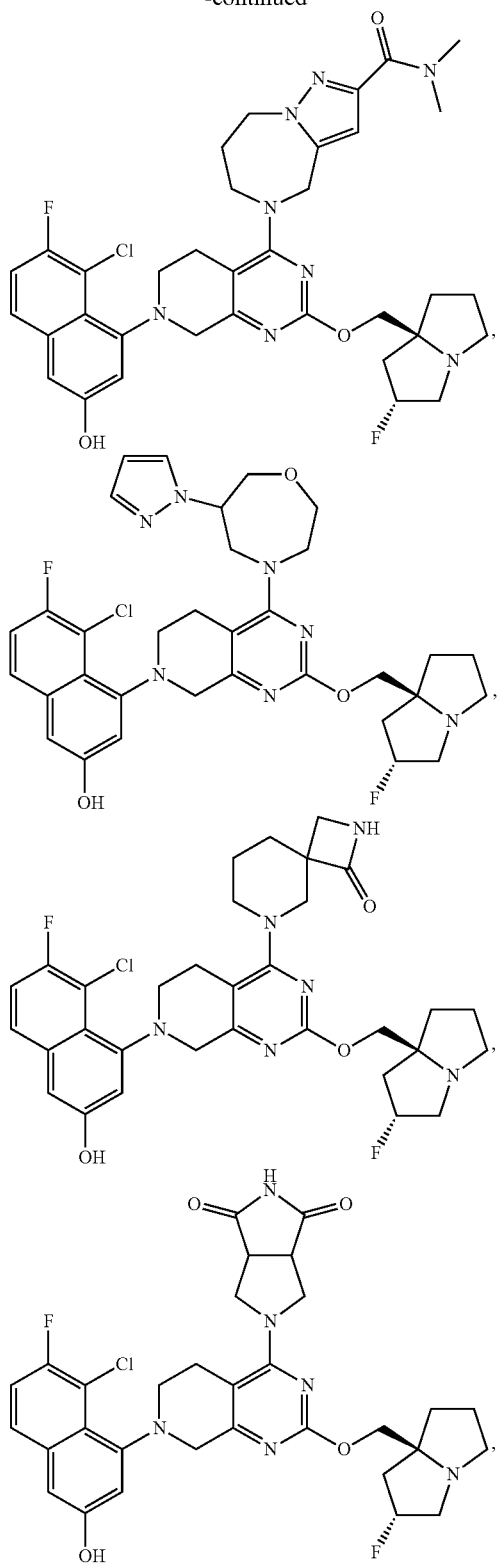

and pharmaceutically acceptable salts thereof.

In one embodiment, the compounds of Formula (I) include bis-hydrochloride, tris-hydrochloride, trifluoroacetic acid, bis-trifluoroacetic acid, and tris-trifluoroacetic acid salts of the above compounds. The compounds of Formula (I) or pharmaceutically acceptable salt thereof may be formulated into pharmaceutical compositions.

Pharmaceutical Compositions

In another aspect, the invention provides pharmaceutical compositions comprising a KRas wild type, KRas G12A, KRas G12C, KRas G12D, KRas G12R, KRas G12S, KRas G12V, KRas G13D and/or KRas Q61H inhibitor according to the invention and a pharmaceutically acceptable carrier, excipient, or diluent. Compounds of the invention may be formulated by any method well known in the art and may be prepared for administration by any route, including, without limitation, parenteral, intraperitoneal, intradermal, intracardiac, intraventricular, intracranial, intracerebrospinal, intrasynovial, intrathecal administration, intramuscular injection, intravitreous injection, intravenous injection, intra-arterial injection, oral, buccal, sublingual, transdermal, topical, intranasal, intratracheal, intrarectal, subcutaneous, and topical administration. In certain embodiments, compounds of the invention are administered intravenously in a hospital setting. In one embodiment, administration may be by the oral route. In some embodiments, the provided pharmaceutical compositions may be administered to a subject in need of treatment by injection systemically, such as by intravenous injection; or by injection or application to the relevant site, such as by direct injection via syringe, or direct application to the site when the site is exposed in surgery; or by topical administration.

Parenteral administration can be by bolus injection or continuous infusion. Pharmaceutical compositions for injection may be presented in unit dosage form, e.g., in ampoules or in multi-dose containers, with an added preservative.

The provided pharmaceutical compositions can also be formulated as a depot preparation. Such long-acting formulations may be administered by implantation (for example subcutaneously or intramuscularly) or by intramuscular injection. Thus, for example, the formulations may be modified with suitable polymeric or hydrophobic materials (for example as an emulsion in an acceptable oil) or ion exchange resins, or as sparingly soluble derivatives, for example, as a sparingly soluble salt.

The pharmaceutical compositions may, if desired, be presented in a vial, pack or a medical device, including but not limited to a dispenser device which may contain one or more unit dosage forms containing the active ingredient. In one embodiment the dispenser device can comprise a syringe having a single dose of the liquid formulation ready for injection. The syringe can be accompanied by instructions for administration.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salt refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. In one embodiment, a dose of the active compound for all of the above-mentioned conditions is in the range from about 0.01 to 300 mg/kg, for example 0.1 to 100 mg/kg per day, and as a further example 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods of use described herein.

Methods of Use

In yet another aspect, the invention provides for methods for inhibiting wild type KRas, KRas G12A, KRas G12C, KRas G12D, KRas G12R, KRas G12S, KRas G12V and/or KRas Q61H activity in a cell, comprising contacting the cell in which inhibition of wild type KRas or KRas G12A, KRas G12C, KRas G12D, KRas G12R, KRas G12S, KRas G12V and/or Q61H activity is desired with an effective amount of a compound of Formula (I), pharmaceutically acceptable salts thereof, or pharmaceutical compositions containing the compound or pharmaceutically acceptable salt thereof. In one embodiment, the contacting is in vitro. In one embodiment, the contacting is in vivo.

As used herein, the term "contacting" refers to the bringing together of indicated moieties in an in vitro system or an in vivo system. For example, "contacting" wild type KRas, KRas G12A, KRas G12C, KRas G12D, KRas G12R, KRas G12S, KRas G12V, KRas G13D and/or KRas Q61H with a compound provided herein includes the administration of a compound provided herein to an individual or patient, such as a human, having wild type KRas or a KRas G12A, KRas G12C, KRas G12D, KRas G12R, KRas G12S, KRas G12V, KRas G13D and/or KRas Q61H mutation, as well as, for example, introducing a compound provided herein into a sample containing a cellular or purified preparation containing wild type KRas or a KRas G12A, KRas G12C, KRas G12D, KRas G12R, KRas G12S, KRas G12V, KRas G13D or KRas Q61H mutation.

In one embodiment, a cell in which inhibition of wild type KRas, KRas G12A, KRas G12C, KRas G12D, KRas G12R, KRas G12S, KRas G12V, KRas G13D and/or KRas Q61H activity is desired is contacted with an effective amount of a compound of Formula (I) or pharmaceutically acceptable salt thereof to negatively modulate the activity of one or more of wild type KRas, KRas G12A, KRas G12C, KRas G12D, KRas G12R, KRas G12S, KRas G12V, KRas G13D and KRas Q61H.

By negatively modulating the activity of one or more of wild type KRas, KRas G12A, KRas G12C, KRas G12D, KRas G12R, KRas G12S, KRas G12V, KRas G13D and KRas Q61H, the methods described herein are designed to inhibit undesired cellular proliferation resulting from enhanced wild type KRas, KRas G12A, KRas G12C, KRas G12D, KRas G12R, KRas G12S, KRas G12V, KRas G13D and/or KRas Q61H activity within the cell. The cells may be contacted in a single dose or multiple doses in accordance with a particular treatment regimen to affect the desired negative modulation of wild type KRas, KRas G12A, KRas G12C, KRas G12D, KRas G12R, KRas G12S, KRas G12V, KRas G13D and/or KRas Q61H. The ability of compounds to bind one or more of wild type KRas, KRas G12A, KRas G12C, KRas G12D, KRas G12R, KRas G12S, KRas G12V, KRas G13D and KRas Q61H may be monitored in vitro using well known methods, including those described in Examples A and B below. In addition, the inhibitory activity of exemplary compounds in cells may be monitored, for example, by measuring the inhibition of one or more of wild type KRas, KRas G12A, KRas G12C, KRas G12D, KRas G12R, KRas G12S, KRas G12V, KRas G13D and/or KRas Q61H activity of the amount of phosphorylated ERK, for example using the method described in Example C below.

In another aspect, methods of treating cancer in a patient in need thereof, comprising administering to said patient a therapeutically effective amount of a compound of Formula (I) or a pharmaceutically acceptable salt thereof, or a pharmaceutical composition comprising the compound or pharmaceutically acceptable salt thereof are provided.

The compositions and methods provided herein may be used for the treatment of a wild type KRas-associated or KRas G12A, KRas G12C, KRas G12D, KRas G12R, KRas G12S, KRas G12V, KRas G13D and/or KRas Q61H-associated cancer in a patient in need thereof, comprising administering to said patient a therapeutically effective amount of a compound of Formula (I), a pharmaceutically acceptable salt thereof, or a pharmaceutical composition comprising the compound or pharmaceutically acceptable salt thereof are provided. In one embodiment, the wild type KRas-associated or KRas G12A, KRas G12C, KRas G12D, KRas G12R, KRas G12S, KRas G12V, KRas G13D and/or KRas Q61H-associated cancer is lung cancer.

The compositions and methods provided herein may be used for the treatment of a wide variety of cancers including tumors such as lung, prostate, breast, brain, skin, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer, small cell lung cancer, colorectal cancer, rectal cancer or pancreatic cancer. In certain embodiments, the cancer is non-small cell lung cancer.

The concentration and route of administration to the patient will vary depending on the cancer to be treated. The compounds, pharmaceutically acceptable salts thereof and pharmaceutical compositions comprising such compounds and salts also may be co-administered with other antineoplastic compounds, e.g., chemotherapy, or used in combination with other treatments, such as radiation or surgical intervention, either as an adjuvant prior to surgery or post-operatively.

Also provided herein is a compound of Formula (I) or a pharmaceutically acceptable salt thereof, or a pharmaceutical composition thereof as defined herein for use in therapy.

Also provided herein is a compound of Formula (I) or a pharmaceutically acceptable salt thereof, or a pharmaceutical composition thereof as defined herein for use in the treatment of cancer.

Also provided herein is a compound of Formula (I) or a pharmaceutically acceptable salt thereof, or a pharmaceutical composition thereof for use in the inhibition of wild type KRas or KRas G12A, KRas G12C, KRas G12D, KRas G12R, KRas G12S, KRas G12V, KRas G13D and/or KRas Q61H.

Also provided herein is a compound of Formula (I) or a pharmaceutically acceptable salt thereof, or a pharmaceutical composition thereof as defined herein, for use in the treatment of a wild type KRas-associated or a KRas G12A, KRas G12C, KRas G12D, KRas G12R, KRas G12S, KRas G12V, KRas G13D and/or KRas Q61H-associated disease or disorder.

Also provided herein is the use of a compound of Formula (I) or a pharmaceutically acceptable salt thereof, as defined herein in the manufacture of a medicament for the treatment of cancer.

Also provided herein is a use of a compound of Formula (I) or a pharmaceutically acceptable salt thereof, as defined herein in the manufacture of a medicament for the inhibition of activity of wild type KRas, KRas G12A, KRas G12C, KRas G12D, KRas G12R, KRas G12S, KRas G12V, KRas G13D and/or KRas Q61H.

Also provided herein is the use of a compound of Formula (I) or a pharmaceutically acceptable salt thereof, as defined herein, in the manufacture of a medicament for the treatment of a wild type KRas-associated or KRas G12A, KRas G12C, KRas G12D, KRas G12R, KRas G12S, KRas G12V, KRas G13D and/or KRas Q61H-associated disease or disorder.

Also provided herein is a method for treating cancer in a patient in need thereof, the method comprising (a) determining that cancer is associated with wild type KRas or a KRas G12A, KRas G12C, KRas G12D, KRas G12R, KRas G12S, KRas G12V, KRas G13D and/or KRas Q61H mutation (e.g., as determined using a regulatory agency-approved, e.g., FDA-approved, assay or kit); and (b) administering to the patient a therapeutically effective amount of a compound of Formula (I), or a pharmaceutically acceptable salt thereof, or a pharmaceutical composition thereof.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

Reaction Schemes and Examples

The compounds of the present invention may be prepared from commercially available reagents using the synthetic methods and reaction schemes described herein, or using other reagents and conventional methods well known to those skilled in the art. For instance, compounds of the present invention may be prepared according to the reaction schemes and examples outlines below.

The compounds of the present invention may have one or more chiral center and may be synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or enantiomers. Unless otherwise indicated, all chiral (enantiomeric and diastereomeric) and racemic forms are within the scope of the invention. Unless otherwise indicated, whenever the specification, including the claims, refers to compounds of the invention, the term "compound" is to be understood to encompass all chiral (enantiomeric and diastereomeric) and racemic forms.

The compounds of the present invention may be in anhydrous, solvated or hydrated forms, and all such forms are included within the scope of the invention.

The following Intermediates are intended to illustrate further certain embodiments of the invention and are not intended to limit the scope of the invention.

Intermediate 1

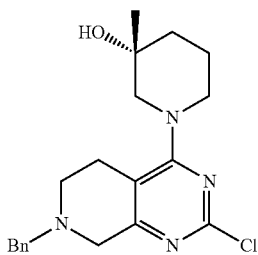 [SMILES: C[C@@]1(O)CCCN(c2nc(Cl)nc3c2CCN(Cc2ccccc2)C3)C1]

(R)-1-(7-benzyl-2-chloro-5,6,7,8-tetrahydropyrido[3,4-d]pyrimidin-4-yl)-3-methylpiperidin-3-ol

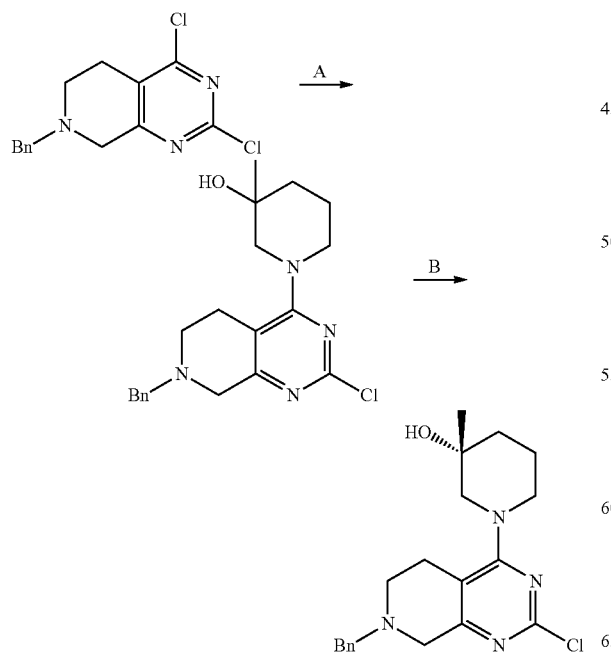

Step A and B. (R)-1-(7-benzyl-2-chloro-5,6,7,8-tetrahydropyrido[3,4-d]pyrimidin-4-yl)-3-methylpiperidin-3-ol: To a solution of 7-benzyl-2,4-dichloro-5,6,7,8-tetrahydropyrido[3,4-d]pyrimidine (5.30 g, 18.0 mmol) in DMA (40.0 mL) were added 3-methylpiperidin-3-ol (3.55 g, 23.42 mmol, HCl) and N-ethyl-N-isopropylpropan-2-amine (6.99 g, 54.0 mmol, 9.41 mL). The mixture was stirred at 20° C. for 1 hour. After completion, the reaction mixture was diluted with $H_2O$ (100 mL) and extracted with ethyl acetate (2×100 mL). The combined organic layers were washed with brine (300 mL) and dried over $Na_2SO_4$. The mixture was filtered and concentrated under reduced pressure to give a residue. The residue was purified by HPLC [C18, 0.1% FA in water, 0-60% MeCN] to give 1-(7-benzyl-2-chloro-5,6,7,8-tetrahydropyrido[3,4-d]pyrimidin-4-yl)-3-methylpiperidin-3-ol (6.0 g) as yellow oil, which was further separated by SFC (column: DAICEL CHIRALPAK AD-H (250 mm×30 mm, 5 um); mobile phase: [0.1% $NH_3 \cdot H_2O$ EtOH]; B %: 30%-30%, 4.1 min; 600 min) to give (R)-1-(7-benzyl-2-chloro-5,6,7,8-tetrahydropyrido[3,4-d]pyrimidin-4-yl)-3-methylpiperidin-3-ol (2.75 g, 40% yield). Yellow solid. $^1$H NMR (400 MHz, chloroform-d) δ=7.38-7.27 (m, 5H), 3.93-3.80 (m, 2H), 3.68 (s, 3H), 3.53-3.45 (m, 1H), 3.37-3.13 (m, 1H), 3.06-2.91 (m, 2H), 2.85-2.70 (m, 2H), 2.67-2.58 (m, 1H), 2.56-2.47 (m, 1H), 1.92-1.75 (m, 2H), 1.67-1.48 (m, 2H), 1.26 (s, 3H); SFC: 99.7%, $t_R$=1.786 min, Column: Chiralpak AD-3 50×4.6 mm I.D., 3 um Mobile phase: Phase A for $CO_2$, and Phase B for EtOH (0.05% DEA); Gradient elution: EtOH (0.05% DEA) in C02 from 5% to 40% Flow rate: 3 mL/min; Detector: 220 nm; Column Temp: 35° C.; Back Pressure: 100 Bar; LCMS (ESI, M+1): m/z 373.0.

Intermediate 2

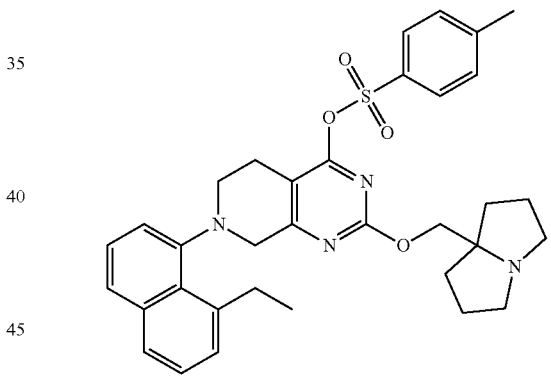

7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl 4-methylbenzenesulfonate

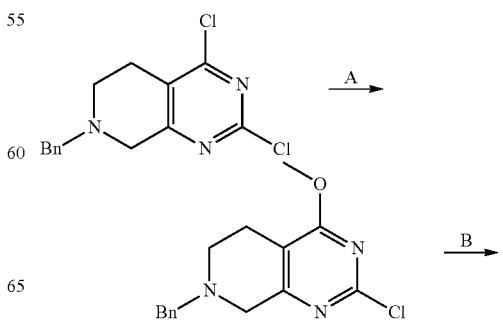

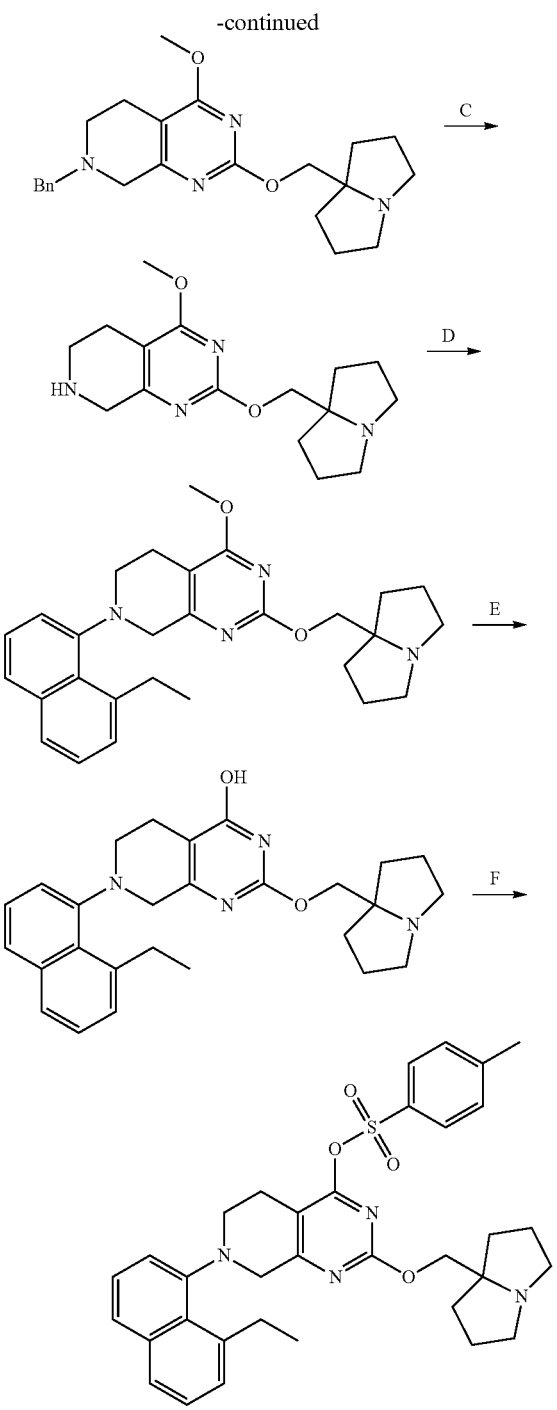

Step A. 7-benzyl-2-chloro-4-methoxy-5,6,7,8-tetrahydropyrido[3,4-d]pyrimidine: To a solution of 7-benzyl-2,4-dichloro-5,6,7,8-tetrahydropyrido[3,4-d]pyrimidine (6.0 g, 20.4 mmol) in MeOH (50 mL) was added NaOMe (2.20 g, 40.8 mmol) at 0° C. The mixture was stirred at 0° C. for 2 hours. The pH of the mixture was adjusted to 7 with aqueous HCl (2 N). Water (100 mL) was added, and the mixture was extracted with DCM (50 mL×3). The combined organic layers were washed with brine (20 mL) and dried over sodium sulfate. The mixture was filtered and concentrated to give a residue. The residue was purified by column chromatography (SiO$_2$, Petroleum ether/Ethyl acetate=1/0 to 10/1) to afford 7-benzyl-2-chloro-4-methoxy-5,6,7,8-tetrahydropyrido[3,4-d]pyrimidine (5.3 g, 90% yield) as yellow oil; $^1$H NMR (400 MHz, CDCl$_3$) δ=7.67 (br d, J 3.7 Hz, 2H), 7.55-7.41 (m, 3H), 5.30 (s, 1H), 4.46 (br s, 1H), 4.24 (br d, J 16.0 Hz, 2H), 4.04 (s, 3H), 3.96-3.67 (m, 2H), 3.49 (br s, 1H), 3.05 (br s, 1H), 2.86 (br d, J 18.6 Hz, 1H). LCMS [ESI, M+1]: m/z 290.1.

Step B. 7-benzyl-2-((hexahydro-1H-pyrrolizin-7a-yl)methoxy)-4-methoxy-5,6,7,8-tetrahydropyrido[3,4-d]pyrimidine: A mixture of 7-benzyl-2-chloro-4-methoxy-5,6,7,8-tetrahydropyrido[3,4-d]pyrimidine (1.30 g, 4.49 mmol), 1,2,3,5,6,7-hexahydropyrrolizin-8-ylmethanol (697 mg, 4.94 mmol), RuPhos (419 mg, 897 µmol), Cs$_2$CO$_3$ (4.39 g, 13.5 mmol) and Pd(OAc)$_2$ (101 mg, 449 µmol) in Toluene (30 mL) was degassed and purged with N$_2$ for 3 times. The mixture was stirred at 110° C. for 8 hours under N2 atmosphere. The reaction mixture was quenched with water 100 mL and extracted with EtOAc (30 mL×3). The combined organic layers were washed with brine (20 mL×2) and dried over Na$_2$SO$_4$. The mixture was filtered and concentrated under reduced pressure to give a residue. The residue was purified by column chromatography (SiO$_2$, DCM/MeOH=1/0 to 5/1) to afford 7-benzyl-2-((hexahydro-1H-pyrrolizin-7a-yl)methoxy)-4-methoxy-5,6,7,8-tetrahydropyrido[3,4-d]pyrimidine (1.2 g, 34% yield). Yellow oil; LCMS [ESI, M+H]: m/z 395.2.

Step C. 2-((hexahydro-1H-pyrrolizin-7a-yl)methoxy)-4-methoxy-5,6,7,8-tetrahydropyrido[3,4-d]pyrimidine: To a solution of 7-benzyl-2-((hexahydro-1H-pyrrolizin-7a-yl)methoxy)-4-methoxy-5,6,7,8-tetrahydropyrido[3,4-d]pyrimidine (3.3 g, 8.36 mmol) in 2-methylpropan-2-ol (200 mL) was added Pd/C (8.0 g, 10% purity) under H2. The suspension was degassed under vacuum and purged with H2 several times. The mixture was stirred under H2 (50 psi) at 40° C. for 30 hours. The reaction mixture was filtered and concentrated under reduced pressure to afford 2-((hexahydro-1H-pyrrolizin-7a-yl)methoxy)-4-methoxy-5,6,7,8-tetrahydropyrido[3,4-d]pyrimidine (2.1 g, crude). Yellow oil; LCMS [ESI, M+H]: m/z 305.2.

Step D. 7-(8-ethylnaphthalen-1-yl)-2-((hexahydro-1H-pyrrolizin-7a-yl)methoxy)-4-methoxy-5,6,7,8-tetrahydropyrido[3,4-d]pyrimidine: A mixture of 1-bromo-8-ethylnaphthalene (1.6 g, 6.81 mmol), 2-((hexahydro-1H-pyrrolizin-7a-yl)methoxy)-4-methoxy-5,6,7,8-tetrahydropyrido[3,4-d]pyrimidine (1.6 g, 5.26 mmol), BINAP (1.31 g, 2.10 mmol), Cs$_2$CO$_3$ (4.28 g, 13.1 mmol) and Pd$_2$(dba)$_3$ (962 mg, 1.05 mmol) in toluene (30 mL) was degassed and purged with N2 for 3 times. The mixture was stirred at 90° C. for 8 hours under N2 atmosphere. The reaction mixture was quenched with water (30 mL) and extracted with EtOAc (10 mL×3). The combined organic layers were washed with brine (5 mL×2) and dried over Na$_2$SO$_4$. The mixture was filtered and concentrated under reduced pressure to give a residue. The residue was purified by prep-TLC (SiO$_2$, EtOAc:MeOH=5:1) to afford 7-(8-ethylnaphthalen-1-yl)-2-((hexahydro-1H-pyrrolizin-7a-yl)methoxy)-4-methoxy-5,6,7,8-tetrahydropyrido[3,4-d]pyrimidine (0.8 g, 1.74 mmol, 33% yield). Brown solid. LCMS [ESI, M+H]: m/z 459.3.

Step E. 7-(8-ethylnaphthalen-1-yl)-2-((hexahydro-1H-pyrrolizin-7a-yl)methoxy)-5,6,7,8-tetrahydropyrido[3,4-d]pyrimidin-4-ol: To a solution of NaH (523 mg, 13.1 mmol, 60% purity) in DMF (10 mL) was added EtSH (1.22 g, 19.6 mmol, 1.45 mL) at 0° C. The mixture was stirred for 30 minutes, and 7-(8-ethylnaphthalen-1-yl)-2-((hexahydro-1H-pyrrolizin-7a-yl)methoxy)-4-methoxy-5,6,7,8-tetrahydropyrido[3,4-d]pyrimidine (600 mg, 1.31 mmol) was added.

The mixture was stirred at 60° C. for 1 hour. The reaction mixture was quenched with water (10 mL). The mixture was extracted with EtOAc (5 mL×2). The combined organic layers were washed with brine (3 mL) and dried over $Na_2SO_4$. The mixture was filtered and concentrated under reduced pressure to afford 7-(8-ethylnaphthalen-1-yl)-2-((hexahydro-1H-pyrrolizin-7a-yl)methoxy)-5,6,7,8-tetrahydropyrido[3,4-d]pyrimidin-4-ol (600 mg, crude) as brown solid. LCMS [ESI, M+H]: m/z 445.2.

Step F. 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate: To a solution of 7-(8-ethylnaphthalen-1-yl)-2-((hexahydro-1H-pyrrolizin-7a-yl)methoxy)-5,6,7,8-tetrahydropyrido[3,4-d]pyrimidin-4-ol (600 mg, 1.35 mmol) and TEA (341 mg, 3.37 mmol) in DCM (10 mL) was added TsCl (257 mg, 1.35 mmol). The mixture was stirred at 20° C. for 1 hour. The reaction mixture was quenched with water (30 mL), and then extracted with DCM (10 mL×2). The combined organic layers were washed with saturated $NaHCO_3$ (10 mL×2) and brine (10 mL). The mixture was dried over $Na_2SO_4$ and filtrate. The solvent was removed under reduced pressure to give a residue. The residue was purified by prep-TLC ($SiO_2$, DCM:MeOH=5:1) to afford 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (530 mg, 52% yield) as yellow solid. LCMS [ESI, M+H]: m/z 559.2.

Intermediate 3

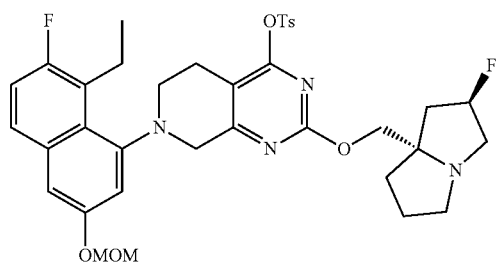

7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl 4-methylbenzenesulfonate

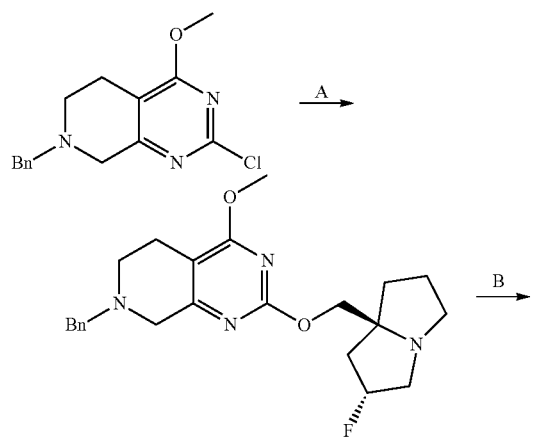

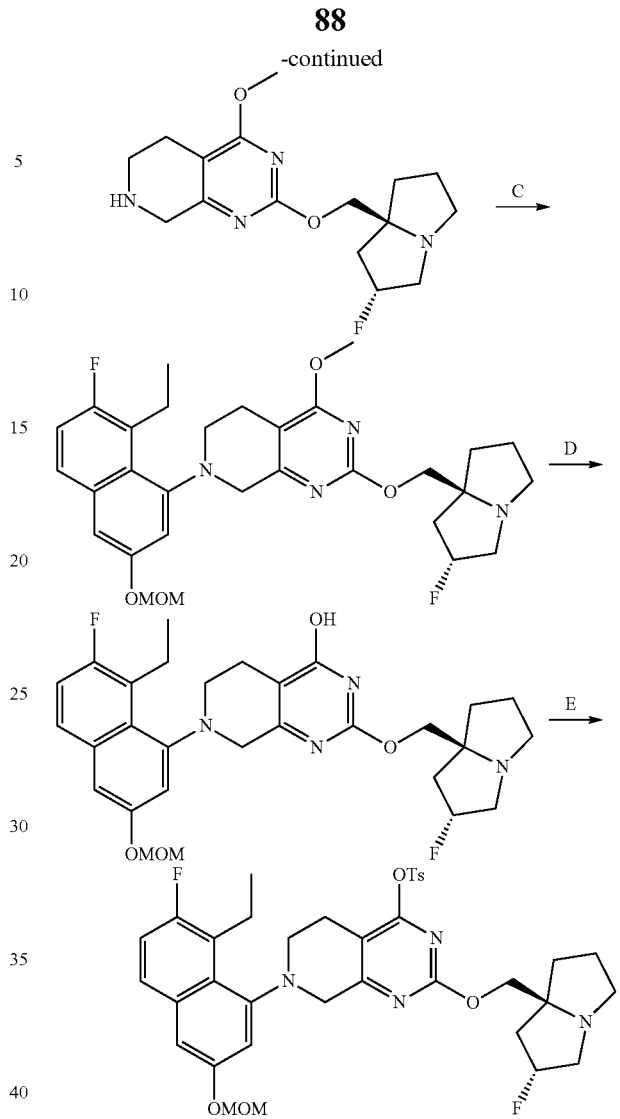

Step A. tert-butyl 2-(((2R,7aS)-2-fluorohexahydro-1H-pyrrolizin-7a-yl)methoxy)-4-methoxy-5,6-dihydropyrido[3,4-d]pyrimidine-7(8H)-carboxylate: To a solution of tert-butyl 2-chloro-4-methoxy-5,6-dihydropyrido[3,4-d]pyrimidine-7(8H)-carboxylate (50 g, 1.0 equiv) and ((2R,7aS)-2-fluorohexahydro-1H-pyrrolizin-7a-yl)methanol (31.9 g, 1.2 equiv) in toluene (500 mL) were added $Cs_2CO_3$ (163 g, 3.0 equiv) and BINAP (20.7 g, 0.2 equiv) at 25° C. The suspension was degassed under vacuum and purged with N2 two times. $Pd(OAc)_2$ (3.74 g, 0.1 equiv) was added. The suspension was degassed under vacuum and purged with N2 three times. Then the reaction was heated to 110° C. and stirred for 12 hours. The mixture was diluted with water (1000 mL) and extracted with ethyl acetate (500 mL×3). The combined organic layers were dried over $Na_2SO_4$ and concentrated under vacuum. The residue was purified by column chromatography ($SiO_2$, DCM/MeOH=10/1) and then by reversed phase flash chromatography [water (FA, 0.1%)/acetonitrile] to afford the title compound (51 g, 72% yield) as yellow oil. LCMS (ESI, M+1): m/z=423.2.

Step B. 2-(((2R,7aS)-2-fluorohexahydro-1H-pyrrolizin-7a-yl)methoxy)-4-methoxy-5,6,7,8-tetrahydropyrido[3,4-d]pyrimidine: To a solution of tert-butyl 2-(((2R,7aS)-2-fluorohexahydro-1H-pyrrolizin-7a-yl)methoxy)-4-methoxy-5,6-dihydropyrido[3,4-d]pyrimidine-7(8H)-carboxylate (50 g, 1.0 equiv) in DCM (200 mL) was added TFA (308 g, 200 mL, 22.8 equiv) dropwise with stirring at 0° C. Then, the reaction was stirred at 25° C. for 2 hours. The mixture was concentrated under vacuum to removed DCM and some TFA. The residue was diluted with ice water (150 mL), and then the pH of the residue was adjusted to 7 with NaHCO₃ (30 g). The mixture was concentrated under oil pump to removed water. Then the residue was diluted with saturation Na₂CO₃ (500 mL) and extracted with ethyl acetate (200 mL×6). The combined organic layer was dried over Na₂SO₄ and concentrated under vacuum to afford the title compound (34.3 g, crude) as white solid. LCMS (ESI, M+1): m/z=323.0.

Step C. 7-(8-ethyl-7-fluoro-3-(methoxymethoxy)naphthalen-1-yl)-2-(((2R,7aS)-2-fluorohexahydro-1H-pyrrolizin-7a-yl)methoxy)-4-methoxy-5,6,7,8-tetrahydropyrido[3,4-d]pyrimidine: To a solution of 2-(((2R,7aS)-2-fluorohexahydro-1H-pyrrolizin-7a-yl)methoxy)-4-methoxy-5,6,7,8-tetrahydropyrido[3,4-d]pyrimidine (50 g, 1.0 equiv) and 8-ethyl-7-fluoro-3-(methoxymethoxy)naphthalen-1-yl trifluoromethanesulfonate (77.1 g, 1.3 equiv) in toluene (500 mL) were added Cs₂CO₃ (152 g, 3.0 equiv) and Xantphos (18.0 g, 0.2 equiv) at 25° C. The suspension was degassed under vacuum and purged with N2 two times. Pd₂(dba)₃ (14.2 g, 0.1 equiv) was added. The suspension was degassed under vacuum and purged with N2 three times. The reaction was stirred at 110° C. for 6 hours. Then the mixture was filtered by Celite, and the residue was washed by ethyl acetate (50 mL×3). The combined organic layer was concentrated under vacuum. The residue was purified by column chromatography (SiO₂, Petroleum ether/Ethyl acetate=3/1 to DCM/MeOH=5/1) and reversed phase flash chromatography [C18, water (FA, 0.1%)/acetonitrile] to afford the title compound (67 g, two steps 77% yield) as brown oil; LCMS (ESI, M+1): m/z=555.2. ¹H NMR (400 MHz, METHANOL-d4) δ=7.59 (dd, J=5.6, 9.2 Hz, 1H), 7.24 (d, J=2.4 Hz, 1H), 7.21-7.11 (m, 2H), 5.33-5.16 (m, 3H), 4.16-4.06 (m, 2H), 4.03 (s, 3H), 3.97 (d, J=17.2 Hz, 1H), 3.72 (d, J=17.2 Hz, 1H), 3.48 (s, 3H), 3.47-3.41 (m, 1H), 3.36-3.30 (m, 2H), 3.25-3.11 (m, 4H), 2.99-2.81 (m, 2H), 2.71-2.64 (m, 1H), 2.31-2.03 (m, 3H), 1.99-1.77 (m, 3H), 1.01 (t, J=7.2 Hz, 3H)

Step D. 7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol: To a solution of EtSH (13.4 g, 16.0 mL, 3.0 equiv) in DMAc (400 mL) was added NaH (8.65 g, 60% purity, 3.0 equiv) at 0° C. The mixture was stirred at 0° C. for 0.5 hour. Then 7-(8-ethyl-7-fluoro-3-(methoxymethoxy)naphthalen-1-yl)-2-(((2R,7aS)-2-fluorohexahydro-1H-pyrrolizin-7a-yl)methoxy)-4-methoxy-5,6,7,8-tetrahydropyrido[3,4-d]pyrimidine (40 g, 1.0 equiv) was added to the mixture. The mixture was stirred at 20° C. for another 1 hour. After completion, water (400 mL) was added, and its pH was adjusted to 6 by 2N HCl. The mixture was extracted with ethyl acetate (400 mL×3). The combined organic layer was washed with brine (400 mL×2), dried over Na₂SO₄, filtered, and concentrated under vacuum to afford the title compound (45 g, crude) as yellow solid. LCMS (ESI, M+1): m/z=541.2.

Step E. 7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl 4-methylbenzenesulfonate: To a mixture of 7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol, N-ethyl-N-isopropylpropan-2-amine (15.1 g, 3 equiv) and DMAP (475 mg, 0.1 equiv) in DCM (200 mL) was added 4-methylbenzene-1-sulfonyl chloride (11.1 g, 1.5 equiv) at 0° C. The mixture was stirred at 25° C. for 0.5 hour. The reaction mixture was concentrated under reduced pressure and purified by column chromatography (Al₂O₃, Petroleum ether/Ethyl acetate=10/1 to 0/1) to afford the title compound (22 g, 82% yield two steps) as yellow solid. LCMS (ESI, M+1): m/z=695.8.

Intermediate 4

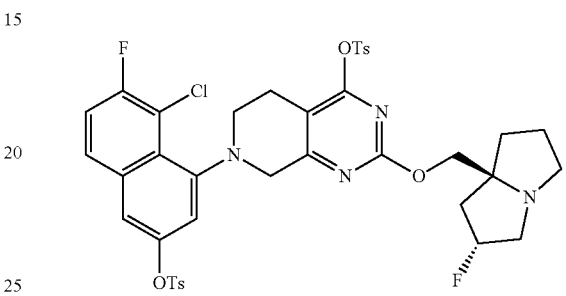

5-chloro-6-fluoro-4-(2-(((2R,7aS)-2-fluorotetrahydro-1H-pyrrolizin-7a(5H)-yl)methoxy)-4-(tosyloxy)-5,8-dihydropyrido[3,4-d]pyrimidin-7(6H)-yl)naphthalen-2-yl 4-__methylbenzenesulfonate

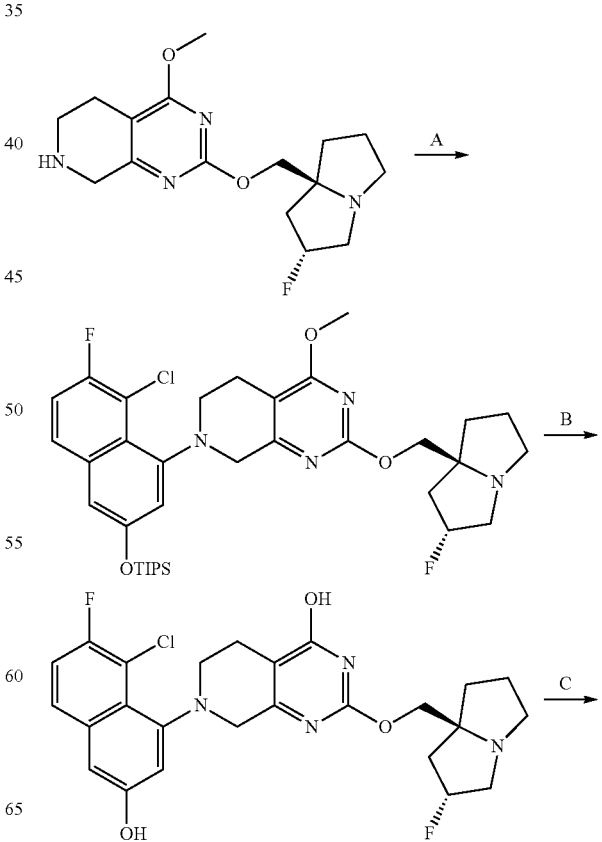

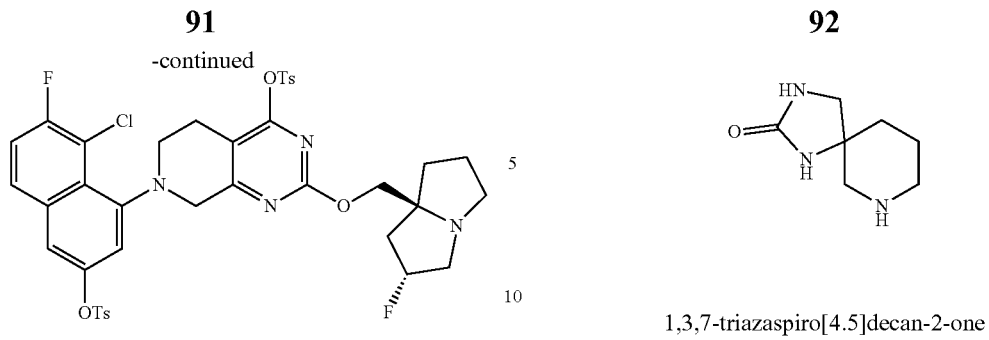

Step A. 7-(8-chloro-7-fluoro-3-((triisopropylsilyl)oxy)naphthalen-1-yl)-2-(((2R,7aS)-2-fluorohexahydro-1H-pyrrolizin-7a-yl)methoxy)-4-methoxy-5,6,7,8-tetrahydropyrido[3,4-d]pyrimidine: A mixture of 2-(((2R,7aS)-2-fluorohexahydro-1H-pyrrolizin-7a-yl)methoxy)-4-methoxy-5,6,7,8-tetrahydropyrido[3,4-d]pyrimidine (4 g, 1.0 equiv), 8-chloro-7-fluoro-3-((triisopropylsilyl)oxy)naphthalen-1-yl trifluoromethanesulfonate (7.46 g, 1.2 equiv), Cs$_2$CO$_3$ (12.1 g, 3.0 equiv), RuPhos (1.16 g, 0.2 equiv), and Pd$_2$(dba)$_3$ (1.14 g, 0.1 equiv) in toluene (80 mL) was degassed and purged with N2 several times. The mixture was stirred at 100° C. for 3 hrs under N2 atmosphere. The mixture was diluted with water (100 mL) and extracted with ethyl acetate (100 mL). The organic layer was dried over sodium sulfate, filtered, and concentrated under vacuum to give a residue and the residue was purified by HPLC [0.1% FA condition] to afford the title compound (3.9 g, 46% yield) as yellow solid. LCMS (ESI, M+1): m/z=673.2.

Step B. 7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol: To a mixture of EtSH (1.99 g, 2.37 mL, 6.0 equiv) in DMAC (30 mL) was added NaH (855 mg, 60% purity, 4.0 equiv) at 0° C. The reaction was stirred at 20° C. for 0.5 hour, and then 7-(8-chloro-7-fluoro-3-((triisopropylsilyl)oxy)naphthalen-1-yl)-2-(((2R,7aS)-2-fluorohexahydro-1H-pyrrolizin-7a-yl)methoxy)-4-methoxy-5,6,7,8-tetrahydropyrido[3,4-d]pyrimidine (3.6 g, 1 equiv) was added. The mixture was stirred at 60° C. for 1 hours. Water (40 mL) was added to the mixture and the pH was adjusted to 6 with 2N HCl. the mixture was extracted with ethyl acetate (3×40 mL). The organic layer was washed with brine (2×40 mL), dried over Na$_2$SO$_4$, filtered, and concentrated under vacuum to afford the title compound (4.2 g, crude) as yellow oil; LCMS (ESI, M+1): m/z=503.0.

Step C. 5-chloro-6-fluoro-4-(2-(((2R,7aS)-2-fluorohexahydro-1H-pyrrolizin-7a-yl)methoxy)-4-(tosyloxy)-5,6-dihydropyrido[3,4-d]pyrimidin-7(8H)-yl)naphthalen-2-yl-4-methylbenzenesulfonate: To a mixture of 7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol (2 g, 1 equiv) and N-ethyl-N-isopropylpropan-2-amine (4.11 g, 8.0 equiv), DMAP (48.6 mg, 0.1 equiv) in DCM (20 mL) was added TsCl (3.03 g, 4.0 equiv) at 0° C. The mixture was stirred at 0° C. for 0.25 hour. The mixture was concentrated and purified by prep-HPLC [column: Welch Xtimate C18 250× 50 mm×10 µm; mobile phase: water (FA)-ACN; B %: 31%-61%, 15 minutes] to afford the title compound (3 g, 45% yield) as yellow solid. LCMS (ESI, M+1): m/z=811.1.

Intermediate 5

1,3,7-triazaspiro[4.5]decan-2-one

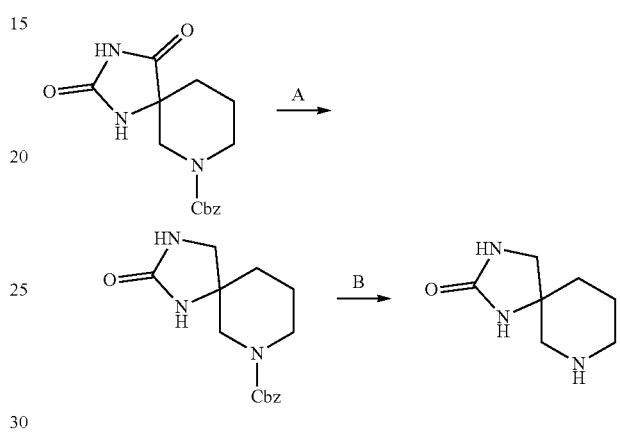

Step A. benzyl 2-oxo-1,3,7-triazaspiro[4.5]decane-7-carboxylate: To a solution of benzyl 2,4-dioxo-1,3,7-triazaspiro[4.5]decane-7-carboxylate (4.0 g, 1.0 equiv) in THF (40 mL) was added BH$_3$-Me$_2$S (10 M, 6.59 mL, 5.0 equiv) in one portion at 0° C. under N$_2$. The reaction was stirred at 10° C. for 0.5 hour. The reaction was stirred at 85° C. for 3 hours. The mixture was quenched with MeOH and stirred at 60° C. for 1 hour. The mixture was diluted with water (20 mL) and extracted with EtOAc (3×20 mL). The combined organic layers were washed with brine (15 mL), dried over anhydrous sodium sulfate, and concentrated. The residue was purified with reversed phase flash chromatography [C18, 0.1% formic acid condition] to afford the title compound (1.40 g, 30.1% yield) as yellow liquid; LCMS (ESI, M+1): m/z=290.1.

Step B. 1,3,7-triazaspiro[4.5]decan-2-one: To a solution of benzyl 2-oxo-1,3,7-triazaspiro[4.5]decane-7-carboxylate (1.40 g, 1.0 equiv) in MeOH (20 mL) was added Pd/C (800 mg, 10% purity) under N$_2$. The suspension was degassed under vacuum and purged with H2 several times. The reaction was stirred under H2 (15 psi) at 20° C. for 2 hours. The mixture was filtered and the solution was concentrated to afford the title compound (800 mg, 87% yield) as yellow solid. LCMS (ESI, M+1): m/z=156.2.

Intermediate 6

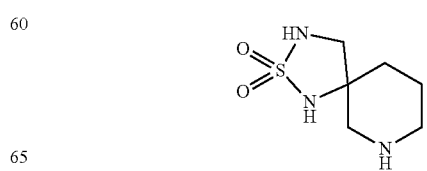

2-thia-1,3,7-triazaspiro[4.5]decane 2,2-dioxide

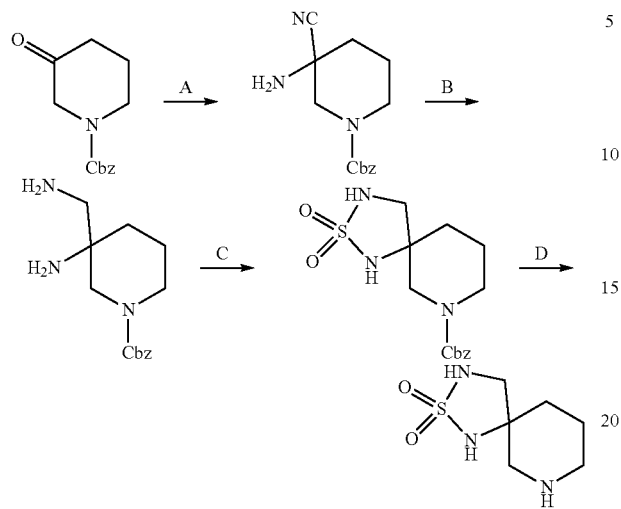

Step A. benzyl 3-amino-3-cyano-piperidine-1-carboxylate: To a mixture of benzyl 3-oxopiperidine-1-carboxylate (10.0 g, 1.0 equiv) and NH₄Cl (9.17 g, 4.0 equiv) in isopropyl alcohol (60 mL) and NH₃·H₂O (120 mL) was added KCN (10.1 g, 3.61 equiv) in one portion at 25° C. under N₂. The mixture was stirred at 25° C. for 12 hours. Water (150 mL) was added to the mixture, and the aqueous phase was extracted with ethyl acetate (3×50 mL). The combined organic phase was washed with brine (100 mL), and dried with anhydrous Na₂SO₄, filtered, and concentrated in vacuum. The residue was purified by column chromatography (SiO₂, Petroleum ether/Ethyl acetate=20/1 to 0/1) to afford the title compound (10.0 g, 89% yield) as yellow oil; LCMS (ESI, 2M+1): m/z=519.2.

Step B. benzyl 3-amino-3-(aminomethyl)piperidine-1-carboxylate: To a mixture of benzyl 3-amino-3-cyano-piperidine-1-carboxylate (200 mg, 1.0 equiv), NH₃·MeOH (1.00 mL, 20% purity, 1.0 equiv) in MeOH (5 mL) was added Raney Ni (30.0 mg) and then the mixture was stirred at 25° C. for 5 hours under H2 atmosphere (15 psi). The reaction mixture was filtered and concentrated under reduced pressure. The residue was purified by prep-HPLC [Waters Xbridge 150×25 mm×5 μm; A: water (10 mM NH₄HCO₃), B: ACN, B %: 9%-39% over 10 min] to afford the title compound (100 mg, 45% yield) as colorless oil; ¹H NMR (400 MHz, chloroform-d₄) δ=7.38-7.30 (m, 5H), 5.23-5.03 (m, 2H), 3.45 (br s, 3H), 3.19 (br d, J=13.2 Hz, 1H), 2.78-2.63 (m, 1H), 2.49 (d, J=13.2 Hz, 1H), 1.66-1.40 (m, 4H).

Step C. benzyl 2-thia-1,3,7-triazaspiro[4.5]decane-7-carboxylate 2,2-dioxide: To a refluxing solution of sulfamide (109 mg, 10.0 equiv) in Pyridine (2 mL) was added benzyl 3-amino-3-(aminomethyl)piperidine-1-carboxylate (30.0 mg, 1.0 equiv). The resulting mixture was stirred at 120° C. for further 12 hours under nitrogen. The reaction mixture was concentrated under reduced pressure to give a residue. The residue was purified by prep-HPLC [Phenomenex Gemini-NX C18 75×30 mm×3 μm; A: water (0.225% FA), B: ACN, B %: 22%-52% over 7 min] to afford the title compound (15.0 mg, 40% yield) as yellow solid. ¹H NMR (400 MHz, chloroform-d₄) δ=7.35 (s, 5H), 5.62 (br d, J=0.8 Hz, 1H), 5.13 (br s, 2H), 5.03 (br s, 1H), 3.65 (br d, J=12.0 Hz, 1H), 3.58-3.31 (m, 4H), 3.22-3.11 (m, 1H), 1.95-1.84 (m, 1H), 1.81-1.67 (m, 2H), 1.54 (br dd, J=2.8, 7.2 Hz, 1H).

Step D. 2-thia-1,3,7-triazaspiro[4.5]decane 2,2-dioxide: A mixture of benzyl 2-thia-1,3,7-triazaspiro[4.5]decane-7-carboxylate 2,2-dioxide (15.0 mg, 1.0 equiv) in MeOH (2 mL) was added Pd/C (3.00 mg, 10% purity) and then the mixture was stirred at 25° C. for 1 hour under H₂ atmosphere (15 psi). The mixture was filtered and concentrated under reduced pressure to afford the title compound (17.0 mg, crude) as yellow solid.

Intermediate 7

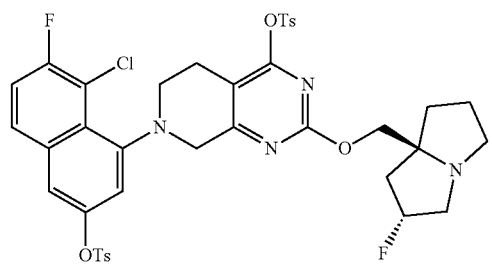 [SMILES: Cc1ccc(S(=O)(=O)Oc2cc(N3CCc4c(nc(OC[C@@]56CCCN5C[C@H](F)C6)nc4OS(=O)(=O)c4ccc(C)cc4)C3)c3c(Cl)c(F)ccc3c2)cc1]

5-chloro-6-fluoro-4-(2-(((2R,7aS)-2-fluorotetrahydro-1H-pyrrolizin-7a(5H)-yl)methoxy)-4-(tosyloxy)-5,8-dihydropyrido[3,4-d]pyrimidin-7(6H)-yl)naphthalen-2-yl 4-methylbenzenesulfonate

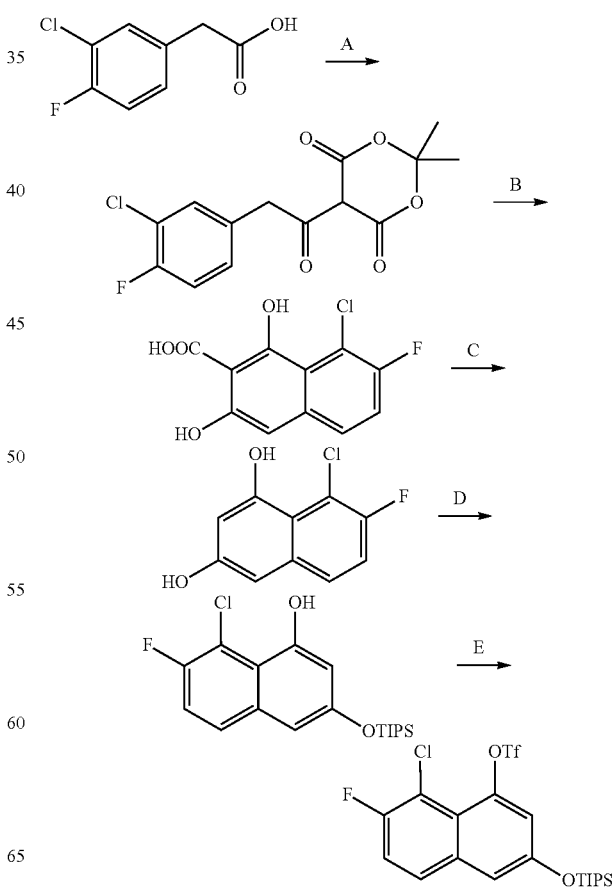

-continued

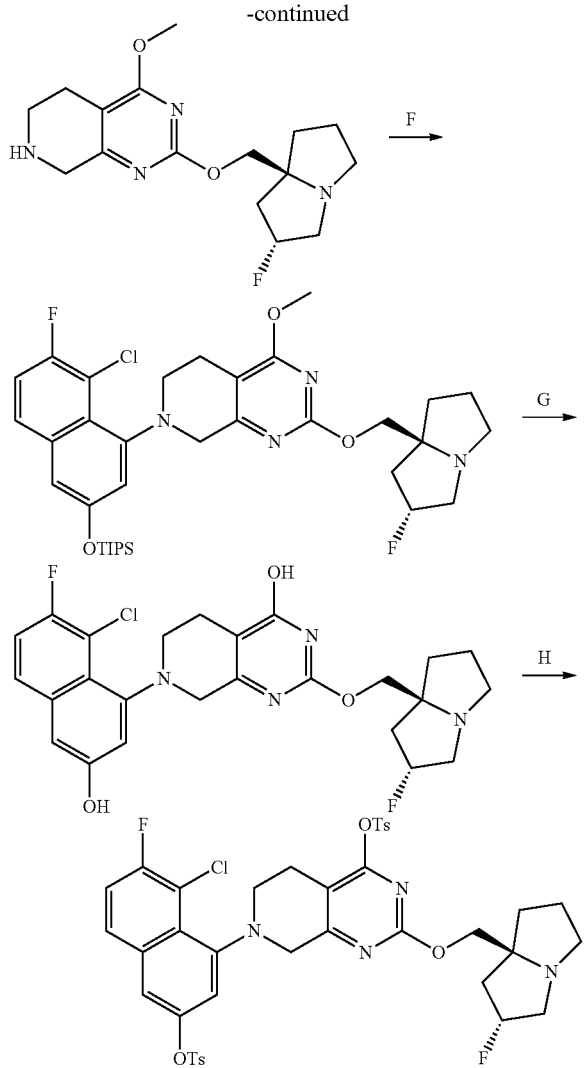

Step A. 5-(2-(3-chloro-4-fluorophenyl)acetyl)-2,2-dimethyl-1,3-dioxane-4,6-dione. To a mixture of 2-(3-chloro-4-fluoro-phenyl)acetic acid (330 g, 1 equiv) and 2,2-dimethyl-1,3-dioxane-4,6-dione (277 g, 1.1 equiv) in MeCN (1500 mL) was added DMAP (18.2 g, 0.09 equiv) at 20° C. N-ethyl-N-isopropylpropan-2-amine (486 g, 2.15 equiv) was added carefully in 1 hour while temperature was controlled between 15 and 30° C. and then 2,2-dimethylpropanoyl chloride (232.10 g, 1.1 equiv) was added during a period of 1 hour. The reaction mixture was stirred at 45° C. for 3 hours. The mixture was cooled to 0° C. and the pH was adjusted to 3 with HCl (4N, ~5 L). The mixture was stirred at 0° C. for 1 hour. The solid was filtered and triturated with MeCN (3 L) to afford the title compound (933 g, 84% yield) as yellow solid, which was used in the next step without further purification. $^1$HNMR (400 MHz, CDCl$_3$) δ=7.46 (dd, J=2.0, 6.8 Hz, 1H), 7.30-7.25 (m, 1H), 7.10 (t, J=8.8 Hz, 1H), 4.39-4.34 (m, 2H), 1.74 (s, 6H).

Step B. 8-chloro-7-fluoro-1,3-dihydroxy-2-naphthoic acid: A mixture of 5-(2-(3-chloro-4-fluorophenyl)acetyl)-2,2-dimethyl-1,3-dioxane-4,6-dione (650 g, 1.0 equiv) in CF$_3$SO$_3$H (1300 mL) was stirred at 5-20° C., and then the mixture was stirred at 10° C. for 2 hours. After completion, the mixture was poured into ice water (2 L) and filtered. The solid was washed with water (5 L) and collected to afford the title compound (2000 g, crude) as yellow solid, which was used in the next step without further purification.

Step C. 8-chloro-7-fluoronaphthalene-1,3-diol: A mixture of 8-chloro-7-fluoro-1,3-dihydroxy-2-naphthoic acid (1.2 kg, 1.0 equiv) in MeCN (700 mL) and H$_2$O (700 mL) was stirred at 85° C. for 12 hours under N$_2$. The mixture was concentrated under vacuum. The residue was extracted with ethyl acetate (2 L× 2), dried over Na$_2$SO$_4$ and concentrated under vacuum. The residue was purified by column chromatography (SiO$_2$, PE/EA=3/1) and prep-HPLC (column: Phenomenex Luna C18 200*40 mm*10 μm; mobile phase: [water (FA)-ACN]; B %: 27%-57%, 10 min). The desired fraction was collected and extracted with ethyl acetate (2 L). The organic combined layers were dried over Na$_2$SO$_4$ and concentrated under vacuum to afford the title compound (17 g, 16% yield two steps) as yellow solid. $^1$H NMR (400 MHz, DMSO-d$_6$) δ 10.17 (s, 1H), 9.71 (s, 1H), 7.58 (dd, J=5.6, 8.8 Hz, 1H), 7.32 (t, J=8.8 Hz, 1H), 6.67 (d, J=2.0 Hz, 1H), 6.63 (d, J=2.0 Hz, 1H).

Step D. 8-chloro-7-fluoro-3-((triisopropylsilyl)oxy)naphthalen-1-ol: To a solution of 8-chloro-7-fluoronaphthalene-1,3-diol (10 g, 1 equiv) and N-ethyl-N-isopropylpropan-2-amine (12.2 g, 2.0 equiv) in DCM (150 mL) was added TIPSCl (8.16 g, 0.9 equiv) at 0° C. The reaction was stirred at 0° C. for 0.5 hour. The mixture was concentrated under vacuum to give a residue and the residue was purified by column chromatography (SiO$_2$, PE/EA=10/1) to afford the title compound (15 g, 86% yield) as yellow oil.

Step E. 8-chloro-7-fluoro-3-((triisopropylsilyl)oxy)naphthalen-1-yl trifluoromethanesulfonate: To a mixture of 8-chloro-7-fluoro-3-((triisopropylsilyl)oxy)naphthalen-1-ol (15 g, 1.0 equiv) and N-ethyl-N-isopropylpropan-2-amine (15.8 g, 3.0 equiv) in DCM (150 mL) was added Tf$_2$O (17.2 g, 1.5 equiv) at −40° C. The reaction was stirred at −40° C. for 0.5 hour. The mixture was concentrated under vacuum and purified by column chromatography (SiO$_2$, PE/EA=10/1) to afford the title compound (19 g, 90% yield) as yellow oil. LCMS (ESI, M+1): m/z=501.0

Step F. 7-(8-chloro-7-fluoro-3-((triisopropylsilyl)oxy)naphthalen-1-yl)-2-(((2R,7aS)-2-fluorohexahydro-1H-pyrrolizin-7a-yl)methoxy)-4-methoxy-5,6,7,8-tetrahydropyrido[3,4-d]pyrimidine: A mixture of 2-(((2R,7aS)-2-fluorohexahydro-1H-pyrrolizin-7a-yl)methoxy)-4-methoxy-5,6,7,8-tetrahydropyrido[3,4-d]pyrimidine (4 g, 1.0 equiv), 8-chloro-7-fluoro-3-((triisopropylsilyl)oxy)naphthalen-1-yl trifluoromethanesulfonate (7.46 g, 1.2 equiv), Cs$_2$CO$_3$ (12.1 g, 3.0 equiv), RuPhos (1.16 g, 0.2 equiv) and Pd$_2$(dba)$_3$ (1.14 g, 0.1 equiv) in toluene (80 mL) was degassed and purged with N$_2$ several times. The mixture was stirred at 100° C. for 3 hours under N$_2$ atmosphere. The mixture was diluted with water (100 mL) and extracted with ethyl acetate (100 mL). The organic layer was dried over sodium sulfate and concentrated under vacuum to give a residue. The residue was purified by HPLC (0.1% FA condition) to afford the title compound (3.9 g, 46% yield) as yellow solid. LCMS (ESI, M+1): m/z=673.2.

Step G. 7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol: To a mixture of EtSH (1.99 g, 2.37 mL, 6.0 equiv) in DMAC (30 mL) was added NaH (855 mg, 60% purity, 4.0 equiv) at 0° C. After the reaction was stirred at 20° C. for 0.5 hour, 7-(8-chloro-7-fluoro-3-((triisopropylsilyl)oxy)naphthalen-1-yl)-2-(((2R,7aS)-2-fluorohexahydro-1H-pyrrolizin-7a-yl)methoxy)-4-methoxy-5,6,7,8-tetrahydropyrido[3,4-d]pyrimidine (3.6 g, 1 equiv) was added. The mixture was stirred at 60° C. for 1 hours. Water (40 mL) was added and the pH of mixture was adjusted to 6 with 2N HCl. The mixture was extracted with ethyl acetate (3×40 mL). The combined organic layers were washed with brine (2×40 mL), dried over Na$_2$SO$_4$ and concentrated under vacuum to afford the title compound (4.2 g, crude) as yellow oil, which was used in the next step without further purification. LCMS (ESI, M+1): m/z=503.1.

Step H. 5-chloro-6-fluoro-4-(2-(((2R,7aS)-2-fluorohexahydro-1H-pyrrolizin-7a-yl)methoxy)-4-(tosyloxy)-5,6-dihydropyrido[3,4-d]pyrimidin-7(8H)-yl)naphthalen-2-yl 4-methylbenzenesulfonate: To a mixture of 7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol (2 g, 1 equiv), N-ethyl-N-isopropylpropan-2-amine (4.11 g, 5.54 mL, 8.0 equiv), and DMAP (48.6 mg, 0.1 equiv) in DCM (20 mL) was added TsCl (3.03 g, 4.0 equiv) at 0° C. The mixture was stirred at 0° C. for 0.25 hour. The mixture was concentrated under vacuum and purified by prep-HPLC (column: Welch Xtimate C18 250*50 mm*10 μm; mobile phase: [water (FA)-ACN]; B %: 31%-61%, 15 min) to afford the title compound (3 g, 45% yield) as yellow solid. LCMS (ESI, M+1): m/z=811.1.

Intermediate 8

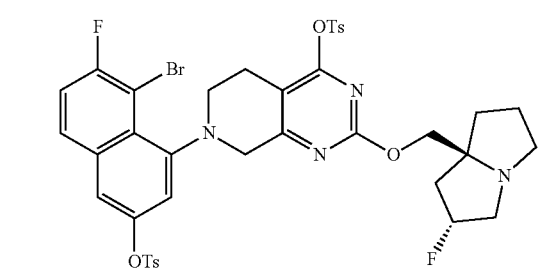 [SMILES: Cc1ccc(S(=O)(=O)Oc2cc(N3CCc4c(nc(OC[C@@]56CCCN5C[C@H](F)C6)nc4OS(=O)(=O)c4ccc(C)cc4)C3)c3c(Br)c(F)ccc3c2)cc1]

5-bromo-6-fluoro-4-(2-(((2R,7aS)-2-fluorotetrahydro-1H-pyrrolizin-7a(5H)-yl)methoxy)-4-(tosyloxy)-5,8-dihydropyrido[3,4-d]pyrimidin-7(6H)-yl)naphthalen-2-yl 4-methylbenzenesulfonate

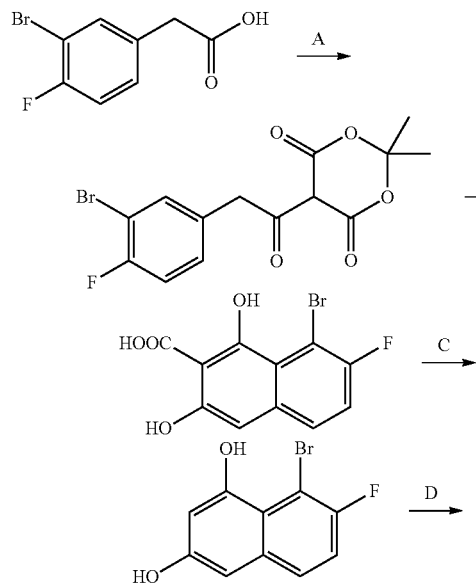

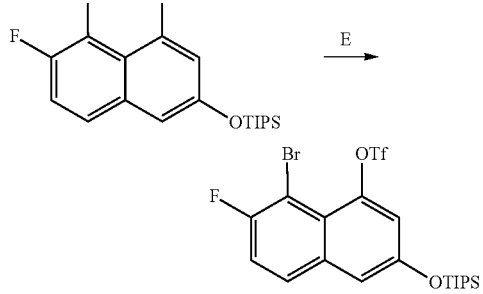

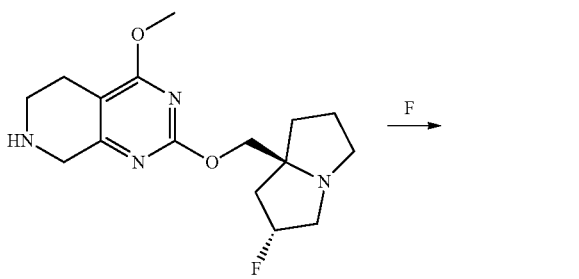

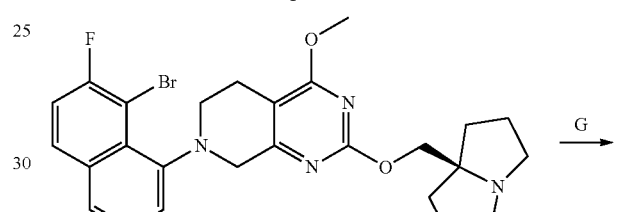

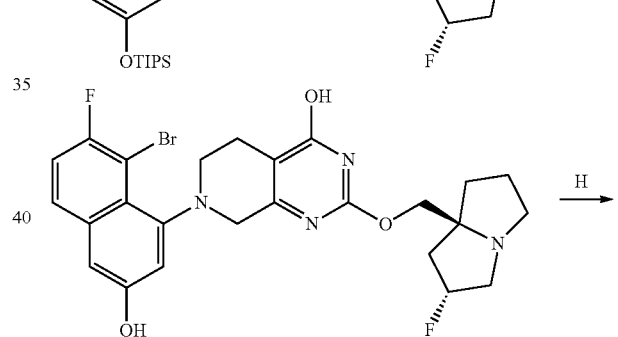

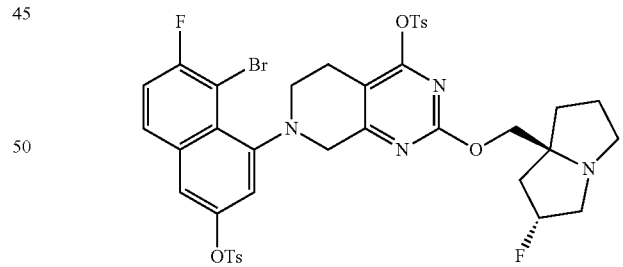

Synthesized according to intermediate 7. The title compound was obtained as yellow solid. LCMS (ESI, M+1): m/z=855.0.

Intermediate 9

99

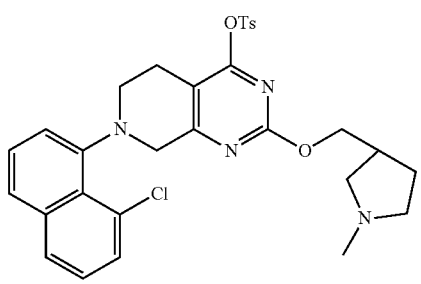 [SMILES: Cc1ccc(S(=O)(=O)Oc2nc(OCC3CCN(C)C3)nc3c2CCN(c2cccc4cccc(Cl)c24)C3)cc1]

(S)-7-(8-chloronaphthalen-1-yl)-2-((1-methylpyrrolidin-2-yl)methoxy)-5,6,7,8-tetrahydropyrido[3,4-d]pyrimidin-4-yl 4-methylbenzenesulfonate

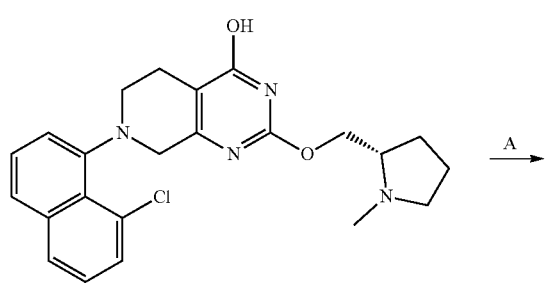

Step A. (S)-7-(8-chloronaphthalen-1-yl)-2-((1-methylpyrrolidin-2-yl)methoxy)-5,6,7,8-tetrahydropyrido[3,4-d]pyrimidin-4-yl 4-methylbenzenesulfonate: To a solution of 7-(8-chloro-1-naphthyl)-2-[[(2S)-1-methylpyrrolidin-2-yl]methoxy]-6,8-dihydro-5H-pyrido[3,4-d]pyrimidin-4-ol (1.50 g, 1.0 equiv) and N-ethyl-N-isopropylpropan-2-amine (1.37 g, 3.0 equiv) in DCM (20 mL) were added DMAP (43.1 mg, 0.1 equiv) and TsCl (1.35 g, 2.0 equiv). The mixture was stirred at 20° C. for 2 hours. After completion, the mixture was diluted with water (40 mL) and extracted with DCM/isopropanol (3×50 mL). The combined organic phase was dried over Na$_2$SO$_4$, filtered and concentrated. The residue was purified by column chromatography (neutral Al$_2$O$_3$, Petroleum ether/Ethyl acetate=10/1 to Ethyl acetate:MeOH=10:1) to afford the title compound (1.0 g, 49% yield) as a brown solid. LCMS (ESI, M+1): m/z=579.2.

100

Example 1

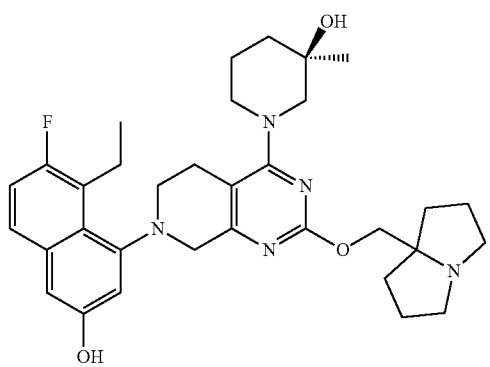 [SMILES: CCc1c(F)ccc2cc(O)cc(N3CCc4c(nc(OCC56CCCN5CCC6)nc4N4CCC[C@@](C)(O)C4)C3)c12]

(R)-1-(7-(8-ethyl-7-fluoro-3-hydroxynaphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol

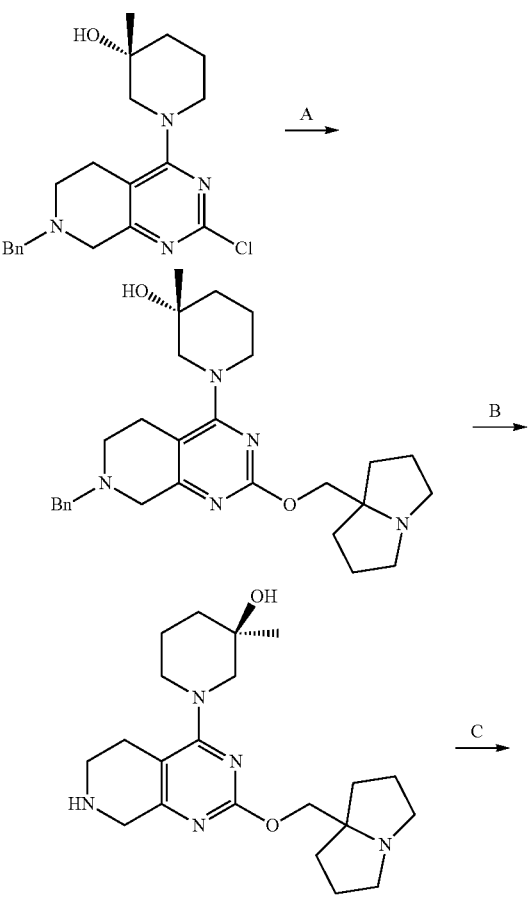

-continued

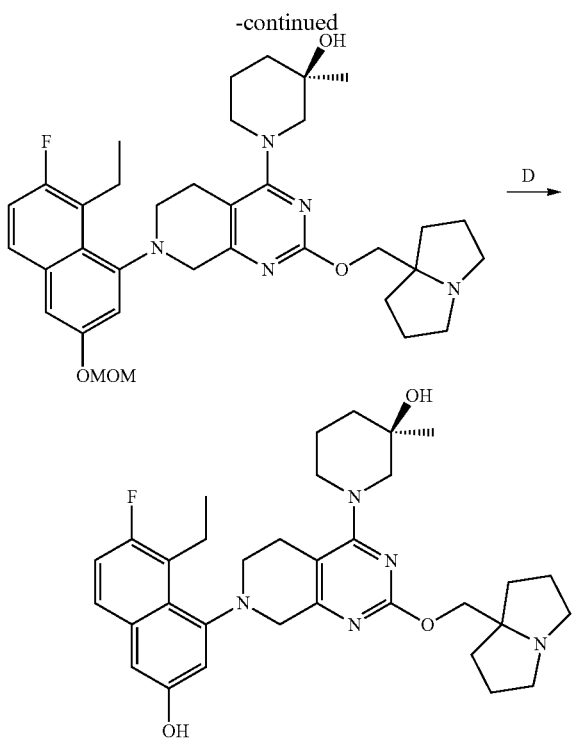

Step A. (R)-1-(7-benzyl-2-((hexahydro-1H-pyrrolizin-7a-yl)methoxy)-5,6,7,8-tetrahydropyrido[3,4-d]pyrimidin-4-yl)-3-methylpiperidin-3-ol: A mixture of (R)-1-(7-benzyl-2-chloro-5,6,7,8-tetrahydropyrido[3,4-d]pyrimidin-4-yl)-3-methylpiperidin-3-ol (1.00 g, 2.68 mmol), (hexahydro-1H-pyrrolizin-7a-yl)methanol (568 mg, 4.02 mmol), BINAP (417 mg, 670 µmol), Cs$_2$CO$_3$ (2.62 g, 8.05 mmol) and Pd(OAc)$_2$ (120 mg, 536 µmol) in toluene (10 mL) was degassed and purged with N$_2$ for 3 times. The mixture was stirred at 110° C. for 3 hours under N$_2$ atmosphere. After completion, the reaction mixture was diluted with H$_2$O (10 mL) and extracted with ethyl acetate (2×10 mL). The combined organic layers were washed with brine (2×30 mL), dried over Na$_2$SO$_4$, filtered, and concentrated under reduced pressure to give a residue. The residue was purified by HPLC [C18, 0.1% FA in water, 0-60% MeCN] to give the title compound (480 mg, 30% yield, 80% purity). Yellow solid. $^1$H NMR (400 MHz, chloroform-d) δ=7.39-7.28 (m, 5H), 4.07-3.96 (m, 2H), 3.96-3.92 (m, 1H), 3.87-3.82 (m, 1H), 3.81-3.74 (m, 1H), 3.71-3.65 (m, 3H), 3.43 (d, J=17.2 Hz, 1H), 3.11-3.04 (m, 2H), 2.98-2.91 (m, 1H), 2.91-2.87 (m, 1H), 2.85-2.77 (m, 1H), 2.76-2.67 (m, 1H), 2.64-2.52 (m, 3H), 2.51-2.43 (m, 1H), 2.07-1.98 (m, 2H), 1.86-1.76 (m, 6H), 1.66-1.57 (m, 3H), 1.26-1.25 (m, 3H); LCMS (ESI, M+1): m/z 478.3.

Step B. (R)-1-(2-((hexahydro-1H-pyrrolizin-7a-yl)methoxy)-5,6,7,8-tetrahydropyrido[3,4-d]pyrimidin-4-yl)-3-methylpiperidin-3-ol: A mixture of (R)-1-(7-benzyl-2-((hexahydro-1H-pyrrolizin-7a-yl)methoxy)-5,6,7,8-tetrahydropyrido[3,4-d]pyrimidin-4-yl)-3-methylpiperidin-3-ol (450 mg, 754 µmol, 80% purity), and Pd(OH)$_2$ (250 mg, 1.78 mmol) in MeOH (5.00 mL) was degassed and purged with H2 for 3 times. The mixture was stirred at 40° C. for 2 hours under H$_2$ (50 psi). After completion, the reaction mixture was filtered through Celite and the filtrate was concentrated. The residue was purified by HPLC [C18, 0.1% FA in water, 0-40% MeCN] to give the title compound (160 mg, 45% yield). White solid. LCMS (ESI, M+1): m/z 388.1.

Step C. (R)-1-(7-(8-ethyl-7-fluoro-3-(methoxymethoxy)naphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol: A mixture of (R)-1-(2-((hexahydro-1H-pyrrolizin-7a-yl)methoxy)-5,6,7,8-tetrahydropyrido[3,4-d]pyrimidin-4-yl)-3-methylpiperidin-3-ol (110 mg, 252 µmol), 8-ethyl-7-fluoro-3-(methoxymethoxy)naphthalen-1-yl trifluoromethanesulfonate (193 mg, 505 µmol), XantPhos Pd G3 (59.9 mg, 63.2 µmol), Xantphos (21.9 mg, 37.9 µmol), Cs$_2$CO$_3$ (247 mg, 758 µmol) and 4 Å MS (50.0 mg) in toluene (2.00 mL) was degassed and purged with N$_2$ for 3 times. The mixture was stirred at 110° C. for 20 hours under N$_2$ atmosphere. After completion, the reaction mixture was diluted with H$_2$O (5 mL) and extracted with ethyl acetate (2×5 mL). The combined organic layers were washed with brine (15 mL), dried over Na$_2$SO$_4$, filtered, and concentrated under reduced pressure to give a residue. The residue was purified by HPLC [C18, 0.1% FA in water, 0-70% MeCN] to give the title compound (48 mg, 29% yield). Yellow solid. LCMS (ESI, M+1): m/z 620.3.

Step D. (R)-1-(7-(8-ethyl-7-fluoro-3-hydroxynaphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol: To a solution of (R)-1-(7-(8-ethyl-7-fluoro-3-(methoxymethoxy)naphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol (30.0 mg, 48.4 µmol) in ACN (0.50 mL) was added HCl·MeOH (4.0 M, 1.00 mL) at 0° C. The mixture was stirred at 0° C. for 20 min. After completion, the reaction mixture was diluted with saturated Na$_2$CO$_3$ solution (2 mL) and extracted with ethyl acetate (2×5.00 mL). The combined organic layers were dried over Na$_2$SO$_4$ and filtered. The mixture was concentrated under reduced pressure to give a residue. The residue was purified by prep-HPLC (column: Phenomenex Luna C18 150×25 mmx 10 µm; mobile phase: [water (0.225% FA)-ACN]; B %: 21%-51%, 10 min) to give (R)-1-(7-(8-ethyl-7-fluoro-3-hydroxynaphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol (8.16 mg, 26.9% yield, FA). Yellow solid. $^1$H NMR (400 MHz, methanol-d$_4$) δ=7.60-7.43 (m, 1H), 7.19-7.10 (t, J=9.6 Hz, 1H), 7.06-6.90 (m, 2H), 4.60 (br s, 2H), 4.47-4.34 (m, 2H), 4.15-4.03 (m, 1H), 3.76-3.62 (m, 2H), 3.59-3.48 (m, 4H), 3.47-3.35 (m, 2H), 3.21-3.11 (m, 4H), 2.82-2.65 (m, 1H), 2.34-1.95 (m, 9H), 1.88-1.63 (m, 3H), 1.24 (d, J=26.4 Hz, 3H), 1.17-1.02 (m, 3H); LCMS (ESI, M+1): m/z 576.3.

Example 2

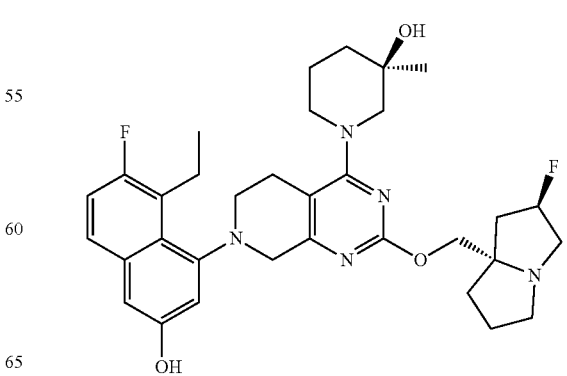

103

(R)-1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol

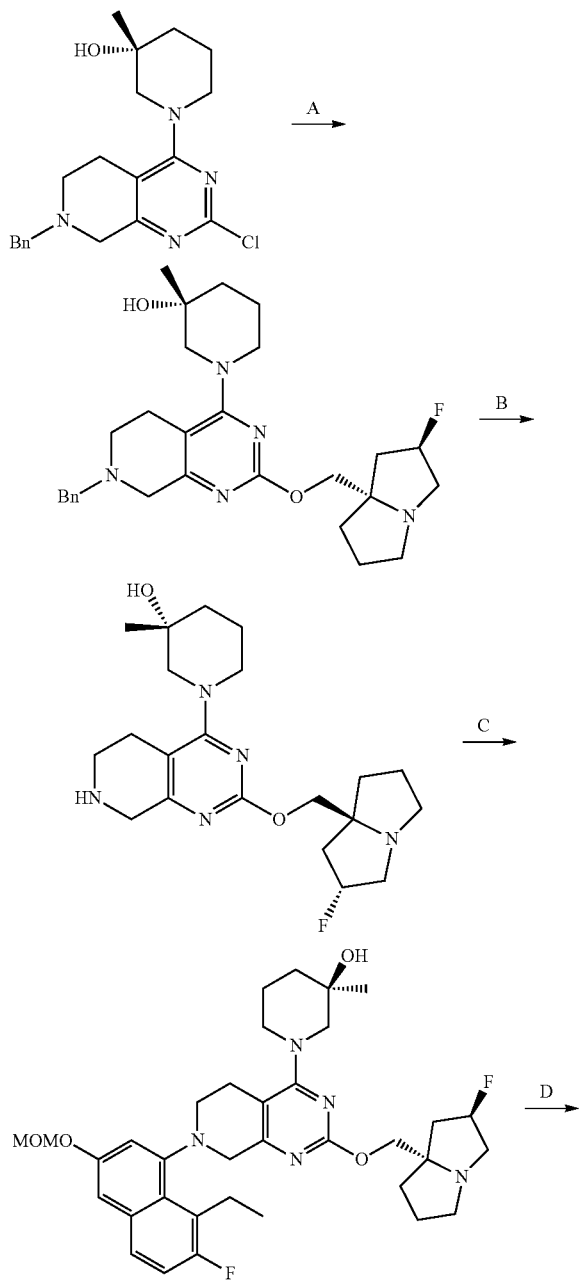

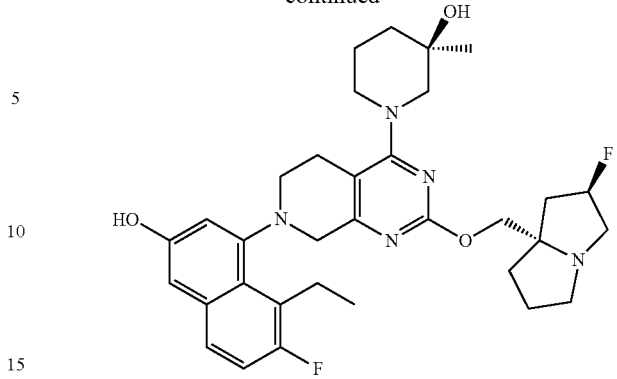

Step A. (R)-1-(7-benzyl-2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol: To a mixture of ((2R,7aS)-2-fluorohexahydro-1H-pyrrolizin-7a-yl)methanol (80.0 mg, 503 µmol) and THF (2 mL) was added NaH (40.0 mg, 1.00 mmol, 60% purity) at 0° C. The reaction was stirred at 0° C. for 0.5 hour and (R)-1-(7-benzyl-2-chloro-5,6,7,8-tetrahydropyrido[3,4-d]pyrimidin-4-yl)-3-methylpiperidin-3-ol (125 mg, 335 µmol) was added at 20° C. over 0.5 hour. The reaction was stirred at 45° C. for 3 hours. The reaction mixture was quenched with sat. NH$_4$Cl (5 mL), diluted with ethyl acetate (10 mL), and extracted with ethyl acetate (10 mL×2). The combined organic phase was washed with brine (10 mL) and dried over anhydrous sodium sulfate. The mixture was filtered and concentrated to give a residue. The residue was purified by reversed phase flash chromatography [water (FA 0.10%)/acetonitrile] to give the title compound (74.0 mg, 44% yield). Yellow Oil; LCMS (ESI, M+1): m/z 496.4.

Step B. (R)-1-(2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol: To a solution of (R)-1-(7-benzyl-2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol (72.0 mg, 145 µmol) in MeOH (2 mL) was added Pd(OH)$_2$/C (36.0 mg, 10% purity) under N$_2$. The suspension was degassed under vacuum and purged with H2 several times. The mixture was stirred under H2 (15 psi) at 20° C. for 2 hours. Upon completion, the mixture was filtered and concentrated to give the title compound (50.0 mg, crude). Colorless Oil; LCMS (ESI, M+1): m/z 406.3.

Step C. (R)-1-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol: To a mixture of (R)-1-(2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol (40.0 mg, 98.6 µmol), 8-ethyl-7-fluoro-3-(methoxymethoxy)naphthalen-1-yl trifluoromethanesulfonate (56.6 mg, 148 µmol), Xantphos (11.4 mg, 19.7 µmol), and Cs$_2$CO$_3$ (96.4 mg, 296 µmol) in toluene (1.5 mL) was added XantPhos Pd G3 (9.35 mg, 9.86 µmol) under N$_2$. The mixture was degassed and purged with N$_2$ for 3 times. The reaction was stirred at 110° C. for 12 hours. Upon completion, the reaction mixture was diluted with ethyl acetate (5 mL) and water (5 mL). The aqueous layer was extracted with ethyl acetate (5 mL). The combined organic phase was washed with brine (5 mL) and dried over anhydrous sodium sulfate. The mixture was filtered and concentrated to give a residue. The residue was purified by reversed phase flash chromatography [water (FA 0.10%)/acetonitrile] to give the title compound (9.00 mg, 14% yield). Yellow Solid. LCMS (ESI, M+1): m/z 638.4.

Step D. (R)-1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol: To a solution of (R)-1-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol (8.00 mg, 12.5 µmol) in MeOH (0.5 mL) was added HCl·MeOH (4 M, 0.5 mL) at 0° C. The mixture was stirred at 0° C. for 0.5 hour. Upon completion, the mixture was concentrated to give a residue. The residue was purified by prep-HPLC (column: Phenomenex Luna C18 150×25 mm×10 µm; mobile phase: [water (0.225% FA)-ACN]; B %: 22%-52%, 10 min) to afford the title compound (6.67 mg, 87% yield, 0.16 FA). Off-white Solid. $^1$H NMR (400 MHz, METHANOL-$d_4$) δ=7.56-7.46 (m, 1H), 7.15 (t, J=9.3 Hz, 1H), 7.02-6.92 (m, 2H), 5.48-5.31 (m, 1H), 4.40-3.90 (m, 2H), 4.14-3.88 (m, 1H), 3.75-3.32 (m, 11H), 3.24-3.09 (m, 3H), 2.84-2.64 (m, 1H), 2.54-1.57 (m, 10H), 1.28-1.18 (m, 3H), 1.16-1.08 (m, 3H); LCMS (ESI, M+1): m/z 594.4.

Example 3

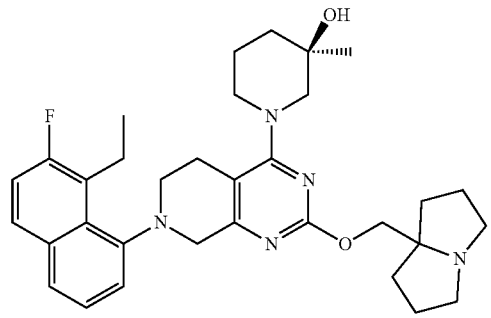 [SMILES: CCc1c(F)ccc2cccc(N3CCc4c(nc(OCC56CCCN5CCC6)nc4N4CCC[C@@](C)(O)C4)C3)c12]

(R)-1-(7-(8-ethyl-7-fluoronaphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol

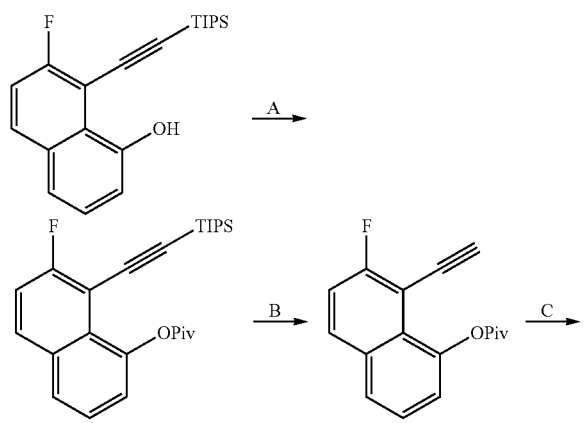

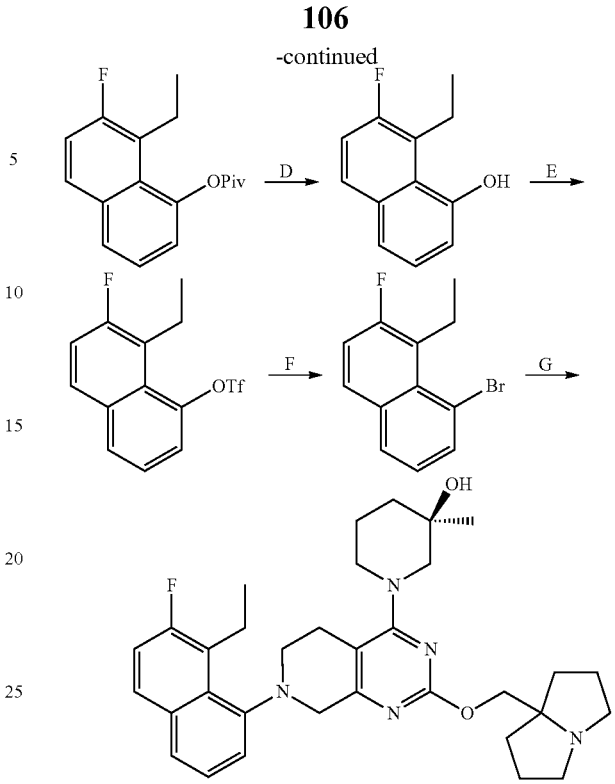

Step A. 7-fluoro-8-((triisopropylsilyl)ethynyl)naphthalen-1-yl pivalate: To a solution of 7-fluoro-8-((triisopropylsilyl)ethynyl)naphthalen-1-ol (5 g, 14.6 mmol) in DCM (50 mL) were added N-ethyl-N-isopropylpropan-2-amine (4.72 g, 36.5 mmol), DMAP (178 mg, 1.46 mmol), and pivaloyl chloride (2.64 g, 21.9 mmol) under $N_2$ atmosphere at 0° C. The mixture was stirred at 0° C. for 0.5 hour. The mixture was diluted with water (50.0 mL) and extracted with DCM (3×25.0 mL). The organic layers were washed with brine, dried over $Na_2SO_4$, and concentrated under reduced pressure to give a residue. The residue was purified by column chromatography (SiO$_2$, Petroleum ether/Ethyl acetate=1/0 to 20/1) to give the title compound (6.00 g, 94% yield) as yellow solid. $^1$H NMR (400 MHz, CHLOROFORM-d) δ 7.84-7.75 (m, 1H), 7.72-7.67 (m, 1H), 7.46-7.40 (t, J=7.6 Hz, 1H), 7.32-7.28 (m, 1H), 7.08 (d, J=8.0 Hz, 1H), 1.51-1.47 (m, 9H), 1.23-1.14 (m, 21H). LCMS (ESI, M+1): m/z 427.2.

Step B. 8-ethynyl-7-fluoronaphthalen-1-yl pivalate: To a solution of 7-fluoro-8-((triisopropylsilyl)ethynyl)naphthalen-1-yl pivalate (5 g, 11.5 mmol) in DMF (50 mL) was added CsF (34.9 g, 220 mmol) under $N_2$ atmosphere. The mixture was stirred at 20° C. for 1 hour. The mixture was diluted with water (150 mL) and extracted with EtOAc (3×50.0 mL). The combined organic layers were washed with brine, dried over $Na_2SO_4$, filtered, and concentrated under reduced pressure. The residue was purified by column chromatography (SiO$_2$, Petroleum ether/Ethyl acetate=100/1 to 20/1) to give the title compound (2.76 g, 87% yield). Yellow solid. $^1$H NMR (400 MHz, CHLOROFORM-d) δ 7.90-7.84 (m, 1H), 7.77-7.71 (m, 1H), 7.46 (t, J=7.6 Hz, 1H), 7.31 (t, J=8.8 Hz, 1H), 7.14-7.09 (m, 1H), 3.63-3.58 (m, 1H), 1.51-1.44 (m, 9H).

Step C. 8-ethyl-7-fluoronaphthalen-1-yl pivalate: To a solution of 8-ethynyl-7-fluoronaphthalen-1-yl pivalate (3.27 g, 11.9 mmol) in MeOH (30.0 mL) was added Pd/C (0.33 g, 10% purity) under $N_2$ atmosphere. The mixture was stirred at 20° C. for 1 hour under H2 (15 psi) atmosphere. The mixture was filtered, and concentrated under reduced pressure to give the title compound (3.23 g, crude). Yellow oil; $^1$H NMR (400 MHz, CHLOROFORM-d) δ 7.76-7.69 (m, 2H), 7.39 (t, J=8.4 Hz, 1H), 7.29-7.23 (m, 1H), 7.05-6.99 (m, 1H), 3.23-3.13 (m, 2H), 1.49-1.45 (m, 9H), 1.25 (t, J=7.2 Hz, 3H). LCMS (ESI, M+1): m/z 275.1.

Step D. 8-ethyl-7-fluoronaphthalen-1-ol: To a solution of 8-ethyl-7-fluoronaphthalen-1-yl pivalate (3.23 g, 11.5 mmol) in MeOH (30.0 mL) was added KOH (2.59 g, 46.2 mmol). The reaction mixture was stirred at 20° C. for 0.5 hour. The mixture was diluted with water (300 mL) and extracted with EtOAc (3×100 mL). The combined organic layers were washed with brine (100 mL) and dried over Na$_2$SO$_4$. The mixture was filtered and concentrated under reduced pressure to give a residue. The residue was purified by column chromatography (SiO$_2$, Petroleum ether/Ethyl acetate=100/1 to 10/1) to give the title compound (2.11 g, 94% yield). Yellow oil; $^1$H NMR (400 MHz, CHLOROFORM-d) δ 7.66-7.59 (m, 1H), 7.44-7.37 (m, 1H), 7.26-7.19 (m, 2H), 6.79-6.74 (m, 1H), 5.24 (s, 1H), 3.43-3.34 (m, 2H), 1.33 (t, J=7.6 Hz, 3H).

Step E. 8-ethyl-7-fluoronaphthalen-1-yl trifluoromethanesulfonate: To a solution of 8-ethyl-7-fluoronaphthalen-1-ol (1.20 g, 6.31 mmol) and 4 Å molecular sieve (1.00 g) in DCM (12.0 mL) was added dropwise N-ethyl-N-isopropylpropan-2-amine (4.89 g, 37.8 mmol, 6.59 mL) at 20° C. The mixture was stirred at this temperature for 10 min, and then trifluoromethylsulfonyl trifluoromethanesulfonate (2.31 g, 8.20 mmol, 1.35 mL) was added dropwise at −40° C. The resulting mixture was stirred at −40° C. for 20 min. The reaction mixture was diluted with H$_2$O (20.0 mL) and extracted with ethyl acetate (2×30.0 mL). The combined organic layers were washed with brine (80.0 mL) and dried over Na$_2$SO$_4$. The mixture was filtered and concentrated under reduced pressure to give a residue. The residue was purified by column chromatography (SiO$_2$, petroleum ether: ethyl acetate=20:1 to 5:1) to give the title compound (1.35 g, 66% yield). Colorless oil, $^1$H NMR (400 MHz, DMSO-d$_6$) δ 8.14-8.09 (m, 1H), 8.08-8.01 (m, 1H), 7.70-7.64 (m, 1H), 7.63-7.52 (m, 2H), 3.22-3.12 (m, 2H), 1.16 (t, J=7.6 Hz, 3H).

Step F. 8-bromo-1-ethyl-2-fluoronaphthalene: A mixture of 8-ethyl-7-fluoronaphthalen-1-yl trifluoromethanesulfonate (500 mg, 1.55 mmol), LiBr (202 mg, 2.33 mmol) and Chloro(pentamethylcyclopentadienyl)ruthenium(II) Tetramer (84.3 mg, 77.6 μmol) in 1,3-dimethylimidazolidin-2-one (4.00 mL) was degassed and purged with N$_2$ for 3 times. The mixture was stirred at 100° C. for 4 hours under N$_2$ atmosphere. After completion, the reaction mixture was diluted with H$_2$O (5.00 mL) and extracted with ethyl acetate (2×10.0 mL). The combined organic layers were washed with brine (20.0 mL) and dried over Na$_2$SO$_4$. The mixture was filtered and concentrated under reduced pressure to give a residue. The residue was purified by column chromatography (SiO$_2$, petroleum ether: ethyl acetate=1:0) to give the title compound (300 mg, 76% yield). Colorless oil; $^1$H NMR (400 MHz, chloroform-d) δ 7.95-7.64 (m, 3H), 7.32-7.18 (m, 2H), 3.63-3.50 (m, 2H), 1.42-1.37 (m, 3H).

Step G. (R)-1-(7-(8-ethyl-7-fluoronaphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol: A mixture of (R)-1-(2-((hexahydro-1H-pyrrolizin-7a-yl)methoxy)-5,6,7,8-tetrahydropyrido[3,4-d]pyrimidin-4-yl)-3-methylpiperidin-3-ol (70 mg, 144 μmol, 80% purity), 8-bromo-1-ethyl-2-fluoronaphthalene (73.1 mg, 289 μmol), Pd$_2$(dba)$_3$ (26.5 mg, 28.9 μmol), Xantphos (12.5 mg, 21.7 μmol), t-BuONa (41.7 mg, 433 μmol) and 4 Å molecular sieve (70 mg) in toluene (2 mL) was degassed and purged with N$_2$ in the glove box. The mixture was stirred at 70° C. for 15 hours under N$_2$ atmosphere. After completion, the reaction mixture was diluted with H$_2$O (3.00 mL) and extracted with ethyl acetate (3×5.00 mL). The combined organic layers were washed with brine (20.0 mL), dried over Na$_2$SO$_4$, filtered, and concentrated under reduced pressure to give a residue. The residue was purified by prep-HPLC (column: Phenomenex Luna C18 150×25 mm×10 μm; mobile phase: [water (0.225% FA)-ACN]; B %: 23%-53%, 10 min) to give the title compound (18.14 mg, 22% yield). Yellow solid. $^1$H NMR (400 MHz, methanol-d$_4$) δ 7.78-7.73 (m, 1H), 7.72-7.65 (m, 1H), 7.44-7.38 (m, 2H), 7.25 (t, J=9.2 Hz, 1H), 4.81-4.44 (m, 2H), 4.28-4.12 (m, 2H), 4.07 (dd, J=3.6 Hz, 17.6 Hz, 1H), 3.74-3.63 (m, 2H), 3.55-3.42 (m, 4H), 3.29-3.08 (m, 5H), 2.85-2.68 (m, 3H), 2.11-1.83 (m, 7H), 1.82-1.61 (m, 5H), 1.27 (s, 3H), 1.17-1.11 (t, J=7.2 Hz, 3H); SFC analysis>99.9%, t$_R$=0.557 min, Column: Chiralcel IC-3 50×4.6 mm I.D., 3 μm Mobile phase: Phase A for CO$_2$, and Phase B for MeOH+ACN (0.05% DEA); Gradient elution: 60% MeOH+ACN (0.05% DEA) in C02. Flow rate: 3 mL/min; Detector: 220 nm; LCMS (ESI, M+1): m/z 560.4.

Example 4

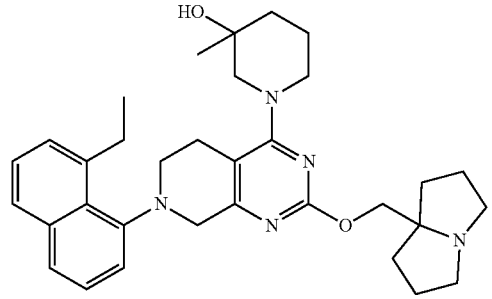 [SMILES: CCc1cccc2cccc(N3CCc4c(nc(OCC56CCCN5CCC6)nc4N4CCCC(C)(O)C4)C3)c12]

1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol

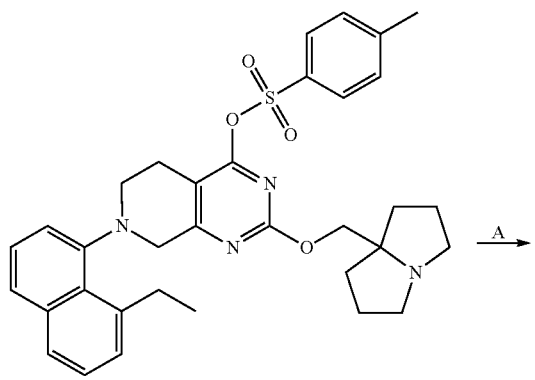

-continued

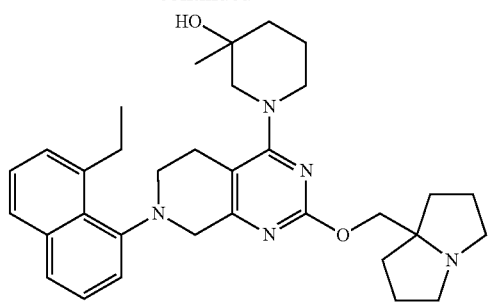

Step A. 1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol: To a solution of 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (100 mg, 167 μmol), 4A molecular sieve (10 mg) and N-ethyl-N-isopropylpropan-2-amine (108 mg, 835 μmol, 145 μL) in DMF (1 mL) was added 3-methylpiperidin-3-ol (50.7 mg, 334 μmol, HCl). The mixture was stirred at 40° C. for 12 hours. After completion, the mixture was purified by prep-HPLC (column: Phenomenex Luna C18 150×25 mm×10 μm; mobile phase: [water (0.225% FA)-ACN]; B %: 25%-55%, 10 min) to afford the title compound (21.2 mg, 23% yield) as white solid. $^1$H NMR (400 MHz, DMSO-$d_6$) δ=7.76 (d, J=8.0 Hz, 1H), 7.70 (d, J=8.0 Hz, 1H), 7.49-7.42 (m, 1H), 7.41-7.36 (m, 1H), 7.36-7.31 (m, 1H), 7.30 (d, J=6.8 Hz, 1H), 4.02 (s, 2H), 3.75-3.68 (m, 1H), 3.65-3.59 (m, 2H), 3.54-3.45 (m, 4H), 3.27-3.18 (m, 2H), 3.16-2.97 (m, 6H), 2.80-2.70 (m, 2H), 1.99-1.71 (m, 7H), 1.71-1.47 (m, 5H), 1.18-1.05 (m, 6H); LCMS [ESI, M+H]: m/z 542.4.

Example 5

7-(8-ethylnaphthalen-1-yl)-2-((hexahydro-1H-pyrrolizin-7a-yl)methoxy)-N-(pyridin-3-yl)-5,6,7,8-tetrahydropyrido[3,4-d]pyrimidin-4-amine

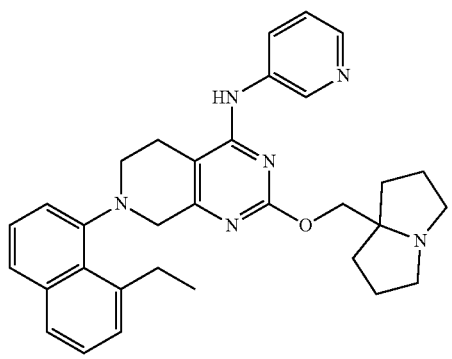 [SMILES: CCc1cccc2cccc(N3CCc4c(nc(OCC56CCCN5CCC6)nc4Nc4cccnc4)C3)c12]

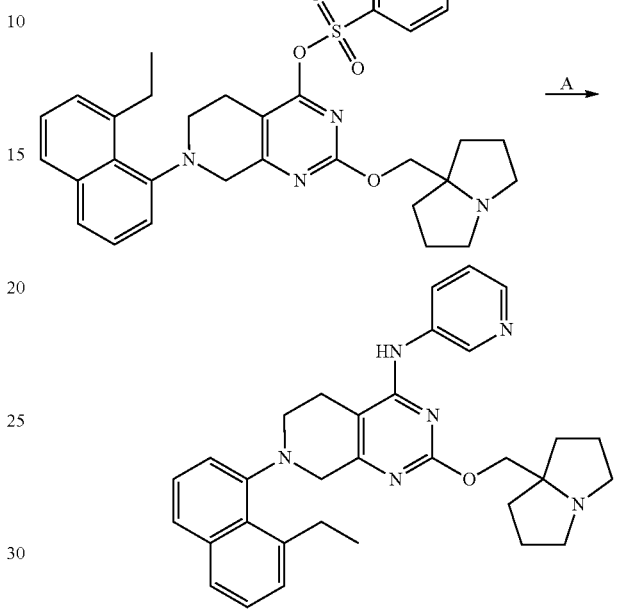

Step A. 7-(8-ethylnaphthalen-1-yl)-2-((hexahydro-1H-pyrrolizin-7a-yl)methoxy)-N-(pyridin-3-yl)-5,6,7,8-tetrahydropyrido[3,4-d]pyrimidin-4-amine: A mixture of 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (80.0 mg, 134 μmol), pyridin-3-amine (50.3 mg, 534 μmol, 28.7 μL), BINAP (16.6 mg, 26.7 μmol), Pd(OAc)$_2$ (3.00 mg, 13.4 μmol) and Cs$_2$CO$_3$ (87.1 mg, 267 μmol) in toluene (1 mL) was degassed and purged with N$_2$ for 3 times. The mixture was stirred at 110° C. for 2 hours under N$_2$ atmosphere. The reaction mixture was quenched with water (10 mL) and extracted with EtOAc (5 mL×3). The combined organic layers were washed with brine (5 mL) and dried over Na$_2$SO$_4$. The mixture was filtered and concentrated under reduced pressure to give a residue. The residue was purified by prep-HPLC twice (column: 3_Phenomenex Luna C18 75×30 mm×3 μm; mobile phase: [water (0.2% FA)-ACN]; B %: 20%-50%, 8 min. column: Phenomenex Gemini-NX 80×30 mm×3 μm; mobile phase: [water (10 mM NH$_4$HCO$_3$)-ACN]; B %: 35%-85%, 10 min) to afford the title compound (5.56 mg, 52% yield) as a yellow solid. $^1$H NMR (400 MHz, CDCl$_3$) δ=8.72 (s, 1H), 8.35 (br d, J=4.9 Hz, 2H), 7.69 (dd, J=8.0, 14.8 Hz, 2H), 7.40 (td, J=7.7, 17.7 Hz, 3H), 7.29 (br d, J=4.8 Hz, 2H), 7.31-7.27 (m, 1H), 6.45 (s, 1H), 4.21-4.09 (m, 3H), 3.85 (br d, J=17.4 Hz, 1H), 3.64 (br s, 1H), 3.47-3.33 (m, 2H), 3.22-3.10 (m, 3H), 2.99-2.88 (m, 1H), 2.71-2.54 (m, 3H), 2.11-2.03 (m, 2H), 1.91-1.82 (m, 5H), 1.69-1.62 (m, 1H), 1.13 (t, J=7.3 Hz, 3H). LCMS (ESI, M+1): m/z 521.3.

General Procedure for Example 6 to 14

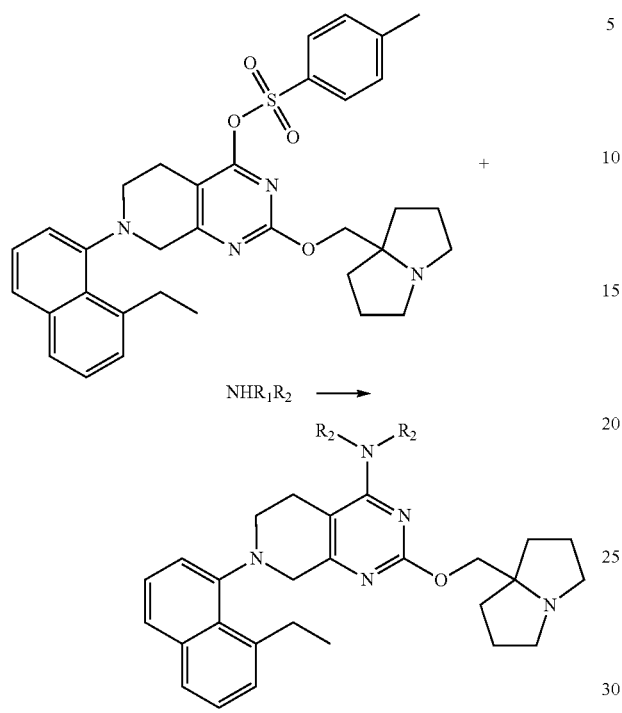

A mixture of 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (1 equiv.), amine (2 equiv.), and N-ethyl-N-isopropylpropan-2-amine (3 equiv. or 5/7 equiv. for amine hydro/dihydro chlorides) in DMSO (1 mL) was heated with stirring at 40° C. for 16 hours. The resulting solution was cooled to room temperature and subjected to HPLC purification (deionized water/HPLC-grade methanol, ammonia) to give the product.

Example 6

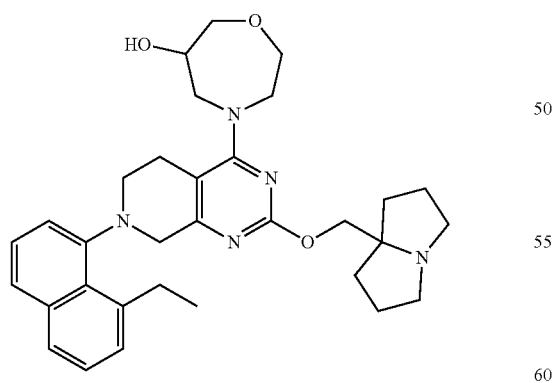

4-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)-1,4-oxazepan-6-ol LCMS (ESI, M+1): m/z 544.2

Example 7

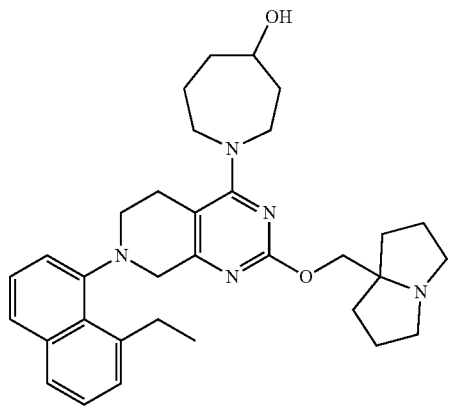 [SMILES: CCc1cccc2cccc(N3CCc4c(nc(OCC56CCCN5CCC6)nc4N4CCCC(O)CC4)C3)c12]

1-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)azepan-4-ol LCMS (ESI, M+1): m/z 542.2

Example 8

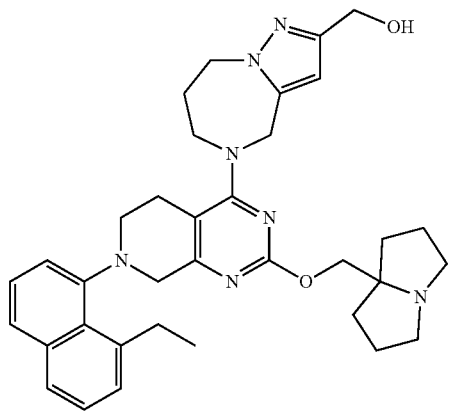 [SMILES: CCc1cccc2cccc(N3CCc4c(nc(OCC56CCCN5CCC6)nc4N4CCCn5nc(CO)cc5C4)C3)c12]

(5-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)-5,6,7,8-tetrahydro-4H-pyrazolo[1,5-a][1,4]diazepin-2-yl)methanol LCMS (ESI, M+1): m/z 594.2

Example 9

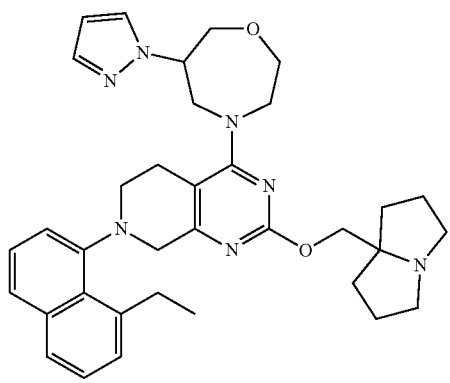 [SMILES: CCc1cccc2cccc(N3CCc4c(nc(OCC56CCCN5CCC6)nc4N4CCOCC(n5cccn5)C4)C3)c12]

4-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-6-(1H-pyrazol-1-yl)-1,4-oxazepane LCMS (ESI, M+1): m/z 594.4

Example 10

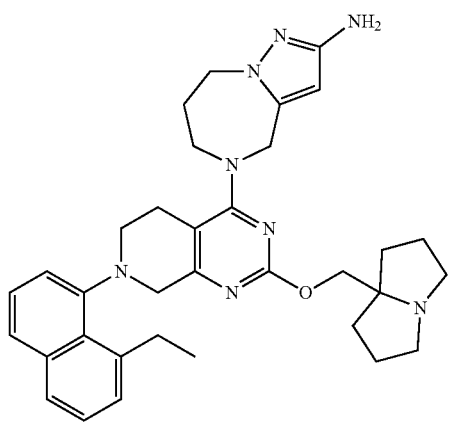 [SMILES: CCc1cccc2cccc(N3CCc4c(nc(OCC56CCCN5CCC6)nc4N4CCCn5nc(N)cc5C4)C3)c12]

5-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-5,6,7,8-tetrahydro-4H-pyrazolo[1,5-a][1,4]diazepin-2-amine LCMS (ESI, M+1): m/z 579.4

Example 11

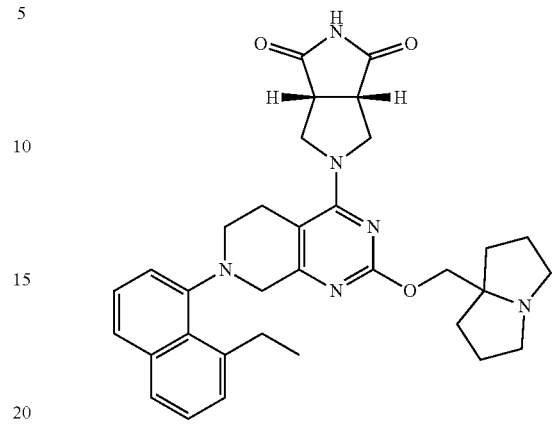

(3aR,6aS)-5-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)tetrahydropyrrolo[3,4-c]pyrrole-1,3(2H,3aH)-dione LCMS (ESI, M+1): m/z 567.4

Example 12

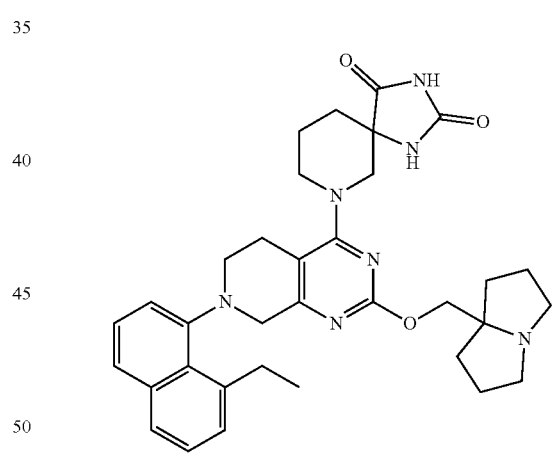

7-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-1,3,7-triazaspiro[4.5]decane-2,4-dione LCMS (ESI, M+1): m/z 596.2

Example 13

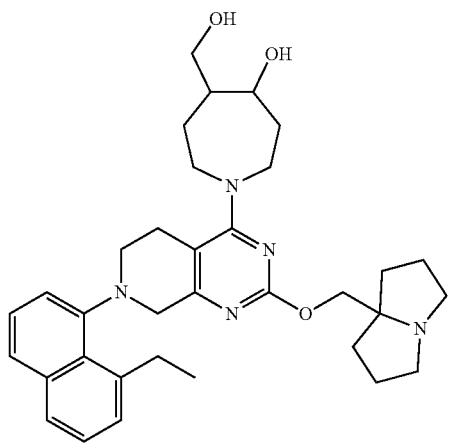 [SMILES: CCc1cccc2cccc(N3CCc4c(nc(OCC56CCCN5CCC6)nc4N4CCC(O)C(CO)CC4)C3)c12]

1-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)-5-(hydroxymethyl)azepan-4-ol LCMS (ESI, M+1): m/z 572.4

Example 14

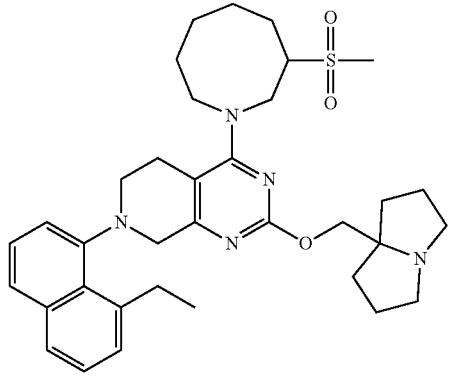 [SMILES: CCc1cccc2cccc(N3CCc4c(nc(OCC56CCCN5CCC6)nc4N4CCCCCC(S(C)(=O)=O)C4)C3)c12]

7-(8-ethylnaphthalen-1-yl)-4-(3-(methylsulfonyl)azocan-1-yl)-2-((tetrahydro-1H-pyrrolizin-7a(5H)-yl)methoxy)-5,6,7,8-tetrahydropyrido[3,4-d]pyrimidine LCMS (ESI, M+1): m/z 618.4

Example 15

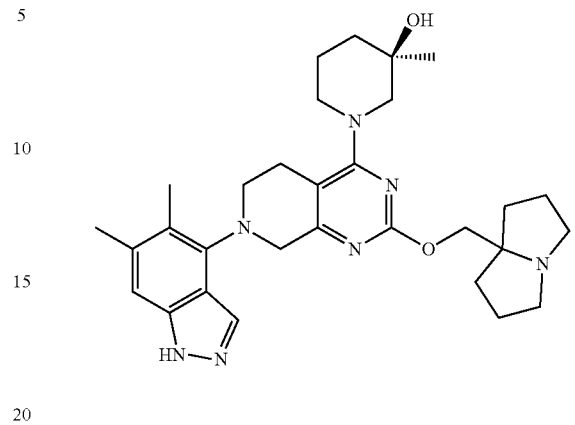

(R)-1-(7-(5,6-dimethyl-1H-indazol-4-yl)-2-((hexahydro-1H-pyrrolizin-7a-yl)methoxy)-5,6,7,8-tetrahydropyrido[3,4-d]pyrimidin-4-yl)-3-methylpiperidin-3-ol

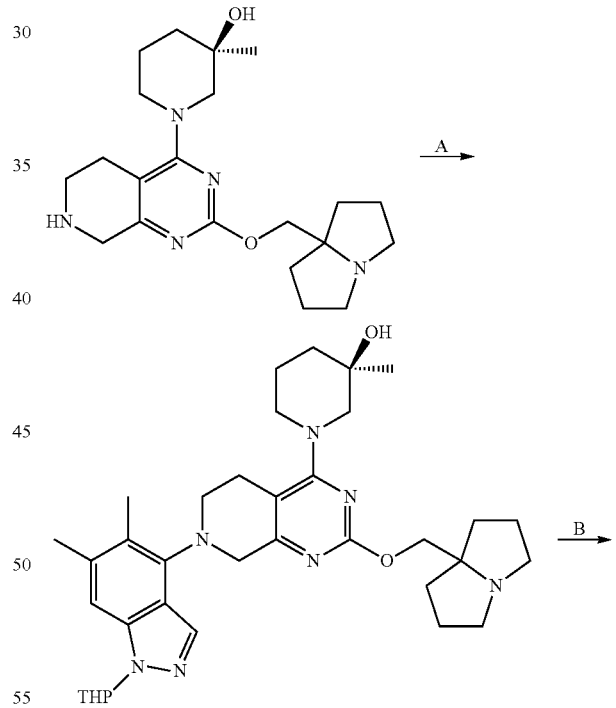

117
-continued

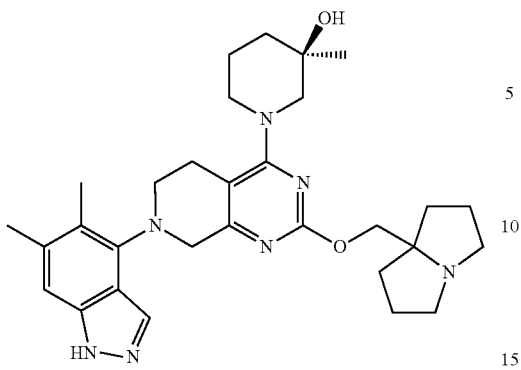

Step A. (3R)-1-(7-(5,6-dimethyl-1-(tetrahydro-2H-pyran-2-yl)-1H-indazol-4-yl)-2-((tetrahydro-1H-pyrrolizin-7a(5H)-yl)methoxy)-5,6,7,8-tetrahydropyrido[3,4-d]pyrimidin-4-yl)-3-methylpiperidin-3-ol: A mixture of (R)-3-methyl-1-(2-((tetrahydro-1H-pyrrolizin-7a(5H)-yl)methoxy)-5,6,7,8-tetrahydropyrido[3,4-d]pyrimidin-4-yl)piperidin-3-ol (100 mg, 1 equiv), 4-bromo-5,6-dimethyl-1-tetrahydropyran-2-yl-indazole (95.8 mg, 1.2 equiv), $Cs_2CO_3$ (252 mg, 3 equiv), RuPhos (48.2 mg, 0.4 equiv), $Pd_2(dba)_3$ (47.3 mg, 0.2 equiv) and 4 Å molecular sieve (10 mg) in toluene (2 mL) was degassed and purged with $N_2$ for 3 times, and then the reaction was stirred at 90° C. for 8 hours under $N_2$ atmosphere. The mixture was filtered and concentrated under vacuum to give a residue. The residue was purified by reversed phase flash chromatography [water (0.10% FA)/acetonitrile]. The desired fractions were collected, neutralized with solid $NaHCO_3$, and concentrated under vacuum to remove acetonitrile. The aqueous layer was extracted with ethyl acetate (2×10 mL). The combined organic layers were dried over anhydrous sodium sulfate and concentrated under vacuum to afford the title compound (90 mg, 56.3% yield) as a white solid. LCMS (ESI, M+1): m/z=616.5.

Step B. ((R)-1-(7-(5,6-dimethyl-1H-indazol-4-yl)-2-((hexahydro-1H-pyrrolizin-7a-yl)methoxy)-5,6,7,8-tetrahydropyrido[3,4-d]pyrimidin-4-yl)-3-methylpiperidin-3-ol: To a solution of (3R)-1-(7-(5,6-dimethyl-1-(tetrahydro-2H-pyran-2-yl)-1H-indazol-4-yl)-2-((tetrahydro-1H-pyrrolizin-7a(5H)-yl)methoxy)-5,6,7,8-tetrahydropyrido[3,4-d]pyrimidin-4-yl)-3-methylpiperidin-3-ol (85 mg, 138 µmol, 1.0 equiv) in DCM (0.5 mL) was added TFA (770 mg, 6.75 mmol, 0.5 mL). The reaction was stirred at 25° C. for 1 hour. The mixture was added dropwise to ice saturated $NaHCO_3$ solution (30 mL) and the pH was adjusted to 8. Then the mixture was extracted with dichloromethane (20 mL). The organic layer was washed with brine (20 mL), dried over anhydrous sodium sulfate, filtered, and concentrated to give a residue. The residue was purified by prep-HPLC [column: Unisil 3-100 C18 Ultra 150×50 mm×3 µm; A: water (FA); B: ACN, B %: 6%-36% over 10 min] to afford the title compound (35.7 mg, 47.9% yield, 98.5% purity) as white solid. $^1$H NMR (400 MHz, Acetic) δ=8.24 (s, 1H), 8.12 (s, 1H), 7.35 (s, 1H), 4.85-4.73 (m, 2H), 4.48-4.22 (m, 4H), 3.90-3.78 (m, 2H), 3.63-3.51 (m, 3H), 3.49-3.36 (m, 1H), 3.27 (td, J=6.2, 11.9 Hz, 2H), 3.20-2.82 (m, 2H), 2.46-2.42 (m, 3H), 2.42-2.35 (m, 5H), 2.29-2.19 (m, 4H), 2.16-2.09 (m, 3H), 1.97-1.89 (m, 1H), 1.83-1.70 (m, 2H), 1.36 (s, 3H); LCMS (ESI, M+1): m/z=532.4.

118
Example 16

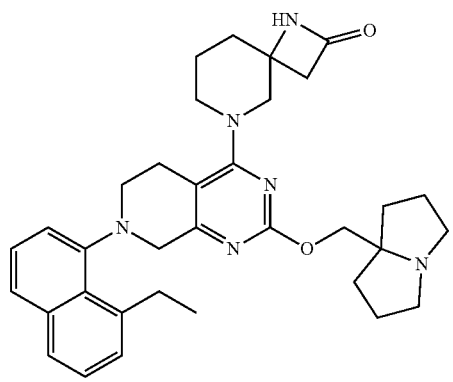 [SMILES: CCc1cccc2cccc(N3CCc4c(nc(OCC56CCCN5CCC6)nc4N4CCCC5(CC(=O)N5)C4)C3)c12]

6-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-1,6-diazaspiro[3.5]nonan-2-one

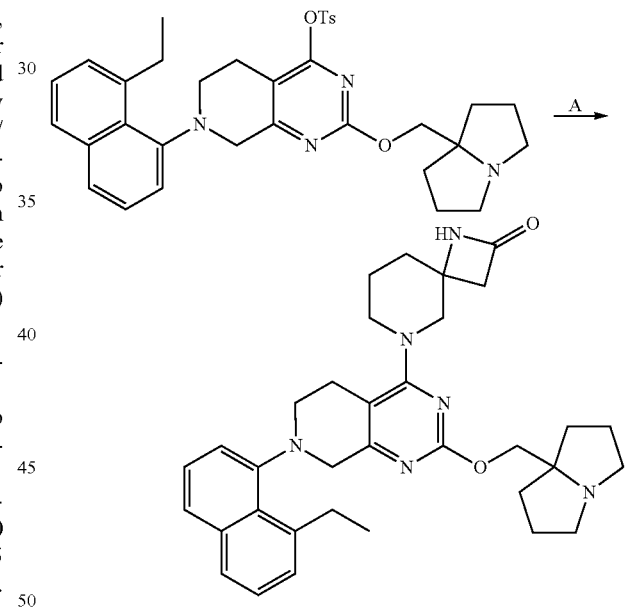

Step A. 6-(7-(8-ethylnaphthalen-1-yl)-2-((hexahydro-H-pyrrolizin-7a-yl)methoxy)-5,6,7,8-tetrahydropyrido[3,4-d]pyrimidin-4-yl)-1,6-diazaspiro[3.5]nonan-2-one: To the mixture of 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (100 mg, 1.0 equiv), 1,6-diazaspiro[3.5]nonan-2-one (32.8 mg, 1.4 equiv) in DMF (1.0 mL) was added N-ethyl-N-isopropylpropan-2-amine (108 mg, 5.0 equiv). The reaction was stirred at 30° C. for 12 hours. The mixture was filtered and purified with prep-HPLC [column: Phenomenex Synergi C18 150×25 mm×10 µm; mobile phase: water (0.225% FA)-ACN; B %: 19%-49%, 10 min] and lyophilized to afford the title compound (53.8 mg, 55% yield) as white solid. $^1$H NMR (400 MHz, methanol-$d_4$): δ=8.53 (s, 1H), 7.74-7.65 (m, 2H), 7.46-7.40 (m, 1H), 7.38-7.27 (m, 3H), 4.45-4.33 (m, 2H), 4.11 (br d, J=18 Hz, 1H), 3.93-3.80 (m, 1H), 3.71-3.66 (m, 1H), 3.65-3.47 (m, 6H), 3.16-3.09 (m, 1H), 3.28-3.08 (m, 1H), 3.07-2.98 (m, 1H), 2.87 (d, J=14.8 Hz, 1H), 2.90-2.65 (m, 1H), 2.26-2.18 (m, 2H), 2.17-2.03 (m, 4H), 1.97 (dt, J=6.8, 12.4 Hz, 4H), 1.90 (br d, J=3.2 Hz, 2H), 1.15 (t, J=7.2 Hz, 3H); LCMS (ESI, M+1): m/z=567.4

Example 17

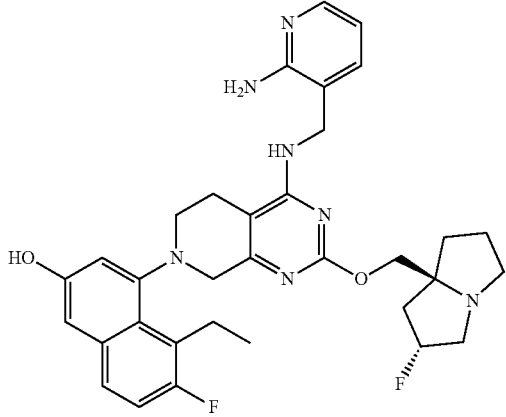 [SMILES: CCc1c(F)ccc2cc(O)cc(N3CCc4c(nc(OC[C@@]56CCCN5C[C@H](F)C6)nc4NCc4cccnc4N)C3)c12]

4-(4-(((2-aminopyridin-3-yl)methyl)amino)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol

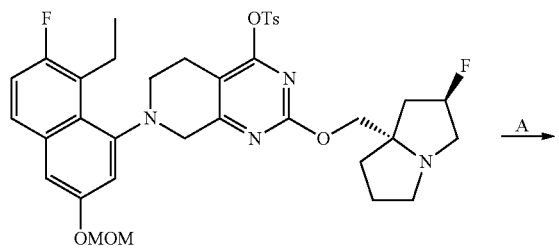

→ A

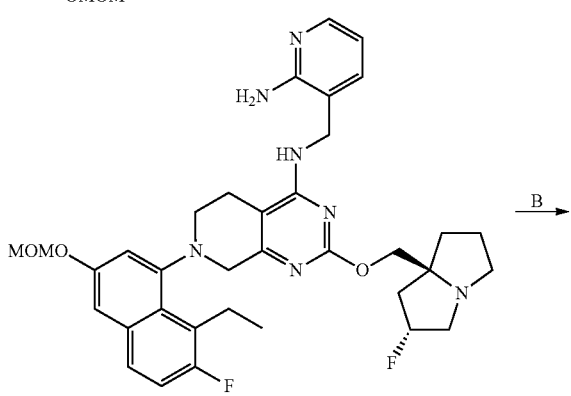

→ B

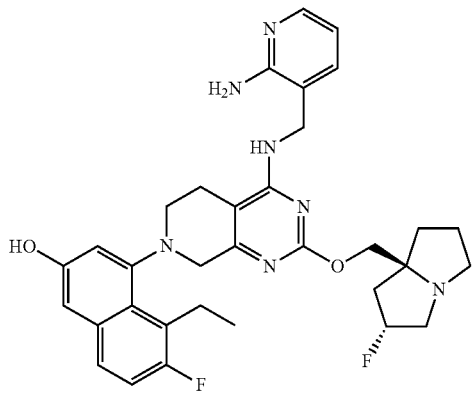

Step A. N-((2-aminopyridin-3-yl)methyl)-7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-amine: To the mixture of 7-(8-ethyl-7-fluoro-3-(methoxymethoxy)naphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl 4-methylbenzenesulfonate (120 mg, 1.0 equiv), 4A molecular sieve (10 mg) and N-ethyl-N-isopropylpropan-2-amine (112 mg, 5.0 equiv) in DMAc (2.0 mL) was added 3-(aminomethyl)pyridin-2-amine (31.9 mg, 1.50 equiv). The mixture was stirred at 40° C. until the reaction was completed. The mixture was quenched with water (5 mL) and extracted with ethyl acetate (3×5 mL). The combined organic layers were dried over anhydrous sodium sulfate, concentrated, and purified by reversed phase flash chromatography [C18, 0.1% formic acid condition] to afford the title compound (40 mg, 36% yield) as yellow solid. LCMS (ESI, M+1): m/z=646.4.

Step B. 4-(4-(((2-aminopyridin-3-yl)methyl)amino)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol: To the solution of N-((2-aminopyridin-3-yl)methyl)-7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-amine (35.0 mg, 1.0 equiv) in DCM (1 mL) was added TFA (1.54 g). The mixture was stirred at 20° C. for 0.5 hour. The mixture was treated with saturated NaHCO₃ aqueous solution to adjust pH to ~8 at 0° C. and extracted with dichloromethane (3×5 mL). The organic layer was dried over anhydrous sodium sulfate, concentrated, and purified by prep-HPLC [column: Phenomenex Gemini-NX C18 75×30 mm×3 μm; mobile phase: water (0.225% FA)-ACN; B %: 18%-28%, 7 min] to afford the title compound (6.19 mg, 19% yield) as yellow solid. ¹H NMR (400 MHz, methanol-d4) δ=8.50 (br s, 1H), 7.87 (dd, J=1.6, 5.2 Hz, 1H), 7.55-7.44 (m, 2H), 7.14 (t, J=9.6 Hz, 1H), 7.02 (d, J=2.4 Hz, 1H), 6.97 (d, J=2.4 Hz, 1H), 6.67 (dd, J=5.2, 7.2 Hz, 1H), 5.54-5.25 (m, 1H), 4.68-4.48 (m, 2H), 4.36-4.15 (m, 2H), 3.90 (br d, J=17.2 Hz, 1H), 3.68 (br d, J=16.8 Hz, 1H), 3.61-3.45 (m, 4H), 3.33 (br s, 2H), 3.26-3.11 (m, 2H), 2.90-2.75 (m, 1H), 2.55 (br d, J=14.4 Hz, 1H), 2.49-2.27 (m, 2H), 2.25-2.06 (m, 3H), 2.05-1.89 (m, 1H), 1.04 (dt, J=1.6, 7.2 Hz, 3H); LCMS (ESI, M+1): m/z=602.3.

Example 18

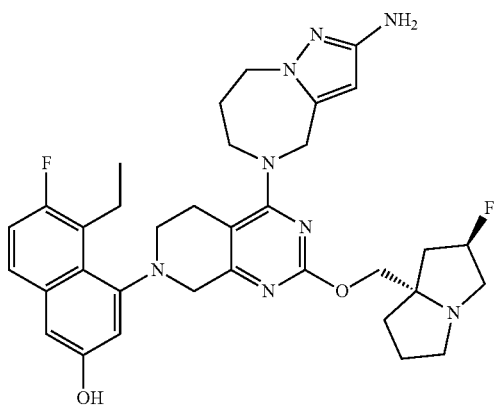 [SMILES: CCc1c(F)ccc2cc(O)cc(N3CCc4c(nc(OC[C@@]56CCCN5C[C@H](F)C6)nc4N4CCCn5nc(N)cc5C4)C3)c12]

4-(4-(2-amino-7,8-dihydro-4H-pyrazolo[1,5-a][1,4]
diazepin-5(6H)-yl)-2-(((2R,7aS)-2-fluorohexahydro-
1H-pyrrolizin-7a-yl)methoxy)-5,6-dihydropyrido[3,
4-d]pyrimidin-7(8H)-yl)-5-ethyl-6-fluoronaphthalen-
2-ol Synthesized according to Example 17. The title compound was obtained as white solid. $^1$H NMR (400 MHz, methanol-d4) δ=7.42 (dd, J=6.0, 9.2 Hz, 1H), 7.05 (t, J=9.2 Hz, 1H), 6.91-6.78 (m, 2H), 5.46 (d, J=2.4 Hz, 1H), 5.26-5.07 (m, 1H), 4.69 (s, 1H), 4.62-4.55 (m, 1H), 4.17-4.09 (m, 2H), 4.03 (dd, J=3.6, 7.2 Hz, 1H), 4.01-3.92 (m, 3H), 3.91-3.83 (m, 1H), 3.62 (dd, J=3.6, 18.0 Hz, 1H), 3.43-3.37 (m, 1H), 3.36-3.27 (m, 2H), 3.16-3.01 (m, 5H), 2.95-2.85 (m, 1H), 2.60 (br d, J=14.4 Hz, 1H), 2.20-2.03 (m, 3H), 2.01-1.91 (m, 2H), 1.90-1.71 (m, 3H), 1.07-0.99 (m, 3H); LCMS (ESI, M+1): m/z=631.4.

Example 19

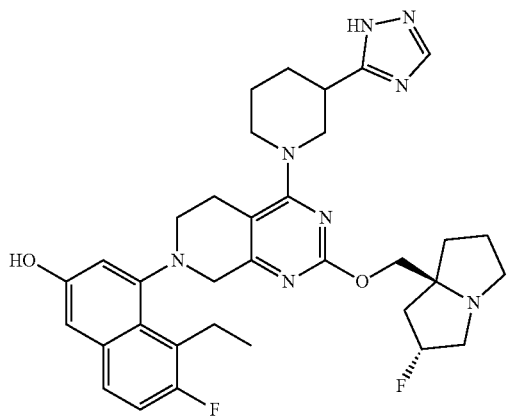 [SMILES: CCc1c(F)ccc2cc(O)cc(N3CCc4c(nc(OC[C@@]56CCCN5C[C@H](F)C6)nc4N4CCCC(c5ncn[nH]5)C4)C3)c12]

4-(4-(3-(1H-1,2,4-triazol-5-yl)piperidin-1-yl)-2-
(((2R,7aS)-2-fluorotetrahydro-1H-pyrrolizin-7a(5H)-
yl)methoxy)-5,8-dihydropyrido[3,4-d]pyrimidin-7
(6H)-yl)-5-ethyl-6-fluoronaphthalen-2-ol Synthesized according to Example 17. The title compound was obtained as yellow solid (TFA). $^1$H NMR (400 MHz, methanol-d4): δ 8.36 (s, 1H), 7.53 (dd, J=5.6, 9.2 Hz, 1H), 7.16 (t, J=9.2 Hz, 1H), 7.05-6.97 (m, 2H), 5.66-5.43 (m, 1H), 4.73-4.53 (m, 3H), 4.38-4.22 (m, 1H), 4.21-4.08 (m, 1H), 4.00-3.83 (m, 3H), 3.82-3.67 (m, 1H), 3.58-3.36 (m, 6H), 3.27-3.12 (m, 3H), 2.80-2.53 (m, 3H), 2.46-2.24 (m, 4H), 2.21-1.69 (m, 4H), 1.12 (t, J=7.2 Hz, 3H); LCMS (ESI, M+1): m/z=631.4.

Example 20

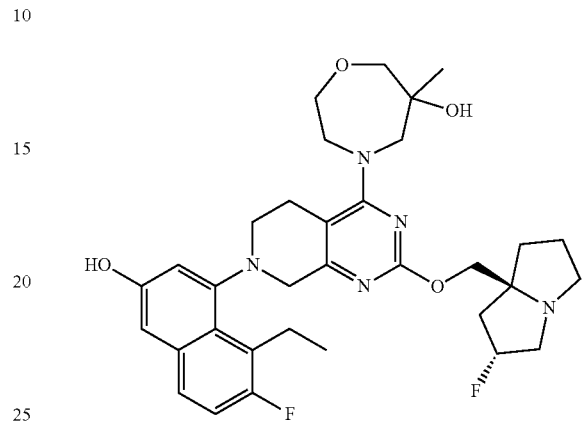

4-(7-(8-ethyl-7-fluoro-3-hydroxynaphthalen-1-yl)-2-
(((2R,7aS)-2-fluorohexahydro-1H-pyrrolizin-7a-yl)
methoxy)-5,6,7,8-tetrahydropyrido[3,4-d]pyrimidin-
4-yl)-6-methyl-1,4-oxazepan-6-ol Synthesized according to Example 17. The title compound was obtained as blue solid. $^1$H NMR (400 MHz, methanol-d4) δ=8.51 (s, 1H), 7.56-7.45 (m, 1H), 7.19-7.08 (m, 1H), 7.05-6.89 (m, 2H), 5.46-5.27 (m, 1H), 4.37-3.91 (m, 6H), 3.90-3.68 (m, 3H), 3.67-3.51 (m, 3H), 3.50-3.35 (m, 6H), 3.26-3.07 (m, 3H), 2.82-2.58 (m, 1H), 2.47-2.25 (m, 2H), 2.23-2.03 (m, 3H), 2.00-1.86 (m, 1H), 1.19 (s, 3H), 1.09 (t, J=7.2 Hz, 3H); LCMS (ESI, M+1): m/z=610.3.

Example 21

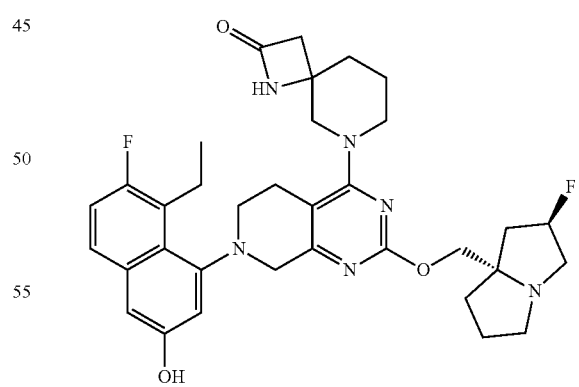

6-(7-(8-ethyl-7-fluoro-3-hydroxynaphthalen-1-yl)-2-
(((2R,7aS)-2-fluorohexahydro-1H-pyrrolizin-7a-yl)
methoxy)-5,6,7,8-tetrahydropyrido[3,4-d]pyrimidin-
4-yl)-1,6-diazaspiro[3.5]nonan-2-one Synthesized according to Example 17. The title compound was obtained as white solid. $^1$H NMR (400 MHz, methanol-d₄) δ=7.51 (dd, J=5.6, 8.8 Hz, 1H), 7.14 (t, J=9.6 Hz, 1H), 7.02-6.94 (m, 2H), 5.35-5.17 (m, 1H), 4.20-4.08 (m, 2H), 4.08-3.84 (m, 2H), 3.83-3.57 (m, 3H), 3.56-3.36 (m, 4H), 3.23-3.13 (m, 5H), 3.04-2.92 (m, 1H), 2.88-2.64 (m, 3H), 2.30-2.03 (m, 3H), 2.02-1.88 (m, 5H), 1.87-1.78 (m, 2H), 1.11 (t, J=7.2 Hz, 3H); LCMS (ESI, M+1): m/z=619.3

Example 22

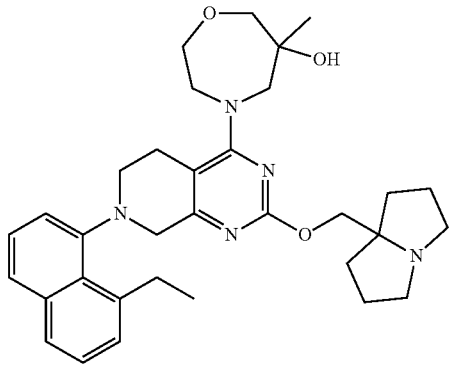 [SMILES: CCc1cccc2cccc(N3CCc4c(nc(OCC56CCCN5CCC6)nc4N4CCOCC(C)(O)C4)C3)c12]

4-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-6-methyl-1,4-oxazepan-6-ol

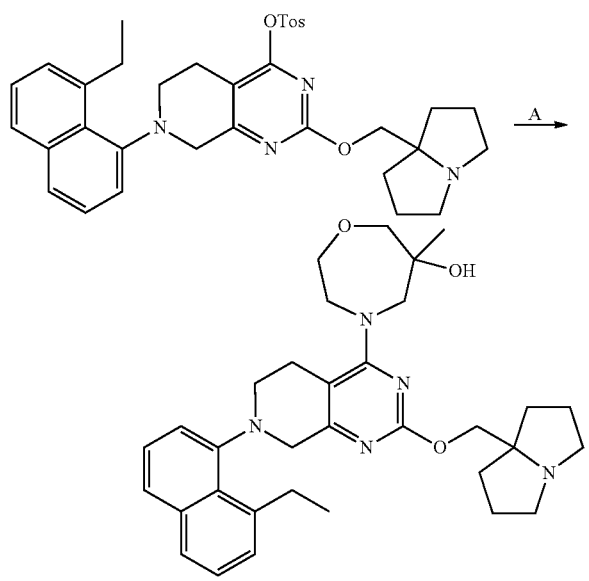

Step A 4-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-6-methyl-1,4-oxazepan-6-ol: A mixture of 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (60 mg, 1.0 equiv), 6-methyl-1,4-oxazepan-6-ol (20 mg, 1.5 equiv), N-ethyl-N-isopropylpropan-2-amine (53 μL, 3.0 equiv) and 4 Å MS (20 mg) in DMF (0.8 mL) was stirred at 40° C. for 15 hours. The reaction mixture was diluted with water (20 mL), and extracted with ethyl acetate (20 mL×4). The combined organic layers were dried over anhydrous sodium sulfate, concentrated, and purified with prep-HPLC [column: Phenomenex Luna C18 150×25 mm×10 μm; mobile phase: water (0.225% FA)-ACN; B %: 20%-50%, 2 min] to afford the title compound (46.5 mg, 77% yield) as yellow solid. ¹H NMR (400 MHz, methanol-d4) δ=7.73-7.63 (m, 2H), 7.46-7.25 (m, 4H), 4.40-4.32 (m, 2H), 4.24-3.98 (m, 3H), 3.96-3.75 (m, 3H), 3.73-3.58 (m, 3H), 3.57-3.42 (m, 5H), 3.28-3.19 (m, 2H), 3.17-2.97 (m, 3H), 2.82-2.60 (m, 1H), 2.26-2.04 (m, 6H), 2.03-1.94 (m, 2H), 1.20 (s, 3H), 1.14 (t, J=7.2 Hz, 3H). LCMS (ESI, M+1): m/z=558.4.

Example 23

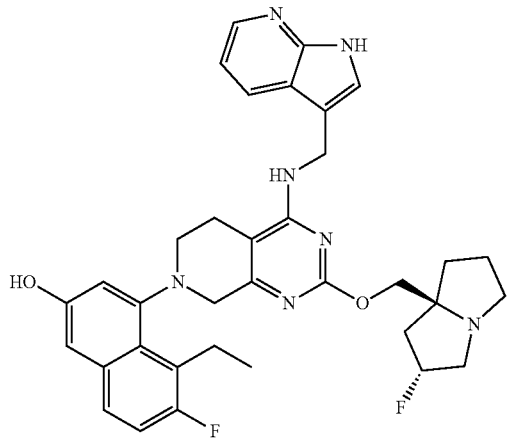 [SMILES: CCc1c(F)ccc2cc(O)cc(N3CCc4c(nc(OC[C@@]56CCCN5C[C@H](F)C6)nc4NCc4c[nH]c5ncccc45)C3)c12]

4-(4-(((1H-pyrrolo[2,3-b]pyridin-3-yl)methyl)amino)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol

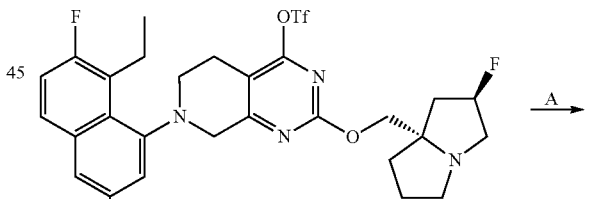

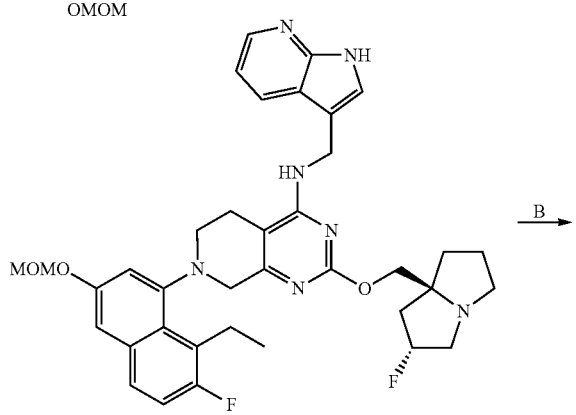

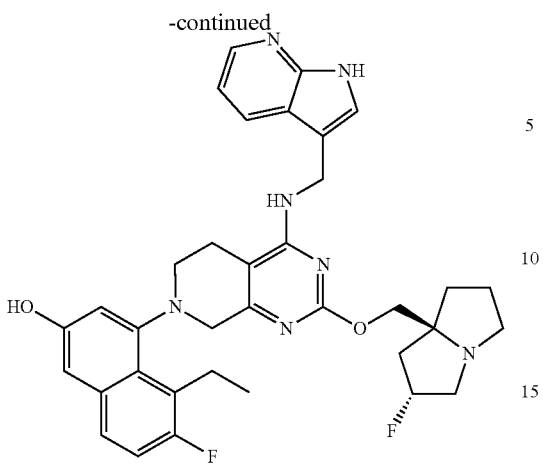

Example 24

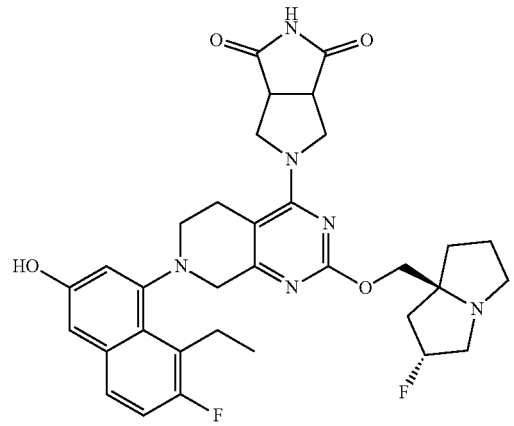 [SMILES: CCc1c(F)ccc2cc(O)cc(N3CCc4c(nc(OC[C@@]56CCCN5C[C@H](F)C6)nc4N4CC5C(=O)NC(=O)C5C4)C3)c12]

5-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)tetrahydropyrrolo[3,4-c]pyrrole-1,3(2H,3aH)-dione Step A. N-((1H-pyrrolo[2,3-b]pyridin-3-yl)methyl)-7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-amine: To a mixture of 7-(8-ethyl-7-fluoro-3-(methoxymethoxy)naphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl trifluoromethanesulfonate (30.0 mg, 1.0 equiv), 4A molecular sieve (10.0 mg) and N-ethyl-N-isopropylpropan-2-amine (28.8 mg, 5.0 equiv) in DMAc (1.0 mL) was added 1H-pyrrolo[2,3-b]pyridin-3-ylmethanamine (13.1 mg, 2.0 equiv). The mixture was stirred at 40° C. until the reaction was completed. The mixture was diluted with water (5 mL) and extracted with ethyl acetate (3×5 mL). The combined organic layers were dried over anhydrous sodium sulfate, concentrated, and purified by reversed phase flash chromatography [C18, 0.1% formic acid condition] to afford the title compound (30 mg, crude) as yellow solid. LCMS (ESI, M+1): m/z=670.4.

Synthesized according to Example 23. The title compound was obtained as white solid. $^1$H NMR (400 MHz, CDCl$_3$) δ=8.38 (s, 1H), 7.47-7.37 (m, 1H), 7.09 (t, J=8.8 Hz, 1H), 6.93 (dd, J=2.0, 8.4 Hz, 1H), 6.75 (d, J=1.2 Hz, 1H), 5.53-5.26 (m, 1H), 4.65-4.52 (m, 1H), 4.52-4.11 (m, 4H), 3.94-3.63 (m, 3H), 3.52-3.41 (m, 1H), 3.40-3.24 (m, 6H), 3.22-3.08 (m, 2H), 3.06-2.87 (m, 1H), 2.82-2.48 (m, 2H), 2.47-2.19 (m, 4H), 2.17-2.08 (m, 2H), 1.05 (t, J=7.2 Hz, 3H); LCMS (ESI, M+1): m/z=619.4.

Step B. 4-(4-(((1H-pyrrolo[2,3-b]pyridin-3-yl)methyl)amino)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol: To the mixture of N-((1H-pyrrolo[2,3-b]pyridin-3-yl)methyl)-7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-amine (20.0 mg, 1.0 equiv) in MeOH (1.0 mL) was added HCl·MeOH (4 M, 1.5 mL). The mixture was stirred at 0° C. for 1 hour. After completion, the mixture was treated with saturated NaHCO$_3$ aqueous solution to adjust pH to ~8 at 0° C. and extracted with dichloromethane (3×5 mL). The combined organic layers were dried over anhydrous sodium sulfate, concentrated, and purified by prep-HPLC [column: Phenomenex Luna C18 150×25 mm×10 μm; mobile phase: water (0.225% FA)-ACN; B %: 16%-46%, 10 min] to afford the title compound (5.20 mg, two steps 28% yield) as off-white solid. $^1$H NMR (400 MHz, methanol-d$_4$) δ=8.51 (s, 1H), 8.19 (dd, J=1.6, 4.8 Hz, 1H), 8.11 (dd, J=1.6, 8.0 Hz, 1H), 7.50 (dd, J=6.0, 9.2 Hz, 1H), 7.41 (s, 1H), 7.17-7.08 (m, 2H), 7.00 (d, J=2.4 Hz, 1H), 6.96 (d, J=2.4 Hz, 1H), 5.47-5.26 (m, 1H), 4.98-4.89 (m, 2H), 4.37-4.28 (m, 1H), 4.27-4.19 (m, 1H), 3.88 (br d, J=17.2 Hz, 1H), 3.66 (br d, J=16.8 Hz, 1H), 3.59-3.43 (m, 4H), 3.35 (br s, 1H), 3.29-3.24 (m, 1H), 3.21-3.11 (m, 1H), 2.86-2.71 (m, 2H), 2.55-2.27 (m, 3H), 2.26-1.84 (m, 5H), 1.02 (dt, J=2.0, 7.2 Hz, 3H); LCMS (ESI, M+1): m/z=626.4.

Example 25

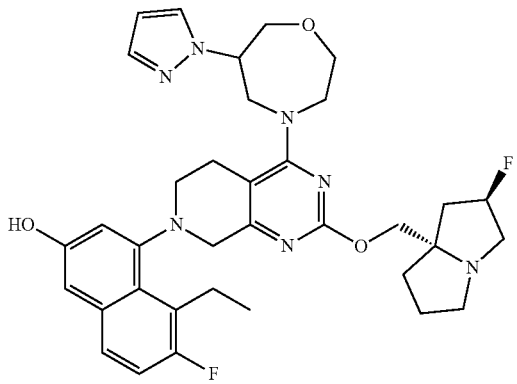 [SMILES: CCc1c(F)ccc2cc(O)cc(N3CCc4c(nc(OC[C@@]56CCCN5C[C@H](F)C6)nc4N4CCOCC(n5cccn5)C4)C3)c12]

4-(4-(6-(1H-pyrazol-1-yl)-1,4-oxazepan-4-yl)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol Synthesized according to Example 23. The title compound was obtained as yellow solid. $^1$H NMR (400 MHz, methanol-d4) δ=7.86-7.78 (m, 1H), 7.58-7.46 (m, 2H), 7.15

(t, J=9.2 Hz, 1H), 7.03-6.93 (m, 2H), 6.39-6.27 (m, 1H), 5.41-5.22 (m, 1H), 5.19-4.67 (m, 1H), 4.64-4.44 (m, 1H), 4.40-4.26 (m, 1H), 4.24-4.05 (m, 5H), 4.05-3.58 (m, 6H), 3.57-3.47 (m, 1H), 3.44-3.32 (m, 3H), 3.26-3.13 (m, 3H), 3.07-3.00 (m, 1H), 2.80-2.63 (m, 1H), 2.43-2.17 (m, 2H), 2.16-2.07 (m, 1H), 2.04-1.95 (m, 2H), 1.94-1.80 (m, 1H), 1.10 (t, J=7.2 Hz, 3H); LCMS (ESI, M+1): m/z=646.2.

Example 26

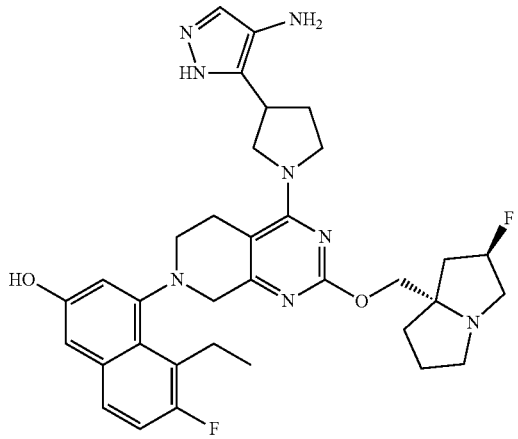 [SMILES: CCc1c(F)ccc2cc(O)cc(N3CCc4c(nc(OC[C@@]56CCCN5C[C@H](F)C6)nc4N4CCC(c5[nH]ncc5N)C4)C3)c12]

4-(4-(3-(4-amino-1H-pyrazol-5-yl)pyrrolidin-1-yl)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol Synthesized according to Example 23. The title compound was obtained as yellow solid. $^1$H NMR (400 MHz, methanol-d4) δ=7.54-7.46 (m, 1H), 7.26-7.18 (m, 1H), 7.16-7.09 (m, 1H), 7.04-6.92 (m, 2H), 5.48-5.19 (m, 1H), 4.32-4.12 (m, 3H), 4.10-3.79 (m, 4H), 3.73-3.55 (m, 2H), 3.54-3.32 (m, 7H), 3.21-3.07 (m, 2H), 3.06-2.93 (m, 1H), 2.42-2.12 (m, 5H), 2.08-1.99 (m, 2H), 1.97-1.86 (m, 1H), 1.15-1.04 (m, 3H); LCMS (ESI, M+1): m/z=631.2.

Example 27

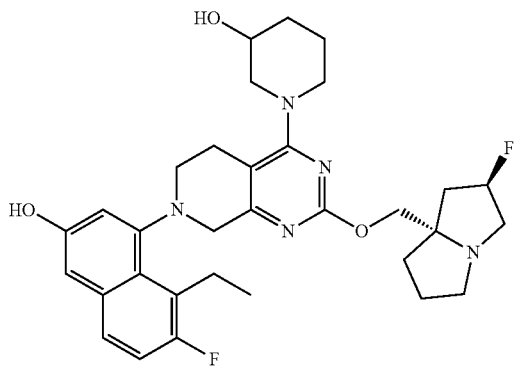 [SMILES: CCc1c(F)ccc2cc(O)cc(N3CCc4c(nc(OC[C@@]56CCCN5C[C@H](F)C6)nc4N4CCCC(O)C4)C3)c12]

1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)piperidin-3-ol

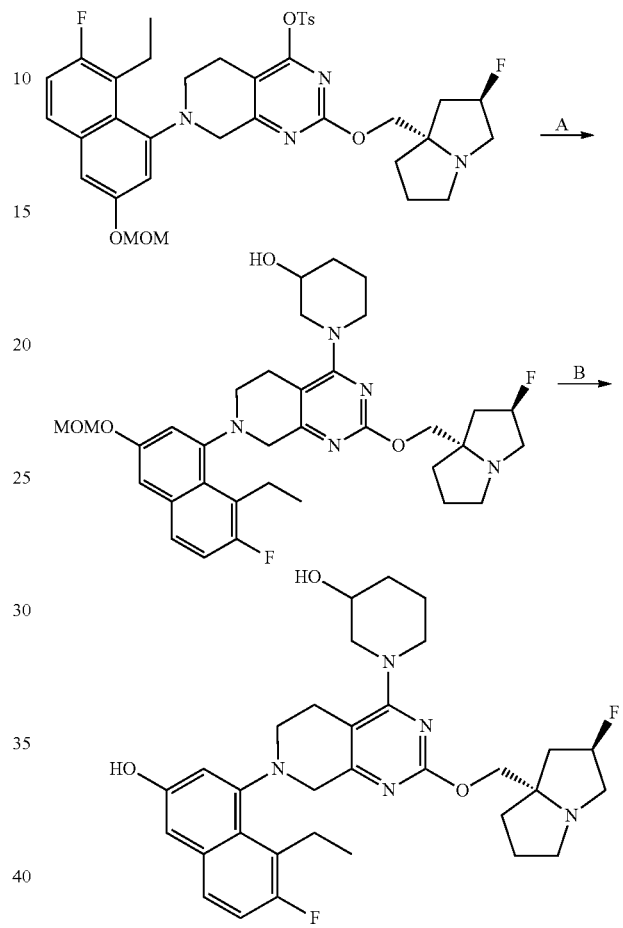

Step A. 1-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)piperidin-3-ol: To a mixture of 7-(8-ethyl-7-fluoro-3-(methoxymethoxy)naphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl 4-methylbenzenesulfonate (150 mg, 1.0 equiv) and 4 Å MS (60 mg) in DMF (2.0 mL) were added N-ethyl-N-isopropylpropan-2-amine (112 mg, 4.0 equiv) and piperidin-3-ol (59.4 mg, 2 equiv, HCl). The mixture was stirred at 40° C. until the reaction was completed. The mixture was filtered, concentrated, and purified with reversed phase flash chromatography [C18, 0.1% FA in water, 0-40% ACN] to afford the title compound (80.0 mg, 58% yield) as yellow solid. LCMS (ESI, M+1): m/z=624.4.

Step B. 1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)piperidin-3-ol: To a solution of 1-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)piperidin-3-ol (70.0 mg, 1.0 equiv) in DCM (1.0 mL) and MeOH (1.0 mL) was added TsOH (58.0 mg, 3.0 equiv). The mixture was stirred at 10° C. for 12 hours. The pH of reaction mixture was adjusted to 8 with saturated NaHCO₃ solution. The mixture was extracted with ethyl acetate (3×5 mL). The combined organic layers were dried over anhydrous sodium sulfate, concentrated, and purified with reversed phase flash chromatography [column: Waters Xbridge 150×25 mm×5 μm; mobile phase: [water (10 mM NH₄HCO₃)-ACN]; B %: 35%-65%, 9 min] to afford the title compound (37.7 mg, 57% yield) as white solid. ¹H NMR (400 MHz, methanol-d4) δ=7.51 (dd, J=6.0, 9.2 Hz, 1H), 7.14 (t, J=9.6 Hz, 1H), 7.03-6.90 (m, 2H), 5.37-5.16 (m, 1H), 4.21-3.98 (m, 4H), 3.95-3.84 (m, 1H), 3.82-3.57 (m, 2H), 3.54-3.35 (m, 3H), 3.29-2.94 (m, 8H), 2.73-2.59 (m, 1H), 2.34-2.13 (m, 2H), 2.12-2.01 (m, 2H), 2.00-1.80 (m, 4H), 1.79-1.50 (m, 2H), 1.11 (t, J=7.2 Hz, 3H); LCMS (ESI, M+1): m/z=580.3.

Example 28

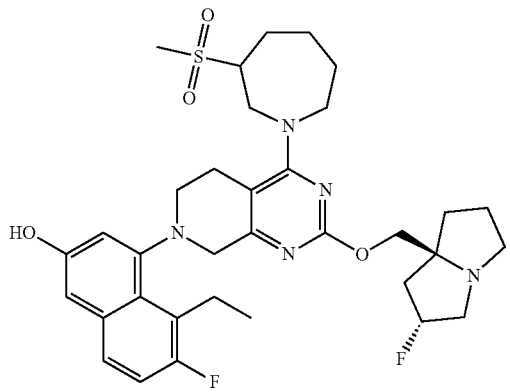 [SMILES: CCc1c(F)ccc2cc(O)cc(N3CCc4c(nc(OC[C@@]56CCCN5C[C@H](F)C6)nc4N4CCCCC(S(C)(=O)=O)C4)C3)c12]

5-ethyl-6-fluoro-4-(2-(((2R,7aS)-2-fluorohexahydro-1H-pyrrolizin-7a-yl)methoxy)-4-(3-(methylsulfonyl)azepan-1-yl)-5,6-dihydropyrido[3,4-d]pyrimidin-7(8H)-yl)naphthalen-2-ol

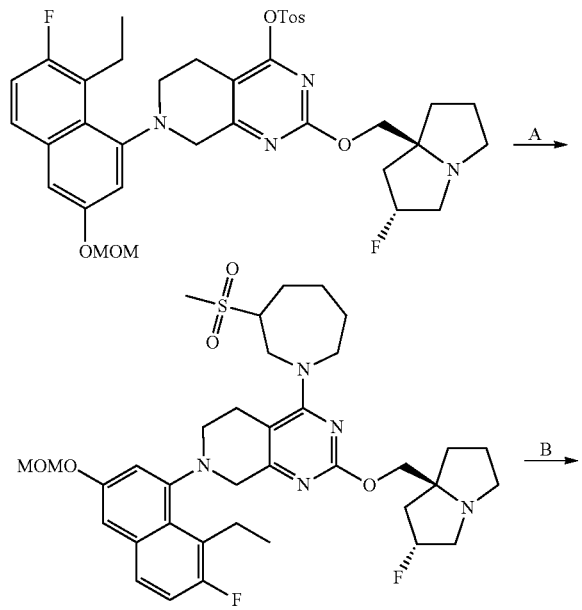

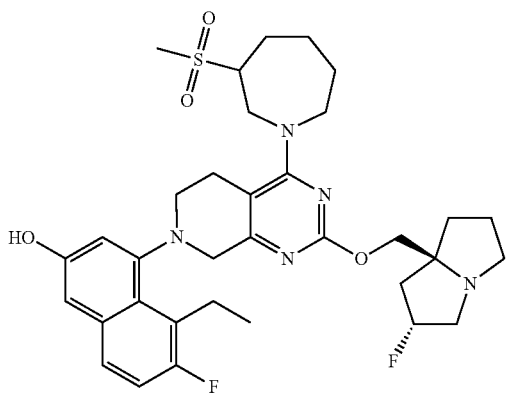

Step A. 7-(8-ethyl-7-fluoro-3-(methoxymethoxy) naphthalen-1-yl)-2-(((2R,7aS)-2-fluorohexahydro-1H-pyrrolizin-7a-yl) methoxy)-4-(3-(methylsulfonyl) azepan-1-yl)-5,6,7,8-tetrahydropyrido[3,4-d]pyrimidine: To a mixture of 7-(8-ethyl-7-fluoro-3-(methoxymethoxy) naphthalen-1-yl)-2-(((2R,7aS)-2-fluorohexahydro-1H-pyrrolizin-7a-yl) methoxy)-5,6,7,8-tetrahydropyrido[3,4-d]pyrimidin-4-yl 4-methylbenzenesulfonate (85 mg, 1 equiv) and 3-(methylsulfonyl) azepane (36.6 mg, 1.4 equiv, HCl) in DMF (1.5 mL) were added 4 Å MS (100 mg) and N-ethyl-N-isopropylpropan-2-amine (79.1 mg, 106 μL, 5.0 equiv). The mixture was stirred at 40° C. until the reaction was completed. The mixture was filtered and purified with HPLC (0.1% FA condition) to afford the title compound (80 mg, 93% yield) as yellow solid. LCMS (ESI, M+1): m/z=700.2.

Step B. 5-ethyl-6-fluoro-4-(2-(((2R,7aS)-2-fluorohexahydro-1H-pyrrolizin-7a-yl)methoxy)-4-(3-(methylsulfonyl)azepan-1-yl)-5,6-dihydropyrido[3,4-d]pyrimidin-7(8H)-yl)naphthalen-2-ol: To a mixture of 7-(8-ethyl-7-fluoro-3-(methoxymethoxy)naphthalen-1-yl)-2-(((2R,7aS)-2-fluorohexahydro-1H-pyrrolizin-7a-yl)methoxy)-4-(3-(methylsulfonyl)azepan-1-yl)-5,6,7,8-tetrahydropyrido[3,4-d]pyrimidine (78 mg, 1 equiv) and ACN (0.5 mL) was added HCl·MeOH (4 M, 279 μL, 10 equiv). The mixture was stirred at 0° C. for 1 hour. The mixture was concentrated under reduced pressure to give a residue. H₂O (10 mL) was added, and the pH of the mixture was adjusted to 8 with solid Na₂CO₃. The mixture was extracted with ethyl acetate (10 mL×3). The combined organic layers were washed with brine (20 mL), dried over anhydrous sodium sulfate, concentrated, and purified by prep-HPLC [column: Phenomenex Gemini-NX C18 75×30 mm×3 μm; mobile phase: water (10 mM NH₄HCO₃)-ACN; B %: 35%-65%, 8 minutes] to give the title compound (30 mg, 40% yield) as white solid. ¹H NMR (400 MHz, CD₃OD) δ 7.54-7.47 (m, 1H), 7.18-7.11 (t, J=9.6 Hz, 1H), 7.03-6.92 (m, 2H), 5.36-5.17 (d, J=963.6 Hz, 1H), 4.78-4.60 (m, 1H), 4.24-4.09 (m, 2H), 4.08-3.97 (m, 2H), 3.96-3.83 (m, 1H), 3.80-3.58 (m, 3H), 3.54-3.45 (m, 1H), 3.42-3.33 (m, 2H), 3.29-3.08 (m, 5H), 3.03-3.00 (m, 3H), 3.00-2.94 (m, 1H), 2.83-2.67 (m, 1H), 2.38-2.03 (m, 5H), 2.00-1.77 (m, 6H), 1.61-1.35 (m, 1H), 1.14-1.06 (m, 3H); LCMS (ESI, M+1): m/z=656.2.

Example 29

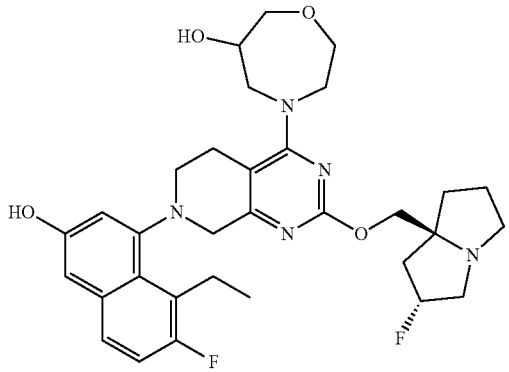 [SMILES: CCc1c(F)ccc2cc(O)cc(N3CCc4c(nc(OC[C@@]56CCCN5C[C@H](F)C6)nc4N4CCOCC(O)C4)C3)c12]

4-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,4-oxazepan-6-ol Synthesized according to Example 28. The title compound was obtained as off-white solid (TFA). $^1$H NMR (400 MHz, methanol-d4) δ=7.53 (dd, J=6.0, 9.2 Hz, 1H), 7.16 (t, J=9.2 Hz, 1H), 7.05-6.98 (m, 2H), 5.65-5.46 (m, 1H), 4.65-4.52 (m, 2H), 4.33-3.71 (m, 14H), 3.69-3.50 (m, 2H), 3.48-3.35 (m, 3H), 3.25-3.14 (m, 1H), 2.98-2.74 (m, 1H), 2.74-2.51 (m, 2H), 2.44-2.27 (m, 3H), 2.24-2.12 (m, 1H), 1.11 (br t, J=7.2 Hz, 3H); LCMS (ESI, M+1, M/2+1): m/z=596.3.

Example 30

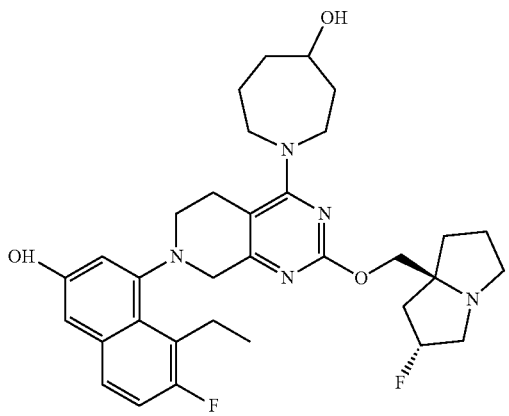 [SMILES: CCc1c(F)ccc2cc(O)cc(N3CCc4c(nc(OC[C@@]56CCCN5C[C@H](F)C6)nc4N4CCCC(O)CC4)C3)c12]

1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)azepan-4-ol Synthesized according to Example 28. The title compound was obtained as white solid. $^1$H NMR (400 MHz, methanol-d4) δ 7.50 (dd, J=5.6, 8.8 Hz, 1H), 7.14 (t, J=9.2 Hz, 1H), 7.01-6.93 (m, 2H), 5.35-5.18 (m, 1H), 4.19-3.98 (m, 3H), 3.96-3.73 (m, 4H), 3.70-3.58 (m, 2H), 3.48 (br d, J=3.2 Hz, 1H), 3.44-3.35 (m, 2H), 3.27-3.09 (m, 5H), 2.98 (m, 1H), 2.79-2.71 (m, 1H), 2.32-1.58 (m, 12H), 1.11 (br t, J=6.8 Hz, 3H); $^{19}$F NMR (400 MHz, methanol-d4) δ=−123.076, −173.617; LCMS (ESI, M+1): m/z=594.3.

Example 31

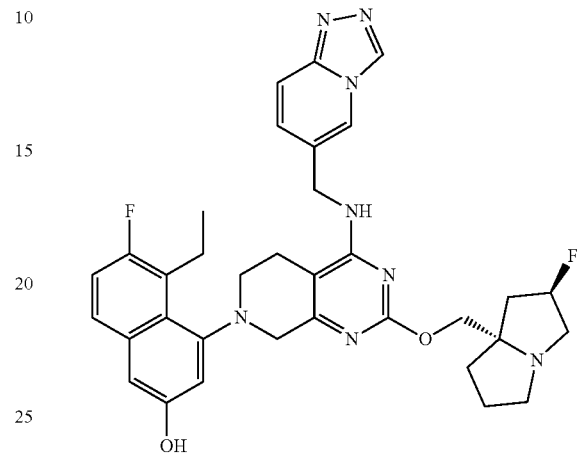

4-(4-(([1,2,4]triazolo[4,3-a]pyridin-6-ylmethyl)amino)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol Synthesized according to Example 28. The title compound was obtained as off-white solid. $^1$H NMR (400 MHz, methanol-d$_4$) δ=9.15 (s, 1H), 8.51 (s, 1H), 7.75 (d, J=9.6 Hz, 1H), 7.68-7.43 (m, 2H), 7.14 (t, J=9.6 Hz, 1H), 7.06-6.89 (m, 2H), 5.42-5.16 (m, 1H), 4.85-4.78 (m, 2H), 4.77-4.63 (m, 1H), 4.22-4.00 (m, 2H), 3.91 (br d, J=16.8 Hz, 1H), 3.67 (br d, J=16.8 Hz, 1H), 3.56 (br dd, J=5.6, 11.2 Hz, 1H), 3.34 (br dd, J=2.4, 4.0 Hz, 4H), 3.28 (br d, J=4.0 Hz, 1H), 3.06 (dt, J=5.2, 9.2 Hz, 1H), 2.85 (ddd, J=6.8, 10.0, 16.0 Hz, 1H), 2.58 (br d, J=15.6 Hz, 1H), 2.36-2.14 (m, 2H), 2.12-1.91 (m, 3H), 1.87-1.69 (m, 1H), 1.05 (dt, J=1.6, 7.2 Hz, 3H); LCMS (ESI, M+1): m/z=627.3.

Example 32

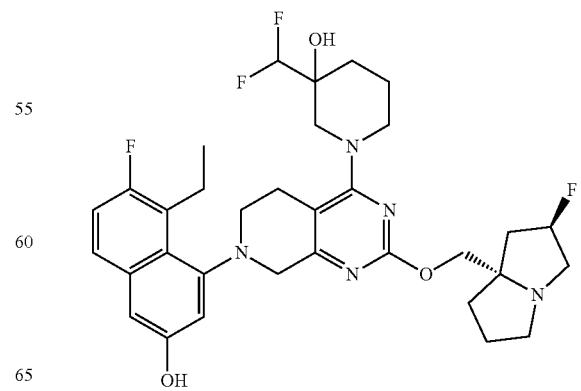

3-(difluoromethyl)-1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)piperidin-3-ol

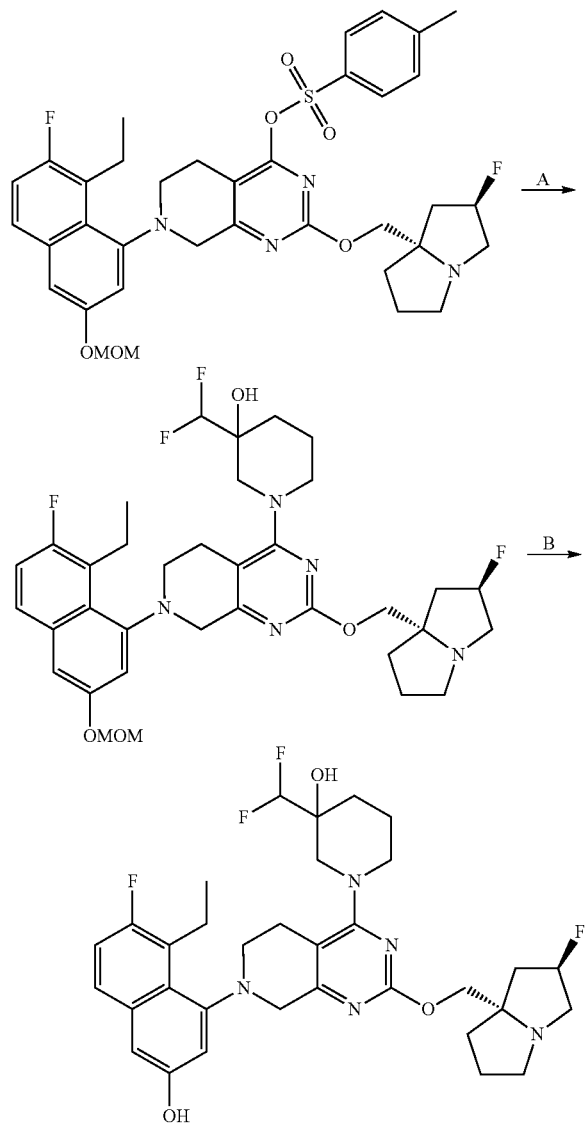

Step A. 3-(difluoromethyl)-1-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)piperidin-3-ol: To a mixture of 7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl 4-methylbenzenesulfonate (100 mg, 1.0 equiv), 3-(difluoromethyl)piperidin-3-ol (54.0 mg, 2.0 equiv, HCl) and 4 Å molecular sieve (20 mg) in DMF (1 mL) was added N-ethyl-N-isopropylpropan-2-amine (74.4 mg, 4.0 equiv). The reaction was stirred at 40-60° C. until the reaction was completed. The mixture was filtered and washed with DMF (1 mL). The reaction was purified with reversed phase flash chromatography [C18, 0.1% formic acid condition] to afford the title compound (85.0 mg, 86% yield) as white solid. LCMS (ESI, M+1): m/z=674.4.

Step B. 3-(difluoromethyl)-1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)piperidin-3-ol: To a solution of 3-(difluoromethyl)-1-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)piperidin-3-ol (80.0 mg, 1.0 equiv) in MeOH (1.5 mL) was added HCl·MeOH (4 M, 57.7 equiv). The mixture was stirred at 0° C. for 0.5 and then its pH was adjusted to 8 with saturated NaHCO₃ aqueous solution (3 mL). The mixture was extracted with EtOAc (3×5 mL). The combined organic layer was dried over anhydrous sodium sulfate, concentrated and purified with prep-HPLC [Phenomenex Synergi C18 150×25 mm×10 μm; A: water (0.225% FA), B: ACN; B %: 17%-47% over 10 min] and lyophilized to afford the title compound (44.1 mg, 59% yield) as off-white solid. ¹H NMR (400 MHz, methanol-d₄) δ=8.50 (s, 1H), 7.51 (dd, J=6.0, 9.2 Hz, 1H), 7.14 (t, J=9.6 Hz, 1H), 7.06-6.91 (m, 2H), 5.97-5.54 (m, 1H), 5.50-5.27 (m, 1H), 4.38-4.20 (m, 2H), 4.18-3.97 (m, 2H), 3.91-3.76 (m, 1H), 3.73-3.60 (m, 1H), 3.59-3.43 (m, 5H), 3.42-3.33 (m, 2H), 3.30-3.11 (m, 3H), 3.11-2.97 (m, 1H), 2.83-2.62 (m, 1H), 2.50-2.26 (m, 2H), 2.24-1.90 (m, 5H), 1.90-1.68 (m, 3H), 1.20-1.04 (m, 3H); LCMS (ESI, M+1): m/z=630.3.

Example 33

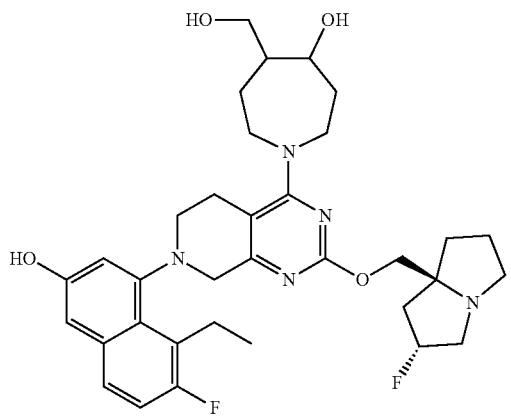 [SMILES: CCc1c(F)ccc2cc(O)cc(N3CCc4c(nc(OC[C@@]56CCCN5C[C@H](F)C6)nc4N4CCC(O)C(CO)CC4)C3)c12]

1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-5-(hydroxymethyl)azepan-4-ol Synthesized according to Example 28. The title compound was obtained as yellow solid. ¹H NMR (400 MHz, methanol-d4) δ 7.56-7.50 (m, 1H), 7.17 (t, J=9.2 Hz, 1H), 7.07-6.98 (m, 2H), 5.55 (d, J=51.6 Hz, 1H), 4.72-4.57 (m, 2H), 4.27-3.99 (m, 4H), 3.98-3.73 (m, 6H), 3.72-3.35 (m, 7H), 3.25-3.12 (m, 1H), 2.96-2.81 (m, 1H), 2.73-2.52 (m, 2H), 2.49-2.29 (m, 3H), 2.24-1.77 (m, 5H), 1.72-1.61 (m, 1H), 1.18-1.09 (m, 3H). LCMS (ESI, M+1, M/2+1): m/z=624.3.

Example 34

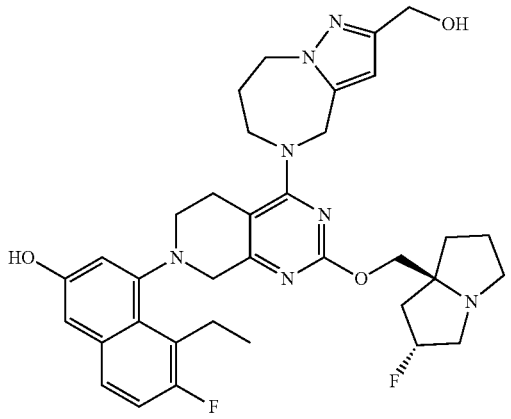 [SMILES: CCc1c(F)ccc2cc(O)cc(N3CCc4c(nc(OC[C@@]56CCCN5C[C@H](F)C6)nc4N4CCCn5nc(CO)cc5C4)C3)c12]

5-ethyl-6-fluoro-4-(2-(((2R,7aS)-2-fluorohexahydro-1H-pyrrolizin-7a-yl)methoxy)-4-(2-(hydroxymethyl)-7,8-dihydro-4H-pyrazolo[1,5-a][1,4]diazepin-5(6H)-yl)-5,6-dihydropyrido[3,4-d]pyrimidin-7(8H)-yl)naphthalen-2-ol Synthesized according to Example 28. The title compound was obtained as white solid. 1H NMR (400 MHz, methanol-d4) δ=7.51 (dd, J=5.6, 8.8 Hz, 1H), 7.18-7.12 (m, 1H), 6.96 (s, 2H), 6.26 (s, 1H), 5.35-5.17 (m, 1H), 4.95 (br d, J=6.0 Hz, 1H), 4.82-4.76 (m, 1H), 4.50 (s, 2H), 4.44 (br d, J=4.4 Hz, 2H), 4.23-4.14 (m, 1H), 4.12-3.92 (m, 4H), 3.72-3.64 (m, 1H), 3.56-3.47 (m, 1H), 3.45-3.39 (m, 2H), 3.26-3.12 (m, 5H), 3.03-2.94 (m, 1H), 2.78-2.69 (m, 1H), 2.32-2.18 (m, 2H), 2.16-2.02 (m, 3H), 2.00-1.81 (m, 3H), 1.18-1.08 (m, 3H); 19F NMR (400 MHz, methanol-d4) δ=−122.947, −173.640; SFC: >99% ee, Chiralpak AD-3 50×4.6 mm I.D., 3 μm column A: 60% MeOH+40% ACN (w/0.05% DEA), B: CO2, 3 mL/min, 220 nm, tR: 0.559 min; LCMS (ESI, M+1): m/z=646.4.

Example 35

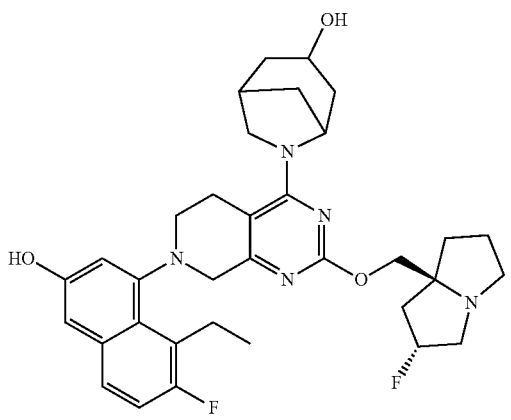 [SMILES: CCc1c(F)ccc2cc(O)cc(N3CCc4c(nc(OC[C@@]56CCCN5C[C@H](F)C6)nc4N4CC5CC(O)CC4C5)C3)c12]

6-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-6-azabicyclo[3.2.1]octan-3-ol Synthesized according to Example 23. The title compound was obtained as off-white solid. ¹H NMR (400 MHz, methanol-d4) δ=8.48 (s, 1H), 7.56-7.45 (m, 1H), 7.13 (t, J=9.2 Hz, 1H), 7.03-6.92 (m, 2H), 5.57-5.35 (m, 1H), 4.84-4.59 (m, 1H), 4.50-4.28 (m, 2H), 4.23-4.09 (m, 1H), 4.05-3.87 (m, 2H), 3.82-3.55 (m, 5H), 3.54-3.45 (m, 1H), 3.43-3.33 (m, 2H), 3.29-2.94 (m, 3H), 2.75-2.35 (m, 4H), 2.33-1.90 (m, 7H), 1.79-1.36 (m, 2H), 1.14-1.05 (m, 3H); LCMS (ESI, M+1): m/z=606.4.

Example 36

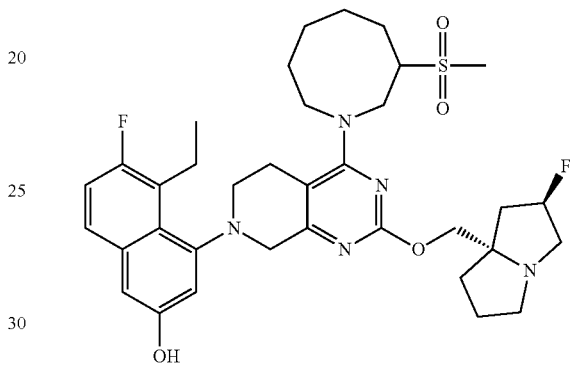

5-ethyl-6-fluoro-4-(2-(((2R,7aS)-2-fluorotetrahydro-1H-pyrrolizin-7a(5H)-yl)methoxy)-4-(3-(methylsulfonyl)azocan-1-yl)-5,8-dihydropyrido[3,4-d]pyrimidin-7(6H)-yl)naphthalen-2-ol Synthesized according to Example 23. The title compound was obtained as off-white solid. ¹H NMR (400 MHz, methanol-d4) δ=8.52 (s, 1H), 7.60-7.45 (m, 1H), 7.14 (t, J=9.2 Hz, 1H), 7.03-6.90 (m, 2H), 5.50-5.26 (m, 1H), 4.89-4.85 (m, 1H), 4.43-4.14 (m, 3H), 4.14-3.96 (m, 1H), 3.86-3.65 (m, 2H), 3.65-3.49 (m, 3H), 3.49-3.39 (m, 3H), 3.39-3.32 (m, 2H), 3.27-3.08 (m, 3H), 3.04-2.94 (m, 3H), 2.81-2.67 (m, 1H), 2.57-2.46 (m, 1H), 2.45-2.16 (m, 3H), 2.14-1.93 (m, 4H), 1.92-1.79 (m, 2H), 1.78-1.55 (m, 3H), 1.46-1.19 (m, 1H), 1.14-1.02 (m, 3H); LCMS (ESI, M+1): m/z=670.4.

Example 37

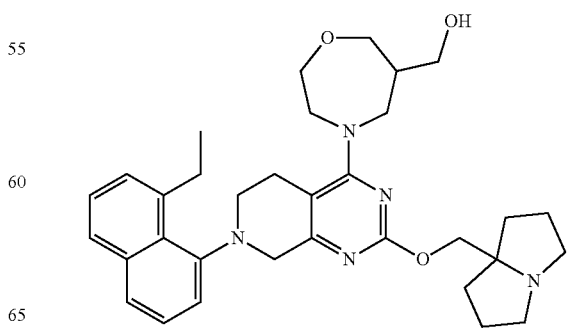

(4-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-1,4-oxazepan-6-yl)methanol

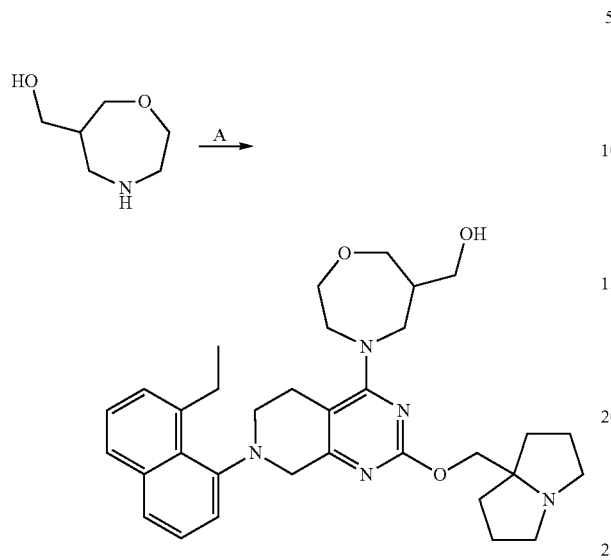

Step A. (4-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-1,4-oxazepan-6-yl)methanol: To a solution of 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (100 mg, 1.0 equiv), 1,4-oxazepan-6-ylmethanol (56.0 mg, 2.0 equiv, HCl) and 4 Å molecular sieve (10 mg) in DMF (1 mL) was added N-ethyl-N-isopropylpropan-2-amine (108 mg, 5.0 equiv). The reaction was stirred at 40° C. until the reaction was completed. The residue was filtered and washed with DMF (1 mL), and purified with prep-HPLC [Phenomenex Luna C18 150×25 mm×10 μm; A: water (FA), B: ACN; B %: 25%-55% over 7 min] to afford the title compound (14.1 mg, 14% yield) as yellow gum; $^1$H NMR (400 MHz, methanol-$d_4$) δ=7.74-7.64 (m, 2H), 7.43 (dt, J=5.6, 7.6 Hz, 1H), 7.39-7.29 (m, 2H), 7.29-7.21 (m, 1H), 4.57 (br s, 2H), 4.39-4.30 (m, 2H), 4.29-4.14 (m, 1H), 4.12-3.97 (m, 1H), 3.97-3.88 (m, 1H), 3.85-3.72 (m, 2H), 3.72-3.62 (m, 2H), 3.61-3.49 (m, 4H), 3.49-3.41 (m, 2H), 3.40-3.32 (m, 2H), 3.30-3.19 (m, 2H), 3.19-3.10 (m, 1H), 3.10-2.98 (m, 2H), 2.77 (br d, J=14.4 Hz, 1H), 2.56-2.34 (m, 1H), 2.24-2.16 (m, 2H), 2.15-2.07 (m, 2H), 2.06-1.97 (m, 2H), 1.97-1.90 (m, 1H), 1.24-1.03 (m, 3H); LCMS (ESI, M+1): m/z=558.5.

Example 38

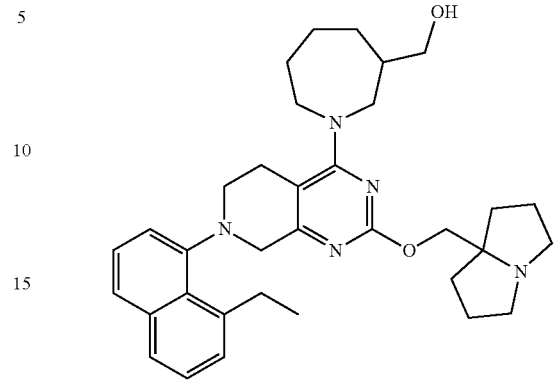

(1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)azepan-3-yl)methanol Synthesized according to Example 37. The title compound was obtained as yellow solid. $^1$H NMR (400 MHz, METHANOL-$d_4$) δ=7.77-7.58 (m, 2H), 7.46-7.37 (m, 1H), 7.37-7.20 (m, 3H), 4.48-4.23 (m, 1H), 4.22-4.13 (m, 2H), 4.12-4.02 (m, 1H), 4.02-3.74 (m, 1H), 3.70-3.57 (m, 2H), 3.56-3.40 (m, 4H), 3.25-3.12 (m, 4H), 3.11-2.98 (m, 1H), 2.86-2.63 (m, 3H), 2.40-2.12 (m, 1H), 2.10-1.99 (m, 3H), 1.98-1.81 (m, 6H), 1.80-1.61 (m, 4H), 1.50-1.32 (m, 2H), 1.21-1.05 (m, 3H); LCMS (ESI, M+1): m/z=556.3.

Example 39

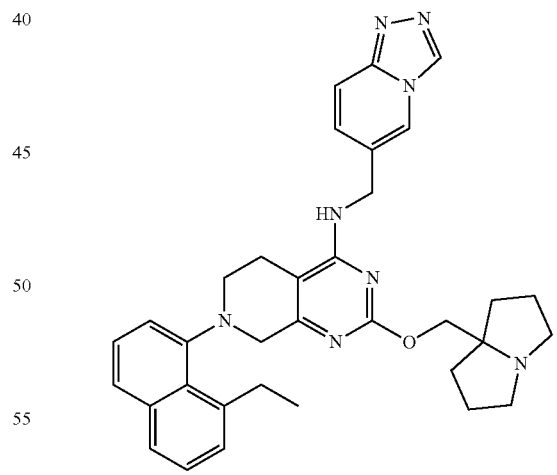

N-([1,2,4]triazolo[4,3-a]pyridin-6-ylmethyl)-7-(8-ethylnaphthalen-1-yl)-2-((hexahydro-1H-pyrrolizin-7a-yl)methoxy)-5,6,7,8-tetrahydropyrido[3,4-d]pyrimidin-4-amine Synthesized according to Example 37. The title compound was obtained as yellow solid. $^1$H NMR (400 MHz, METHANOL-$d_4$) δ=9.28 (s, 1H), 8.71 (s, 1H), 7.90 (d, J=9.6 Hz, 1H), 7.80 (dd, J=1.2, 9.6 Hz, 1H), 7.72 (dd, J=4.0, 7.2 Hz, 2H), 7.45 (t, J=7.6 Hz, 1H), 7.40-7.37 (m, 2H), 7.31 (d, J=6.4 Hz, 1H), 4.95 (t, J=15.2 Hz, 2H), 4.64 (q, J=11.6 Hz, 2H), 4.05 (d, J=17.6 Hz, 1H), 3.84 (d, J=17.6 Hz, 1H), 3.66-3.62 (m, 3H), 3.46-3.41 (m, 2H), 3.28-3.23 (m, 2H), 3.15-3.07 (m, 1H), 2.90-2.83 (m, 1H), 2.64 (br d, J=16.0 Hz, 1H), 2.28-2.09 (m, 8H), 1.11 (t, J=7.2 Hz, 3H); LCMS (ESI, M+1): m/z=575.4.

Example 40

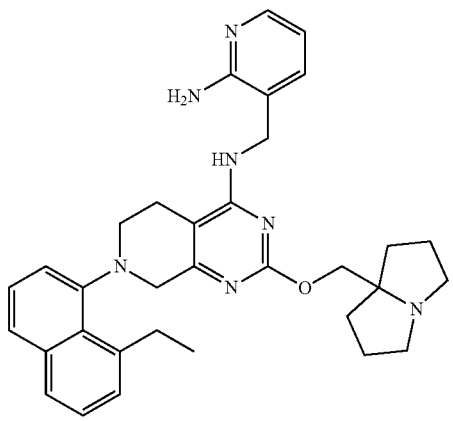 [SMILES: CCc1cccc2cccc(N3CCc4c(nc(OCC56CCCN5CCC6)nc4NCc4cccnc4N)C3)c12]

N-((2-aminopyridin-3-yl)methyl)-7-(8-ethylnaphthalen-1-yl)-2-((hexahydro-1H-pyrrolizin-7a-yl)methoxy)-5,6,7,8-tetrahydropyrido[3,4-d]pyrimidin-4-amine Synthesized according to Example 37. The title compound was obtained as white solid. $^1$H NMR (400 MHz, METHANOL-d$_4$) δ=7.87 (dd, J=1.6, 5.2 Hz, 1H), 7.69 (ddd, J=0.8, 8.0, 14.4 Hz, 2H), 7.52 (dd, J=1.6, 7.2 Hz, 1H), 7.43-7.41 (m, 1H), 7.37-7.35 (m, 2H), 7.33-7.28 (m, 1H), 6.67 (dd, J=5.2, 7.2 Hz, 1H), 4.58 (q, J=15.6 Hz, 2H), 4.39 (s, 2H), 3.92 (br d, J=17.2 Hz, 1H), 3.68 (br d, J=17.2 Hz, 1H), 3.60-3.55 (m, 4H), 3.37 (br dd, J=7.2, 11.2 Hz, 1H), 3.20 (td, J=6.0, 11.6 Hz, 2H), 3.05 (br dd, J=7.2, 13.2 Hz, 1H), 2.93-2.79 (m, 1H), 2.57 (br d, J=16.0 Hz, 1H), 2.21-2.01 (m, 8H), 1.09 (t, J=7.2 Hz, 3H); LCMS (ESI, M+1): m/z=550.4.

Example 41

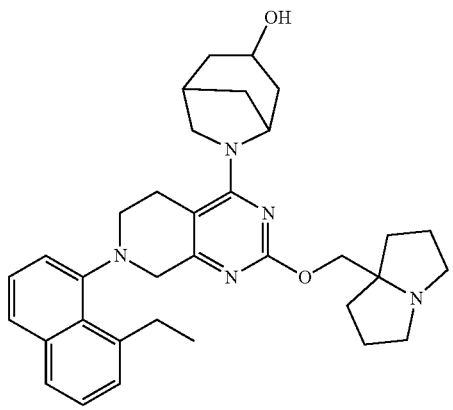 [SMILES: CCc1cccc2cccc(N3CCc4c(nc(OCC56CCCN5CCC6)nc4N4CC5CC(O)CC4C5)C3)c12]

6-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-6-azabicyclo[3.2.1]octan-3-ol Synthesized according to Example 37. The title compound was obtained as off-white solid (TFA); $^1$H NMR (400 MHz, METHANOL-d$_4$) δ=7.71-7.65 (m, 2H), 7.43-7.41 (m, 1H), 7.35-7.34 (m, 2H), 7.28-7.26 (m, 1H), 4.67-4.64 (m, 1H), 4.34-4.29 (m, 2H), 4.21-4.13 (m, 1H), 4.06-3.87 (m, 2H), 3.83-3.48 (m, 4H), 3.43-3.35 (m, 2H), 3.22-2.97 (m, 6H), 2.77-2.37 (m, 2H), 2.20-2.17 (m, 2H), 2.15-1.99 (m, 8H), 1.87-1.63 (m, 2H), 1.61-1.22 (m, 1H), 1.16-1.11 (m, 3H); LCMS (ESI, M+1): m/z=554.5.

Example 42

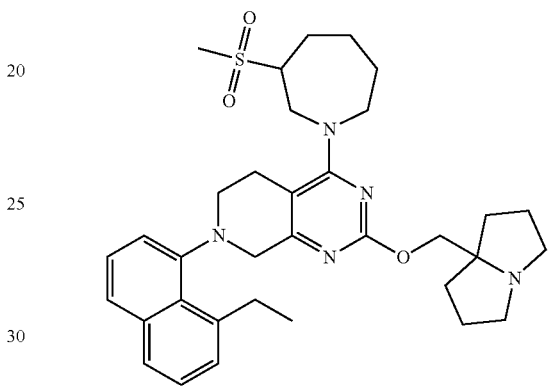

7-(8-ethylnaphthalen-1-yl)-2-((hexahydro-1H-pyrrolizin-7a-yl)methoxy)-4-(3-(methylsulfonyl)azepan-1-yl)-5,6,7,8-tetrahydropyrido[3,4-d]pyrimidine Synthesized according to Example 37. The title compound was obtained as off-white solid (0.44 equiv formic acid). 1H NMR (400 MHz, METHANOL-d$_4$): δ=7.73-7.63 (m, 2H), 7.46-7.25 (m, 4H), 4.70-4.62 (m, 1H), 4.42-4.26 (m, 2H), 4.12-3.94 (m, 2H), 3.91-3.43 (m, 6H), 3.38-3.32 (m, 2H), 3.29-3.08 (m, 2H), 3.08-2.91 (m, 6H), 2.86-2.71 (m, 1H), 2.08-2.06 (m, 1H), 2.34-2.06 (m, 3H), 2.06-2.06 (m, 1H), 2.06-1.82 (m, 8H), 1.58-1.35 (m, 1H), 1.18-1.09 (m, 3H); LCMS (ESI, M+1): m/z=604.3.

Example 43

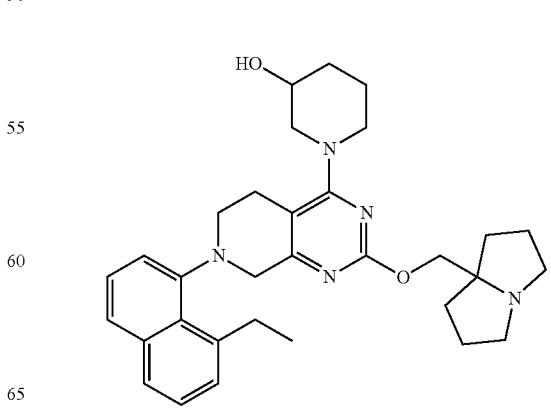

141

1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)piperidin-3-ol Synthesized according to Example 37. The title compound was obtained as off-white solid. $^1$H NMR (400 MHz, DMSO+D$_2$O) δ=7.77-7.66 (m, 2H), 7.51-7.23 (m, 4H), 4.12 (s, 2H), 4.00-3.74 (m, 3H), 3.65-3.36 (m, 4H), 3.26-3.08 (m, 4H), 3.04-2.81 (m, 5H), 2.62-2.53 (m, 1H), 2.01-1.71 (m, 10H), 1.62-1.31 (m, 2H), 1.07 (dt, J=1.6, 7.2 Hz, 3H); LCMS (ESI, M+1): m/z=528.4.

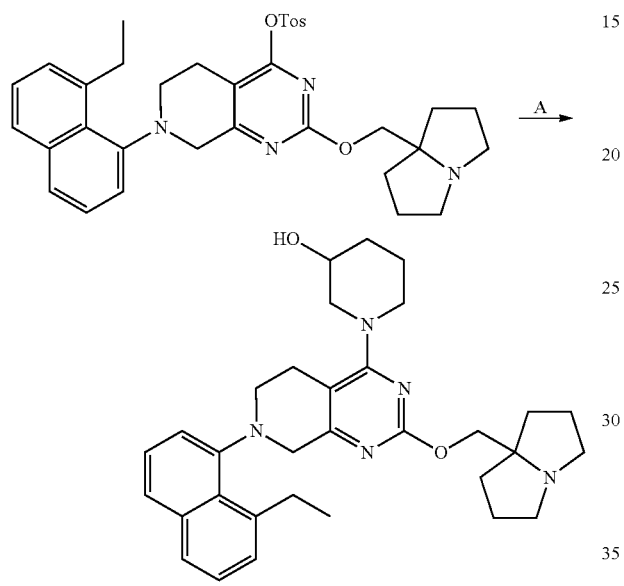

Step A. 1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)piperidin-3-ol: To a mixture of 7-(8-ethyl-naphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (90 mg, 1.0 equiv), piperidin-3-ol (31 mg, 2.04 equiv) and 4 Å molecular sieve (20 mg) in DMF (1.0 mL) was added N-ethyl-N-isopropylpropan-2-amine (83.1 mg, 112 µL, 4.28 equiv). The mixture was stirred at 40° C. for 15 hours. The reaction mixture was diluted with water (20 mL) and extracted with ethyl acetate (20 mL×4). The combined organic phase was dried over anh Na$_2$SO$_4$, concentrated and purified with prep-HPLC [Phenomenex Luna C18 150×25 mm×10 µm; A: water (0.2% FA), B: ACN, B %: 17%-47% over 10 min] to afford the title compound (26.2 mg, 33% yield) as off-white solid. $^1$H NMR (400 MHz, DMSO+D$_2$O) δ=7.77-7.66 (m, 2H), 7.51-7.23 (m, 4H), 4.12 (s, 2H), 4.00-3.74 (m, 3H), 3.65-3.36 (m, 4H), 3.26-3.08 (m, 4H), 3.04-2.81 (m, 5H), 2.62-2.53 (m, 1H), 2.01-1.71 (m, 10H), 1.62-1.31 (m, 2H), 1.07 (dt, J=1.6, 7.2 Hz, 3H); LCMS (ESI, M+1): m/z=528.4.

142

Example 44

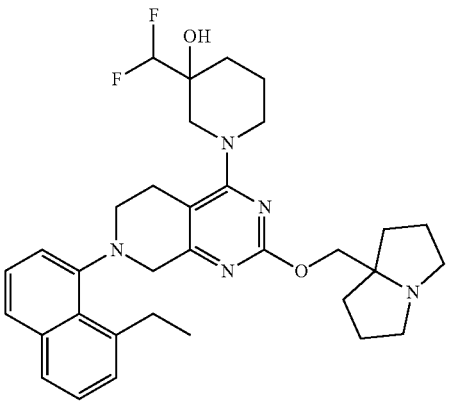 [SMILES: CCc1cccc2cccc(N3CCc4c(nc(OCC56CCCN5CCC6)nc4N4CCCC(O)(C(F)F)C4)C3)c12]

3-(difluoromethyl)-1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)piperidin-3-ol Synthesized according to Example 37. The title compound was obtained as white solid. $^1$H NMR (400 MHz, METHANOL-d$_4$) δ=7.75-7.63 (m, 2H), 7.47-7.24 (m, 4H), 5.92-5.57 (m, 1H), 4.40-4.29 (m, 2H), 4.20-3.98 (m, 2H), 3.93-3.76 (m, 1H), 3.72-3.51 (m, 3H), 3.48-3.33 (m, 3H), 3.27-3.14 (m, 2H), 3.14-2.95 (m, 4H), 2.84-2.63 (m, 1H), 2.23-2.02 (m, 6H), 2.00-1.66 (m, 6H), 1.15 (dt, J=4.4, 7.2 Hz, 3H). LCMS (ESI, M+1): m/z=578.4.

Example 45

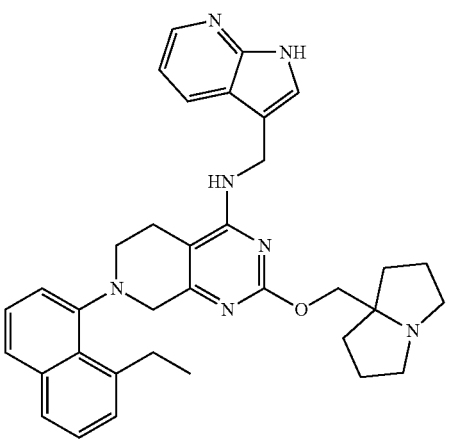 [SMILES: CCc1cccc2cccc(N3CCc4c(nc(OCC56CCCN5CCC6)nc4NCc4c[nH]c5ncccc45)C3)c12]

N-((1H-pyrrolo[2,3-b]pyridin-3-yl)methyl)-7-(8-ethylnaphthalen-1-yl)-2-((hexahydro-1H-pyrrolizin-7a-yl)methoxy)-5,6,7,8-tetrahydropyrido[3,4-d]pyrimidin-4-amine Synthesized according to Example 37. The title compound was obtained as off-white solid. $^1$H NMR (400 MHz, METHANOL-d$_4$) δ=8.47 (dd, J=1.2, 8.0 Hz, 1H), 8.35 (d, J=4.8 Hz, 1H), 7.72-7.71 (m, 2H), 7.67 (s, 1H), 7.44 (t, J=7.6 Hz, 1H), 7.39-7.38 (m, 3H), 7.37-7.31 (m, 1H), 5.07 (q, J=15.2 Hz, 2H), 4.70 (q, J=11.6 Hz, 2H), 4.04 (d, J=18.0 Hz, 1H), 3.84 (d, J=17.6 Hz, 1H), 3.68-3.58 (m, 3H), 3.44-3.40 (m, 2H), 3.29-3.26 (m, 2H), 3.11 (dd, J=7.2, 13.2 Hz, 1H), 2.84-2.80 (m, 1H), 2.56 (br d, J=16.4 Hz, 1H), 2.27-2.10 (m, 8H), 1.10 (t, J=7.2 Hz, 3H); LCMS (ESI, M+1): m/z=574.5.

METHANOL-$d_4$): δ=7.76-7.70 (m, 2H), 7.45 (t, J=7.6 Hz, 1H), 7.40-7.30 (m, 3H), 4.63 (d, J=1.2 Hz, 2H), 4.19-4.06 (m, 4H), 4.05-3.98 (m, 1H), 3.96-3.85 (m, 3H), 3.84-3.73 (m, 2H), 3.70-3.50 (m, 4H), 3.30-3.21 (m, 4H), 3.16-3.05 (m, 1H), 2.90-2.82 (m, 1H), 2.34-2.25 (m, 2H), 2.25-2.06 (m, 7H), 2.04-1.95 (m, 1H), 1.17 (t, J=7.2 Hz, 3H); LCMS (ESI, M+1): m/z=528.3.

Example 46

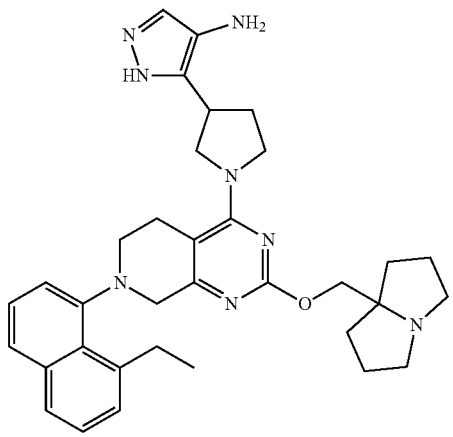 [SMILES: CCc1cccc2cccc(N3CCc4c(nc(OCC56CCCN5CCC6)nc4N4CCC(c5[nH]ncc5N)C4)C3)c12]

5-(1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)pyrrolidin-3-yl)-1H-pyrazol-4-amine Synthesized according to Example 37. The title compound was obtained as gray solid. $^1$H NMR (400 MHz, METHANOL-$d_4$) δ=7.73-7.63 (m, 2H), 7.46-7.39 (m, 1H), 7.38-7.30 (m, 2H), 7.30-7.25 (m, 1H), 7.25-7.20 (m, 1H), 4.52-4.40 (m, 2H), 4.33-4.14 (m, 1H), 4.12-3.82 (m, 4H), 3.74-3.51 (m, 6H), 3.50-3.37 (m, 1H), 3.27-3.17 (m, 3H), 3.14 (br s, 2H), 2.36 (s, 1H), 2.29-2.08 (m, 7H), 2.04 (br dd, J=6.5, 12.0 Hz, 2H), 1.19-1.09 (m, 3H). LCMS (ESI, M+1): m/z=579.4

Example 47

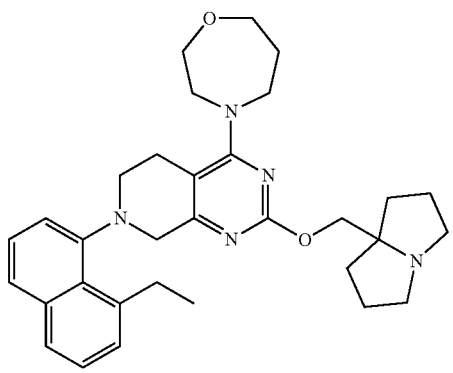 [SMILES: CCc1cccc2cccc(N3CCc4c(nc(OCC56CCCN5CCC6)nc4N4CCCOCC4)C3)c12]

4-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-1,4-oxazepane Synthesized according to Example 37. The title compound was obtained as yellow solid. $^1$H NMR (400 MHz, Example 48

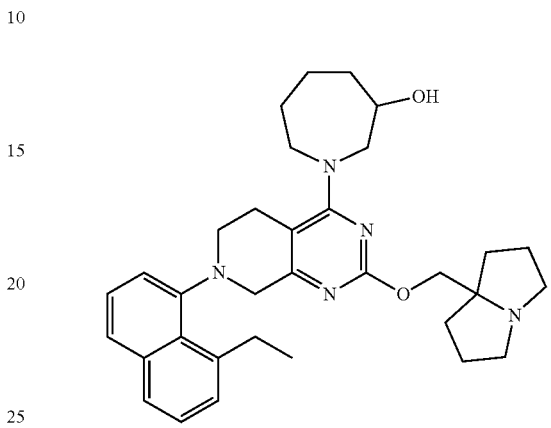

1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)azepan-3-ol Synthesized according to Example 37. The title compound was obtained as light yellow solid. $^1$H NMR (400 MHz, METHANOL-$d_4$): δ=8.54 (s, 1H), 7.69 (dd, J=8.0, 16.4 Hz, 2H), 7.42 (dt, J=2.8, 7.6 Hz, 1H), 7.37-7.26 (m, 3H), 4.35 (d, J=5.6 Hz, 2H), 4.29-3.98 (m, 4H), 3.72-3.54 (m, 4H), 3.53-3.36 (m, 3H), 3.29-3.15 (m, 2H), 3.12-2.98 (m, 3H), 2.83-2.75 (m, 1H), 2.19 (td, J=6.0, 12.4 Hz, 2H), 2.15-2.00 (m, 4H), 1.99-1.90 (m, 3H), 1.89-1.72 (m, 3H), 1.69-1.58 (m, 1H), 1.52-1.28 (m, 1H), 1.14 (t, J=7.2 Hz, 3H); LCMS (ESI, M+1): m/z=542.3.

Example 49

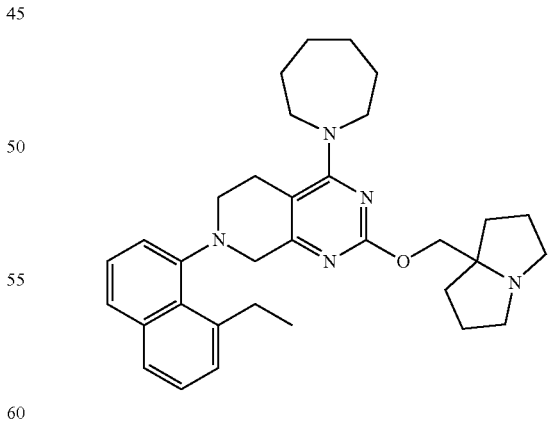

4-(azepan-1-yl)-7-(8-ethylnaphthalen-1-yl)-2-((hexahydro-1H-pyrrolizin-7a-yl)methoxy)-5,6,7,8-tetrahydropyrido[3,4-d]pyrimidine Synthesized according to Example 37. The title compound was obtained as yellow solid. $^1$H NMR (400 MHz, METHANOL-d$_4$) δ=7.69 (ddd, J=0.8, 8.0, 17.2 Hz, 2H), 7.43 (t, J=7.6 Hz, 1H), 7.38-7.30 (m, 2H), 7.30-7.26 (m, 1H), 4.41-4.31 (m, 2H), 4.02 (d, J=17.2 Hz, 1H), 3.94-3.85 (m, 2H), 3.82-3.73 (m, 2H), 3.67-3.54 (m, 3H), 3.53-3.44 (m, 2H), 3.29-3.17 (m, 2H), 3.14-2.99 (m, 3H), 2.84-2.73 (m, 1H), 2.25-2.16 (m, 2H), 2.16-2.02 (m, 4H), 2.01-1.79 (m, 6H), 1.69 (br dd, J=4.8, 7.2 Hz, 2H), 1.62-1.51 (m, 2H), 1.14 (t, J=7.2 Hz, 3H); LCMS (ESI, M+1): m/z=526.5.

Example 50

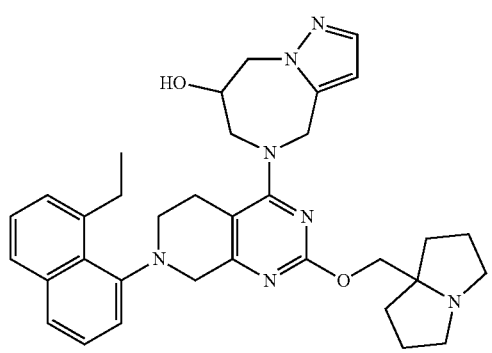 [SMILES: CCc1cccc2cccc(N3CCc4c(nc(OCC56CCCN5CCC6)nc4N4Cc5ccnn5CC(O)C4)C3)c12]

5-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-5,6,7,8-tetrahydro-4H-pyrazolo[1,5-a][1,4]diazepin-7-ol Synthesized according to Example 37. The title compound was obtained as white solid. $^1$H NMR (400 MHz, METHANOL-d$_4$) δ=7.69 (dd, J=8.0, 16.0 Hz, 2H), 7.46-7.36 (m, 1H), 7.36-7.22 (m, 4H), 6.30-6.19 (m, 1H), 5.16-4.91 (m, 1H), 4.79 (br d, J=16.4 Hz, 1H), 4.62-4.50 (m, 1H), 4.47-4.40 (m, 1H), 4.39-4.17 (m, 4H), 4.15-3.87 (m, 2H), 3.82-3.72 (m, 1H), 3.67-3.54 (m, 2H), 3.51-3.34 (m, 1H), 3.29-3.01 (m, 4H), 2.97-2.86 (m, 2H), 2.85-2.72 (m, 1H), 2.15-2.06 (m, 2H), 2.05-1.90 (m, 4H), 1.88-1.78 (m, 2H), 1.17 (t, J=7.2 Hz, 3H); LCMS (ESI, M+1): m/z=580.5.

Example 51

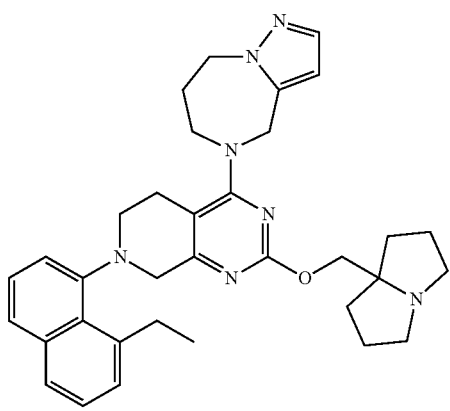 [SMILES: CCc1cccc2cccc(N3CCc4c(nc(OCC56CCCN5CCC6)nc4N4CCCn5nccc5C4)C3)c12]

4-(7,8-dihydro-4H-pyrazolo[1,5-a][1,4]diazepin-5(6H)-yl)-7-(8-ethylnaphthalen-1-yl)-2-((hexahydro-1H-pyrrolizin-7a-yl)methoxy)-5,6,7,8-tetrahydropyrido[3,4-d]pyrimidine Synthesized according to Example 37. The title compound was obtained as light yellow solid. $^1$H NMR (400 MHz, METHANOL-d$_4$) δ=7.68 (br dd, J=8.0, 16.4 Hz, 2H), 7.44-7.36 (m, 1H), 7.35-7.26 (m, 4H), 6.25 (s, 1H), 5.04 (br d, J=16.4 Hz, 1H), 4.78 (br s, 1H), 4.56-4.42 (m, 2H), 4.19 (s, 3H), 4.07 (br d, J=17.6 Hz, 1H), 4.00-3.91 (m, 1H), 3.66 (br d, J=17.6 Hz, 1H), 3.61-3.50 (m, 2H), 3.29-3.18 (m, 4H), 3.12 (br dd, J=7.1, 13.3 Hz, 1H), 2.93-2.83 (m, 2H), 2.73 (br d, J=12.0 Hz, 1H), 2.35-2.23 (m, 1H), 2.11-2.03 (m, 3H), 1.97 (ddd, J=6.4, 13.4, 20.0 Hz, 4H), 1.85-1.76 (m, 2H), 1.16 (br t, J=7.2 Hz, 3H); LCMS (ESI, M+1): m/z=564.4.

Example 52

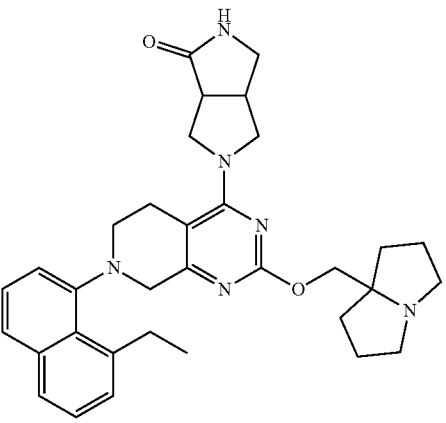 [SMILES: CCc1cccc2cccc(N3CCc4c(nc(OCC56CCCN5CCC6)nc4N4CC5CNC(=O)C5C4)C3)c12]

5-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)hexahydropyrrolo[3,4-c]pyrrol-1(2H)-one Synthesized according to Example 37. The title compound was obtained as white solid. $^1$H NMR (400 MHz, METHANOL-d$_4$) δ=7.71-7.65 (m, 2H), 7.42 (q, J=7.2 Hz, 1H), 7.36-7.26 (m, 3H), 4.39-4.24 (m, 3H), 4.12-3.96 (m, 3H), 3.80-3.73 (m, 1H), 3.68-3.58 (m, 5H), 3.43-3.42 (m, 2H), 3.22-3.16 (m, 4H), 3.06-3.04 (m, 4H), 2.18-2.16 (m, 2H), 2.09-2.04 (m, 4H), 2.03-1.94 (m, 2H), 1.16-1.10 (m, 3H); LCMS (ESI, M+1): m/z=553.4.

Example 53

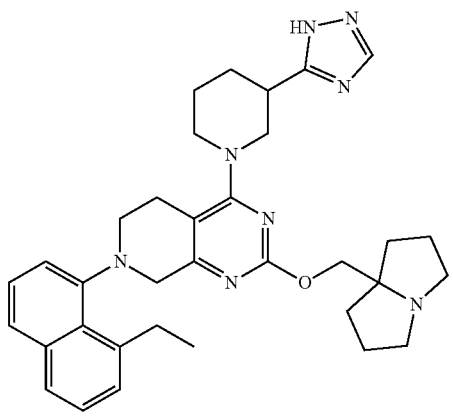 [SMILES: CCc1cccc2cccc(N3CCc4c(nc(OCC56CCCN5CCC6)nc4N4CCCC(c5ncn[nH]5)C4)C3)c12]

4-(3-(1H-1,2,4-triazol-5-yl)piperidin-1-yl)-7-(8-ethylnaphthalen-1-yl)-2-((hexahydro-1H-pyrrolizin-7a-yl)methoxy)-5,6,7,8-tetrahydropyrido[3,4-d]pyrimidine Synthesized according to Example 37. The title compound was obtained as yellow solid. $^1$H NMR (400 MHz, METHANOL-$d_4$) δ=8.43 (d, J=2.8 Hz, 1H), 7.75-7.69 (m, 2H), 7.48-7.42 (m, 1H), 7.40-7.31 (m, 3H), 4.81-4.61 (m, 3H), 4.52-4.33 (m, 1H), 4.27-4.13 (m, 1H), 3.90-3.75 (m, 1H), 3.71-3.62 (m, 3H), 3.62-3.47 (m, 3H), 3.44-3.35 (m, 1H), 3.29-3.23 (m, 3H), 3.23-3.04 (m, 2H), 2.81-2.72 (m, 1H), 2.35-2.26 (m, 3H), 2.25-2.14 (m, 4H), 2.13-1.99 (m, 4H), 1.97-1.72 (m, 1H), 1.17 (t, J=7.2 Hz, 3H); LCMS (ESI, M+1): m/z=579.4.

Example 54

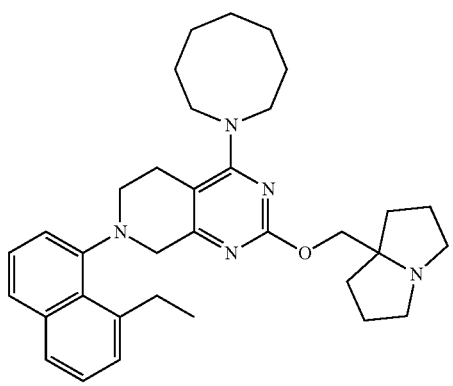 [SMILES: CCc1cccc2cccc(N3CCc4c(nc(OCC56CCCN5CCC6)nc4N4CCCCCCC4)C3)c12]

4-(azocan-1-yl)-7-(8-ethylnaphthalen-1-yl)-2-((hexahydro-1H-pyrrolizin-7a-yl)methoxy)-5,6,7,8-tetrahydropyrido[3,4-d]pyrimidine Synthesized according to Example 37. The title compound was obtained as yellow solid. $^1$H NMR (400 MHz, METHANOL-$d_4$) δ=7.73-7.63 (m, 2H), 7.41 (t, J=7.6 Hz, 1H), 7.37-7.25 (m, 3H), 4.22-4.11 (m, 2H), 4.02 (br d, J=17.6 Hz, 1H), 3.93-3.84 (m, 2H), 3.82-3.73 (m, 2H), 3.66-3.51 (m, 3H), 3.23-3.11 (m, 4H), 3.07 (dd, J=7.2, 13.2 Hz, 1H), 2.83-2.68 (m, 3H), 2.10-2.01 (m, 2H), 1.99-1.80 (m, 8H), 1.79-1.65 (m, 4H), 1.58 (br s, 4H), 1.14 (t, J=7.2 Hz, 3H); LCMS (ESI, M+1): m/z=540.5.

Example 55

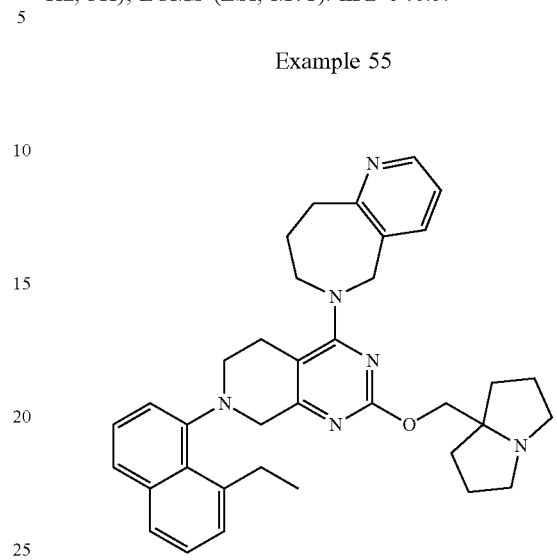

6-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-6,7,8,9-tetrahydro-5H-pyrido[3,2-c]azepine Synthesized according to Example 37. The title compound was obtained as yellow solid. $^1$H NMR (400 MHz, METHANOL-$d_4$) δ=8.31 (dd, J=1.2, 4.8 Hz, 1H), 7.78 (dd, J=1.2, 7.6 Hz, 1H), 7.69 (dd, J=7.2, 16.0 Hz, 2H), 7.42 (t, J=7.6 Hz, 1H), 7.38-7.33 (m, 1H), 7.32-7.23 (m, 3H), 5.03-4.96 (m, 1H), 4.90-4.79 (m, 1H), 4.41-4.32 (m, 1H), 4.27-4.15 (m, 2H), 4.11-3.97 (m, 2H), 3.65 (br d, J=18.0 Hz, 1H), 3.62-3.52 (m, 4H), 3.27-3.23 (m, 2H), 3.23-3.17 (m, 3H), 3.11 (dd, J=7.6, 13.6 Hz, 1H), 2.73 (br d, J=14.8 Hz, 1H), 2.30-1.97 (m, 11H), 1.16 (t, J=7.6 Hz, 3H); LCMS (ESI, M+1): m/z=575.4.

Example 56

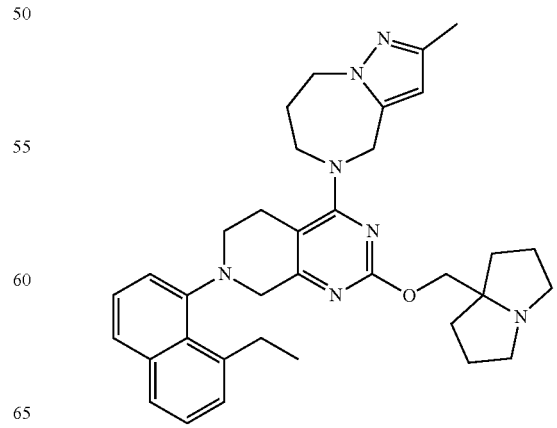

7-(8-ethylnaphthalen-1-yl)-2-((hexahydro-1H-pyrrolizin-7a-yl)methoxy)-4-(2-methyl-7,8-dihydro-4H-pyrazolo[1,5-a][1,4]diazepin-5(6H)-yl)-5,6,7,8-tetrahydropyrido[3,4-d]pyrimidine Synthesized according to Example 37. The title compound was obtained as yellow solid. ¹H NMR (400 MHz, methanol-d₄) δ=7.77-7.63 (m, 2H), 7.43 (t, J=7.6 Hz, 1H), 7.39-7.33 (m, 1H), 7.32-7.20 (m, 2H), 6.03 (s, 1H), 5.01 (d, J=16.4 Hz, 1H), 4.75 (d, J=16.4 Hz, 1H), 4.47-4.34 (m, 4H), 4.31-4.21 (m, 1H), 4.08 (d, J=17.6 Hz, 1H), 3.97-3.86 (m, 1H), 3.73-3.50 (m, 5H), 3.30-3.19 (m, 4H), 3.18-3.09 (m, 1H), 2.81-2.70 (m, 1H), 2.32-2.24 (m, 2H), 2.23-1.98 (m, 11H), 1.17 (t, J=7.2 Hz, 3H); LCMS (ESI, M+1): m/z=578.5.

Example 57

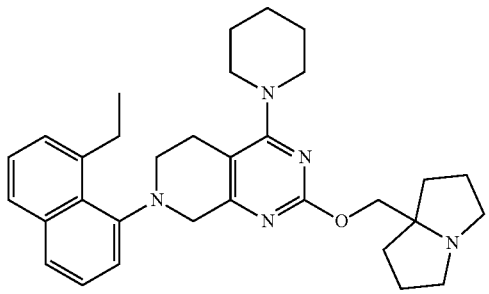 [SMILES: CCc1cccc2cccc(N3CCc4c(nc(OCC56CCCN5CCC6)nc4N4CCCCC4)C3)c12]

7-(8-ethylnaphthalen-1-yl)-2-((hexahydro-1H-pyrrolizin-7a-yl)methoxy)-4-(piperidin-1-yl)-5,6,7,8-tetrahydropyrido[3,4-d]pyrimidine Synthesized according to Example 37. The title compound was obtained as white solid. ¹H NMR (400 MHz, METHANOL-d4) δ=7.68 (dd, J=7.6, 17.6 Hz, 2H), 7.42 (t, J=7.7 Hz, 1H), 7.37-7.25 (m, 3H), 4.27-4.15 (m, 2H), 4.09 (d, J=17.6 Hz, 1H), 3.68-3.57 (m, 4H), 3.56-3.48 (m, 3H), 3.27-3.11 (m, 4H), 3.06 (dd, J=7.2, 13.2 Hz, 1H), 2.90-2.79 (m, 2H), 2.69-2.58 (m, 1H), 2.15-2.04 (m, 2H), 2.03-1.86 (m, 4H), 1.85-1.62 (m, 8H), 1.15 (t, J=7.2 Hz, 3H); LCMS (ESI, M+1): m/z=512.4.

Example 58

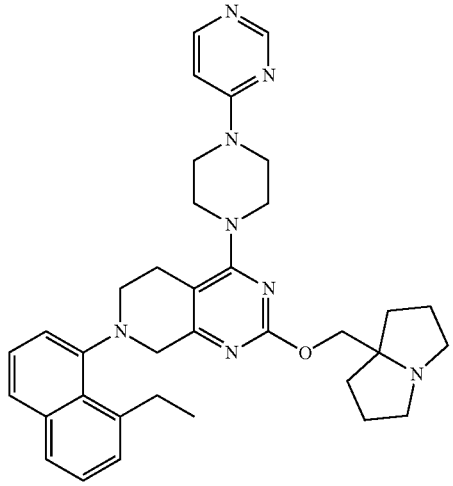 [SMILES: CCc1cccc2cccc(N3CCc4c(nc(OCC56CCCN5CCC6)nc4N4CCN(c5ccncn5)CC4)C3)c12]

7-(8-ethylnaphthalen-1-yl)-2-((hexahydro-1H-pyrrolizin-7a-yl)methoxy)-4-(4-(pyrimidin-4-yl)piperazin-1-yl)-5,6,7,8-tetrahydropyrido[3,4-d]pyrimidine Synthesized according to Example 37. The title compound was obtained as pink solid. ¹H NMR (400 MHz, METHANOL-d₄) δ=8.55 (s, 1H), 8.18 (d, J=6.4 Hz, 1H), 7.71 (dd, J=7.2, 16.4 Hz, 2H), 7.44 (t, J=7.6 Hz, 1H), 7.40-7.28 (m, 3H), 6.84 (d, J=6.4 Hz, 1H), 4.41-4.31 (m, 2H), 4.14 (d, J=17.6 Hz, 1H), 4.01-3.92 (m, 2H), 3.89-3.79 (m, 4H), 3.73-3.55 (m, 5H), 3.48-3.38 (m, 2H), 3.28-3.18 (m, 2H), 3.14-3.01 (m, 3H), 2.82-2.71 (m, 1H), 2.24-2.15 (m, 2H), 2.14-1.99 (m, 4H), 1.99-1.90 (m, 2H), 1.17 (t, J=7.2 Hz, 3H); LCMS (ESI, M+1): m/z=591.4.

Example 59

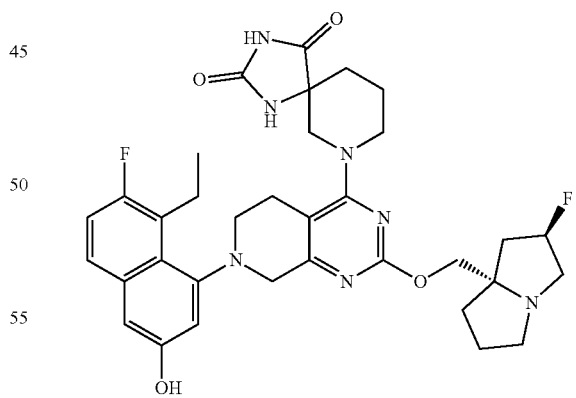

7-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,3,7-triazaspiro[4.5]decane-2,4-dione Synthesized according to Example 32. The title compound was obtained as orange solid. ¹H NMR (400 MHz, METHANOL-d₄) δ=7.52 (dd, J=6.0, 8.8 Hz, 1H), 7.15 (t, J=9.6 Hz, 1H), 7.04-6.93 (m, 2H), 5.61-5.30 (m, 1H), 4.49-4.28 (m, 2H), 4.27-4.14 (m, 1H), 4.14-3.93 (m, 2H), 3.80-3.56 (m, 4H), 3.56-3.32 (m, 5H), 3.29-3.20 (m, 1H), 3.20-3.01 (m, 2H), 2.86-2.68 (m, 1H), 2.61-2.33 (m, 2H), 2.32-2.03 (m, 5H), 2.02-1.72 (m, 3H), 1.10 (t, J=7.2 Hz, 3H); LCMS (ESI, M+1): m/z=648.3.

Example 60

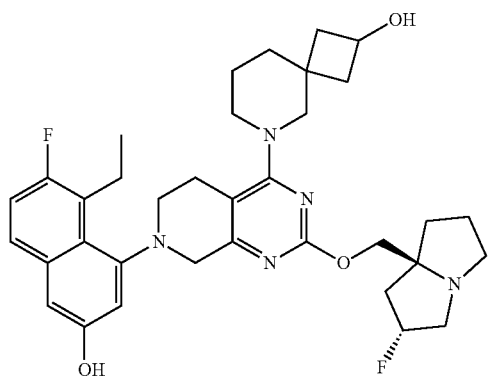 [SMILES: CCc1c(F)ccc2cc(O)cc(N3CCc4c(nc(OC[C@@]56CCCN5C[C@H](F)C6)nc4N4CCCC5(CC(O)C5)C4)C3)c12]

6-(7-(8-ethyl-7-fluoro-3-hydroxynaphthalen-1-yl)-2-
(((2R,7aS)-2-fluorohexahydro-1H-pyrrolizin-7a-yl)
methoxy)-5,6,7,8-tetrahydropyrido[3,4-d]pyrimidin-
4-yl)-6-azaspiro[3.5]nonan-2-ol Synthesized according to Example 28. The title compound was obtained as yellow solid. ¹H NMR (400 MHz, METHANOL-d4) δ=7.51 (dd, J=5.6, 8.8 Hz, 1H), 7.14 (t, J=9.2 Hz, 1H), 6.98 (m, 2H), 5.47-5.22 (m, 1H), 4.33-4.13 (m, 3H), 4.07 (d, J=17.6 Hz, 1H), 3.90-3.72 (m, 1H), 3.70-3.59 (m, 2H), 3.58-3.48 (m, 1H), 3.47-3.35 (m, 1H), 3.45-3.33 (m, 5H), 3.28-3.07 (m, 4H), 2.75-2.55 (m, 1H), 2.46-2.12 (m, 5H), 2.11-2.01 (m, 2H), 2.00-1.90 (m, 1H), 1.89-1.55 (m, 6H), 1.21-1.04 (m, 3H); LCMS (ESI, M+1): m/z=620.1.

Example 61

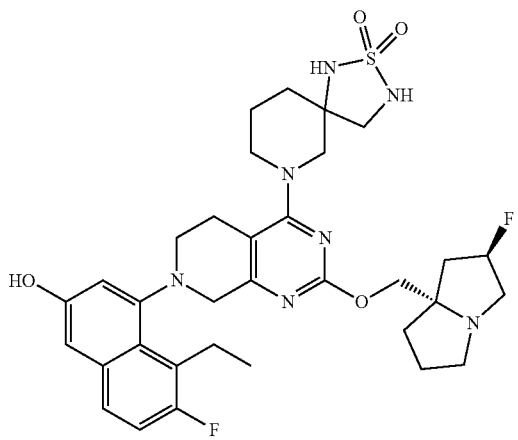 [SMILES: CCc1c(F)ccc2cc(O)cc(N3CCc4c(nc(OC[C@@]56CCCN5C[C@H](F)C6)nc4N4CCCC5(CNS(=O)(=O)N5)C4)C3)c12]

7-(7-(8-ethyl-7-fluoro-3-hydroxynaphthalen-1-yl)-2-
(((2R,7aS)-2-fluorohexahydro-1H-pyrrolizin-7a-yl)
methoxy)-5,6,7,8-tetrahydropyrido[3,4-d]pyrimidin-
4-yl)-2-thia-1,3,7-triazaspiro[4.5]decane 2,2-dioxide Synthesized according to Example 32. The title compound was obtained as white solid. ¹H NMR (400 MHz, METHANOL-d4) δ=8.50 (br s, 1H), 7.60-7.43 (m, 1H), 7.15 (dt, J=2.8, 9.4 Hz, 1H), 7.06-6.88 (m, 2H), 5.53-5.31 (m, 1H), 4.41-4.25 (m, 2H), 4.17-3.97 (m, 2H), 3.72-3.48 (m, 7H), 3.45-3.33 (m, 3H), 3.25-3.14 (m, 4H), 2.76-2.44 (m, 2H), 2.43-2.26 (m, 2H), 2.24-1.92 (m, 5H), 1.90-1.65 (m, 3H), 1.16-1.06 (m, 3H); LCMS (ESI, M+1): m/z=670.3.

Example 62

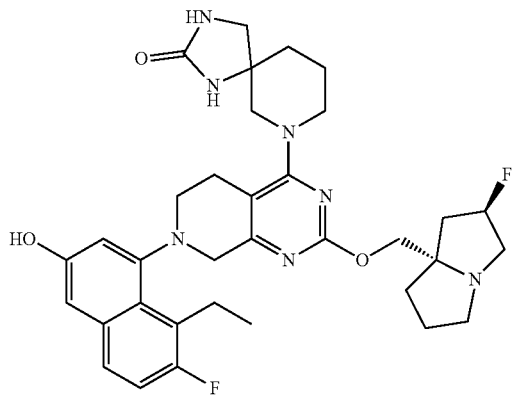 [SMILES: CCc1c(F)ccc2cc(O)cc(N3CCc4c(nc(OC[C@@]56CCCN5C[C@H](F)C6)nc4N4CCCC5(CNC(=O)N5)C4)C3)c12]

7-(7-(8-ethyl-7-fluoro-3-hydroxynaphthalen-1-yl)-2-
(((2R,7aS)-2-fluorohexahydro-1H-pyrrolizin-7a-yl)
methoxy)-5,6,7,8-tetrahydropyrido[3,4-d]pyrimidin-
4-yl)-1,3,7-triazaspiro[4.5]decan-2-one Synthesized according to Example 32. The title compound was obtained as yellow solid. ¹H NMR (400 MHz, METHANOL-d₄) δ=8.50 (br s, 1H), 7.52 (dd, J=6.0, 8.8 Hz, 1H), 7.15 (t, J=9.6 Hz, 1H), 7.02-6.95 (m, 2H), 5.49-5.29 (m, 1H), 4.67-4.49 (m, 1H), 4.39-4.19 (m, 2H), 4.16-4.04 (m, 1H), 3.76-3.60 (m, 4H), 3.59-3.34 (m, 8H), 3.25-3.14 (m, 3H), 2.79-2.65 (m, 1H), 2.47-2.27 (m, 2H), 2.25-2.17 (m, 1H), 2.15-2.05 (m, 2H), 2.04-1.95 (m, 1H), 1.94-1.67 (m, 4H), 1.11 (dt, J=2.8, 7.2 Hz, 3H). LCMS (ESI, M+1): m/z=634.3.

Example 63

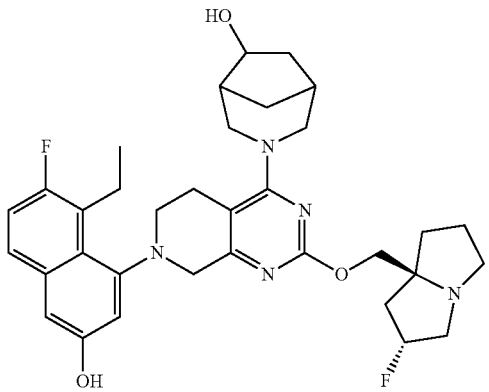 [SMILES: CCc1c(F)ccc2cc(O)cc(N3CCc4c(nc(OC[C@@]56CCCN5C[C@H](F)C6)nc4N4CC5CC(O)C(C5)C4)C3)c12]

3-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-azabicyclo[3.2.1]octan-6-ol Synthesized according to Example 32. The title compound was obtained as white solid. $^1$H NMR (400 MHz, METHANOL-$d_4$) δ=7.57-7.46 (m, 1H), 7.21-7.09 (m, 1H), 7.03-6.92 (m, 2H), 5.45-5.25 (m, 1H), 4.66-4.47 (m, 1H), 4.36-4.23 (m, 2H), 4.23-4.02 (m, 2H), 4.07 (br d, J=17.6 Hz, 1H), 3.85-3.74 (m, 1H), 3.68-3.58 (m, 1H), 3.51-3.34 (m, 7H), 3.23-3.07 (m, 3H), 3.06-2.99 (m, 1H), 3.06-2.69 (m, 1H), 2.45-2.25 (m, 3H), 2.24-2.12 (m, 3H), 2.12-2.00 (m, 2H), 1.99-1.87 (m, 1H), 1.82-1.69 (m, 2H), 1.61-1.24 (m, 1H), 1.15-1.05 (m, 3H); LCMS (ESI, M+1): m/z=606.3.

Example 64

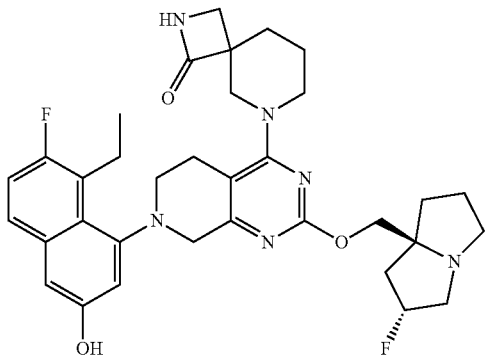 [SMILES: CCc1c(F)ccc2cc(O)cc(N3CCc4c(nc(OC[C@@]56CCCN5C[C@H](F)C6)nc4N4CCCC5(CNC5=O)C4)C3)c12]

6-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-2,6-diazaspiro[3.5]nonan-1-one Synthesized according to Example 27. The title compound was obtained as pink solid. $^1$HNMR (400 MHz, METHANOL-d4) δ=7.52-7.49 (m, 1H), 7.15 (t, J=9.2 Hz, 1H), 7.04-6.93 (m, 2H), 5.40 (d, J=53.2 Hz, 1H), 4.69-4.53 (m, 1H), 4.51-4.32 (m, 2H), 4.16-4.03 (m, 1H), 4.03-3.77 (m, 3H), 3.76-3.62 (m, 4H), 3.57-3.47 (m, 1H), 3.46-3.33 (m, 3H), 3.27-3.08 (m, 4H), 2.74-2.41 (m, 3H), 2.36-2.17 (m, 3H), 2.16-1.76 (m, 5H), 1.11 (m, 3H); LCMS (ESI, M+1): m/z=619.4.

Example 65

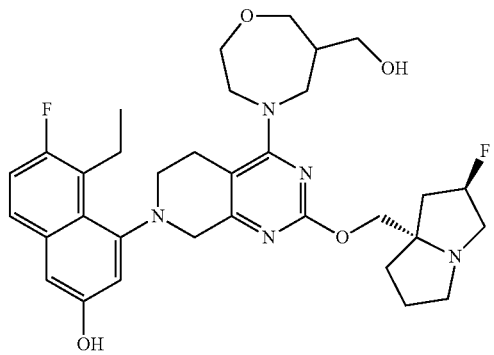 [SMILES: CCc1c(F)ccc2cc(O)cc(N3CCc4c(nc(OC[C@@]56CCCN5C[C@H](F)C6)nc4N4CCOCC(CO)C4)C3)c12]

5-ethyl-6-fluoro-4-(2-(((2R,7aS)-2-fluorohexahydro-1H-pyrrolizin-7a-yl)methoxy)-4-(6-(hydroxymethyl)-1,4-oxazepan-4-yl)-5,6-dihydropyrido[3,4-d]pyrimidin-7(8H)-yl)naphthalen-2-ol Synthesized according to Example 32. The title compound was obtained as yellow solid. 1H NMR (400 MHz, METHANOL-d4) δ=8.52 (s, 1H), 7.68-7.46 (m, 1H), 7.21-7.10 (m, 1H), 7.09-6.90 (m, 2H), 6.90-6.87 (m, 1H), 5.48-5.23 (m, 1H), 4.49-4.14 (m, 4H), 4.11-3.77 (m, 4H), 3.75-3.36 (m, 12H), 3.28-3.08 (m, 3H), 2.81-2.70 (m, 1H), 2.52-1.89 (m, 4H), 2.14-1.82 (m, 3H), 1.26-1.05 (m, 3H); LCMS (ESI, M+1): m/z=610.5.

Example 66

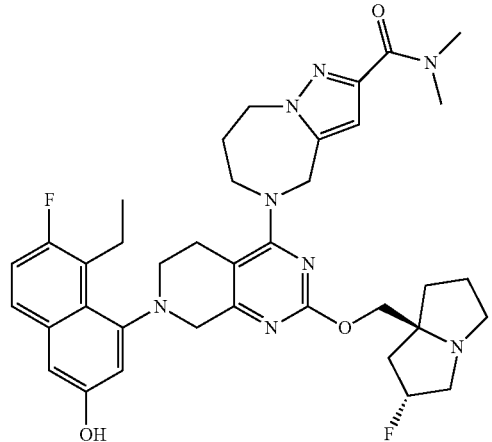 [SMILES: CCc1c(F)ccc2cc(O)cc(N3CCc4c(nc(OC[C@@]56CCCN5C[C@H](F)C6)nc4N4CCCn5nc(C(=O)N(C)C)cc5C4)C3)c12]

155

5-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide

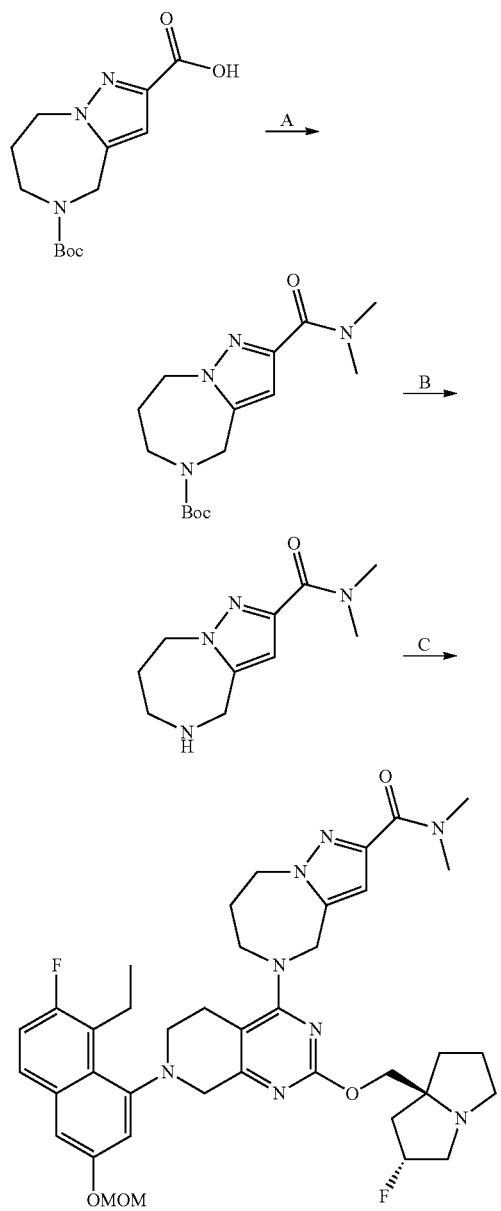

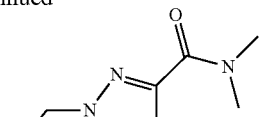

Step A. tert-butyl 2-(dimethylcarbamoyl)-7,8-dihydro-4H-pyrazolo[1,5-a][1,4]diazepine-5(6H)-carboxylate: To a solution of 5-(tert-butoxycarbonyl)-5,6,7,8-tetrahydro-4H-pyrazolo[1,5-a][1,4]diazepine-2-carboxylic acid (1.0 g, 1.0 equiv) and N-methylmethanamine (3.55 mL, 2.0 equiv) in DCM (10 mL) was added HATU (2.03 g, 1.5 equiv) and N-ethyl-N-isopropylpropan-2-amine (1.38 g, 1.86 mL, 3.0 equiv). The mixture was stirred at 20° C. for 1 hr. The mixture was concentrated under vacuum. The residue was purified by reversed phase flash chromatography [water (FA, 0.1%)/acetonitrile]. The desire fractions were combined. Its pH was adjusted to 8 by NaHCO₃ (4.0 g) and solvent was removed to afford the title compound (1.0 g, 91% yield) as yellow solid. LCMS [ESI, M+1]: m/z=309.2.

Step B. N,N-dimethyl-5,6,7,8-tetrahydro-4H-pyrazolo[1,5-a][1,4]diazepine-2-carboxamide: A mixture of tert-butyl 2-(dimethylcarbamoyl)-7,8-dihydro-4H-pyrazolo[1,5-a][1,4]diazepine-5(6H)-carboxylate and HCl/dioxane (9.50 mL, 12.3 equiv) in MeCN (9.5 mL) was stirred at 0° C. for 1 hour. The mixture was concentrated under vacuum. The pH of the residue was adjusted to 8 with saturated sodium bicarbonate (4 mL). The residue was purified by prep HPLC [column: YMC Triart C18 250×50 mm×7 µm; mobile phase: water (ammonia hydroxide v/v)-ACN; B %: 2%-32%, 8 minutes] to afford the title compound (0.50 g, 77% yield) as yellow solid. LCMS [ESI, M+1]: m/z=209.2.

Step C. 5-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide: A mixture of 7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl 4-methylbenzenesulfonate (100 mg, 1.0 equiv), N,N-dimethyl-5,6,7,8-tetrahydro-4H-pyrazolo[1,5-a][1,4]diazepine-2-carboxamide (60.0 mg, 2.0 equiv), 4A molecular sieve (10.0 mg) and N-ethyl-N-isopropylpropan-2-amine (74.4 mg, 4.0 equiv) in DMF (0.3 mL) was stirred at 40° C. for 12 hours. The reaction mixture was filtered and purified with prep-HPLC column: Phenomenex Luna C18 100×30 mm×5 µm; mobile phase: water (FA)-ACN; B %: 19%-49%, 8 minutes]. The desire fractions were combined, and solvents were removed. The pH of the residue was adjusted to 8 with saturated sodium bicarbonate. The residue was extracted with ethyl acetate (0.1 ml×3), dried over Na₂SO₄ and concentrated under vacuum to afford the title compound (71.0 mg, 67% yield) as yellow solid. LCMS (ESI, M+1): m/z=731.4.

Step D. 5-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide: A mixture of 5-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide (80.0 mg, 1.0 equiv) and HCl·MeOH (2.00 mL, 73 equiv) was stirred at 0° C. for 1 hours. The mixture was concentrated under vacuum. The pH of the residue was adjusted to 8 with saturated sodium bicarbonate solution. The mixture was diluted with ethyl acetate (3×1 mL), dried over Na$_2$SO$_4$, concentrated and purified by prep-HPLC [column: Waters xbridge 150×25 mm×10 μm; mobile phase: water (NH$_4$HCO$_3$)-ACN; B %: 35%-65%, 11 minutes] to afford the title compound (27.0 mg, 34% yield) as yellow solid. $^1$H NMR (400 MHz, METHANOL-d4) δ=9.18 (s, 1H), 8.58-8.43 (m, 1H), 7.81 (dd, J=5.2, 9.2 Hz, 1H), 7.43-7.35 (m, 2H), 7.21 (d, J=2.4 Hz, 1H), 6.76 (s, 1H), 5.48-5.18 (m, 3H), 4.54 (br d, J=6.4 Hz, 2H), 4.48-4.36 (m, 4H), 3.63-3.41 (m, 3H), 3.33 (s, 3H), 3.23-3.16 (m, 1H), 3.08 (s, 3H), 2.47-2.23 (m, 5H), 2.18-1.98 (m, 3H); LCMS (ESI, M+1): m/z=687.3.

Example 67

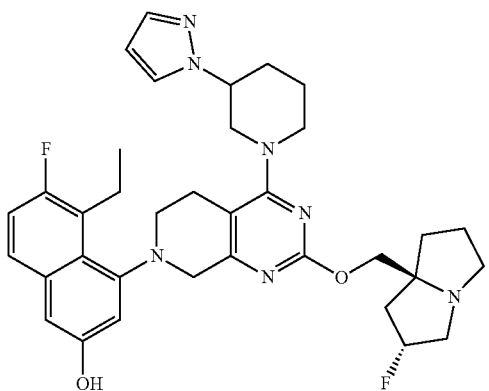 [SMILES: CCc1c(F)ccc2cc(O)cc(N3CCc4c(nc(OC[C@@]56CCCN5C[C@H](F)C6)nc4N4CCCC(n5cccn5)C4)C3)c12]

4-(4-(3-(1H-pyrazol-1-yl)piperidin-1-yl)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol Synthesized according to Example 28. The title compound was obtained as off-white solid. $^1$H NMR (400 MHz, methanol-d$_4$) δ=7.78-7.73 (m, 1H), 7.56-7.47 (m, 2H), 7.14 (t, J=9.4 Hz, 1H), 7.02-6.94 (m, 2H), 6.32 (td, J=2.0, 4.0 Hz, 1H), 5.45-5.14 (m, 1H), 4.66-4.64 (m, 1H), 4.74-4.55 (m, 1H), 4.51-4.25 (m, 2H), 4.24-3.94 (m, 4H), 3.66 (dd, J=11.2, 17.6 Hz, 1H), 3.55-3.46 (m, 1H), 3.43-3.33 (m, 3H), 3.26 (br d, J=9.2 Hz, 2H), 3.22-3.14 (m, 2H), 3.13-2.94 (m, 2H), 2.74-2.57 (m, 1H), 2.41-2.15 (m, 4H), 2.14-2.07 (m, 1H), 2.05-1.97 (m, 3H), 1.96-1.87 (m, 1H), 1.87-1.63 (m, 1H), 1.17-1.02 (m, 3H); LCMS (ESI, M+1): m/z=630.4.

Example 68

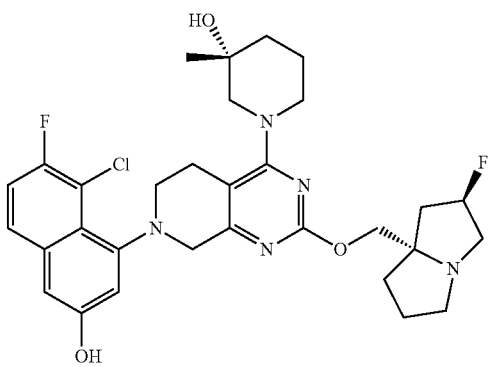 [SMILES: C[C@@]1(O)CCCN(c2nc(OC[C@@]34CCCN3C[C@H](F)C4)nc3c2CCN(c2cc(O)cc4ccc(F)c(Cl)c24)C3)C1]

(R)-1-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol

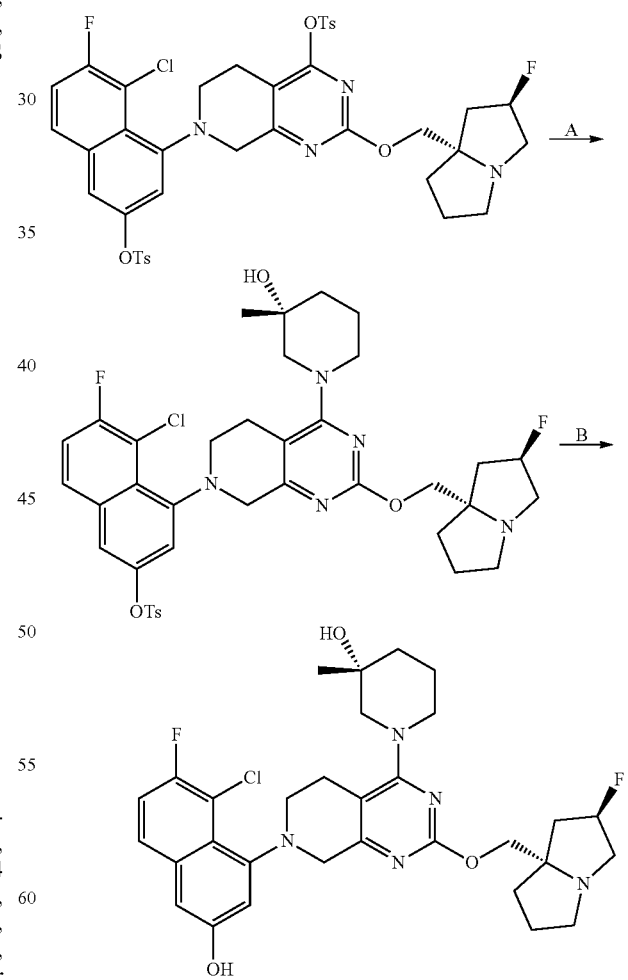

Step A. 5-chloro-6-fluoro-4-(2-(((2R,7aS)-2-fluorotetrahydro-1H-pyrrolizin-7a(5H)-yl)methoxy)-4-((R)-3-hydroxy-3-methylpiperidin-1-yl)-5,8-dihydropyrido[3,4-d]pyrimidin-7(6H)-yl)naphthalen-2-yl 4-methylbenzenesulfonate: To a mixture of 5-chloro-6-fluoro-4-(2-(((2R,7aS)-2-fluorotetrahydro-1H-pyrrolizin-7a(5H)-yl)methoxy)-4-(tosyloxy)-5,8-dihydropyrido[3,4-d]pyrimidin-7(6H)-yl)naphthalen-2-yl 4-methylbenzenesulfonate (100 mg, 1.0 equiv) and (3R)-3-methylpiperidin-3-ol (28.4 mg, 2.0 equiv) in DMF (1 mL) were added N-ethyl-N-isopropylpropan-2-amine (63.7 mg, 4.0 equiv) and 4 Å molecular sieve (10.0 mg). The mixture was stirred at 40-60° C. until the reaction was completed. The mixture was diluted with ethyl acetate (10 mL) and washed with water (5 mL×3). The organic layers were washed with saturated brine (5 mL), dried over anhydrous sodium sulfate, and concentrated to afford the title compound (81.0 mg, crude) as yellow oil; LCMS (ESI, M−1): m/z=754.3.

Step B. (R)-1-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol: A mixture of 5-chloro-6-fluoro-4-(2-(((2R,7aS)-2-fluorotetrahydro-1H-pyrrolizin-7a(5H)-yl)methoxy)-4-((R)-3-hydroxy-3-methylpiperidin-1-yl)-5,8-dihydropyrido[3,4-d]pyrimidin-7(6H)-yl)naphthalen-2-yl 4-methylbenzenesulfonate (70 mg, 1.0 equiv) and NaOH (371 mg, 100 equiv) in MeOH (2 mL) was stirred at 25° C. for 1 hour. The reaction mixture was diluted with water (3 mL), concentrated under vacuum to remove MeOH, extracted with ethyl acetate (5 mL×3). The combined organic layers were washed with brine (3×5 mL), dried over anhydrous sodium sulfate, concentrated, and purified with prep-HPLC [column: Phenomenex Luna C18 150×25 mm×10 μm; mobile phase: water (FA)-ACN; B %: 14%-44%, 8 minutes] to afford the title compound (8.71 mg, 15% yield) as off-white solid. $^1$H NMR (400 MHz, METHANOL-d$_4$) δ=7.62 (dd, J=5.6, 8.8 Hz, 1H), 7.28 (t, J=8.8 Hz, 1H), 6.95 (d, J=2.0 Hz, 2H), 5.55-5.32 (m, 1H), 4.41-4.16 (m, 3H), 4.03-3.37 (m, 8H), 3.28-3.02 (m, 4H), 2.77-2.59 (m, 1H), 2.54-2.30 (m, 2H), 1.89-1.62 (m, 3H), 2.25-1.60 (m, 5H), 1.30-1.18 (m, 3H); LCMS (ESI, M+1): m/z=600.5.

Example 69

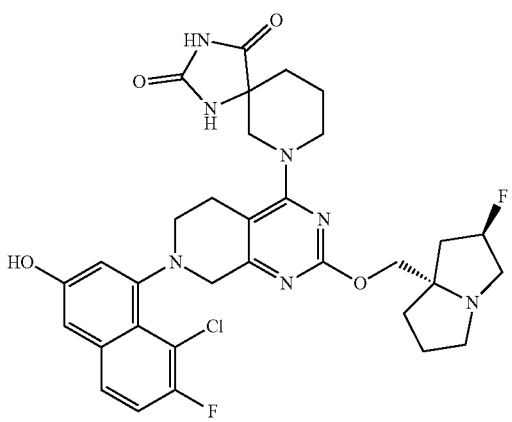 [SMILES: O=C1NC(=O)C2(CCCN(c3nc(OC[C@@]45CCCN4C[C@H](F)C5)nc4c3CCN(c3cc(O)cc5ccc(F)c(Cl)c35)C4)C2)N1]

7-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,3,7-triazaspiro[4.5]decane-2,4-dione Synthesized according to Example 68. The title compound was obtained as pink solid. $^1$H NMR (400 MHz, METHANOL-d$_4$) δ=7.62 (dd, J=5.6, 9.2 Hz, 1H), 7.28 (t, J=8.8 Hz, 1H), 6.98-6.92 (m, 2H), 5.55-5.30 (m, 1H), 4.44-4.29 (m, 2H), 4.25-3.98 (m, 2H), 3.71-3.64 (m, 1H), 3.61-3.52 (m, 3H), 3.45-3.35 (m, 2H), 3.27-3.00 (m, 4H), 2.80-2.64 (m, 1H), 2.56-2.33 (m, 2H), 2.32-2.22 (m, 1H), 2.19-1.76 (m, 8H). LCMS (ESI, M+1): m/z=654.2.

Example 70

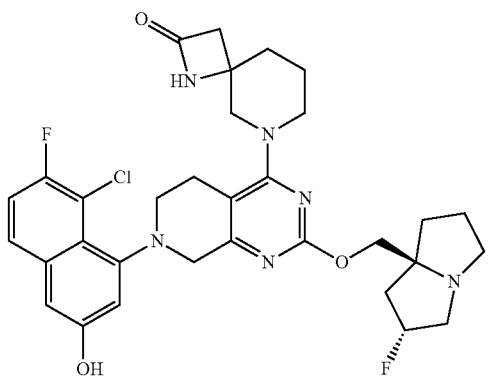 [SMILES: O=C1CC2(CCCN(c3nc(OC[C@@]45CCCN4C[C@H](F)C5)nc4c3CCN(c3cc(O)cc5ccc(F)c(Cl)c35)C4)C2)N1]

6-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,6-diazaspiro[3.5]nonan-2-one Synthesized according to Example 68. The title compound was obtained as pink solid. $^1$H NMR (400 MHz, METHANOL-d4) δ=7.62 (dd, J=5.6, 9.2 Hz, 1H), 7.27 (t, J=8.8 Hz, 1H), 6.95 (d, J=2.0 Hz, 2H), 5.36-5.19 (m, 1H), 4.27 (br d, J=17.6 Hz, 1H), 4.22-4.03 (m, 2H), 3.92-3.48 (m, 6H), 3.26-3.10 (m, 5H), 3.00 (dt, J=5.6, 9.2 Hz, 1H), 2.88-2.59 (m, 3H), 2.34-2.04 (m, 3H), 2.03-1.78 (m, 7H); LCMS (ESI, M+1): m/z=625.3.

Example 71

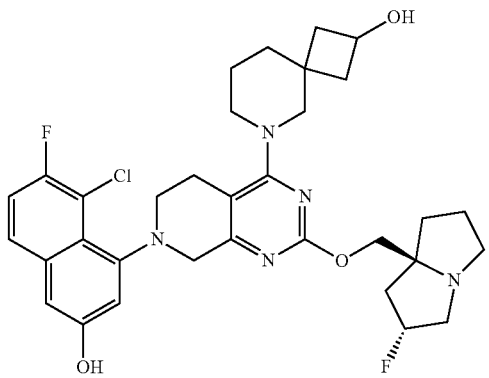 [SMILES: Oc1cc(N2CCc3c(nc(OC[C@@]45CCCN4C[C@H](F)C5)nc3N3CCCC4(CC(O)C4)C3)C2)c2c(Cl)c(F)ccc2c1]

6-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-6-azaspiro[3.5]nonan-2-ol Synthesized according to Example 68. The title compound was obtained as pink solid. $^1$H NMR (400 MHz, METHANOL-d₄) δ=8.64-8.48 (m, 1H), 7.62 (dd, J=5.6, 9.2 Hz, 1H), 7.27 (t, J=8.8 Hz, 1H), 6.95 (s, 2H), 5.45-5.13 (m, 1H), 4.32-4.06 (m, 4H), 3.79-3.39 (m, 5H), 3.30-2.97 (m, 7H), 2.66-2.55 (m, 1H), 2.38-2.08 (m, 5H), 2.04-1.59 (m, 9H); LCMS (ESI, M+1): m/z=626.3.

Example 72

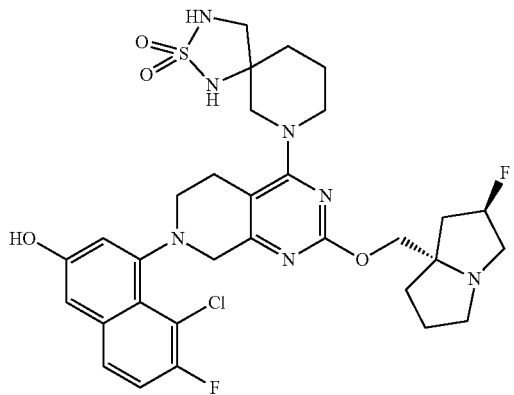 [SMILES: O=S1(=O)NCC2(CCCN(c3nc(OC[C@@]45CCCN4C[C@H](F)C5)nc4c3CCN(c3cc(O)cc5ccc(F)c(Cl)c35)C4)C2)N1]

7-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-2-thia-1,3,7-triazaspiro[4.5]decane 2,2-dioxide Synthesized according to Example 68. The title compound was obtained as off-white solid. ¹H NMR (400 MHz, METHANOL-d4) δ=7.67-7.60 (m, 1H), 7.29 (dt, J=3.2, 8.8 Hz, 1H), 7.01-6.93 (m, 2H), 5.40-5.20 (m, 1H), 4.29 (d, J=17.6 Hz, 1H), 4.22-4.09 (m, 2H), 3.98-3.80 (m, 1H), 3.75-3.35 (m, 6H), 3.29-3.23 (m, 2H), 3.23-3.17 (m, 3H), 3.16-2.96 (m, 2H), 2.74-2.59 (m, 1H), 2.39-2.11 (m, 3H), 2.08-1.92 (m, 4H), 1.91-1.68 (m, 3H); LCMS (ESI, M+1): m/z=676.3.

Example 73

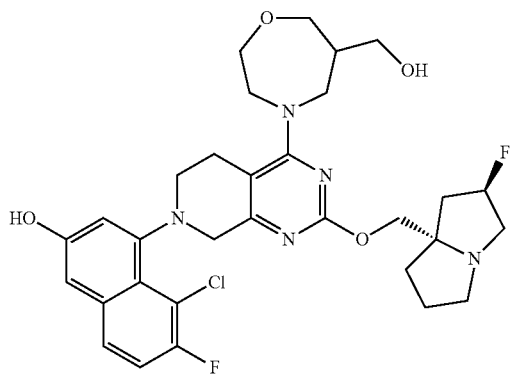 [SMILES: OCC1COCCN(c2nc(OC[C@@]34CCCN3C[C@H](F)C4)nc3c2CCN(c2cc(O)cc4ccc(F)c(Cl)c24)C3)C1]

5-chloro-6-fluoro-4-(2-(((2R,7aS)-2-fluorohexahydro-1H-pyrrolizin-7a-yl)methoxy)-4-(6-(hydroxymethyl)-1,4-oxazepan-4-yl)-5,6-dihydropyrido[3,4-d]pyrimidin-7(8H)-yl)naphthalen-2-ol Synthesized according to Example 68. The title compound was obtained as white solid. ¹H NMR (400 MHz, METHANOL-d4) δ=7.70-7.53 (m, 1H), 7.27 (t, J=8.8 Hz, 1H), 6.95 (dd, J=2.8, 5.1 Hz, 2H), 5.39-5.16 (m, 1H), 4.46-4.26 (m, 1H), 4.26-4.15 (m, 2H), 4.15-4.02 (m, 2H), 3.98-3.76 (m, 3H), 3.76-3.64 (m, 2H), 3.60 (br s, 1H), 3.57-3.37 (m, 4H), 3.28-3.20 (m, 2H), 3.20-2.95 (m, 4H), 2.75-2.64 (m, 1H), 2.53-2.32 (m, 1H), 2.26-2.05 (m, 3H), 2.02-1.80 (m, 3H); LCMS (ESI, M+1): m/z=616.3.

Example 74

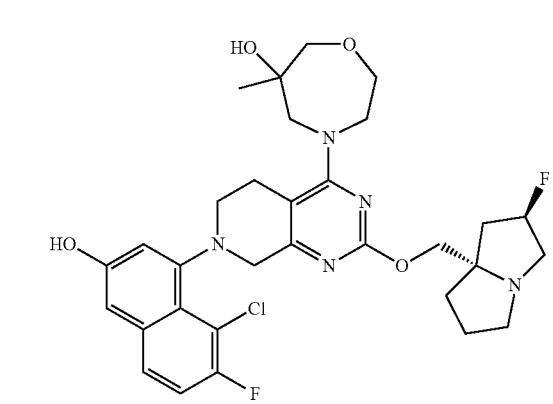 [SMILES: CC1(O)COCCN(c2nc(OC[C@@]34CCCN3C[C@H](F)C4)nc3c2CCN(c2cc(O)cc4ccc(F)c(Cl)c24)C3)C1]

4-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-6-methyl-1,4-oxazepan-6-ol Synthesized according to Example 68. The title compound was obtained as yellow solid. ¹H NMR (400 MHz, METHANOL-d4) δ=7.62 (td, J=6.4, 8.8 Hz, 1H), 7.31-7.24 (m, 1H), 6.99-6.87 (m, 2H), 5.50-5.31 (m, 1H), 4.35-4.29 (m, 1H), 4.28-4.17 (m, 2H), 4.10-4.00 (m, 1H), 4.00-3.92 (m, 1H), 3.91-3.85 (m, 1H), 3.84-3.73 (m, 2H), 3.69-3.59 (m, 2H), 3.58-3.49 (m, 4H), 3.49-3.41 (m, 2H), 3.26-3.17 (m, 2H), 3.16-3.04 (m, 1H), 2.76-2.56 (m, 1H), 2.53-2.31 (m, 2H), 2.26-2.07 (m, 3H), 2.06-1.90 (m, 1H), 1.24-1.14 (m, 3H); LCMS (ESI, M+1): m/z=616.3.

Example 75

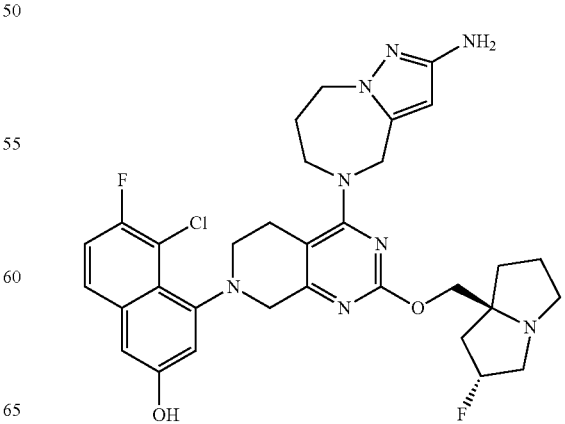

163

4-(4-(2-amino-7,8-dihydro-4H-pyrazolo[1,5-a][1,4]
diazepin-5(6H)-yl)-2-(((2R,7aS)-2-fluorohexahydro-
1H-pyrrolizin-7a-yl)methoxy)-5,6-dihydropyrido[3,
4-d]pyrimidin-7(8H)-yl)-5-chloro-6-
fluoronaphthalen-2-ol Synthesized according to Example 68. The title compound was obtained as white solid. $^1$H NMR (400 MHz, METHANOL-d$_4$) δ=7.62 (dd, J=5.6, 9.1 Hz, 1H), 7.27 (t, J=8.8 Hz, 1H), 6.96 (d, J=2.0 Hz, 1H), 6.91 (s, 1H), 5.55 (s, 1H), 5.40-5.26 (m, 1H), 4.75 (br d, J=2.4 Hz, 1H), 4.70-4.63 (m, 2H), 4.27 (s, 1H), 4.29-4.16 (m, 3H), 4.15-4.09 (m, 1H), 4.08-3.91 (m, 2H), 3.72 (br d, J=17.2 Hz, 1H), 3.57-3.48 (m, 1H), 3.35 (br d, J=1.2 Hz, 2H), 3.23-3.12 (m, 2H), 3.12-3.02 (m, 1H), 2.71-2.59 (m, 1H), 2.40-2.27 (m, 1H), 2.27-2.11 (m, 3H), 2.10-1.97 (m, 3H), 1.97-1.84 (m, 1H); LCMS (ESI, M+1): m/z=637.2.

Example 76 and Example 77

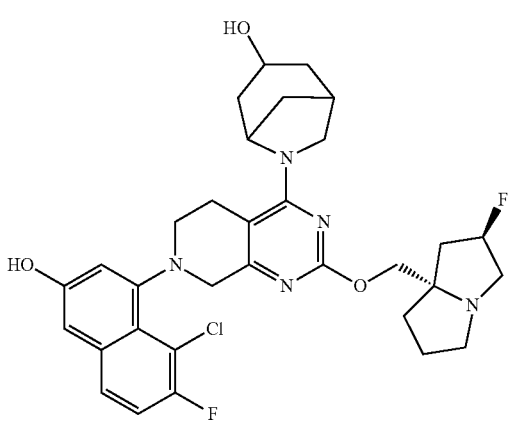 [SMILES: Oc1cc(N2CCc3c(nc(OC[C@@]45CCCN4C[C@H](F)C5)nc3N3CC4CC(O)CC3C4)C2)c2c(Cl)c(F)ccc2c1]

6-(7-(8-chloro-7-fluoro-3-hydroxynaphthalen-1-yl)-
2-(((2R,7aS)-2-fluorohexahydro-1H-pyrrolizin-7a-
yl)methoxy)-5,6,7,8-tetrahydropyrido[3,4-d]pyrimi-
din-4-yl)-6-azabicyclo[3.2.1]octan-3-ol Synthesized according to Example 68. Two isomers of the title compounds were separated with HPLC in the final step. Isomer 1: yellow solid. 1H NMR (400 MHz, METHANOL-d4) δ=7.58 (br dd, J=6.0, 8.8 Hz, 1H), 7.26-7.20 (m, 1H), 6.98-6.87 (m, 1H), 5.39-5.17 (m, 1H), 4.19-4.15 (m, 1H), 4.13-4.07 (m, 3H), 4.03-3.74 (m, 2H), 3.72-3.56 (m, 1H), 3.55-3.43 (m, 2H), 3.24-3.13 (m, 4H), 3.09-2.93 (m, 4H), 2.70-2.48 (m, 2H), 2.23-2.05 (m, 3H), 2.00-1.91 (m, 5H), 1.76-1.63 (m, 2H), 1.35-1.28 (m, 1H); LCMS (ESI, M+1): m/z=612.5. Isomer 2: yellow oil; 1H NMR (400 MHz, METHANOL-d4) δ=7.57 (dd, J=6.0, 8.8 Hz, 1H), 7.22 (t, J=8.8 Hz, 1H), 6.98-6.84 (m, 2H), 5.40-5.17 (m, 1H), 4.87 (br s, 1H), 4.19-4.11 (m, 2H), 4.08-4.02 (m, 1H), 4.00-3.90 (m, 1H), 3.81-3.58 (m, 3H), 3.57-3.34 (m, 2H), 3.26-3.13 (m, 4H), 3.02-2.87 (m, 2H), 2.80-2.52 (m, 2H), 2.50-2.16 (m, 2H), 2.13-2.05 (m, 2H), 2.01-1.91 (m, 3H), 1.89-1.80 (m, 1H), 1.71 (br d, J=11.2 Hz, 1H), 1.55-1.46 (m, 1H), 1.44-1.35 (m, 1H); LCMS (ESI, M+1): m/z=612.5.

164

Example 78

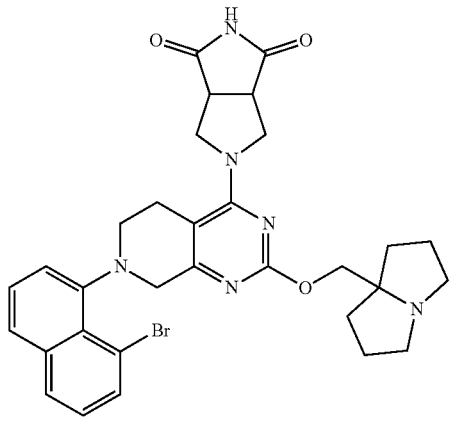 [SMILES: O=C1NC(=O)C2CN(c3nc(OCC45CCCN4CCC5)nc4c3CCN(c3cccc5cccc(Br)c35)C4)CC12]

5-(7-(8-bromonaphthalen-1-yl)-2-((hexahydro-1H-
pyrrolizin-7a-yl)methoxy)-5,6,7,8-tetrahydropyrido
[3,4-d]pyrimidin-4-yl)tetrahydropyrrolo[3,4-c]pyr-
role-1,3(2H,3aH)-dione

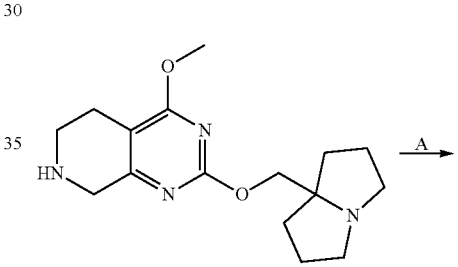

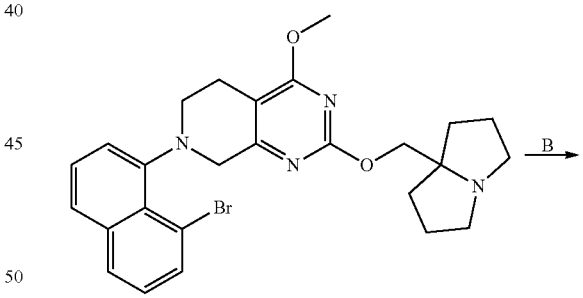

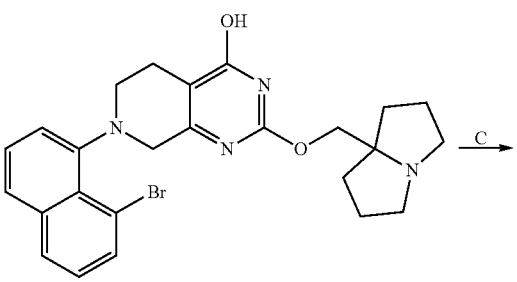

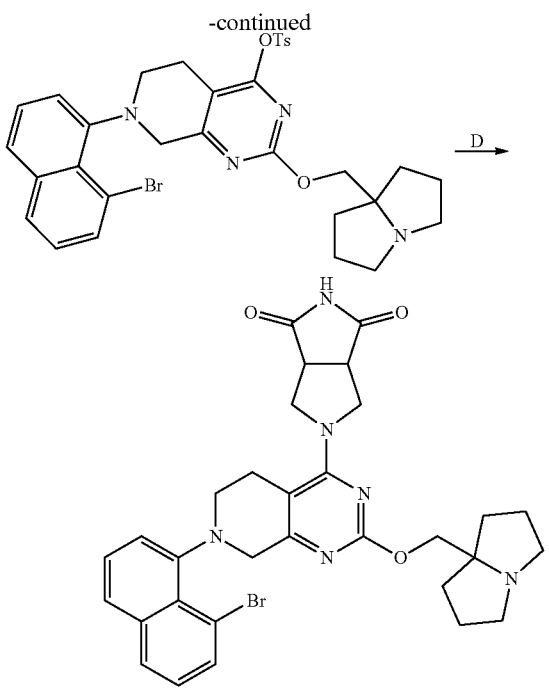

Step A. 7-(8-bromonaphthalen-1-yl)-2-((hexahydro-1H-pyrrolizin-7a-yl)methoxy)-4-methoxy-5,6,7,8-tetrahydropyrido[3,4-d]pyrimidine: A mixture of 2-((hexahydro-1H-pyrrolizin-7a-yl)methoxy)-4-methoxy-5,6,7,8-tetrahydropyrido[3,4-d]pyrimidine (500 mg, 1.0 equiv), 1,8-dibromonaphthalene (1.41 g, 3.0 equiv), BINAP (306 mg, 0.3 equiv), t-BuONa (237 mg, 1.5 equiv) and Pd$_2$(dba)$_3$ (150 mg, 0.1 equiv) in toluene (20 mL) was degassed and purged with N$_2$ for 3 times, and then the mixture was stirred at 90° C. for 3 hours under N$_2$ atmosphere. The mixture was diluted with H$_2$O (10 mL) and extracted with ethyl acetate (3×10 mL). The combined organic layers were dried over anhydrous sodium sulfate, concentrated, and purified by reversed phase flash chromatography [C18, 0.1% formic acid condition] to afford the tittle compound (400 mg, 41% yield) as yellow solid. LCMS (ESI, M+1): m/z=511.2.

Step B. 7-(8-bromonaphthalen-1-yl)-2-((hexahydro-1H-pyrrolizin-7a-yl)methoxy)-5,6,7,8-tetrahydropyrido[3,4-d]pyrimidin-4-ol: To a solution of NaH (47.1 mg, 60% purity, 2.0 equiv) in DMAC (1 mL) was added EtSH (256 mg, 7.0 equiv) at 0° C. under N$_2$ atmosphere. The mixture was stirred at 0° C. for 10 minutes, and then 7-(8-bromonaphthalen-1-yl)-2-((hexahydro-1H-pyrrolizin-7a-yl)methoxy)-4-methoxy-5,6,7,8-tetrahydropyrido[3,4-d]pyrimidine (300 mg, 1.0 equiv) in DMAC (2 mL) was added. The mixture was stirred at 60° C. for 1 hour. The mixture was quenched with saturated NH$_4$Cl (20 mL) at 0° C., and extracted with ethyl acetate (3×10 mL). The combined organic layers were dried over anhydrous Na$_2$SO$_4$, concentrated, and purified by reversed phase flash chromatography [C18, 0.1% formic acid condition] to afford the title compound (125 mg, 82% yield) as yellow solid. LCMS (ESI, M+1): m/z=495.1.

Step C. 7-(8-bromonaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate: To a solution of 7-(8-bromonaphthalen-1-yl)-2-((hexahydro-1H-pyrrolizin-7a-yl)methoxy)-5,6,7,8-tetrahydropyrido[3,4-d]pyrimidin-4-ol (120 mg, 1.0 equiv) in THF (3 mL) were added N-ethyl-N-isopropylpropan-2-amine (78.26 mg, 2.5 equiv) and DMAP (2.96 mg, 0.1 equiv). Then 4-methylbenzene-1-sulfonyl chloride (60.0 mg, 1.3 equiv) was added at 0° C. The solution was stirred at 20° C. for 2 hours. The mixture was diluted with H$_2$O (10 mL) at 0° C. and extracted with ethyl acetate (3×10 mL). The combined organic layers were dried over anhydrous sodium sulfate, concentrated, and purified by reversed phase flash chromatography [C18, 0.1% formic acid condition] to afford the title compound (120 mg, 76% yield) as yellow solid.

Step D. 5-(7-(8-bromonaphthalen-1-yl)-2-((hexahydro-1H-pyrrolizin-7a-yl)methoxy)-5,6,7,8-tetrahydropyrido[3,4-d]pyrimidin-4-yl)tetrahydropyrrolo[3,4-c]pyrrole-1,3(2H,3aH)-dione: To a solution of 7-(8-bromonaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (100 mg, 1.0 equiv) and tetrahydropyrrolo[3,4-c]pyrrole-1,3(2H,3aH)-dione (28.5 mg, 1.3 equiv) in DMF (1 mL) were added N-ethyl-N-isopropylpropan-2-amine (59.7 mg, 3 equiv), and 4 Å molecular sieve (30 mg). The reaction mixture was stirred at 40° C. for 12 hours. The mixture was filtered and purified with prep-HPLC [Waters Xbridge 150×25 mm×5 μm; A: water (10 mM NH$_4$HCO$_3$), B: ACN, B %: 40%-70%, 10 minutes] to afford the title compound (24 mg, 22% yield,) as yellow solid. $^1$H NMR (400 MHz, METHANOL-d4) δ=7.88-7.85 (m, 1H), 7.79 (dd, J=0.8, 7.6 Hz, 1H), 7.73-7.66 (m, 1H), 7.50 (t, J=8.0 Hz, 1H), 7.39-7.32 (m, 1H), 7.31-7.25 (m, 1H), 4.62 (d, J=10.4 Hz, 1H), 4.40-4.15 (m, 4H), 3.80-3.74 (m, 1H), 3.66-3.55 (m, 2H), 3.54-3.44 (m, 3H), 3.43-3.35 (m, 2H), 3.29-3.12 (m, 2H), 3.07-2.96 (m, 2H), 2.74-2.65 (m, 1H), 2.23-2.13 (m, 2H), 2.12-1.97 (m, 4H), 1.95-1.82 (m, 2H); LCMS (ESI, M+1): m/z=617.2.

Example 79

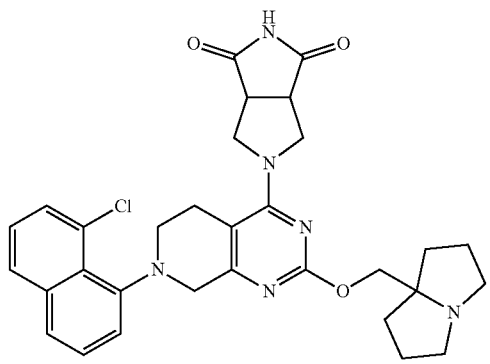 [SMILES: O=C1NC(=O)C2CN(c3nc(OCC45CCCN4CCC5)nc4c3CCN(c3cccc5cccc(Cl)c35)C4)CC12]

5-(7-(8-chloronaphthalen-1-yl)-2-((hexahydro-1H-pyrrolizin-7a-yl)methoxy)-5,6,7,8-tetrahydropyrido[3,4-d]pyrimidin-4-yl)tetrahydropyrrolo[3,4-c]pyrrole-1,3(2H,3aH)-dione

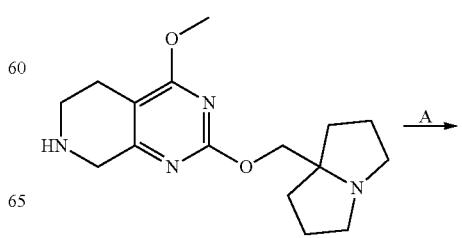

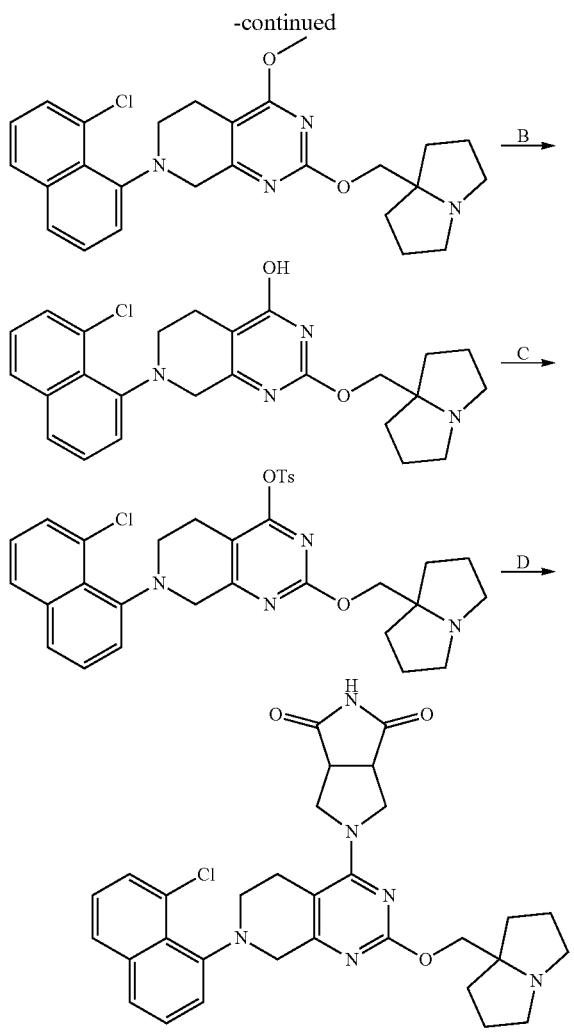

Step A. 7-(8-chloronaphthalen-1-yl)-2-((hexahydro-1H-pyrrolizin-7a-yl)methoxy)-4-methoxy-5,6,7,8-tetrahydropyrido[3,4-d]pyrimidine: To a mixture of 1-bromo-8-chloronaphthalene (600 mg, 1.0 equiv), 2-((hexahydro-1H-pyrrolizin-7a-yl)methoxy)-4-methoxy-5,6,7,8-tetrahydropyrido[3,4-d]pyrimidine (832 mg, 1.1 equiv), $Cs_2CO_3$ (2.43 g, 3.0 equiv), Xantphos (287 mg, 0.2 equiv) in toluene (12 mL) was added $Pd_2(dba)_3$ (227 mg, 0.1 equiv) under $N_2$. The mixture was stirred at 110° C. for 10 hours. The reaction mixture was filtered. The mixture was diluted with water (10 mL) and extracted with ethyl acetate (3×15 mL). The combined organic phase was washed with brine (30 mL), dried over anhydrous sodium sulfate, concentrated, and purified with reversed phase flash chromatography [C18, 0.1% formic acid condition] to afford the title compound (760 mg, 56% yield) as yellow oil; LCMS (ESI, M+1): m/z=465.1. Step B. 7-(8-chloronaphthalen-1-yl)-2-((hexahydro-1H-pyrrolizin-7a-yl)methoxy)-5,6,7,8-tetrahydropyrido[3,4-d]pyrimidin-4-ol: To a mixture of NaH (120 mg, 60% purity, 2.0 equiv) in DMAc (7 mL) was added EtSH (654 mg, 7.0 equiv) at 0° C. and the mixture was stirred at 0° C. for minutes. 7-(8-chloronaphthalen-1-yl)-2-((hexahydro-1H-pyrrolizin-7a-yl)methoxy)-4-methoxy-5,6,7,8-tetrahydropyrido[3,4-d]pyrimidine (700 mg, 1.0 equiv) in DMAc (7 mL) was added at 0° C. and the mixture was stirred at 60° C. for 1 hour. The reaction mixture was quenched with saturated $NH_4Cl$ aqueous (50 mL) at 0° C. and extracted with ethyl acetate (3×50 mL). The combined organic layers were dried over anhydrous $Na_2SO_4$, concentrated, and purified with reversed phase flash chromatography [C18, 0.1% formic acid condition] to afford the title compound (420 mg, 57% yield) as yellow solid. LCMS (ESI, M+1): m/z=451.1.

Step C. 7-(8-chloronaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate: To a solution of 7-(8-chloronaphthalen-1-yl)-2-((hexahydro-1H-pyrrolizin-7a-yl)methoxy)-5,6,7,8-tetrahydropyrido[3,4-d]pyrimidin-4-ol (150 mg, 1.0 equiv), DMAP (4.06 mg, 0.1 equiv), N-ethyl-N-isopropylpropan-2-amine (129 mg, 3.0 equiv) in dichloromethane (3 mL) was added TsCl (88.8 mg, 1.4 equiv) at 0° C. The mixture was stirred at 15° C. for 1 hour. The reaction mixture was quenched with water (5 mL) and extracted with dichloromethane (10 mL). The organic phase was washed with brine (10 mL), dried over anhydrous sodium sulfate, concentrated, and purified by column chromatography [$Al_2O_3$, petroleum ether/ethyl acetate=20/1 to 0/1] to afford the title compound (120 mg, 57% yield) as yellow solid. LCMS (ESI, M+1): m/z=605.1.

Step D. 5-(7-(8-chloronaphthalen-1-yl)-2-((hexahydro-1H-pyrrolizin-7a-yl)methoxy)-5,6,7,8-tetrahydropyrido[3,4-d]pyrimidin-4-yl)tetrahydropyrrolo[3,4-c]pyrrole-1,3(2H,3aH)-dione: A mixture of 7-(8-chloronaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (110 mg, 1.0 equiv), tetrahydropyrrolo[3,4-c]pyrrole-1,3(2H,3aH)-dione (50.9 mg, 2.0 equiv), N-ethyl-N-isopropylpropan-2-amine (70.5 mg, 3.0 equiv), and 4 Å molecular sieve (30 mg) in DMF (1 mL) was stirred at 40° C. for 10 hours. The reaction was filtered and purified with prep-HPLC [column: Phenomenex Synergi C18 150×25 mm×10 μm; mobile phase: water (0.225% FA)-ACN; B %: 11%-41%, 10 minutes] to afford the title compound (64.5 mg, 56% yield, FA) as light yellow solid. $^1$H NMR (400 MHz, methanol-$d_4$) δ=7.82 (dd, J=0.8, 8.0 Hz, 1H), 7.68 (d, J=7.6 Hz, 1H), 7.58-7.44 (m, 2H), 7.40-7.34 (m, 1H), 7.31 (dd, J=0.8, 7.6 Hz, 1H), 4.64-4.56 (m, 1H), 4.53-4.39 (m, 2H), 4.30-4.19 (m, 2H), 3.84-3.57 (m, 5H), 3.55-3.45 (m, 3H), 3.29-3.09 (m, 4H), 2.69 (br d, J=14.8 Hz, 1H), 2.35-2.23 (m, 2H), 2.23-2.11 (m, 4H), 2.10-1.98 (m, 2H); LCMS (ESI, M+1): m/z=573.2.

Example 80

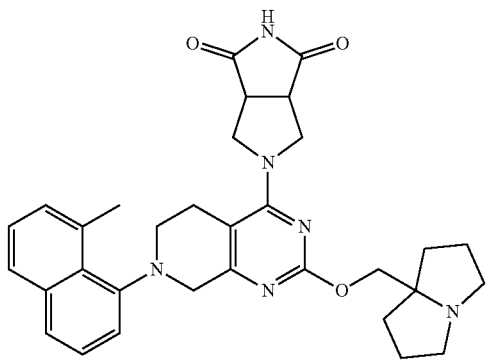 [SMILES: Cc1cccc2cccc(N3CCc4c(nc(OCC56CCCN5CCC6)nc4N4CC5C(=O)NC(=O)C5C4)C3)c12]

5-(2-((hexahydro-1H-pyrrolizin-7a-yl)methoxy)-7-(8-methylnaphthalen-1-yl)-5,6,7,8-tetrahydropyrido[3,4-d]pyrimidin-4-yl)tetrahydropyrrolo[3,4-c]pyrrole-1,3(2H,3aH)-dione

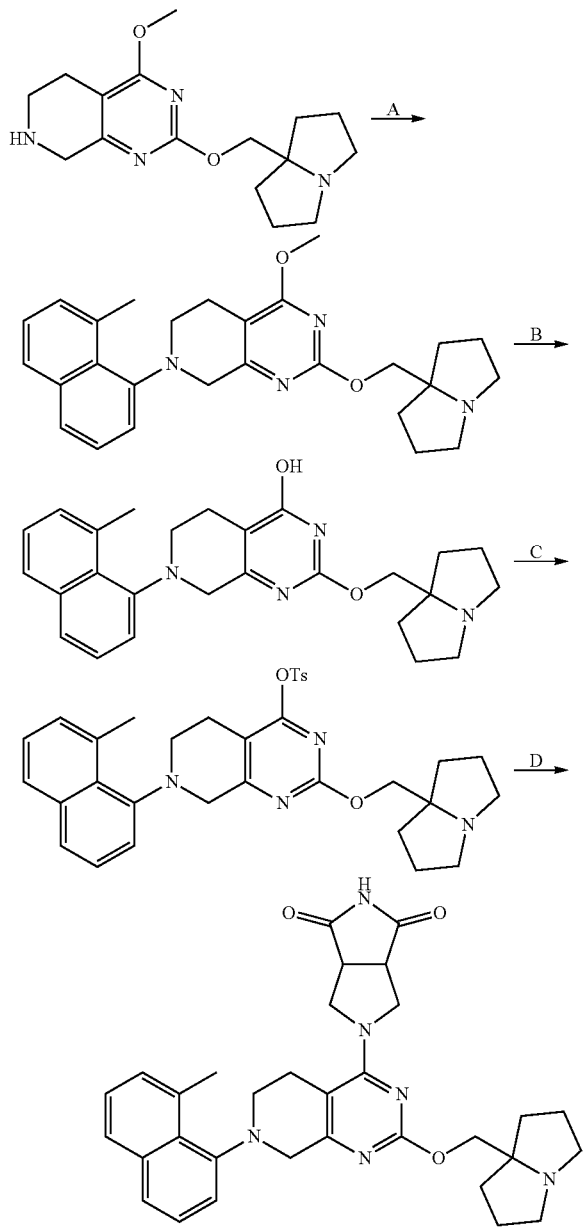

Step A. 2-((hexahydro-1H-pyrrolizin-7a-yl)methoxy)-4-methoxy-7-(8-methylnaphthalen-1-yl)-5,6,7,8-tetrahydropyrido[3,4-d]pyrimidine: To a mixture of 4-methoxy-2-((tetrahydro-1H-pyrrolizin-7a(5H)-yl)methoxy)-5,6,7,8-tetrahydropyrido[3,4-d]pyrimidine (500 mg, 1.0 equiv), 1-bromo-8-methyl-naphthalene (436 mg, 1.2 equiv), Cs$_2$CO$_3$ (1.61 g, 3.0 equiv), Xantphos (190 mg, 0.2 equiv) in toluene (10 mL) was added Pd$_2$(dba)$_3$ (150 mg, 0.1 equiv) under N$_2$. The reaction was stirred at 110° C. for 8 hours. The reaction was filtered and diluted with water (15 mL). The mixture was extracted with ethyl acetate (2×30 mL). The combined organic phase was washed with brine (50 mL), dried over anhydrous Na$_2$SO$_4$, concentrated and purified with reversed phase flash chromatography [C18, 0.1% formic acid condition] to afford the title compound (490 mg, 60% yield) as yellow oil; LCMS (ESI, M+1): m/z=445.1.

Step B. 2-((hexahydro-1H-pyrrolizin-7a-yl)methoxy)-7-(8-methylnaphthalen-1-yl)-5,6,7,8-tetrahydropyrido[3,4-d]pyrimidin-4-ol: To the mixture of NaH (86.0 mg, 60% purity, 2.0 equiv) in DMAC (5 mL) was added EtSH (467 mg, 7.0 equiv) at 0° C. for 5 minutes and the mixture was stirred at 0° C. for 10 minutes. 2-((hexahydro-1H-pyrrolizin-7a-yl)methoxy)-4-methoxy-7-(8-methylnaphthalen-1-yl)-5,6,7,8-tetrahydropyrido[3,4-d]pyrimidine (478 mg, 1.0 equiv) in DMAC (5 mL) was added at 0° C. The mixture was stirred at 60° C. for 1 hour. The reaction was quenched with saturated NH$_4$Cl aqueous (20 mL) at 0° C. The mixture was diluted with H$_2$O (60 mL) and extracted with ethyl acetate (3×20 mL). The combined organic layers were dried over anhydrous Na$_2$SO$_4$, concentrated and purified with reversed phase flash chromatography [C18, 0.1% formic acid condition] to afford the title compound (100 mg, 17% yield) as yellow solid. LCMS (ESI, M+1): m/z=431.2.

Step C. 2-((hexahydro-1H-pyrrolizin-7a-yl)methoxy)-7-(8-methylnaphthalen-1-yl)-5,6,7,8-tetrahydropyrido[3,4-d]pyrimidin-4-yl 4-methylbenzenesulfonate: To a solution of 2-((hexahydro-1H-pyrrolizin-7a-yl)methoxy)-7-(8-methylnaphthalen-1-yl)-5,6,7,8-tetrahydropyrido[3,4-d]pyrimidin-4-ol (100 mg, 1.0 equiv), DMAP (2.84 mg, 0.1 equiv), N-ethyl-N-isopropylpropan-2-amine (90.0 mg, 3.0 equiv) in DCM (3 mL) was added TsCl (62.0 mg, 1.4 equiv) at 0° C. The mixture was stirred at 15° C. for 1 hour. The reaction mixture was quenched with water (5 mL) and extracted with DCM (10 mL). The combined organic phase was washed with brine (10 mL), dried over anhydrous Na$_2$SO$_4$, concentrated, and purified with column chromatography [Al$_2$O$_3$, petroleum ether/ethyl acetate=20/1 to 0/1] to afford the title compound (90.0 mg, 61% yield) as yellow oil; LCMS (ESI, M+1): m/z=585.2.

Step D. 5-(2-((hexahydro-1H-pyrrolizin-7a-yl)methoxy)-7-(8-methylnaphthalen-1-yl)-5,6,7,8-tetrahydropyrido[3,4-d]pyrimidin-4-yl)tetrahydropyrrolo[3,4-c]pyrrole-1,3(2H,3aH)-dione: A mixture of 2-((hexahydro-1H-pyrrolizin-7a-yl)methoxy)-7-(8-methylnaphthalen-1-yl)-5,6,7,8-tetrahydropyrido[3,4-d]pyrimidin-4-yl 4-methylbenzenesulfonate (90.0 mg, 1.0 equiv), 2,3,3a,6a-tetrahydro-1H-pyrrolo[3,4-c]pyrrole-4,6-dione (43.1 mg, 2.0 equiv), N-ethyl-N-isopropylpropan-2-amine (59.7 mg, 3.0 equiv) and 4 Å molecular sieve (30.0 mg) in DMF (1 mL) was stirred at 40° C. for 10 hours. The mixture was filtered and purified with prep-HPLC [column: Phenomenex Synergi C18 150×25 mm×10 μm; mobile phase: water (0.225% FA)-ACN; B %: 11%-44%, 11 minutes] to afford the title compound (36.6 mg, 39% yield, 0.67FA) as white solid. $^1$H NMR (400 MHz, methanol-d$_4$) δ=7.67 (dd, J=8.0, 16.4 Hz, 2H), 7.41 (t, J=7.6 Hz, 1H), 7.35-7.25 (m, 2H), 7.23 (d, J=7.2 Hz, 1H), 4.65-4.54 (m, 1H), 4.44-4.30 (m, 2H), 4.26 (d, J=12.0 Hz, 1H), 4.02 (d, J=17.6 Hz, 1H), 3.78 (dd, J=8.0, 11.6 Hz, 1H), 3.67 (d, J=17.6 Hz, 1H), 3.58-3.39 (m, 6H), 3.23-3.14 (m, 2H), 3.12-3.03 (m, 2H), 2.87 (s, 3H), 2.76-2.62 (m, 1H), 2.26-2.16 (m, 2H), 2.15-2.01 (m, 4H), 2.00-1.90 (m, 2H); LCMS (ESI, M+1): m/z=553.2.

Example 81

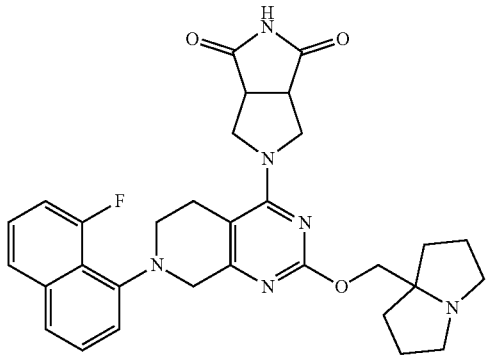

5-(7-(8-fluoronaphthalen-1-yl)-2-((hexahydro-1H-pyrrolizin-7a-yl)methoxy)-5,6,7,8-tetrahydropyrido[3,4-d]pyrimidin-4-yl)tetrahydropyrrolo[3,4-c]pyrrole-1,3(2H,3aH)-dione

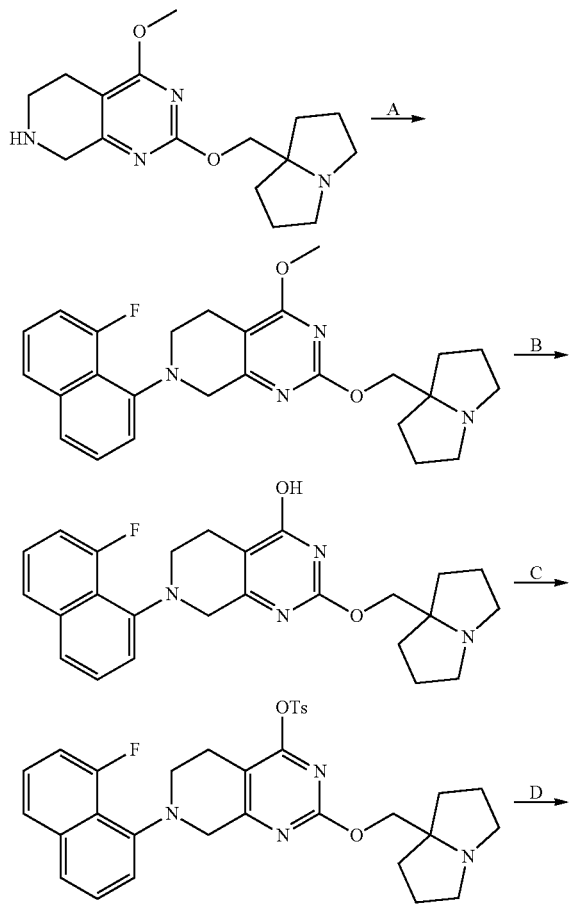

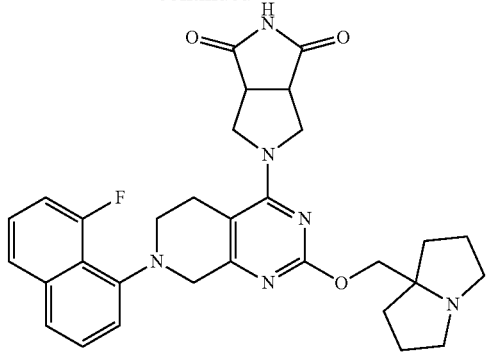 [SMILES: O=C1NC(=O)C2CN(c3nc(OCC45CCCN4CCC5)nc4c3CCN(c3cccc5cccc(F)c35)C4)CC12]

Step A. 7-(8-fluoronaphthalen-1-yl)-2-((hexahydro-1H-pyrrolizin-7a-yl)methoxy)-4-methoxy-5,6,7,8-tetrahydropyrido[3,4-d]pyrimidine: To a solution of 4-methoxy-2-((tetrahydro-1H-pyrrolizin-7a(5H)-yl)methoxy)-5,6,7,8-tetrahydropyrido[3,4-d]pyrimidine (200 mg, 1.0 equiv), 1-bromo-8-fluoro-naphthalene (148 mg, 1.0 equiv), RuPhos (61.3 mg, 0.2 equiv) and $Cs_2CO_3$ (642 mg, 3.0 equiv) in toluene (2 mL) was added $Pd_2(dba)_3$ (60.2 mg, 0.1 equiv). The mixture was stirred at 110° C. for 12 hours. The mixture was diluted with water (10 mL) and extracted with ethyl acetate (3×10 mL). The combined organic layers were dried over anhydrous sodium sulfate, concentrated, and purified by reversed phase flash chromatography [C18, 0.1% formic acid condition] to afford the title compound (110 mg, 34% yield) as yellow liquid; LCMS (ESI, M+1): m/z=449.2.

Step B. 7-(8-fluoronaphthalen-1-yl)-2-((hexahydro-1H-pyrrolizin-7a-yl)methoxy)-5,6,7,8-tetrahydropyrido[3,4-d]pyrimidin-4-ol: To a solution of NaH (44.6 mg, 60% purity, 2.0 equiv) in DMAC (3 mL) was added EtSH (200 mg, 5.8 equiv) at 10° C. The mixture was stirred at 10° C. for 0.5 hour. Then 7-(8-fluoronaphthalen-1-yl)-2-((hexahydro-1H-pyrrolizin-7a-yl)methoxy)-4-methoxy-5,6,7,8-tetrahydropyrido[3,4-d]pyrimidine (250 mg, 1.0 equiv) was added to the reaction. The reaction was stirred at 60° C. for 1 hour. The mixture was diluted with water (10 mL) and extracted with ethyl acetate (3×10 mL). The combined organic layers were dried over anhydrous sodium sulfate, concentrated to afford the title compound (270 mg, crude) as yellow liquid; LCMS (ESI, M+1): m/z=435.1.

Step C. 7-(8-fluoronaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate: To a solution of 7-(8-fluoronaphthalen-1-yl)-2-((hexahydro-1H-pyrrolizin-7a-yl)methoxy)-5,6,7,8-tetrahydropyrido[3,4-d]pyrimidin-4-ol (270 mg, 1 equiv), N-ethyl-N-isopropylpropan-2-amine (241 mg, 3.0 equiv) and DMAP (7.59 mg, 0.1 equiv) in DCM (4 mL) was added TsCl (178 mg, 1.5 equiv) at 0° C. The mixture was stirred at 20° C. for 12 hours. The mixture was diluted with water (10 mL) and extracted with ethyl acetate (3×10 mL). The combined organic layers were dried over anhydrous sodium sulfate, concentrated and purified by column chromatography [$Al_2O_3$, Petroleum ether/Ethyl acetate=10/1 to 1/1] to afford the title compound (120 mg, 33% yield) as yellow liquid; LCMS (ESI, M+1): m/z=589.2.

Step D. 5-(7-(8-fluoronaphthalen-1-yl)-2-((hexahydro-1H-pyrrolizin-7a-yl)methoxy)-5,6,7,8-tetrahydropyrido[3,4-d]pyrimidin-4-yl)tetrahydropyrrolo[3,4-c]pyrrole-1,3(2H,3aH)-dione: To a solution of 7-(8-fluoronaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (110 mg, 1.0 equiv), 2,3,3a,6a- tetrahydro-1H-pyrrolo[3,4-c]pyrrole-4,6-dione (78.6 mg, 3.0 equiv) and 4 Å molecular sieve (10 mg) in DMF (1 mL) was added N-ethyl-N-isopropylpropan-2-amine (72.4 mg, 3.0 equiv). The mixture was stirred at 40° C. for 12 hours. The residue was filtered and washed with DMF (1 mL), and purified with prep-HPLC [Waters Xbridge 150×25 mm×5 μm; A: water (10 mM $NH_4HCO_3$), B: ACN; B %: 25%-55% over 9 min] to give a crude product. The crude product was purified with prep-HPLC [Phenomenex Gemini-NX C18 75×30 mm×3 μm; A: water (0.225% FA), B: ACN; B %: 12%-42%, 7 minutes] to afford the title compound (11.0 mg, 10% yield) as yellow solid. $^1$H NMR (400 MHz, METHANOL-$d_4$) δ=7.69 (d, J=7.8 Hz, 1H), 7.61 (d, J=8.4 Hz, 1H), 7.49-7.39 (m, 2H), 7.23-7.12 (m, 2H), 4.67-4.54 (m, 1H), 4.41 (br d, J=1.6 Hz, 2H), 4.35-4.11 (m, 2H), 4.09-3.92 (m, 1H), 3.86-3.63 (m, 2H), 3.61-3.46 (m, 5H), 3.30-3.22 (m, 1H), 3.19-3.10 (m, 2H), 3.05-2.83 (m, 1H), 2.67 (br dd, J=5.6, 10.4 Hz, 1H), 2.29-2.20 (m, 2H), 2.20-2.06 (m, 4H), 2.05-1.96 (m, 2H); LCMS (ESI, M+1): m/z=557.1.

General procedure for the preparation of EXAMPLE 82 to 171: A mixture of 7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl 4-methylbenzenesulfonate (33 μmol, 1 equiv), amine (2 equiv), and N-ethyl-N-isopropylpropan-2-amine (5 equiv) in NMP (1 mL) was stirred at 120° C. for 16 hours. Then the mixture was cooled to room temperature, the solvent was evaporated under reduced pressure, and the residue was dissolved in the DMSO (1 mL). DMSO solution was filtered, analyzed by LCMS and subjected to HPLC purification (acetonitrile/methanol, ammonia) to give the product.

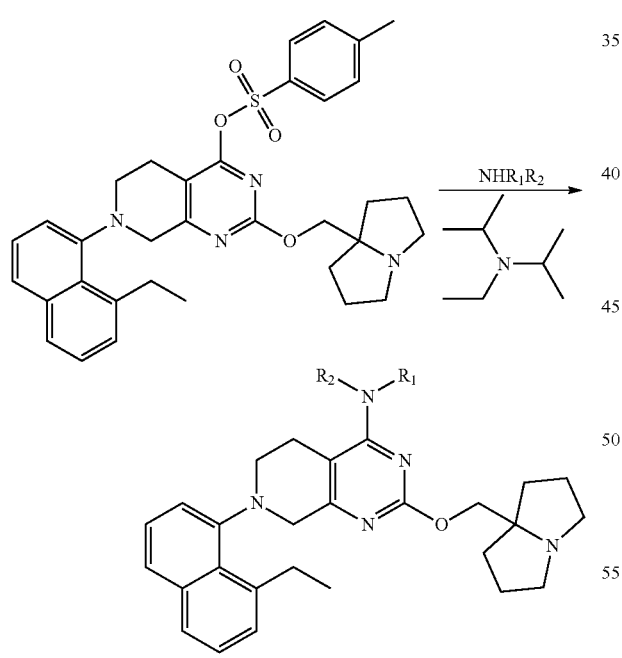

TABLE 1

| MS for EXAMPLE 82 to 171. | |
|---|---|
| EXAMPLE No. | Obs. M + 1 |
| 82 | 578.4 |

TABLE 1-continued

| MS for EXAMPLE 82 to 171. | |
|---|---|
| EXAMPLE No. | Obs. M + 1 |
| 83 | 645.2 |
| 84 | 608.2 |
| 85 | 631.4 |
| 86 | 558.4 |
| 87 | 594.2 |
| 88 | 595.4 |
| 89 | 585.2 |
| 90 | 604.4 |
| 91 | 598.4 |
| 92 | 556.4 |
| 93 | 593.6 |
| 94 | 592.4 |
| 95 | 570.4 |
| 96 | 579.4 |
| 97 | 542.4 |
| 98 | 528.4 |
| 99 | 579.4 |
| 100 | 592.4 |
| 101 | 560.4 |
| 102 | 621.4 |
| 103 | 571.2 |
| 104 | 595.2 |
| 105 | 569.4 |
| 106 | 619.2 |
| 107 | 556.6 |
| 108 | 619.2 |
| 109 | 558.4 |
| 110 | 596.2 |
| 111 | 542.4 |
| 112 | 588.4 |
| 113 | 530.4 |
| 114 | 557.4 |
| 115 | 578.4 |
| 116 | 578.4 |
| 117 | 576.2 |
| 118 | 593.4 |
| 119 | 540.4 |
| 120 | 606.4 |
| 121 | 540.4 |
| 122 | 594.4 |
| 123 | 622.2 |
| 124 | 562.2 |
| 125 | 605.2 |
| 126 | 607.4 |
| 127 | 539.2 |
| 128 | 509.4 |
| 129 | 584.4 |
| 130 | 586.4 |
| 131 | 556.4 |
| 132 | 579.2 |
| 133 | 556.4 |
| 134 | 555.2 |
| 135 | 609.2 |
| 136 | 541.4 |
| 137 | 595.4 |
| 138 | 554.2 |
| 139 | 567.2 |
| 140 | 690.2 |
| 141 | 567.4 |
| 142 | 602.2 |
| 143 | 635.4 |
| 144 | 628.4 |
| 145 | 550.4 |
| 146 | 629.4 |
| 147 | 542.4 |
| 148 | 541.6 |
| 149 | 554.2 |
| 150 | 576.2 |
| 151 | 579.4 |
| 152 | 607.2 |
| 153 | 541.2 |
| 154 | 589.4 |
| 155 | 606.4 |
| 156 | 541.4 |
| 157 | 576.2 |
| 158 | 564.2 |

TABLE 1-continued
MS for EXAMPLE 82 to 171.
| EXAMPLE No. | Obs. M + 1 |
|---|---|
| 159 | 590.2 |
| 160 | 566.4 |
| 161 | 585.3 |
| 162 | 594.4 |
| 163 | 648.2 |
| 164 | 565.2 |
| 165 | 627.2 |
| 166 | 623.2 |
| 167 | 542.2 |
| 168 | 581.2 |
| 169 | 539.2 |
| 170 | 524.3 |
| 171 | 544.2 |
Example 82
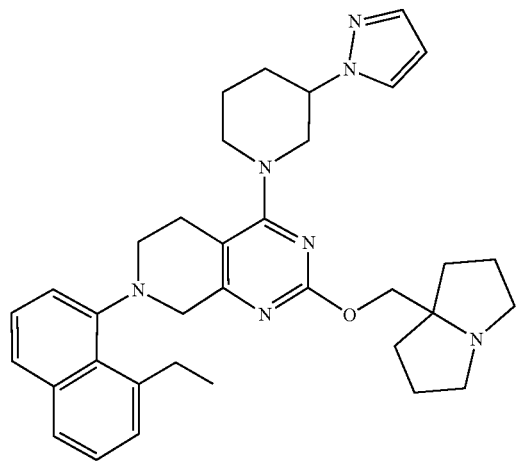
4-(3-(1H-pyrazol-1-yl)piperidin-1-yl)-7-(8-ethyl-naphthalen-1-yl)-2-((tetrahydro-1H-pyrrolizin-7a (5H)-yl)methoxy)-5,6,7,8-tetrahydropyrido[3,4-d] pyrimidine
Example 83
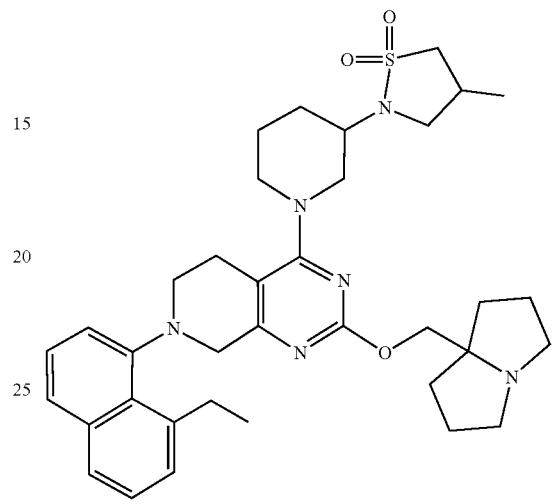
2-(1-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)piperidin-3-yl)-4-methylisothiazolidine 1,1-dioxide
Example 84
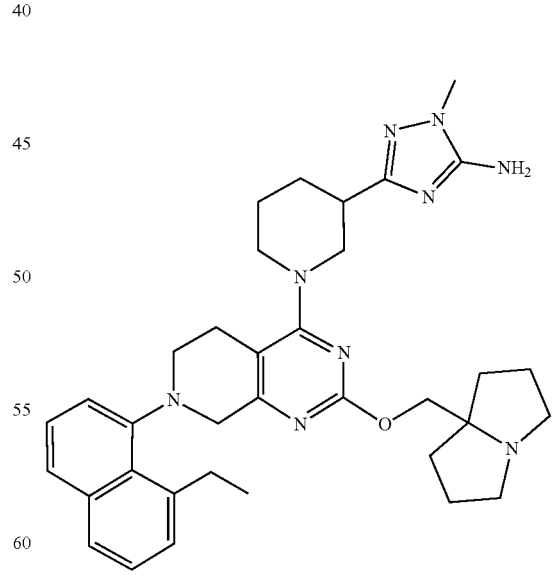

177

3-(1-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)piperidin-3-yl)-1-methyl-1H-1,2,4-triazol-5-amine Example 85

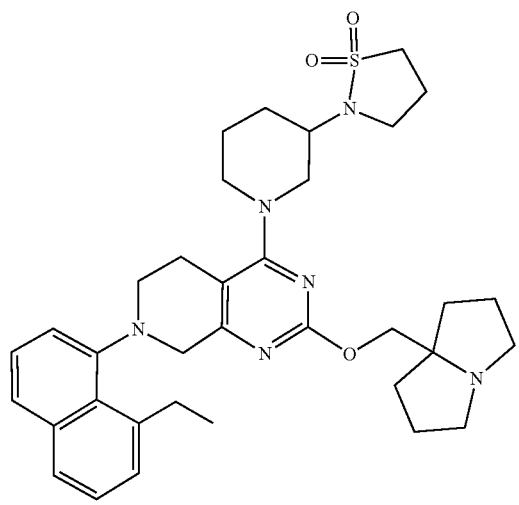

2-(1-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)piperidin-3-yl)isothi-azolidine 1,1-dioxide Example 86

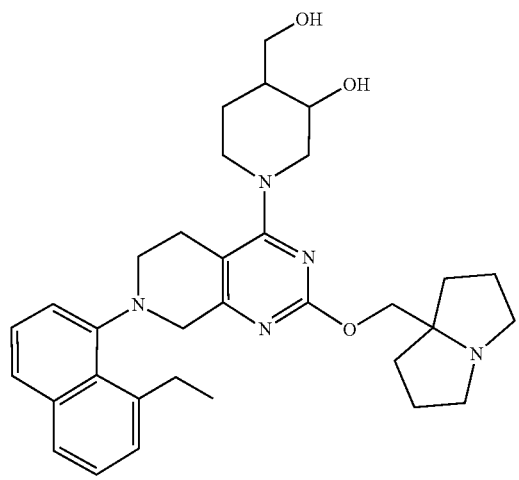 [SMILES: CCc1cccc2cccc(N3CCc4c(nc(OCC56CCCN5CCC6)nc4N4CCC(CO)C(O)C4)C3)c12]

178

1-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)-4-(hydroxymethyl)piperidin-3-ol Example 87

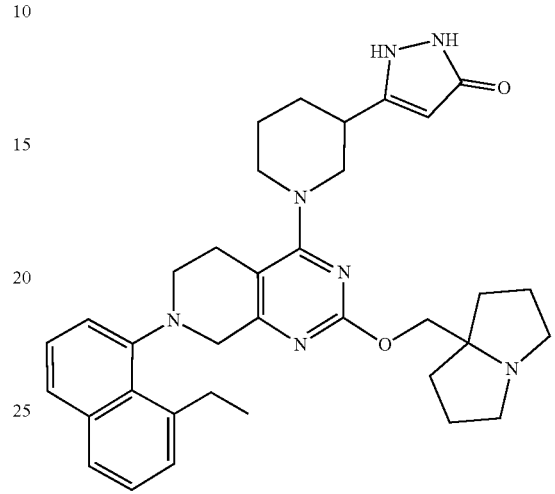

5-(1-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)piperidin-3-yl)-1,2-dihydro-3H-pyrazol-3-one Example 88

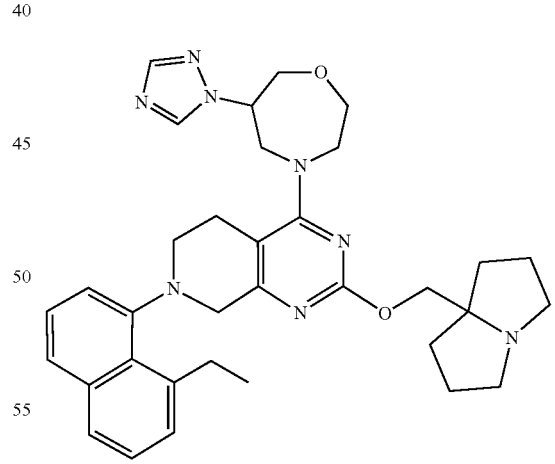

4-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)-6-(1H-1,2,4-triazol-1-yl)-1,4-oxazepane Example 89

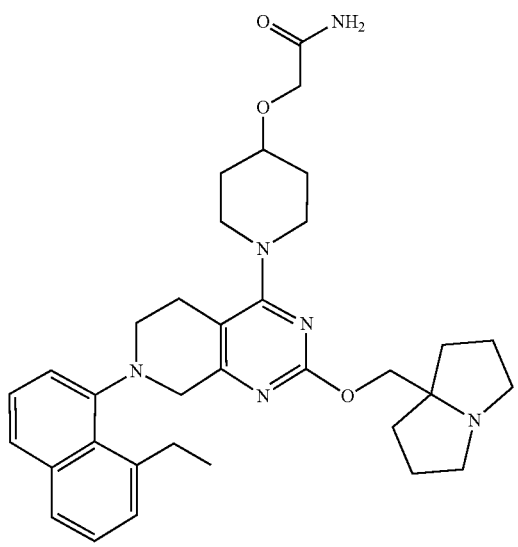 [SMILES: CCc1cccc2cccc(N3CCc4c(nc(OCC56CCCN5CCC6)nc4N4CCC(OCC(N)=O)CC4)C3)c12]

2-((1-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)piperidin-4-yl)oxy)acetamide Example 90

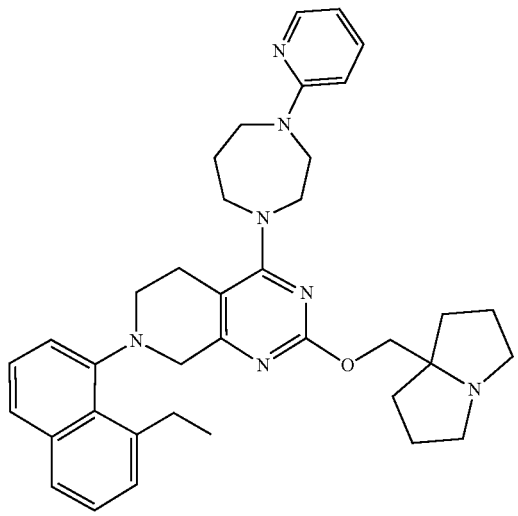 [SMILES: CCc1cccc2cccc(N3CCc4c(nc(OCC56CCCN5CCC6)nc4N4CCCN(c5ccccn5)CC4)C3)c12]

7-(8-ethylnaphthalen-1-yl)-4-(4-(pyridin-2-yl)-1,4-diazepan-1-yl)-2-((tetrahydro-1H-pyrrolizin-7a(5H)-yl)methoxy)-5,6,7,8-tetrahydropyrido[3,4-d]pyrimidine Example 91

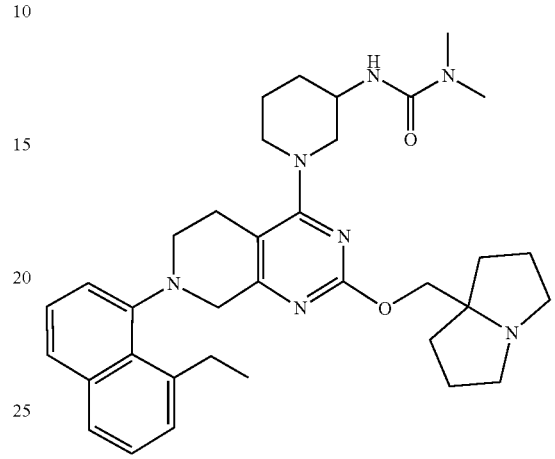

3-(1-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)piperidin-3-yl)-1,1-dimethylurea Example 92

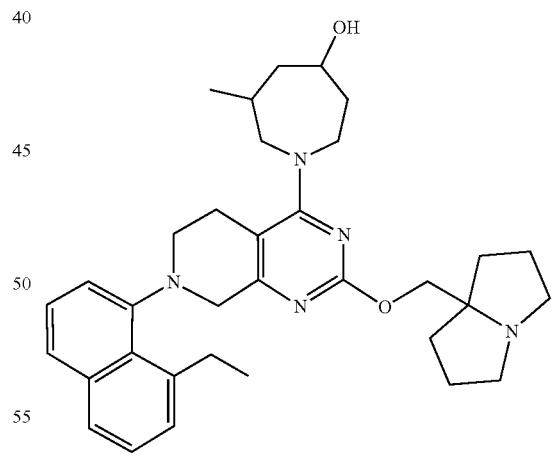

181

1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-6-methylazepan-4-ol Example 93

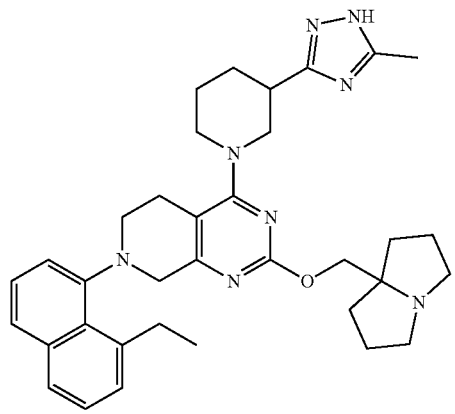 [SMILES: CCc1cccc2cccc(N3CCc4c(nc(OCC56CCCN5CCC6)nc4N4CCCC(c5n[nH]c(C)n5)C4)C3)c12]

7-(8-ethylnaphthalen-1-yl)-4-(3-(5-methyl-1H-1,2,4-triazol-3-yl)piperidin-1-yl)-2-((tetrahydro-1H-pyrrolizin-7a(5H)-yl)methoxy)-5,6,7,8-tetrahydropyrido[3,4-d]pyrimidine Example 94

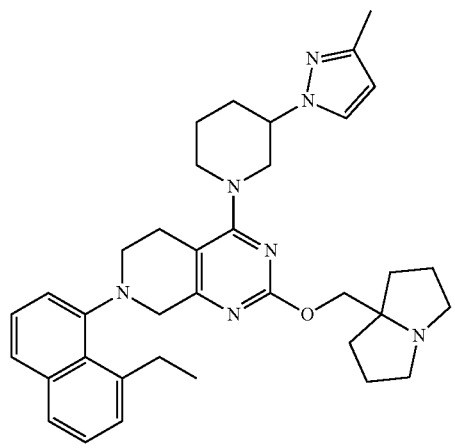 [SMILES: CCc1cccc2cccc(N3CCc4c(nc(OCC56CCCN5CCC6)nc4N4CCCC(n5ccc(C)n5)C4)C3)c12]

182

7-(8-ethylnaphthalen-1-yl)-4-(3-(3-methyl-1H-pyrazol-1-yl)piperidin-1-yl)-2-((tetrahydro-1H-pyrrolizin-7a(5H)-yl)methoxy)-5,6,7,8-tetrahydropyrido[3,4-d]pyrimidine Example 95

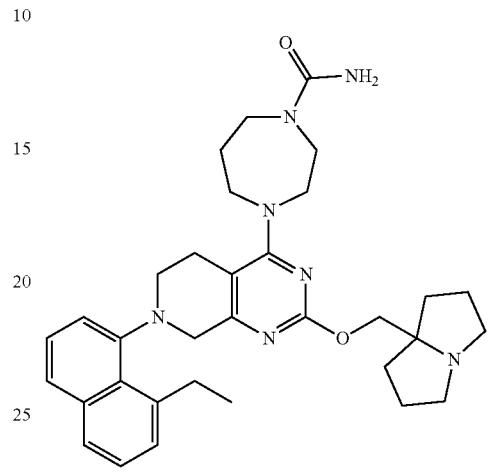

4-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-1,4-diazepane-1-carboxamide Example 96

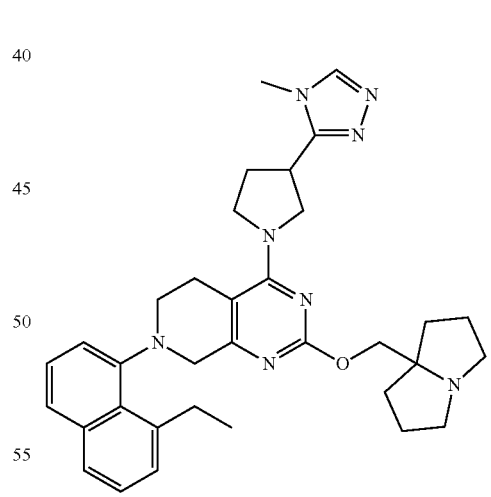

183

7-(8-ethylnaphthalen-1-yl)-4-(3-(4-methyl-4H-1,2,4-triazol-3-yl)pyrrolidin-1-yl)-2-((tetrahydro-1H-pyrrolizin-7a(5H)-yl)methoxy)-5,6,7,8-tetrahydropyrido[3,4-d]pyrimidine Example 97

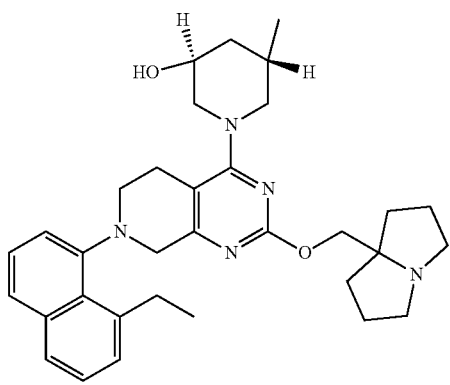 [SMILES: CCc1cccc2cccc(N3CCc4c(nc(OCC56CCCN5CCC6)nc4N4C[C@@H](C)C[C@H](O)C4)C3)c12]

(3S,5S)-1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-5-methylpiperidin-3-ol Example 98

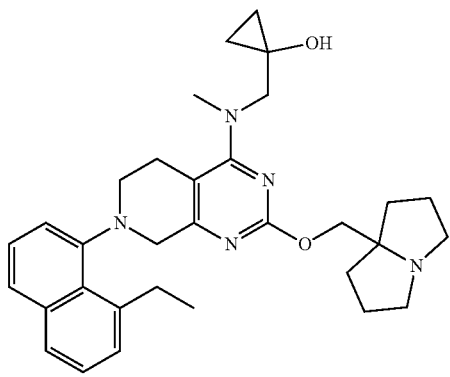 [SMILES: CCc1cccc2cccc(N3CCc4c(nc(OCC56CCCN5CCC6)nc4N(C)CC4(O)CC4)C3)c12]

184

1-(((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)methyl)cyclopropan-1-ol Example 99

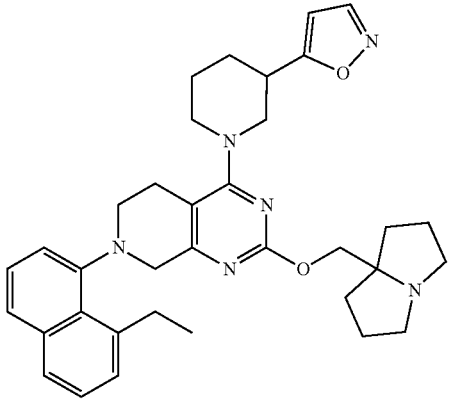 [SMILES: CCc1cccc2cccc(N3CCc4c(nc(OCC56CCCN5CCC6)nc4N4CCCC(c5ccno5)C4)C3)c12]

5-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)isoxazole Example 100

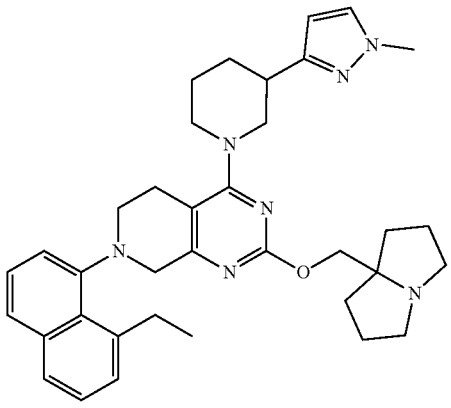 [SMILES: CCc1cccc2cccc(N3CCc4c(nc(OCC56CCCN5CCC6)nc4N4CCCC(c5ccn(C)n5)C4)C3)c12]

185

7-(8-ethylnaphthalen-1-yl)-4-(3-(1-methyl-1H-pyra-
zol-3-yl)piperidin-1-yl)-2-((tetrahydro-1H-pyr-
rolizin-7a(5H)-yl)methoxy)-5,6,7,8-tetrahydropyrido
[3,4-d]pyrimidine Example 101

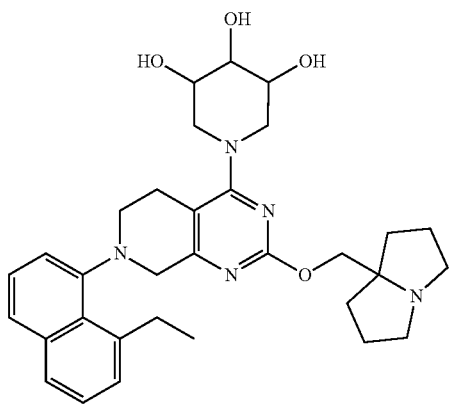 [SMILES: CCc1cccc2cccc(N3CCc4c(nc(OCC56CCCN5CCC6)nc4N4CC(O)C(O)C(O)C4)C3)c12]

1-(7-(8-ethylnaphthalen-1-yl)-2-((tetrahydro-1H-
pyrrolizin-7a(5H)-yl)methoxy)-5,6,7,8-tetrahydro-
pyrido[3,4-d]pyrimidin-4-yl)piperidine-3,4,5-triol Example 102

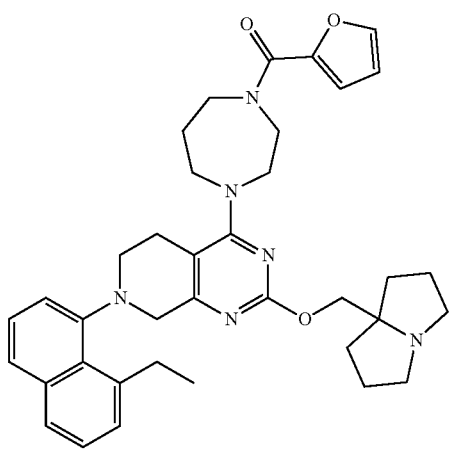 [SMILES: CCc1cccc2cccc(N3CCc4c(nc(OCC56CCCN5CCC6)nc4N4CCCN(C(=O)c5ccco5)CC4)C3)c12]

186

(4-(7-(8-ethylnaphthalen-1-yl)-2-((tetrahydro-1H-
pyrrolizin-7a(5H)-yl)methoxy)-5,6,7,8-tetrahydro-
pyrido[3,4-d]pyrimidin-4-yl)-1,4-diazepan-1-yl)
(furan-2-yl)methanone Example 103

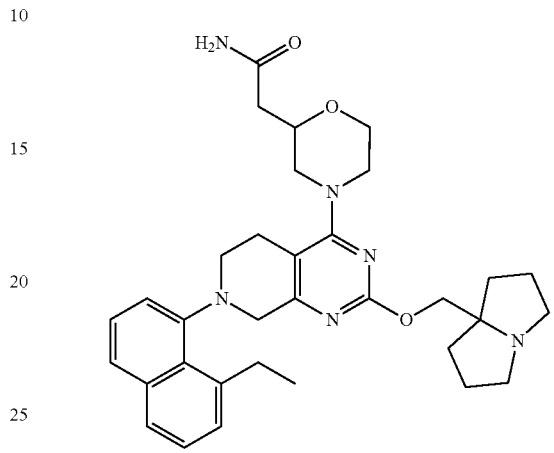

2-(4-(7-(8-ethylnaphthalen-1-yl)-2-((tetrahydro-1H-
pyrrolizin-7a(5H)-yl)methoxy)-5,6,7,8-tetrahydro-
pyrido[3,4-d]pyrimidin-4-yl)morpholin-2-yl)acet-
amide Example 104

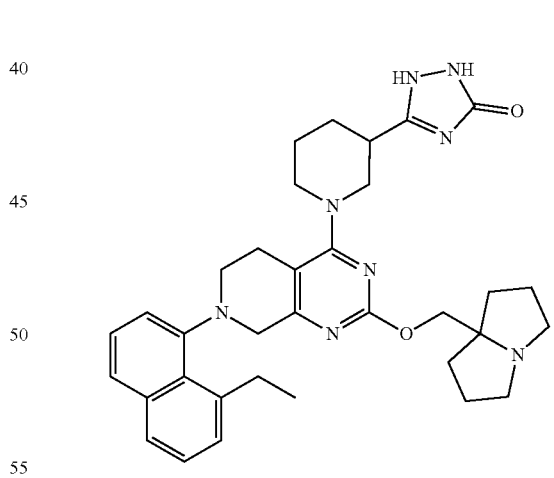

187

5-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-1,2-dihydro-3H-1,2,4-triazol-3-one Example 105

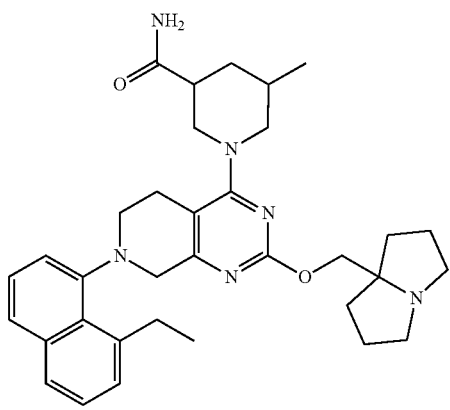 [SMILES: CCc1cccc2cccc(N3CCc4c(nc(OCC56CCCN5CCC6)nc4N4CC(C)CC(C(N)=O)C4)C3)c12]

1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-5-methylpiperidine-3-carboxamide Example 106

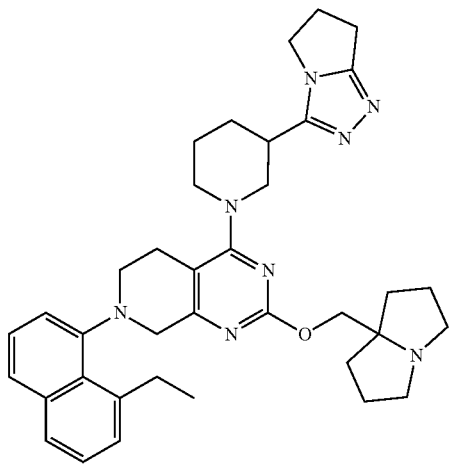 [SMILES: CCc1cccc2cccc(N3CCc4c(nc(OCC56CCCN5CCC6)nc4N4CCCC(c5nnc6n5CCC6)C4)C3)c12]

188

4-(3-(6,7-dihydro-5H-pyrrolo[2,1-c][1,2,4]triazol-3-yl)piperidin-1-yl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidine Example 107

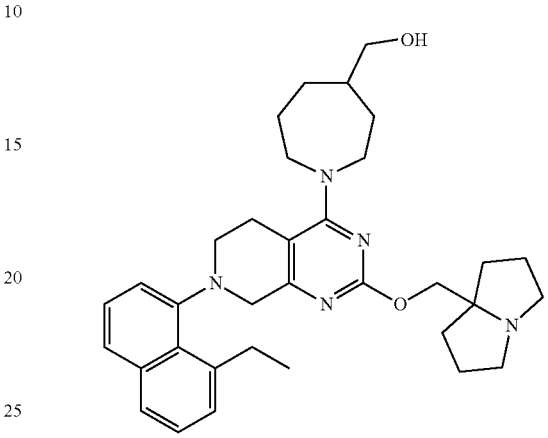

(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)azepan-4-yl)methanol Example 108

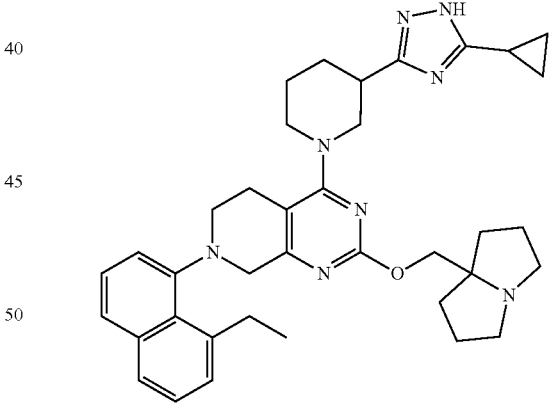

| 189 | 190 |
|---|---|
| 4-(3-(5-cyclopropyl-1H-1,2,4-triazol-3-yl)piperidin-1-yl)-7-(8-ethylnaphthalen-1-yl)-2-((tetrahydro-1H-pyrrolizin-7a(5H)-yl)methoxy)-5,6,7,8-tetrahydro-pyrido[3,4-d]pyrimidine | 1-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)-3-(trifluoromethyl)piperidin-3-ol |
| Example 109 | Example 111 |

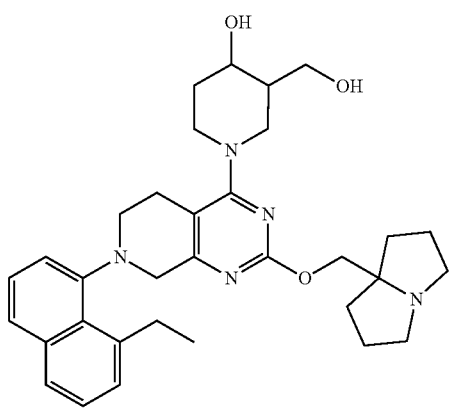 [SMILES: CCc1cccc2cccc(N3CCc4c(nc(OCC56CCCN5CCC6)nc4N4CCC(O)C(CO)C4)C3)c12]

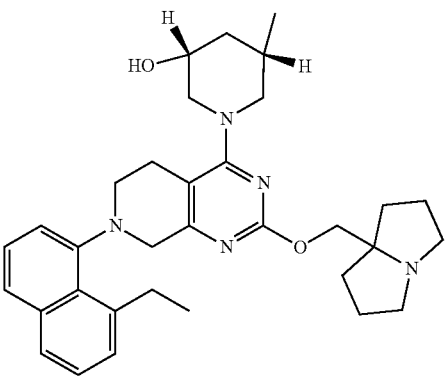 [SMILES: CCc1cccc2cccc(N3CCc4c(nc(OCC56CCCN5CCC6)nc4N4C[C@@H](C)C[C@@H](O)C4)C3)c12]

1-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)-3-(hydroxymethyl)piperidin-4-ol (3R,5S)-1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-5-methylpiperidin-3-ol Example 110

Example 112

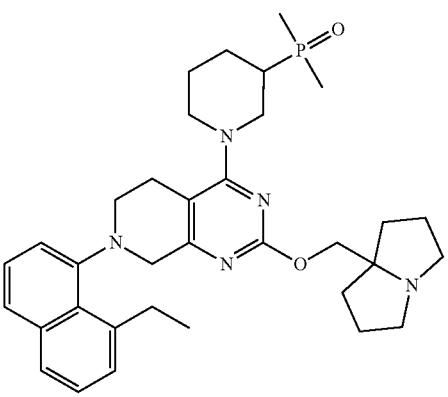 [SMILES: CCc1cccc2cccc(N3CCc4c(nc(OCC56CCCN5CCC6)nc4N4CCCC(P(C)(C)=O)C4)C3)c12]

| 191 | 192 |
|---|---|
| (1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)dimethylphosphine oxide | 4-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)morpholine-2-carboxamide |

Example 113

Example 115

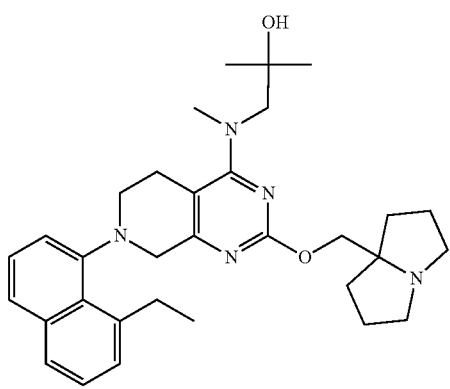 [SMILES: CCc1cccc2cccc(N3CCc4c(nc(OCC56CCCN5CCC6)nc4N(C)CC(C)(C)O)C3)c12]

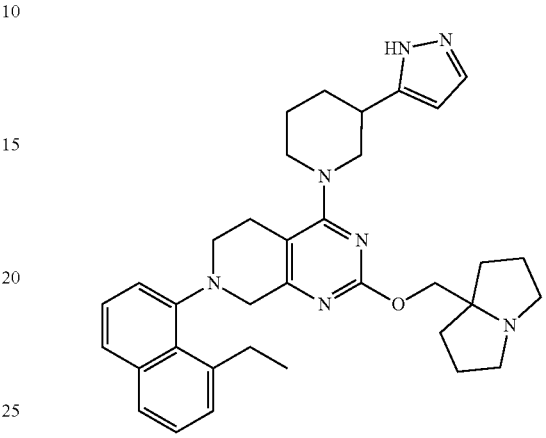

1-((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)-2-methylpropan-2-ol 4-(3-(1H-pyrazol-5-yl)piperidin-1-yl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidine Example 114

Example 116

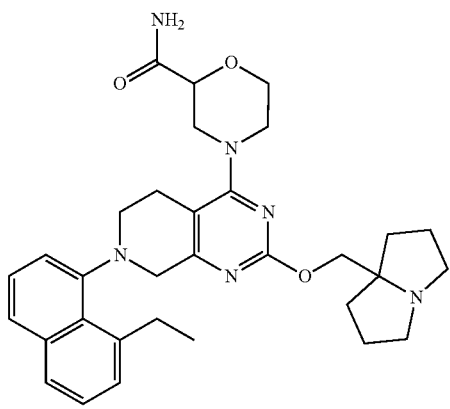 [SMILES: CCc1cccc2cccc(N3CCc4c(nc(OCC56CCCN5CCC6)nc4N4CCOC(C(N)=O)C4)C3)c12]

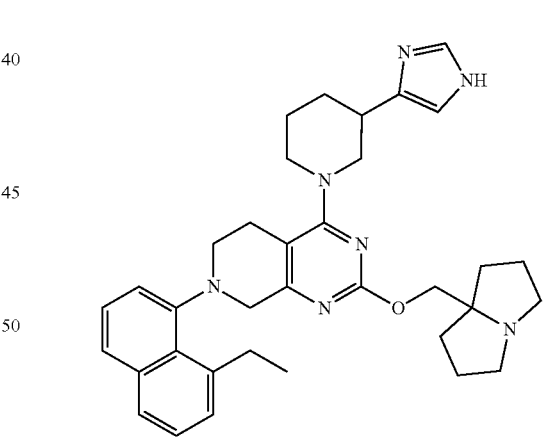

4-(3-(1H-imidazol-4-yl)piperidin-1-yl)-7-(8-ethyl-naphthalen-1-yl)-2-((tetrahydro-1H-pyrrolizin-7a(5H)-yl)methoxy)-5,6,7,8-tetrahydropyrido[3,4-d]pyrimidine Example 117

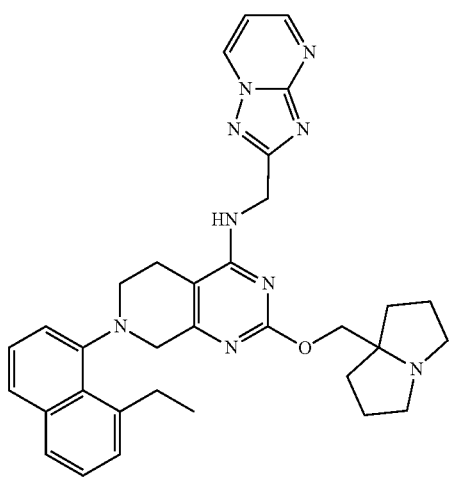 [SMILES: CCc1cccc2cccc(N3CCc4c(nc(OCC56CCCN5CCC6)nc4NCc4nc5ncccn5n4)C3)c12]

N-([1,2,4]triazolo[1,5-a]pyrimidin-2-ylmethyl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-amine Example 118

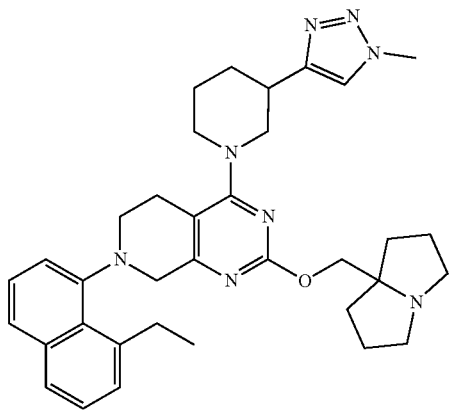 [SMILES: CCc1cccc2cccc(N3CCc4c(nc(OCC56CCCN5CCC6)nc4N4CCCC(c5cn(C)nn5)C4)C3)c12]

7-(8-ethylnaphthalen-1-yl)-4-(3-(1-methyl-1H-1,2,3-triazol-4-yl)piperidin-1-yl)-2-((tetrahydro-1H-pyrrolizin-7a(5H)-yl)methoxy)-5,6,7,8-tetrahydropyrido[3,4-d]pyrimidine Example 119

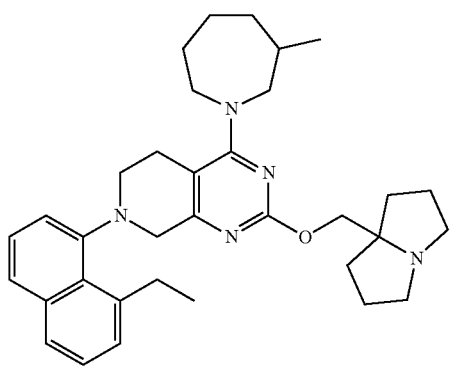 [SMILES: CCc1cccc2cccc(N3CCc4c(nc(OCC56CCCN5CCC6)nc4N4CCCCC(C)C4)C3)c12]

7-(8-ethylnaphthalen-1-yl)-4-(3-(1-methyl-1H-1,2,3-triazol-4-yl)piperidin-1-yl)-2-((tetrahydro-1H-pyrrolizin-7a(5H)-yl)methoxy)-5,6,7,8-tetrahydropyrido[3,4-d]pyrimidine Example 120

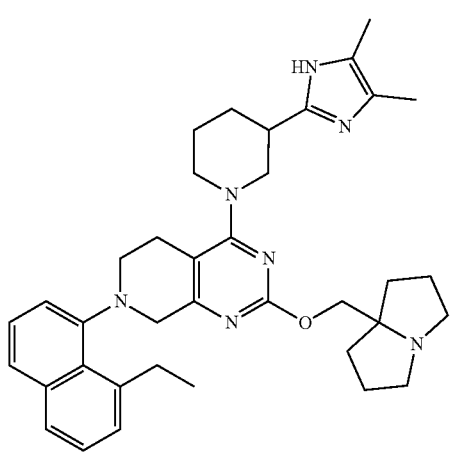 [SMILES: CCc1cccc2cccc(N3CCc4c(nc(OCC56CCCN5CCC6)nc4N4CCCC(c5nc(C)c(C)[nH]5)C4)C3)c12]

195

4-(3-(4,5-dimethyl-1H-imidazol-2-yl)piperidin-1-yl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidine Example 121

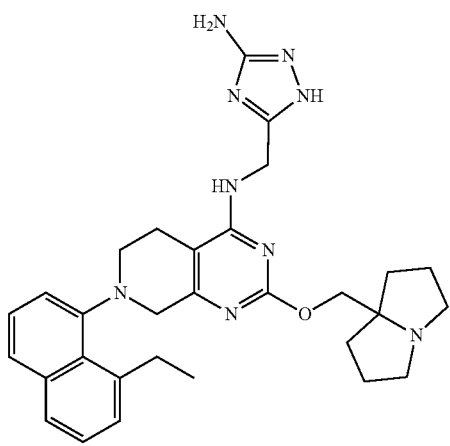 [SMILES: CCc1cccc2cccc(N3CCc4c(nc(OCC56CCCN5CCC6)nc4NCc4nc(N)n[nH]4)C3)c12]

N-((3-amino-1H-1,2,4-triazol-5-yl)methyl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-amine Example 122

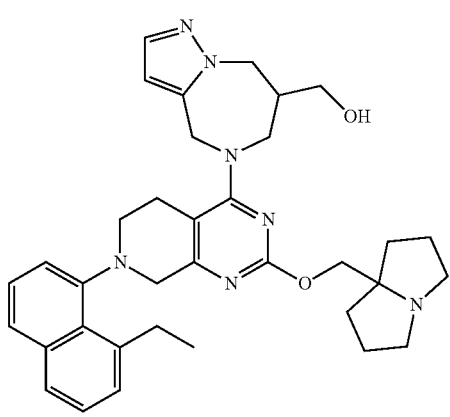 [SMILES: CCc1cccc2cccc(N3CCc4c(nc(OCC56CCCN5CCC6)nc4N4Cc5ccnn5CC(CO)C4)C3)c12]

196

(5-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-5,6,7,8-tetrahydro-4H-pyrazolo[1,5-a][1,4]diazepin-7-yl)methanol Example 123

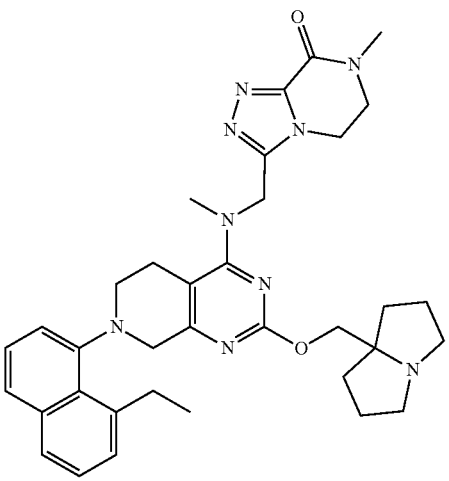 [SMILES: CCc1cccc2cccc(N3CCc4c(nc(OCC56CCCN5CCC6)nc4N(C)Cc4nnc5n4CCN(C)C5=O)C3)c12]

3-(((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)methyl)-7-methyl-6,7-dihydro-[1,2,4]triazolo[4,3-a]pyrazin-8(5H)-one Example 124

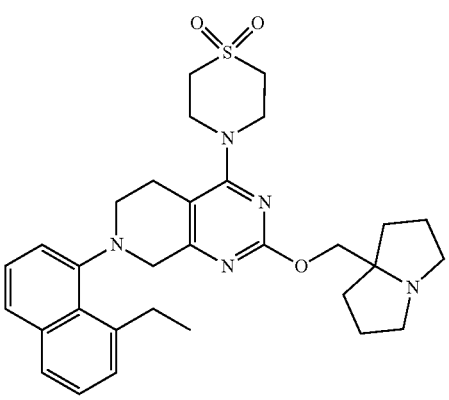 [SMILES: CCc1cccc2cccc(N3CCc4c(nc(OCC56CCCN5CCC6)nc4N4CCS(=O)(=O)CC4)C3)c12]

| 197 | 198 |
|---|---|
| 4-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)thiomorpholine 1,1-dioxide | 4-((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)-1-(1-methyl-1H-pyrazol-4-yl)pyrrolidin-2-one |
| Example 125 | Example 127 |

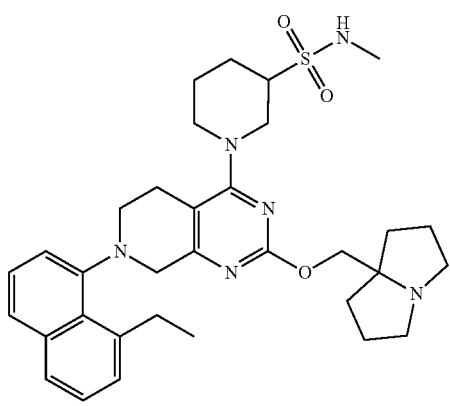 [SMILES: CCc1cccc2cccc(N3CCc4c(nc(OCC56CCCN5CCC6)nc4N4CCCC(S(=O)(=O)NC)C4)C3)c12]

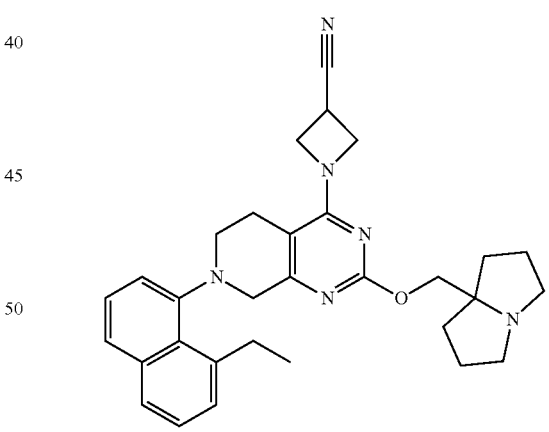

1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-N-methylpiperidine-3-sulfonamide N-((1H-1,2,3-triazol-4-yl)methyl)-7-(8-ethylnaphthalen-1-yl)-N-methyl-2-((tetrahydro-1H-pyrrolizin-7a(5H)-yl)methoxy)-5,6,7,8-tetrahydropyrido[3,4-d]pyrimidin-4-amine Example 126

Example 128

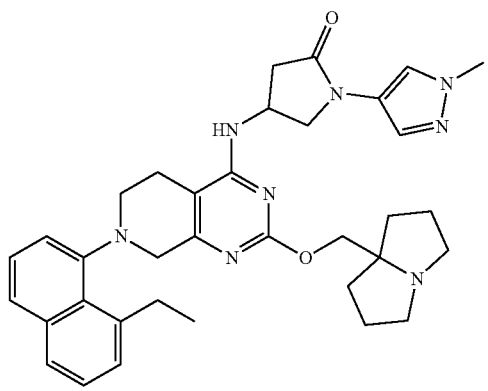 [SMILES: CCc1cccc2cccc(N3CCc4c(nc(OCC56CCCN5CCC6)nc4NC4CC(=O)N(c5cnn(C)c5)C4)C3)c12]

199

1-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)azetidine-3-carbonitrile Example 129

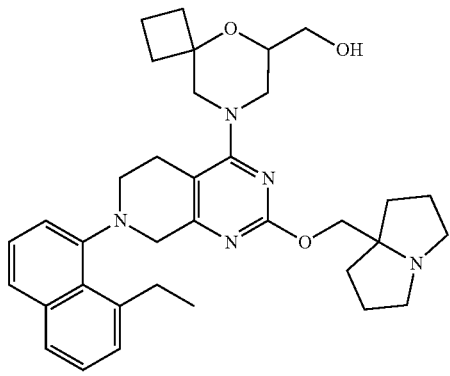 [SMILES: CCc1cccc2cccc(N3CCc4c(nc(OCC56CCCN5CCC6)nc4N4CC(CO)OC5(CCC5)C4)C3)c12]

(8-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)-5-oxa-8-azaspiro[3.5]nonan-6-yl)methanol Example 130

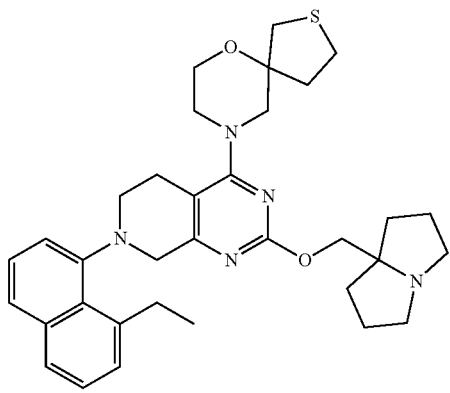 [SMILES: CCc1cccc2cccc(N3CCc4c(nc(OCC56CCCN5CCC6)nc4N4CCOC5(CCSC5)C4)C3)c12]

200

9-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)-6-oxa-2-thia-9-azaspiro[4.5]decane Example 131

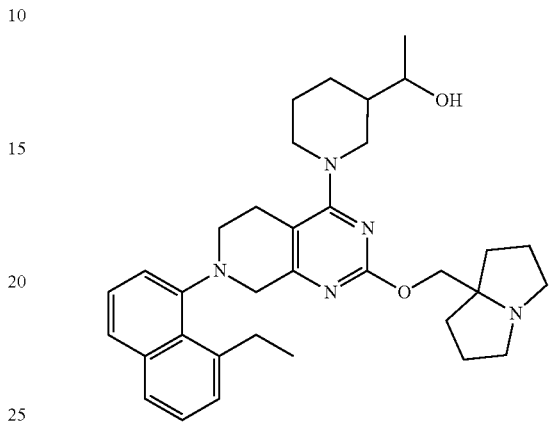

1-(1-(7-(8-ethylnaphthalen-1-yl)-2-((tetrahydro-1H-pyrrolizin-7a(5H)-yl)methoxy)-5,6,7,8-tetrahydro-pyrido[3,4-d]pyrimidin-4-yl)piperidin-3-yl)ethan-1-ol Example 132

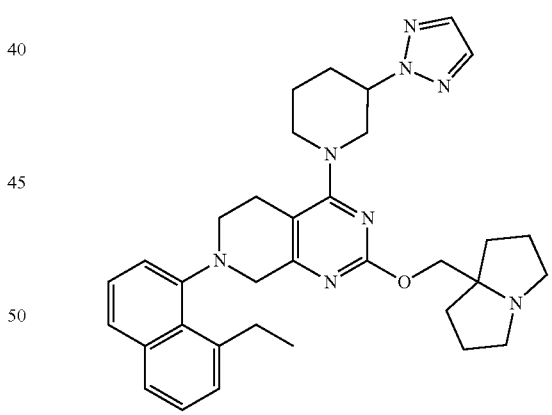

201

4-(3-(2H-1,2,3-triazol-2-yl)piperidin-1-yl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidine Example 133

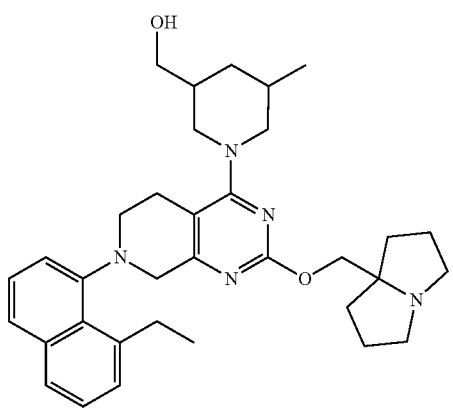 [SMILES: CCc1cccc2cccc(N3CCc4c(nc(OCC56CCCN5CCC6)nc4N4CC(C)CC(CO)C4)C3)c12]

(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-5-methylpiperidin-3-yl)methanol Example 134

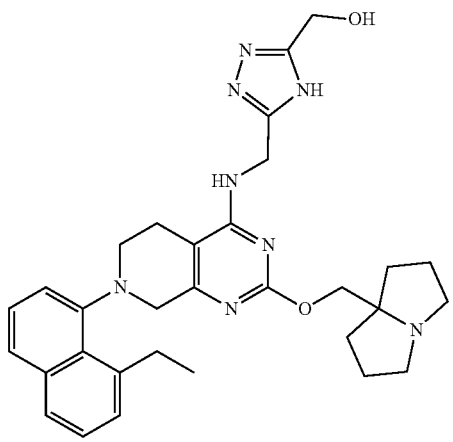 [SMILES: CCc1cccc2cccc(N3CCc4c(nc(OCC56CCCN5CCC6)nc4NCc4nnc(CO)[nH]4)C3)c12]

202

(5-(((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)methyl)-4H-1,2,4-triazol-3-yl)methanol Example 135

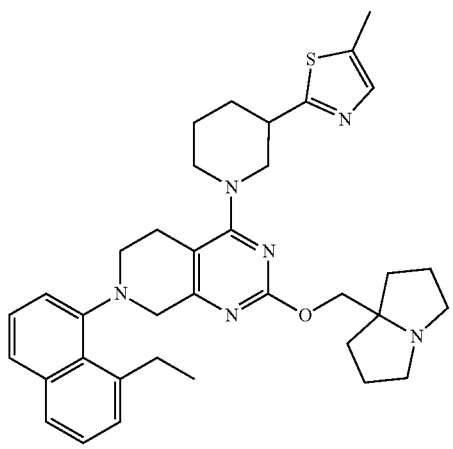 [SMILES: CCc1cccc2cccc(N3CCc4c(nc(OCC56CCCN5CCC6)nc4N4CCCC(c5ncc(C)s5)C4)C3)c12]

2-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-5-methylthiazole Example 136

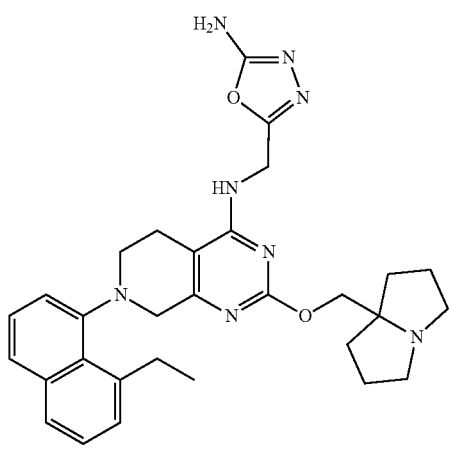 [SMILES: CCc1cccc2cccc(N3CCc4c(nc(OCC56CCCN5CCC6)nc4NCc4nnc(N)o4)C3)c12]

| 203 | 204 |
|---|---|
| 5-(((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)methyl)-1,3,4-oxadiazol-2-amine | N-(2-(3-amino-1H-1,2,4-triazol-5-yl)ethyl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-amine |

Example 137

Example 139

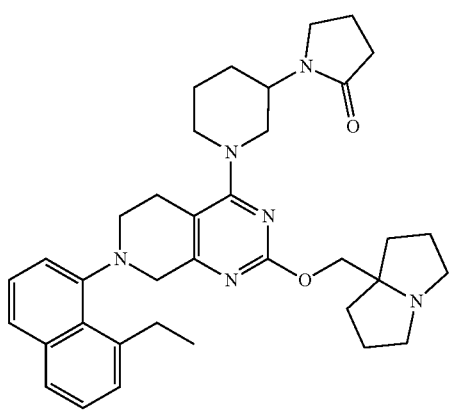 [SMILES: CCc1cccc2cccc(N3CCc4c(nc(OCC56CCCN5CCC6)nc4N4CCCC(N5CCCC5=O)C4)C3)c12]

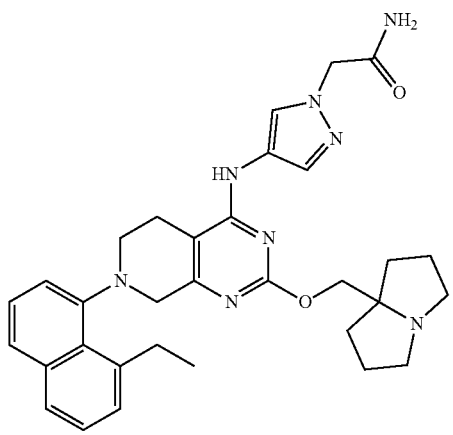

1-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)pyrrolidin-2-one 2-(4-((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)-1H-pyrazol-1-yl)acetamide Example 138

Example 140

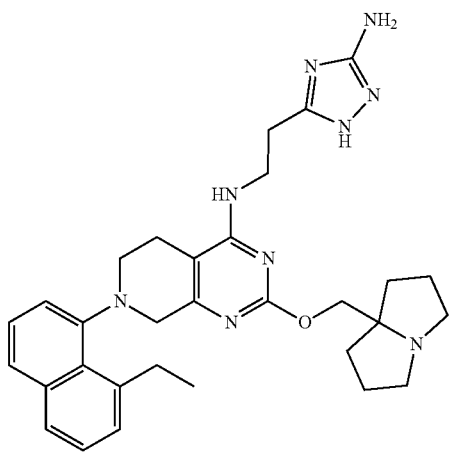 [SMILES: CCc1cccc2cccc(N3CCc4c(nc(OCC56CCCN5CCC6)nc4NCCc4nc(N)n[nH]4)C3)c12]

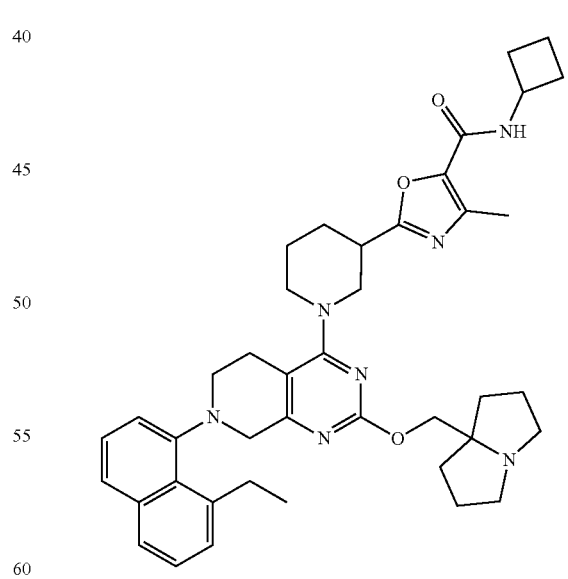

205

N-cyclobutyl-2-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-4-methyloxazole-5-carboxamide Example 141

206

N-((2-(1H-1,2,4-triazol-1-yl)pyridin-3-yl)methyl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-amine Example 143

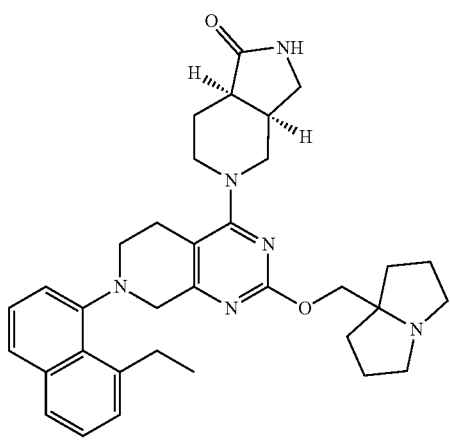 [SMILES: CCc1cccc2cccc(N3CCc4c(nc(OCC56CCCN5CCC6)nc4N4CC[C@H]5C(=O)NC[C@H]5C4)C3)c12]

(3aS,7aR)-5-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)octahydro-1H-pyrrolo[3,4-c]pyridin-1-one Example 142

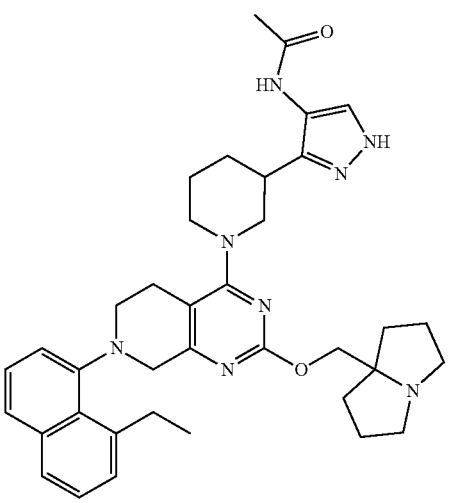

N-(3-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-1H-pyrazol-4-yl)acetamide Example 144

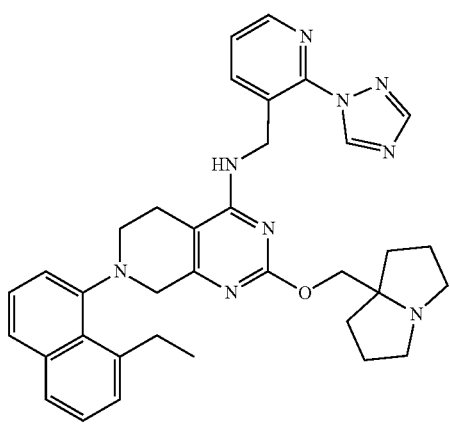 [SMILES: CCc1cccc2cccc(N3CCc4c(nc(OCC56CCCN5CCC6)nc4NCc4cccnc4-n4cncn4)C3)c12]

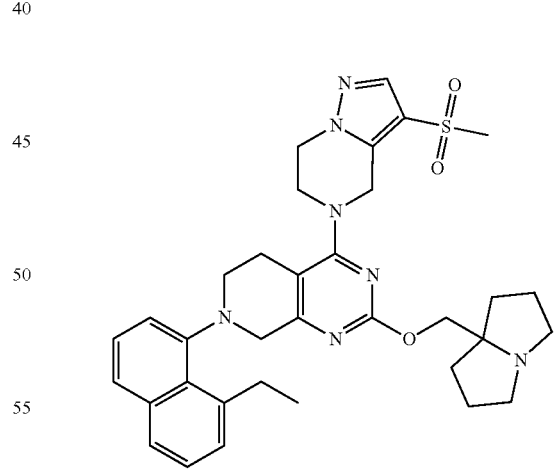

207

7-(8-ethylnaphthalen-1-yl)-4-(3-(methylsulfonyl)-6,
7-dihydropyrazolo[1,5-a]pyrazin-5(4H)-yl)-2-((tetra-
hydro-1H-pyrrolizin-7a(5H)-yl)methoxy)-5,6,7,8-
tetrahydropyrido[3,4-d]pyrimidine Example 145

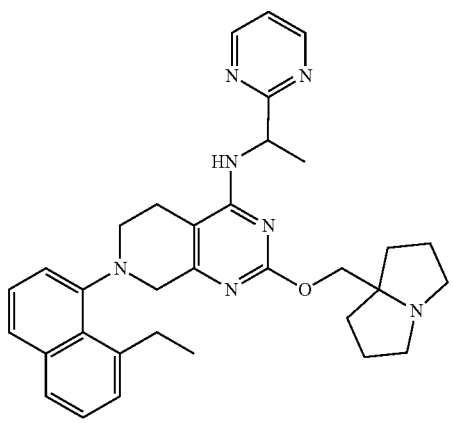 [SMILES: CCc1cccc2cccc(N3CCc4c(nc(OCC56CCCN5CCC6)nc4NC(C)c4ncccn4)C3)c12]

7-(8-ethylnaphthalen-1-yl)-N-(1-(pyrimidin-2-yl)
ethyl)-2-((tetrahydro-1H-pyrrolizin-7a(5H)-yl)
methoxy)-5,6,7,8-tetrahydropyrido[3,4-d]pyrimidin-
4-amine Example 146

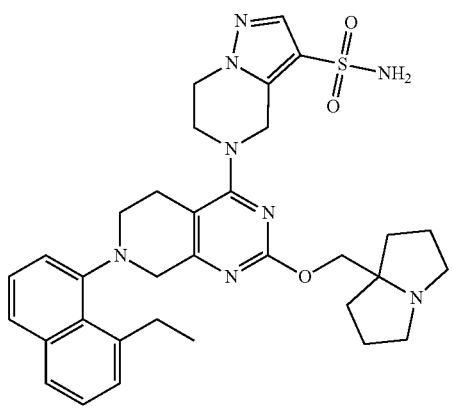 [SMILES: CCc1cccc2cccc(N3CCc4c(nc(OCC56CCCN5CCC6)nc4N4CCn5ncc(S(N)(=O)=O)c5C4)C3)c12]

208

5-(7-(8-ethylnaphthalen-1-yl)-2-((tetrahydro-1H-
pyrrolizin-7a(5H)-yl)methoxy)-5,6,7,8-tetrahydro-
pyrido[3,4-d]pyrimidin-4-yl)-4,5,6,7-tetrahydropyra-
zolo[1,5-a]pyrazine-3-sulfonamide Example 147

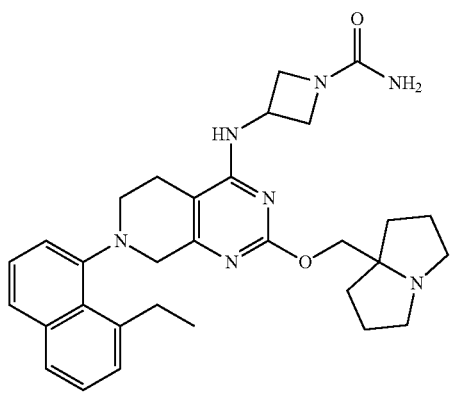 [SMILES: CCc1cccc2cccc(N3CCc4c(nc(OCC56CCCN5CCC6)nc4NC4CN(C(N)=O)C4)C3)c12]

3-((7-(8-ethylnaphthalen-1-yl)-2-((tetrahydro-1H-
pyrrolizin-7a(5H)-yl)methoxy)-5,6,7,8-tetrahydro-
pyrido[3,4-d]pyrimidin-4-yl)amino)azetidine-1-car-
boxamide Example 148

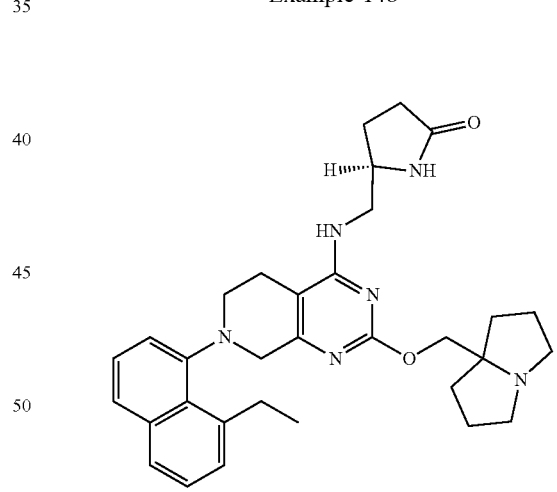

209

(R)-5-(((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)methyl)pyrrolidin-2-one Example 149

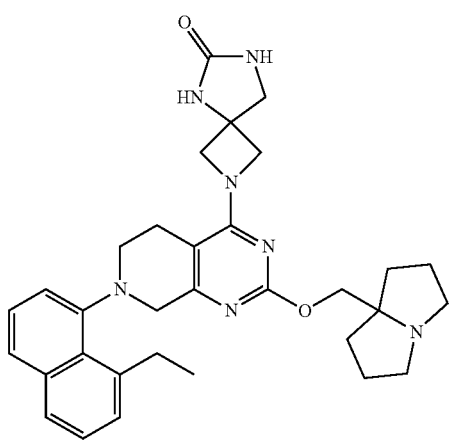 [SMILES: CCc1cccc2cccc(N3CCc4c(nc(OCC56CCCN5CCC6)nc4N4CC5(CNC(=O)N5)C4)C3)c12]

2-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-2,5,7-triazaspiro[3.4]octan-6-one Example 150

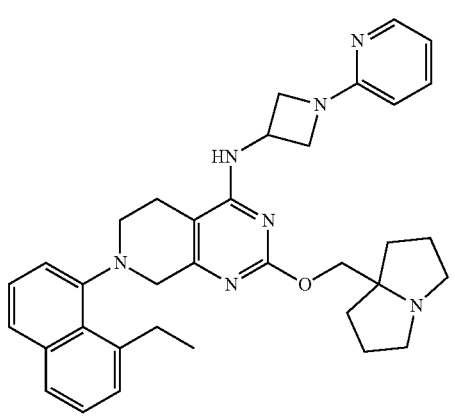 [SMILES: CCc1cccc2cccc(N3CCc4c(nc(OCC56CCCN5CCC6)nc4NC4CN(c5ccccn5)C4)C3)c12]

210

7-(8-ethylnaphthalen-1-yl)-N-(1-(pyridin-2-yl)azetidin-3-yl)-2-((tetrahydro-1H-pyrrolizin-7a(5H)-yl)methoxy)-5,6,7,8-tetrahydropyrido[3,4-d]pyrimidin-4-amine Example 151

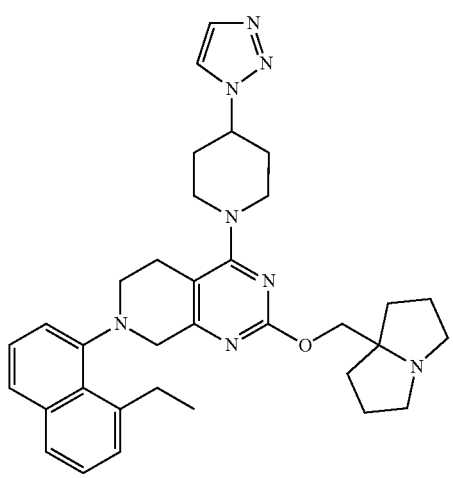 [SMILES: CCc1cccc2cccc(N3CCc4c(nc(OCC56CCCN5CCC6)nc4N4CCC(n5ccnn5)CC4)C3)c12]

4-(4-(1H-1,2,3-triazol-1-yl)piperidin-1-yl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidine Example 152

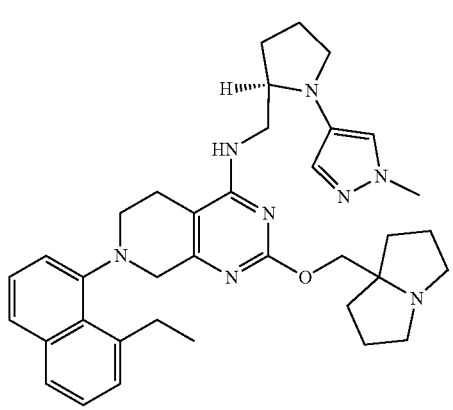 [SMILES: CCc1cccc2cccc(N3CCc4c(nc(OCC56CCCN5CCC6)nc4NC[C@H]4CCCN4c4cnn(C)c4)C3)c12]

211

(R)-7-(8-ethylnaphthalen-1-yl)-N-((1-(1-methyl-1H-pyrazol-4-yl)pyrrolidin-2-yl)methyl)-2-((tetrahydro-1H-pyrrolizin-7a(5H)-yl)methoxy)-5,6,7,8-tetrahydropyrido[3,4-d]pyrimidin-4-amine Example 153

212

2-((2-((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)ethyl)amino)nicotinonitrile Example 155

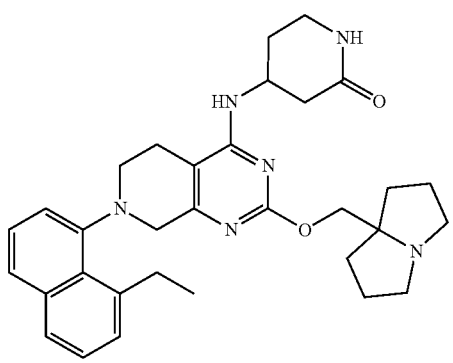 [SMILES: CCc1cccc2cccc(N3CCc4c(nc(OCC56CCCN5CCC6)nc4NC4CCNC(=O)C4)C3)c12]

4-((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)piperidin-2-one Example 154

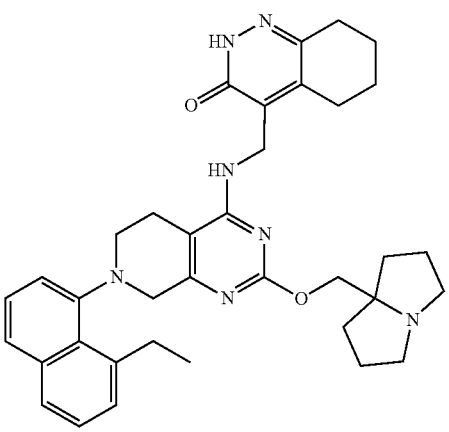

4-(((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)methyl)-5,6,7,8-tetrahydrocinnolin-3(2H)-one Example 156

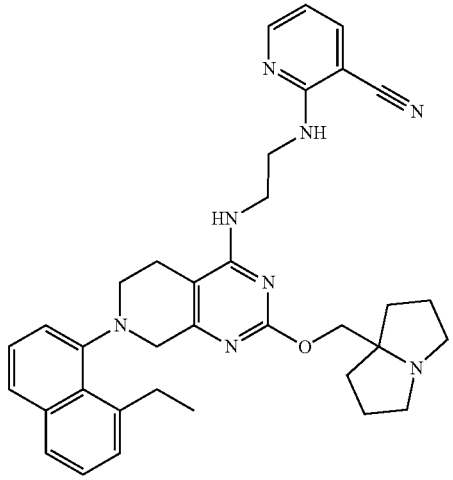 [SMILES: CCc1cccc2cccc(N3CCc4c(nc(OCC56CCCN5CCC6)nc4NCCNc4ncccc4C#N)C3)c12]

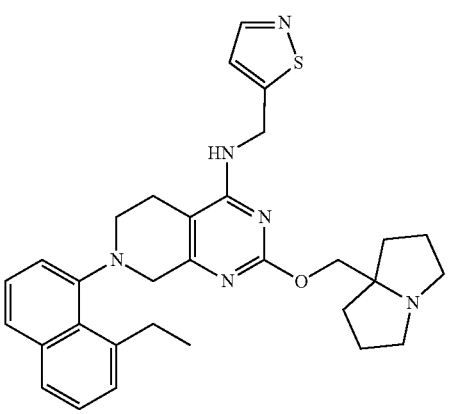 [SMILES: CCc1cccc2cccc(N3CCc4c(nc(OCC56CCCN5CCC6)nc4NCc4ccns4)C3)c12]

213

7-(8-ethylnaphthalen-1-yl)-N-(isothiazol-5-ylm-
ethyl)-2-((tetrahydro-1H-pyrrolizin-7a(5H)-yl)
methoxy)-5,6,7,8-tetrahydropyrido[3,4-d]pyrimidin-
4-amine Example 157

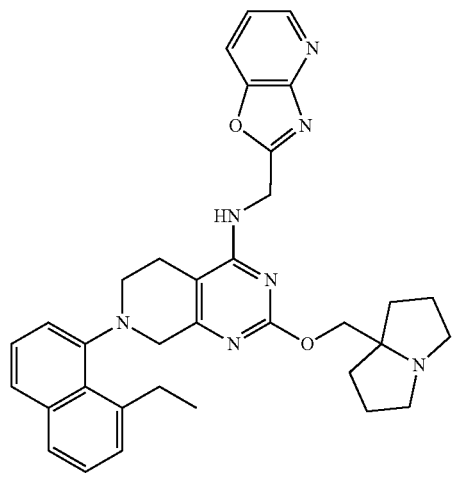 [SMILES: CCc1cccc2cccc(N3CCc4c(nc(OCC56CCCN5CCC6)nc4NCc4nc5ncccc5o4)C3)c12]

7-(8-ethylnaphthalen-1-yl)-N-(oxazolo[4,5-b]pyri-
din-2-ylmethyl)-2-((tetrahydro-1H-pyrrolizin-7a
(5H)-yl)methoxy)-5,6,7,8-tetrahydropyrido[3,4-d]
pyrimidin-4-amine Example 158

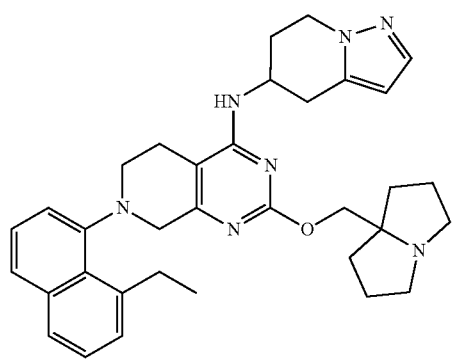 [SMILES: CCc1cccc2cccc(N3CCc4c(nc(OCC56CCCN5CCC6)nc4NC4CCn5nccc5C4)C3)c12]

214

7-(8-ethylnaphthalen-1-yl)-2-((tetrahydro-1H-pyr-
rolizin-7a(5H)-yl)methoxy)-N-(4,5,6,7-tetrahydropy-
razolo[1,5-a]pyridin-5-yl)-5,6,7,8-tetrahydropyrido
[3,4-d]pyrimidin-4-amine Example 159

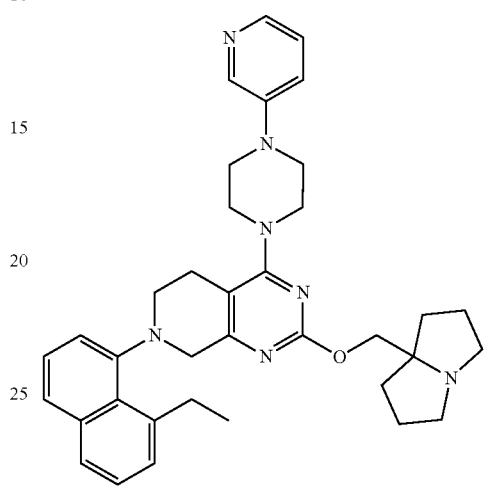

7-(8-ethylnaphthalen-1-yl)-4-(4-(pyridin-3-yl)piper-
azin-1-yl)-2-((tetrahydro-1H-pyrrolizin-7a(5H)-yl)
methoxy)-5,6,7,8-tetrahydropyrido[3,4-d]pyrimidine Example 160

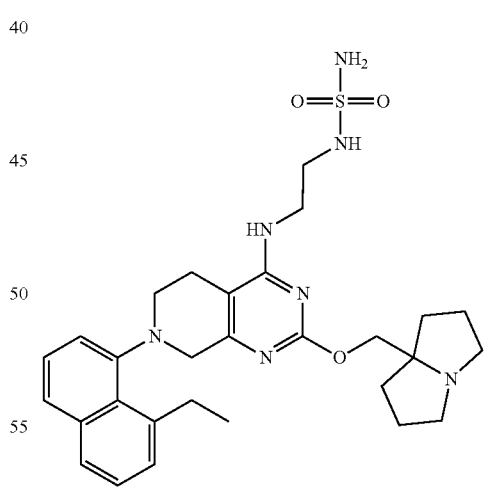

215

N-(2-((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)ethyl)sulfamide Example 161

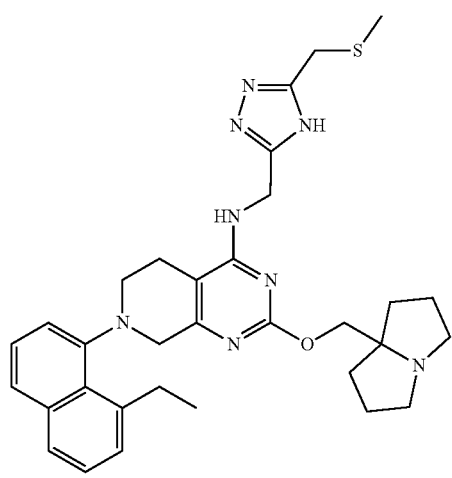 [SMILES: CCc1cccc2cccc(N3CCc4c(nc(OCC56CCCN5CCC6)nc4NCc4nnc(CSC)[nH]4)C3)c12]

7-(8-ethylnaphthalen-1-yl)-N-((5-((methylthio)methyl)-4H-1,2,4-triazol-3-yl)methyl)-2-((tetrahydro-1H-pyrrolizin-7a(5H)-yl)methoxy)-5,6,7,8-tetrahydropyrido[3,4-d]pyrimidin-4-amine Example 162

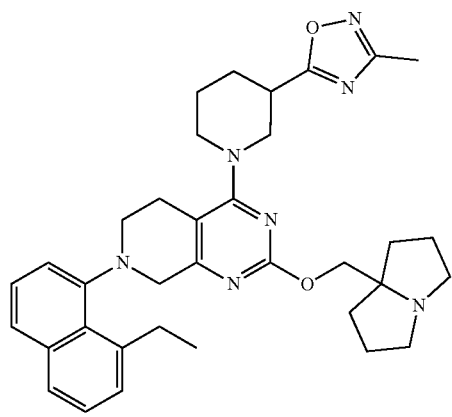 [SMILES: CCc1cccc2cccc(N3CCc4c(nc(OCC56CCCN5CCC6)nc4N4CCCC(c5nc(C)no5)C4)C3)c12]

216

5-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-3-methyl-1,2,4-oxadiazole Example 163

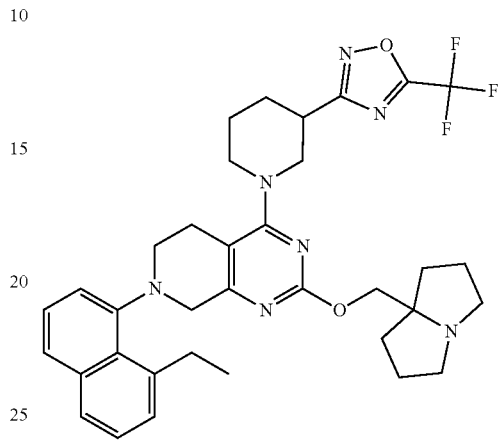

3-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-5-(trifluoromethyl)-1,2,4-oxadiazole Example 164

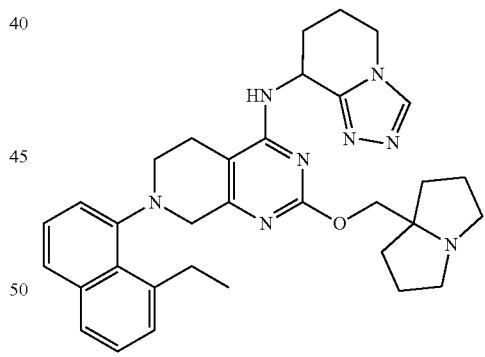

217

7-(8-ethylnaphthalen-1-yl)-2-((tetrahydro-1H-pyr-rolizin-7a(5H)-yl)methoxy)-N-(5,6,7,8-tetrahydro-[1,2,4]triazolo[4,3-a]pyridin-8-yl)-5,6,7,8-tetrahydropyrido[3,4-d]pyrimidin-4-amine Example 165

218

(5-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-4-methyl-4H-1,2,4-triazol-3-yl)methanol Example 167

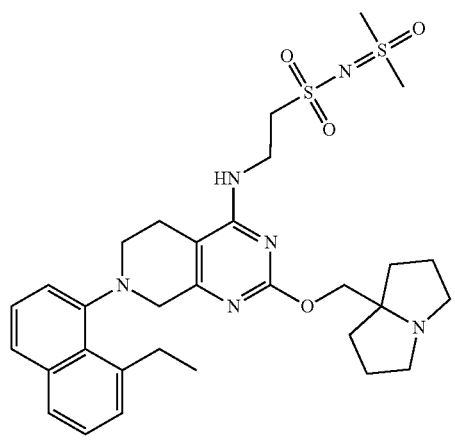 [SMILES: CCc1cccc2cccc(N3CCc4c(nc(OCC56CCCN5CCC6)nc4NCCS(=O)(=O)N=S(C)(C)=O)C3)c12]

N-(dimethyl(oxo)-16-sulfaneylidene)-2-((7-(8-ethyl-naphthalen-1-yl)-2-((tetrahydro-1H-pyrrolizin-7a(5H)-yl)methoxy)-5,6,7,8-tetrahydropyrido[3,4-d]pyrimidin-4-yl)amino)ethane-1-sulfonamide Example 166

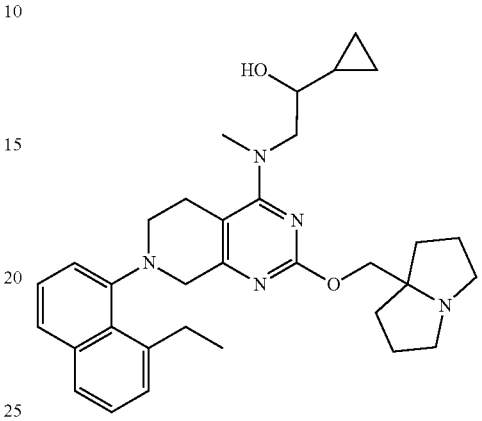

1-cyclopropyl-2-((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)ethan-1-ol Example 168

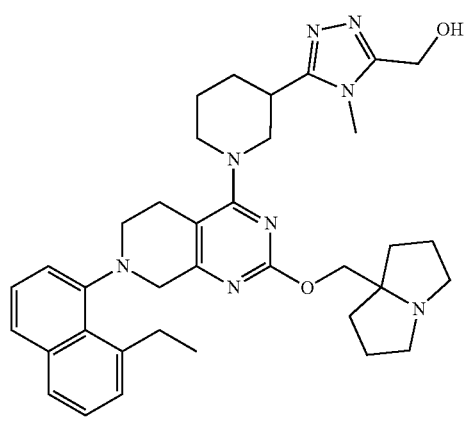 [SMILES: CCc1cccc2cccc(N3CCc4c(nc(OCC56CCCN5CCC6)nc4N4CCCC(c5nnc(CO)n5C)C4)C3)c12]

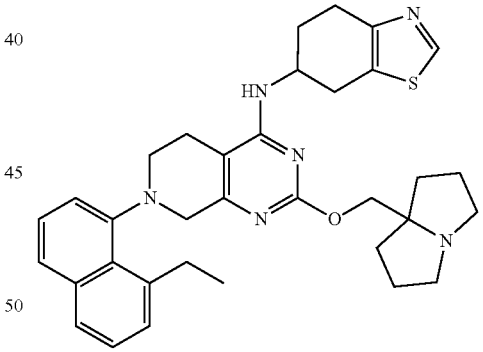

219

N-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-4,5,6,7-tetrahydrobenzo[d]thiazol-6-amine Example 169

220

N-(bicyclo[3.1.0]hexan-3-yl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-amine Example 171

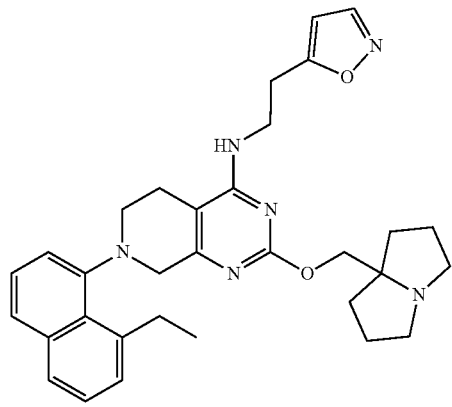 [SMILES: CCc1cccc2cccc(N3CCc4c(nc(OCC56CCCN5CCC6)nc4NCCc4ccno4)C3)c12]

7-(8-ethylnaphthalen-1-yl)-N-(2-(isoxazol-5-yl)ethyl)-2-((tetrahydro-1H-pyrrolizin-7a(5H)-yl)methoxy)-5,6,7,8-tetrahydropyrido[3,4-d]pyrimidin-4-amine Example 170

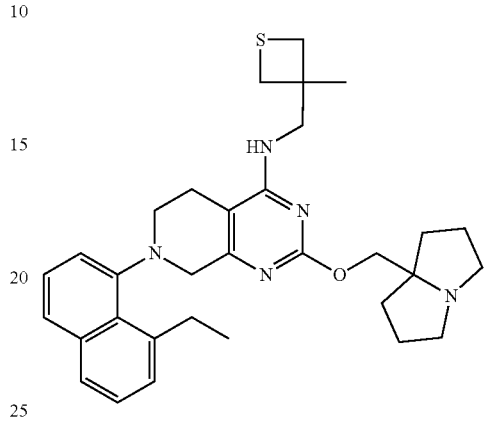

7-(8-ethylnaphthalen-1-yl)-N-((3-methylthietan-3-yl)methyl)-2-((tetrahydro-1H-pyrrolizin-7a(5H)-yl)methoxy)-5,6,7,8-tetrahydropyrido[3,4-d]pyrimidin-4-amine Example 172

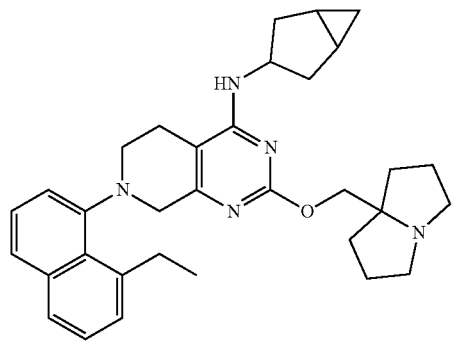 [SMILES: CCc1cccc2cccc(N3CCc4c(nc(OCC56CCCN5CCC6)nc4NC4CC5CC5C4)C3)c12]

Isomer 1

1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-6-(hydroxymethyl)azepan-4-ol

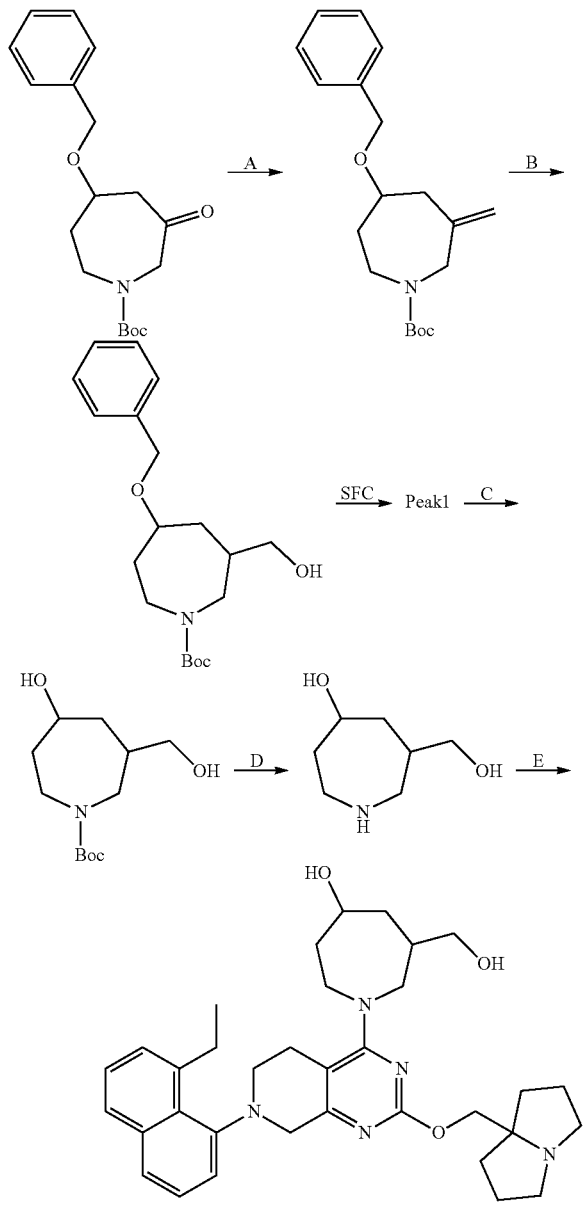

Step A. tert-butyl 5-(benzyloxy)-3-methyleneazepane-1-carboxylate: To a mixture of methyl(triphenyl)phosphonium; bromide (8.39 g, 2.5 equiv) in THF (15 mL) was added n-BuLi (2.5 M, 10.5 mL, 2.8 equiv) at 0° C. The reaction was stirred at 0° C. for 0.5 hours, and then tert-butyl 5-(benzyloxy)-3-oxoazepane-1-carboxylate (3.00 g, 1.0 equiv) was added at 0° C. The reaction was stirred at 0° C. for 1 hour. The mixture was quenched with sat. NH$_4$Cl (10 mL) and extracted with ethyl acetate (10 ml×2). The combined organic layers were dried over Na$_2$SO$_4$ and concentrated. The residue was purified by column chromatography (SiO$_2$, Petroleum ether/Ethyl acetate=50/1 to 2/1) to afford the title compound (1.4 g, 37% yield) as yellow oil; $^1$H NMR (400 MHz, METHANOL-d$_4$) δ=7.44-7.26 (m, 4H), 5.08-4.91 (m, 2H), 4.84-4.42 (m, 3H), 4.23-4.08 (m, 1H), 4.04-3.84 (m, 1H), 3.67-3.38 (m, 2H), 3.22-3.05 (m, 1H), 2.61-2.25 (m, 2H), 2.03-1.67 (m, 2H), 1.46 (d, J=6.8 Hz, 9H); LCMS (ESI, M−99): m/z=218.2.

Step B. tert-butyl 5-(benzyloxy)-3-(hydroxymethyl)azepane-1-carboxylate: To a solution of tert-butyl 5-(benzyloxy)-3-methyleneazepane-1-carboxylate (600 mg, 1.0 equiv) in THF (5 mL) was added BH$_3$·Me$_2$S (10 M, 567 μL, 3.0 equiv) at 0° C., and the mixture was stirred at 0° C. for 1.5 hours. NaOH (3 M, 2.52 mL, 4.0 equiv) and H$_2$O$_2$ (7.94 g, 6.73 mL, 30% purity, 37 equiv) were added and the reaction was stirred at 0° C. for 1.5 hours. The reaction was quenched with sat. Na$_2$SO$_3$, and extracted with ethyl acetate (10 mL×2). The combined organic layers were dried over Na$_2$SO$_4$, concentrated, and purified with reversed phase flash chromatography [C18, 0.1% formic acid condition] to give mixture of stereoisomers (280 mg) which was separated by SFC (column: DAICEL CHIRALCEL OJ (250 mm×30 mm, 10 μm); mobile phase: [0.1% NH$_3$H$_2$O MEOH]; B %: 15%-15%, 2.2 min) to afford three peaks. Peak 1 (95 mg, 15% yield) as yellow oil; $^1$H NMR (400 MHz, METHANOL-d$_4$) δ=7.44-7.17 (m, 5H), 4.62-4.39 (m, 2H), 3.88-3.75 (m, 1H), 3.56-3.34 (m, 5H), 3.30-3.15 (m, 1H), 2.30 (td, J=3.0, 5.6 Hz, 1H), 2.13-1.93 (m, 2H), 1.80 (br dd, J=4.4, 9.2 Hz, 1H), 1.51-1.46 (m, 1H), 1.44 (d, J=4.4 Hz, 9H); LCMS (ESI, M+1): m/z=336.1. Peak 2 (35 mg, 4.7% yield) as yellow oil; $^1$H NMR (400 MHz, METHANOL-d$_4$) δ=7.39-7.19 (m, 5H), 4.63-4.47 (m, 2H), 3.63-3.33 (m, 6H), 3.14 (s, 1H), 2.23-1.96 (m, 2H), 1.92-1.77 (m, 1H), 1.74-1.58 (m, 1H), 1.44 (d, J=6.0 Hz, 9H), 1.29 (br s, 1H); LCMS (ESI, M−99): m/z=236.1. Peak 3 (40 mg, 6% yield) as yellow oil; $^1$H NMR (400 MHz, METHANOL-d$_4$) δ=7.42-7.15 (m, 4H), 4.64-4.45 (m, 2H), 3.64-3.40 (m, 5H), 3.34 (br d, J=5.2 Hz, 1H), 3.27 (br s, 1H), 3.20-3.04 (m, 1H), 2.23-2.04 (m, 2H), 1.85 (br dd, J=4.8, 8.4 Hz, 1H), 1.68 (dt, J=4.4, 9.2 Hz, 1H), 1.44 (d, J=6.0 Hz, 9H), 1.40-1.25 (m, 1H); LCMS (ESI, M−99): m/z=236.1.

Step C. tert-butyl 5-hydroxy-3-(hydroxymethyl)azepane-1-carboxylate: To a solution of tert-butyl 5-(benzyloxy)-3-(hydroxymethyl)azepane-1-carboxylate (peak 1, 400 mg, 1.0 equiv) in MeOH (10 mL) was added Pd/C (100 mg, 10% purity) under N$_2$. The suspension was degassed under vacuum and purged with H2 several times and the mixture was stirred under H2 (15 psi) at 50° C. for 2 hours. The mixture was filtered and concentrated to afford the title compound (303 mg, crude) as yellow oil; $^1$H NMR (400 MHz, METHANOL-d$_4$) δ=4.04 (td, J=1.6, 3.2 Hz, 1H), 3.57-3.43 (m, 3H), 3.35 (s, 1H), 3.43-3.34 (m, 1H), 3.30-3.10 (m, 1H), 2.29 (br s, 1H), 1.92-1.69 (m, 3H), 1.63-1.52 (m, 1H), 1.46 (s, 9H).

Step D. 6-(hydroxymethyl)azepan-4-ol: To a solution of tert-butyl 5-hydroxy-3-(hydroxymethyl)azepane-1-carboxylate (150 mg, 1.0 equiv) in DCM (0.8 mL) was added HCl·dioxane (4 M, 153 μL, 1.0 equiv) at 0° C. The mixture was stirred at 0° C. for 30 minutes. After completion, the reaction mixture was concentrated under reduced pressure to afford the title compound (110 mg, crude) as colorless oil.

Step E. 1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-6-(hydroxymethyl)azepan-4-ol: To a solution of 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (120 mg, 1.0 equiv) and N-ethyl-N-isopropylpropan-2-amine (77.7 mg, 105 μL, 3.0 equiv) in DMF (1 mL) was added 6-(hydroxymethyl)azepan-4-ol (100 mg, 3.4 equiv) and 4 Å molecular sieve (30.0 mg, 1.0 equiv). The reaction mixture was degassed and purged with N₂ for three times. The reaction mixture was stirred at 40° C. for 12 hours. The mixture was filtered and the filtrate was purified by prep-HPLC [column: Phenomenex C18 150×25 mm×10 μm; mobile phase: water (FA)-ACN; B %: 11%-41%, 10 minutes] to afford the title compound (25.9 mg, 21% yield) as yellow gum; ¹H NMR (400 MHz, METHANOL-d₄) δ=7.69 (dd, J=7.6, 16.7 Hz, 2H), 7.43 (dt, J=3.2, 7.6 Hz, 1H), 7.38-7.30 (m, 2H), 7.29-7.26 (m, 1H), 4.51-4.37 (m, 2H), 4.26-3.90 (m, 4H), 3.78-3.35 (m, 10H), 3.27-3.15 (m, 3H), 3.11-2.94 (m, 1H), 2.91-2.71 (m, 1H), 2.61-2.31 (m, 1H), 2.29-1.97 (m, 9H), 1.96-1.56 (m, 3H), 1.15 (q, J=7.6 Hz, 3H); LCMS (ESI, M+1): m/z=572.5.

Example 173

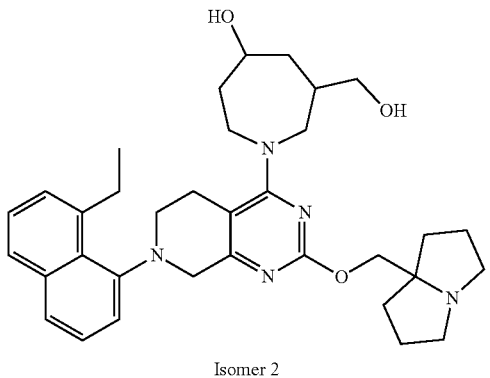 [SMILES: CCc1cccc2cccc(N3CCc4c(nc(OCC56CCCN5CCC6)nc4N4CCC(O)CC(CO)C4)C3)c12]

Isomer 2

1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-6-(hydroxymethyl)azepan-4-ol Synthesized according to Example 172 (step C-E, peak 2 of tert-butyl 5-(benzyloxy)-3-(hydroxymethyl)azepane-1-carboxylate was used). The title compound was obtained as yellow solid. ¹H NMR (400 MHz, METHANOL-d₄) δ=7.78-7.59 (m, 2H), 7.46-7.39 (m, 1H), 7.38-7.31 (m, 2H), 7.31-7.26 (m, 1H), 4.42 (br d, J=2.8 Hz, 2H), 4.22-3.98 (m, 2H), 3.85-3.46 (m, 10H), 3.37 (br dd, J=10.4, 13.6 Hz, 2H), 3.23-3.11 (m, 3H), 3.10-2.97 (m, 1H), 2.88-2.71 (m, 1H), 2.38-1.84 (m, 12H), 1.59-1.47 (m, 1H), 1.23-1.07 (m, 3H). LCMS (ESI, M+1): m/z=572.4.

Example 174

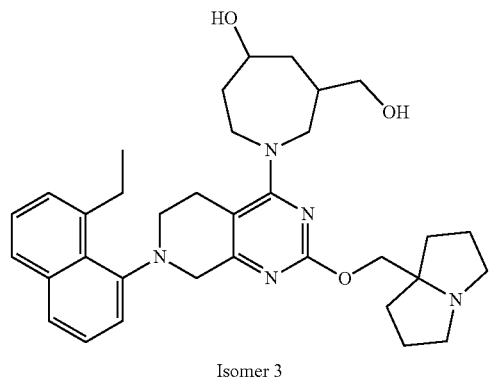 [SMILES: CCc1cccc2cccc(N3CCc4c(nc(OCC56CCCN5CCC6)nc4N4CCC(O)CC(CO)C4)C3)c12]

Isomer 3

1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-6-(hydroxymethyl)azepan-4-ol Synthesized according to Example 172 (step C-E, peak 3 of tert-butyl 5-(benzyloxy)-3-(hydroxymethyl)azepane-1-carboxylate was used). The title compound was obtained as yellow solid. ¹H NMR (400 MHz, METHANOL-d₄) δ=7.69 (br dd, J=8.0, 15.6 Hz, 2H), 7.48-7.39 (m, 1H), 7.39-7.31 (m, 2H), 7.31-7.26 (m, 1H), 4.43 (br d, J=3.2 Hz, 2H), 4.22-3.97 (m, 2H), 3.91-3.48 (m, 10H), 3.37 (br dd, J=10.4, 13.6 Hz, 2H), 3.27-3.13 (m, 3H), 3.10-2.95 (m, 1H), 2.91-2.69 (m, 1H), 2.38-1.66 (m, 12H), 1.60-1.42 (m, 1H), 1.23-1.06 (m, 3H); LCMS (ESI, M+1): m/z=572.5.

Example 175

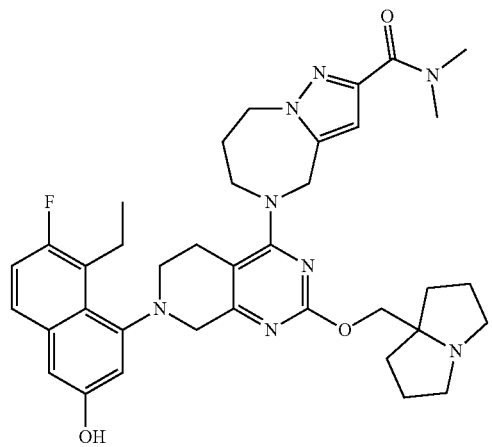 [SMILES: CCc1c(F)ccc2cc(O)cc(N3CCc4c(nc(OCC56CCCN5CCC6)nc4N4CCCn5nc(C(=O)N(C)C)cc5C4)C3)c12]

225

5-[7-(8-ethyl-7-fluoro-3-hydroxy-1-naphthyl)-2-(1,2,3,5,6,7-hexahydropyrrolizin-8-ylmethoxy)-6,8-dihydro-5H-pyrido[3,4-d]pyrimidin-4-yl]-N,N-dimethyl-4,6,7,8-tetrahydropyrazolo[1,5-a][1,4]diazepine-2-carboxamide

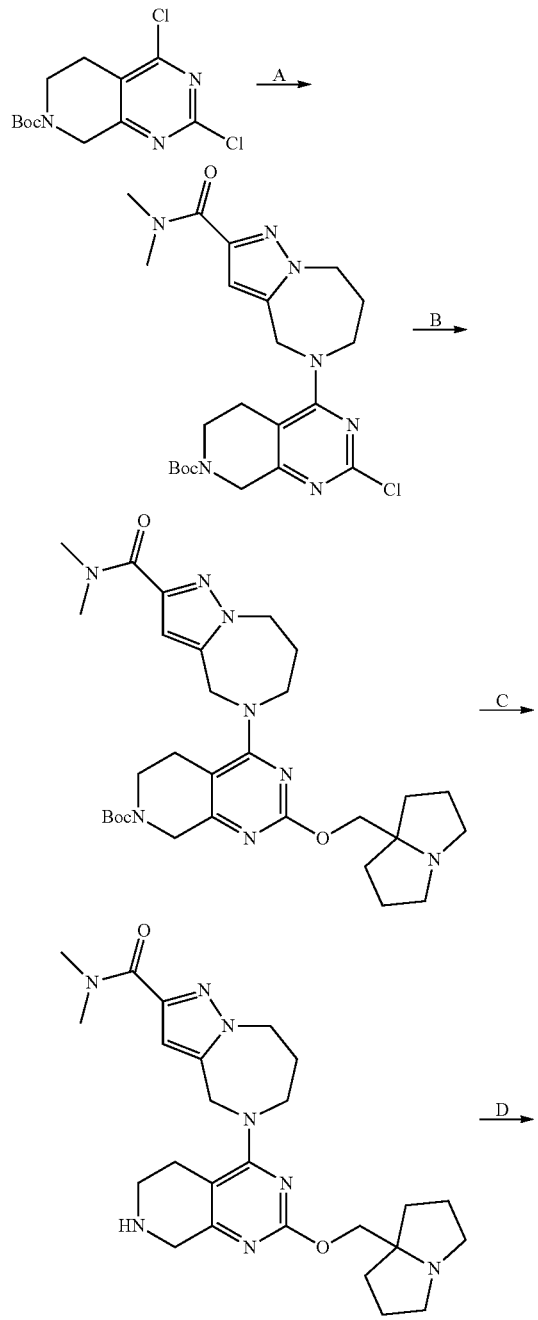

226

-continued

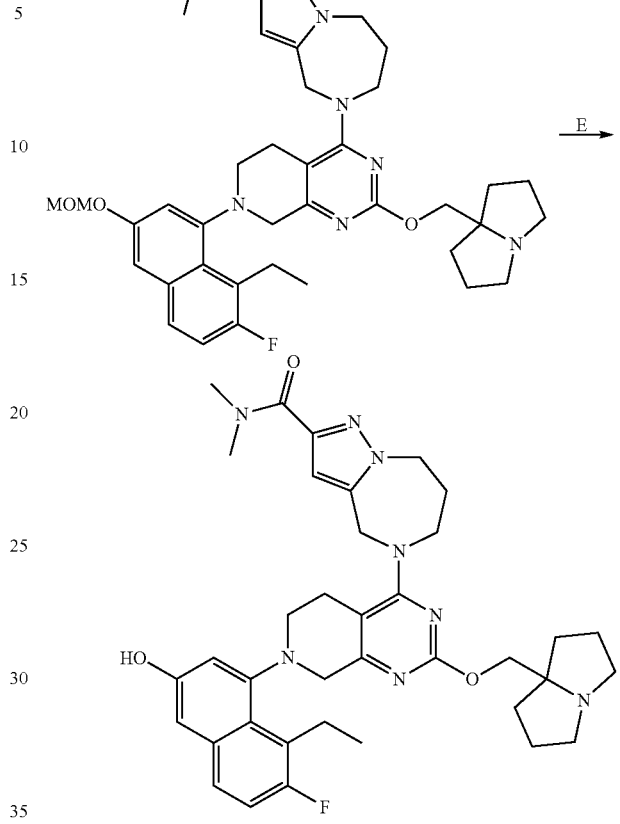

Step A tert-butyl 2-chloro-4-(2-(dimethylcarbamoyl)-7,8-dihydro-4H-pyrazolo[1,5-a][1,4]diazepin-5(6H)-yl)-5,6-dihydropyrido[3,4-d]pyrimidine-7(8H)-carboxylate: To a solution of N,N-dimethyl-5,6,7,8-tetrahydro-4H-pyrazolo[1,5-a][1,4]diazepine-2-carboxamide (1.4 g, 1.09 equiv) in DMSO (30 mL) were added N-ethyl-N-isopropylpropan-2-amine (3.40 g, 5 equiv) and tert-butyl 2,4-dichloro-6,8-dihydro-5H-pyrido[3,4-d]pyrimidine-7-carboxylate (1.6 g, 1 equiv). The mixture was stirred at 60° C. for 12 hours. The reaction mixture was diluted with water (150 mL) and extracted with EtOAc (3×100 mL). The combined organic layers were washed with brine (3×20 mL), dried over anhydrous sodium sulfate, concentrated and purified with column chromatography (SiO$_2$, Petroleum ether/Ethyl acetate=1/1 to 1/2) to afford the title compound as a yellow oil; $^1$H NMR (400 MHz, CHLOROFORM-d) δ=6.61 (s, 1H), 4.71 (br s, 2H), 4.61-4.44 (m, 4H), 3.92 (br d, J=4.4 Hz, 2H), 3.58 (br s, 2H), 3.34 (br s, 3H), 3.10 (br s, 3H), 2.71 (br s, 2H), 2.18 (br s, 2H), 1.51 (s, 9H); LCMS (ESI, M+1): m/z=476.3.

Step B. tert-butyl 4-(2-(dimethylcarbamoyl)-7,8-dihydro-4H-pyrazolo[1,5-a][1,4]diazepin-5(6H)-yl)-2-((tetrahydro-1H-pyrrolizin-7a(5H)-yl)methoxy)-5,8-dihydropyrido[3,4-d]pyrimidine-7(6H)-carboxylate: A mixture of tert-butyl 2-chloro-4-[2-(dimethylcarbamoyl)-4,6,7,8-tetrahydropyrazolo[1,5-a][1,4]diazepin-5-yl]-6,8-dihydro-5H-pyrido[3,4-d]pyrimidine-7-carboxylate (400 mg, 1.0 equiv), 1,2,3,5,6,7-hexahydropyrrolizin-8-ylmethanol (142 mg, 1.2 equiv), BINAP (131 mg, 0.3 equiv), Pd(OAc)$_2$ (37.7 mg, 0.2 equiv) and Cs$_2$CO$_3$ (685 mg, 2.5 equiv) in toluene (7 mL) was degassed and purged with N₂ for 3 times, and then the reaction was stirred at 110° C. for 8 hours under N₂ atmosphere. The reaction was quenched with water (15 mL) at 25° C. and extracted with ethyl acetate (10 mL×3). The combined organic layers were washed with saturated salt solution (5 mL), dried over anhydrous sodium sulfate, and concentrated under reduced pressure. The residue was purified by prep-HPLC (column: Phenomenex luna C18 150×40 mm×15 μm; mobile phase: [water (FA)-ACN]; B %: 20%-50%, 10 min) to afford the title compound (223 mg, 45% yield) as a yellow solid. LCMS (ESI, M+1): m/z=581.2.

Step C. N,N-dimethyl-5-(2-((tetrahydro-1H-pyrrolizin-7a (5H)-yl)methoxy)-5,6,7,8-tetrahydropyrido[3,4-d]pyrimidin-4-yl)-5,6,7,8-tetrahydro-4H-pyrazolo[1,5-a][1,4]diazepine-2-carboxamide: To a solution of tert-butyl 4-(2-(dimethylcarbamoyl)-7,8-dihydro-4H-pyrazolo[1,5-a][1,4]diazepin-5(6H)-yl)-2-((tetrahydro-1H-pyrrolizin-7a(5H)-yl)methoxy)-5,8-dihydropyrido[3,4-d]pyrimidine-7(6H)-carboxylate (200 mg, 1.0 equiv) in dioxane (0.5 mL) was added HCl/dioxane (2 M, 5.00 mL). The mixture was stirred at 0° C. at 25° C. for 1 hour. The reaction mixture was concentrated under reduced pressure. The residue was dissolved in MeOH (3 mL), and its pH was adjusted to 9 with NaHCO₃. The mixture was stirred for 0.3 hour. The reaction mixture was filtered and concentrated under reduced pressure to afford the title compound (185 mg, 90% yield) as a yellow oil; LCMS (ESI, M+1): m/z=481.3.

Step D. 5-(7-(8-ethyl-7-fluoro-3-(methoxymethoxy) naphthalen-1-yl)-2-((tetrahydro-1H-pyrrolizin-7a(5H)-yl) methoxy)-5,6,7,8-tetrahydropyrido[3,4-d]pyrimidin-4-yl)-N,N-dimethyl-5,6,7,8-tetrahydro-4H-pyrazolo[1,5-a][1,4] diazepine-2-carboxamide: A mixture of N,N-dimethyl-5-(2-((tetrahydro-1H-pyrrolizin-7a(5H)-yl)methoxy)-5,6,7,8-tetrahydropyrido[3,4-d]pyrimidin-4-yl)-5,6,7,8-tetrahydro-4H-pyrazolo[1,5-a][1,4]diazepine-2-carboxamide (160 mg, 1.0 equiv), [8-ethyl-7-fluoro-3-(methoxymethoxy)-1-naphthyl]trifluoromethanesulfonate (140 mg, 1.1 equiv), Pd₂(dba)₃ (45.7 mg, 0.2 equiv), Xantphos (48.2 mg, 0.3 equiv) and Cs₂CO₃ (325 mg, 3 equiv) in toluene (1 mL) was degassed and purged with N₂ for 3 times. The mixture was stirred at 110° C. for 14 hours under N₂ atmosphere. The mixture was concentrated in vacuum to give a residue. The residue was purified by prep-HPLC (column: Phenomenex luna C18 150×40 mm×15 μm; mobile phase: [water (FA)-ACN]; B %: 23%-53%, 10 min) to afford the title compound (30 mg, 12.51% yield) as a yellow solid.

Step E. 5-(7-(8-ethyl-7-fluoro-3-hydroxynaphthalen-1-yl)-2-((tetrahydro-1H-pyrrolizin-7a(5H)-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide: To a solution of 5-(7-(8-ethyl-7-fluoro-3-(methoxymethoxy)naphthalen-1-yl)-2-((tetrahydro-1H-pyrrolizin-7a(5H)-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide (27.0 mg, 1.0 equiv) in MeOH (3 mL) was added HCl/MeOH (4 M, 3 mL). The mixture was stirred at 0° C. for 0.5 hours. The reaction mixture was adjusted pH to 9 with NaHCO₃ and stirred at 0° C. for 0.3 hours. The reaction mixture was filtered and concentrated under reduced pressure. The residue was purified by prep-HPLC (FA condition; column: Phenomenex Luna C18 150×25 mm×10 μm; mobile phase: [water (FA)-ACN]; B %: 17%-47%, 10 min) to afford the title compound (11.2 mg, 44% yield) as an off-white solid. ¹H NMR (400 MHz, METHANOL-d4) δ=8.66-8.37 (m, 1H), 7.54 (dd, J=5.6, 8.8 Hz, 1H), 7.17 (t, J=9.6 Hz, 1H), 7.00 (s, 2H), 6.65 (s, 1H), 4.95 (br s, 2H), 4.59-4.50 (m, 2H), 4.48-4.36 (m, 2H), 4.23-4.12 (m, 2H), 4.09 (br d, J=17.6 Hz, 1H), 3.71 (br d, J=17.6 Hz, 1H), 3.67-3.60 (m, 2H), 3.60-3.53 (m, 1H), 3.44-3.34 (m, 5H), 3.31-3.17 (m, 5H), 3.10 (s, 3H), 2.78 (br d, J=14.4 Hz, 1H), 2.37-2.26 (m, 3H), 2.25-2.13 (m, 4H), 2.12-2.04 (m, 3H), 1.12 (t, J=7.2 Hz, 3H); ¹⁹F NMR (377 MHz, METHANOL-d4) δ=−122.91 (s, 1F); LCMS (ESI, M+1): m/z=669.4.

Example 176

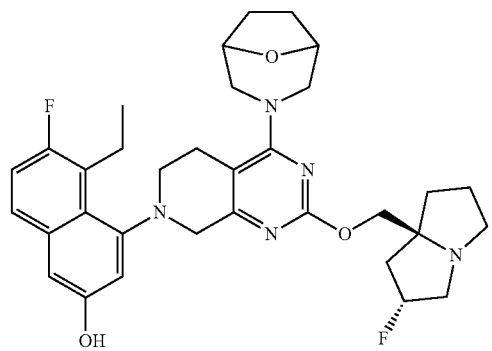 [SMILES: CCc1c(F)ccc2cc(O)cc(N3CCc4c(nc(OC[C@@]56CCCN5C[C@H](F)C6)nc4N4CC5CCC(C4)O5)C3)c12]

4-(4-(8-oxa-3-azabicyclo[3.2.1]octan-3-yl)-2-(((2R, 7aS)-2-fluorotetrahydro-1H-pyrrolizin-7a(5H)-yl) methoxy)-5,8-dihydropyrido[3,4-d]pyrimidin-7(6H)-yl)-5-ethyl-6-fluoronaphthalen-2-ol Synthesized according to Example 32. The title compound was obtained as white solid. ¹H NMR (400 MHz, METHANOL-d₄) δ=7.53-7.58 (m, 1H), 7.14 (t, J=9.2 Hz, 1H), 7.00-6.93 (m, 2H), 5.37-5.17 (m, 1H), 4.42 (s, 2H), 4.26-4.00 (m, 4H), 3.69 (d, J=10.0 Hz, 2H), 3.50-3.35 (m, 4H), 3.26-3.09 (m, 6H), 2.99 (dt, J=5.6, 9.4 Hz, 1H), 2.70-2.60 (m, 1H), 2.10 (d, J=8.0 Hz, 4H), 2.01-1.79 (m, 6H), 1.10 (t, J=7.2 Hz, 3H); LCMS (ESI, M+1): m/z=592.3.

Example 177

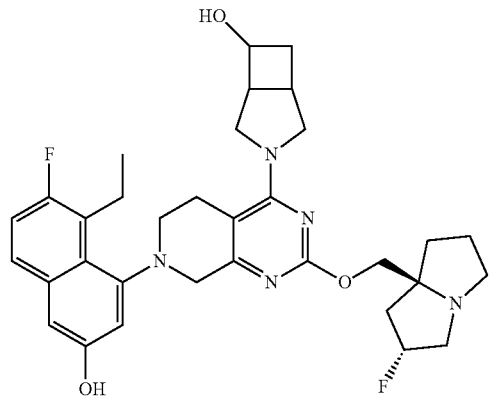 [SMILES: CCc1c(F)ccc2cc(O)cc(N3CCc4c(nc(OC[C@@]56CCCN5C[C@H](F)C6)nc4N4CC5CC(O)C5C4)C3)c12]

3-(7-(8-ethyl-7-fluoro-3-hydroxynaphthalen-1-yl)-2-(((2R,7aS)-2-fluorohexahydro-1H-pyrrolizin-7a-yl) methoxy)-5,6,7,8-tetrahydropyrido[3,4-d]pyrimidin-4-yl)-3-azabicyclo[3.2.0]heptan-6-ol Synthesized according to Example 32. The title compound was obtained as white solid. ¹H NMR (400 MHz, METHANOL-d4) δ=7.54-7.46 (m, 1H), 7.16-7.01 (m, 1H), 7.00-6.99 (m, 1H), 6.98-6.94 (m, 1H), 5.35-5.16 (m, 1H), 4.69-4.41 (m, 1H), 4.35-4.27 (m, 1H), 4.25-4.07 (m, 2H), 4.07-3.80 (m, 2H), 3.70-3.55 (m, 2H), 3.54-3.46 (m, 1H), 3.44-3.32 (m, 4H), 3.25-3.11 (m, 5H), 3.06-2.92 (m, 2H), 2.72-2.63 (m, 1H), 2.63-2.54 (m, 1H), 2.33-2.13 (m, 2H), 2.12-2.04 (m, 1H), 2.00-1.89 (m, 2H), 1.88-1.80 (m, 1H), 1.77-1.68 (m, 1H), 1.12-1.08 (m, 3H); LCMS (ESI, M+1): m/z=592.4.

Example 178

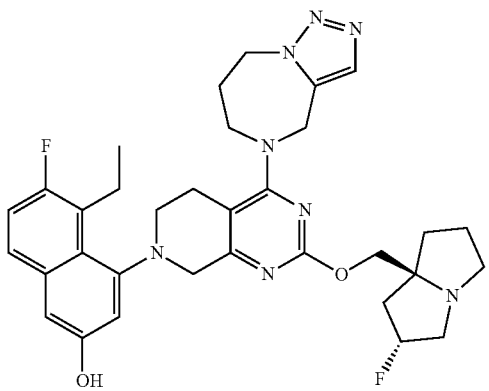 [SMILES: CCc1c(F)ccc2cc(O)cc(N3CCc4c(nc(OC[C@@]56CCCN5C[C@H](F)C6)nc4N4CCCn5nncc5C4)C3)c12]

4-(4-(7,8-dihydro-4H-[1,2,3]triazolo[1,5-a][1,4]diazepin-5(6H)-yl)-2-(((2R,7aS)-2-fluorotetrahydro-1H-pyrrolizin-7a(5H)-yl)methoxy)-5,8-dihydropyrido[3,4-d]pyrimidin-7(6H)-yl)-5-ethyl-6-fluoronaphthalen-2-ol Synthesized according to Example 32. The title compound was obtained as light yellow solid. $^1$H NMR (400 MHz, METHANOL-d$_4$) δ=7.71 (s, 1H), 7.51 (dd, J=5.6, 8.8 Hz, 1H), 7.14 (t, J=9.2 Hz, 1H), 6.97 (s, 2H), 5.20 (br s, 1H), 5.09-4.95 (m, 2H), 4.79-4.53 (m, 2H), 4.26-3.94 (m, 5H), 3.67 (br d, J=18.0 Hz, 1H), 3.53 (br s, 1H), 3.39 (br dd, J=2.4, 7.2 Hz, 2H), 3.28-3.14 (m, 5H), 3.00 (dt, J=6.0, 9.2 Hz, 1H), 2.72 (br d, J=11.2 Hz, 1H), 2.35-2.04 (m, 5H), 2.01-1.79 (m, 3H), 1.11 (br t, J=7.2 Hz, 3H); LCMS (M+1): m/z=617.5.

Example 179

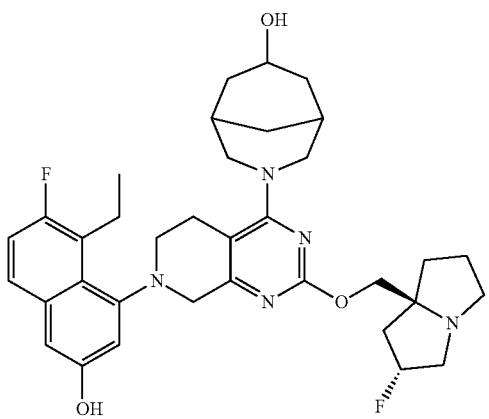 [SMILES: CCc1c(F)ccc2cc(O)cc(N3CCc4c(nc(OC[C@@]56CCCN5C[C@H](F)C6)nc4N4CC5CC(O)CC(C5)C4)C3)c12]

3-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-azabicyclo[3.3.1]nonan-7-ol Synthesized according to Example 32. The title compound was obtained as yellow solid. $^1$H NMR (400 MHz, DMSO-d$_6$) δ=9.70 (s, 1H), 7.59 (dd, J=6.0, 8.8 Hz, 1H), 7.24 (t, J=9.2 Hz, 1H), 6.99 (s, 2H), 5.37-5.11 (m, 1H), 4.67 (d, J=8.0 Hz, 1H), 4.03-3.95 (m, 2H), 3.95-3.91 (m, 1H), 3.85 (dd, J=7.2, 10.0 Hz, 1H), 3.77-3.70 (m, 1H), 3.70-3.66 (m, 1H), 3.64 (s, 1H), 3.16-3.09 (m, 2H), 3.06 (br d, J=5.6 Hz, 3H), 2.98 (br s, 1H), 2.86-2.74 (m, 3H), 2.67 (br d, J=1.6 Hz, 1H), 2.13 (br s, 2H), 2.09-2.02 (m, 2H), 2.02-1.97 (m, 2H), 1.95 (br s, 1H), 1.83 (br s, 1H), 1.78-1.71 (m, 2H), 1.71-1.61 (m, 2H), 1.42 (br d, J=12.0 Hz, 2H), 1.05 (t, J=7.2 Hz, 3H); LCMS (ESI, M+1): m/z=620.5.

Example 180

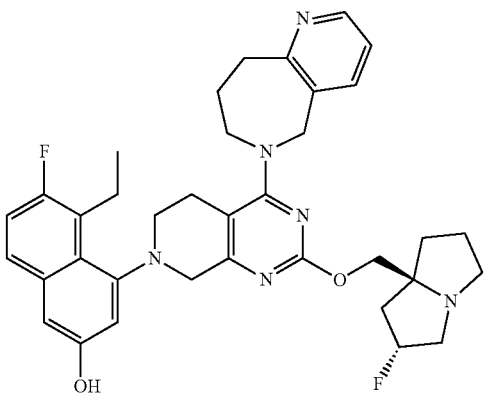 [SMILES: CCc1c(F)ccc2cc(O)cc(N3CCc4c(nc(OC[C@@]56CCCN5C[C@H](F)C6)nc4N4CCCc5ncccc5C4)C3)c12]

4-(4-(8,9-dihydro-5H-pyrido[3,2-c]azepin-6(7H)-yl)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol Synthesized according to Example 32. The title compound was obtained as white solid. $^1$H NMR (400 MHz, METHANOL-d$_4$) δ=8.51 (d, J=5.6 Hz, 1H), 8.36 (br s, 1H), 7.78-7.63 (m, 1H), 7.59-7.47 (m, 1H), 7.15 (t, J=9.6 Hz, 1H), 7.06-6.92 (m, 2H), 5.74-5.42 (m, 1H), 5.11-4.98 (m, 2H), 4.43 (t, J=11.6 Hz, 1H), 4.33-4.21 (m, 1H), 4.20-4.04 (m, 3H), 3.96-3.80 (m, 3H), 3.69 (br dd, J=6.6, 17.6 Hz, 1H), 3.58-3.49 (m, 1H), 3.47-3.35 (m, 5H), 3.28-3.15 (m, 2H), 2.81-2.73 (m, 1H), 2.66-2.48 (m, 2H), 2.39-2.27 (m, 4H), 2.22-2.06 (m, 2H), 1.11 (t, J=7.2 Hz, 3H); LCMS (ESI, M+1): m/z=627.5.

Example 181

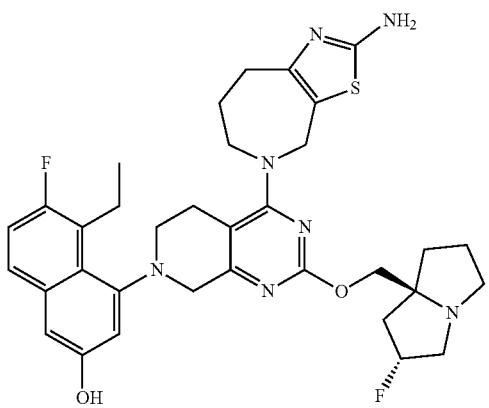 [SMILES: CCc1c(F)ccc2cc(O)cc(N3CCc4c(nc(OC[C@@]56CCCN5C[C@H](F)C6)nc4N4CCCc5nc(N)sc5C4)C3)c12]

4-(4-(2-amino-7,8-dihydro-4H-thiazolo[5,4-c]aze-pin-5(6H)-yl)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol Synthesized according to Example 32. The title compound was obtained as white solid. $^1$H NMR (400 MHz, METHANOL-d4) δ=7.52-7.48 (m, 1H), 7.14 (t, J=9.6 Hz, 1H), 7.00-6.93 (m, 2H), 5.37-5.15 (m, 1H), 4.77-4.71 (m, 1H), 4.65-4.57 (m, 1H), 4.21-4.04 (m, 3H), 4.04-3.99 (m, 2H), 3.67-3.63 (m, 1H), 3.53-3.46 (m, 1H), 3.44-3.37 (m, 2H), 3.24-3.09 (m, 5H), 3.13-2.96 (m, 1H), 2.89-2.77 (m, 1H), 2.76-2.65 (m, 2H), 2.31-2.17 (m, 1H), 2.17-2.04 (m, 3H), 2.01-1.83 (m, 4H), 1.11 (t, J=7.2 Hz, 3H); LCMS (ESI, M+1): m/z=648.4.

Example 182

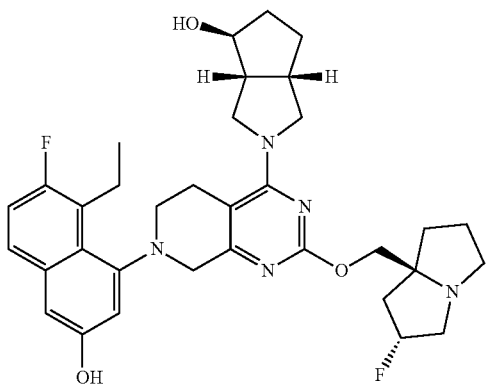 [SMILES: CCc1c(F)ccc2cc(O)cc(N3CCc4c(nc(OC[C@@]56CCCN5C[C@H](F)C6)nc4N4C[C@H]5CC[C@H](O)[C@H]5C4)C3)c12]

(3aR,4S,6aS)-2-(7-(8-ethyl-7-fluoro-3-hydroxynaph-thalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)octahydrocyclopenta[c]pyrrol-4-ol Synthesized according to Example 32. The title compound was obtained as light-yellow solid. $^1$H NMR (400 MHz, METHONL-d) δ=7.53-7.47 (m, 1H), 7.17-7.10 (m, 1H), 7.00-6.97 (m, 1H), 6.95 (d, J=2.4 Hz, 1H), 5.19 (br s, 1H), 4.07 (s, 2H), 4.05-3.94 (m, 3H), 3.78-3.70 (m, 2H), 3.68-3.62 (m, 1H), 3.61-3.54 (m, 1H), 3.52-3.45 (m, 1H), 3.42-3.32 (m, 3H), 3.27-3.13 (m, 5H), 3.02-2.86 (m, 3H), 2.68-2.53 (m, 1H), 2.32-2.11 (m, 3H), 2.11-2.01 (m, 2H), 1.86 (br d, J=7.8 Hz, 1H), 1.74-1.63 (m, 1H), 1.48 (br d, J=6.0 Hz, 1H), 1.30 (br d, J=4.3 Hz, 1H), 1.12-1.07 (m, 3H); LCMS[ESI, M+1]: m/z=606.3.

Example 183

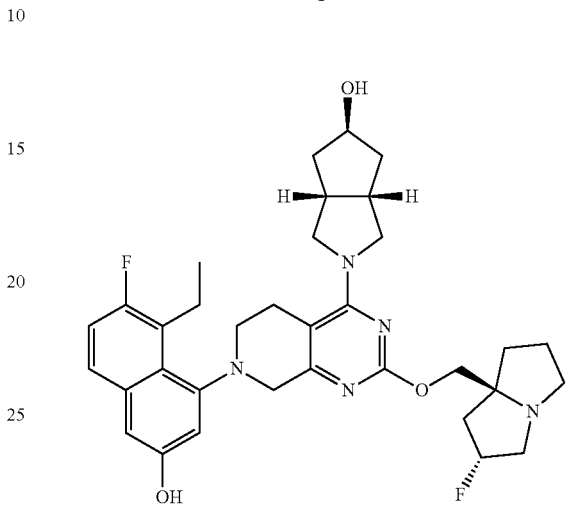

(3aR,5R,6aS)-2-(7-(8-ethyl-7-fluoro-3-hydroxynaph-thalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)octahydrocyclopenta[c]pyrrol-5-ol Synthesized according to Example 32. The title compound was obtained as yellow solid. $^1$H NMR (400 MHz, METHANOL-d$_4$) δ=7.53-7.48 (m, 1H), 7.14 (t, J=9.6 Hz, 1H), 7.01-6.94 (m, 2H), 5.36-5.17 (m, 1H), 4.44 (s, 1H), 4.14 (d, J=12.0 Hz, 1H), 4.09-3.92 (m, 3H), 3.82-3.69 (m, 2H), 3.67-3.54 (m, 2H), 3.50-3.34 (m, 3H), 3.29-3.11 (m, 5H), 3.03-2.83 (m, 4H), 2.15 (s, 2H), 2.13-2.04 (m, 1H), 2.01-1.79 (m, 6H), 1.75-1.64 (m, 1H), 1.14-1.05 (m, 3H); LCMS (ESI, M+1): m/z=606.3.

Example 184

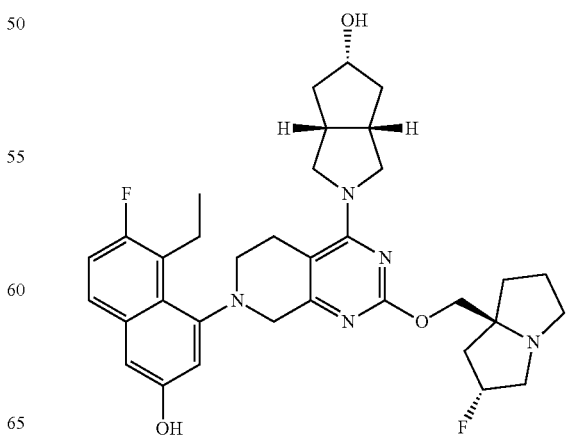

233

(3aR,5S,6aS)-2-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)octahydrocyclopenta[c]pyrrol-5-ol Synthesized according to Example 28. The title compound was obtained as yellow solid. ¹H NMR (400 MHz, METHANOL-d4) δ=7.50 (dd, J=6.0, 9.2 Hz, 1H), 7.13 (t, J=9.2 Hz, 1H), 7.02-6.93 (m, 2H), 5.36-5.17 (m, 1H), 4.30 (m, 1H), 4.21-3.91 (m, 5H), 3.84-3.75 (m, 1H), 3.71 (dd, J=2.4, 12.0 Hz, 1H), 3.62 (br d, J=17.6 Hz, 1H), 3.53-3.34 (m, 3H), 3.28-3.10 (m, 5H), 3.03-2.87 (m, 2H), 2.78-2.66 (m, 2H), 2.34-2.04 (m, 5H), 2.02-1.79 (m, 3H), 1.63-1.45 (m, 2H), 1.10 (m, 3H); LCMS (ESI, M+): m/z=606.5.

Example 185

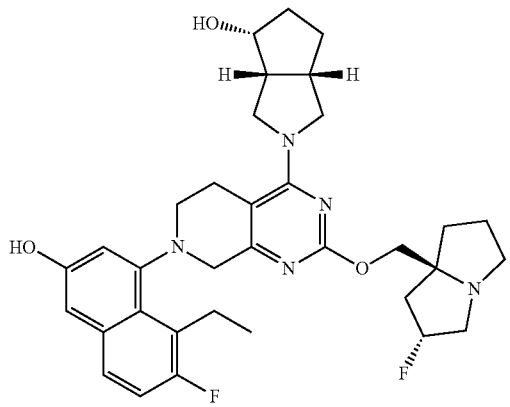 [SMILES: CCc1c(F)ccc2cc(O)cc(N3CCc4c(nc(OC[C@@]56CCCN5C[C@H](F)C6)nc4N4C[C@H]5CC[C@@H](O)[C@H]5C4)C3)c12]

(3aR,4R,6aS)-2-(7-(8-ethyl-7-fluoro-3-hydroxynaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)octahydrocyclopenta[c]pyrrol-4-ol Synthesized according to Example 32. The title compound was obtained as yellow solid. ¹H NMR (400 MHz, METHANOL-d₄) δ=7.53-7.48 (m, 1H), 7.14 (t, J=9.6 Hz, 1H), 7.01-6.94 (m, 2H), 5.36-5.17 (m, 1H), 4.38-4.00 (m, 5H), 3.98-3.72 (m, 2H), 3.65-3.54 (m, 2H), 3.55-3.35 (m, 3H), 3.24-3.14 (m, 5H), 3.12-2.95 (m, 2H), 2.90-2.65 (m, 2H), 1.99-1.94 (m, 3H), 1.93-1.76 (m, 7H), 1.21-1.11 (m, 3H); LCMS (ESI, M+): m/z=606.3.

Example 186

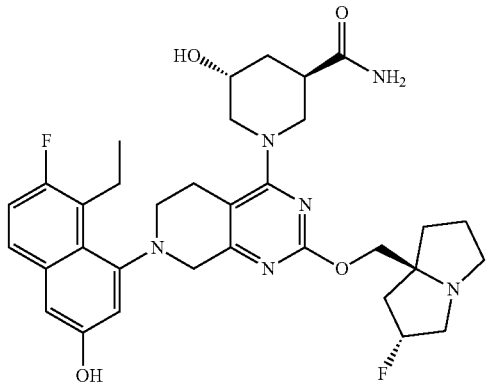 [SMILES: CCc1c(F)ccc2cc(O)cc(N3CCc4c(nc(OC[C@@]56CCCN5C[C@H](F)C6)nc4N4C[C@H](O)C[C@@H](C(N)=O)C4)C3)c12]

(3R,5R)-1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-5-hydroxypiperidine-3-carboxamide

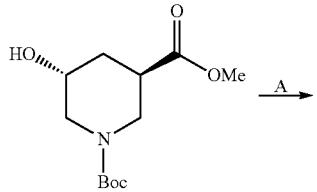

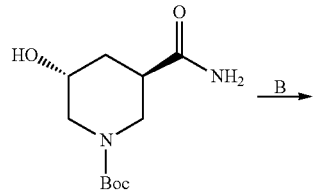

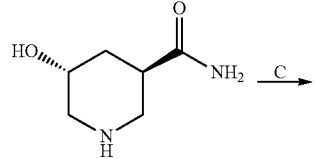

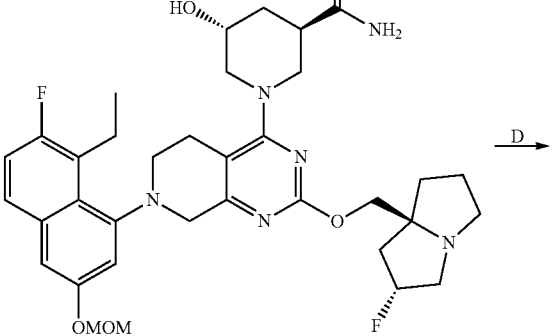

235

-continued

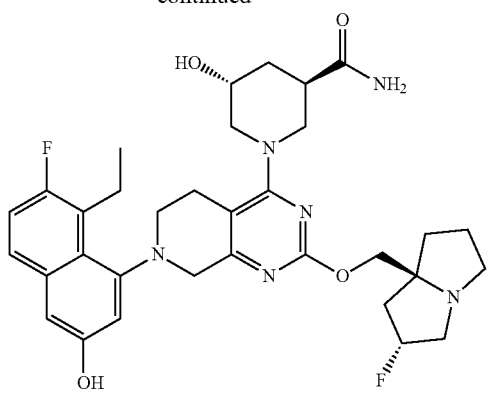

Step A. trans-tert-butyl 3-carbamoyl-5-hydroxypiperidine-1-carboxylate: A solution of O1-tert-butyl O3-methyl trans-5-hydroxypiperidine-1,3-dicarboxylate (200 mg, 1.0 equiv) in NH$_3$·MeOH (5 mL) was stirred in a sealed tube at 60° C. for 96 hours. The residue was concentrated to afford the title compound (180 mg, crude) as white solid. $^1$H NMR (400 MHz, DMSO-d$_6$) δ=7.47-7.28 (m, 1H), 6.94-6.71 (m, 1H), 4.66 (br s, 1H), 4.05-3.47 (m, 3H), 3.13-2.54 (m, 3H), 1.82-1.47 (m, 2H), 1.43-1.34 (m, 9H); LCMS (ESI, M+1): m/z=245.3.

Step B. trans-5-hydroxypiperidine-3-carboxamide: To a solution of tert-butyl trans-3-carbamoyl-5-hydroxy-piperidine-1-carboxylate (160 mg, 1.0 equiv) in MeCN (1 mL) was added HCl·dioxane (4 M, 2 mL, 12.2 equiv). The mixture was stirred at 0° C. for 0.5 hour. The residue was concentrated to afford the title compound (190 mg, HCl, crude) as colorless liquid.

Step C and D: Synthesized according to Example 32. The title compound was obtained as yellow solid. $^1$H NMR (400 MHz, METHANOL-d$_4$) δ=7.51 (dd, J=6.0, 9.2 Hz, 1H), 7.14 (t, J=9.6 Hz, 1H), 7.06-6.92 (m, 2H), 5.50-5.34 (m, 1H), 4.47-4.23 (m, 3H), 4.22-3.86 (m, 4H), 3.79-3.60 (m, 2H), 3.59-3.47 (m, 4H), 3.43-3.35 (m, 2H), 3.25-3.12 (m, 3H), 3.00-2.84 (m, 1H), 2.66 (br d, J=14.4 Hz, 1H), 2.53-2.33 (m, 2H), 2.23 (br d, J=9.6 Hz, 1H), 2.20-1.95 (m, 5H), 1.17-1.06 (m, 3H); LCMS (ESI, M+1): m/z=623.5.

Example 187

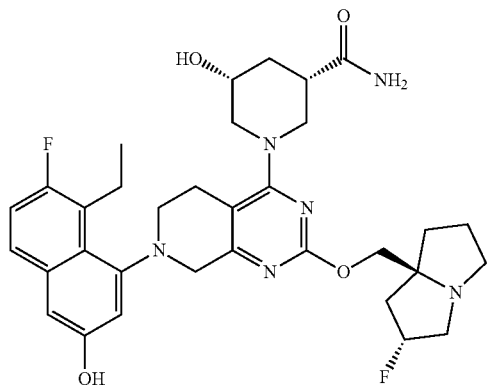 [SMILES: CCc1c(F)ccc2cc(O)cc(N3CCc4c(nc(OC[C@@]56CCCN5C[C@H](F)C6)nc4N4C[C@H](O)C[C@H](C(N)=O)C4)C3)c12]

236

(3S,5R)-1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-5-hydroxypiperidine-3-carboxamide Step A. cis-tert-butyl 3-carbamoyl-5-hydroxypiperidine-11-carboxylate: A solution of cis-1-tert-butyl 3-methyl 5-hydroxypiperidine-1,3-dicarboxylate (200 mg, 1.0 equiv) in NH$_3$/MeOH (5.0 mL) was stirred at 60° C. in a sealed tube for 48 hours. The solvent was removed under reduce pressure to afford the title compound (180 mg, crude) as a white solid. $^1$H NMR (400 MHz, CDCl$_3$,) δ=6.53-6.14 (m, 1H), 5.74-5.38 (m, 1H), 3.89-3.74 (m, 1H), 3.73-3.48 (m, 3H), 3.45-3.07 (m, 2H), 2.59-2.39 (m, 1H), 2.05 (s, 2H), 1.49-1.45 (m, 9H).

Step B. cis-5-hydroxypiperidine-3-carboxamide: To a solution of tert-butyl cis-3-carbamoyl-5-hydroxy-piperidine-1-carboxylate (180 mg, 1 equiv) in MeOH (1 mL) was added HCl/MeOH (4 M, 1.71 mL, 6.98 equiv) at 25° C. The mixture was stirred at 25° C. for 2 hours. The reaction mixture was concentrated under reduce pressure to afford the title compound (140 mg, crude, HCl) as a white solid.

Step C-D: Synthesized according to Example 32. The title compound was obtained as white solid. $^1$H NMR (400 MHz, METHANOL-d4) δ=7.53-7.47 (m, 1H), 7.17-7.10 (m, 1H), 7.00-6.93 (m, 2H), 5.35-5.16 (m, 1H), 4.25-4.03 (m, 5H), 3.97-3.56 (m, 2H), 3.53-3.33 (m, 3H), 3.24-3.12 (m, 5H), 3.10-2.90 (m, 2H), 2.90-2.52 (m, 3H), 2.32-2.04 (m, 4H), 1.69 (q, J=11.8 Hz, 4H), 1.15-1.07 (m, 3H); LCMS (ESI, M+1): m/z=623.3.

Example 188

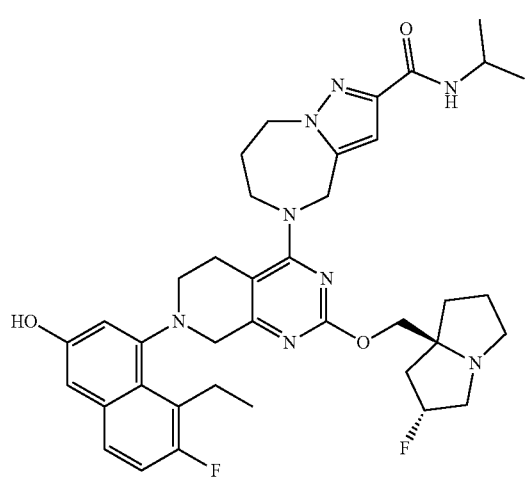 [SMILES: CCc1c(F)ccc2cc(O)cc(N3CCc4c(nc(OC[C@@]56CCCN5C[C@H](F)C6)nc4N4CCCn5nc(C(=O)NC(C)C)cc5C4)C3)c12]

5-(7-(8-ethyl-7-fluoro-3-hydroxynaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-N-isopropyl-5,6,7,8-tetrahydro-4H-pyrazolo[1,5-a][1,4]diazepine-2-carboxamide

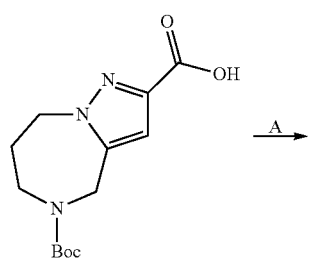

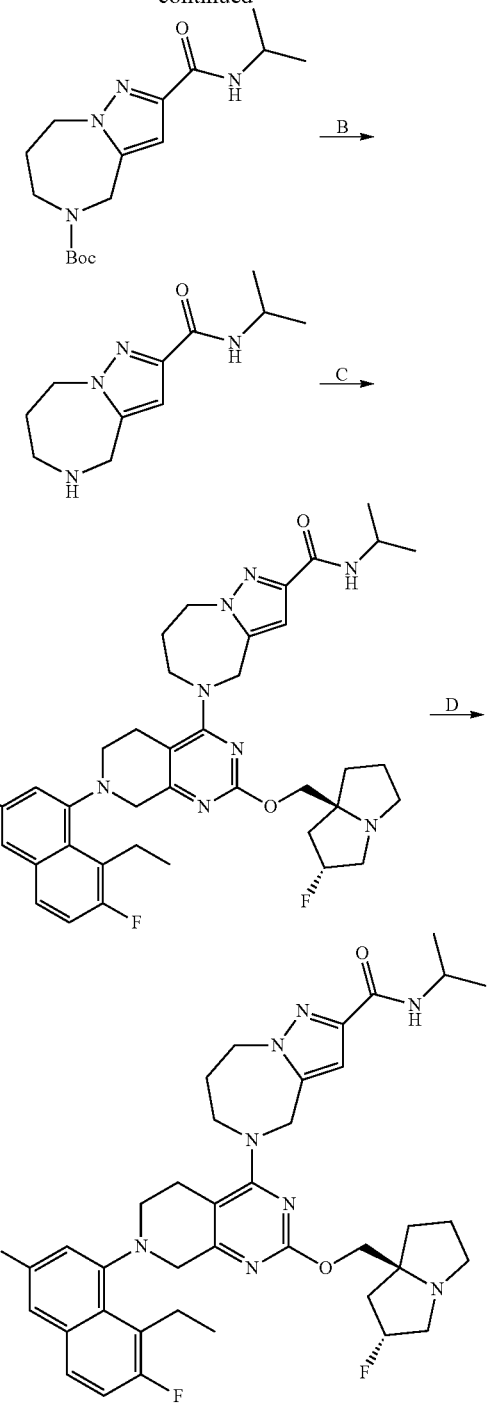

Step A. tert-butyl 2-(isopropylcarbamoyl)-4,6,7,8-tetrahydropyrazolo[1,5-a][1,4]diazepine-5-carboxylate: To a solution of 5-tert-butoxycarbonyl-4,6,7,8-tetrahydropyrazolo[1,5-a][1,4]diazepine-2-carboxylic acid (150 mg, 1.0 equiv) and propan-2-amine (63.0 mg, 2.0 equiv) in DMF (3 mL) were added HATU (304 mg, 1.5 equiv) and N-ethyl-N-isopropylpropan-2-amine (207 mg, 3.0 equiv) at 0° C. The mixture was stirred at 25° C. for 0.5 hour. The reaction mixture was diluted with water (50 mL) and extracted with ethyl acetate (30 mL×3). The combined organic layers were washed with brine (50 mL×3), dried over sodium sulfate, and concentrated under reduced pressure. The residue was purified by column chromatography (SiO₂, Petroleum ether/Ethyl acetate=3/1 to 1/2) to afford the title compound (135 mg, 78% yield) as a white solid. LCMS (ESI, M+1): m/z=323.2.

Step B. N-isopropyl-5,6,7,8-tetrahydro-4H-pyrazolo[1,5-a][1,4]diazepine-2-carboxamide: To a solution of tert-butyl 2-(isopropylcarbamoyl)-4,6,7,8-tetrahydropyrazolo[1,5-a][1,4]diazepine-5-carboxylate (160 mg, 1.0 equiv) in DCM (2 mL) was added TFA (0.8 mL). The reaction was stirred at 25° C. for 0.5 hour. The mixture was concentrated and then dissolved in MeOH (5 mL). NaHCO₃ was added to neutralize the mixture and then it was stirred at 25° C. for 0.5 hour. MeOH was removed through evaporation. The residue was taken up with ethyl acetate (10 mL), filtered, and concentrated under reduced pressure to afford the title compound (110 mg, 97.72% yield) as a white solid. LCMS (ESI, M+1): m/z=223.1

Step C-D: Synthesized according to Example 32. The title compound was obtained as pink solid. ¹H NMR (400 MHz, methanol-d4) δ=7.56-7.43 (m, 1H), 7.19-7.08 (m, 1H), 7.01-6.93 (m, 2H), 6.69 (s, 1H), 5.34-5.16 (m, 1H), 5.01-4.95 (m, 1H), 4.79 (br s, 1H), 4.66-4.45 (m, 3H), 4.27-4.11 (m, 2H), 4.10-3.93 (m, 4H), 3.65 (br d, J=18.0 Hz, 1H), 3.54 (br d, J=9.2 Hz, 1H), 3.47-3.34 (m, 2H), 3.19 (br t, J=8.0 Hz, 3H), 3.15-3.11 (m, 1H), 3.03-2.93 (m, 1H), 2.72 (br d, J=14.0 Hz, 1H), 2.40-2.27 (m, 1H), 2.27-2.01 (m, 4H), 2.00-1.89 (m, 2H), 1.89-1.76 (m, 1H), 1.23 (d, J=6.4 Hz, 6H), 1.11 (br t, J=7.2 Hz, 3H); ¹⁹F NMR (377 MHz, METHANOL-d4) δ=-122.86 (br s, 1F), -170.30--181.06 (m, 1F); LCMS (ESI, M+1): m/z=701

Example 189

5-(7-(8-ethyl-7-fluoro-3-hydroxynaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-N,N,3-trimethyl-5,6,7,8-tetrahydro-4H-pyrazolo[1,5-a][1,4]diazepine-2-carboxamide

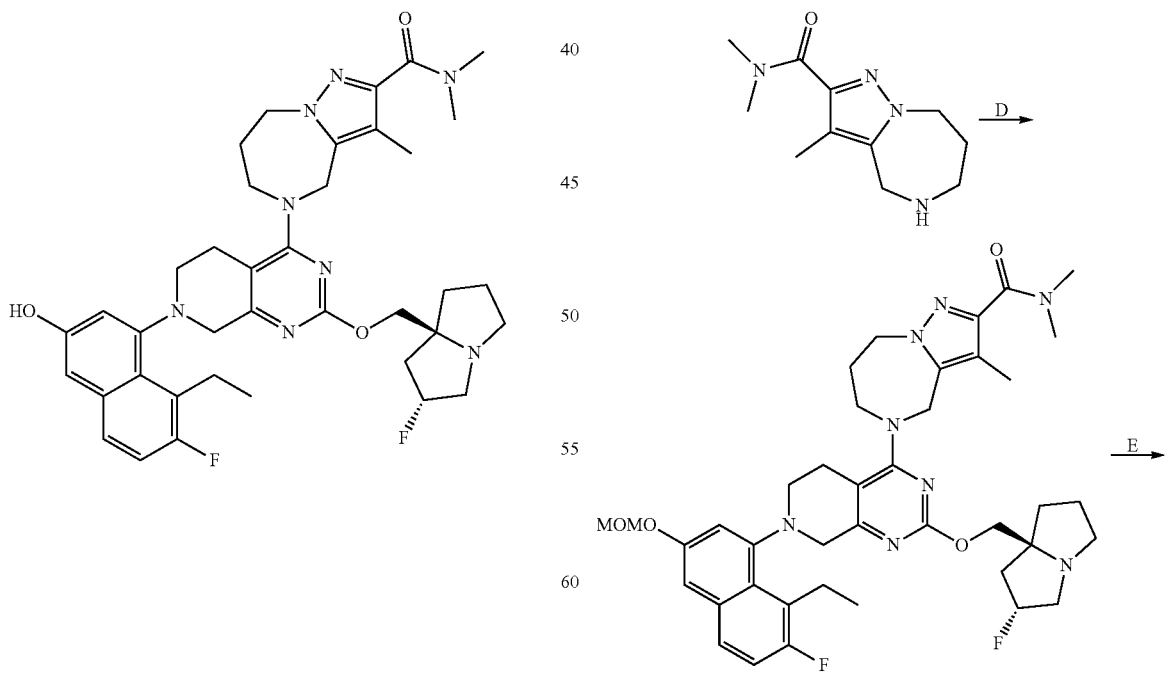

-continued

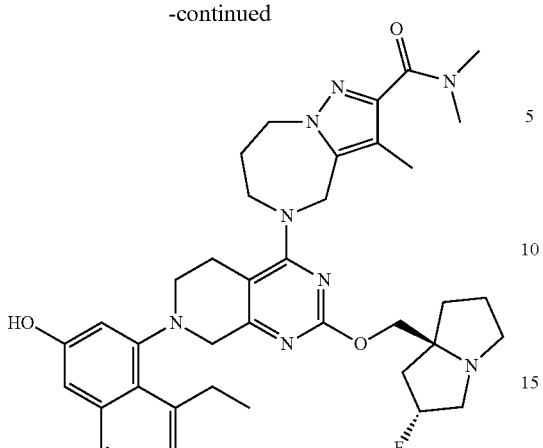

Step A. tert-butyl 2-(dimethylcarbamoyl)-3-iodo-7,8-dihydro-4H-pyrazolo[1,5-a][1,4]diazepine-5(6H)-carboxylate: To a solution of tert-butyl 2-(dimethylcarbamoyl)-4,6,7,8-tetrahydropyrazolo[1,5-a][1,4]diazepine-5-carboxylate (500 mg, 1.0 equiv) in AcOH (5 mL) was added NIS (720 mg, 2.0 equiv). The reaction was stirred at 80° C. for 2 hours. The reaction mixture was diluted with EtOAc (40 mL). The mixture was washed with saturated salt solution (3×20 mL), dried over anhydrous sodium sulfate, filtered, and concentrated under reduced pressure to give a residue. The residue was purified by column chromatography (SiO$_2$, Petroleum ether/Ethyl acetate=1/1 to 0/1) to afford the title compound (560 mg, 79% yield) as a brown solid. LCMS (ESI, M+1): m/z=435.1.

Step B. tert-butyl 2-(dimethylcarbamoyl)-3-methyl-7,8-dihydro-4H-pyrazolo[1,5-a][1,4]diazepine-5(6H)-carboxylate: A mixture of tert-butyl 2-(dimethylcarbamoyl)-3-iodo-4,6,7,8-tetrahydropyrazolo[1,5-a][1,4]diazepine-5-carboxylate (200 mg, 1.0 equiv), methylboronic acid (55.1 mg, 2.0 equiv), Ad$_2$nBuP Pd G$_3$ (cataCXium® A Pd G3) (33.5 mg, 0.1 equiv), and K$_3$PO$_4$ (195 mg, 2.0 equiv) in dioxane (3 mL) and H$_2$O (1 mL) was degassed and purged with N$_2$ for 3 times. The reaction was stirred at 80° C. for 2 hours under N$_2$ atmosphere. The reaction mixture was filtered and concentrated under reduced pressure. The residue was purified by prep-HPLC (column: Waters Xbridge C18 150×50 mm×10 μm; mobile phase: [water (NH$_4$HCO$_3$)-ACN]; B %: 22%-52%, 10 minutes) to afford the title compound (50.0 mg, 34% yield) as a white solid. LCMS (ESI, M+1): m/z=323.1.

Step C. N,N,3-trimethyl-5,6,7,8-tetrahydro-4H-pyrazolo[1,5-a][1,4]diazepine-2-carboxamide: To a solution of tert-butyl 2-(dimethylcarbamoyl)-3-methyl-4,6,7,8-tetrahydro-pyrazolo[1,5-a][1,4]diazepine-5-carboxylate (50.0 mg, 1.0 equiv) in dioxane (1 mL) was added HCl/dioxane (4 M, 1 mL). The mixture was stirred at 25° C. for 1 hour. The reaction mixture was filtered and concentrated under reduced pressure to afford the title compound (28.0 mg, 81% yield) as yellow oil, which was used in the the next step without further purification; LCMS (ESI, M+1): m/z=223.2.

Step D-E: Synthesized according to Example 32. The title compound was obtained as a white solid. $^1$H NMR (400 MHz, METHANOL-d$_4$) δ=7.51 (dd, J=6.0, 8.8 Hz, 1H), 7.19-7.09 (m, 1H), 6.96 (s, 2H), 5.35 (br s, 1H), 5.02-5.00 (m, 1H), 4.71 (br dd, J=3.2, 16.4 Hz, 1H), 4.58 (br s, 1H), 4.53-4.37 (m, 2H), 4.14-4.01 (m, 4H), 4.00-3.90 (m, 1H), 3.67 (br d, J=18.0 Hz, 1H), 3.50 (br d, J=10.4 Hz, 1H), 3.41 (br d, J=7.2 Hz, 2H), 3.29-3.22 (m, 3H), 3.21-3.17 (m, 2H), 3.13 (s, 3H), 3.08 (s, 3H), 3.06-2.97 (m, 1H), 2.70 (br d, J=14.0 Hz, 1H), 2.38-2.25 (m, 2H), 2.23-2.05 (m, 5H), 2.02-1.92 (m, 2H), 1.91-1.78 (m, 1H), 1.10 (br t, J=7.2 Hz, 3H); $^{19}$F NMR (377 MHz, METHANOL-d4) δ=−123.04 (br s, 1F), −171.19--176.12 (m, 1F); LCMS (ESI, M+1): m/z=701.5.

Example 190

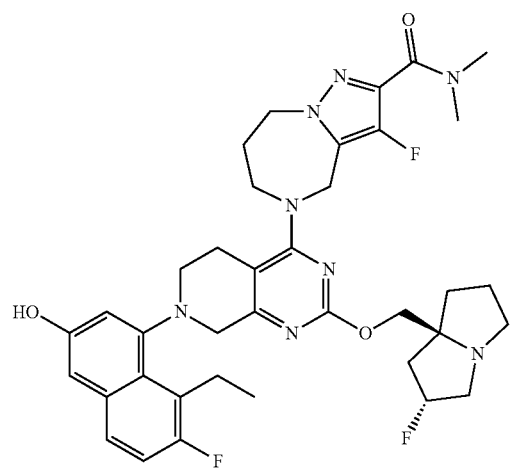 [SMILES: CCc1c(F)ccc2cc(O)cc(N3CCc4c(nc(OC[C@@]56CCCN5C[C@H](F)C6)nc4N4CCCn5nc(C(=O)N(C)C)c(F)c5C4)C3)c12]

5-(7-(8-ethyl-7-fluoro-3-hydroxynaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-3-fluoro-N,N-dimethyl-5,6,7,8-tetrahydro-4H-pyrazolo[1,5-a][1,4]diazepine-2-carboxamide

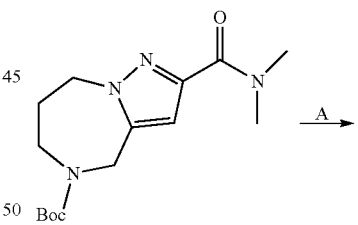

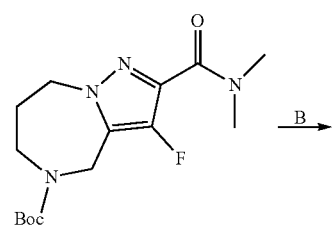

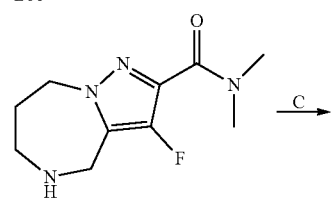

243
-continued

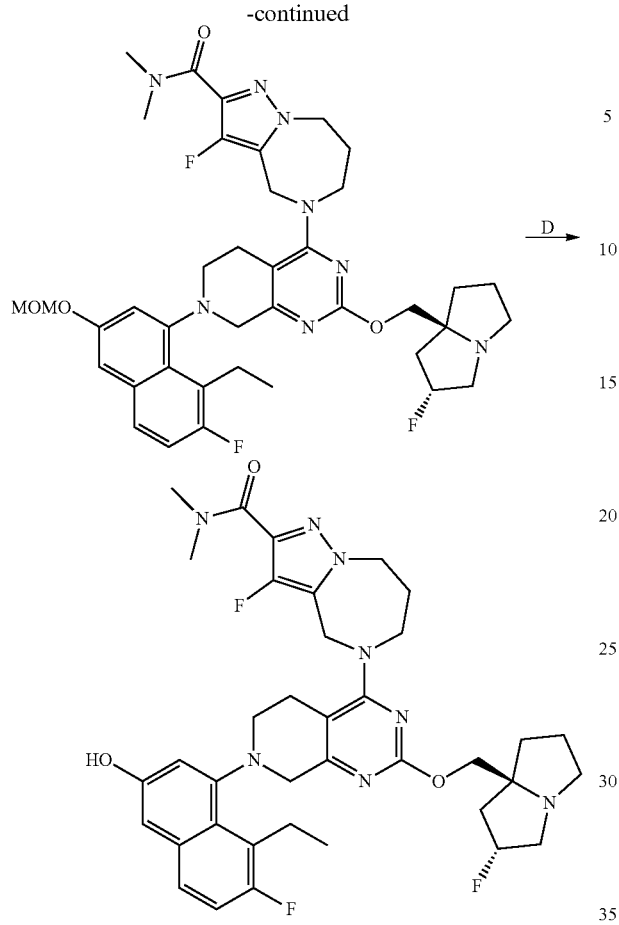

2H), 3.01-2.91 (m, 4H), 2.80 (s, 1H), 2.62 (s, 1H), 2.24-1.57 (m, 9H), 1.04 (t, J=7.2 Hz, 3H); LCMS (ESI, M+1): m/z=705.5.

Example 191

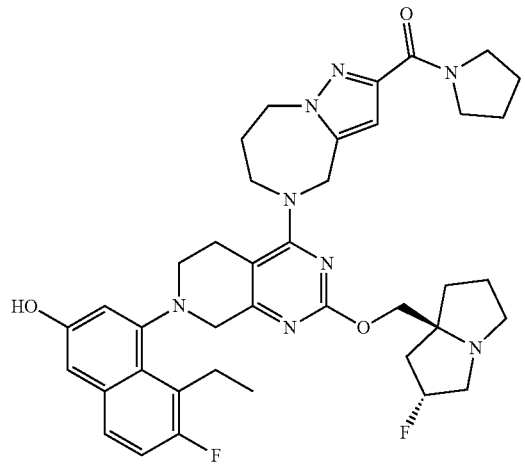 [SMILES: CCc1c(F)ccc2cc(O)cc(N3CCc4c(nc(OC[C@@]56CCCN5C[C@H](F)C6)nc4N4CCCn5nc(C(=O)N6CCCC6)cc5C4)C3)c12]

(5-(7-(8-ethyl-7-fluoro-3-hydroxynaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-5,6,7,8-tetrahydro-4H-pyrazolo[1,5-a][1,4]diazepin-2-yl)(pyrrolidin-1-yl)methanone

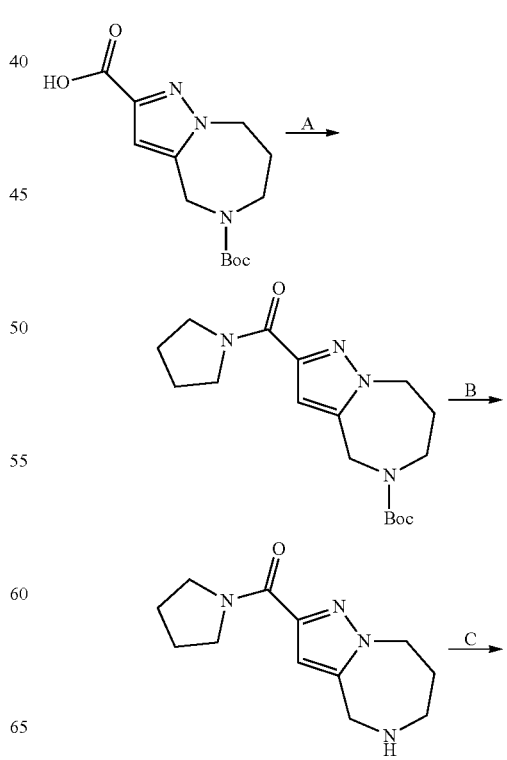

Step A. tert-butyl 2-(dimethylcarbamoyl)-3-fluoro-7,8-dihydro-4H-pyrazolo[1,5-a][1,4]diazepine-5(6H)-carboxylate: To a solution of tert-butyl 2-(dimethylcarbamoyl)-4,6,7,8-tetrahydropyrazolo[1,5-a][1,4]diazepine-5-carboxylate (760 mg, 1 equiv) in ACN (10 mL) was added 1-(chloromethyl)-4-fluoro-1,4-diazoniabicyclo[2.2.2]octane; ditetrafluoroborate (4.37 g, 5 equiv). The reaction was stirred at 25° C. for 16 hours. After completion, the reaction mixture was concentrated and purified with prep-HPLC (column: Phenomenex luna C18 200×40 mm×10 µm; mobile phase: [water (FA)-MeCN]; B %: 25%-55%, 10 min) to afford the title compound (107 mg, 13.17% yield) as a yellow oil; LCMS (ESI, M+1): m/z=326.9.

Step B. 3-fluoro-N,N-dimethyl-5,6,7,8-tetrahydro-4H-pyrazolo[1,5-a][1,4]diazepine-2-carboxamide: To a solution of tert-butyl 2-(dimethylcarbamoyl)-3-fluoro-4,6,7,8-tetrahydropyrazolo[1,5-a][1,4]diazepine-5-carboxylate (56 mg, 1 equiv) in DCM (0.25 mL) was added TFA (0.25 mL). The reaction was stirred at 25° C. for 1 hour. The reaction was concentrated under the reduced pressure and filtered to afford the title compound (91 mg, crude, TFA) as a yellow oil; LCMS (ESI, M+1): m/z=226.9.

Step C-D: Synthesized according to Example 32. The title compound was obtained as white solid. $^1$H NMR (400 MHz, DMSO-d$_6$) δ=9.68 (s, 1H), 8.16 (s, 1H), 7.67-7.51 (m, 1H), 7.24 (s, 1H), 6.98 (s, 2H), 5.17 (s, 1H), 4.94 (d, J=16.0 Hz, 1H), 4.73 (d, J=16.0 Hz, 1H), 4.44 (t, J=6.8 Hz, 2H), 4.15-4.00 (m, 1H), 3.98-3.76 (m, 4H), 3.62 (d, J=16.8 Hz, 1H), 3.40 (s, 2H), 3.28-3.21 (m, 2H), 3.10 (s, 3H), 3.04 (s,

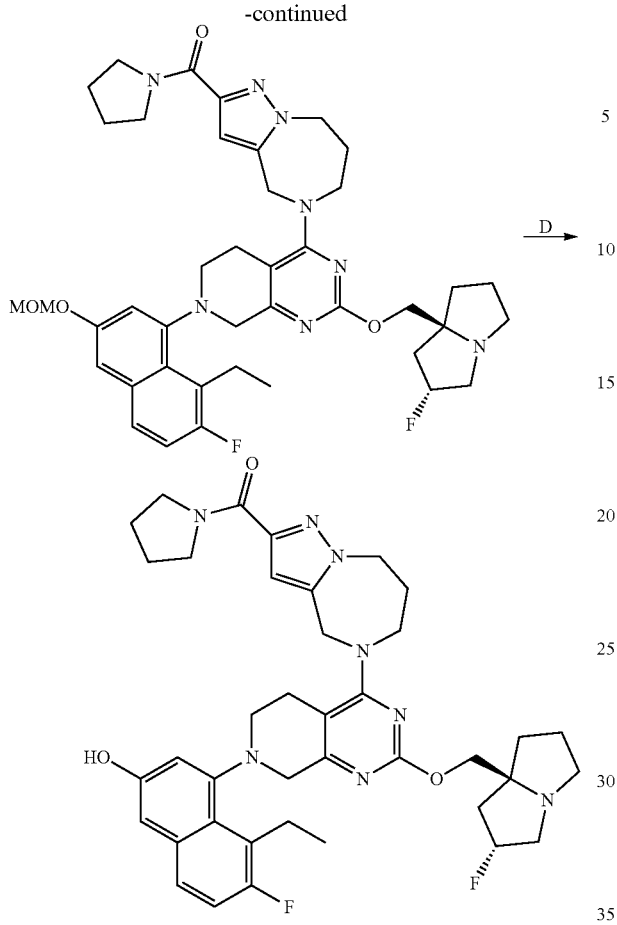

Step A. tert-butyl 2-(pyrrolidine-1-carbonyl)-4,6,7,8-tetrahydropyrazolo[1,5-a][1,4]diazepine-5-carboxylate: To a solution of 5-tert-butoxycarbonyl-4,6,7,8-tetrahydropyrazolo[1,5-a][1,4]diazepine-2-carboxylic acid (200 mg, 1.0 equiv), pyrrolidine (101 mg, 2.0 equiv) and N-ethyl-N-isopropylpropan-2-amine (276 mg, 3.0 equiv) in DMF (1 mL) was added HATU (405 mg, 1.5 equiv) at 0° C. The mixture was stirred at 25° C. for 1 hour. The reaction mixture was quenched with water (5 mL) at 25° C., diluted with water (20 mL) and extracted with ethyl acetate (30 mL×2). The combined organic layers were washed with brine (5 mL), dried over anhydrous sodium sulfate, filtered, and concentrated under reduced pressure. The residue was purified by column chromatography (SiO₂, Petroleum ether/Ethyl acetate=10/1 to 0/1) to afford the title compound (240 mg, 99% yield) as a yellow solid. LCMS (ESI, M+1): m/z=335.2.

Step B. pyrrolidin-1-yl(5,6,7,8-tetrahydro-4H-pyrazolo[1,5-a][1,4]diazepin-2-yl)methanone: To a solution of tert-butyl 2-(pyrrolidine-1-carbonyl)-4,6,7,8-tetrahydropyrazolo[1,5-a][1,4]diazepine-5-carboxylate (240 mg, 1.0 equiv) in DCM (1 mL) was added TFA (3 mL). The mixture was stirred at 25° C. for 0.5 hour. The reaction mixture was concentrated under reduced pressure to remove solvent. The residue was dissolved with MeOH (10 mL), and pH was adjusted to 9 with NH₃·H₂O (4 mL). The mixture was stirred for 0.3 hours. The reaction mixture was diluted with water (10 mL) and extracted with trichloromethane:isopropanol=4:1 (10 mL×3). The organic layer was separated, washed with brine (10 mL×2), dried over anhydrous sodium sulfate, filtered and concentrated under reduced pressure to afford the title compound (160 mg, 95% yield) as a yellow oil; ¹H NMR (400 MHz, DMSO-d₆) δ=6.44 (s, 1H), 4.37-4.31 (m, 2H), 3.81 (s, 2H), 3.80-3.77 (m, 2H), 3.43 (t, J=6.4 Hz, 2H), 3.06-2.99 (m, 2H), 1.89-1.67 (m, 6H).

Step C-D: Synthesized according to Example 32. The title compound was obtained as yellow solid. ¹H NMR (400 MHz, METHANOL-d4) δ=7.51 (dd, J=5.6, 9.0 Hz, 1H), 7.14 (t, J=9.2 Hz, 1H), 6.97 (s, 2H), 6.68 (s, 1H), 5.37-5.15 (m, 1H), 5.03-4.97 (m, 1H), 4.64-4.51 (m, 3H), 4.25-4.15 (m, 1H), 4.13-3.96 (m, 4H), 3.90 (t, J=6.4 Hz, 2H), 3.66 (d, J=17.6 Hz, 1H), 3.62-3.50 (m, 3H), 3.39 (br dd, J=2.0, 5.9 Hz, 1H), 3.26-3.13 (m, 5H), 3.03-2.95 (m, 1H), 2.72 (br d, J=13.6 Hz, 1H), 2.37-2.12 (m, 3H), 2.11-2.03 (m, 2H), 2.00-1.90 (m, 6H), 1.89-1.81 (m, 1H), 1.38-1.27 (m, 1H), 1.15-1.07 (m, 3H); ¹⁹F NMR (377 MHz, METHANOL-d4) δ=−122.92 (br s, 1F), −173.58 (br d, J=22.9 Hz, 1F); LCMS [ESI, M+1]: m/z=713.4.

Example 192

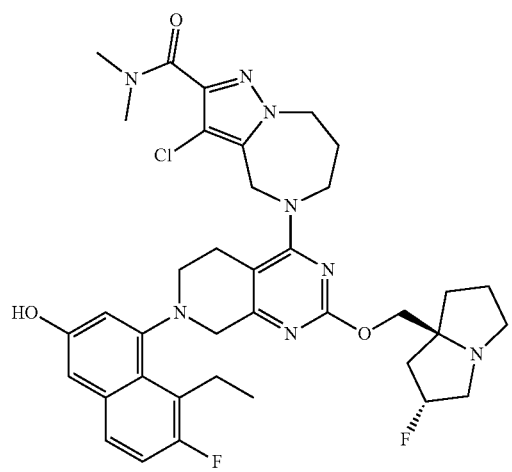 [SMILES: CCc1c(F)ccc2cc(O)cc(N3CCc4c(nc(OC[C@@]56CCCN5C[C@H](F)C6)nc4N4CCCn5nc(C(=O)N(C)C)c(Cl)c5C4)C3)c12]

3-chloro-5-(7-(8-ethyl-7-fluoro-3-hydroxynaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide

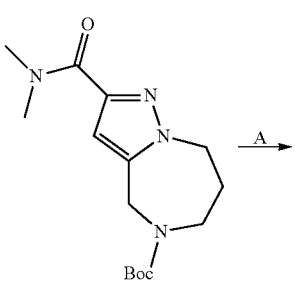

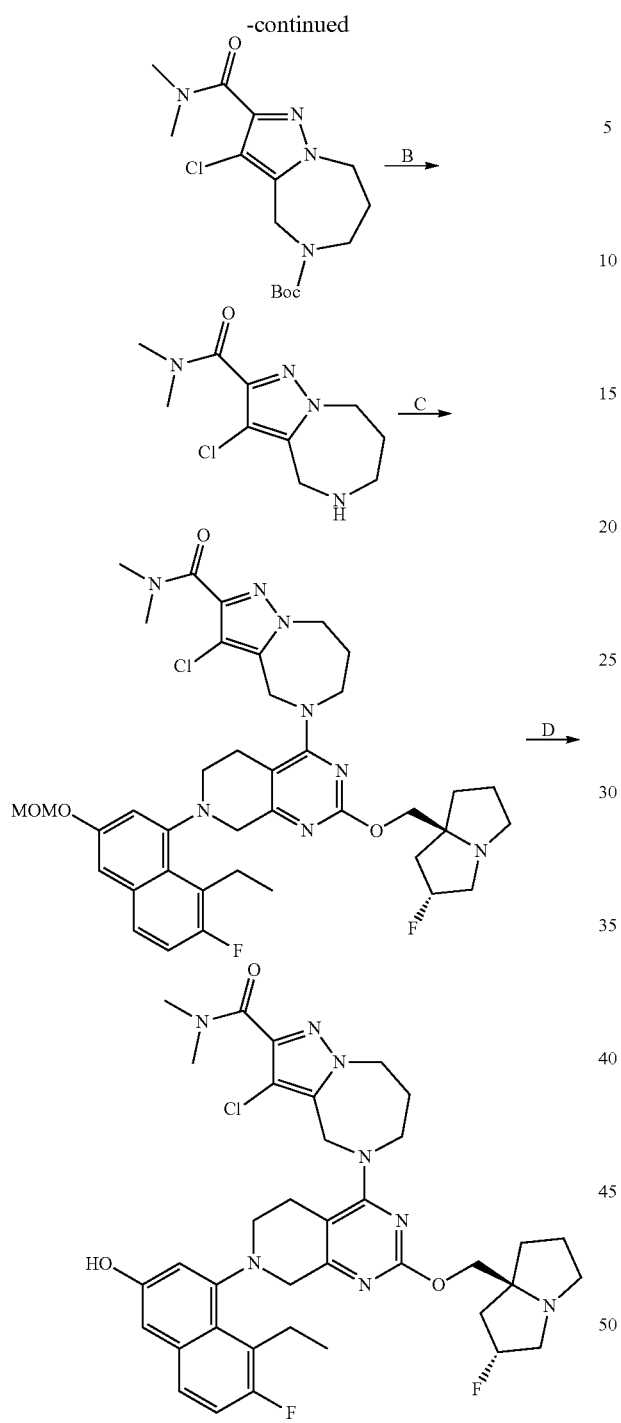

Step A. tert-butyl 3-chloro-2-(dimethylcarbamoyl)-7,8-dihydro-4H-pyrazolo[1,5-a][1,4]diazepine-5(6H)-carboxylate: To a mixture of tert-butyl 2-(dimethylcarbamoyl)-4,6,7,8-tetrahydropyrazolo[1,5-a][1, 4]diazepine-5-carboxylate (1.2 g, 1 equiv) in DMF (12 mL) was added NCS (779.44 mg, 1.5 equiv) at 0° C. The reaction was stirred at 55° C. for 1 hour. The reaction mixture was diluted with H$_2$O (10 mL×3) and extracted with EtOAc (10 mL×3), the combined organic layers were washed with brine (10 mL×3), dried, filtered, and concentrated to give a residue, which was purified by column chromatography (SiO$_2$, Petroleum ether/Ethyl acetate=10/1 to 1/1) to afford the title compound (740 mg, 51.59% yield) as a light yellow oil; 1H NMR (400 MHz, CDCl$_3$) δ=4.50 (s, 2H), 4.45-4.35 (m, 2H), 3.75 (s, 2H), 3.10 (s, 6H), 1.97 (s, 2H), 1.44 (s, 9H); LCMS (ESI, M+1): m/z=343.4.

Step B. 3-chloro-N,N-dimethyl-5,6,7,8-tetrahydro-4H-pyrazolo[1,5-a][1,4]diazepine-2-carboxamide: A mixture of tert-butyl 3-chloro-2-(dimethylcarbamoyl)-4,6,7,8-tetrahydropyrazolo[1,5-a][1,4]diazepine-5-carboxylate (170 mg, 1 equiv) and HCl/dioxane (1 mL) was stirred at 20° C. for 1 hour. The mixture was concentrated to afford the title compound (115 mg, crude) as light-yellow solid.

Step C-D: Synthesized according to Example 32. The title compound was obtained as yellow gum; $^1$H NMR (400 MHz, DMSO-d$_6$) δ=11.23-10.98 (m, 1H), 7.60 (dd, J=6.0 Hz, 8.8 Hz, 1H), 7.30-7.20 (m, 1H), 7.08-6.97 (m, 2H), 5.67-5.46 (m, 1H), 5.05 (d, J=16.0 Hz, 1H), 4.92-4.77 (m, 1H), 4.50-4.35 (m, 4H), 4.19-4.13 (m, 1H), 4.03 (d, J=17.2 Hz, 3H), 3.43 (d, J=8.0 Hz, 2H), 3.33-3.21 (m, 4H), 3.16-3.08 (m, 1H), 2.99 (d, J=16.0 Hz, 6H), 2.79-2.64 (m, 2H), 2.44-2.38 (m, 1H), 2.35-1.96 (m, 8H), 1.10-0.98 (m, 3H); LCMS (ESI, M+1): m/z=721.3.

Example 193

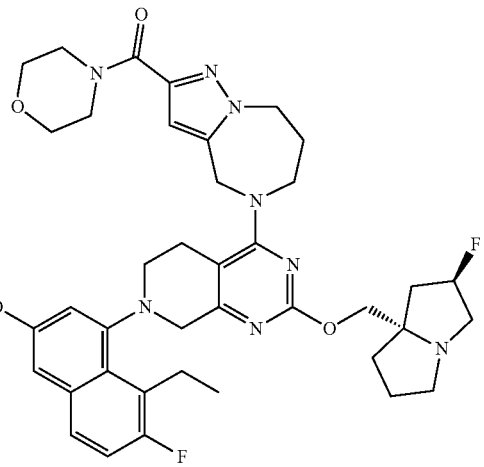

(5-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-5,6,7,8-tetrahydro-4H-pyrazolo[1,5-a][1,4]diazepin-2-yl)(morpholino)methanone

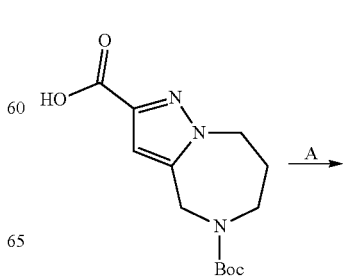

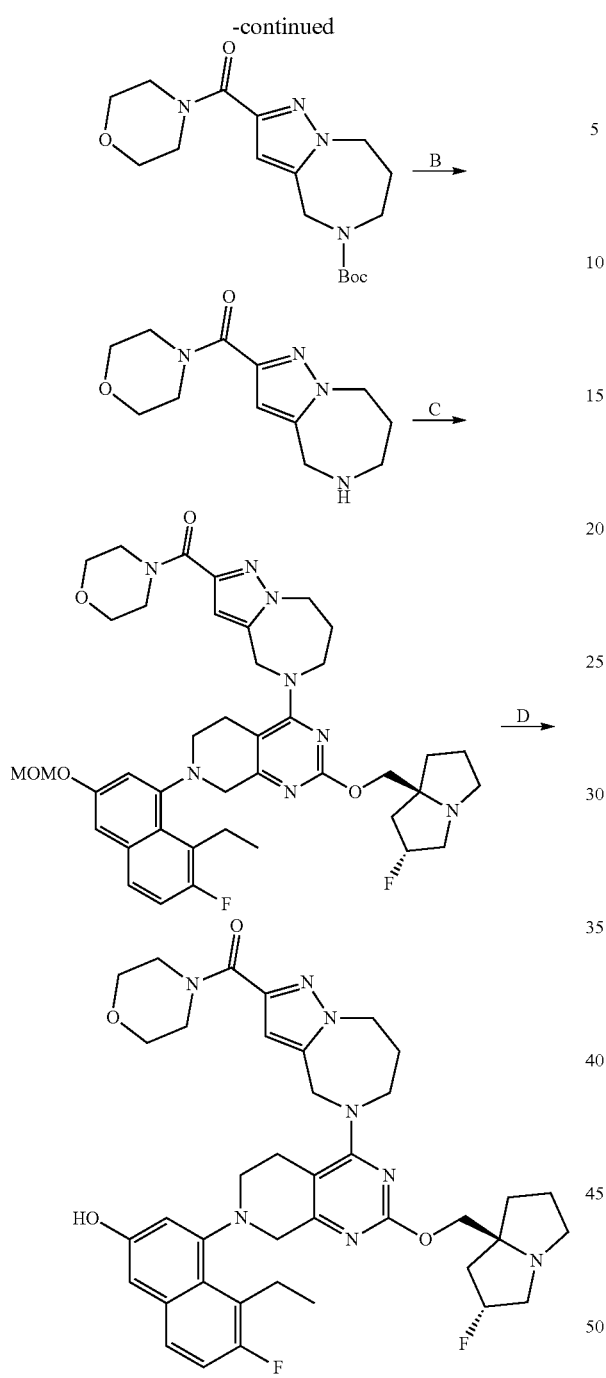

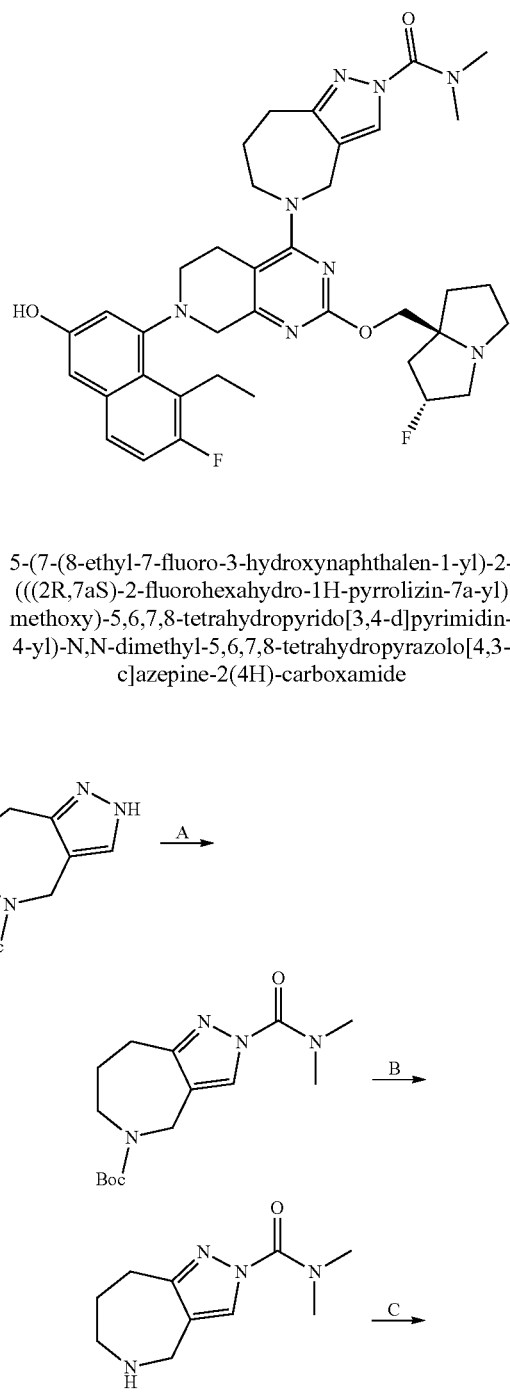

Example 194

5-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-N,N-dimethyl-5,6,7,8-tetrahydropyrazolo[4,3-c]azepine-2(4H)-carboxamide Synthesized according to Example 191. The title compound was obtained as off-white solid. $^1$H NMR (400 MHz, methanol-$d_4$) δ=7.51 (dd, J=5.6, 8.8 Hz, 1H), 7.14 (t, J=9.2 Hz, 1H), 6.96 (s, 2H), 6.62 (s, 1H), 5.38-5.14 (m, 1H), 5.04-4.98 (m, 1H), 4.86-4.80 (m, 1H), 4.69-4.57 (m, 1H), 4.56-4.50 (m, 2H), 4.27-4.15 (m, 1H), 4.12-4.08 (m, 1H), 4.08-3.94 (m, 5H), 3.73 (br s, 3H), 3.70-3.63 (m, 3H), 3.57-3.48 (m, 1H), 3.45-3.35 (m, 2H), 3.26-3.18 (m, 3H), 3.18-3.11 (m, 2H), 2.98 (dt, J=5.2, 9.2 Hz, 1H), 2.72 (br d, J=13.6 Hz, 1H), 2.34-2.11 (m, 3H), 2.11-2.02 (m, 2H), 2.00-1.91 (m, 2H), 1.90-1.79 (m, 1H), 1.15-1.07 (m, 3H); $^{19}$F NMR (377 MHz, methanol-$d_4$) δ=−123, −173; LCMS (ESI, M+1): m/z=729.5.

-continued

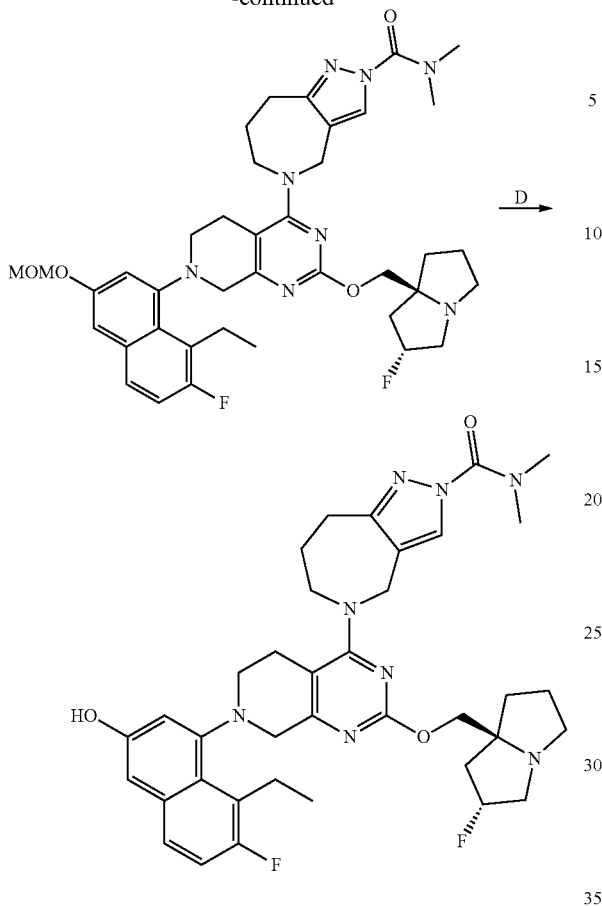

1.99-1.82 (m, 4H), 1.09 (br t, J=6.4 Hz, 3H); ¹⁹F NMR (377 MHz, METHANOL-d4) δ=−123, −173; LCMS (ESI, M+1): m/z=687.6.

Example 195

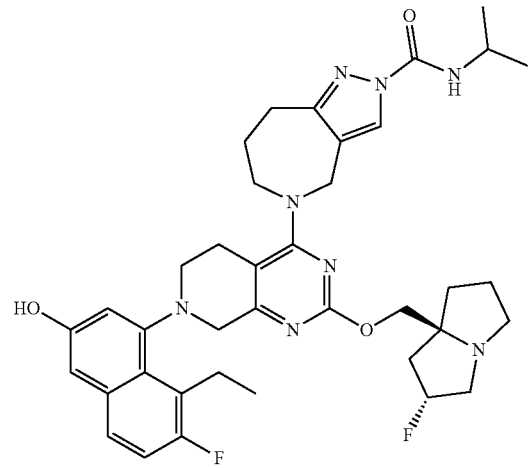 [SMILES: CCc1c(F)ccc2cc(O)cc(N3CCc4c(nc(OC[C@@]56CCCN5C[C@H](F)C6)nc4N4CCCc5nn(C(=O)NC(C)C)cc5C4)C3)c12]

5-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-N-isopropyl-5,6,7,8-tetrahydropyrazolo[4,3-c]azepine-2(4H)-carboxamide

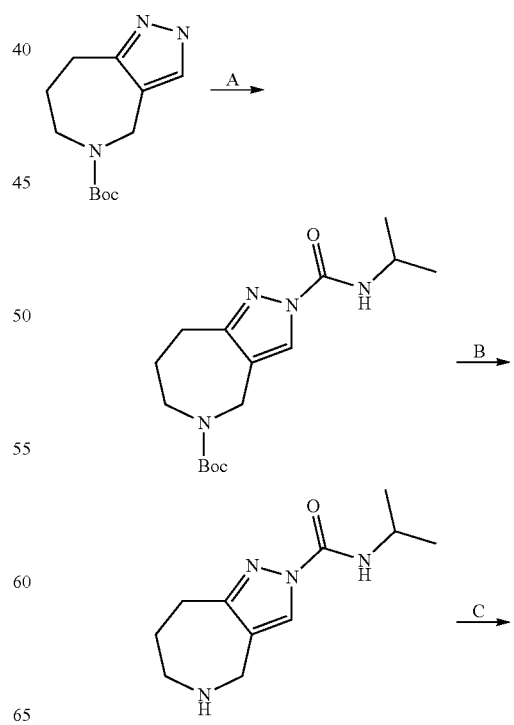

Step A. tert-butyl 2-(dimethylcarbamoyl)-4,6,7,8-tetrahydropyrazolo[4,3-c]azepine-5(2H)-carboxylate: To a solution of tert-butyl 4,6,7,8-tetrahydro-2H-pyrazolo[4,3-c]azepine-5-carboxylate (1.00 g, 1.0 equiv) in THF (10 mL) were added sodium amide (843 mg, 5.0 equiv) and N,N-dimethylcarbamoyl chloride (906 mg, 2.0 equiv) at 0° C. The mixture was stirred at 25° C. for 2 hours. The reaction mixture was quenched with water (20 mL) at 0° C., and then extracted with ethyl acetate (3×30 mL). The combined organic layers were washed with brine (30 mL), dried over Na₂SO₄, filtered, and concentrated under reduced pressure to afford the title compound (1.10 g, 85% yield) as a white solid. LCMS (ESI, M+1): m/z=309.3.

Step B. N,N-dimethyl-5,6,7,8-tetrahydropyrazolo[4,3-c]azepine-2(4H)-carboxamide: To a solution of tert-butyl 2-(dimethylcarbamoyl)-4,6,7,8-tetrahydropyrazolo[4,3-c]azepine-5-carboxylate (780 mg, 1.0 equiv) in DCM (5 mL) was added TFA (3.16 g, 11 equiv). The mixture was stirred at 25° C. for 0.5 hour. The reaction mixture was concentrated under reduced pressure to afford the title compound (200 mg, 38% yield) as a white solid. LCMS (ESI, M+1): m/z=209.1.

Step C-D: Synthesized according to Example 32. The title compound was obtained as white solid. ¹H NMR (400 MHz, methanol-d4) δ=8.05 (br d, J=3.2 Hz, 1H), 7.50 (br dd, J=6.0, 8.8 Hz, 1H), 7.13 (br t, J=9.2 Hz, 1H), 6.95 (s, 2H), 5.36-5.16 (m, 1H), 4.76-4.71 (m, 1H), 4.66-4.50 (m, 1H), 4.20-4.12 (m, 1H), 4.12-4.02 (m, 3H), 4.00 (br d, J=8.4 Hz, 1H), 3.65 (br d, J=17.2 Hz, 1H), 3.50 (br d, J=6.4 Hz, 1H), 3.36 (br d, J=7.2 Hz, 2H), 3.18 (br s, 11H), 2.97 (br d, J=3.2 Hz, 3H), 2.72 (br d, J=12.4 Hz, 1H), 2.27-2.05 (m, 4H),

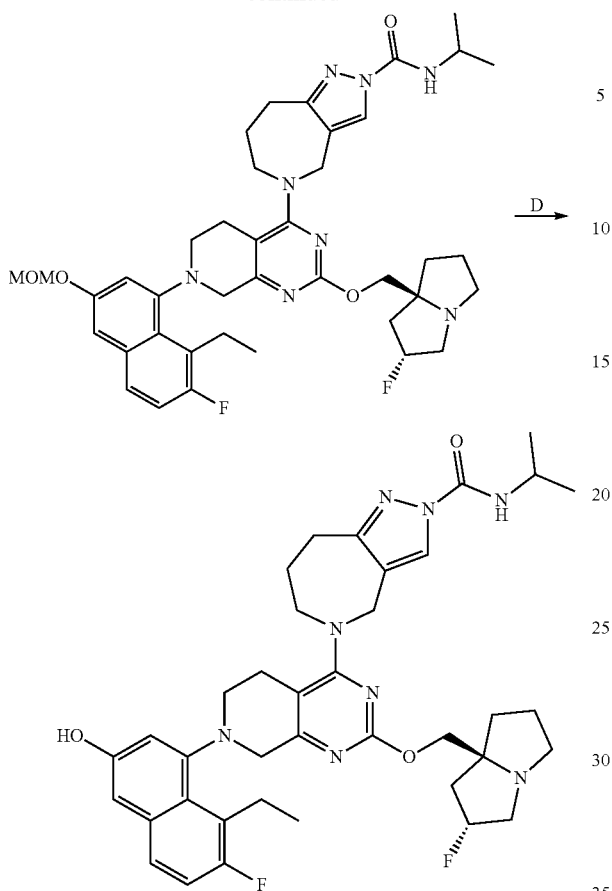

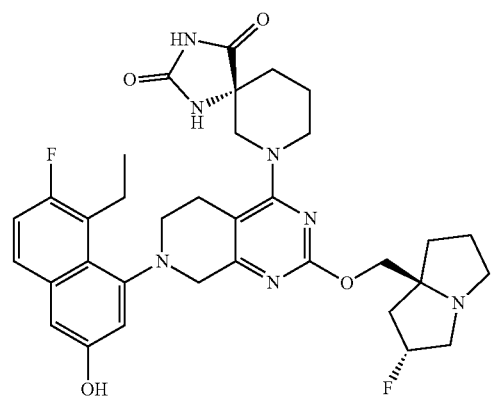 [SMILES: CCc1c(F)ccc2cc(O)cc(N3CCc4c(nc(OC[C@@]56CCCN5C[C@H](F)C6)nc4N4CCC[C@]5(C4)NC(=O)NC5=O)C3)c12]

Example 196

(R)-7-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,3,7-triazaspiro[4.5]decane-2,4-dione

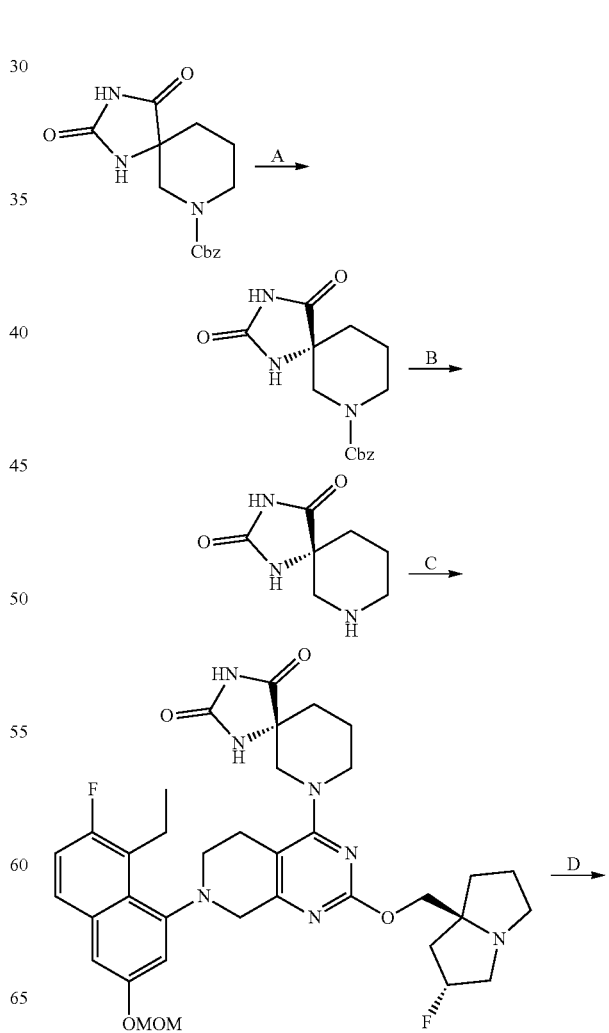

Step A. tert-butyl 2-(isopropylcarbamoyl)-4,6,7,8-tetrahydropyrazolo[4,3-c]azepine-5-carboxylate: To a solution of tert-butyl 4,6,7,8-tetrahydro-2H-pyrazolo[4,3-c]azepine-5-carboxylate (4.0 g, 1.0 equiv) in THF (20 mL) was added CDI (2.73 g, 1 equiv) dropwise at 25° C. for 1 hour. Then isopropyl amine (1.1 g, 1.1 equiv) was added dropwise at 25° C. The mixture was concentrated and purified with column chromatography [SiO$_2$, petroleum ether/ethyl acetate=3/1 to 0/1] to afford the title compound (4.5 g, 82% yield) as white solid. LCMS (ESI, M+1): m/z=323.2.

Step B. N-isopropyl-5,6,7,8-tetrahydropyrazolo[4,3-c]azepine-2(4H)-carboxamide: A solution of tert-butyl 2-(isopropylcarbamoyl)-4,6,7,8-tetrahydropyrazolo[4,3-c]azepine-5-carboxylate (6.0 g, 1 equiv) in HCl/MeOH (30 mL) was stirred at 25° C. for 0.5 hour. The mixture was concentrated to afford the title compound (3.2 g, 77% yield) as white solid. LCMS (ESI, M+1): m/z=223.2.

Step C-D: Synthesized according to Example 32. The title compound was obtained as yellow solid. 1H NMR (400 MHz, DMSO-d6) δ=8.21 (d, J=1.6 Hz, 1H), 7.99 (dd, J=2.0, 8.4 Hz, 1H), 7.59 (dd, J=6.0, 9.1 Hz, 1H), 7.24 (t, J=9.6 Hz, 1H), 7.05-6.95 (m, 2H), 5.66-5.44 (m, 1H), 4.86-4.61 (m, 2H), 4.44-4.21 (m, 2H), 4.07 (br d, J=4.0 Hz, 2H), 3.97-3.79 (m, 3H), 3.75-3.66 (m, 2H), 3.28-3.03 (m, 7H), 2.92 (br t, J=5.6 Hz, 2H), 2.75-2.57 (m, 2H), 2.45-2.40 (m, 1H), 2.37-2.22 (m, 2H), 2.18-1.95 (m, 4H), 1.76-1.66 (m, 1H), 1.17 (d, J=6.8 Hz, 6H), 1.02 (t, J=7.2 Hz, 3H); LCMS (ESI, M+1): m/z=701.5.

255
-continued

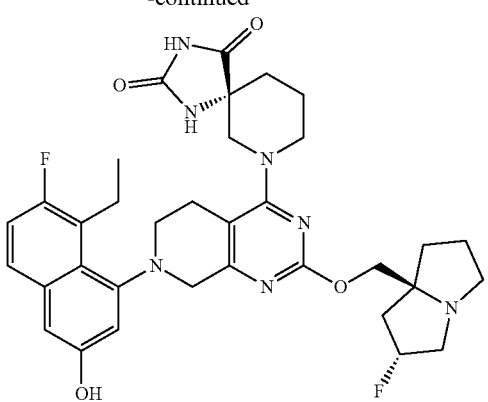

Step A. (R)-benzyl 2,4-dioxo-1,3,7-triazaspiro[4.5]decane-7-carboxylate: Benzyl 2,4-dioxo-1,3,7-triazaspiro[4.5]decane-7-carboxylate (30 g, 1 equiv) was purified with SFC [DAICEL CHIRALPAK AS (250 mm×30 mm, 10 μm); A: 0.1% NH₃H₂O, B: MeOH; B %: 27%-27%, 3.4 over 918 minutes]. The first peak was collected and concentrated to afford the title compound (14.5 g, 48% yield) as white solid. SFC: >99% ee, Chiralpak IG-3 50×4.6 mm I.D., 3 μm, Mobile phase: Phase A for CO2, and Phase B for MeOH (0.05% DEA); Gradient elution: 40% MeOH (0.05% DEA) in CO2, 3 mL/min, 220 nm, $t_R$: 1.640 min; LCMS (ESI, M+1): m/z=304.1.

Step B. (R)-1,3,7-triazaspiro[4.5]decane-2,4-dione: To a solution of (R)-benzyl 2,4-dioxo-1,3,7-triazaspiro[4.5]decane-7-carboxylate (14 g, 1.0 equiv) in MeOH (700 mL) was added Pd/C (1.4 g, 10% purity) under N₂. The suspension was degassed and purged with H₂ several times. The mixture was stirred at 25° C. for 1 hour under H₂ (15 psi) atmosphere. The mixture was filtered, and concentrated to afford the title compound (7.63 g, 88% yield) as white solid. LCMS (ESI, M+1): m/z=170.1.

Step C-D: Synthesized according to Example 32. The title compound was obtained as yellow solid. ¹H NMR (400 MHz, METHANOL-d₄) δ=7.55-7.46 (m, 1H), 7.18-7.10 (m, 1H), 7.02-6.93 (m, 2H), 5.36-5.15 (m, 1H), 4.22-4.09 (m, 3H), 4.08-4.04 (m, 1H), 4.04-3.93 (m, 1H), 3.69-3.61 (m, 1H), 3.54-3.34 (m, 4H), 3.27-3.11 (m, 5H), 3.10-2.93 (m, 2H), 2.83-2.68 (m, 1H), 2.34-2.19 (m, 1H), 2.17-2.05 (m, 3H), 2.01-1.80 (m, 6H), 1.15-1.08 (m, 7.2 Hz, 3H); ¹⁹F NMR (400 MHz, METHANOL-d₄) δ=−123, −173; LCMS (ESI, M+1): m/z=648.4.

256

Example 197

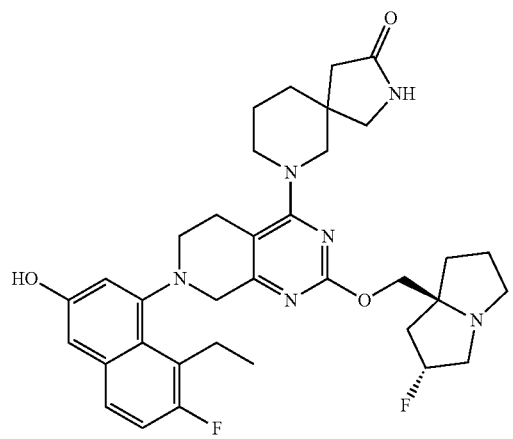 [SMILES: CCc1c(F)ccc2cc(O)cc(N3CCc4c(nc(OC[C@@]56CCCN5C[C@H](F)C6)nc4N4CCCC5(CNC(=O)C5)C4)C3)c12]

7-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-2,7-diazaspiro[4.5]decan-3-one Synthesized according to Example 32. The title compound was obtained as white solid. ¹H NMR (400 MHz, METHANOL-d₄) δ=7.52 (dd, J=5.8, 8.9 Hz, 1H), 7.15 (t, J=9.4 Hz, 1H), 7.03-6.91 (m, 2H), 5.55-5.27 (m, 1H), 4.39-4.16 (m, 2H), 4.09 (dd, J=10.0, 17.8 Hz, 1H), 3.89-3.75 (m, 1H), 3.74-3.63 (m, 2H), 3.62-3.34 (m, 9H), 3.29-3.04 (m, 5H), 2.67 (br d, J=12.1 Hz, 1H), 2.47 (br d, J=3.3 Hz, 1H), 2.39-2.15 (m, 4H), 2.11 (br dd, J=5.7, 10.8 Hz, 2H), 1.89-1.65 (m, 4H), 1.16-1.05 (m, 3H); LCMS (ESI, M+1): m/z=633.5.

Example 198

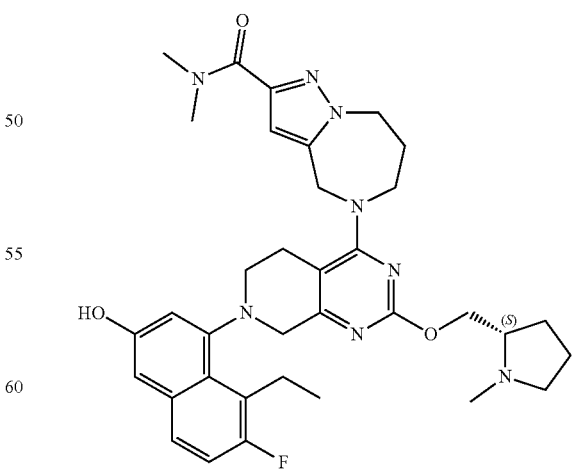

257

5-[7-(8-ethyl-7-fluoro-3-hydroxy-1-naphthyl)-2-[[(2S)-1-methylpyrrolidin-2-yl]methoxy]-6,8-dihydro-5H-pyrido[3,4-d]pyrimidin-4-yl]-N,N-dimethyl-4,6,7,8-tetrahydropyrazolo[1,5-a][1,4]diazepine-2-carboxamide

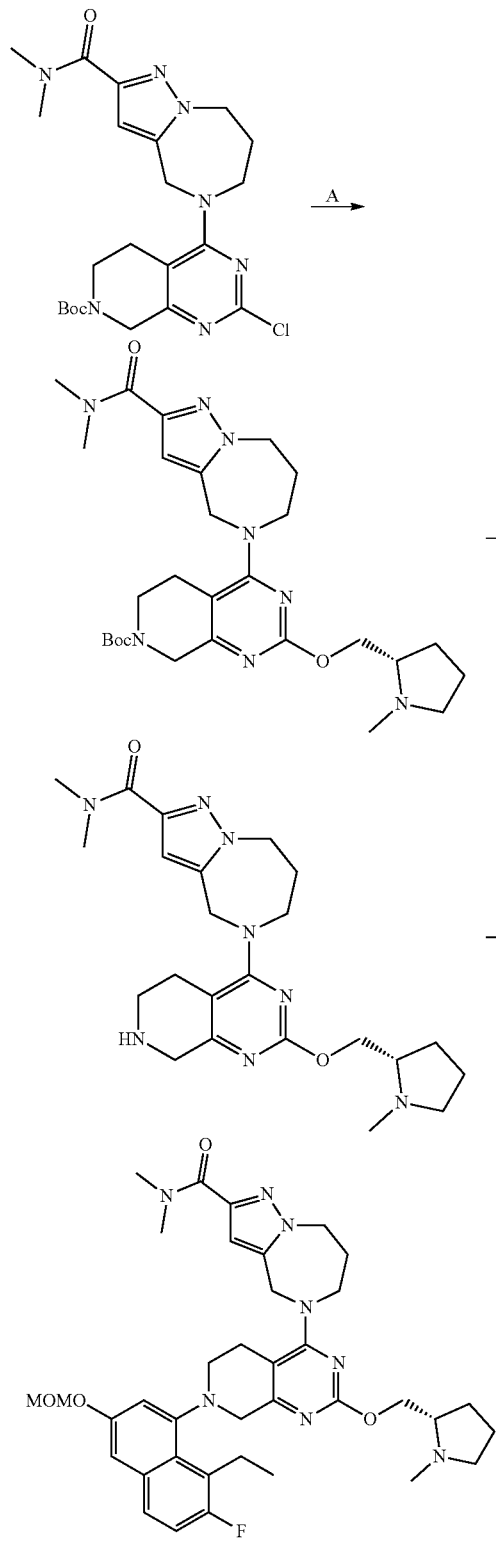

258

-continued

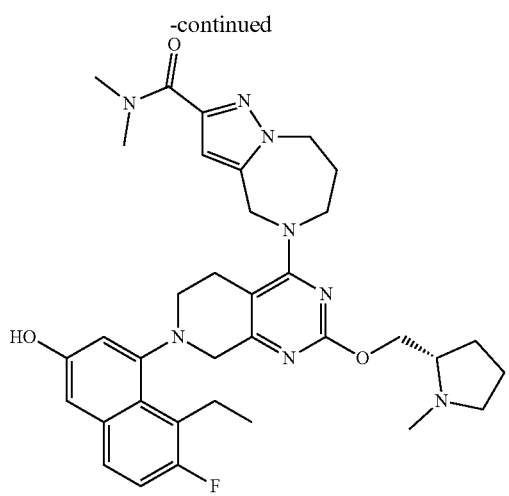

Step A. tert-butyl 4-[2-(dimethylcarbamoyl)-4,6,7,8-tetrahydropyrazolo[1,5-a][1,4]diazepin-5-yl]-2-[[(2S)-1-methylpyrrolidin-2-yl]methoxy]-6,8-dihydro-5H-pyrido[3,4-d]pyrimidine-7-carboxylate: A mixture of tert-butyl 2-chloro-4-[2-(dimethylcarbamoyl)-4,6,7,8-tetrahydropyrazolo[1,5-a][1,4]diazepin-5-yl]-6,8-dihydro-5H-pyrido[3,4-d]pyrimidine-7-carboxylate (560 mg, 1.0 equiv), [(2S)-1-methylpyrrolidin-2-yl]methanol (163 mg, 1.2 equiv), Pd(OAc)$_2$ (52.8 mg, 0.2 equiv), 2,2'-bis(diphenylphosphino)-1,1'-binaphthalene (183 mg, 0.3 equiv) and Cs$_2$CO$_3$ (767 mg, 2.0 equiv) in toluene (12 mL) was degassed and purged with nitrogen for 3 times. The mixture was stirred at 110° C. for 3 hours under nitrogen atmosphere. The mixture was concentrated to remove the solvent. The residue was diluted with water (10 mL) and extracted with dichloromethane:methanol=10:1 (2×10 mL). The combined organic layer was washed with brine (10 mL), dried over anhydrous sodium sulfate, concentrated, and purified with prep-HPLC [column: Phenomenex luna C18 150×25 mm×10 μm; mobile phase: water (FA)-ACN; B %: 28%-58%, 10 minutes] to afford the title compound (222 mg, 34.0% yield) as yellow solid. LCMS (ESI, M+1): m/z=555.5.

Step B. N,N-dimethyl-5-[2-[[(2S)-1-methylpyrrolidin-2-yl]methoxy]-5,6,7,8-tetrahydropyrido [3,4-d]pyrimidin-4-yl]-4,6,7,8-tetrahydropyrazolo[1,5-a][1,4]diazepine-2-carboxamide: To a solution of tert-butyl 4-[2-(dimethylcarbamoyl)-4,6,7,8-tetrahydropyrazolo[1,5-a][1,4]diazepin-5-yl]-2-[[(2S)-1-methylpyrrolidin-2-yl]methoxy]-6,8-dihydro-5H-pyrido[3,4-d]pyrimidine-7-carboxylate (200 mg, 1.0 equiv) in dioxane (6 mL) was added HCl/dioxane (4.0 M, 6.00 mL). The mixture was stirred at 0° C. for 1 hour. The mixture was concentrated. The residue was dissolved in methanol (3 mL) and basified (pH ~8) with NaHCO$_3$ solid. The mixture was stirred for 0.3 hour, filtered, and concentrated to afford the title compound (156 mg, 95.2% yield) as white solid.

Step C. 5-[7-[8-ethyl-7-fluoro-3-(methoxymethoxy)-1-naphthyl]-2-[[(2S)-1-methylpyrrolidin-2-yl]methoxy]-6,8-dihydro-5H-pyrido[3,4-d]pyrimidin-4-yl]-N,N-dimethyl-4,6,7,8-tetrahydropyrazolo[1,5-a][1,4]diazepine-2-carboxamide: A mixture of N,N-dimethyl-5-[2-[[(2S)-1-methylpyrrolidin-2-yl]methoxy]-5,6,7,8-tetrahydropyrido [3,4-d]pyrimidin-4-yl]-4,6,7,8-tetrahydropyrazolo[1,5-a][1,4]diazepine-2-carboxamide (156 mg 1.0 equiv), [8-ethyl-7-fluoro-3-(methoxymethoxy)-1-naphthyl] trifluoromethanesulfonate (144 mg, 1.1 equiv), tris(dibenzylideneacetone)dipalladium(0) (47.1 mg, 0.2 equiv), (5-diphenylphosphanyl-9,9-dimethylxanthen-4-yl)-diphenylphosphane (49.6 mg, 0.3 equiv) and Cs$_2$CO$_3$ (335 mg, 3.0 equiv) in toluene (1 mL) was degassed and purged with N$_2$ for 3 times. The mixture was stirred at 110° C. for 14 hours under N$_2$ atmosphere. The mixture was diluted with water (20 mL) and extracted with ethyl acetate (2×15 mL). The combined organic layers were washed with brine (20 mL), dried over anhydrous sodium sulfate, concentrated and purified with prep-HPLC [column: Phenomenex luna C18 150× 40 mm×15 µm; mobile phase: water (FA)-ACN; B %: 23%-53%, 10 minutes] to afford the title compound (45.0 mg, 18.7% yield) as white solid.

Step D. 5-[7-(8-ethyl-7-fluoro-3-hydroxy-1-naphthyl)-2-[[(2S)-1-methylpyrrolidin-2-yl]methoxy]-6,8-dihydro-5H-pyrido[3,4-d]pyrimidin-4-yl]-N,N-dimethyl-4,6,7,8-tetrahydropyrazolo[1,5-a][1,4]diazepine-2-carboxamide: To a solution of 5-[7-[8-ethyl-7-fluoro-3-(methoxymethoxy)-1-naphthyl]-2-[[(2S)-1-methylpyrrolidin-2-yl]methoxy]-6,8-dihydro-5H-pyrido[3,4-d]pyrimidin-4-yl]-N,N-dimethyl-4,6,7,8-tetrahydropyrazolo[1,5-a][1,4]diazepine-2-carboxamide (38.0 mg, 1.0 equiv) in methanol (3 mL) was added HCl/MeOH (4.00 M, 3 mL). The mixture was stirred at 0° C. for 1 hour. The mixture was diluted with methanol (4 mL) and basified (pH ~8) with NaHCO$_3$ solid. The mixture was stirred at 0° C. for 0.3 hour, filtered, concentrated, and purified with prep-HPLC [column: Phenomenex luna C18 150×25 mm×10 µm; mobile phase: water (FA)-ACN; B %: 15%-45%, 10 minutes] to afford the title compound (15.3 mg, 42.9% yield) as white solid. $^1$H NMR (400 MHz, METHANOL-d4) δ=7.51 (dd, J=6.0, 8.8 Hz, 1H), 7.15 (t, J=9.6 Hz, 1H), 6.97 (s, 2H), 6.60 (d, J=0.8 Hz, 1H), 5.05-4.96 (m, 1H), 4.66-4.46 (m, 4H), 4.44-4.34 (m, 1H), 4.25-4.15 (m, 1H), 4.06 (br d, J=17.6 Hz, 2H), 3.68 (br d, J=17.6 Hz, 1H), 3.54 (br d, J=10.4 Hz, 1H), 3.51-3.43 (m, 2H), 3.42-3.35 (m, 2H), 3.33-3.32 (m, 3H), 3.28-3.14 (m, 2H), 3.08 (s, 3H), 2.98-2.89 (m, 1H), 2.84 (d, J=3.6 Hz, 3H), 2.74 (br d, J=13.6 Hz, 1H), 2.38-2.19 (m, 2H), 2.13-1.87 (m, 4H), 1.11 (t, J=7.2 Hz, 3H); $^{19}$F NMR (377 MHz, METHANOL-d$_4$) δ=−122; LCMS (ESI, M+1): m/z=643.5.

Example 199

(R)-1-(2-((1-((dimethylamino)methyl)cyclopropyl)methoxy)-7-(8-ethyl-7-fluoro-3-hydroxynaphthalen-1-yl)-5,6,7,8-tetrahydropyrido[3,4-d]pyrimidin-4-yl)-3-methylpiperidin-3-ol

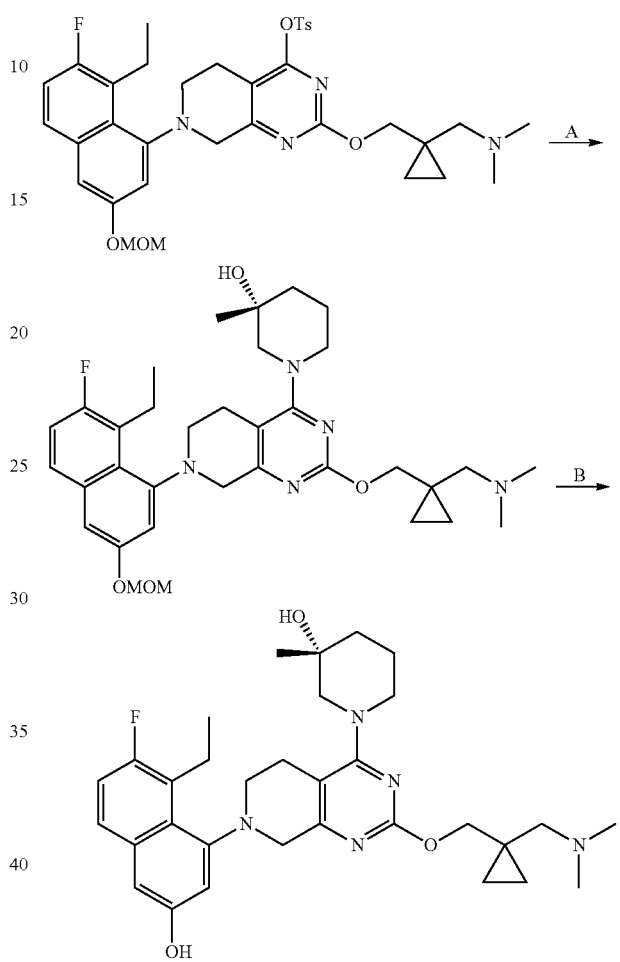

Synthesized according to Example 32. The title compound was obtained as white solid. $^1$H NMR (400 MHz, METHANOL-d$_4$) δ=7.53-7.48 (m, 1H), 7.14 (t, J=9.6 Hz, 1H), 7.05-6.94 (m, 2H), 4.26-4.15 (m, 2H), 4.12-4.00 (m, 2H), 3.90-3.65 (m, 1H), 3.64-3.58 (m, 1H), 3.55-3.85 (m, 5H), 3.24-3.05 (m, 2H), 2.85-2.70 (m, 1H), 2.65-3.51 (m, 2H), 2.49-2.30 (m, 6H), 2.08-1.60 (m, 4H), 1.33-1.15 (m, 3H), 1.13-1.01 (m, 3H), 0.77-0.65 (m, 2H), 0.61-0.48 (m, 2H); LCMS (ESI, M+1): m/z=564.3.

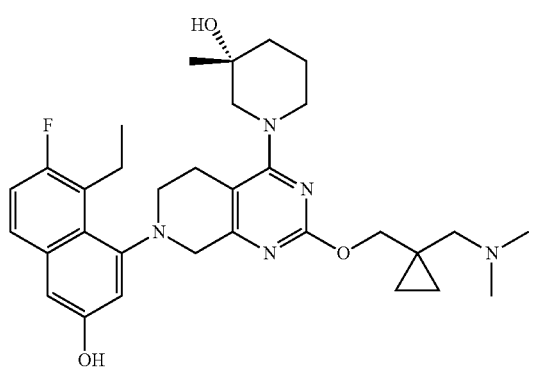 [SMILES: CCc1c(F)ccc2cc(O)cc(N3CCc4c(nc(OCC5(CN(C)C)CC5)nc4N4CCC[C@@](C)(O)C4)C3)c12]

Example 200

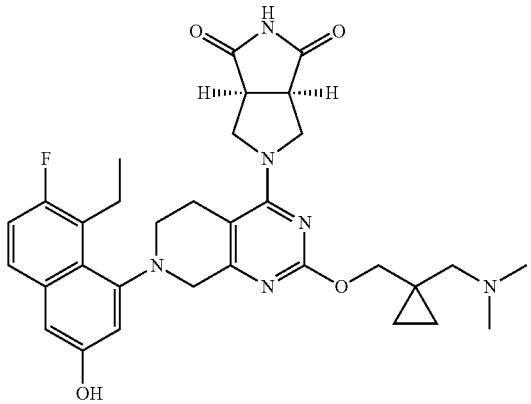 [SMILES: CCc1c(F)ccc2cc(O)cc(N3CCc4c(nc(OCC5(CN(C)C)CC5)nc4N4C[C@@H]5C(=O)NC(=O)[C@@H]5C4)C3)c12]

(3aS,6aR)-5-[2-[[1-[(dimethylamino)methyl]cyclopropyl]methoxy]-7-(8-ethyl-7-fluoro-3-hydroxy-1-naphthyl)-6,8-dihydro-5H-pyrido[3,4-d]pyrimidin-4-yl]-3a,4,6,6a-tetrahydropyrrolo[3,4-c]pyrrole-1,3-dione

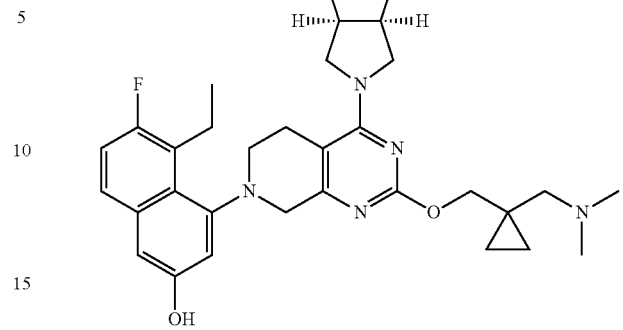

Synthesized according to Example 32. The title compound was obtained as white solid. $^1$H NMR (400 MHz, METHANOL-$d_4$) δ=7.51 (dd, J=6.0, 9.2 Hz, 1H), 7.14 (t, J=9.2 Hz, 1H), 7.04-6.93 (m, 2H), 4.61 (br d, J=10.8 Hz, 2H), 4.31-4.17 (m, 3H), 4.01 (d, J=17.2 Hz, 1H), 3.77 (br s, 1H), 3.66 (d, J=17.6 Hz, 1H), 3.55-3.45 (m, 4H), 3.34 (br d, J=2.8 Hz, 1H), 3.23-3.15 (m, 2H), 2.85 (br s, 2H), 2.76-2.69 (m, 1H), 2.62 (s, 6H), 1.10 (t, J=7.2 Hz, 3H), 0.83-0.76 (m, 2H), 0.66 (s, 2H); LCMS (ESI, M+1): m/z=589.1.

Example 201

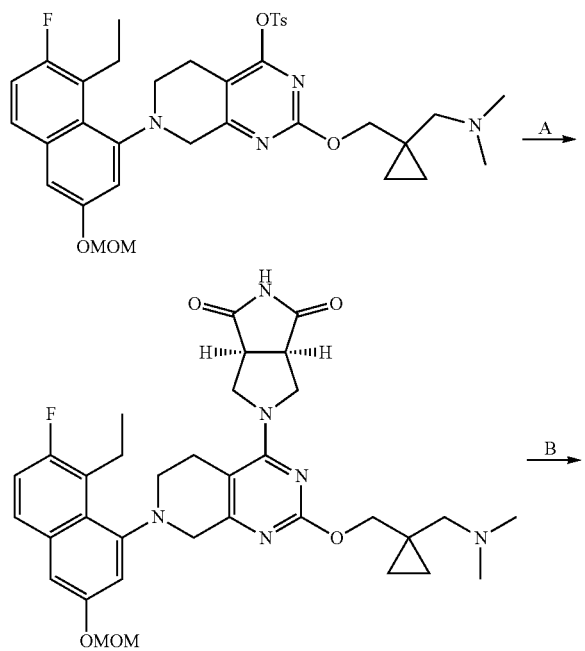

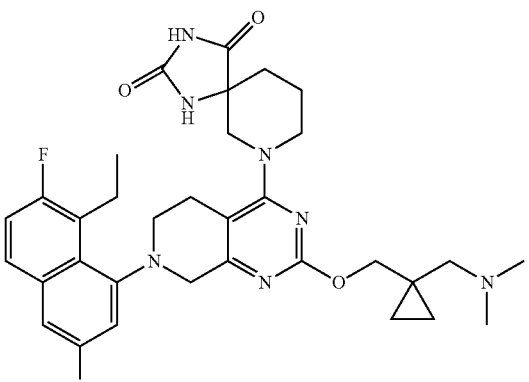

7-(2-((1-(((dimethylamino)methyl)cyclopropyl)methoxy)-7-(8-ethyl-7-fluoro-3-hydroxynaphthalen-1-yl)-5,6,7,8-tetrahydropyrido[3,4-d]pyrimidin-4-yl)-1,3,7-triazaspiro[4.5]decane-2,4-dione

263
-continued

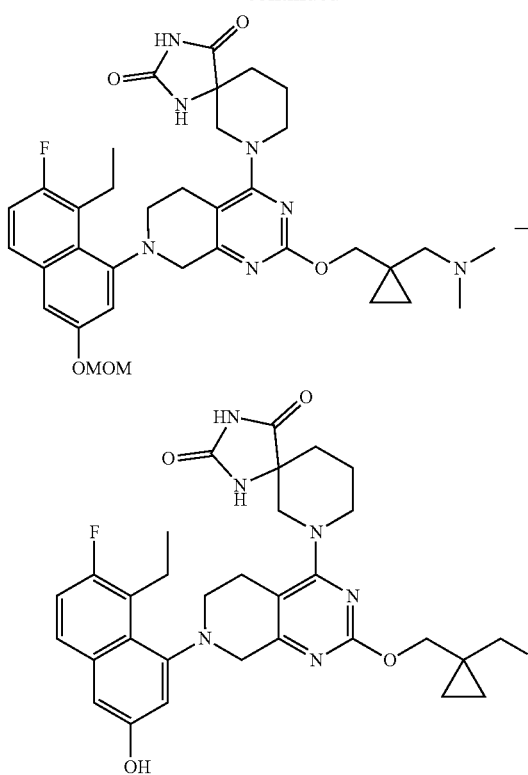

Synthesized according to Example 32. The title compound was obtained as yellow solid. $^1$H NMR (400 MHz, METHANOL-d$_4$) δ=7.51 (dd, J=6.0, 8.98 Hz, 1H), 7.15 (t, J=9.6 Hz, 1H), 7.07-6.91 (m, 2H), 4.27-3.92 (m, 5H), 3.66 (dd, J=6.8, 17.6 Hz, 1H), 3.58-3.32 (m, 5H), 3.24-3.10 (m, 2H), 3.05-2.93 (m, 2H), 2.85-2.75 (m, 1H), 2.72 (br d, J=13.2 Hz, 6H), 2.20-2.07 (m, 1H), 2.05-1.77 (m, 3H), 1.10 (t, J=7.2 Hz, 3H), 0.89-0.78 (m, 2H), 0.73-0.62 (m, 2H); LCMS (ESI, M+1): m/z=618.4.

Example 202

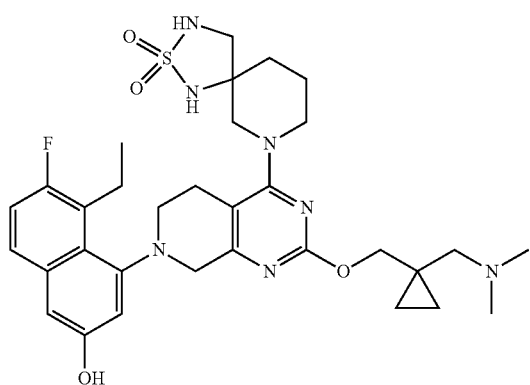 [SMILES: CCc1c(F)ccc2cc(O)cc(N3CCc4c(nc(OCC5(CN(C)C)CC5)nc4N4CCCC5(CNS(=O)(=O)N5)C4)C3)c12]

264

7-(2-((1-(((dimethylamino)methyl)cyclopropyl)methoxy)-7-(8-ethyl-7-fluoro-3-hydroxynaphthalen-1-yl)-5,6,7,8-tetrahydropyrido[3,4-d]pyrimidin-4-yl)-2-thia-1,3,7-triazaspiro[4.5]decane 2,2-dioxide

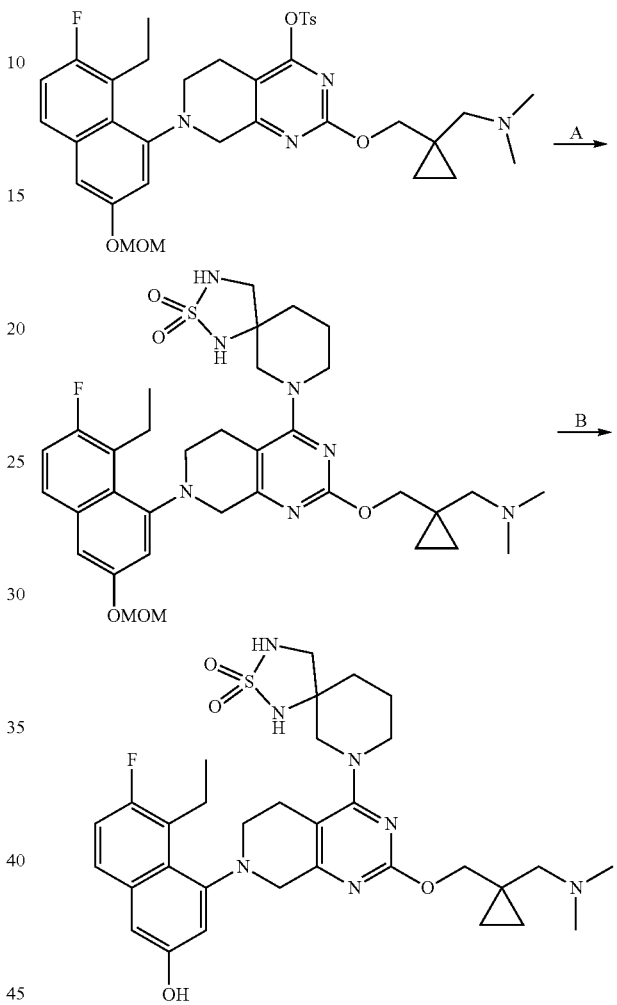

Synthesized according to Example 32. The title compound was obtained as yellow solid. $^1$H NMR (400 MHz, METHANOL-d4) δ=7.56-7.47 (m, 1H), 7.20-7.08 (m, 1H), 7.05-6.92 (m, 2H), 4.31-4.19 (m, 2H), 4.13-4.06 (m, 1H), 3.99-3.87 (m, 1H), 3.70-3.47 (m, 4H), 3.46-3.33 (m, 3H), 3.30-3.08 (m, 4H), 3.18-3.01 (m, 2H), 2.79-2.61 (m, 7H), 1.82 (br s, 4H), 1.17-1.04 (m, 3H), 0.85 (br s, 2H), 0.78-0.67 (m, 2H); LCMS (ESI, M+1): m/z=640.4.

265

Example 203

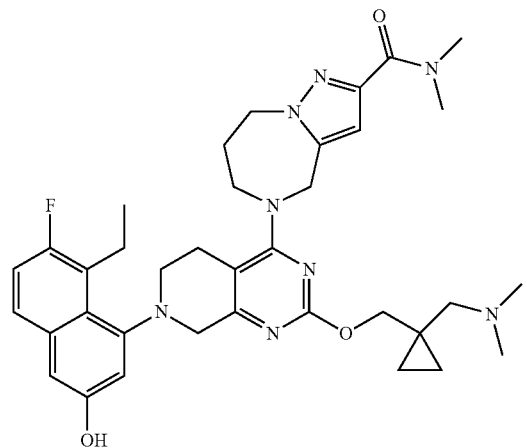 [SMILES: CCc1c(F)ccc2cc(O)cc(N3CCc4c(nc(OCC5(CN(C)C)CC5)nc4N4CCCn5nc(C(=O)N(C)C)cc5C4)C3)c12]

5-(2-((1-(((dimethylamino)methyl)cyclopropyl)methoxy)-7-(8-ethyl-7-fluoro-3-hydroxynaphthalen-1-yl)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide

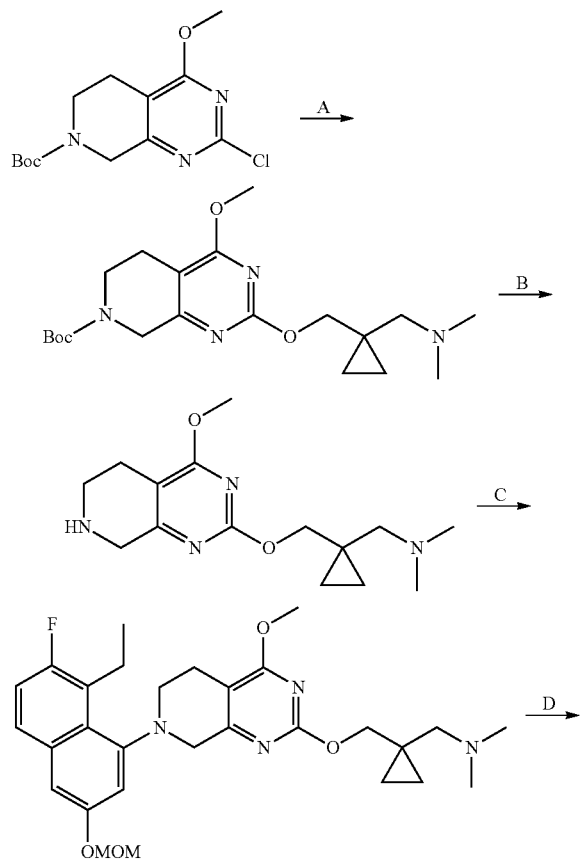

Step A. tert-butyl 2-((1-(((dimethylamino)methyl)cyclopropyl)methoxy)-4-methoxy-5,6-dihydropyrido[3,4-d]pyrimidine-7(8H)-carboxylate: To a solution of tert-butyl 2-chloro-4-methoxy-6,8-dihydro-5H-pyrido[3,4-d]pyrimidine-7-carboxylate (20.0 g, 1.0 equiv), [1-[(dimethylamino)methyl]cyclopropyl]methanol (12.9 g, 1.5 equiv), BINAP (8.31 g, 0.2 equiv) and $Cs_2CO_3$ (65.2 g, 3.0 equiv) in toluene (200 mL) was added $Pd(OAc)_2$ (1.50 g, 0.1 equiv) under nitrogen atmosphere. The mixture was stirred at 110° C. for 12 hours. The mixture was diluted with water (30 mL) and extracted with ethyl acetate (3×20 mL). The combined organic layers were dried over anhydrous sodium sulfate, concentrated, and purified by column chromatography

[SiO₂, Petroleum ether/Ethyl acetate=20/1 to Ethyl acetate/MeOH=5/1] to give a crude product. The crude product was purified by reversed phase flash chromatography [C18, 0.1% formic acid condition] to afford the title compound (17.0 g, 64% yield) as yellow liquid. ¹H NMR (400 MHz, CHLOROFORM-d) δ=4.41 (s, 2H), 4.20 (s, 2H), 3.98-3.94 (m, 3H), 3.60 (br t, J=5.6 Hz, 2H), 2.55 (br t, J=5.2 Hz, 2H), 2.33 (s, 2H), 2.24 (s, 6H), 1.46 (s, 9H), 0.67-0.56 (m, 2H), 0.48-0.37 (m, 2H); LCMS (ESI, M+1): m/z=393.3.

Step B. 1-(1-(((4-methoxy-5,6,7,8-tetrahydropyrido[3,4-d]pyrimidin-2-yl)oxy)methyl)cyclopropyl)-N,N-dimethyl-methanamine: To a solution of tert-butyl 2-[[1-[(dimethylamino)methyl]cyclopropyl]methoxy]-4-methoxy-6,8-dihydro-5H-pyrido[3,4-d]pyrimidine-7-carboxylate (17.0 g, 1.0 equiv) in DCM (90 mL) was added TFA (92.4 g, 19 equiv). The reaction was stirred at 20° C. for 1 hour. The mixture was concentrated to dryness and dissolved in ethyl acetate (50 mL). The mixture was basified to pH 8 with Na₂CO₃ and the aqueous solution was extracted with ethyl acetate (2×50 mL). The combined organic layers were dried over anhydrous sodium sulfate and concentrated to afford the title compound (7.00 g, crude) as yellow liquid; LCMS (ESI, M+1): m/z=293.4.

Step C. 1-(1-(((7-(8-ethyl-7-fluoro-3-(methoxymethoxy)naphthalen-1-yl)-4-methoxy-5,6,7,8-tetrahydropyrido[3,4-d]pyrimidin-2-yl)oxy)methyl)cyclopropyl)-N,N-dimethyl-methanamine: To a solution of 1-[1-[(4-methoxy-5,6,7,8-tetrahydropyrido[3,4-d]pyrimidin-2-yl)oxymethyl]cyclopropyl]-N,N-dimethyl-methanamine (7.00 g, 1.0 equiv), [8-ethyl-7-fluoro-3-(methoxymethoxy)-1-naphthyl] trifluoromethanesulfonate (13.7 g, 1.5 equiv), Cs₂CO₃ (23.4 g, 3.0 equiv) and Xantphos (3.46 g, 0.25 equiv) in toluene (70 mL) was added Pd₂(dba)₃ (3.29 g, 0.15 equiv). The suspension was degassed under vacuum and purged with N₂ several times. The mixture was stirred at 110° C. for 14 hours. The reaction was stirred at 20° C. for 12 hours. The mixture was diluted with water (30 mL) and extracted with ethyl acetate (3×20 mL). The combined organic layers were dried over anhydrous sodium sulfate, concentrated, and purified by reversed phase flash chromatography [C18, 0.1% formic acid condition] to afford the title compound (6.00 g, 48% yield) as yellow liquid; ¹H NMR (400 MHz, CHLOROFORM-d) δ=7.54 (dd, J=6.0, 8.8 Hz, 1H), 7.22-7.14 (m, 2H), 7.06 (d, J=2.4 Hz, 1H), 5.27 (s, 2H), 4.25-4.17 (m, 2H), 4.03 (s, 3H), 3.75 (br d, J=17.2 Hz, 1H), 3.58-3.43 (m, 4H), 3.33 (dq, J=2.8, 7.2 Hz, 2H), 3.19 (dt, J=4.0, 11.2 Hz, 1H), 2.87 (ddd, J=6.0, 10.4, 16.4 Hz, 1H), 2.68 (br d, J=16.4 Hz, 1H), 2.39-2.30 (m, 2H), 2.24 (s, 6H), 2.00 (br d, J=4.4 Hz, 1H), 1.26 (t, J=7.2 Hz, 3H), 0.70-0.59 (m, 2H), 0.48-0.39 (m, 2H); LCMS (ESI, M+1): m/z=525.4.

Step D. 2-((1-((dimethylamino)methyl)cyclopropyl)methoxy)-7-(8-ethyl-7-fluoro-3-(methoxymethoxy)naphthalen-1-yl)-5,6,7,8-tetrahydropyrido[3,4-d]pyrimidin-4-ol: To a solution of EtSH (2.86 g, 4.0 equiv) in DMAc (60 mL) was added NaH (915 mg, 60% purity, 2.0 equiv) at 10° C. The mixture was stirred at 10° C. for 0.5 hour. 1-[1-[[7-[8-ethyl-7-fluoro-3-(methoxymethoxy)-1-naphthyl]-4-methoxy-6,8-dihydro-5H-pyrido[3,4-d]pyrimidin-2-yl]oxymethyl]cyclopropyl]-N,N-dimethyl-methanamine (6.00 g, 1.0 equiv) was added and the reaction mixture was stirred at 60° C. for 1 hour. The mixture was diluted with water (30 mL) and extracted with ethyl acetate (3×20 mL). The combined organic layers were dried over anhydrous sodium sulfate, filtered, and concentrated to afford the title compound (7.00 g, crude) as yellow liquid; LCMS (ESI, M+1): m/z=511.3.

Step E. 2-((1-((dimethylamino)methyl)cyclopropyl)methoxy)-7-(8-ethyl-7-fluoro-3-(methoxymethoxy)naphthalen-1-yl)-5,6,7,8-tetrahydropyrido[3,4-d]pyrimidin-4-yl 4-methylbenzenesulfonate: To a solution of 2-[[1-[(dimethylamino)methyl]cyclopropyl]methoxy]-7-[8-ethyl-7-fluoro-3-(methoxymethoxy)-1-naphthyl]-6,8-dihydro-5H-pyrido[3,4-d]pyrimidin-4-ol (7.00 g, 1.0 equiv) and DMAP (167 mg, 0.1 equiv) and N-ethyl-N-isopropylpropan-2-amine (5.32 g, 3.0 equiv) in DCM (70 mL) was added TsCl (3.92 g, 1.5 equiv) at 0° C. The mixture was stirred at 20° C. for 2 hours. The mixture was diluted with water (30 mL) and extracted with ethyl acetate (3×20 mL). The combined organic layers were dried over anhydrous sodium sulfate, filtered, concentrated, and purified by column chromatography [Al₂O₃, Petroleum ether/Ethyl acetate=10/1 to Ethyl acetate] to afford the title compound (2.00 g, 22% yield) as yellow liquid; 1H NMR (400 MHz, CHLOROFORM-d) δ=8.02 (d, J=8.4 Hz, 2H), 7.55 (dd, J=6.0, 8.8 Hz, 1H), 7.39 (d, J=8.0 Hz, 2H), 7.24-7.16 (m, 2H), 7.04 (d, J=2.4 Hz, 1H), 5.30-5.24 (m, 2H), 3.97 (s, 2H), 3.80 (br d, J=18.0 Hz, 1H), 3.54-3.47 (m, 4H), 3.31-3.18 (m, 3H), 3.02-2.99 (m, 1H), 2.88-2.80 (m, 1H), 2.48 (s, 3H), 2.33 (br s, 2H), 2.26 (s, 6H), 2.05 (s, 1H), 1.04 (t, J=7.2 Hz, 3H), 0.61-0.56 (m, 2H), 0.46 (br s, 2H); LCMS (ESI, M+1): m/z=665.4.

Step F-G: Synthesized according to Example 32. The title compound was obtained as white solid. ¹H NMR (400 MHz, METHANOL-d₄) δ=7.51 (dd, J=5.6, 8.8 Hz, 1H), 7.14 (t, J=9.6 Hz, 1H), 6.96 (s, 2H), 6.57 (s, 1H), 5.03-4.95 (m, 2H), 4.59-4.49 (m, 2H), 4.22-4.12 (m, 3H), 4.10-3.95 (m, 2H), 3.66 (br d, J=17.6 Hz, 1H), 3.52 (br d, J=10.4 Hz, 1H), 3.38 (td, J=3.2, 7.2 Hz, 2H), 3.32 (br s, 3H), 3.26-3.06 (m, 5H), 2.76-2.63 (m, 3H), 2.49 (s, 6H), 2.35-2.01 (m, 2H), 1.10 (t, J=7.2 Hz, 3H), 0.72 (br s, 2H), 0.58 (s, 2H); LCMS (ESI, M+1): m/z=657.5.

Example 204

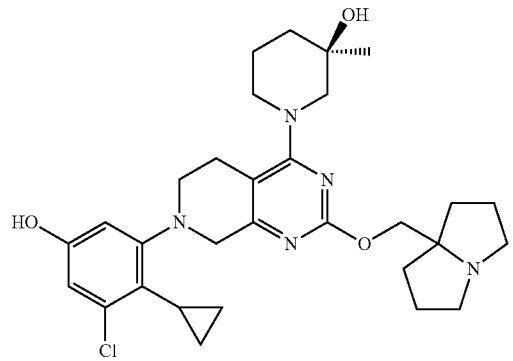 [SMILES: C[C@@]1(O)CCCN(c2nc(OCC34CCCN3CCC4)nc3c2CCN(c2cc(O)cc(Cl)c2C2CC2)C3)C1]

(R)-1-(7-(3-chloro-2-cyclopropyl-5-hydroxyphenyl)-2-((hexahydro-1H-pyrrolizin-7a-yl)methoxy)-5,6,7,8-tetrahydropyrido[3,4-d]pyrimidin-4-yl)-3-methylpiperidin-3-ol

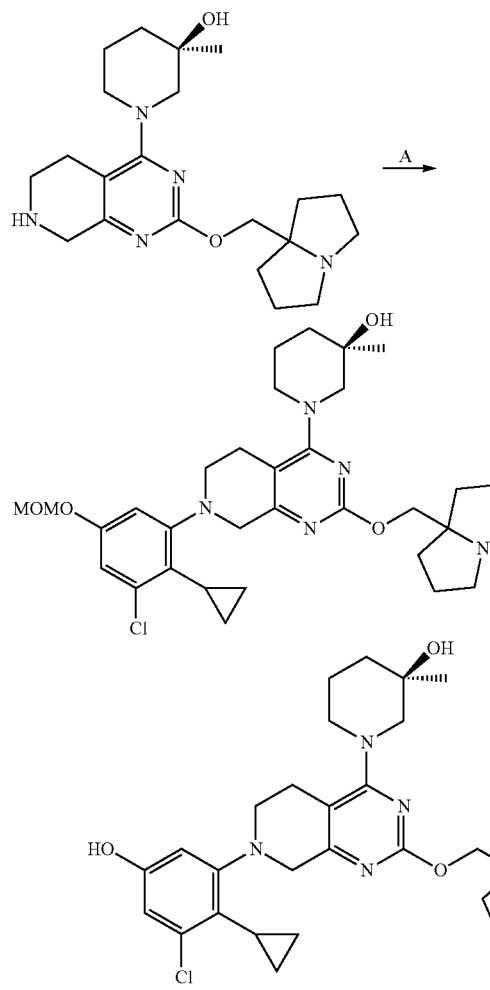

Step A. (R)-1-(7-(3-chloro-2-cyclopropyl-5-(methoxymethoxy)phenyl)-2-((hexahydro-1H-pyrrolizin-7a-yl)methoxy)-5,6,7,8-tetrahydropyrido[3,4-d]pyrimidin-4-yl)-3-methylpiperidin-3-ol: A mixture of (R)-3-methyl-1-(2-((tetrahydro-1H-pyrrolizin-7a(5H)-yl)methoxy)-5,6,7,8-tetrahydropyrido[3,4-d]pyrimidin-4-yl)piperidin-3-ol (100 mg, 258 µmol, 1.0 equiv), 1-bromo-3-chloro-2-cyclopropyl-5-(methoxymethoxy)benzene (90.3 mg, 310 µmol, 1.2 equiv), RuPhos (48.2 mg, 103 µmol, 0.4 equiv), 4A molecular sieve (10 mg), Cs$_2$CO$_3$ (252 mg, 774 µmol, 3.0 equiv) and Pd$_2$(dba)$_3$ (47.3 mg, 51.6 µmol, 0.2 equiv) in toluene (2 mL) was degassed and purged with N$_2$ for 3 times, and then the mixture was stirred at 90° C. for 8 hours under N$_2$ atmosphere. The mixture was filtered, and the filtrate was concentrated under vacuum to give a residue. The residue was purified by reversed phase flash chromatography [water (0.10% FA)/acetonitrile]. The desired fractions were collected, neutralized with solid NaHCO$_3$, and concentrated under vacuum to remove acetonitrile. The resulting mixture was extracted with ethyl acetate (2×5 mL). The combined organic layers were dried over anhydrous sodium sulfate and concentrated under vacuum to afford the title compound (27 mg, 16.7% yield, 95.5% purity) as yellow solid. LCMS (ESI, M+1): m/z=598.4.

Step B. (R)-1-(7-(3-chloro-2-cyclopropyl-5-hydroxyphenyl)-2-((hexahydro-1H-pyrrolizin-7a-yl)methoxy)-5,6,7,8-tetrahydropyrido[3,4-d]pyrimidin-4-yl)-3-methylpiperidin-3-ol: To a solution of (R)-1-(7-(3-chloro-2-cyclopropyl-5-(methoxymethoxy)phenyl)-2-((hexahydro-1H-pyrrolizin-7a-yl)methoxy)-5,6,7,8-tetrahydropyrido[3,4-d]pyrimidin-4-yl)-3-methylpiperidin-3-ol (45.0 mg, 75.2 µmol, 1.0 equiv) in MeCN (0.5 mL) was added HCl·MeOH (4 M, 1 mL). The reaction mixture was stirred at 0° C. for 1 hour. The mixture was added dropwise into ice-cold saturated NaHCO$_3$ solution (20 mL). Then the mixture was extracted with ethyl acetate (2×8 mL). The combined organic layers were washed with saturated brine (10 mL), dried over anhydrous sodium sulfate, and concentrated under vacuum to give a residue. The residue was purified by prep-HPLC [column: Phenomenex luna C18 150×25 mm×10 µm; A: water (FA); B: ACN, B %: 14%-44% over 10 min] to afford the title compound (28.3 mg, 66.2% yield, 97.4% purity) as yellow solid. $^1$H NMR (400 MHz, METHANOL-d4) δ=8.53 (s, 1H), 6.53 (s, 1H), 6.39 (s, 1H), 4.44-4.32 (m, 2H), 4.15-3.98 (m, 2H), 3.83-3.72 (m, 1H), 3.63 (br d, J=13.2 Hz, 1H), 3.55-3.44 (m, 2H), 3.35 (s, 1H), 3.24 (br s, 1H), 3.16-3.04 (m, 2H), 2.97-2.76 (m, 2H), 2.29-1.87 (m, 10H), 1.82-1.55 (m, 4H), 1.22 (s, 3H), 1.04-0.94 (m, 2H), 0.71-0.62 (m, 2H); LCMS [ESI, M+1]: 554.4;

Example 205

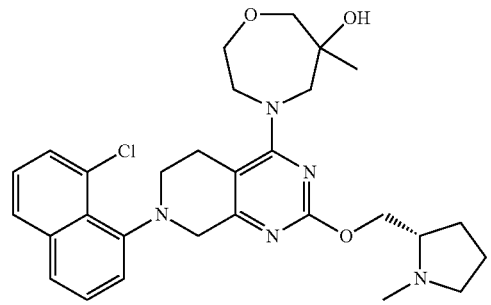 [SMILES: CN1CCC[C@H]1COc1nc2c(c(N3CCOCC(C)(O)C3)n1)CCN(c1cccc3cccc(Cl)c13)C2]

4-[7-(8-chloro-1-naphthyl)-2-[[(2S)-1-methylpyrrolidin-2-yl]methoxy]-6,8-dihydro-5H-pyrido[3,4-d]pyrimidin-4-yl]-6-methyl-1,4-oxazepan-6-ol

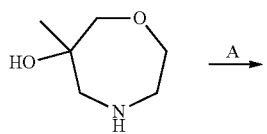

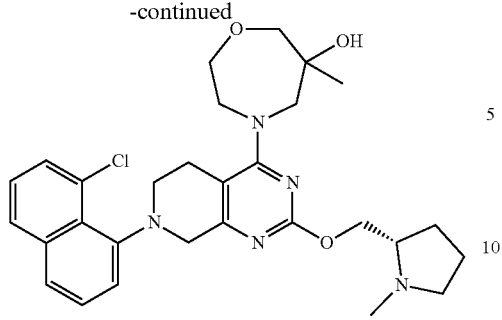

Step A. 4-[7-(8-chloro-1-naphthyl)-2-[[(2S)-1-methylpyrrolidin-2-yl]methoxy]-6,8-dihydro-5H-pyrido[3,4-d]pyrimidin-4-yl]-6-methyl-1,4-oxazepan-6-ol: A mixture of (S)-7-(8-chloronaphthalen-1-yl)-2-((1-methylpyrrolidin-2-yl)methoxy)-5,6,7,8-tetrahydropyrido[3,4-d]pyrimidin-4-yl 4-methylbenzenesulfonate (70 mg, 1.0 equiv), 6-methyl-1,4-oxazepan-6-ol (19.03 mg, 1.2 equiv), N-ethyl-N-isopropylpropan-2-amine (46.87 mg, 3.0 equiv), 4A molecular sieve (20 mg) in DMF (2 mL) was degassed and purged with $N_2$ for 3 times. The reaction was stirred at 60° C. under $N_2$ atmosphere until the reaction was completed. The mixture was concentrated and purified by prep-HPLC (column: Waters Xbridge 150×25 mm×5 μm; mobile phase: [water ($NH_4HCO_3$)-ACN]; B %: 54%-84%, 10 minutes) to afford the title compound (21.61 mg, 32% yield) as a yellow solid. $^1$H NMR (400 MHz, methanol-d4) δ=7.85-7.79 (m, 1H), 7.71-7.63 (m, 1H), 7.55-7.43 (m, 2H), 7.40-7.24 (m, 2H), 4.37-4.26 (m, 3H), 4.25-3.89 (m, 3H), 3.88-3.75 (m, 3H), 3.71-3.41 (m, 5H), 3.24-3.12 (m, 1H), 3.07 (dt, J=5.4, 9.8 Hz, 1H), 2.80-2.57 (m, 2H), 2.52-2.47 (m, 3H), 2.43-2.28 (m, 1H), 2.14-2.01 (m, 1H), 1.87-1.76 (m, 2H), 1.75-1.61 (m, 1H), 1.20-1.16 (m, 3H); LCMS (ESI, M): m/z=538.2.

Example 206

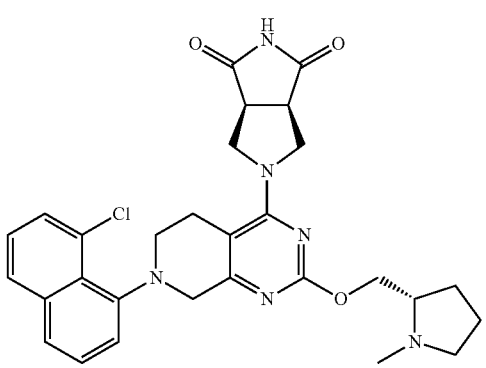 [SMILES: CN1CCC[C@H]1COc1nc2c(c(N3C[C@@H]4C(=O)NC(=O)[C@@H]4C3)n1)CCN(c1cccc3cccc(Cl)c13)C2]

(3aS,6aR)-5-[7-(8-chloro-1-naphthyl)-2-[[(2S)-1-methylpyrrolidin-2-yl]methoxy]-6,8-dihydro-5H-pyrido[3,4-d]pyrimidin-4-yl]-3a,4,6,6a-tetrahydropyrrolo[3,4-c]pyrrole-1,3-dione Synthesized according to Example 205. The title compound was obtained as yellow solid $^1$H NMR (400 MHz, methanol-d4) δ=8.56 (s, 1H), 7.84 (d, J=8.0 Hz, 1H), 7.69 (d, J=8.0 Hz, 1H), 7.54 (d, J=7.6 Hz, 1H), 7.52-7.46 (m, 1H), 7.38 (t, J=7.6 Hz, 1H), 7.32 (d, J=7.6 Hz, 1H), 4.61 (br dd, J=4.8, 10.4 Hz, 1H), 4.56-4.48 (m, 1H), 4.48-4.40 (m, 1H), 4.27 (br d, J=3.2 Hz, 1H), 4.24 (br d, J=9.2 Hz, 1H), 3.78 (br dd, J=8.0, 11.6 Hz, 1H), 3.70 (br d, J=17.2 Hz, 1H), 3.64-3.56 (m, 1H), 3.56-3.45 (m, 3H), 3.44-3.36 (m, 1H), 3.31-3.21 (m, 2H), 3.20-3.10 (m, 1H), 2.84-2.79 (m, 1H), 2.78 (s, 3H), 2.68 (br d, J=14.4 Hz, 1H), 2.32-2.19 (m, 1H), 2.06-1.93 (m, 2H), 1.92-1.82 (m, 1H); LCMS (ESI, M): m/z=547.2.

Example 207

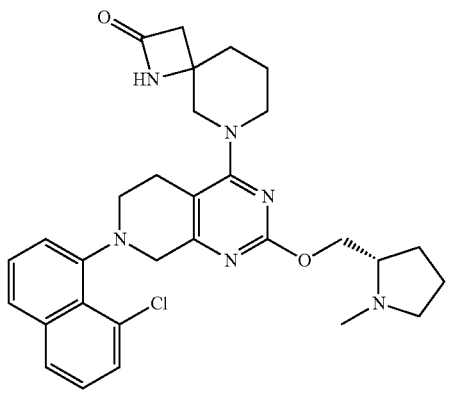 [SMILES: CN1CCC[C@H]1COc1nc2c(c(N3CCCC4(CC(=O)N4)C3)n1)CCN(c1cccc3cccc(Cl)c13)C2]

8-[7-(8-chloro-1-naphthyl)-2-[[(2S)-1-methylpyrrolidin-2-yl]methoxy]-6,8-dihydro-5H-pyrido[3,4-d]pyrimidin-4-yl]-1,8-diazaspiro[3.5]nonan-2-one Synthesized according to Example 205 except using $K_3PO_4$ as the base. The title compound was obtained as yellow solid. $^1$H NMR (400 MHz, METHANOL-$d_4$) δ=7.84 (dd, J=0.8, 8.0 Hz, 1H), 7.69 (d, J=7.6 Hz, 1H), 7.55 (dd, J=1.2, 7.6 Hz, 1H), 7.50 (t, J=7.6 Hz, 1H), 7.42-7.36 (m, 1H), 7.33 (d, J=7.2 Hz, 1H), 4.44-4.36 (m, 1H), 4.35-4.26 (m, 2H), 3.95-3.81 (m, 1H), 3.80-3.62 (m, 2H), 3.62-3.54 (m, 2H), 3.27-3.13 (m, 3H), 3.09 (td, J=4.8, 9.6 Hz, 1H), 2.91-2.61 (m, 4H), 2.51 (s, 3H), 2.36 (q, J=8.8 Hz, 1H), 2.16-2.05 (m, 1H), 2.04-1.77 (m, 6H), 1.77-1.66; LCMS (ESI, M+1): m/z=547.3.

Example 208

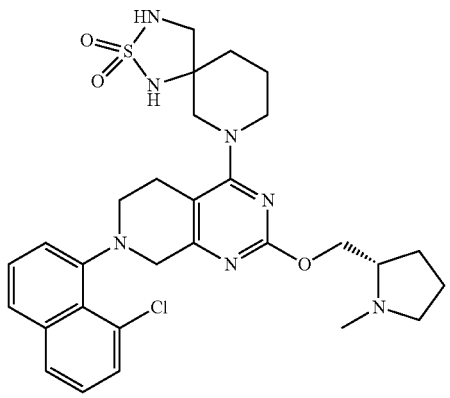 [SMILES: CN1CCC[C@H]1COc1nc2c(c(N3CCCC4(CNS(=O)(=O)N4)C3)n1)CCN(c1cccc3cccc(Cl)c13)C2]

9-[7-(8-chloro-1-naphthyl)-2-[[(2S)-1-methylpyrrolidin-2-yl]methoxy]-6,8-dihydro-5H-pyrido[3,4-d]pyrimidin-4-yl]-2λ6-thia-1,3,9-triazaspiro[4.5]decane 2,2-dioxide Synthesized according to Example 205 except using K$_3$PO$_4$ as the base. The title compound was obtained as yellow solid. $^1$H NMR (400 MHz, methanol-d4) δ=7.83 (dd, J=3.6, 8.0 Hz, 1H), 7.68 (dd, J=3.6, 8.0 Hz, 1H), 7.57-7.52 (m, 1H), 7.50 (td, J=4.0, 7.6 Hz, 1H), 7.38 (dt, J=2.4, 7.6 Hz, 1H), 7.36-7.30 (m, 1H), 4.45-4.38 (m, 1H), 4.38-4.28 (m, 2H), 3.97-3.83 (m, 1H), 3.78-3.69 (m, 1H), 3.69-3.63 (m, 1H), 3.62-3.53 (m, 2H), 3.53-3.36 (m, 2H), 3.27-3.15 (m, 3H), 3.11 (td, J=4.4, 9.6 Hz, 1H), 2.85-2.76 (m, 1H), 2.75-2.61 (m, 1H), 2.53 (s, 3H), 2.39 (q, J=8.8 Hz, 1H), 2.18-2.04 (m, 1H), 2.04-1.89 (m, 2H), 1.88-1.67 (m, 5H); LCMS (ESI, M+1): m/z=598.2

Example 209

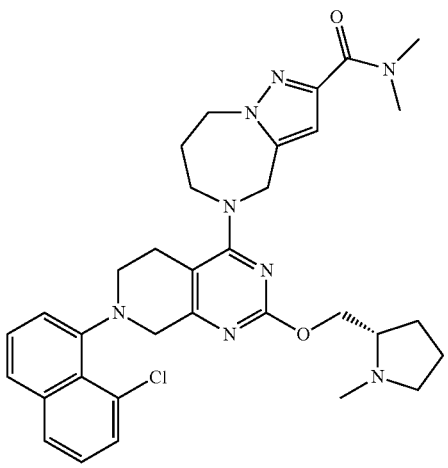 [SMILES: CN(C)C(=O)c1cc2n(n1)CCCN(c1nc(OC[C@@H]3CCCN3C)nc3c1CCN(c1cccc4cccc(Cl)c14)C3)C2]

(S)-5-(7-(8-chloronaphthalen-1-yl)-2-((1-methylpyrrolidin-2-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide Synthesized according to Example 205 except using K$_3$PO$_4$ as the base. The title compound was obtained as yellow solid. $^1$H NMR (400 MHz, METHANOL-d$_4$) δ=8.48 (br s, 1H), 7.82 (br d, J=8.0 Hz, 1H), 7.68 (br d, J=8.0 Hz, 1H), 7.55-7.45 (m, 2H), 7.37 (br t, J=7.6 Hz, 1H), 7.29 (br d, J=7.2 Hz, 1H), 6.58 (s, 1H), 5.00-4.89 (m, 3H), 4.72-4.39 (m, 5H), 4.26 (br d, J=17.6 Hz, 1H), 4.19-4.02 (m, 2H), 3.84-3.49 (m, 5H), 3.18 (br d, J=10.8 Hz, 2H), 3.08 (s, 3H), 2.98 (br d, J=3.2 Hz, 3H), 2.69 (br d, J=14.4 Hz, 1H), 2.38-1.92 (m, 3H), 2.20-1.91 (m, 4H); LCMS (ESI, M+1): m/z=615.4.

Example 210

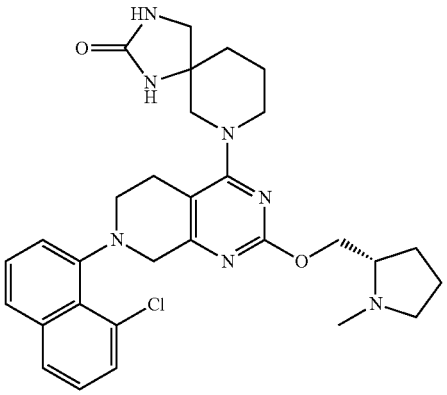 [SMILES: CN1CCC[C@H]1COc1nc2c(c(N3CCCC4(CNC(=O)N4)C3)n1)CCN(c1cccc3cccc(Cl)c13)C2]

7-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1,3,7-triazaspiro[4.5]decan-2-one Synthesized according to Example 205. The title compound was obtained as yellow solid. $^1$H NMR (400 MHz, methanol-d4) δ=7.82 (d, J=8.0 Hz, 1H), 7.67 (dd, J=2.0, 8.0 Hz, 1H), 7.56-7.45 (m, 2H), 7.40-7.28 (m, 2H), 4.43-4.20 (m, 3H), 3.77-3.62 (m, 3H), 3.62-3.44 (m, 3H), 3.28-3.24 (m, 1H), 3.23-3.11 (m, 2H), 3.10-3.03 (m, 1H), 2.79-2.61 (m, 2H), 2.49 (s, 3H), 2.34 (q, J=9.2 Hz, 1H), 2.17-1.60 (m, 9H); LCMS (ESI, M+1): m/z=562.2

Example 211

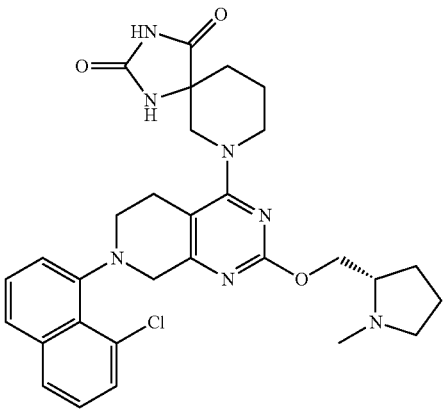 [SMILES: CN1CCC[C@H]1COc1nc2c(c(N3CCCC4(C3)NC(=O)NC4=O)n1)CCN(c1cccc3cccc(Cl)c13)C2]

9-[7-(8-chloro-1-naphthyl)-2-[[(2S)-1-methylpyrrolidin-2-yl]methoxy]-6,8-dihydro-5H-pyrido[3,4-d]pyrimidin-4-yl]-1,3,9-triazaspiro[4.5]decane-2,4-dione Synthesized according to Example 205. The title compound was obtained as white solid. $^1$H NMR (400 MHz, METHANOL-d4) δ=8.56 (s, 1H), 7.84 (d, J=8.0 Hz, 1H), 7.70 (dd, J=3.6, 7.4 Hz, 1H), 7.56-7.53 (m, 1H), 7.51 (td, J=3.6, 8.0 Hz, 1H), 7.42-7.37 (m, 1H), 7.34 (dd, J=7.6, 11.2 Hz, 1H), 4.63 (br s, 1H), 4.53-4.37 (m, 2H), 4.37-4.29 (m, 1H), 4.28-3.98 (m, 2H), 3.70 (br d, J=17.6 Hz, 1H), 3.65-3.56 (m, 1H), 3.43 (td, J=2.4, 13.2 Hz, 1H), 3.31-3.24 (m, 1H), 3.24-3.13 (m, 2H), 3.12-2.99 (m, 1H), 2.78 (br d, J=14.0 Hz, 1H), 2.71 (br d, J=4.0 Hz, 2H), 2.67 (d, J=3.2 Hz, 2H), 2.24-2.06 (m, 2H), 2.03-1.77 (m, 6H); LCMS (ESI, M+1): m/z=576.3.

Example 212

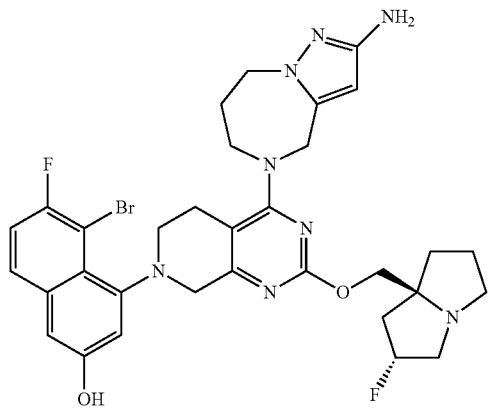 [SMILES: Nc1cc2n(n1)CCCN(c1nc(OC[C@@]34CCCN3C[C@H](F)C4)nc3c1CCN(c1cc(O)cc4ccc(F)c(Br)c14)C3)C2]

4-(4-(2-amino-7,8-dihydro-4H-pyrazolo[1,5-a][1,4]diazepin-5(6H)-yl)-2-(((2R,7aS)-2-fluorohexahydro-1H-pyrrolizin-7a-yl)methoxy)-5,6-dihydropyrido[3,4-d]pyrimidin-7(8H)-yl)-5-bromo-6-fluoronaphthalen-2-ol

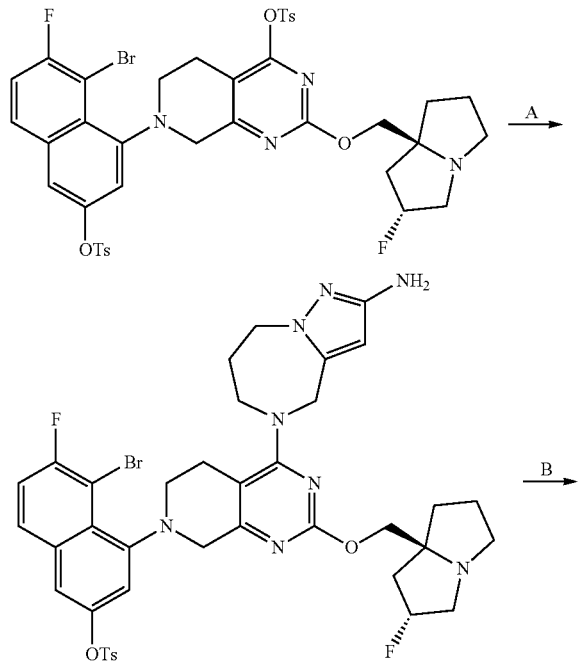

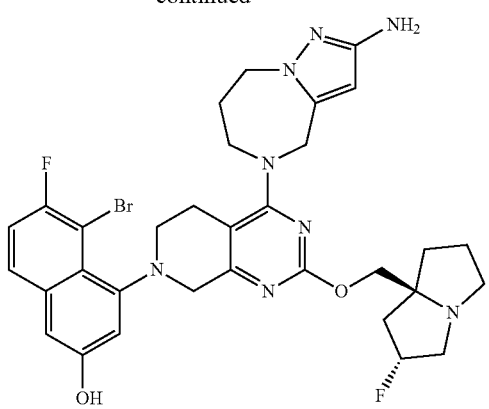

Step A. 4-(4-(2-amino-7,8-dihydro-4H-pyrazolo[1,5-a][1,4]diazepin-5(6H)-yl)-2-(((2R,7aS)-2-fluorohexahydro-1H-pyrrolizin-7a-yl)methoxy)-5,6-dihydropyrido[3,4-d]pyrimidin-7(8H)-yl)-5-bromo-6-fluoronaphthalen-2-yl 4-methylbenzenesulfonate: To a mixture of 5-bromo-6-fluoro-4-(2-(((2R,7aS)-2-fluorohexahydro-1H-pyrrolizin-7a-yl)methoxy)-4-(tosyloxy)-5,6-dihydropyrido[3,4-d]pyrimidin-7(8H)-yl)naphthalen-2-yl 4-methylbenzenesulfonate (50 mg, 1 equiv), 5,6,7,8-tetrahydro-4H-pyrazolo[1,5-a][1,4]diazepin-2-amine (17.8 mg, 2 equiv) and 4 Å molecular sieve (20 mg) in DMF (0.5 mL) was added N-ethyl-N-isopropylpropan-2-amine (37.8 mg, 5 equiv). The mixture was stirred at 40° C. for 12 hours. The reaction mixture was filtered and purified with HPLC [0.1% FA condition] to afford the title compound (45 mg, 87% yield) as yellow solid. LCMS (ESI, M+1,): m/z=835.2.

Step B. 4-(4-(2-amino-7,8-dihydro-4H-pyrazolo[1,5-a][1,4]diazepin-5(6H)-yl)-2-(((2R,7aS)-2-fluorohexahydro-1H-pyrrolizin-7a-yl)methoxy)-5,6-dihydropyrido[3,4-d]pyrimidin-7(8H)-yl)-5-bromo-6-fluoronaphthalen-2-ol: To a solution of 4-(4-(2-amino-7,8-dihydro-4H-pyrazolo[1,5-a][1,4]diazepin-5(6H)-yl)-2-(((2R,7aS)-2-fluorohexahydro-1H-pyrrolizin-7a-yl)methoxy)-5,6-dihydropyrido[3,4-d]pyrimidin-7(8H)-yl)-5-bromo-6-fluoronaphthalen-2-yl 4-methylbenzenesulfonate (20 mg, 1.0 equiv) in MeOH (0.5 mL) was added NaOH (19.0 mg, 20 equiv). The mixture was stirred at 25° C. for 0.5 hour. The reaction mixture was diluted with H$_2$O (1.5 mL) and extracted with ethyl acetate (3×1.5 mL). The combined organic layers were concentrated and purified by prep-HPLC [Phenomenex luna C18 150×25 mm×10 µm; mobile phase: [water (FA)-ACN]; B %: 10%-40%, 10 min] to afford the title compound (16.5 mg, 45% yield) as pink solid. $^1$H NMR (400 MHz, METHANOL-d4) δ=7.68 (dd, J=5.6, 9.2 Hz, 1H), 7.25 (t, J=8.4 Hz, 1H), 6.97 (dd, J=2.4, 15.2 Hz, 2H), 5.38 (s, 1H), 4.79 (br d, J=4.4 Hz, 1H), 4.72-4.63 (m, 1H), 4.30-4.16 (m, 5H), 4.13-4.03 (m, 1H), 4.01-3.91 (m, 1H), 3.65 (br d, J=17.6 Hz, 1H), 3.56-3.41 (m, 4H), 3.30-3.11 (m, 4H), 2.72-2.62 (m, 1H), 2.49-2.29 (m, 2H), 2.27-2.16 (m, 2H), 2.14-1.94 (m, 4H); LCMS (ESI, M+1): m/z=681.2.

Example 213 and Example 214

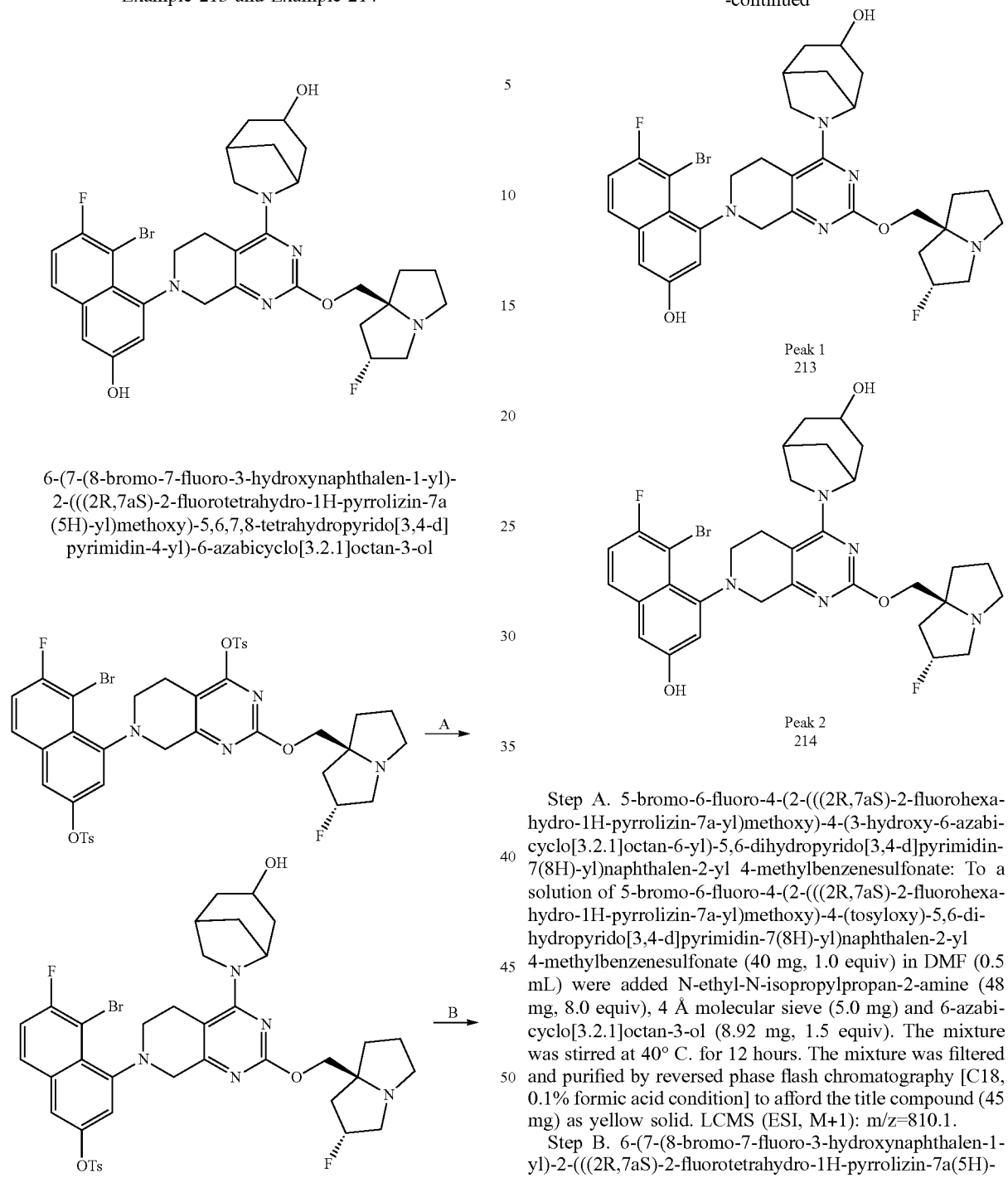

6-(7-(8-bromo-7-fluoro-3-hydroxynaphthalen-1-yl)-
2-(((2R,7aS)-2-fluorotetrahydro-1H-pyrrolizin-7a
(5H)-yl)methoxy)-5,6,7,8-tetrahydropyrido[3,4-d]
pyrimidin-4-yl)-6-azabicyclo[3.2.1]octan-3-ol Peak 1
213

Peak 2
214

Step A. 5-bromo-6-fluoro-4-(2-(((2R,7aS)-2-fluorohexahydro-1H-pyrrolizin-7a-yl)methoxy)-4-(3-hydroxy-6-azabicyclo[3.2.1]octan-6-yl)-5,6-dihydropyrido[3,4-d]pyrimidin-7(8H)-yl)naphthalen-2-yl 4-methylbenzenesulfonate: To a solution of 5-bromo-6-fluoro-4-(2-(((2R,7aS)-2-fluorohexahydro-1H-pyrrolizin-7a-yl)methoxy)-4-(tosyloxy)-5,6-dihydropyrido[3,4-d]pyrimidin-7(8H)-yl)naphthalen-2-yl 4-methylbenzenesulfonate (40 mg, 1.0 equiv) in DMF (0.5 mL) were added N-ethyl-N-isopropylpropan-2-amine (48 mg, 8.0 equiv), 4 Å molecular sieve (5.0 mg) and 6-azabicyclo[3.2.1]octan-3-ol (8.92 mg, 1.5 equiv). The mixture was stirred at 40° C. for 12 hours. The mixture was filtered and purified by reversed phase flash chromatography [C18, 0.1% formic acid condition] to afford the title compound (45 mg) as yellow solid. LCMS (ESI, M+1): m/z=810.1.

Step B. 6-(7-(8-bromo-7-fluoro-3-hydroxynaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-6-azabicyclo[3.2.1]octan-3-ol: To a solution of 5-bromo-6-fluoro-4-(2-(((2R,7aS)-2-fluorohexahydro-1H-pyrrolizin-7a-yl)methoxy)-4-(3-hydroxy-6-azabicyclo[3.2.1]octan-6-yl)-5,6-dihydropyrido[3,4-d]pyrimidin-7(8H)-yl) naphthalen-2-yl 4-methylbenzenesulfonate (37 mg, crude) in MeOH (0.5 mL) was added NaOH (4.0 M, 20.0 equiv). The mixture was stirred at 22° C. for 0.5 hour. The mixture was filtered and purified with reversed phase flash chromatography [C18, 0.1% formic acid condition] and prep-HPLC [Welch Xtimate C18 150×25 mm×5 µm; mobile phase: water (NH₃H₂O)-ACN; B %: 27%-57%, 8 min] to afford two peaks: peak 1/Example 213 (3.16 mg, 10% yield) as yellow solid. ¹H NMR (400 MHz, METHANOL-d₄) δ=7.69-7.60 (m, 1H), 7.22 (t, J=8.8 Hz, 1H), 7.05-6.90 (m, 2H), 5.39-5.17 (m, 1H), 4.65-4.55 (m, 1H), 4.13-3.95 (m, 4H), 4.37-3.92 (m, 2H), 3.70-3.37 (m, 3H), 3.25-3.13 (m, 4H), 3.05-2.93 (m, 2H), 2.44-2.27 (m, 1H), 2.22-2.08 (m, 2H), 2.71-2.08 (m, 1H), 2.06-1.83 (m, 6H), 1.80-1.63 (m, 2H); LCMS (ESI, M+1): m/z=656.3. Peak 2/Example 214 (3.65 mg, 12% yield) as yellow solid. ¹H NMR (400 MHz, METHANOL-d4) δ=7.66 (dd, J=5.6, 8.8 Hz, 1H), 7.23 (t, J=8.8 Hz, 1H), 7.02-6.92 (m, 2H), 5.39-5.16 (m, 1H), 4.64 (br s, 1H), 4.19-3.89 (m, 4H), 3.81-3.36 (m, 5H), 3.23-3.09 (m, 5H), 3.02-2.89 (m, 2H), 2.60 (br s, 2H), 2.22-2.07 (m, 3H), 1.95 (br d, J=7.6 Hz, 4H), 1.75-1.68 (m, 1H), 1.56-1.45 (m, 1H), 1.43-1.34 (m, 1H); LCMS (ESI, M+1): m/z=656.2.

Example 215

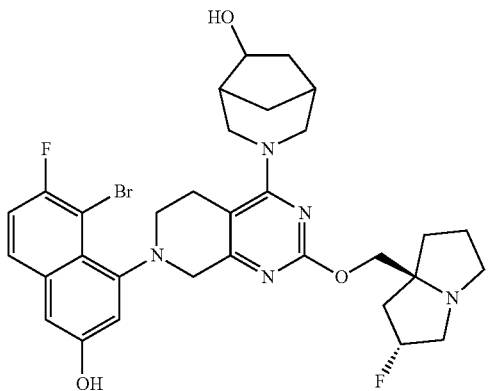 [SMILES: Oc1cc(N2CCc3c(nc(OC[C@@]45CCCN4C[C@H](F)C5)nc3N3CC4CC(O)C(C4)C3)C2)c2c(Br)c(F)ccc2c1]

3-(7-(8-bromo-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-azabicyclo[3.2.1]octan-6-ol Synthesized according to Example 212. The title compound was obtained as pink solid. ¹H NMR (400 MHz, METHANOL-d4) δ=7.69-7.64 (m, 1H), 7.24 (dt, J=2.4, 8.8 Hz, 1H), 7.02-6.95 (m, 2H), 5.45-5.25 (m, 1H), 4.66-4.56 (m, 1H), 4.36-4.29 (m, 1H), 4.28-4.19 (m, 3H), 4.18-4.11 (m, 1H), 3.62-3.43 (m, 3H), 3.43-3.34 (m, 3H), 3.23-3.07 (m, 3H), 3.07-2.99 (m, 1H), 2.68 (br d, J=14.4 Hz, 1H), 2.55-2.35 (m, 1H), 2.34-2.23 (m, 3H), 2.22-2.11 (m, 3H), 2.09-2.00 (m, 2H), 1.99-1.89 (m, 1H), 1.82-1.68 (m, 2H); LCMS (ESI, M+1): m/z=656.

Example 216

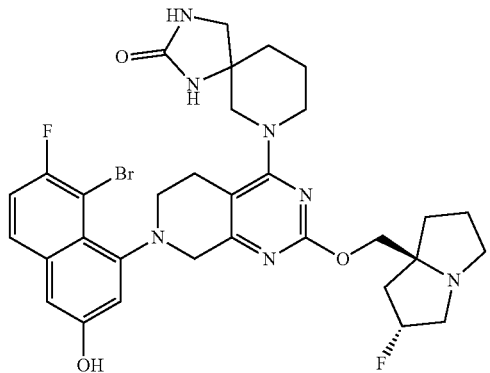 [SMILES: O=C1NCC2(CCCN(c3nc(OC[C@@]45CCCN4C[C@H](F)C5)nc4c3CCN(c3cc(O)cc5ccc(F)c(Br)c35)C4)C2)N1]

7-(7-(8-bromo-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,3,7-triazaspiro[4.5]decan-2-one Synthesized according to Example 212. The title compound was obtained as white solid. ¹H NMR (400 MHz, METHANOL-d4) δ=7.68 (ddd, J=3.2, 5.6, 9.0 Hz, 1H), 7.37-7.18 (m, 1H), 7.08-6.92 (m, 2H), 5.73-5.42 (m, 1H), 4.69-4.44 (m, 2H), 4.33-3.97 (m, 2H), 3.92-3.34 (m, 10H), 3.28-3.12 (m, 3H), 2.77-2.51 (m, 3H), 2.44-2.12 (m, 4H), 2.03-1.67 (m, 4H). LCMS (ESI, M+1): m/z=684.1.

Example 217

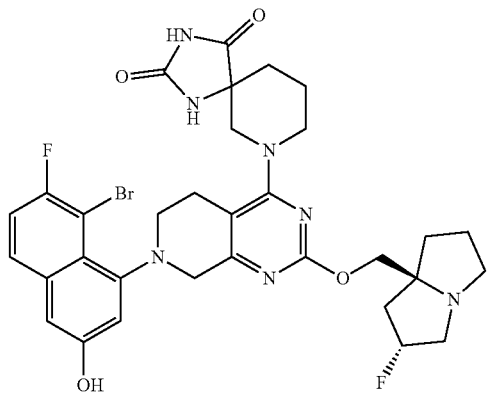 [SMILES: O=C1NC(=O)C2(CCCN(c3nc(OC[C@@]45CCCN4C[C@H](F)C5)nc4c3CCN(c3cc(O)cc5ccc(F)c(Br)c35)C4)C2)N1]

7-(7-(8-bromo-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,3,7-triazaspiro[4.5]decane-2,4-dione Synthesized according to Example 212. The title compound was obtained as white solid. ¹H NMR (400 MHz, METHANOL-d4) δ=7.67 (dd, J 5.6, 9.2 Hz, 1H), 7.24 (t, J 8.8 Hz, 1H), 7.05-6.94 (m, 2H), 5.52-5.25 (m, 1H), 4.40-4.22 (m, 3H), 4.17-3.95 (m, 2H), 3.67-3.48 (m, 3H), 3.45-3.37 (m, 3H), 3.20-2.98 (m, 3H), 2.79-2.65 (m, 1H), 2.49-2.27 (m, 2H), 2.26-2.01 (m, 5H), 2.01-1.76 (m, 4H); LCMS (ESI, M+1): m/z=698.1.

Example 218

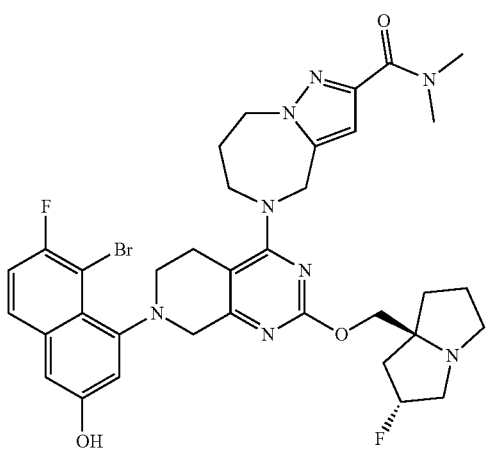 [SMILES: CN(C)C(=O)c1cc2n(n1)CCCN(c1nc(OC[C@@]34CCCN3C[C@H](F)C4)nc3c1CCN(c1cc(O)cc4ccc(F)c(Br)c14)C3)C2]

5-(7-(8-bromo-7-fluoro-3-hydroxynaphthalen-1-yl)-
2-(((2R,7aS)-2-fluorohexahydro-1H-pyrrolizin-7a-
yl)methoxy)-5,6,7,8-tetrahydropyrido[3,4-d]pyrimi-
din-4-yl)-N,N-dimethyl-5,6,7,8-tetrahydro-4H-
pyrazolo[1,5-a][1,4]diazepine-2-carboxamide Synthesized according to Example 212. The title compound was obtained as yellow solid. $^1$H NMR (400 MHz, METHANOL-d4) δ=7.67 (dd, J=5.6, 9.2 Hz, 1H), 7.31-7.15 (m, 1H), 6.98 (br d, J=3.2 Hz, 2H), 6.61 (d, J=2.4 Hz, 1H), 5.53-5.28 (m, 1H), 5.04-4.93 (m, 1H), 4.57-4.47 (m, 2H), 4.32-4.14 (m, 4H), 4.10-3.99 (m, 1H), 3.65-3.44 (m, 5H), 3.37 (br s, 4H), 3.23-3.12 (m, 3H), 3.08 (s, 3H), 2.75-2.63 (m, 1H), 2.51-1.90 (m, 5H), 2.15-1.90 (m, 4H); LCMS (ESI, M+1): m/z=737.1.

Example 219

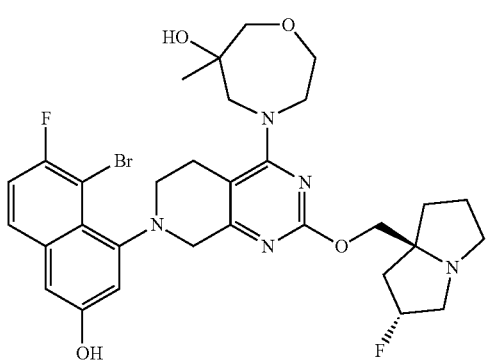 [SMILES: CC1(O)COCCN(c2nc(OC[C@@]34CCCN3C[C@H](F)C4)nc3c2CCN(c2cc(O)cc4ccc(F)c(Br)c24)C3)C1]

4-(7-(8-bromo-7-fluoro-3-hydroxynaphthalen-1-yl)-
2-(((2R,7aS)-2-fluorohexahydro-1H-pyrrolizin-7a-
yl)methoxy)-5,6,7,8-tetrahydropyrido[3,4-d]pyrimi-
din-4-yl)-6-methyl-1,4-oxazepan-6-ol Synthesized according to Example 212. The title compound was obtained as as white solid. $^1$H NMR (400 MHz, METHANOL-d4) δ=8.54 (s, 5H), 7.74-7.60 (m, 1H), 7.24 (dt, J=5.6, 8.6 Hz, 1H), 7.05-6.86 (m, 2H), 5.48-5.20 (m, 1H), 4.33-4.19 (m, 2H), 4.19-4.10 (m, 2H), 4.09-3.92 (m, 2H), 3.91-3.70 (m, 3H), 3.69-3.59 (m, 1H), 3.59-3.49 (m, 3H), 3.49-3.43 (m, 1H), 3.42-3.34 (m, 2H), 3.26-3.02 (m, 3H), 2.75-2.56 (m, 1H), 2.43-2.29 (m, 1H), 2.29-2.21 (m, 1H), 2.17-2.09 (m, 1H), 2.08-1.97 (m, 2H), 1.96-1.84 (m, 1H), 1.18 (dd, J=2.0, 5.9 Hz, 3H); LCMS (ESI, M+1): m/z=660.

Example 220

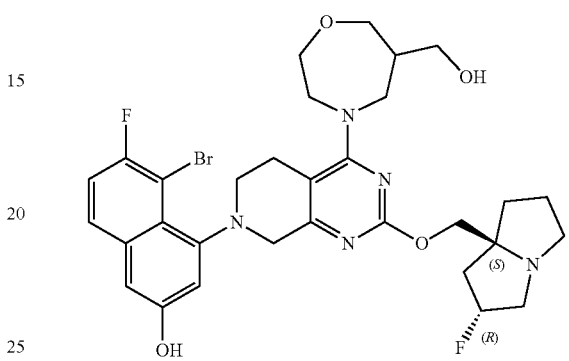

5-bromo-6-fluoro-4-(2-(((2R,7aS)-2-fluorohexa-
hydro-1H-pyrrolizin-7a-yl)methoxy)-4-(6-(hy-
droxymethyl)-1,4-oxazepan-4-yl)-5,6-dihydropyrido
[3,4-d]pyrimidin-7(8H)-yl)naphthalen-2-ol Synthesized according to Example 212. The title compound was obtained as yellow solid. $^1$H NMR (400 MHz, METHANOL-d4) δ=7.73-7.63 (m, 1H), 7.24 (t, J=8.8 Hz, 1H), 7.02-6.95 (m, 2H), 5.59-5.18 (m, 1H), 4.55-4.01 (m, 6H), 3.97-3.88 (m, 1H), 3.84-3.75 (m, 2H), 3.73-3.62 (m, 2H), 3.59-3.48 (m, 4H), 3.46-3.37 (m, 3H), 3.24-3.08 (m, 3H), 2.70 (br d, J=13.6 Hz, 1H), 2.50-2.39 (m, 1H), 2.35-2.29 (m, 1H), 2.22 (br s, 2H), 2.12-1.92 (m, 3H); LCMS (ESI, M+1): m/z=660.3.

Example 221

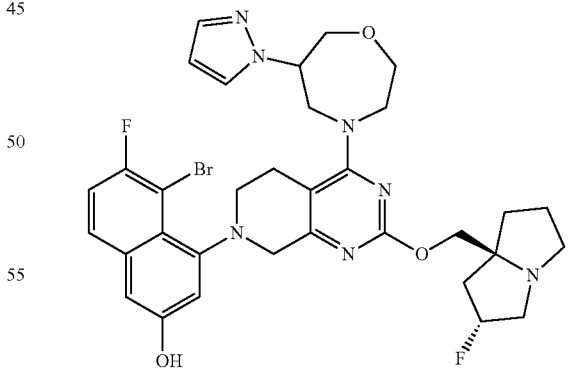

4-(4-(6-(1H-pyrazol-1-yl)-1,4-oxazepan-4-yl)-2-
(((2R,7aS)-2-fluorotetrahydro-1H-pyrrolizin-7a(5H)-
yl)methoxy)-5,8-dihydropyrido[3,4-d]pyrimidin-7
(6H)-yl)-5-bromo-6-fluoronaphthalen-2-ol Synthesized according to Example 212. The title compound was obtained as yellow solid. $^1$H NMR (400 MHz, METHANOL-d4) δ=7.88-7.80 (m, 1H), 7.73-7.64 (m, 1H), 7.54 (s, 1H), 7.26 (t, J=8.4 Hz, 1H), 7.07-6.92 (m, 2H), 6.36 (s, 1H), 5.68-5.46 (m, 1H), 5.22-5.06 (m, 1H), 4.67-4.42 (m, 3H), 4.35-4.20 (m, 2H), 4.20-4.09 (m, 2H), 4.07-3.97 (m, 2H), 3.97-3.91 (m, 2H), 3.91-3.84 (m, 3H), 3.83-3.73 (m, 1H), 3.64-3.57 (m, 1H), 3.51-3.42 (m, 1H), 3.30-3.20 (m, 1H), 3.20-3.10 (m, 1H), 2.83-2.69 (m, 1H), 2.68-2.47 (m, 2H), 2.45-2.29 (m, 3H), 2.27-2.07 (m, 1H); LCMS (ESI, M+1): m/z=696.1.

Example 222

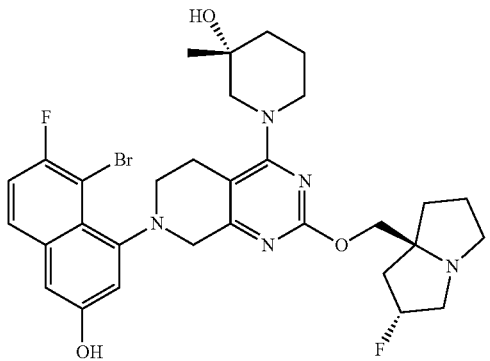 [SMILES: C[C@@]1(O)CCCN(c2nc(OC[C@@]34CCCN3C[C@H](F)C4)nc3c2CCN(c2cc(O)cc4ccc(F)c(Br)c24)C3)C1]

(R)-1-(7-(8-bromo-7-fluoro-3-hydroxynaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-3-methylpiperidin-3-ol Synthesized according to Example 212. The title compound was obtained as yellow solid. ¹H NMR (400 MHz, METHANOL-d4) δ=7.73-7.64 (m, 1H), 7.26 (t, J=8.4 Hz, 1H), 7.04-6.97 (m, 2H), 5.53-5.31 (m, 1H), 4.41-4.22 (m, 3H), 3.76-3.39 (m, 8H), 3.13 (br d, J=0.8 Hz, 3H), 2.78-2.61 (m, 1H), 2.52-2.31 (m, 2H), 2.27-1.96 (m, 5H), 1.93-1.60 (m, 4H), 1.30-1.21 (m, 3H); LCMS (ESI, M+1): m/z=644.1.

Example 223

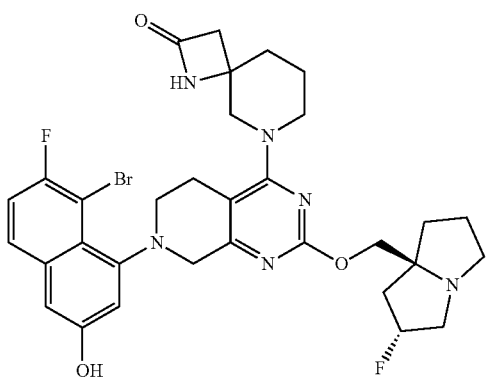 [SMILES: O=C1CC2(CCCN(c3nc(OC[C@@]45CCCN4C[C@H](F)C5)nc4c3CCN(c3cc(O)cc5ccc(F)c(Br)c35)C4)C2)N1]

6-(7-(8-bromo-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,6-diazaspiro[3.5]nonan-2-one Synthesized according to Example 212. The title compound was obtained as white solid. ¹H NMR (400 MHz, METHANOL-d4) δ=7.71-7.66 (m, 1H), 7.26 (t, J=8.8 Hz, 1H), 7.06-6.95 (m, 2H), 5.40-5.19 (m, 1H), 4.32-4.04 (m, 3H), 3.99-3.47 (m, 6H), 3.27-3.13 (m, 5H), 3.04-2.97 (m, 1H), 2.89-2.63 (m, 3H), 2.36-2.07 (m, 3H), 2.05-1.78 (m, 7H). LCMS (ESI, M+1): m/z=669.

Example 224

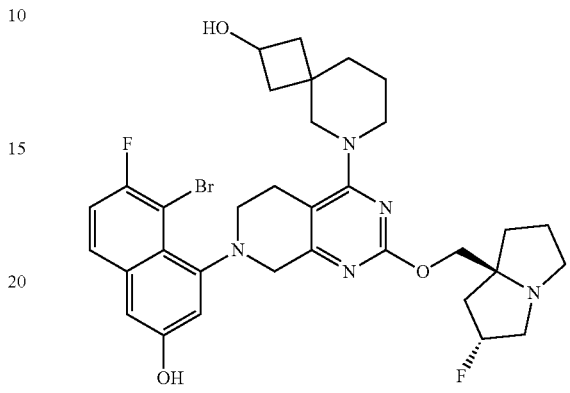

6-(7-(8-bromo-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-6-azaspiro[3.5]nonan-2-ol Synthesized according to Example 212. ¹H NMR (400 MHz, METHANOL-d4) δ=7.69 (dd, J=5.6, 8.8 Hz, 1H), 7.31-7.22 (m, 1H), 7.01 (s, 2H), 5.61-5.25 (m, 1H), 4.43-4.23 (m, 4H), 3.88-3.76 (m, 1H), 3.71-3.65 (m, 2H), 3.60-3.45 (m, 5H), 3.27-3.16 (m, 3H), 2.68-2.33 (m, 4H), 2.29-1.98 (m, 6H), 1.89-1.61 (m, 6H); LCMS (ESI, M+1): m/z=670.2.

Example 225

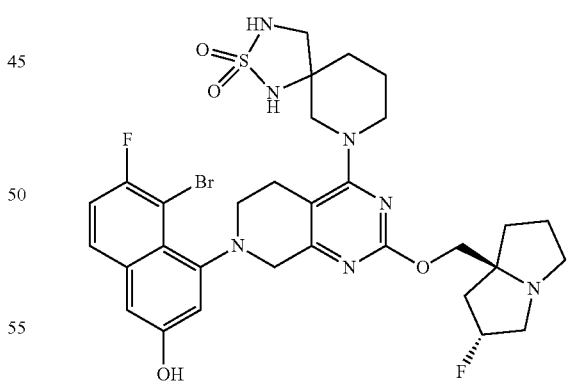

7-(7-(8-bromo-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-2-thia-1,3,7-triazaspiro[4.5]decane 2,2-dioxide Synthesized according to Example 212. The title compound was obtained as yellow solid. ¹H NMR (400 MHz, METHANOL-d₄) δ=7.64 (td, J=5.6, 9.2 Hz, 1H), 7.22 (dt, J=4.0, 8.8 Hz, 1H), 7.05-6.88 (m, 2H), 5.39-5.17 (m, 1H), 4.25 (br d, J=17.6 Hz, 1H), 4.18-4.02 (m, 2H), 4.00-3.77 (m, 1H), 3.59 (br d, J=10.0 Hz, 1H), 3.54 (br dd, J=7.2, 11.6 Hz, 2H), 3.51-3.44 (m, 1H), 3.44-3.33 (m, 2H), 3.29-3.19 (m, 3H), 3.18-3.08 (m, 3H), 3.04-2.94 (m, 1H), 2.71-2.57 (m, 1H), 2.40-2.07 (m, 3H), 2.06-1.64 (m, 7H); LCMS (ESI, M+1): m/z=720.3.

Example 226

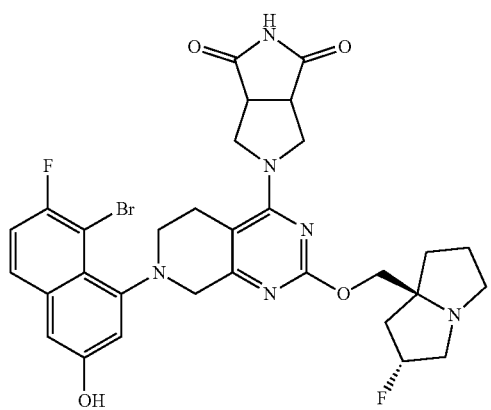 [SMILES: O=C1NC(=O)C2CN(c3nc(OC[C@@]45CCCN4C[C@H](F)C5)nc4c3CCN(c3cc(O)cc5ccc(F)c(Br)c35)C4)CC12]

5-(7-(8-bromo-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)tetrahydropyrrolo[3,4-c]pyrrole-1,3(2H,3aH)-dione Synthesized according to Example 212. The title compound was obtained as yellow solid. ¹H NMR (400 MHz, METHANOL-d4) δ=7.73-7.62 (m, 1H), 7.24 (br t, J=8.4 Hz, 1H), 6.99 (s, 2H), 5.60-5.21 (m, 1H), 4.66-4.60 (m, 1H), 4.41-4.14 (m, 4H), 3.81-3.72 (m, 1H), 3.70-3.46 (m, 8H), 3.27-3.11 (m, 3H), 2.70 (br d, J=14.5 Hz, 1H), 2.56-2.30 (m, 2H), 2.28-1.95 (m, 4H); LCMS (ESI, M+1): m/z=669.

Example 227

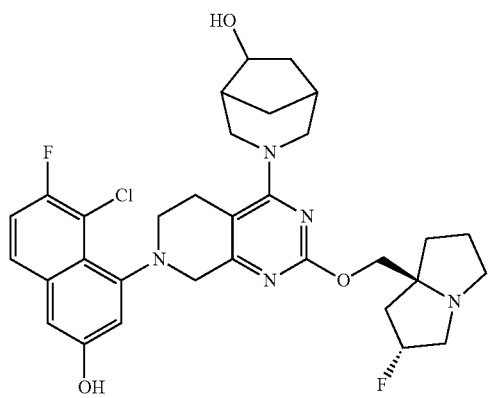 [SMILES: Oc1cc(N2CCc3c(nc(OC[C@@]45CCCN4C[C@H](F)C5)nc3N3CC4CC(O)C(C4)C3)C2)c2c(Cl)c(F)ccc2c1]

3-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-azabicyclo[3.2.1]octan-6-ol

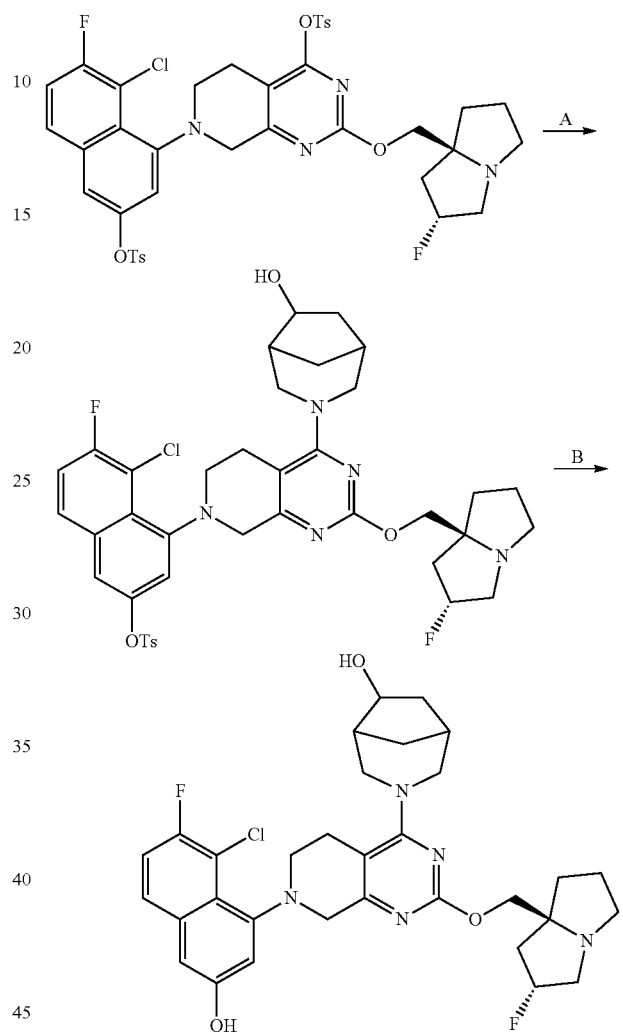

Step A. 5-chloro-6-fluoro-4-(2-(((2R,7aS)-2-fluorotetrahydro-1H-pyrrolizin-7a(5H)-yl)methoxy)-4-(6-hydroxy-3-azabicyclo[3.2.1]octan-3-yl)-5,8-dihydropyrido[3,4-d]pyrimidin-7(6H)-yl)naphthalen-2-yl 4-methylbenzenesulfonate: To a solution of 5-chloro-6-fluoro-4-(2-(((2R,7aS)-2-fluorotetrahydro-1H-pyrrolizin-7a(5H)-yl)methoxy)-4-(tosyloxy)-5,8-dihydropyrido[3,4-d]pyrimidin-7(6H)-yl)naphthalen-2-yl 4-methylbenzenesulfonate (110 mg, 1 equiv) and 3-azabicyclo[3.2.1]octan-6-ol (66.6 mg, crude, HCl) in DMF (0.5 mL) were added N-ethyl-N-isopropylpropan-2-amine (175 mg, 10 equiv) and 4 Å molecular sieve (5 mg). The mixture was stirred at 40° C. until reaction was completed. The residue was purified by reversed phase flash chromatography [C18, 0.1% formic acid] to afford the title compound (80 mg, 77% yield) as white solid. LCMS (ESI, M+1): m/z=766.2.

Step B 3-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-

3-azabicyclo[3.2.1]octan-6-ol: To a solution of 5-chloro-6-fluoro-4-(2-(((2R,7aS)-2-fluorotetrahydro-1H-pyrrolizin-7a(5H)-yl)methoxy)-4-(6-hydroxy-3-azabicyclo[3.2.1]octan-3-yl)-5,8-dihydropyrido[3,4-d]pyrimidin-7(6H)-yl)naphthalen-2-yl 4-methylbenzenesulfonate (50 mg, 1 equiv) in MeOH (0.5 mL) was added NaOH (26.1 mg, 10 equiv). The mixture was stirred at 25° C. for 20 minutes. The mixture was purified by prep-HPLC (column: Phenomenex luna C18 150×25 mm×10 μm; mobile phase A: water (FA), B: ACN; B %: 15%-45%, 10 min) afford the title compound (5.58 mg, 13% yield) as a yellow solid. $^1$H NMR (400 MHz, METHANOL-d4) δ=7.64 (br dd, J=6.0, 7.6 Hz, 1H), 7.29 (br t, J=8.8 Hz, 1H), 6.97 (br s, 2H), 5.56-5.36 (m, 1H), 4.69-4.48 (m, 1H), 4.44-3.84 (m, 5H), 3.74-3.48 (m, 5H), 3.45-3.36 (m, 1H), 3.30-3.18 (m, 2H), 3.16-3.01 (m, 2H), 2.97-2.67 (m, 1H), 2.60-2.35 (m, 2H), 2.34-2.12 (m, 6H), 2.11-1.99 (m, 1H), 1.86-1.69 (m, 2H), 1.62-1.29 (m, 1H). LCMS (ESI, M+1): m/z=612.3.

Example 228

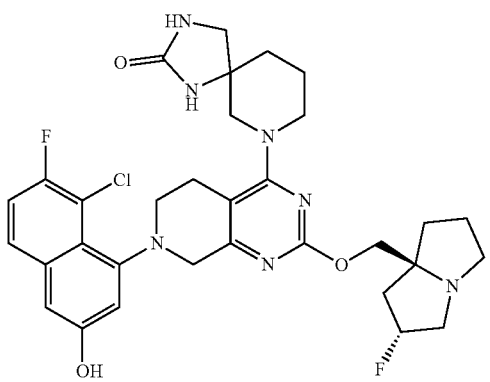 [SMILES: O=C1NCC2(CCCN(c3nc(OC[C@@]45CCCN4C[C@H](F)C5)nc4c3CCN(c3cc(O)cc5ccc(F)c(Cl)c35)C4)C2)N1]

7-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,3,7-triazaspiro[4.5]decan-2-one Synthesized according to Example 212. The title compound was obtained as yellow solid. $^1$H NMR (400 MHz, METHANOL-d4) δ=7.62 (dd, J=5.6, 9.1 Hz, 1H), 7.27 (t, J=8.8 Hz, 1H), 6.97-6.88 (m, 2H), 5.40-5.15 (m, 1H), 4.27 (dd, J=8.8, 17.3 Hz, 1H), 4.22-4.02 (m, 2H), 3.76-3.58 (m, 3H), 3.57-3.48 (m, 2H), 3.44-3.33 (m, 1H), 3.29-3.07 (m, 7H), 3.03-2.95 (m, 1H), 2.72-2.61 (m, 1H), 2.35-2.14 (m, 2H), 2.14-2.06 (m, 1H), 2.01-1.69 (m, 7H); LCMS (ESI, M+1): m/z=640.2.

Example 229

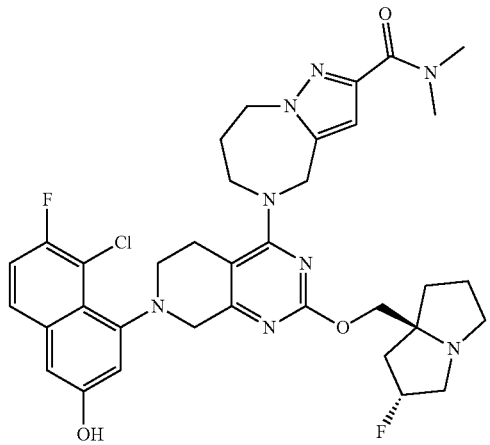 [SMILES: CN(C)C(=O)c1cc2n(n1)CCCN(c1nc(OC[C@@]34CCCN3C[C@H](F)C4)nc3c1CCN(c1cc(O)cc4ccc(F)c(Cl)c14)C3)C2]

5-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide Synthesized according to Example 212. The title compound was obtained as yellow solid. $^1$H NMR (400 MHz, METHANOL-d4) δ=7.64 (dd, J=5.6, 9.2 Hz, 1H), 7.29 (t, J=8.8 Hz, 1H), 7.01-6.91 (m, 2H), 6.60 (d, J=1.6 Hz, 1H), 5.53-5.15 (m, 1H), 5.03-4.93 (m, 1H), 4.60-4.49 (m, 2H), 4.29-4.10 (m, 4H), 4.09-3.98 (m, 1H), 3.76-3.34 (m, 5H), 3.33-3.27 (m, 4H), 3.18-3.06 (m, 5H), 2.69 (br d, J=14.8 Hz, 1H), 2.43-1.82 (m, 9H). LCMS (ESI, M+1): m/z=693.3.

Example 230

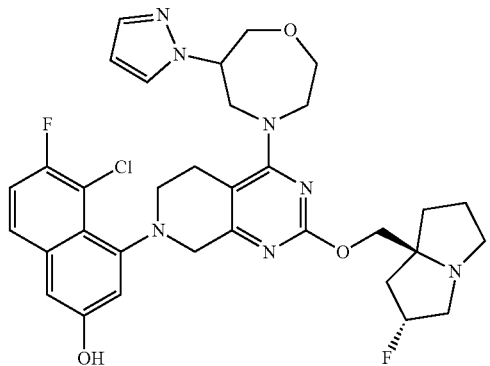 [SMILES: Oc1cc(N2CCc3c(nc(OC[C@@]45CCCN4C[C@H](F)C5)nc3N3CCOCC(n4cccn4)C3)C2)c2c(Cl)c(F)ccc2c1]

4-(4-(6-(1H-pyrazol-1-yl)-1,4-oxazepan-4-yl)-2-(((2R,7aS)-2-fluorohexahydro-1H-pyrrolizin-7a-yl)methoxy)-5,6-dihydropyrido[3,4-d]pyrimidin-7(8H)-yl)-5-chloro-6-fluoronaphthalen-2-ol Synthesized according to Example 212. The title compound was obtained as yellow solid. $^1$H NMR (400 MHz, METHANOL-d$_4$) δ=7.87-7.80 (m, 1H), 7.69-7.60 (m, 1H), 7.57-7.50 (m, 1H), 7.30 (t, J=8.8 Hz, 1H), 7.05-6.91 (m, 2H), 6.42-6.31 (m, 1H), 5.69-5.47 (m, 1H), 5.21-5.03 (m, 1H), 4.70-4.46 (m, 3H), 4.37-4.21 (m, 2H), 4.20-4.08 (m, 2H), 4.08-3.92 (m, 4H), 3.91-3.65 (m, 4H), 3.64-3.51 (m, 1H), 3.50-3.40 (m, 1H), 3.29-3.19 (m, 1H), 3.18-3.06 (m, 1H), 2.81-2.71 (m, 1H), 2.71-2.61 (m, 1H), 2.61-2.52 (m, 1H), 2.43-2.28 (m, 3H), 2.27-2.09 (m, 1H); LCMS (ESI, M+1): m/z=652.4.

Example 231

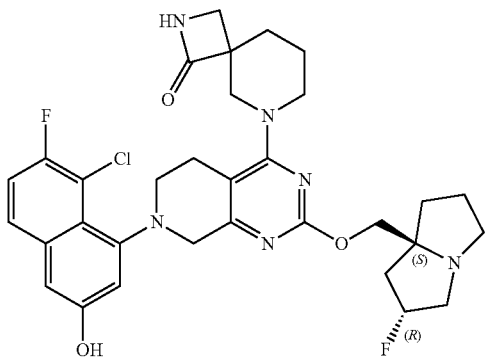

6-(7-(8-chloro-7-fluoro-3-hydroxynaphthalen-1-yl)-2-(((2R,7aS)-2-fluorotetrahydro-1H-pyrrolizin-7a (5H)-yl)methoxy)-5,6,7,8-tetrahydropyrido[3,4-d]pyrimidin-4-yl)-2,6-diazaspiro[3.5]nonan-1-one Synthesized according to Example 212. The title compound was obtained as white solid. $^1$H NMR (400 MHz, METHANOL-d4) δ=7.71-7.63 (m, 1H), 7.31 (t, J=8.8 Hz, 1H), 7.06-6.92 (m, 2H), 5.69-5.46 (m, 1H), 4.67-4.51 (m, 2H), 4.32 (br d, J=17.6 Hz, 1H), 4.21-3.83 (m, 6H), 3.83-3.72 (m, 1H), 3.71-3.40 (m, 4H), 3.25-3.11 (m, 3H), 2.79-2.56 (m, 3H), 2.47-2.28 (m, 3H), 2.26-1.82 (m, 5H); LCMS (ESI, M+1): m/z=625.3.

Example 232

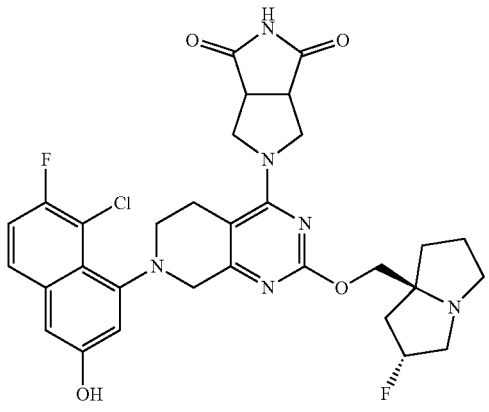 [SMILES: O=C1NC(=O)C2CN(c3nc(OC[C@@]45CCCN4C[C@H](F)C5)nc4c3CCN(c3cc(O)cc5ccc(F)c(Cl)c35)C4)CC12]

5-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)tetrahydropyrrolo[3,4-c]pyrrole-1,3(2H,3aH)-dione Synthesized according to Example 212. The title compound was obtained as white solid. $^1$H NMR (400 MHz, METHANOL-d4) δ=7.65 (dd, J=5.6, 8.8 Hz, 1H), 7.30 (t, J=8.8 Hz, 1H), 6.99 (s, 2H), 5.69-5.46 (m, 1H), 4.68-4.50 (m, 3H), 4.37-4.20 (m, 2H), 4.02-3.93 (m, 1H), 3.95-3.85 (m, 3H), 3.78-3.66 (m, 2H), 3.65-3.53 (m, 3H), 3.47 (dt, J=5.6, 10.4 Hz, 1H), 3.28 (br d, J=1.6 Hz, 1H), 3.24-3.11 (m, 1H), 2.80 (br d, J=14.4 Hz, 1H), 2.69 (br t, J=4.4 Hz, 2H), 2.47-2.30 (m, 3H), 2.26-2.12 (m, 1H); LCMS (ESI, M+1): m/z=625.1.

Example A

KRas Binding Assay

This Example illustrates that exemplary compounds of the present invention bind to KRas and are capable of displacing a labeled tracer ligand occupying the KRas binding site. $KRas^{WT}$, $KRas^{G12A}$, $KRas^{G12C}$, $KRas^{G12D}$, $KRas^{G12R}$, $KRas^{G12S}$, $KRas^{G12V}$, $KRas^{G13D}$, or $KRas^{Q61H}$ was used in the assay.

The ability of a compound to bind to KRas was measured using a TR-FRET displacement assay. Biotinylated KRas (corresponding to amino acids 1-169, produced at Accelegan Inc.) was incubated with custom made Cy5 labelled tracer, terbium streptavidin (Cisbio Inc.) and compound (1% DMSO final) in buffer (50 mM HEPES, pH 7.5, 5 mM $MgCl_2$, 0.005% Tween-20 and 1 mM DTT). After a 60-minute incubation at room temperature, the reaction was measured using a BMG LABTECH CLARIO star Plus via TR-FRET. 100 percent of control (POC) is determined by using a DMSO control and 0 POC is determined using a concentration of control compound that completely inhibits binding of the tracer to KRas. The POC values were fit to a 4-parameter $IC_{50}$ equation and the $IC_{50}$ value reported.

TABLE 2

Binding to KRas ($IC_{50}$ nM) by Exemplary Compounds of Formula (I)

| Ex. No. | G12D | G12V | G12R | G12A | G12S | G12C | WT | G13D | Q61H |
|---|---|---|---|---|---|---|---|---|---|
| 1 | ≤2 | ≤2 | ≤2 | ≤2 | ≤2 | ≤2 | ≤2 | ≤2 | ≤2 |
| 2 | ≤2 | ≤2 | ≤2 | ≤2 | ≤2 | ≤2 | ≤2 | 52 | ≤2 |
| 3 | 16 | 17 | 25 | | | | | | |
| 4 | 97 | 90 | 127 | | | | | | |
| 5 | 19070 | 7652 | 8070 | | | | | | |
| 6 | 310 | 118 | 71 | 86 | 100 | 88 | 104 | 159 | 132 |
| 7 | 121 | 68 | 50 | 92 | 107 | 89 | 143 | 143 | 173 |
| 8 | 43 | 137 | 102 | 316 | 175 | 139 | 271 | 628 | 567 |
| 9 | 192 | 165 | 168 | 128 | 154 | 115 | 54 | 66 | 76 |
| 10 | 67 | 81 | 74 | 169 | 101 | 81 | 171 | 375 | 291 |
| 11 | 22 | 18 | 42 | 45 | 15 | 41 | 51 | 42 | 50 |
| 12 | 3 | ≤2 | ≤2 | ≤2 | ≤2 | ≤2 | ≤2 | ≤2 | ≤2 |
| 13 | 290 | 73 | 99 | 51 | 70 | 82 | 41 | 40 | 57 |
| 14 | 256 | 112 | 233 | 145 | 171 | 173 | 119 | 118 | 135 |
| 15 | 126 | 103 | 144 | | | | | | |
| 16 | 63 | 18 | 28 | 45 | 45 | 37 | 66 | 65 | 55 |
| 17 | 26 | ≤2 | ≤2 | | | | | | |
| 18 | ≤2 | ≤2 | ≤2 | | | | | | |
| 19 | 26 | 6 | 4 | 4 | 9 | 5 | 8 | 11 | 9 |
| 20 | ≤2 | ≤2 | 52 | | | | | | |
| 21 | ≤2 | ≤2 | ≤2 | | | | | | |
| 22 | 68 | 71 | 123 | 93 | 89 | 72 | 105 | 101 | 95 |
| 23 | 69 | 5 | 4 | 9 | 12 | 7 | 36 | 42 | 38 |
| 24 | ≤2 | ≤2 | ≤2 | | | | | | |

TABLE 2-continued

Binding to KRas (IC$_{50}$ nM) by Exemplary Compounds of Formula (I)

| Ex. No. | G12D | G12V | G12R | G12A | G12S | G12C | WT | G13D | Q61H |
|---|---|---|---|---|---|---|---|---|---|
| 25 | 3 | 3 | 4 | | | | | | |
| 26 | 110 | 4 | 5 | 7 | 10 | 7 | 24 | 34 | 22 |
| 27 | ≤2 | ≤2 | ≤2 | | | | | | |
| 28 | ≤2 | ≤2 | ≤2 | | | | | | |
| 29 | ≤2 | ≤2 | ≤2 | | | | | | |
| 30 | ≤2 | ≤2 | ≤2 | | | | | | |
| 31 | 31 | ≤2 | ≤2 | | | | | | |
| 32 | ≤2 | ≤2 | 3 | | | | | | |
| 33 | 5 | ≤2 | ≤2 | | | | | | |
| 34 | ≤2 | ≤2 | ≤2 | | | | | | |
| 35 | 7 | 52 | ≤2 | | | | | | |
| 36 | 5 | ≤2 | 5 | | | | | | |
| 37 | 479 | 221 | 168 | | | | 214 | | |
| 38 | ≤2 | 204 | 485 | | | | 445 | | |
| 39 | 7110 | 221 | 239 | 425 | 592 | 317 | 1366 | 1530 | 1637 |
| 40 | 2371 | 155 | 51 | 115 | 158 | 63 | 566 | 1030 | 854 |
| 41 | 1300 | 206 | 245 | 452 | 255 | 520 | 543 | 583 | 685 |
| 42 | 223 | 160 | 276 | 175 | 190 | 263 | 127 | 128 | 157 |
| 43 | 552 | 271 | 198 | | | 271 | | | |
| 44 | 162 | 200 | 308 | 202 | 202 | 232 | 191 | 163 | 226 |
| 45 | 7870 | 394 | 354 | 922 | 1128 | 328 | 7538 | 3967 | 4409 |
| 46 | 6753 | 232 | 277 | 448 | 611 | 401 | 1822 | 2857 | 2231 |
| 47 | 222 | 87 | 61 | 82 | 86 | 65 | 137 | 179 | 172 |
| 48 | 192 | 94 | 141 | 101 | 124 | 82 | 159 | 80 | 214 |
| 49 | 465 | 184 | 167 | 317 | 364 | 273 | 579 | 662 | 703 |
| 50 | 219 | 342 | 284 | 569 | 330 | 299 | 613 | 800 | 808 |
| 51 | 309 | 652 | 492 | 1257 | 669 | 564 | 1373 | 2030 | 1930 |
| 52 | 1234 | 348 | 723 | 1275 | 584 | 662 | 2217 | 1153 | 1418 |
| 53 | 2720 | 937 | 397 | 548 | 854 | 741 | 894 | 1184 | 1150 |
| 54 | 1463 | 707 | 663 | 767 | 924 | 755 | 943 | 1075 | 1232 |
| 55 | 1155 | 1095 | 744 | 2080 | 1155 | 893 | 2902 | 3861 | 4546 |
| 56 | 874 | 1617 | 1808 | 3009 | 2028 | 1647 | 5122 | 5722 | 5563 |
| 57 | 4798 | 3609 | 1288 | 2034 | 2294 | 2100 | 2977 | 3315 | 3451 |
| 58 | 19970 | 2858 | 7914 | | | 6572 | | | |
| 59 | ≤2 | ≤2 | ≤2 | | | | | | |
| 60 | ≤2 | ≤2 | ≤2 | | | | | | |
| 61 | 4 | 4 | 9 | | | | | | |
| 62 | ≤2 | ≤2 | ≤2 | | | | | | |
| 63 | 8 | ≤2 | ≤2 | | | | | | |
| 64 | ≤2 | ≤2 | ≤2 | | | | | | |
| 65 | 3 | ≤2 | ≤2 | | | | | | |
| 66 | ≤2 | ≤2 | ≤2 | | | | | | |
| 67 | 11 | 7 | ≤2 | | | | | | |
| 68 | ≤2 | ≤2 | 3 | | | | | | |
| 69 | ≤2 | 52 | ≤2 | | | | | | |
| 70 | ≤2 | ≤2 | ≤2 | | | | | | |
| 71 | 4 | ≤2 | ≤2 | | | | | | |
| 72 | ≤2 | ≤2 | ≤2 | | | | | | |
| 73 | 5 | 3 | 3 | | | | | | |
| 74 | ≤2 | 3 | 4 | | | | | | |
| 75 | ≤2 | 3 | ≤2 | | | | | | |
| 76 | 37 | 7 | 7 | | | | | | |
| 77 | 740 | 188 | 165 | | | | | | |
| 78 | 30 | 41 | 81 | 59 | 22 | 80 | 73 | 67 | 112 |
| 79 | 53 | 67 | 135 | 128 | 35 | 116 | 109 | 111 | 151 |
| 80 | 121 | 130 | 285 | 428 | 68 | 211 | 200 | 213 | 260 |
| 81 | 5404 | 3398 | 4022 | 4047 | 1159 | 3557 | 3606 | 3716 | 5329 |
| 82 | 1121 | 958 | 291 | 628 | 696 | 475 | 712 | 552 | 606 |
| 83 | 929 | 427 | 311 | 206 | 240 | 190 | 83 | 139 | 189 |
| 84 | 2106 | 291 | 104 | 215 | 351 | 161 | 838 | 696 | 734 |
| 85 | 1028 | 491 | 399 | 223 | 263 | 274 | 140 | 186 | 213 |
| 86 | 1320 | 498 | 465 | 225 | 304 | 576 | 158 | 151 | 194 |
| 87 | 4876 | 1875 | 165 | 1136 | 1149 | 470 | 1007 | 1470 | 844 |
| 88 | 1114 | 403 | 470 | 475 | 505 | 482 | 215 | 176 | 228 |
| 89 | 7108 | 593 | 219 | 427 | 721 | 465 | 959 | 1133 | 929 |
| 90 | 6278 | 2123 | 1071 | 1028 | 1872 | 1164 | 225 | 440 | 321 |
| 91 | 1040 | 435 | 229 | 292 | 459 | 382 | 765 | 919 | 963 |
| 92 | 532 | 295 | 279 | 303 | 342 | 348 | 232 | 247 | 325 |
| 93 | 2617 | 701 | 234 | 427 | 698 | 256 | 678 | 1099 | 1235 |
| 94 | 2124 | 1293 | 244 | 793 | 883 | 525 | 860 | 699 | 757 |
| 95 | 4696 | 990 | 724 | 655 | 953 | 656 | 255 | 254 | 343 |
| 96 | 3283 | 357 | 1159 | 304 | 348 | 304 | 747 | 1326 | 1275 |
| 97 | 1161 | 567 | 499 | 484 | 520 | 558 | 321 | 336 | 400 |
| 98 | 1072 | 341 | 514 | 453 | 482 | 330 | 444 | 629 | 537 |
| 99 | 3012 | 958 | 338 | 1251 | 1252 | 1004 | 1236 | 1561 | 1125 |
| 100 | 4424 | 2032 | 339 | 1006 | 1427 | 828 | 1145 | 1366 | 1397 |
| 101 | 1215 | 546 | 400 | 487 | 383 | 355 | 515 | 673 | 740 |
| 102 | 15040 | 6447 | 3076 | 805 | 3092 | 2988 | 357 | 363 | 424 |
| 103 | 2581 | 1390 | 364 | 785 | 791 | 427 | 718 | 691 | 690 |
| 104 | 4203 | 852 | 365 | 755 | 1123 | 894 | 1589 | 1795 | 1978 |
| 105 | 607 | 368 | 461 | 382 | 385 | 457 | 469 | 566 | 600 |
| 106 | 2232 | 1303 | 1786 | 628 | 752 | 369 | 1418 | 1073 | 1457 |
| 107 | 1448 | 406 | 638 | 423 | 535 | 487 | 369 | 465 | 528 |
| 108 | 4087 | 948 | 381 | 656 | 975 | 485 | 1548 | 1292 | 1596 |
| 109 | 1765 | 690 | 387 | 735 | 612 | 456 | 519 | 893 | 898 |
| 110 | 726 | 566 | 788 | 595 | 551 | 639 | 400 | 412 | 491 |
| 111 | 602 | 404 | 546 | 440 | 486 | 417 | 411 | 544 | 513 |
| 112 | 7286 | 1581 | 2094 | 1339 | 1329 | 1566 | 412 | 581 | 64" |
| 113 | 843 | 450 | 756 | 464 | 601 | 418 | 509 | 654 | 523 |
| 114 | 3729 | 997 | 455 | 1924 | 704 | 1307 | 1094 | 1206 | 1184 |
| 115 | 3036 | 1805 | 460 | 1107 | 1351 | 928 | 1152 | 1396 | 1215 |
| 116 | 3295 | 1788 | 462 | 1160 | 1495 | 1112 | 2097 | 1674 | 1642 |
| 117 | 2270 | 495 | 3979 | 5283 | 3417 | 2365 | 6165 | 7027 | 9679 |
| 118 | 1797 | 948 | 558 | 880 | 917 | 652 | 1947 | 1574 | 1494 |
| 119 | 1050 | 564 | 836 | 644 | 797 | 811 | 967 | 735 | 778 |
| 120 | 6382 | 4209 | 1315 | 1532 | 2475 | 573 | 1810 | 2008 | 2100 |
| 121 | 2298 | 612 | 2368 | 4551 | 3416 | 2339 | 3617 | 5146 | 6355 |
| 122 | 1903 | 613 | 689 | 1415 | 1200 | 941 | 1748 | 2574 | 2088 |
| 123 | 4231 | 639 | 1524 | 1930 | 1667 | 884 | 2484 | 6144 | 4626 |
| 124 | 30770 | 5019 | 645 | 5236 | 3432 | 4129 | 5876 | 7464 | 7700 |
| 125 | 1027 | 1410 | 1490 | 1324 | 665 | 1198 | 651 | 720 | 1045 |
| 126 | 720 | 2747 | 3291 | 5901 | 2909 | 2741 | 4255 | 5681 | 5449 |
| 127 | 2039 | 739 | 1355 | 2072 | 1402 | 1151 | 1543 | 1826 | 1747 |
| 128 | 10550 | 744 | 1041 | 2076 | 1670 | 1512 | 3588 | 4575 | 3833 |
| 129 | 16010 | 2410 | 760 | 2968 | 2140 | 1296 | 2210 | 3216 | 2428 |
| 130 | 5071 | 1258 | 1227 | 1457 | 1300 | 1096 | 772 | 1156 | 950 |
| 131 | 2123 | 1256 | 774 | 1197 | 1352 | 1067 | 1415 | 1358 | 1480 |
| 132 | 3901 | 1643 | 775 | 1184 | 1656 | 1316 | 1432 | 1454 | 1716 |
| 133 | 945 | 936 | 781 | 1025 | 1018 | 871 | 1338 | 1503 | 1438 |
| 134 | 1546 | 828 | 3219 | 4629 | 3342 | 2592 | 6361 | 9181 | 8678 |
| 135 | 4096 | 2853 | 850 | 2671 | 2423 | 1933 | 2833 | 2811 | 2848 |
| 136 | 3393 | 868 | 1628 | 1537 | 1987 | 969 | 1564 | 3278 | 2300 |
| 137 | 3236 | 1472 | 1142 | 948 | 1076 | 1034 | 1664 | 1349 | 1471 |
| 138 | 7755 | 1009 | 1842 | 2739 | 4146 | 1372 | 6052 | 7305 | 7302 |
| 139 | 12400 | 1173 | 1408 | 2536 | 2833 | 1491 | 3479 | 5443 | 4575 |
| 140 | 5214 | 2385 | 1437 | 1655 | 2002 | 1179 | 1922 | 1763 | 2234 |
| 141 | 8519 | 1260 | 1636 | 2953 | 2490 | 2299 | 1615 | 1198 | 1610 |
| 142 | 10540 | 1381 | 1721 | 2325 | 1873 | 1250 | 7522 | 13130 | 7246 |
| 143 | 5925 | 4146 | 2014 | 2227 | 2472 | 1915 | 2048 | 1324 | 1251 |
| 144 | 1261 | 6276 | 11100 | 8494 | 5681 | 4975 | 7514 | 10150 | 10630 |
| 145 | 11550 | 1271 | 1593 | 2528 | 2695 | 1857 | 4723 | 7071 | 10710 |
| 146 | 1324 | 6012 | 8206 | 9311 | 5253 | 4463 | 8417 | 10550 | 10450 |
| 147 | 1325 | 1449 | 1487 | 2707 | 2154 | 1653 | 2451 | 3631 | 3213 |
| 148 | 7622 | 1353 | 4351 | 3245 | 2895 | 3071 | 7312 | 7152 | 7799 |
| 149 | 43040 | 1422 | 1816 | 2535 | 3349 | 1846 | 4755 | 6889 | 6314 |
| 150 | 5528 | 2552 | 1556 | 5031 | 4866 | 1953 | 4731 | 5980 | 5160 |
| 151 | 30860 | 5410 | 1613 | 2689 | 4715 | 3473 | 3649 | 2700 | 4575 |
| 152 | 16860 | 5221 | 17800 | 6423 | 10060 | 1729 | 6202 | 9414 | 10990 |
| 153 | 1734 | 3364 | 4661 | 7284 | 4170 | 3507 | 8434 | 6440 | 8150 |
| 154 | 35690 | 3073 | 2372 | 4041 | 7122 | 1794 | 6788 | 8229 | 6912 |
| 155 | 22420 | 7306 | 4916 | 1856 | 3401 | 4419 | 3169 | 4863 | 4673 |
| 156 | 14670 | 2861 | 2099 | 2744 | 2679 | 1902 | 3572 | 4233 | 5546 |
| 157 | 6300 | 1949 | 9035 | 24250 | 10570 | 7016 | 17340 | 15500 | 19910 |
| 158 | 24760 | 3483 | 2209 | 5035 | 4720 | 2679 | 8254 | 10410 | 10410 |
| 159 | 13830 | 6748 | 7634 | 10010 | 8845 | 7575 | 7338 | 9818 | 2358 |
| 160 | 4445 | 2564 | 7653 | 9262 | 6739 | 4236 | 8741 | 10020 | 11020 |
| 161 | 7688 | 2744 | 14610 | 21680 | 14990 | 6788 | 27380 | 25160 | 21280 |
| 162 | 7513 | 8353 | 2788 | 5218 | 3429 | 3793 | 4081 | 3413 | 3984 |
| 163 | 7111 | 5166 | 3465 | | | | | | |
| 164 | 11240 | 6272 | 10890 | 7494 | 7320 | 3803 | 9409 | 14500 | 15480 |
| 165 | 14170 | 4344 | 7468 | 8672 | 8075 | 3870 | 5920 | 6712 | 6550 |
| 166 | 9853 | 7319 | 4652 | 5509 | 5134 | 4153 | 4815 | 4796 | 4581 |
| 167 | 25200 | 4211 | 5543 | 8097 | 7345 | 5409 | 5856 | 5195 | 7330 |
| 168 | 26360 | 7121 | 4948 | 11050 | 9628 | 5391 | 15050 | 21940 | 14620 |
| 169 | 8483 | 7172 | 5122 | | | | | | |
| 170 | 25030 | 5872 | 11870 | 27860 | 16450 | 15070 | 16990 | 16370 | 17040 |
| 171 | 16630 | 8802 | 8276 | | | | | | |
| 172 | 224 | 153 | 153 | | | | | | |
| 173 | 1155 | 535 | 307 | | | | | | |
| 174 | 287 | 38 | 24 | | | | | | |

TABLE 2-continued

Binding to KRas (IC$_{50}$ nM) by Exemplary Compounds of Formula (I)

| Ex. No. | G12D | G12V | G12R | G12A | G12S | G12C | WT | G13D | Q61H |
|---|---|---|---|---|---|---|---|---|---|
| 175 | ≤2 | ≤2 | ≤2 | | | | | | |
| 176 | 78 | 11 | ≤2 | | | | | | |
| 177 | 19 | 9 | 15 | | | | | | |
| 178 | ≤2 | ≤2 | ≤2 | | | | | | |
| 179 | 207 | 101 | 80 | | | | | | |
| 180 | 4 | 8 | 6 | | | | | | |
| 181 | ≤2 | ≤2 | ≤2 | | | | | | |
| 182 | 209 | 75 | 118 | | | | | | |
| 183 | 150 | 54 | 23 | | | | | | |
| 184 | 23 | 12 | 11 | | | | | | |
| 185 | 143 | 52 | 46 | | | | | | |
| 186 | ≤2 | ≤2 | ≤2 | | | | | | |
| 187 | 4 | ≤2 | ≤2 | | | | | | |
| 188 | ≤2 | ≤2 | ≤2 | | | | | | |
| 189 | ≤2 | 52 | ≤2 | | | | | | |
| 190 | ≤2 | ≤2 | ≤2 | | | | | | |
| 191 | ≤2 | 52 | ≤2 | | | | | | |
| 192 | ≤2 | ≤2 | 3 | | | | | | |
| 193 | ≤2 | ≤2 | ≤2 | | | | | | |
| 194 | ≤2 | ≤2 | ≤2 | | | | | | |
| 195 | 17 | 8 | 20 | | | | | | |
| 196 | ≤2 | ≤2 | ≤2 | | | | | | |
| 197 | ≤2 | ≤2 | ≤2 | | | | | | |
| 198 | ≤2 | ≤2 | 5 | | | | | | |
| 199 | ≤2 | ≤2 | ≤2 | | | | | | |
| 200 | ≤2 | ≤2 | ≤2 | | | | | | |
| 201 | ≤2 | ≤2 | 4 | | | | | | |
| 202 | ≤2 | ≤2 | 7 | | | | | | |
| 203 | ≤2 | 52 | 3 | | | | | | |
| 204 | 6 | 6 | 9 | | | | | | |
| 205 | 4688 | 4696 | 6430 | | | | | | |
| 206 | 932 | 833 | 1625 | | | | | | |
| 207 | 765 | 404 | 553 | | | | | | |
| 208 | 136 | 197 | 350 | | | | | | |
| 209 | 1123 | 1903 | 4139 | | | | | | |
| 210 | 579 | 497 | 699 | | | | | | |
| 211 | 101 | 38 | 34 | | | | | | |
| 212 | ≤2 | ≤2 | ≤2 | | | | | | |
| 213 | 11 | 3 | 3 | | | | | | |
| 214 | 558 | 118 | 54 | | | | | | |
| 215 | 10 | 3 | 3 | | | | | | |
| 216 | ≤2 | ≤2 | 3 | | | | | | |
| 217 | ≤2 | ≤2 | ≤2 | | | | | | |
| 218 | ≤2 | ≤2 | ≤2 | | | | | | |
| 219 | 3 | 3 | 4 | | | | | | |
| 220 | ≤2 | ≤2 | ≤2 | | | | | | |
| 221 | 4 | 3 | 5 | | | | | | |
| 222 | ≤2 | ≤2 | ≤2 | | | | | | |
| 223 | ≤2 | ≤2 | ≤2 | | | | | | |
| 224 | ≤2 | ≤2 | ≤2 | | | | | | |
| 225 | ≤2 | ≤2 | ≤2 | | | | | | |
| 226 | ≤2 | ≤2 | ≤2 | | | | | | |
| 227 | 20 | 4 | 6 | | | | | | |
| 228 | ≤2 | ≤2 | ≤2 | | | | | | |
| 229 | ≤2 | ≤2 | ≤2 | | | | | | |
| 230 | 5 | 3 | 5 | | | | | | |
| 231 | 12 | 15 | 26 | | | | | | |
| 232 | ≤2 | ≤2 | ≤2 | | | | | | |

Example B

Inhibition of KRas Phosphorylation of ERK by Exemplary Compounds of Formula (I)

This Example illustrates that exemplary compounds of the present invention inhibit the phosphorylation of ERK downstream of KRas WT, G12C, G12D, G12R, G12S, G12V, G13D, Q61H.

AsPC-1 (G12D, ATCC CRL-1682), A549 (G12S, ATCC CCL-185), HCT116 (G13D, ATCC CCL-247) cells were grown in DMEM medium supplemented with 10% fetal bovine serum and Penicillin/Streptomycin. NCI-H358 (G12C, ATCC CRL-5807), NCI-H460 (Q61H, ATCC HTB-117), NCI-H727 (G12V, ATCC CRL-5815), MKN1 (WT-dep, JCRB JCRB0252), PSN-1 (G12R, ATCC CRM-CRL-3211) cells were grown in RPMI medium supplemented with 10% fetal bovine serum, 10 mM HEPES, 10 mM Sodium Pyruvate, and Penicillin/Streptomycin. Cells were plated in black well clear bottom tissue culture treated 96 well plates (Corning, 3904) at a density of 20,000 cells/well and allowed to attach for 12-14 hours. Diluted compounds were then added in a final concentration of 0.5% DMSO. After 3 hours, 50 µL of 4.0% formaldehyde was added and the plates incubated at room temperature for 20 minutes. The plates were then dumped and permeabilized with 150 µL of ice cold 100% methanol for 10 minutes. Non-specific antibody binding to the plates was blocked using 100 µL Odyssey blocking buffer (LI-COR Biosciences, 927-60010) for 1 hour at room temperature.

The amount of phospho-ERK was determined using an antibody specific for the phosphorylated form of ERK and compared to the amount of GAPDH. Primary antibodies used for the detection were added as follows: Phospho-ERK (Cell Signaling CS-9101) diluted 1:500 and GAPDH (Millipore MAB374) diluted 1:5000 in Odyssey blocking buffer+0.05% Tween 20. The plates were incubated overnight at 4 C. The plates were washed 3× with 150 uL PBS+0.1% Tween 20.

Secondary antibodies used to visualize primary antibodies were added as follows: Goat Anti-Rabbit-800 (LI-COR, 926-32211) and Goat Anti-Mouse-680 (LI-COR, 926-68070) diluted 1:800 both in Odyssey blocking buffer+0.05% Tween 20 and were incubated for 1 hour at room temperature. The plates were washed 3× with 150 uL PBS+0.100 Tween 20. Plates were imaged dry on a Li—COR Odyssey CLX plate reader.

The phospho-ERK (Thr202/Tyr204) signal was normalized to the GAPDH signal for each well and percent of DMSO control values were calculated. IC50 values were generated using a 4-parameter fit of the dose response curve.

TABLE 3

Inhibition (IC$_{50}$ nM) of KRas-mediated Phosphorylation of ERK by Exemplary Compounds of Formula (I)

| Ex. No. | AsPC-1 | H727 | H358 | HCT116 | H460 | A549 | PSN1 |
|---|---|---|---|---|---|---|---|
| 1 | 398 | 1262 | 236 | 601 | 357 | 1020 | 1396 |
| 2 | 280 | 798 | 252 | 863 | 184 | 241 | 3529 |
| 17 | | 1127 | 232 | 10000 | | 189 | >10000 |
| 18 | 182 | 503 | | | 317 | | |
| 19 | 2685 | 2929 | | | 1290 | | |
| 20 | | 747 | 314 | 860 | | 446 | >10000 |
| 21 | 204 | 466 | | | 202 | | |
| 23 | 3851 | 2418 | | | 1769 | | |
| 24 | 25 | 134 | | | 65 | | |
| 25 | 448 | 540 | | | 171 | | |
| 26 | 10000 | 3125 | | | 3263 | | |
| 27 | 808 | 549 | | | 282 | | |
| 28 | 1007 | 987 | | | 494 | | |
| 29 | 509 | 542 | | | 285 | | |
| 30 | 447 | 399 | | | 309 | | |
| 31 | 3544 | 3320 | | | >10000 | | |
| 32 | 624 | 1094 | | | 381 | | |
| 33 | 1360 | 1862 | | | 398 | | |
| 34 | 258 | 1041 | | | 774 | | |
| 35 | 2361 | 1616 | | | 1428 | | |
| 36 | 1764 | 1734 | | | 731 | | |
| 59 | 44 | 181 | | | 17 | | |
| 67 | 1568 | 876 | | | 225 | | |

Example C

Inhibition of KRas Phosphorylation of ERK (HTRF) by Exemplary Compounds of Formula (I)

Cisbio HTRF Advanced pERK Assay Catalog #64AER-PEH

Cells: MKN1, PSN1

Procedure:
- Day 1: Seed 6,000 cells/well ~25 µl/well in 384-well white solid bottom plate; RPM1_10% FBS. Incubate overnight at 37° C./5% CO2.
- Day 2: Echo transfer 25 nl of 10 mM compound 10 point dilution at 1:3 (Cf=10 uM) and incubate for 3 hour at 37° C./5% CO2.
- Add 8.5 µl/well of 4× Lysis Buffer/25× Blocking reagent (do not dump media) and incubate for 30 min at room temperature on shaker.
- Add conjugate mixture of 4.25 ul/well 1X-pERK-D2 and 1X-pERK-K diluted in Detection Buffer for a total of 8.5 µl/well.
- Incubate for 4 hours at room temperature covered.
- Read HTRF using ClarioStar Cells: ASPC1, H727, A549, H460, HCT116, H358
Culture/Assay Media: RPMI-1640+10% FBS Procedure:

Cell Seeding
1. To harvest cells from flask using 0.05% Trypsin/EDTA solution. Add 10 mL of media to stop trypsinizing. Pipette the cells into a conical bottom 50 mL centrifuge tube and centrifuge 5 min×1000 rpm.
2. Re-suspend the cell pellet in media, take a cell count, and then adjust the cell density using fresh media.
3. Seed 6,000 cells into cell culture plate with 50 µL media.
4. Incubate cell plate overnight in a 37° C., 5% CO2 incubator.

Compound Titrations
1. Use Tecan to complete the compound addition. Compounds start from 10 uM top, 3-fold dilution, and 10 doses. The final DMSO concentration is 0.8%. Dispensed 0.2 uM Trametinib as Min control.
2. Incubate cell plate for 3 hrs in the incubator.

Detection with Cisbio pERK HTRF Kit
1. Dilute 1 volume of 4× lysis buffer with 3 volumes of deionized water. Then, add 100× the blocking reagent. Keep lysis buffer on the ice.
2. At the end of the compound treatment, flick-off the media.
3. Add 35 µL of lysis buffer per well using a Multidrop Combi. Then place on a plate agitator shaking at 300 rpm at 4° C. for 40 mins.
4. Make up the HTRF antibody buffer. For each assay plate, mix 50 µL of d2-conjugate antibody with 950 µL of detection buffer. Similarly, mix 50 µL of Cryptate antibody with 950 µL of detection buffer. Then mix the two diluted antibodies together.
5. Dispense 3.4 µL the antibody buffer to wells of an empty assay plate. Seal the plate and centrifuge plate 30 sec×1000 rpm.
6. At the end of the 4° C. lysis, centrifuge the lysate plates 3 mins×1500 rpm.
7. Use the Bravo to transfer 13.6 µL of lysate from cell culture plate to assay plate. Then incubate assay plate for 2 hrs at room temperature.
8. At the end of incubation, read plate on the Envision after centrifuging plate 30 sec×1000 rpm.

TABLE 4

Inhibition (HTRF $IC_{50}$ nM) of KRas -mediated Phosphorylation of ERK by ExemplaryCompounds of Formula (I)

| Ex. No. | AsPC-1 | H727 | MKN1 | PSN1 | A549 | H460 | HCT116 | H358 |
|---|---|---|---|---|---|---|---|---|
| 2 | 29 | 315 | | | 144 | 146 | 426 | |
| 15 | 1114 | 3186 | | | | | | |
| 18 | | | 22 | ≥10000 | | | | |
| 19 | | | 389 | ≥10000 | | | | |
| 21 | | | 9 | 645.5 | | | | |
| 23 | | | 53 | ≥10000 | | | | |
| 24 | 10 | 35 | 6 | 2952 | 17 | 59 | 148 | |
| 25 | 180 | 767 | 51 | 8319 | | | 521 | |
| 27 | | | 9 | 2718 | | | | |
| 28 | | | 36 | ≥10000 | | | | |
| 29 | 318 | 906 | 20 | 5809 | | | 1313 | |
| 30 | 86 | 227 | 16 | 3511 | | 203 | 480 | 83 |
| 31 | | | 637 | ≥10000 | | | | |
| 32 | | | 31 | 1545 | | | | |
| 33 | | | 11 | ≥10000 | | | | |
| 34 | 31 | 217 | 134 | ≥10000 | 351 | 784 | 1270 | 38 |
| 35 | | | 159 | 5722 | | | | |
| 36 | | | 37 | ≥10000 | | | | |
| 59 | 8 | 40 | 5 | 25.32 | 3 | 9 | 16 | 4 |
| 60 | 556 | 258 | 29 | 6607 | | | 1116 | |
| 61 | 211 | 1200 | 51 | 3651 | | | 2377 | |
| 62 | 15 | 81 | 4 | 324.8 | 25 | 69 | 125 | 11 |
| 63 | 457 | 608 | 33 | 6956 | | | 1174 | |
| 64 | 595 | 778 | 83 | 2629 | | | 891 | |
| 65 | 1293 | 739 | 26 | 4423 | | | 1214 | |
| 66 | 1 | 5 | 1 | | 5 | 36 | 62 | 2 |
| 67 | | | 112 | ≥10000 | | | | |
| 68 | 112 | 423 | 71 | 2259 | | 421 | 1167 | |
| 69 | 122 | 194 | 41 | 578.3 | 59 | 68 | 164 | |
| 70 | 705 | 471 | 40 | 749.8 | | | 1490 | |
| 71 | 1169 | 848 | 211 | 6042 | | | | |
| 72 | 10 | 59 | 7 | 148.4 | 32 | 59 | 126 | 8 |
| 73 | 661 | 871 | 85 | 6383 | | | | |
| 74 | 253 | 790 | 78 | 4054 | | | 1449 | |
| 75 | 128 | 242 | 128 | ≥10000 | | | 2162 | |
| 76 | 2074 | 1782 | 468 | 5629 | | | | |
| 77 | 9106 | 8303 | 2665 | ≥10000 | | | | |
| 175 | 53 | 85 | 58 | 7861 | 326 | 750 | 1115 | 50 |
| 176 | 5940 | 984 | | | | | | |
| 177 | 1307 | 1385 | 479 | ≥10000 | | | | |
| 178 | 17 | 68 | 20 | 7625 | | | | |
| 179 | 5171 | 4794 | 1206 | ≥10000 | | | | |
| 180 | 383 | 600 | 462 | ≥10000 | | 1563 | | |
| 181 | 228 | 191 | 90 | ≥10000 | | | | |
| 182 | 3921 | 4664 | 1298 | ≥10000 | | | | |
| 183 | 1545 | 2924 | 498 | ≥10000 | | | | |
| 184 | 770 | 796 | 652 | ≥10000 | | | | |
| 185 | 5120 | 3722 | 1545 | ≥10000 | | | | |
| 186 | 4361 | 2667 | | | | | | |
| 187 | 5327 | 1319 | | | | | | |
| 188 | 2 | 4 | 7 | 2876 | | 49 | | 3 |
| 189 | 2 | 3 | 4 | 2676 | | 39 | | 1 |
| 190 | 2 | 6 | 6 | 5450 | | 49 | | 3 |
| 191 | 3 | 3 | 10 | 2965 | | 33 | | 3 |
| 192 | 24 | 29 | 11 | ≥10000 | | | | |
| 193 | 3 | 5 | 4 | 2101 | | 38 | 74 | 2 |
| 194 | 71 | 115 | 100 | ≥10000 | | 426 | | 63 |
| 195 | 1110 | 373 | 1515 | ≥10000 | | | | |
| 196 | 6 | 11 | 5 | 18 | 2 | 2 | 5 | 1 |
| 197 | 136 | 313 | 12 | 1690 | | 285 | 499 | |
| 198 | 185 | 344 | 185 | ≥10000 | 671 | 1242 | 1953 | |
| 199 | 43 | 262 | 31 | 2503 | 201 | 242 | 441 | 65 |
| 200 | 62 | 264 | 27 | 9113 | 142 | 578 | 832 | 77 |
| 201 | 49 | 176 | 49 | 80.45 | 14 | 26 | 49 | 12 |
| 202 | 543 | 1346 | 101 | 3905 | | | | |
| 203 | 132 | 283 | 181 | ≥10000 | 524 | 1102 | 1699 | |
| 204 | 1528 | 1667 | | | | | | |
| 205 | ≥10000 | ≥10000 | | | | | | |
| 206 | ≥10000 | ≥10000 | | | | | | |
| 207 | ≥10000 | ≥10000 | | | | | | |
| 208 | 4053 | 6941 | | | | | | |
| 209 | 7196 | 8520 | | | | | | |
| 210 | ≥10000 | ≥10000 | | | | | | |
| 211 | 4891 | 2877 | | | | | | |

TABLE 4-continued

Inhibition (HTRF IC$_{50}$ nM) of KRas-mediated Phosphorylation of ERK by ExemplaryCompounds of Formula (I)

| Ex. No. | AsPC-1 | H727 | MKN1 | PSN1 | A549 | H460 | HCT116 | H358 |
|---|---|---|---|---|---|---|---|---|
| 212 | 111 | 268 | 61 | ≥10000 | | 545 | 1108 | |
| 213 | 1743 | 1171 | 148 | 6504 | | | | |
| 214 | ≥10000 | 7428 | 1705 | ≥10000 | | | | |
| 215 | 1295 | 957 | 203 | 7584 | | | | |
| 216 | 92 | 300 | 19 | 1264 | 206 | 293 | 531 | 27 |
| 217 | 234 | 390 | 21 | 269 | 160 | 132 | 227 | |
| 218 | 46 | 86 | 85 | 6067 | 294 | 845 | 1338 | 61 |
| 219 | 448 | 1581 | 97 | 6116 | | 1022 | | |
| 220 | 668 | 616 | 29 | 4102 | | | | |
| 221 | 1363 | 1465 | 145 | ≥10000 | | | | |
| 222 | 179 | 530 | 37 | 2823 | | 352 | 672 | |
| 223 | 320 | 234 | 19 | 606.6 | | 325 | | |
| 224 | 976 | 651 | 62 | ≥10000 | | | | |
| 225 | 23 | 82 | 3 | 327.9 | | 56 | 158 | 9 |
| 226 | 45 | 43 | 7 | 2788 | | 169 | | 22 |
| 227 | 4047 | 1301 | 524 | 7048 | | | | |
| 228 | 108 | 197 | 24 | 696.4 | 146 | 253 | 405 | |
| 229 | 220 | 260 | 317 | 2141 | 705 | 1402 | 1981 | |
| 230 | 1092 | 1751 | 112 | ≥10000 | | | | |
| 231 | 2364 | 4376 | 929 | ≥10000 | | | | |
| 232 | 125 | 114 | 34 | 2772 | 98 | 331 | 709 | |

Example D: Anti-Proliferative Activity of Pan-KRas Inhibitors Against Mutations That Confer Resistance to Adagrasib To test the anti-proliferative activity of a prototype pan KRas inhibitor against mutations that confer resistance to adagrasib, mouse 3T3 fibroblasts were transduced with retroviruses that expressed various engineered human KRas mutant constructs. Cells were selected with puromycin to select for cells that were successfully transduced by the retrovirus and plated in ultra-low attachment plates where cells grew as 3 dimensional cultures. Cells were treated with a serial dilution of MRTX849 or Example 5 of co-pending patent application 63/125,776 and 50% inhibitory concentration (IC50) values were calculated (Table 5). Example 5 of 63/125,776 demonstrated activity against numerous codon 12 mutations including the G12W mutation predicted to result from a single nucleotide substitution from the cysteine 12 codon.

TABLE 5

IC50 Values of the KRas G12C Inhibitor MRTX849 and the Pan KRas Inhibitor Example 5 of 63/125,776 in a 5-day Viability Assay in 3T3 Cells Engineered to Express MRTX849 Resistance Mutations

| | MRTX849 (nM) | Example 5 (of 63/125,776) (nM) |
|---|---|---|
| G12A | >3000 | 32 |
| G12C | 16.62 | 28.1 |
| G12D | >3000 | 20.25 |
| G12R | >3000 | 1742 |
| G12V | >3000 | 94 |
| G12W | >3000 | 50 |
| G13D | >3000 | 610 |
| Q61H | >3000 | 58 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The invention claimed is:

1. A method for inhibiting wild type KRas or KRas G12A, KRas G12C, KRas G12D, KRas G12R, KRas G12S, KRas G12V, KRas G13D or KRas Q61H activity in a cell, comprising contacting the cell in which inhibition of KRas activity is desired with an effective amount of a compound selected from:

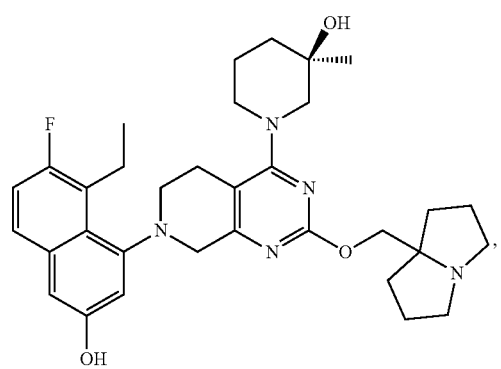

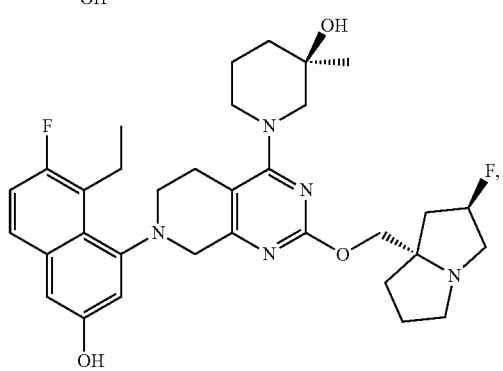

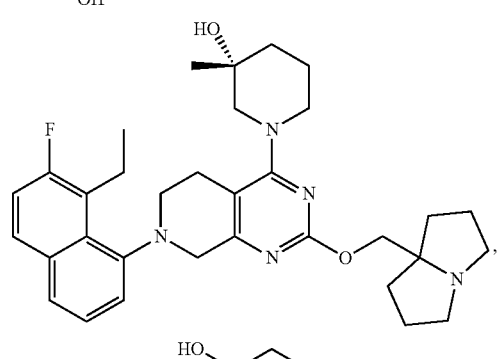

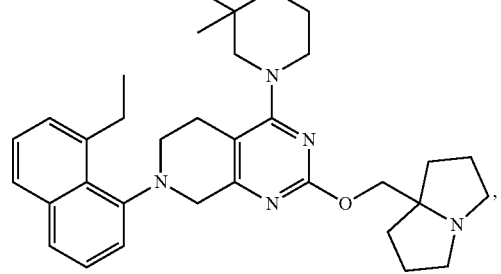

299
-continued
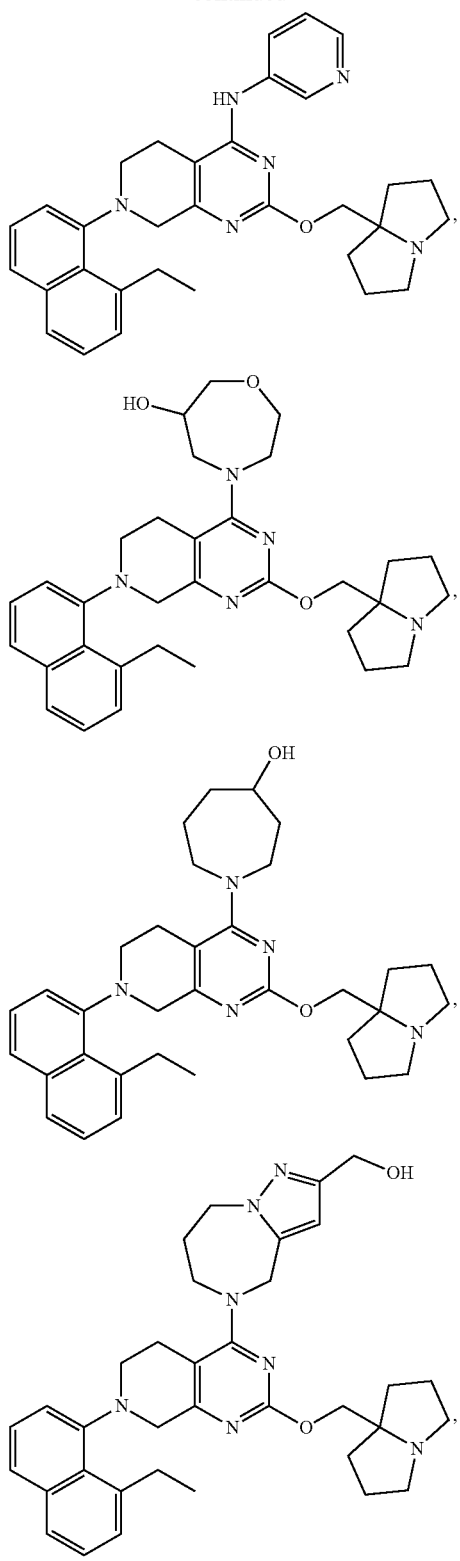
300
-continued
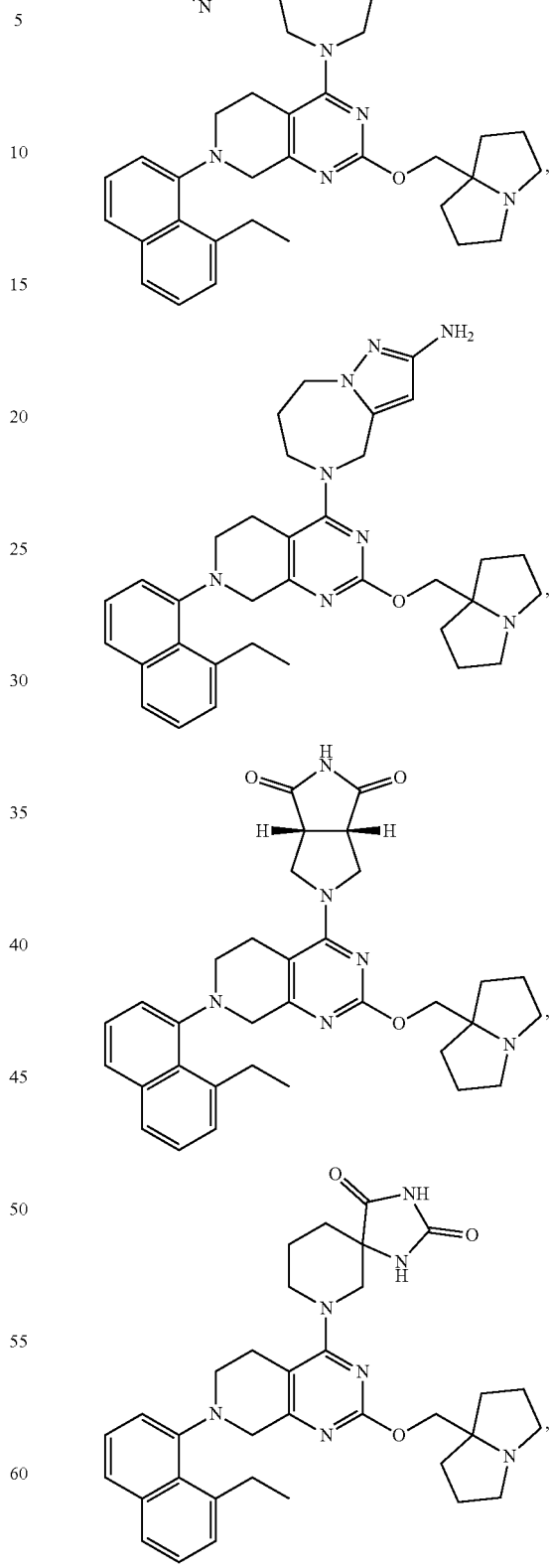

301
-continued
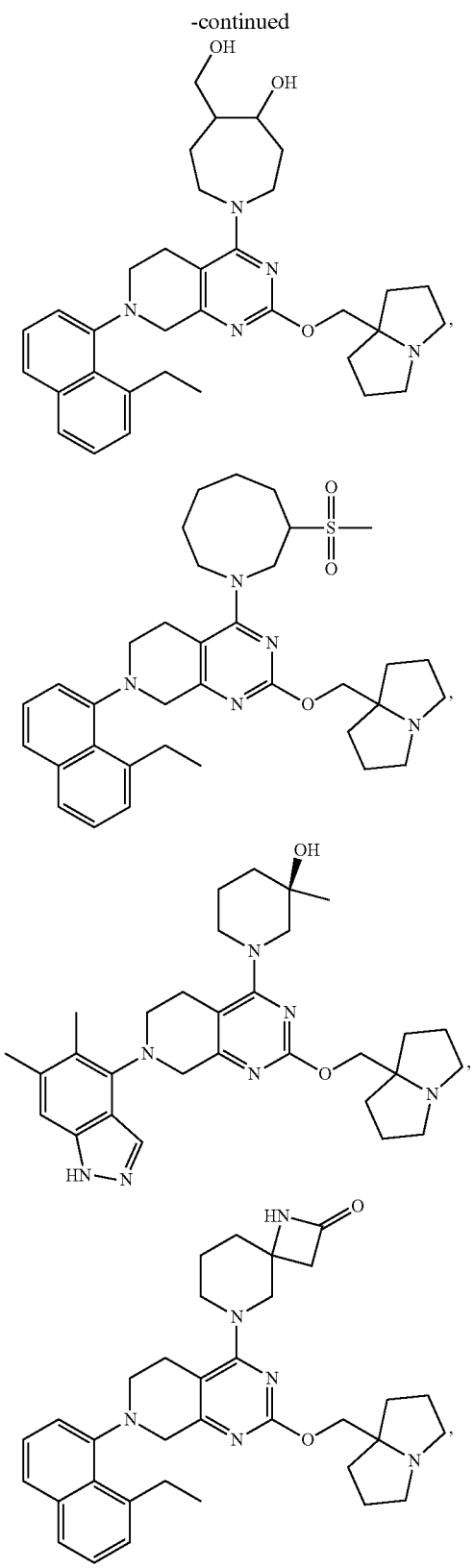
302
-continued
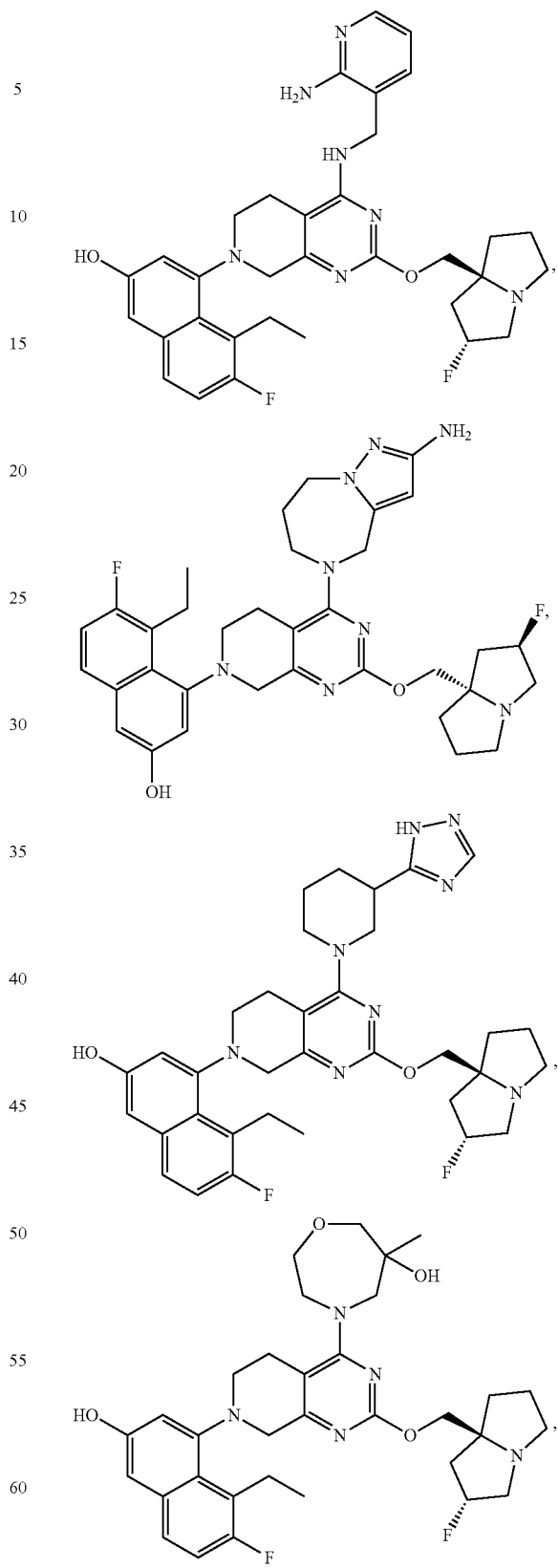

303
-continued
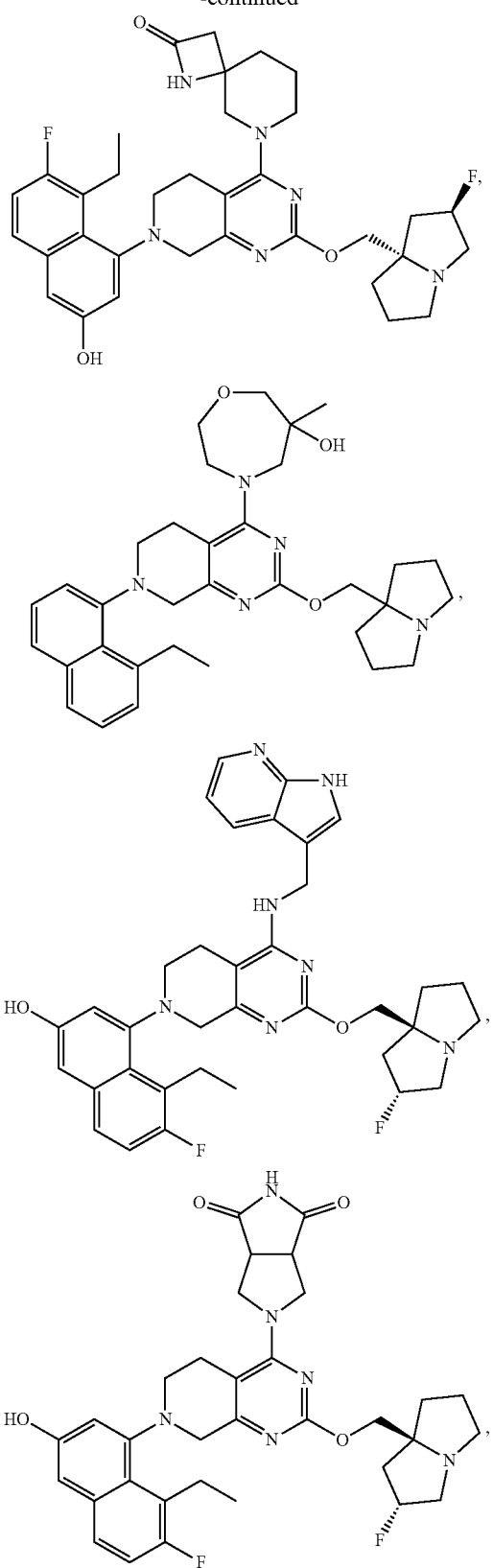
304
-continued
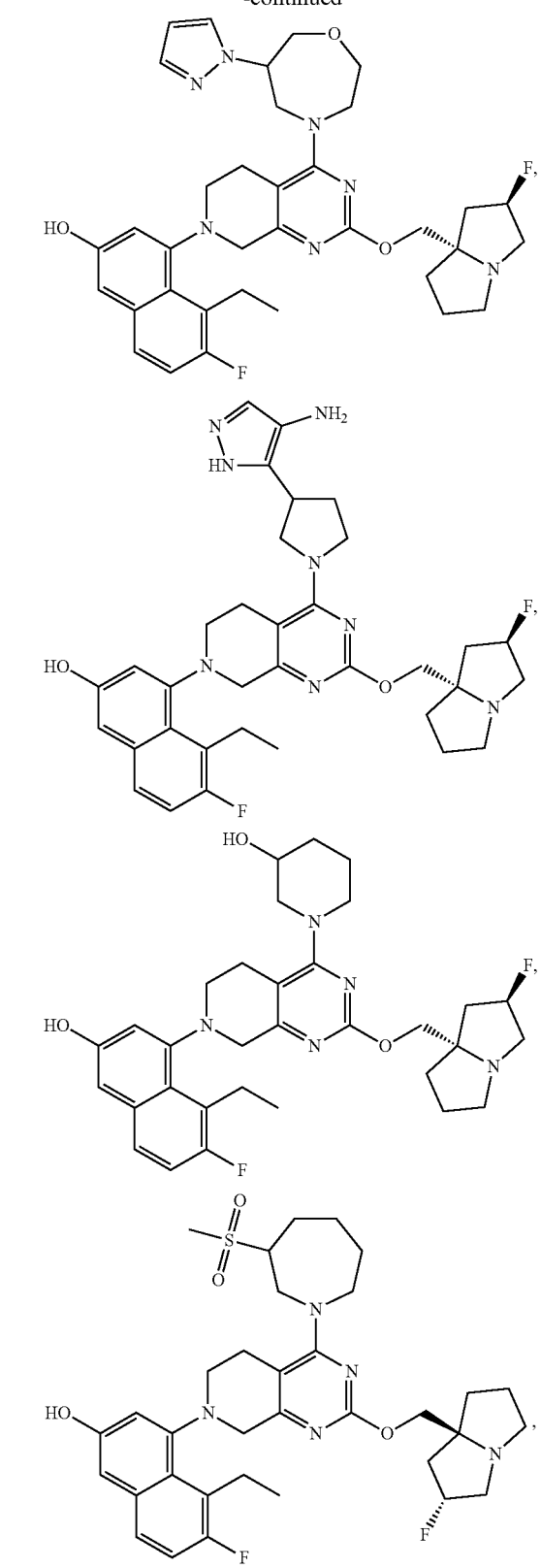

305
-continued
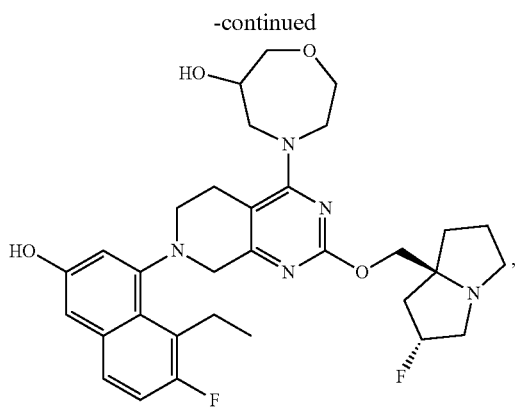
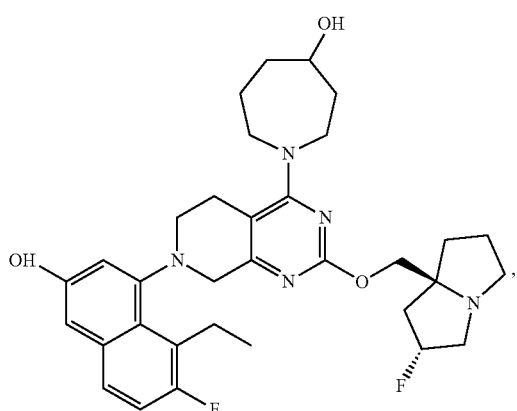
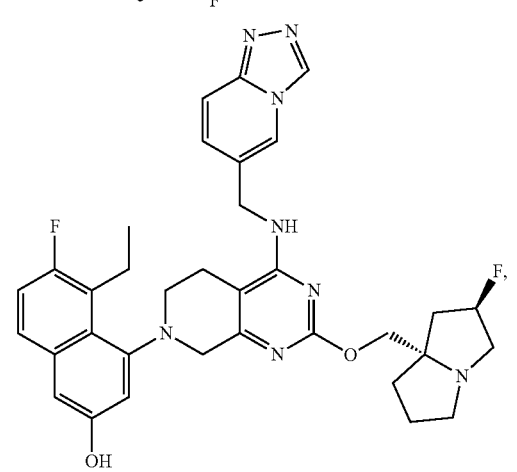
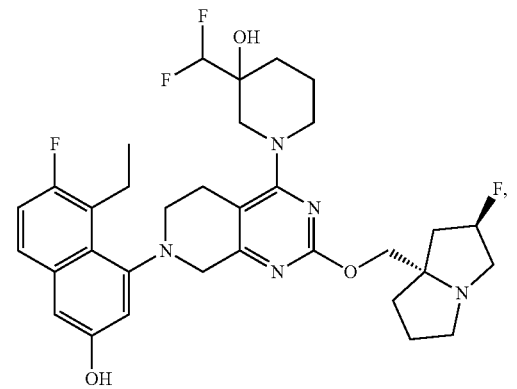
306
-continued
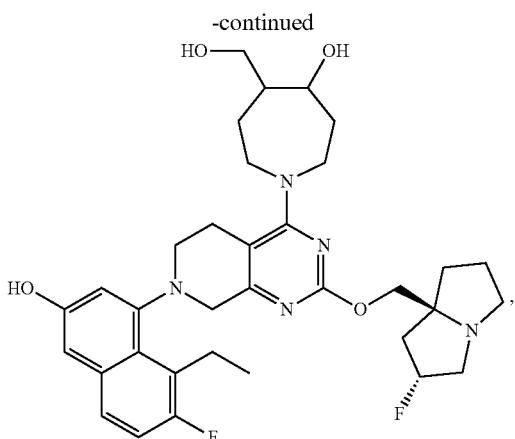
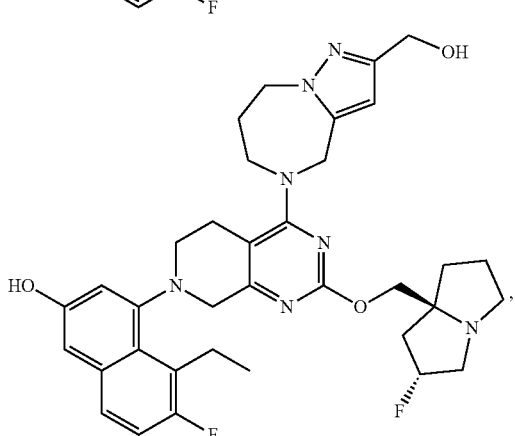
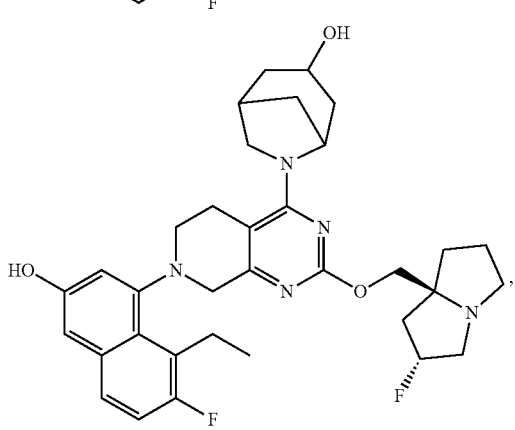
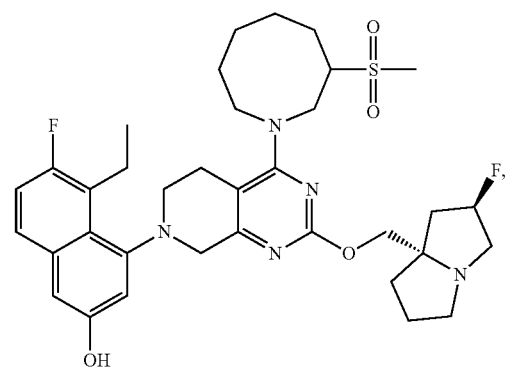

307
-continued
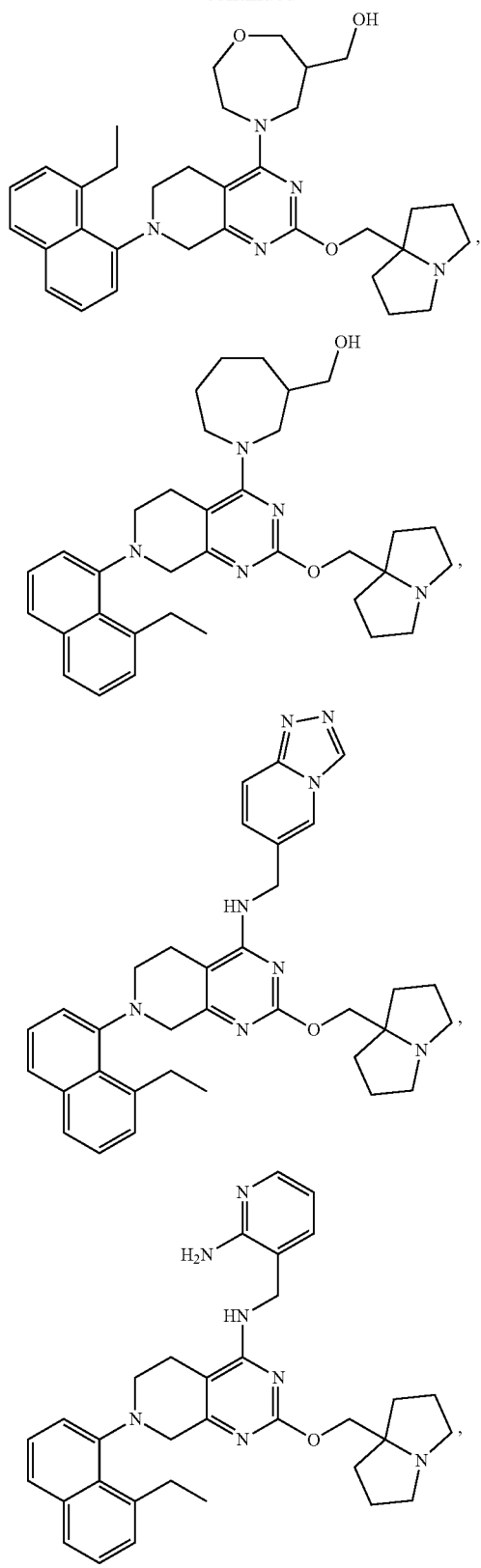
308
-continued
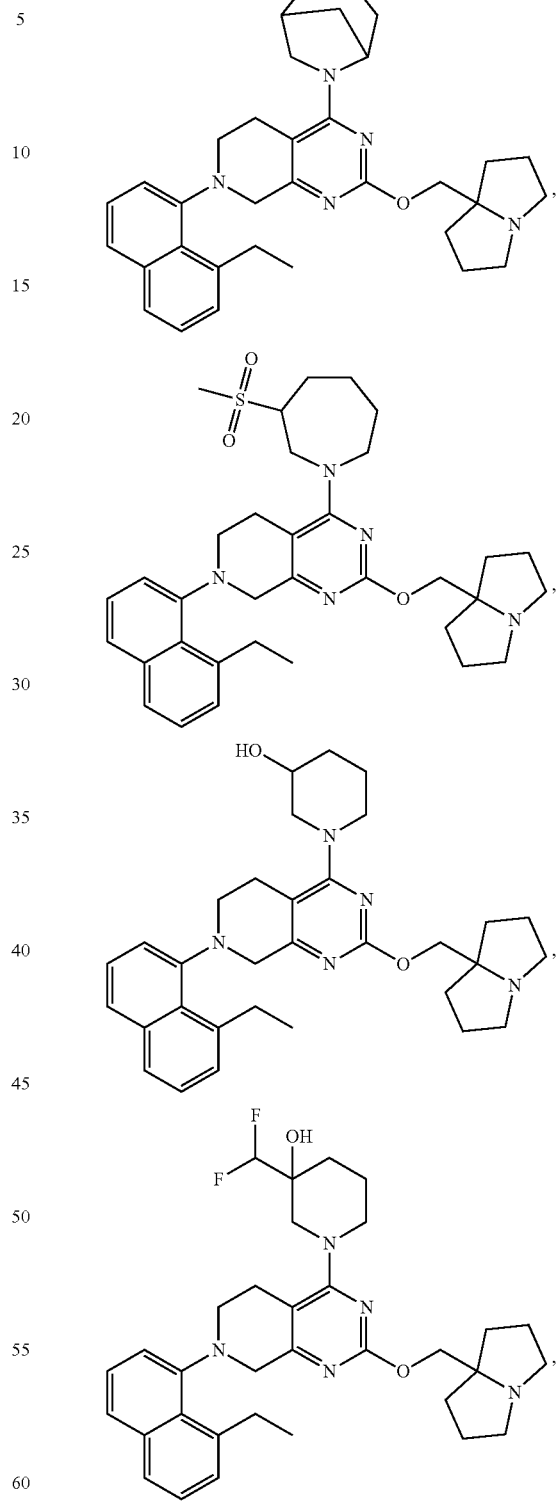

309
-continued
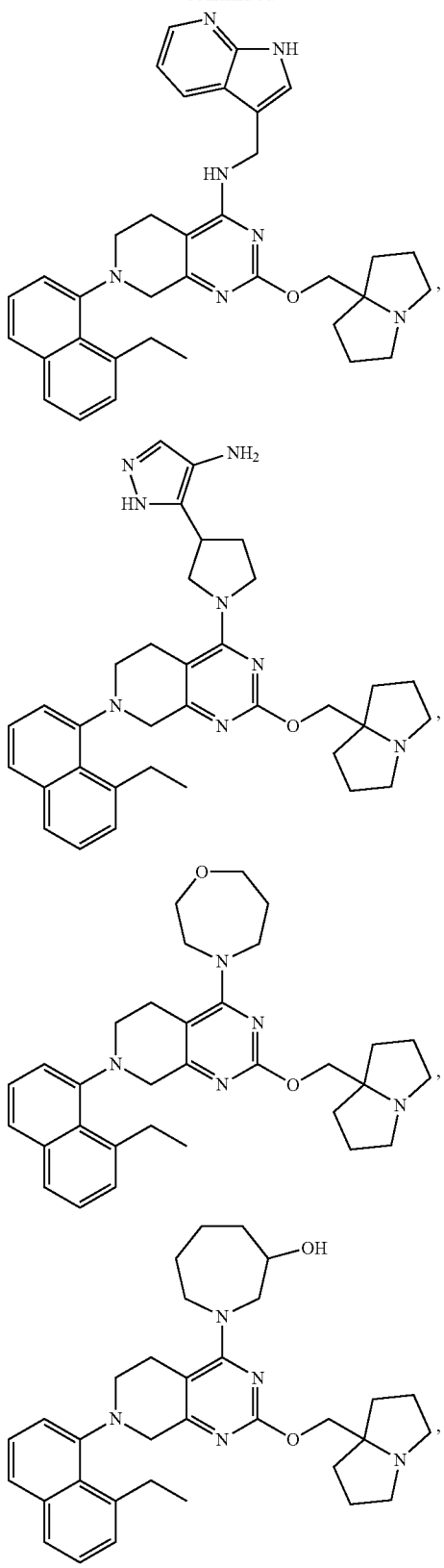
310
-continued
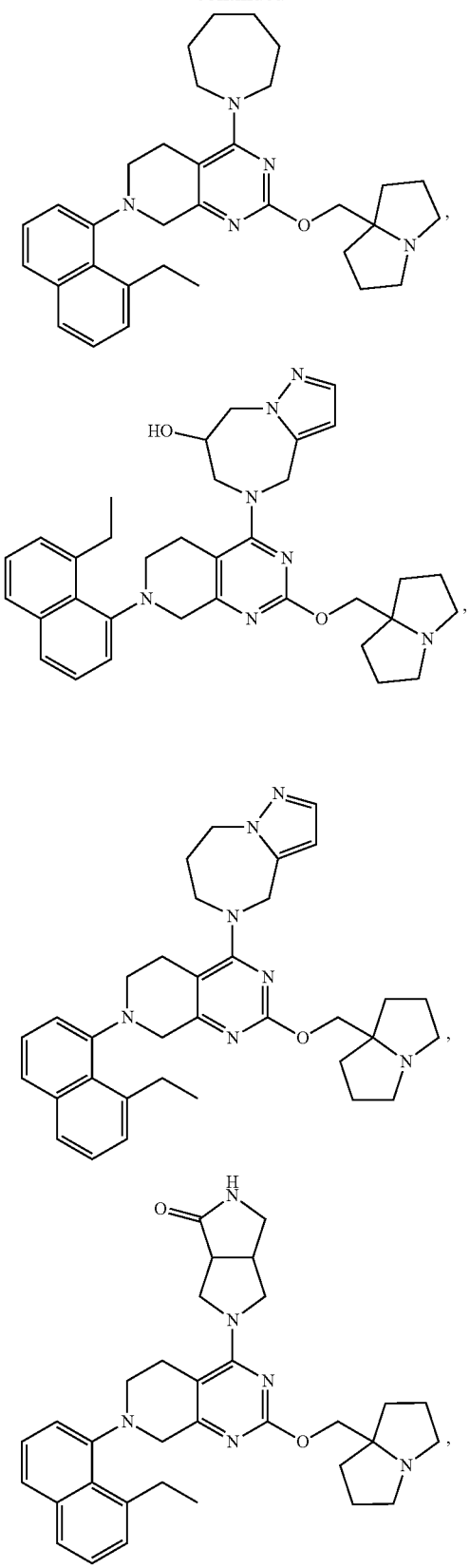

311
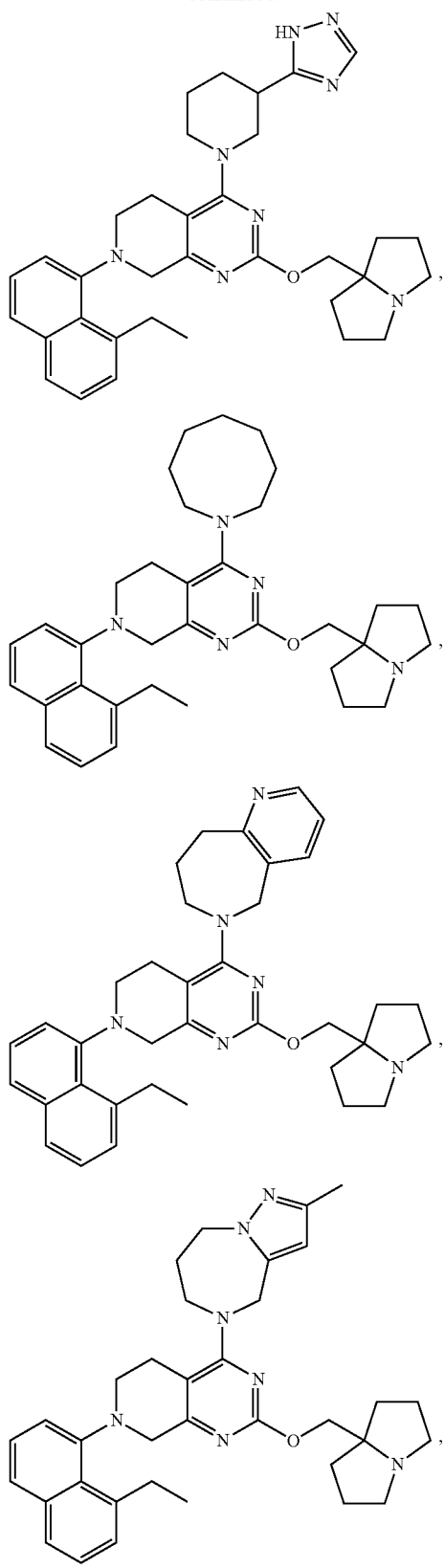
312
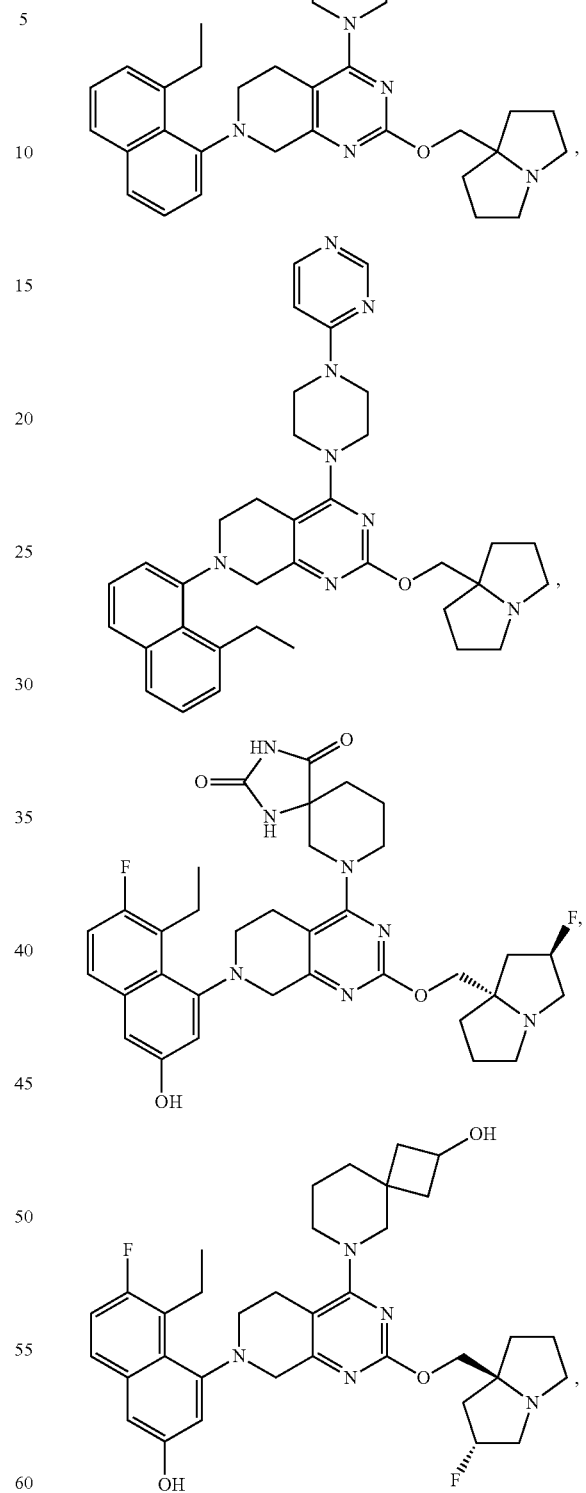

313
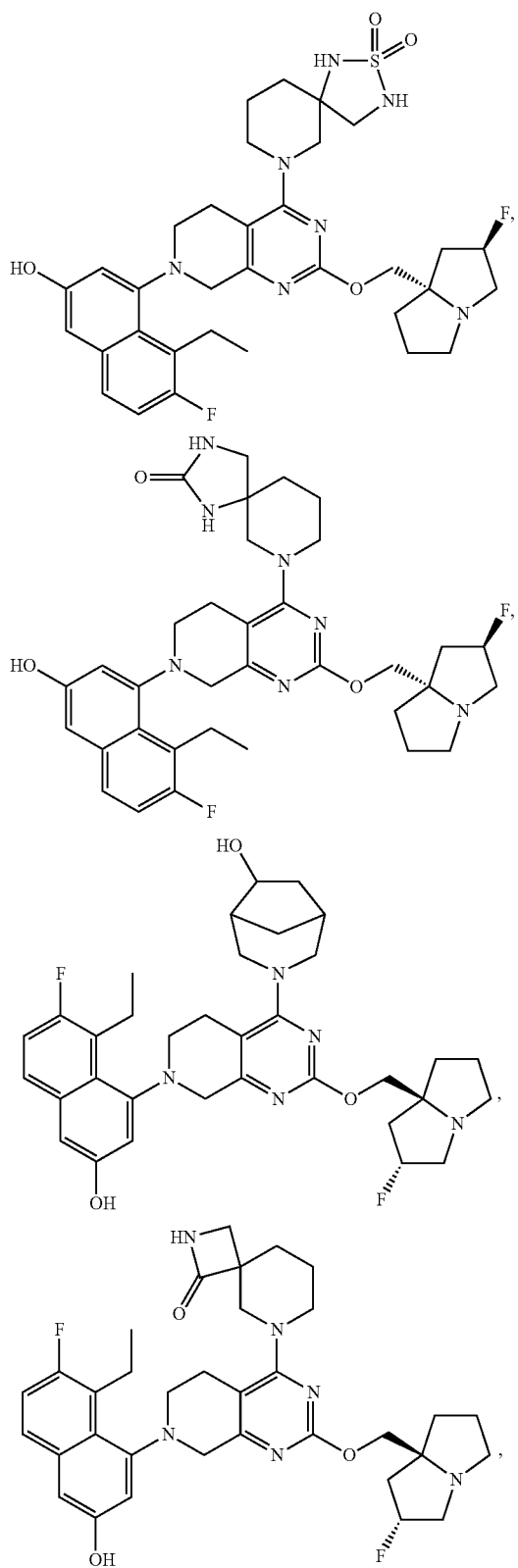
314
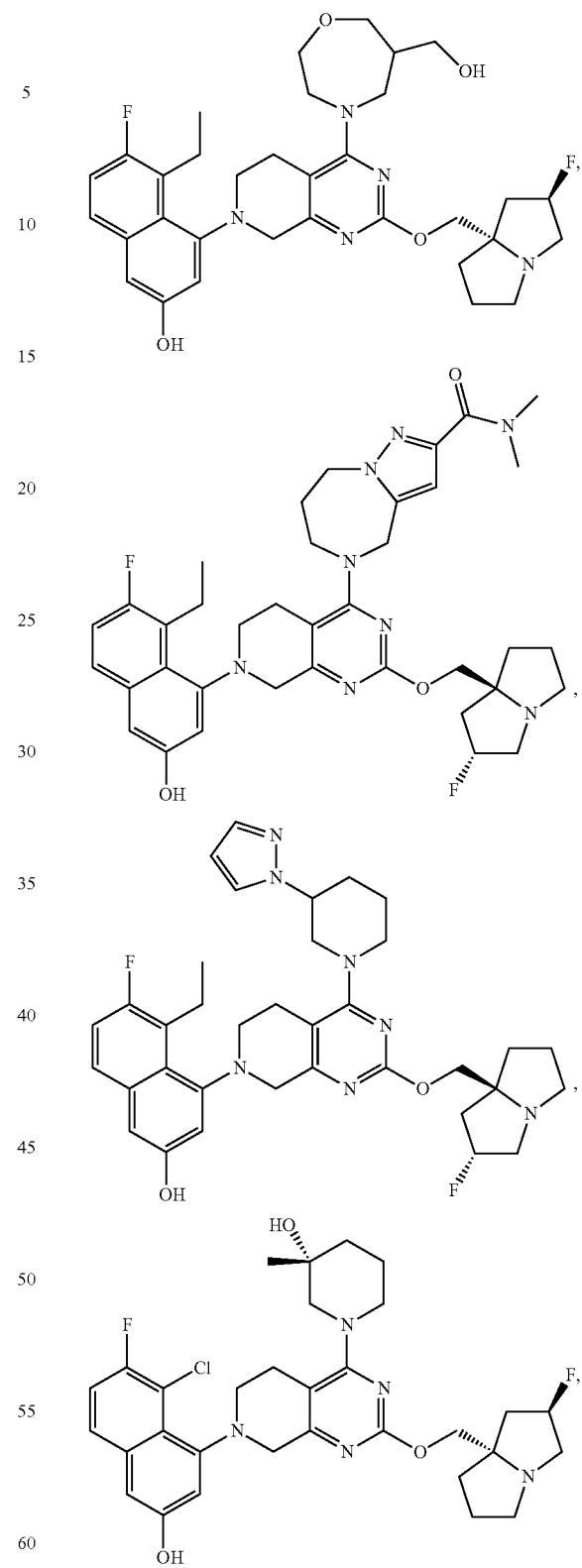

315
-continued
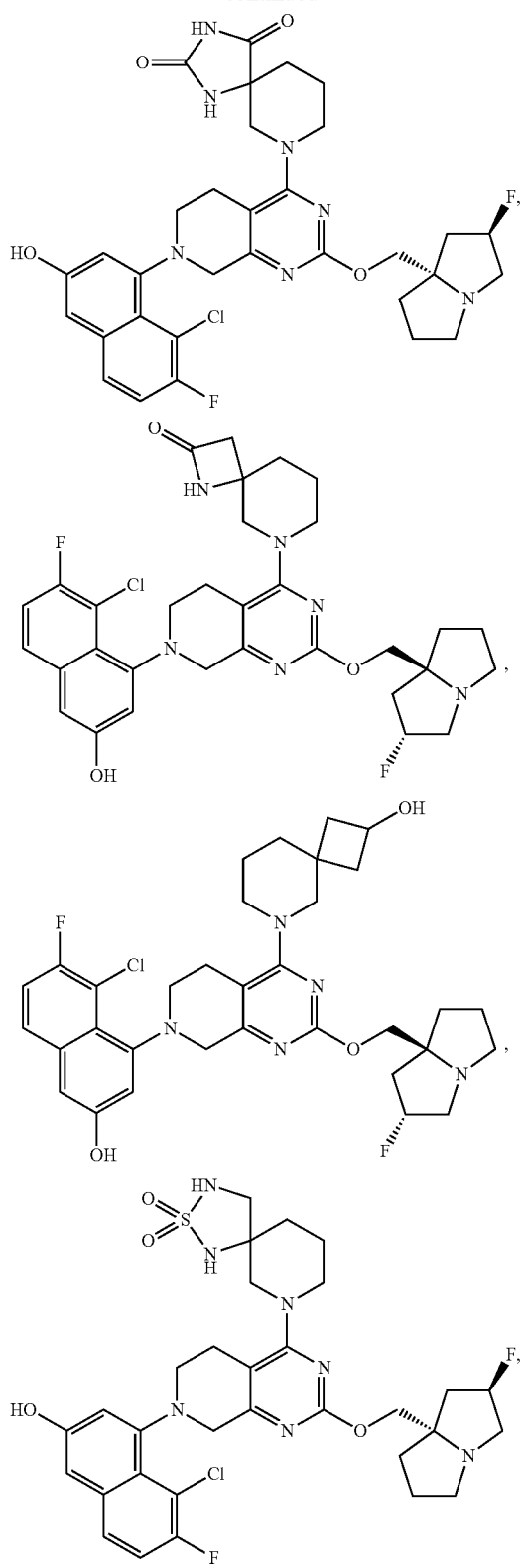
316
-continued
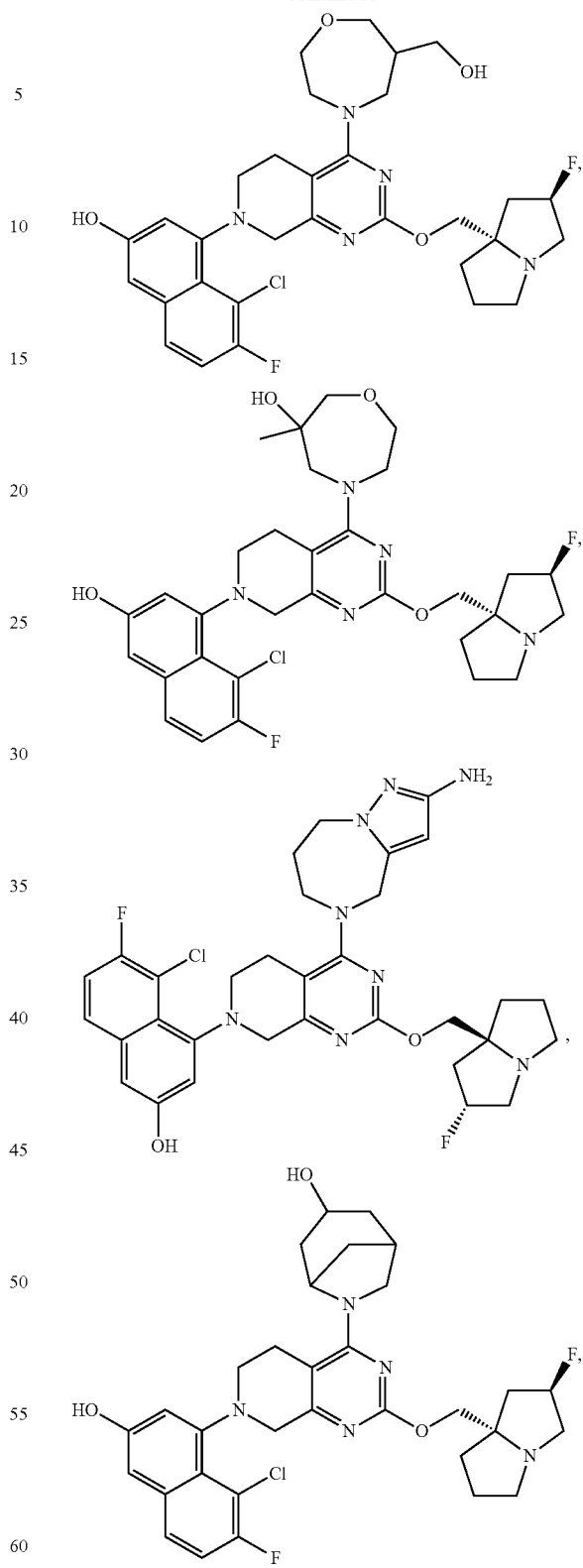

317
-continued
318
-continued
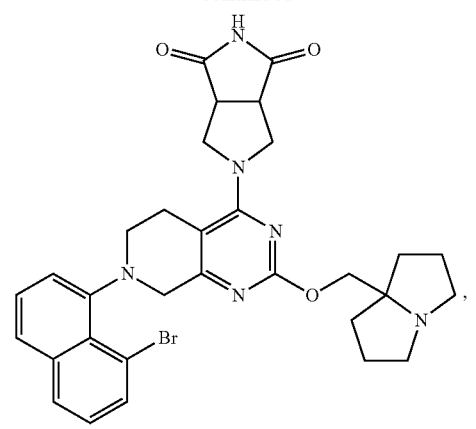
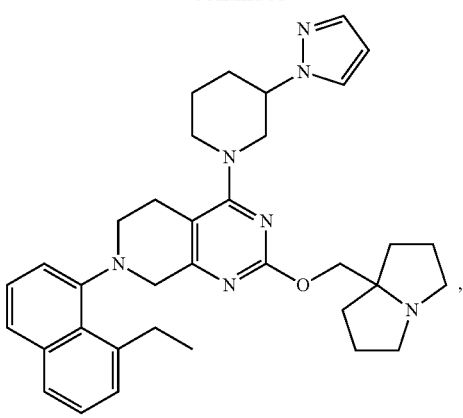
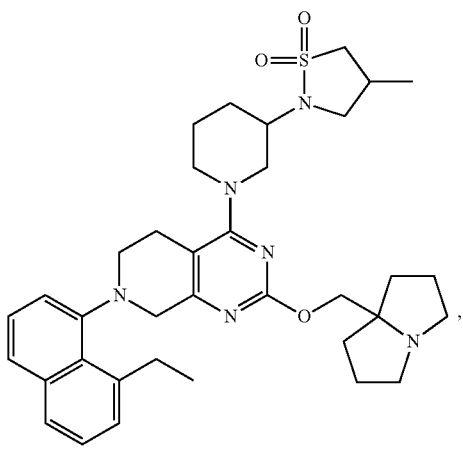
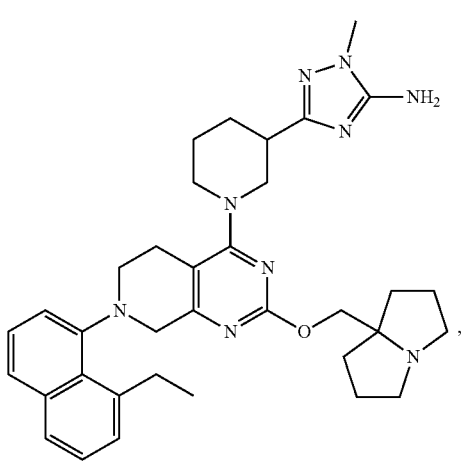

319
-continued
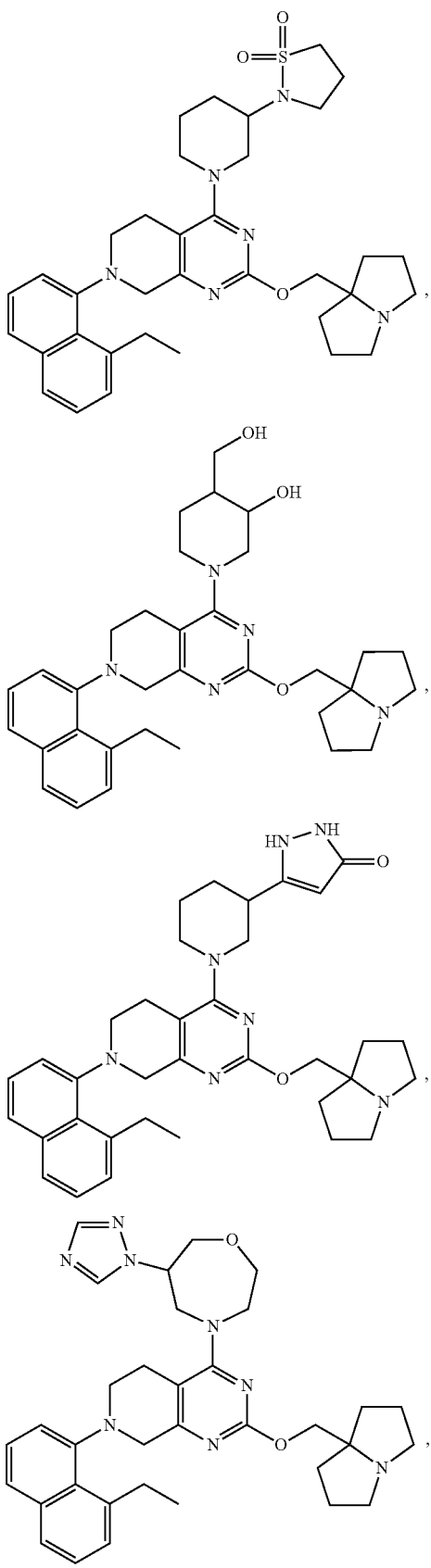
320
-continued
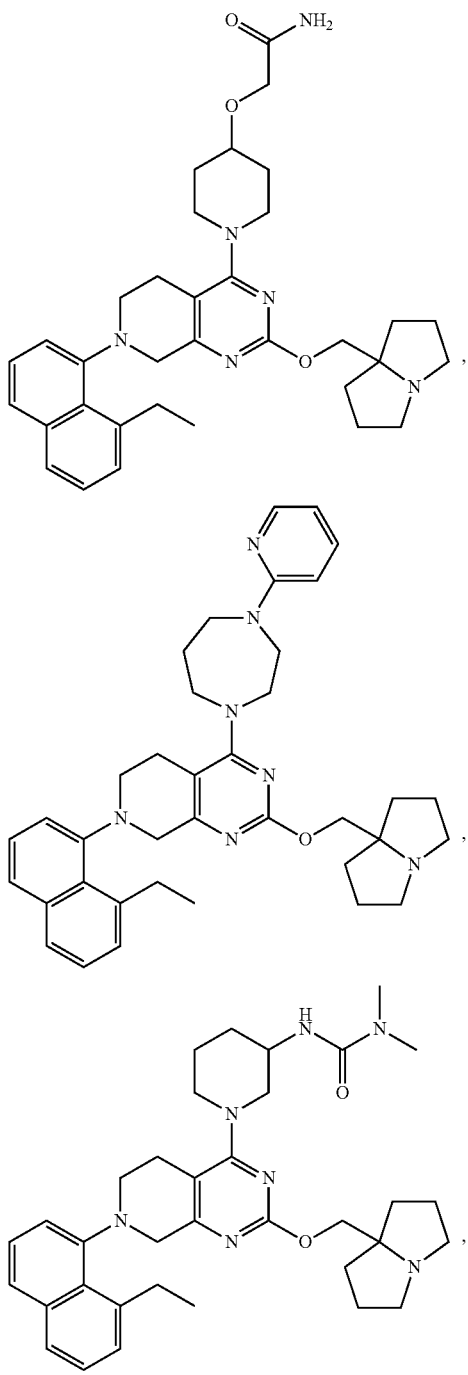

321
-continued
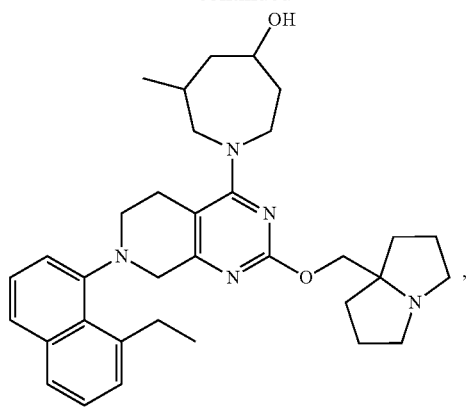
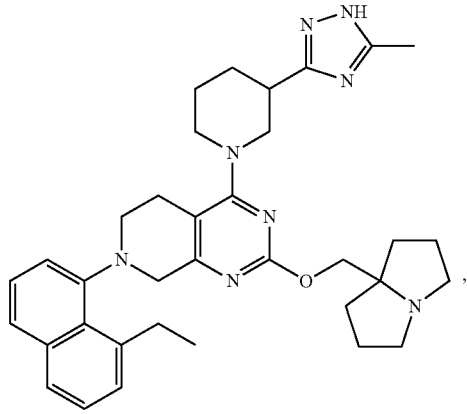
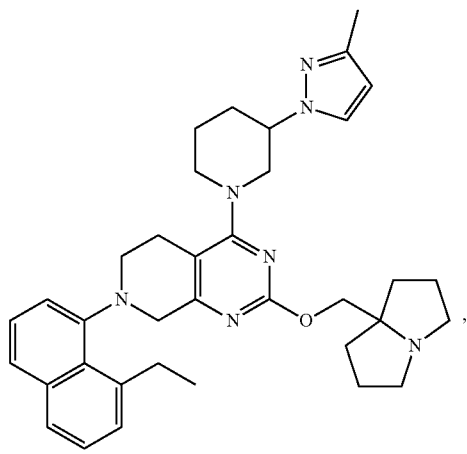
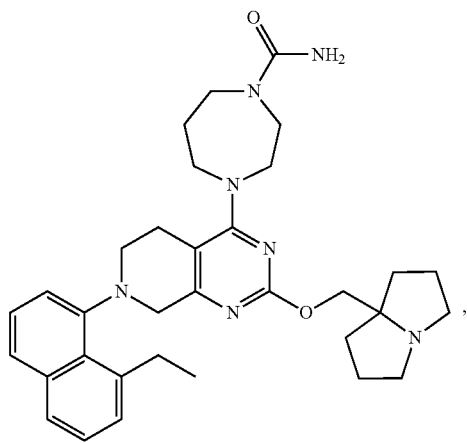
322
-continued
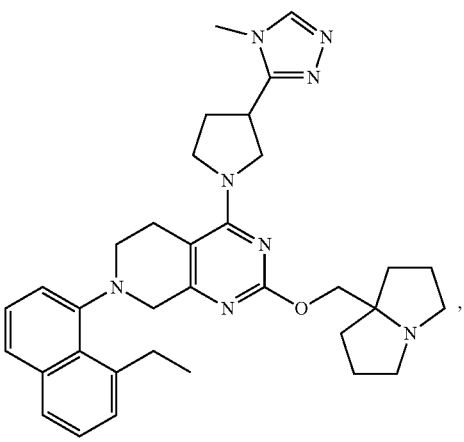
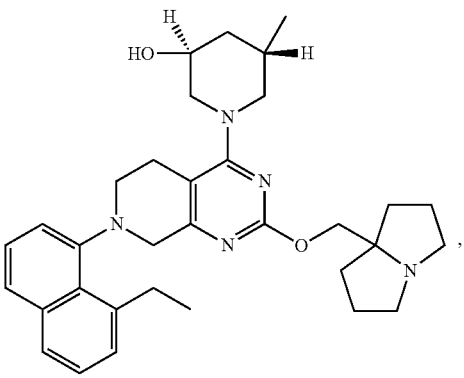
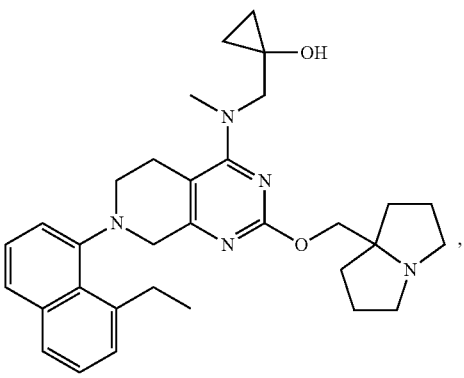
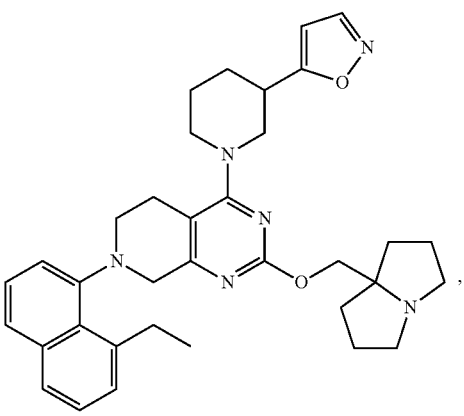

323
-continued
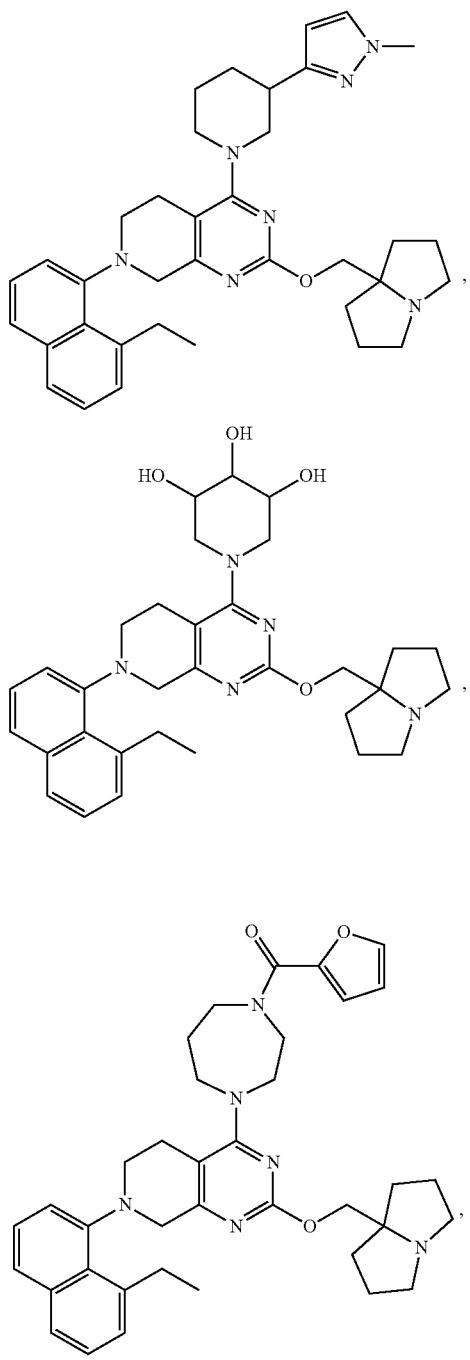
324
-continued
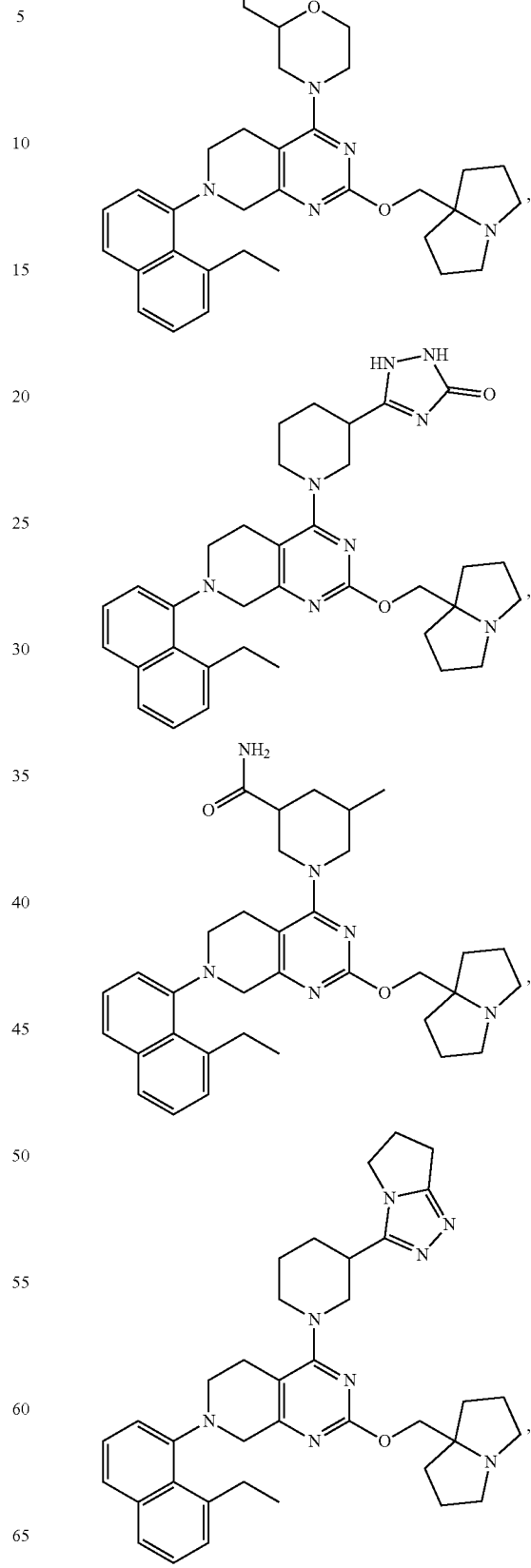

325
-continued
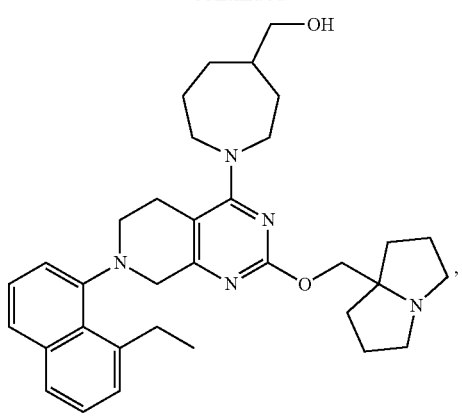
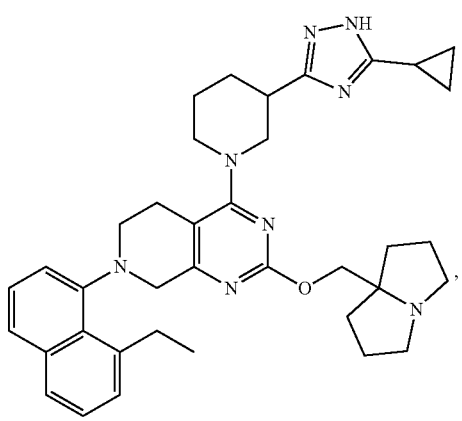
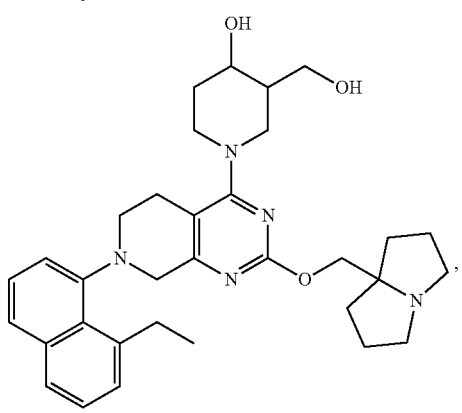
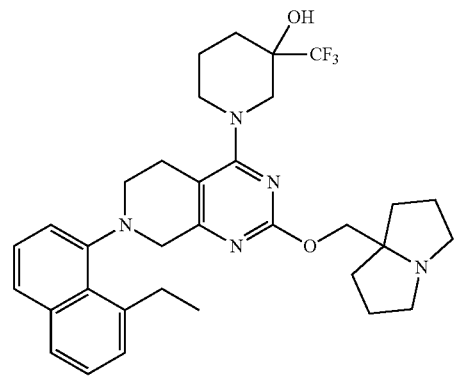
326
-continued
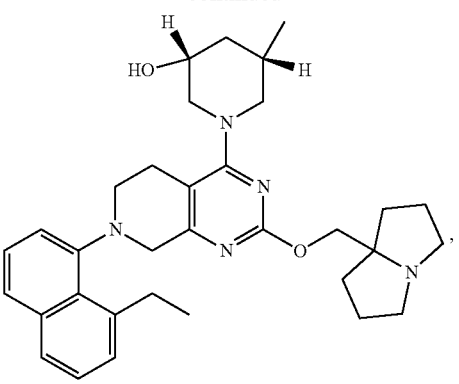
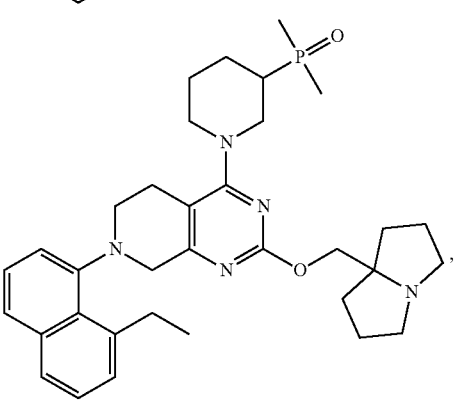
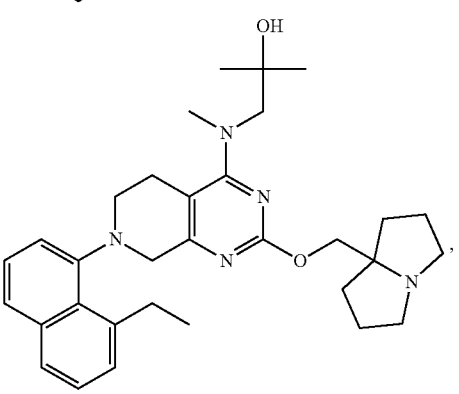
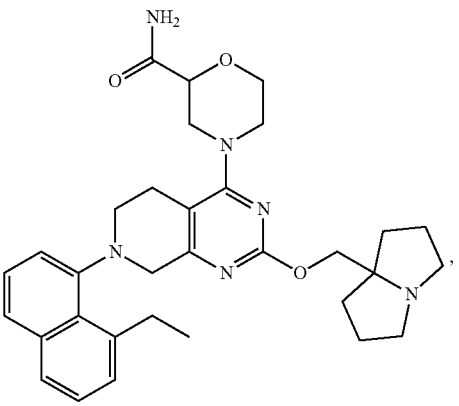

327
-continued
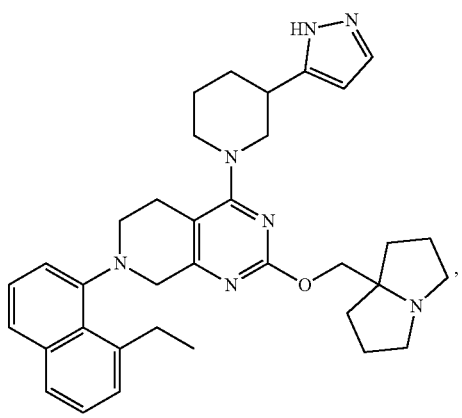
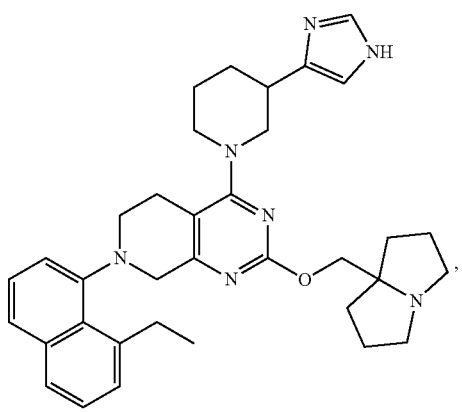
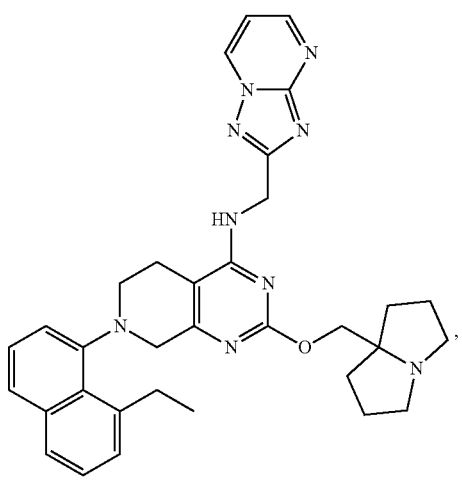
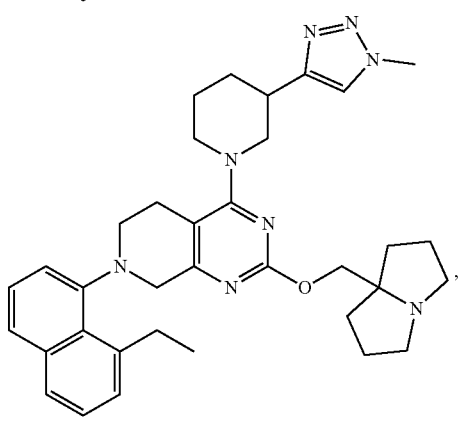
328
-continued
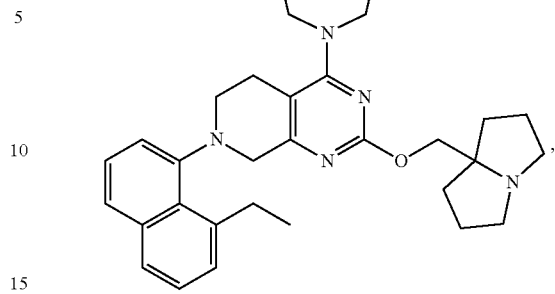
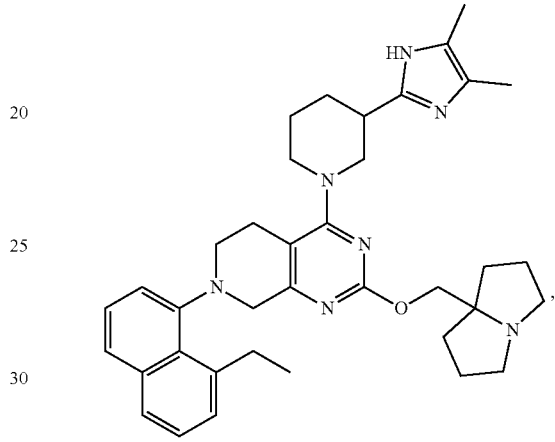
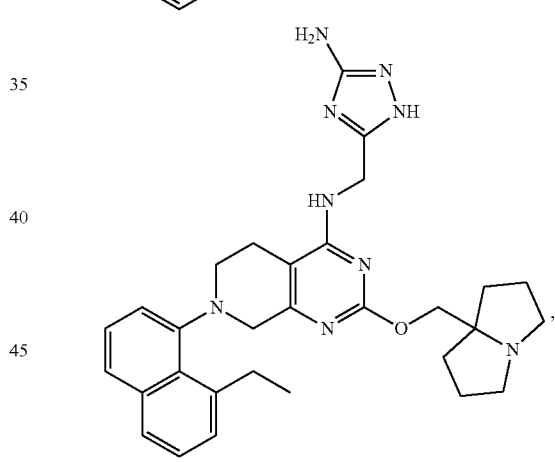
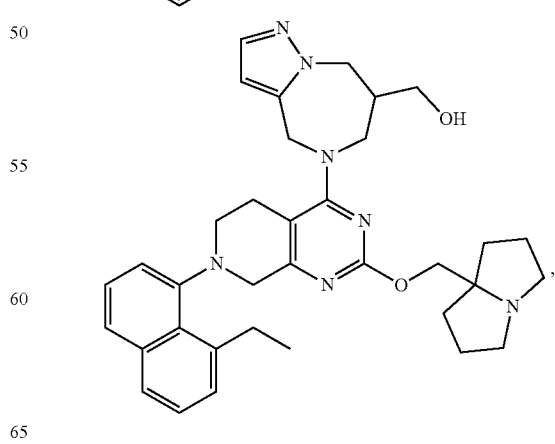

329
-continued
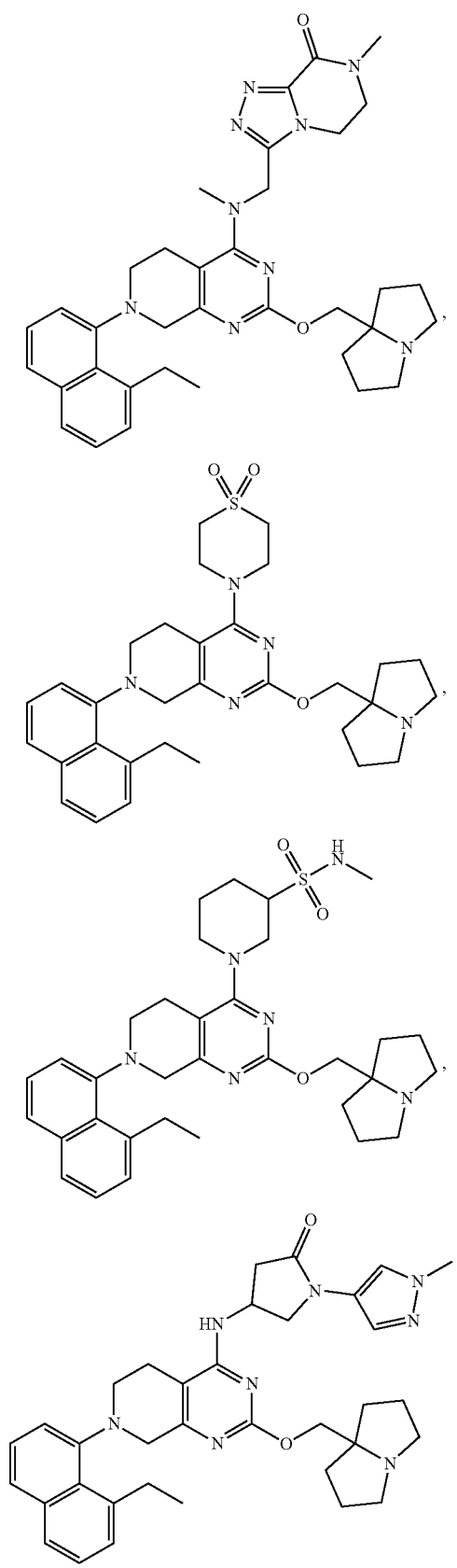
330
-continued
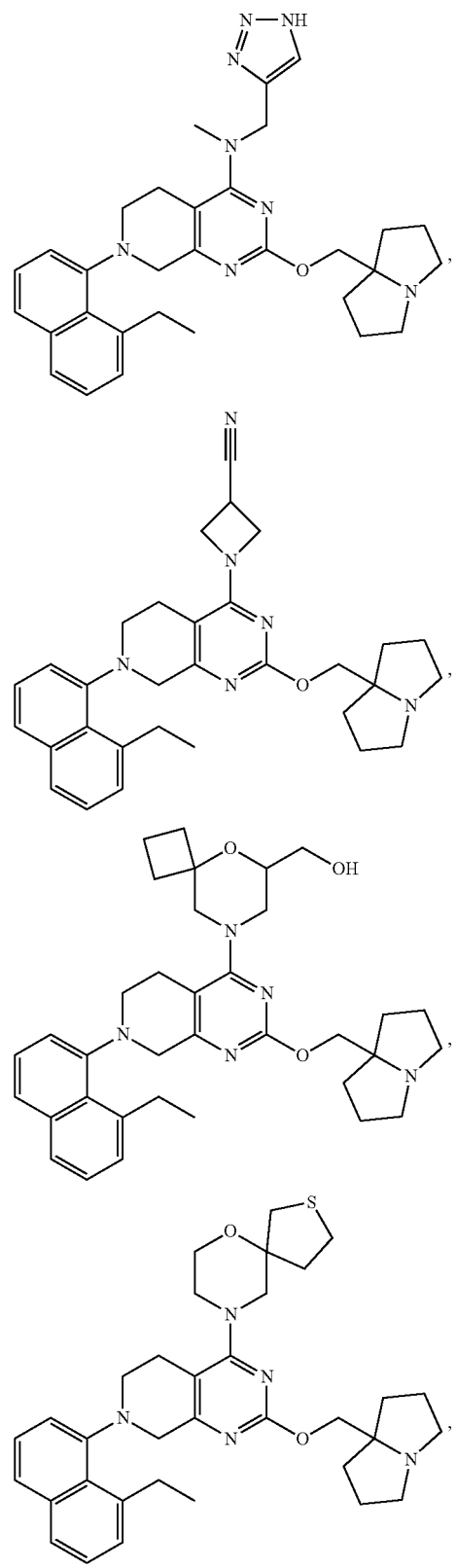

331
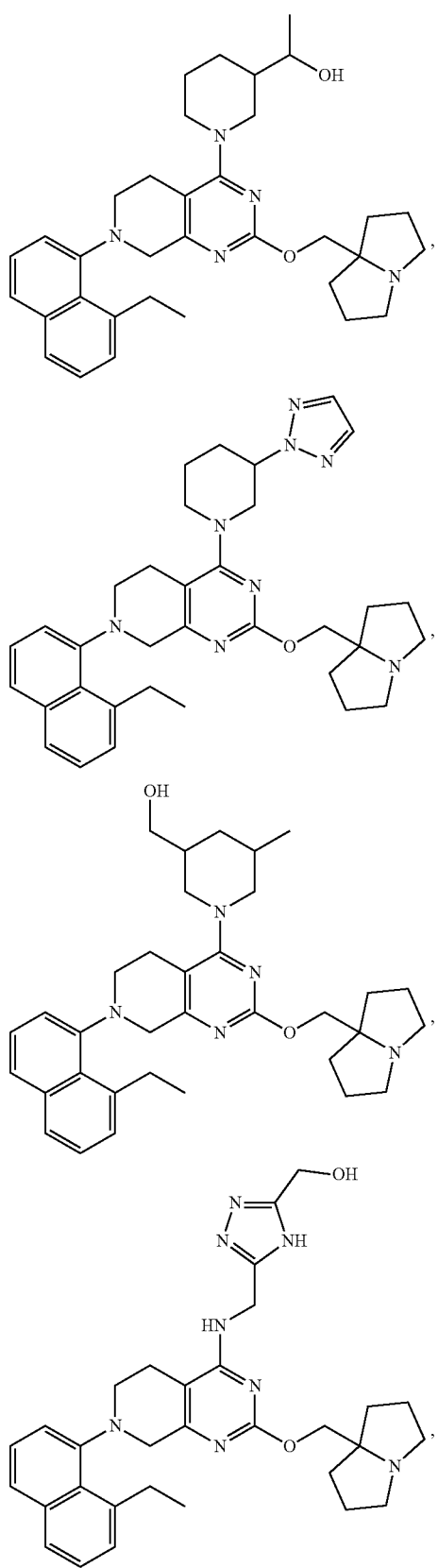
332
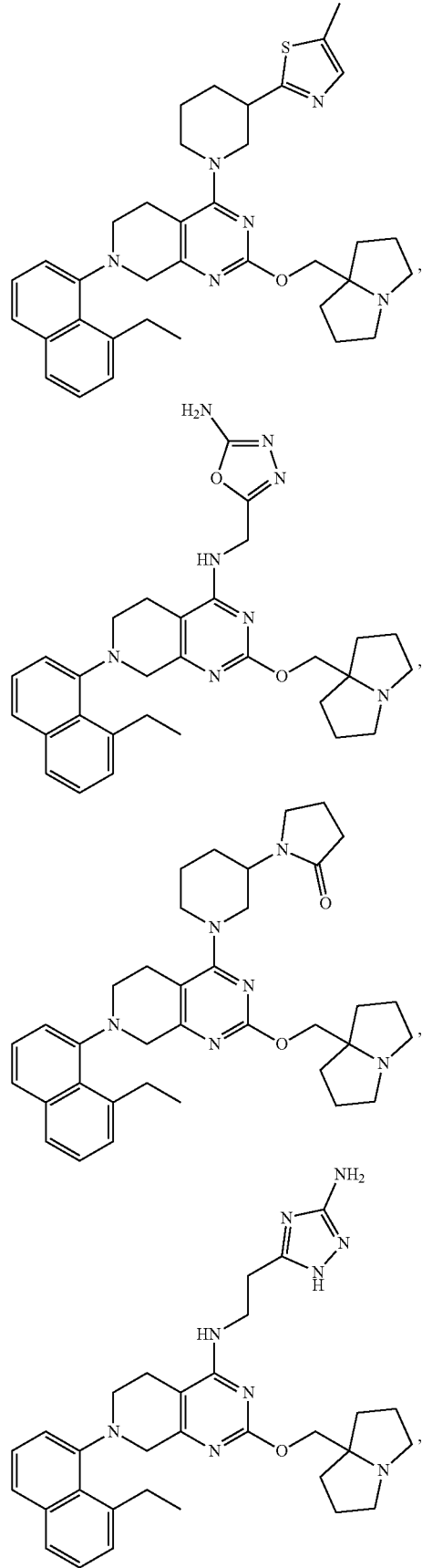

333
-continued
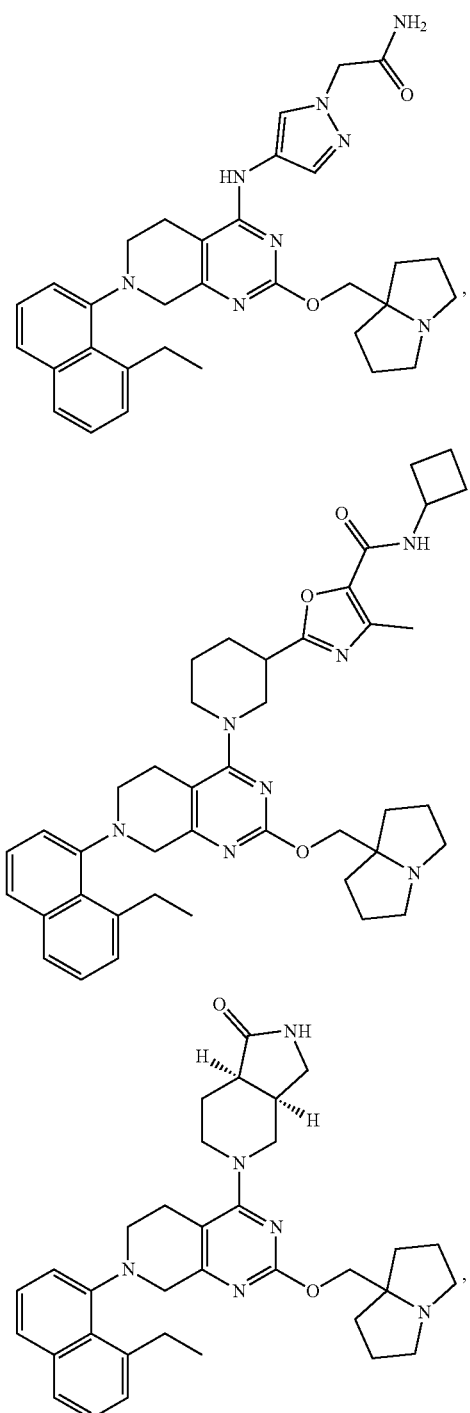
334
-continued
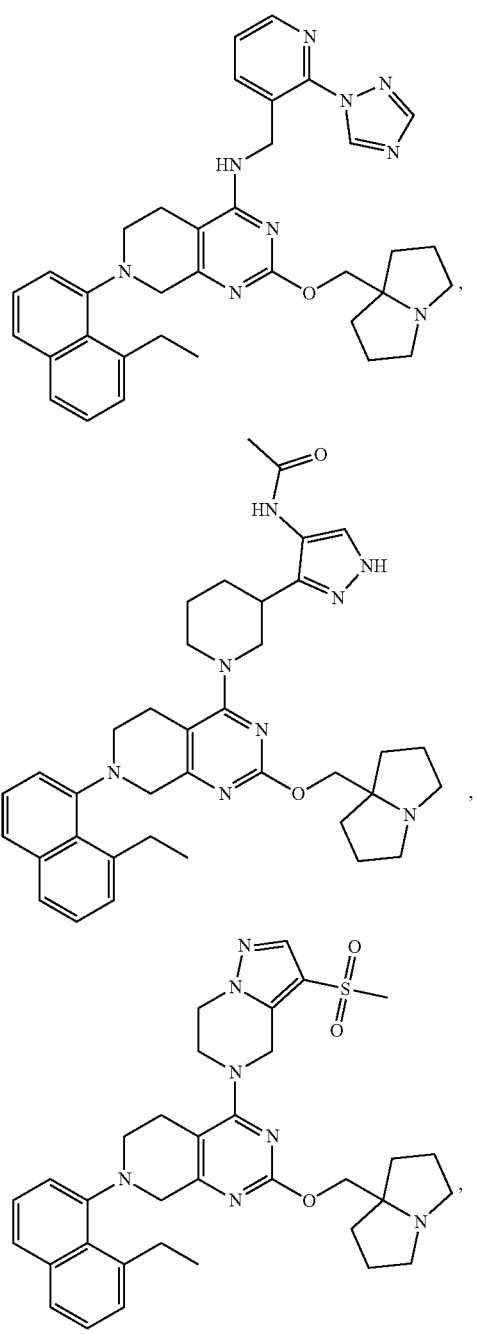

335
-continued
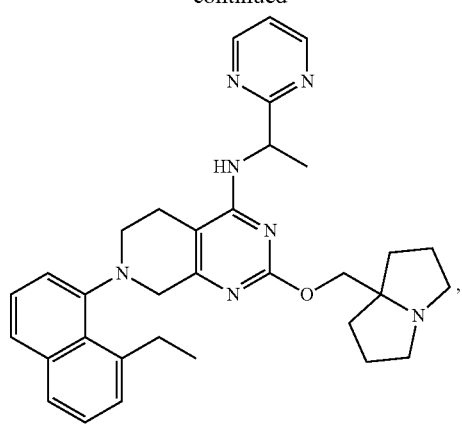
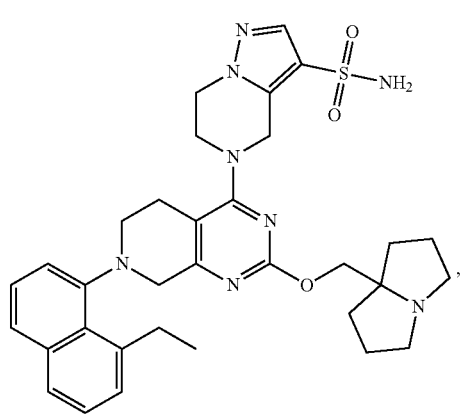
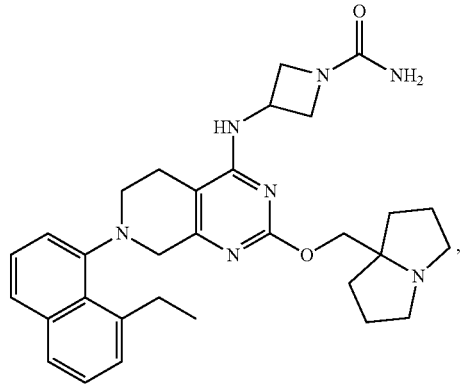
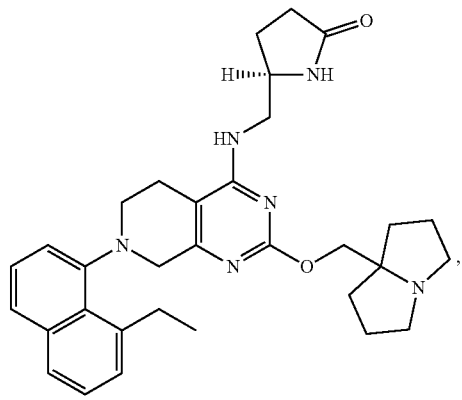
336
-continued
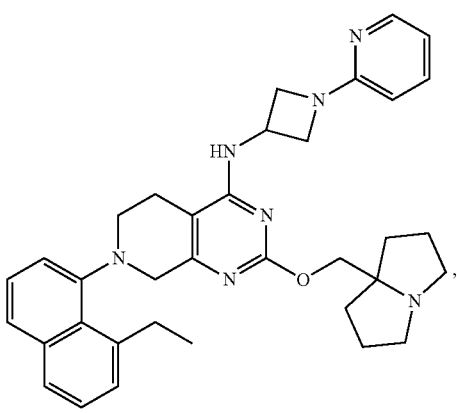
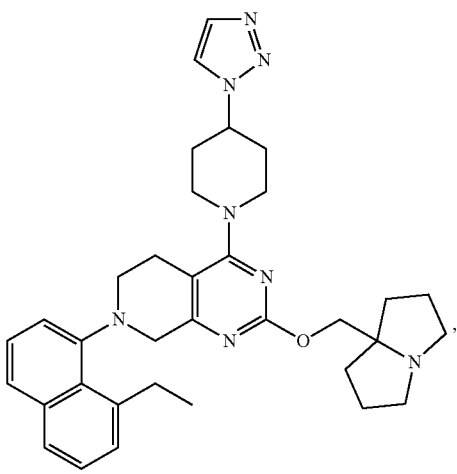
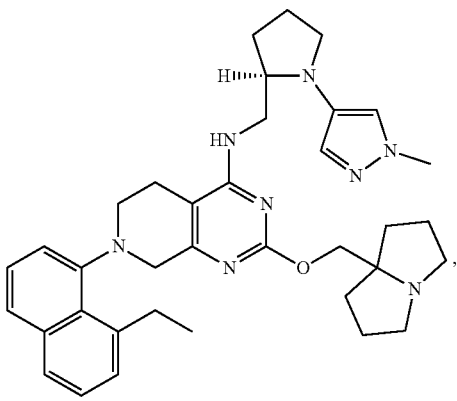

337
-continued
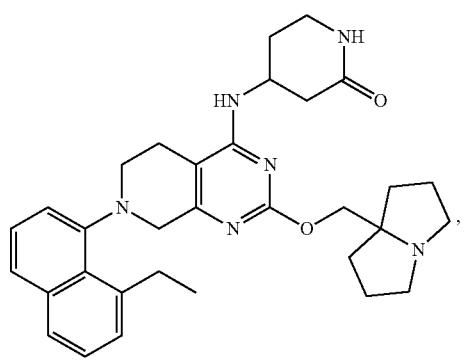
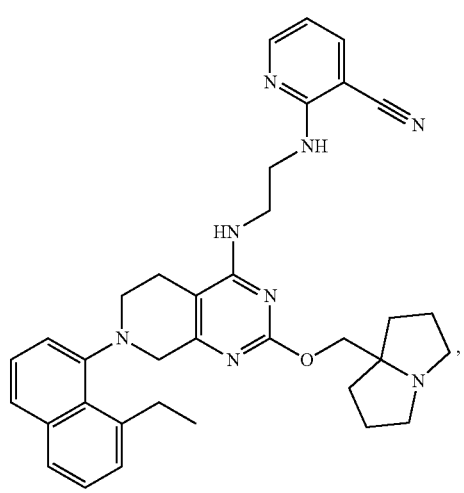
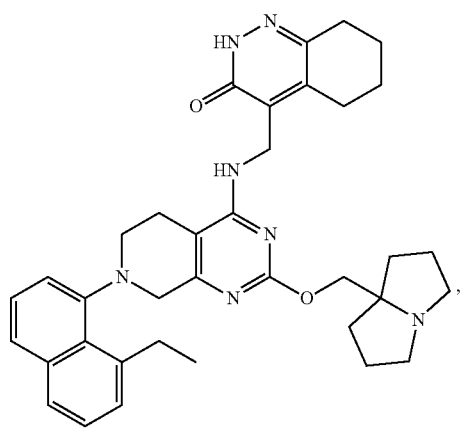
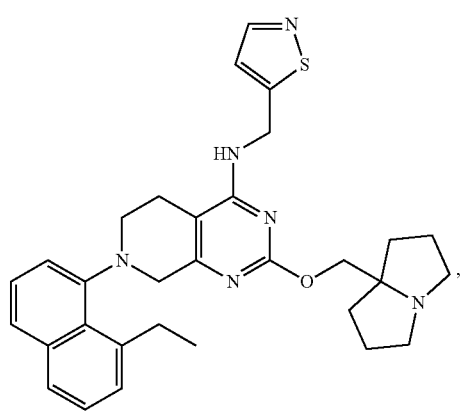
338
-continued
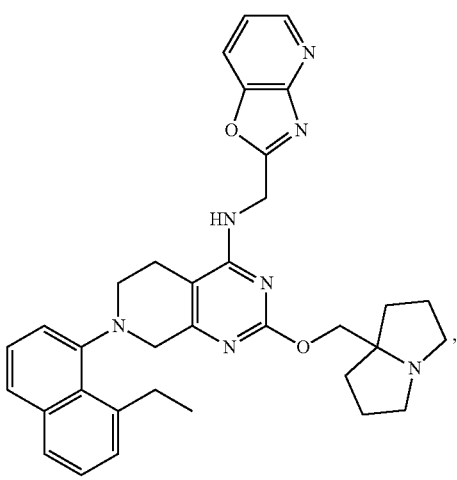
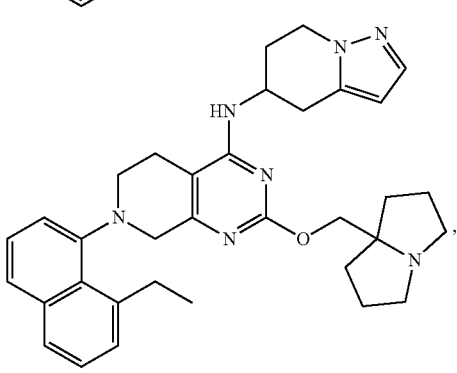
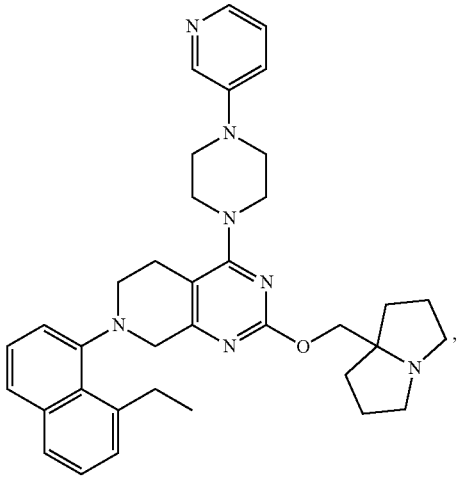

339
-continued
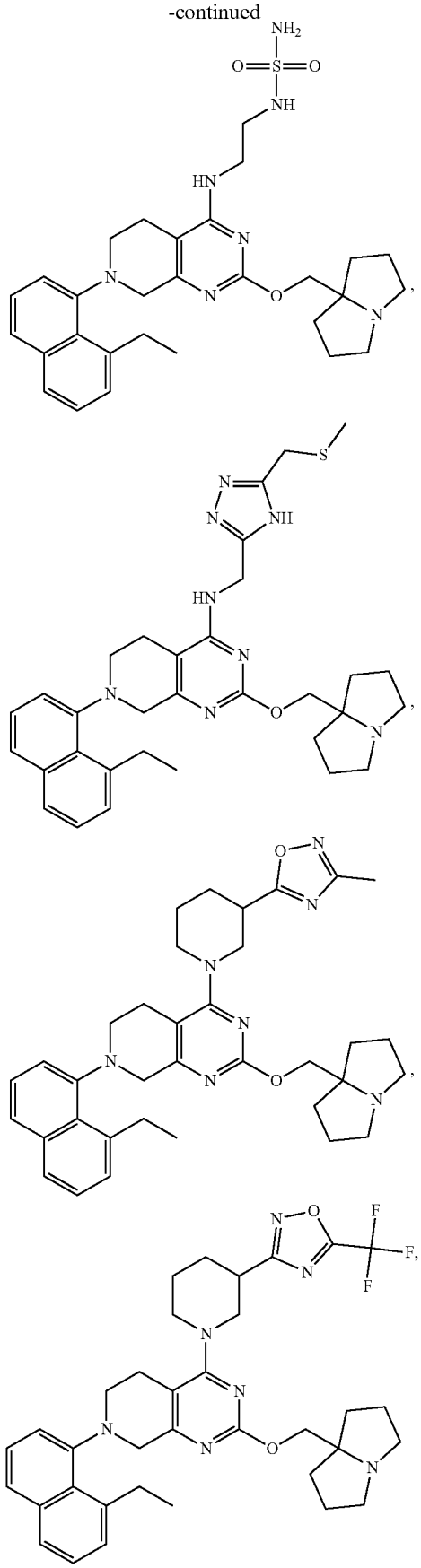
340
-continued
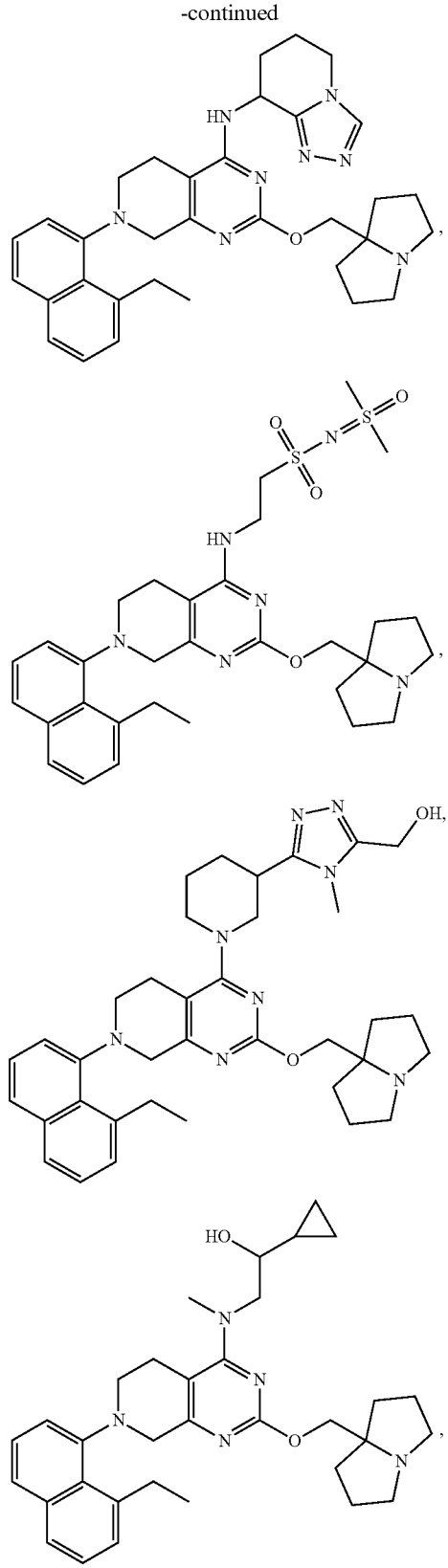

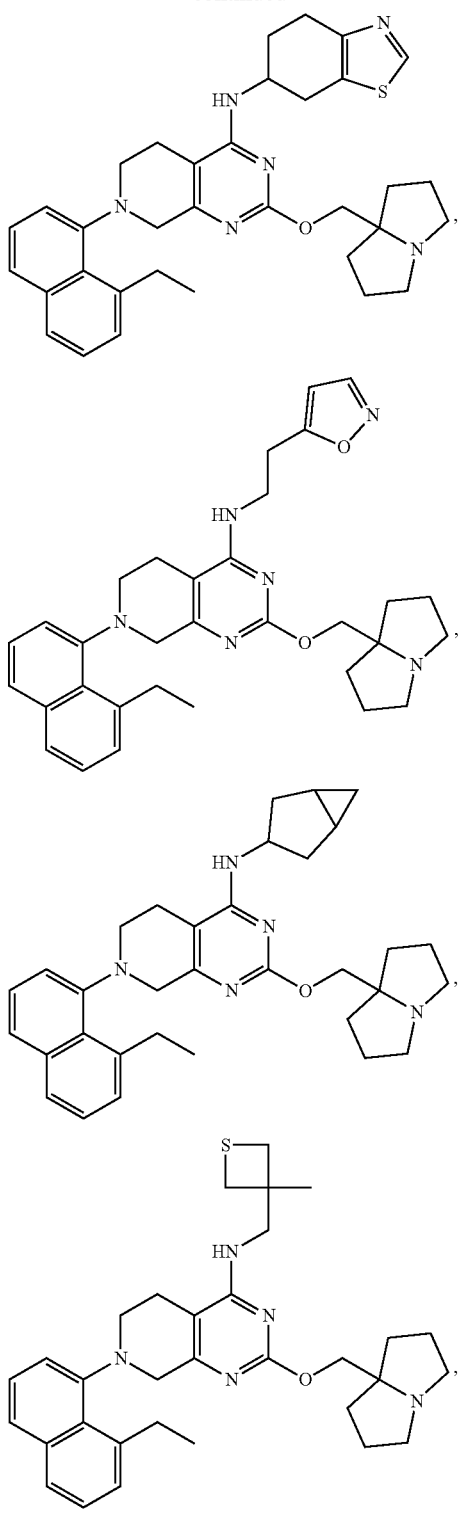
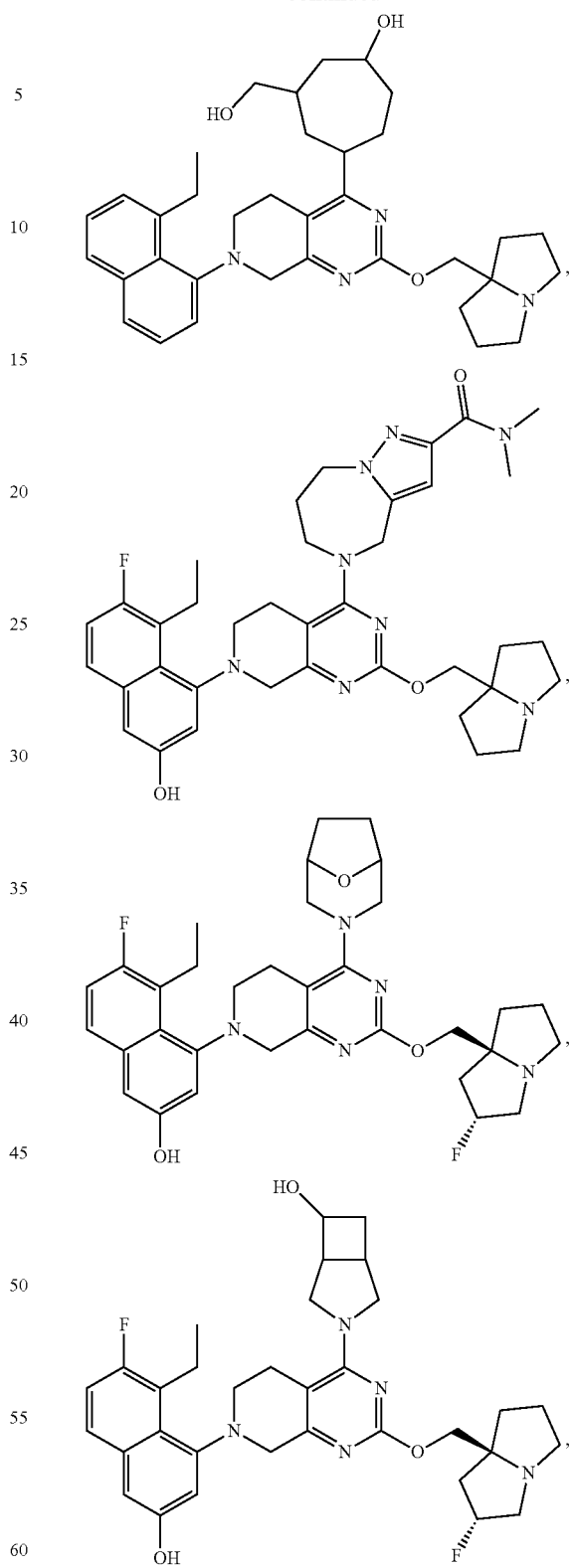

343
-continued
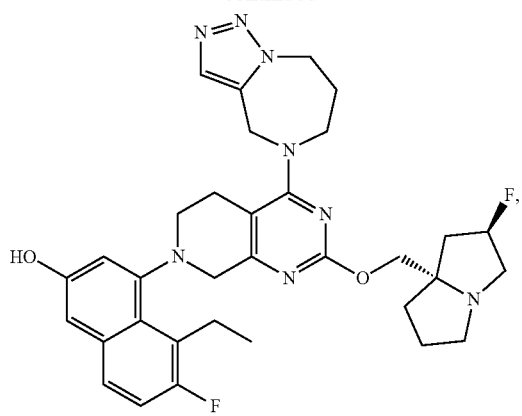
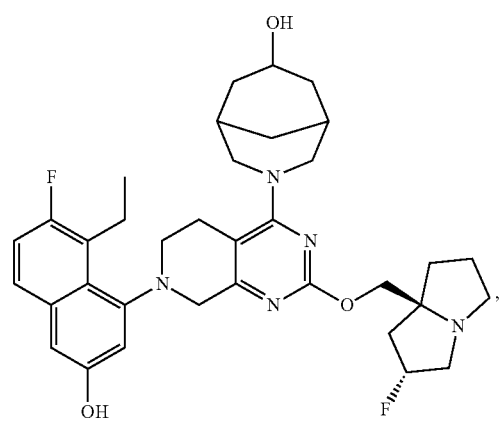
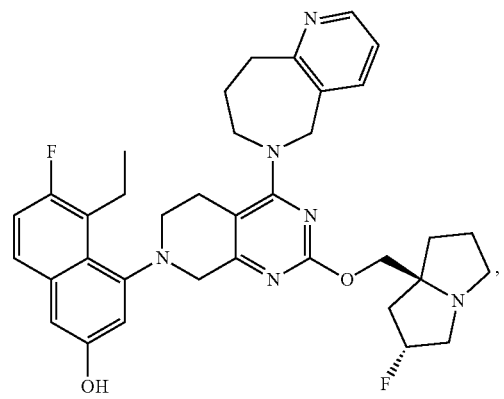
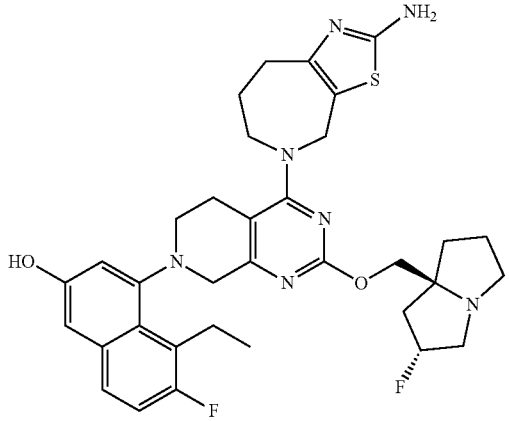
344
-continued
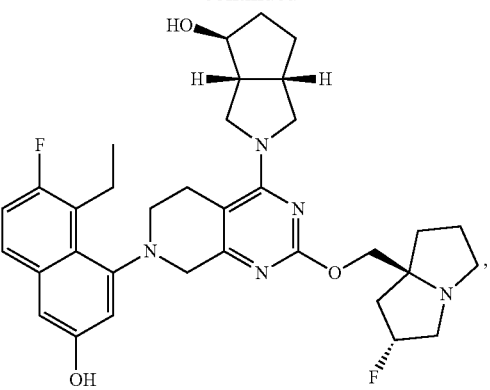
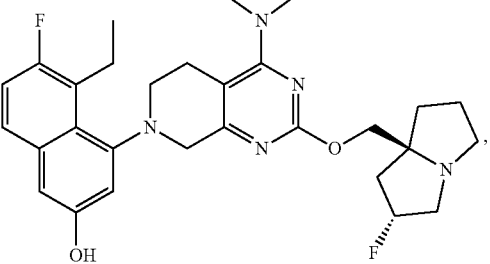
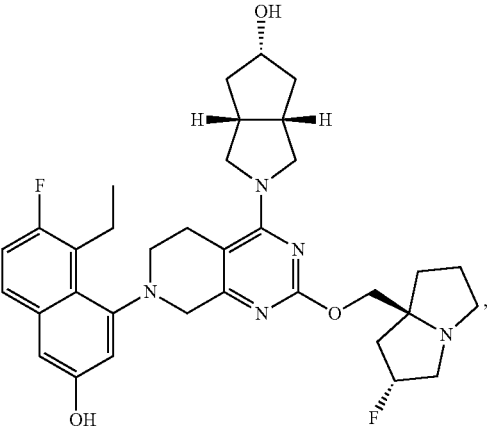
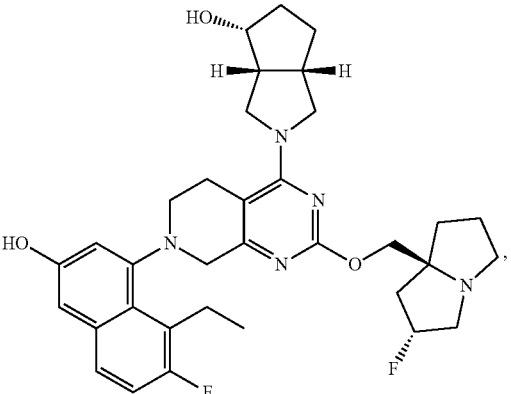

345
-continued
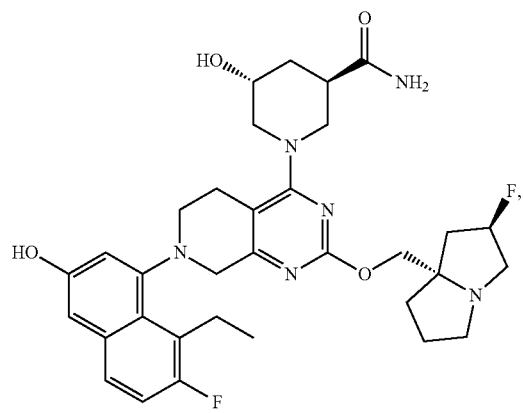
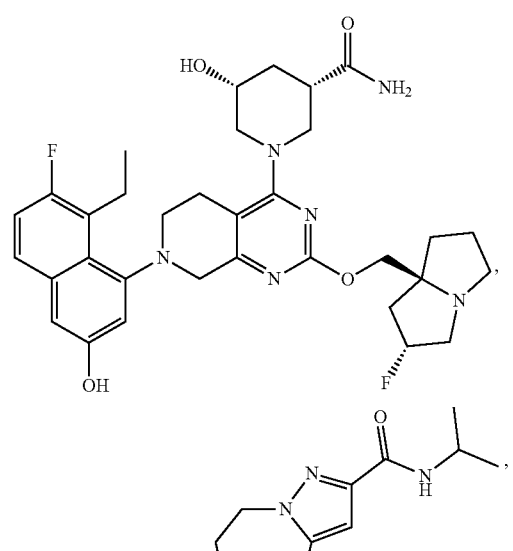
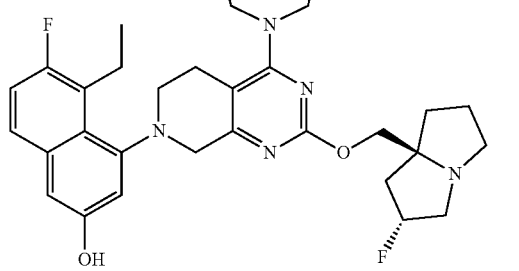
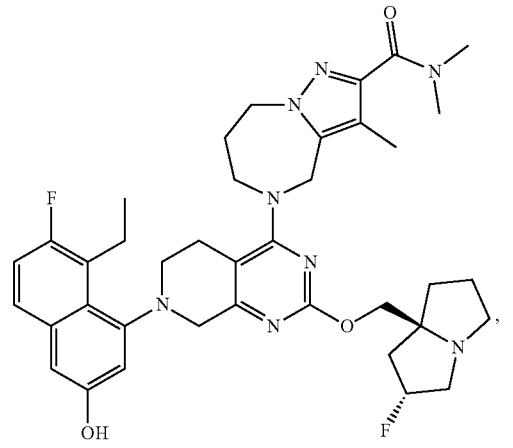
346
-continued
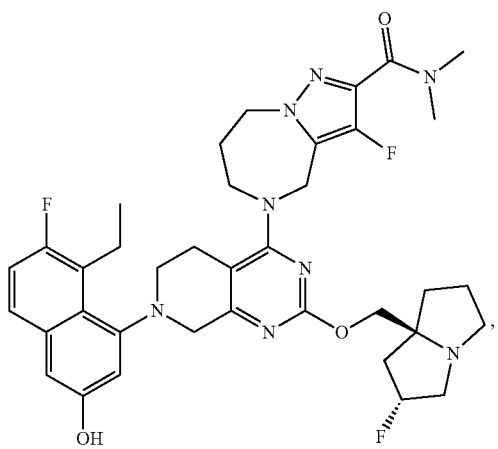
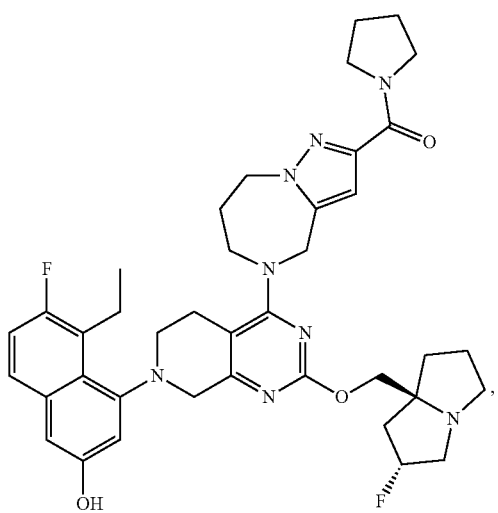 [SMILES: CCc1c(F)ccc2cc(O)cc(N3CCc4c(nc(OC[C@@]56CCCN5C[C@H](F)C6)nc4N4CCCn5nc(C(=O)N6CCCC6)cc5C4)C3)c12]
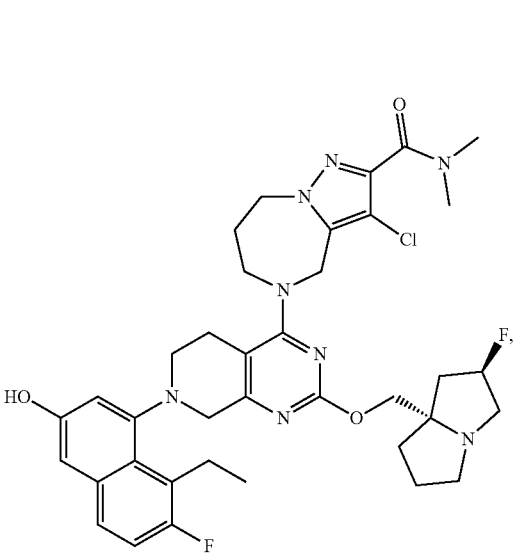

347
-continued
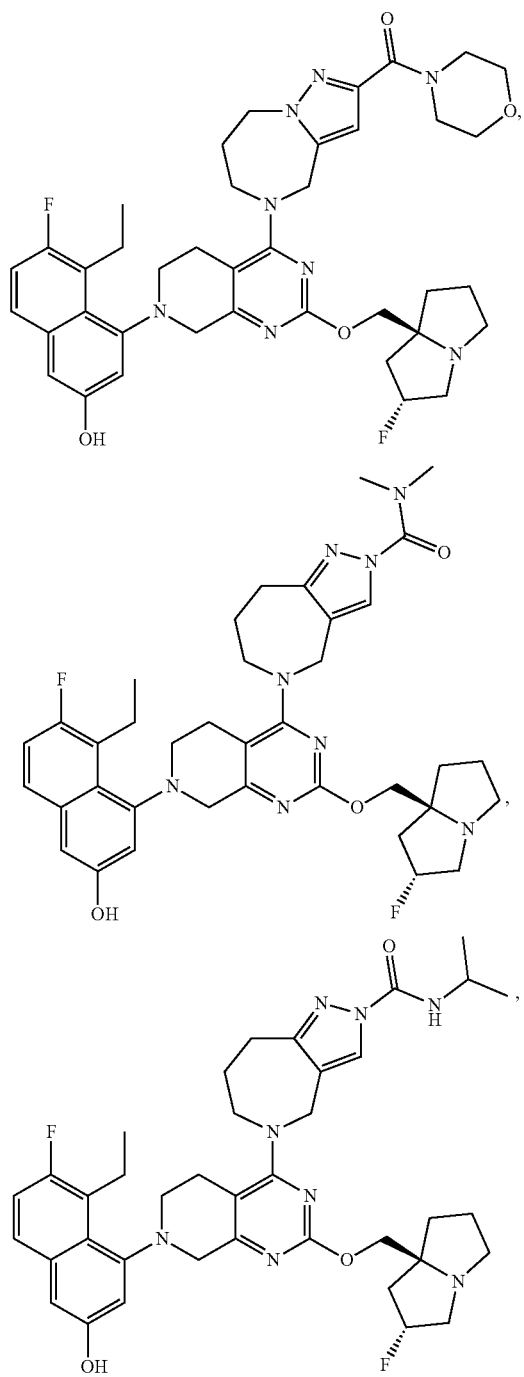
348
-continued
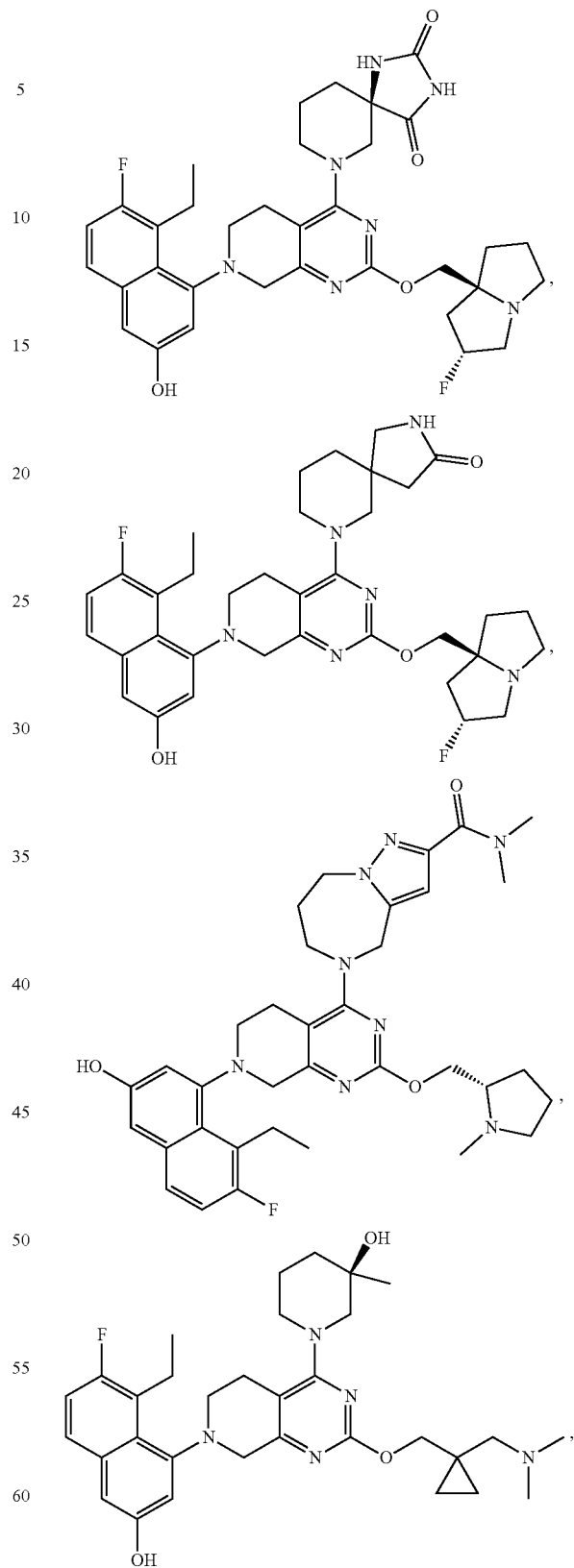

349
-continued
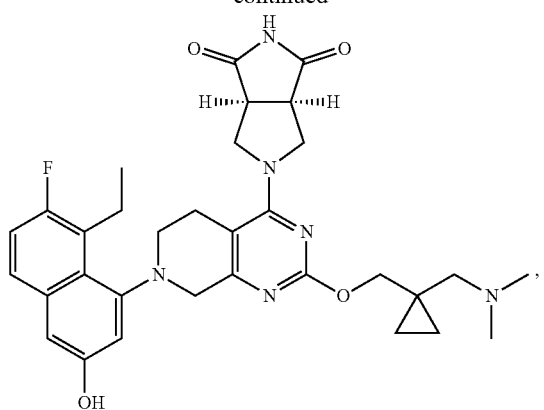
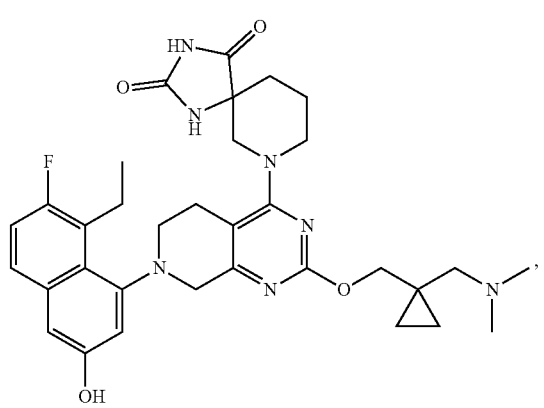
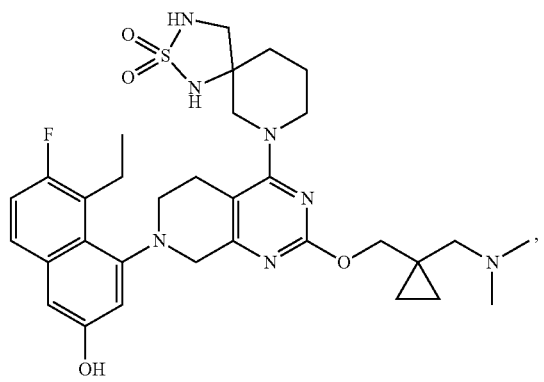
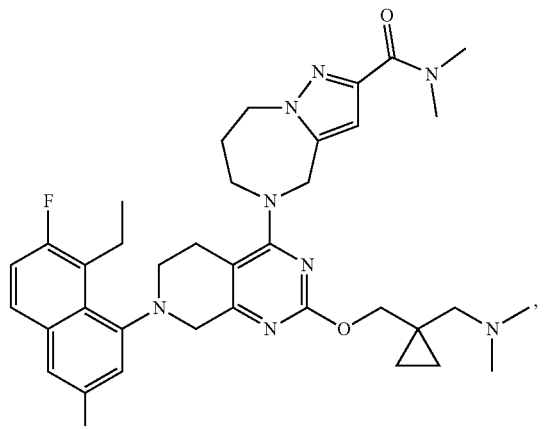
350
-continued
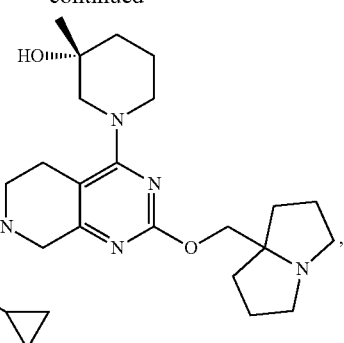
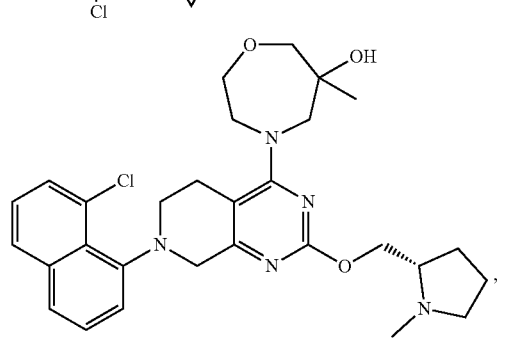
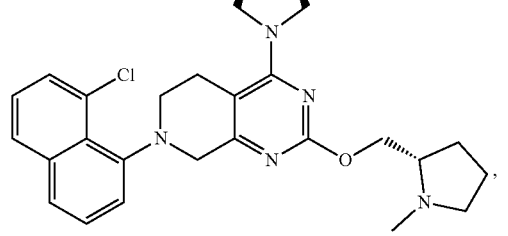
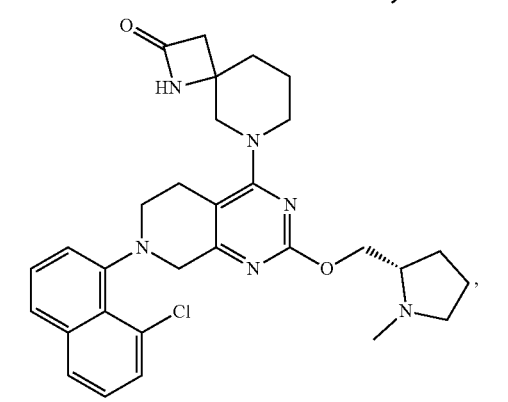

351
-continued
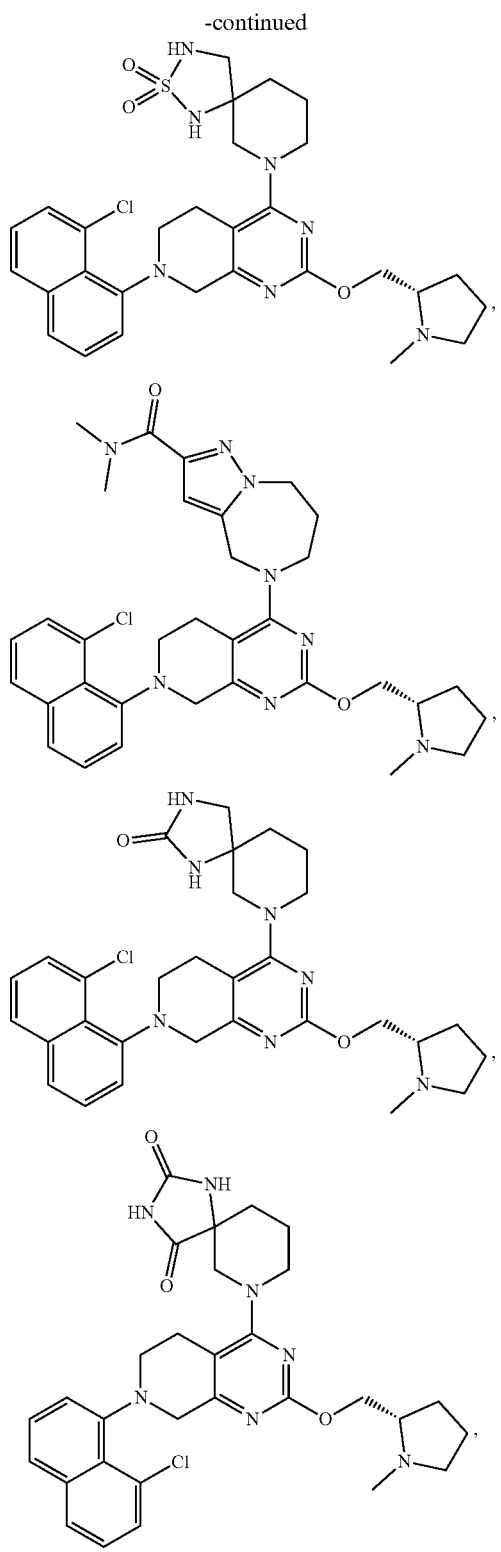
352
-continued
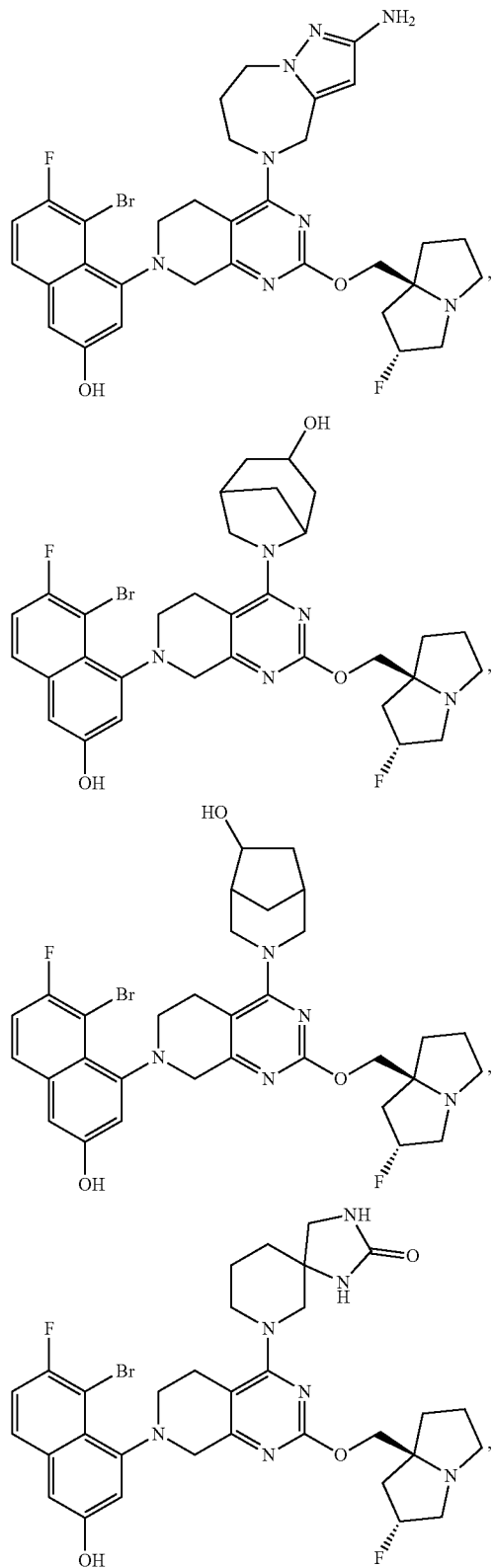

353
-continued
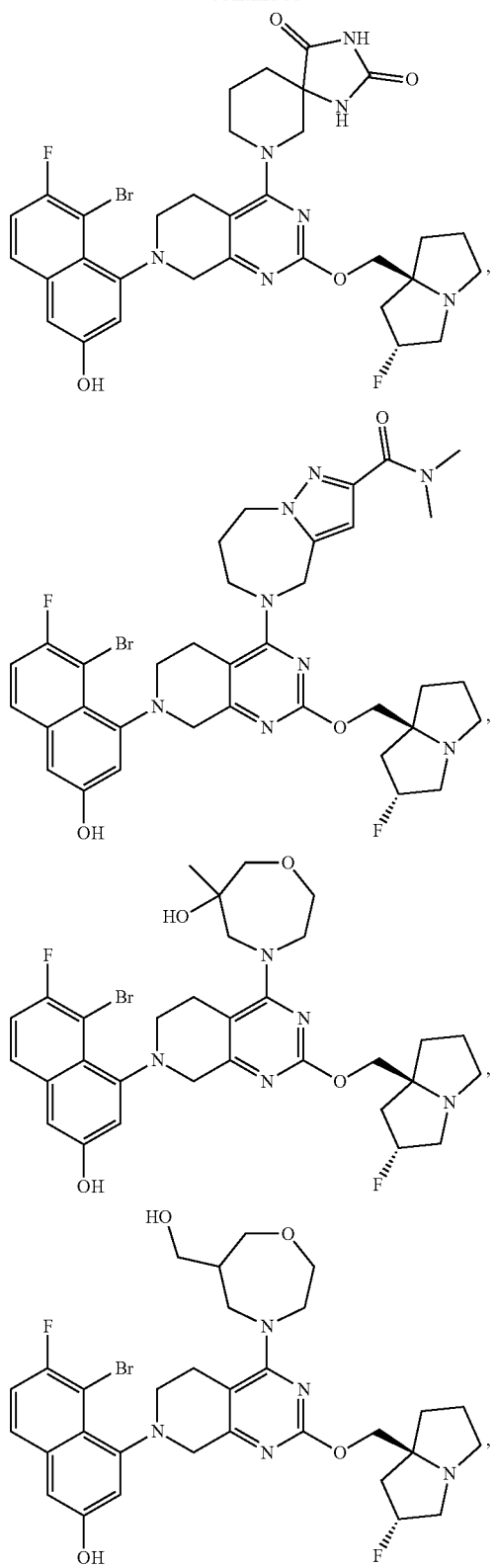
354
-continued
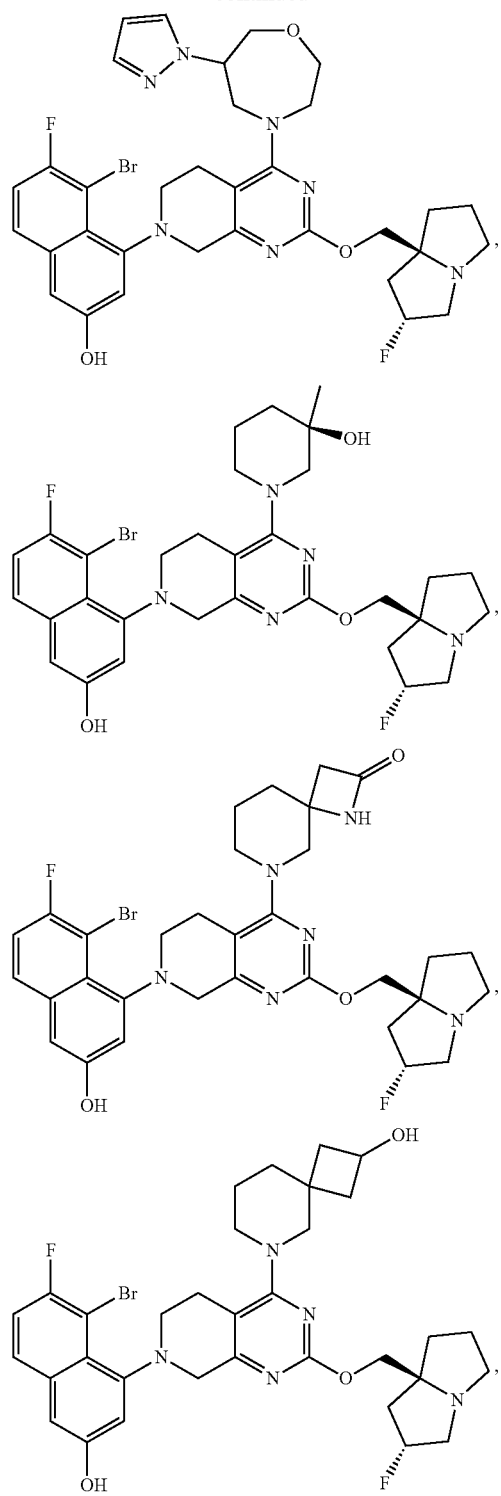

-continued
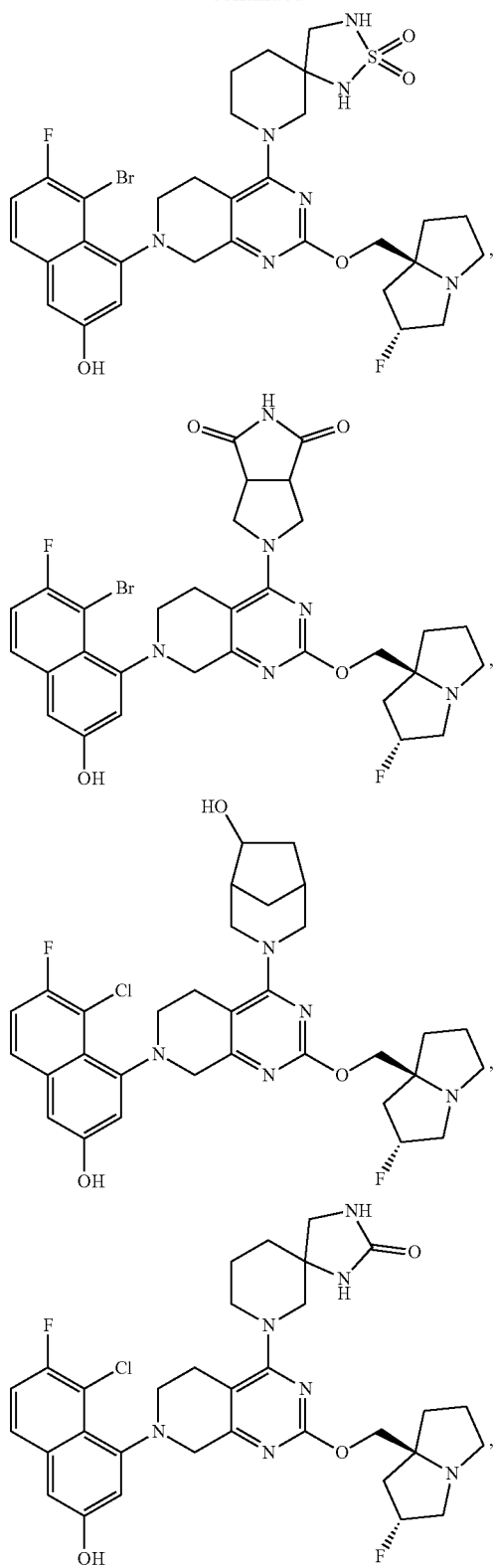
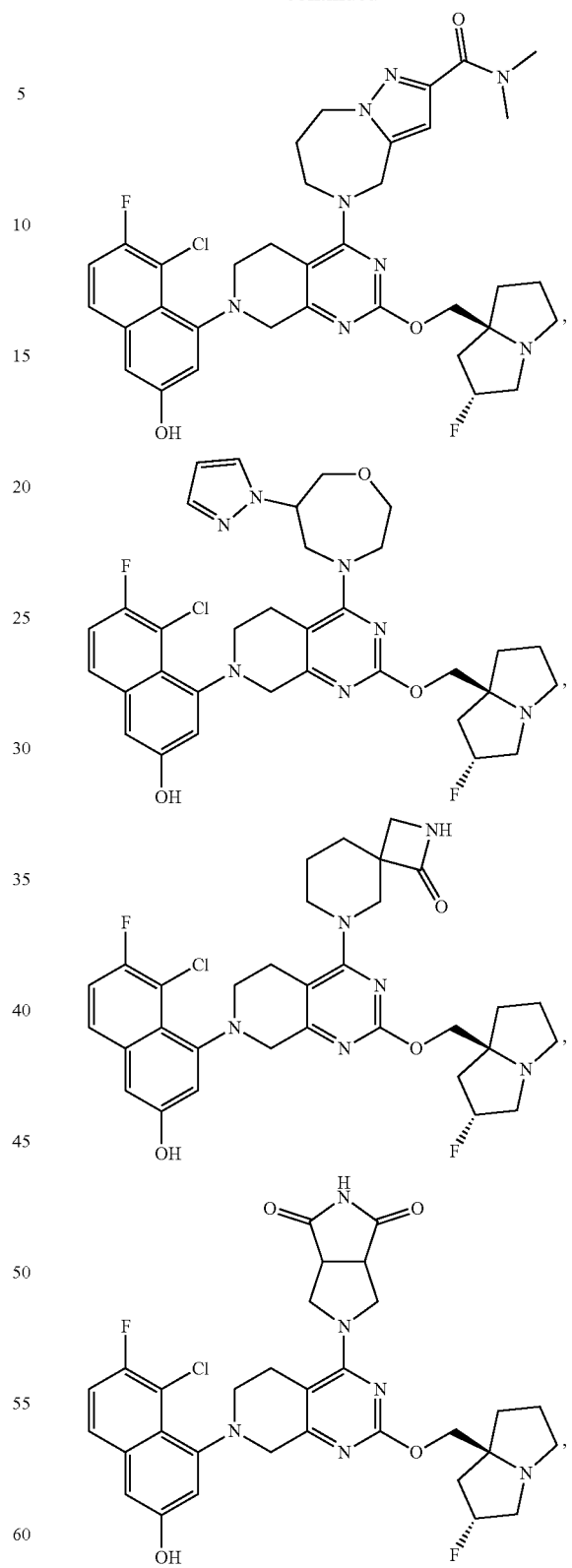
and a pharmaceutically acceptable salt thereof.
2. The method of claim 1, wherein the compound is

357

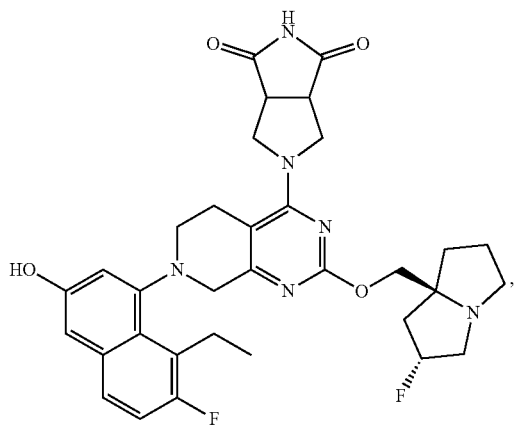 [SMILES: CCc1c(F)ccc2cc(O)cc(N3CCc4c(nc(OC[C@@]56CCCN5C[C@H](F)C6)nc4N4CC5C(=O)NC(=O)C5C4)C3)c12]

or a pharmaceutically acceptable salt thereof.

3. The method of claim 1, wherein the compound is

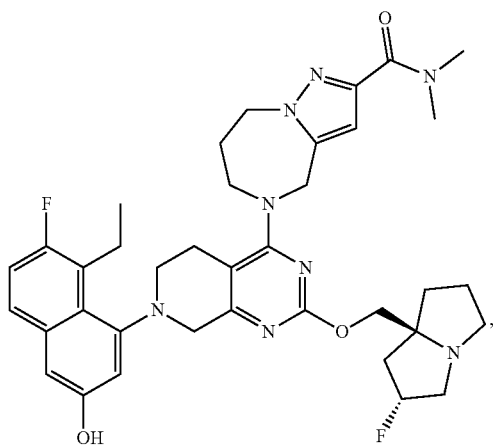 [SMILES: CCc1c(F)ccc2cc(O)cc(N3CCc4c(nc(OC[C@@]56CCCN5C[C@H](F)C6)nc4N4CCCn5nc(C(=O)N(C)C)cc5C4)C3)c12]

or a pharmaceutically acceptable salt thereof.

4. The method of claim 1, wherein the compound is

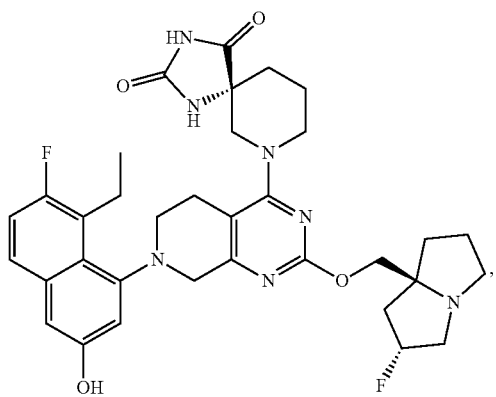 [SMILES: CCc1c(F)ccc2cc(O)cc(N3CCc4c(nc(OC[C@@]56CCCN5C[C@H](F)C6)nc4N4CCC[C@]5(C4)NC(=O)NC5=O)C3)c12]

or a pharmaceutically acceptable salt thereof.

5. A method for treating cancer comprising administering to a patient having cancer a therapeutically effective amount of a compound selected from:

358

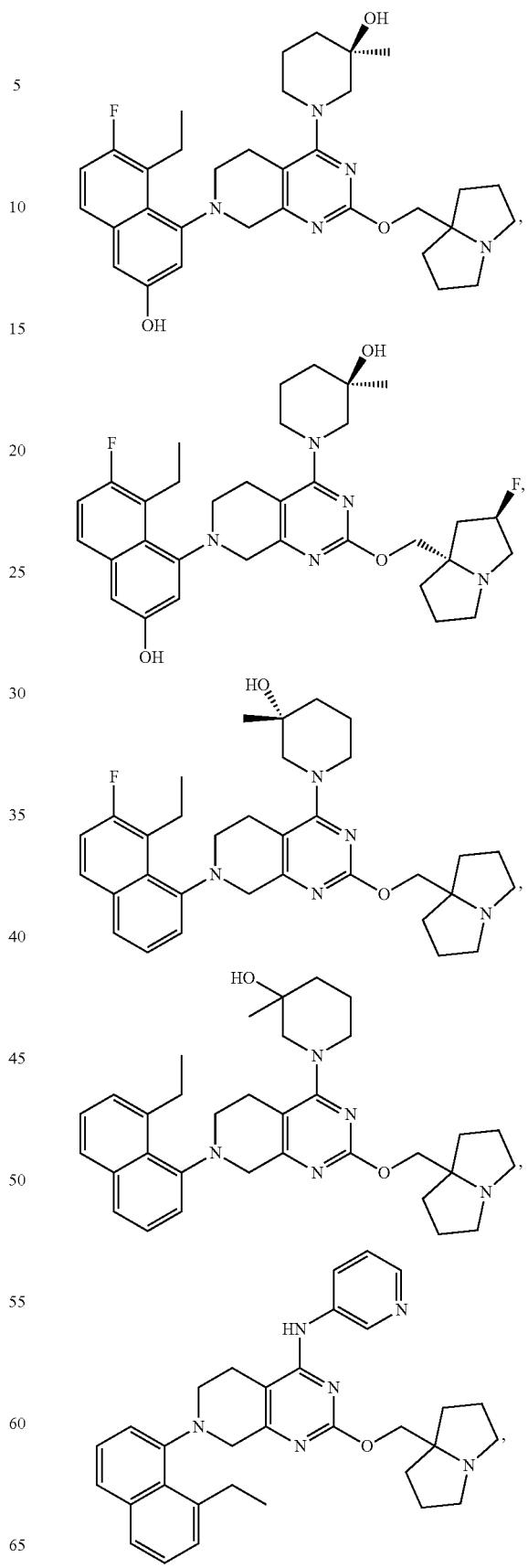

359
-continued
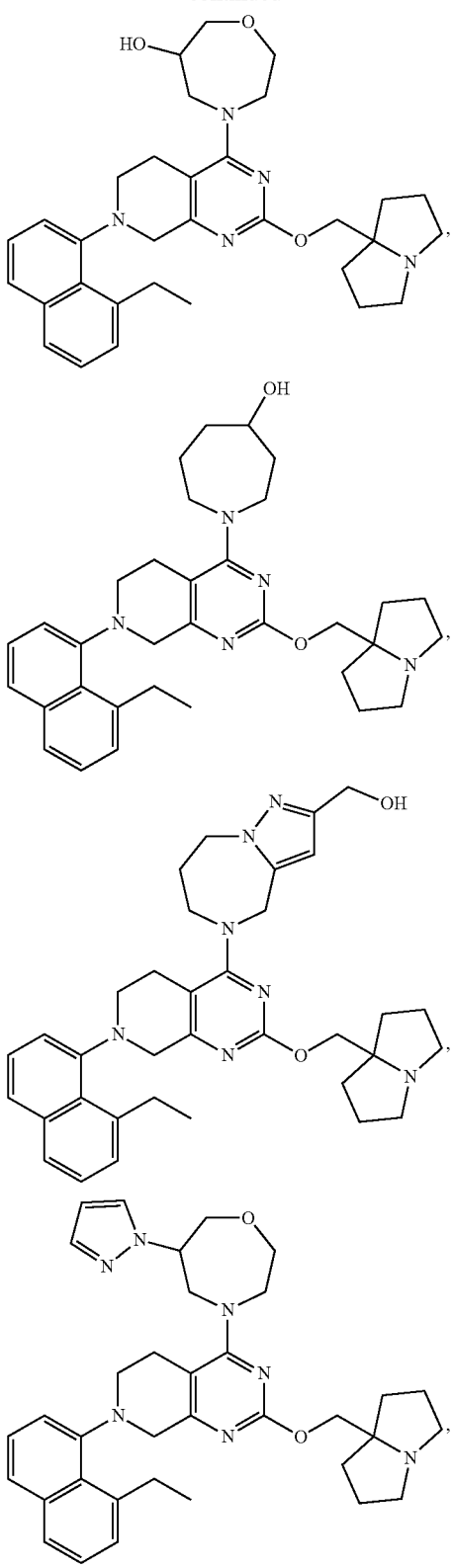
360
-continued
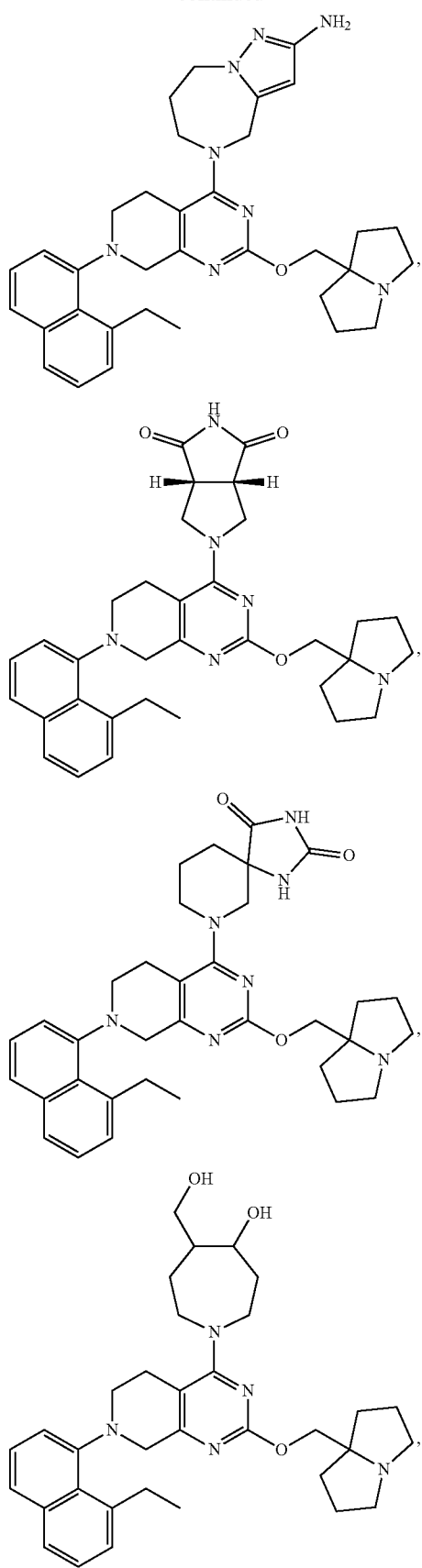

361
-continued
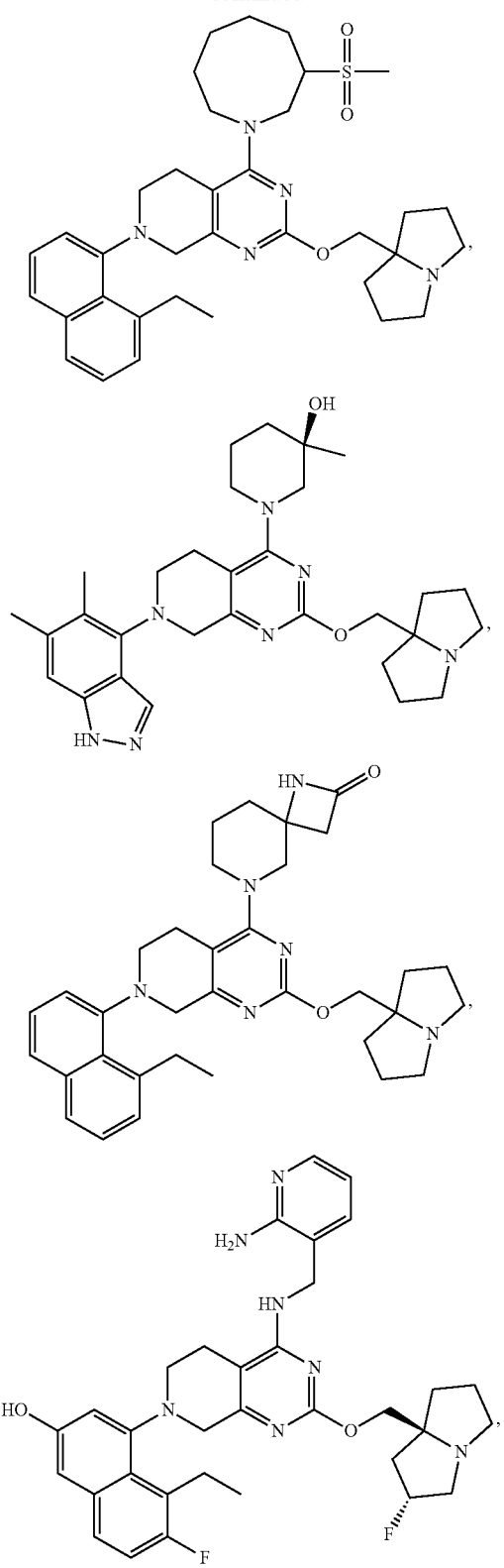
362
-continued
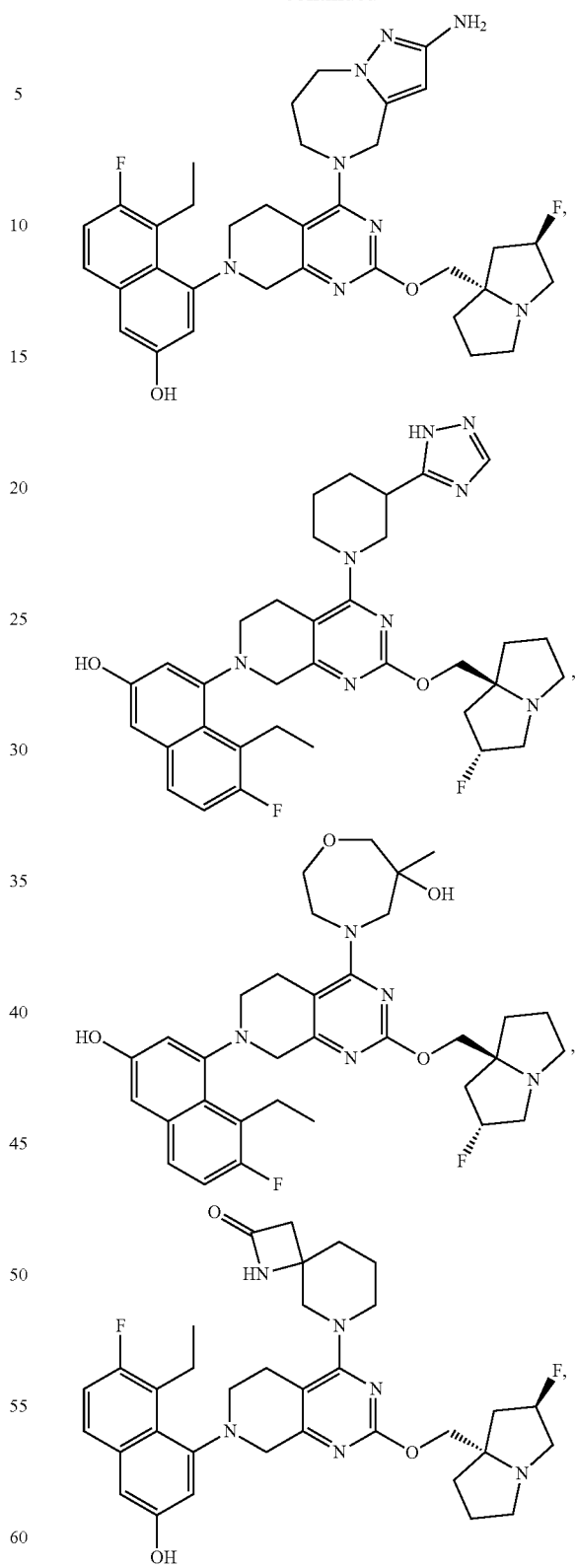

363
-continued
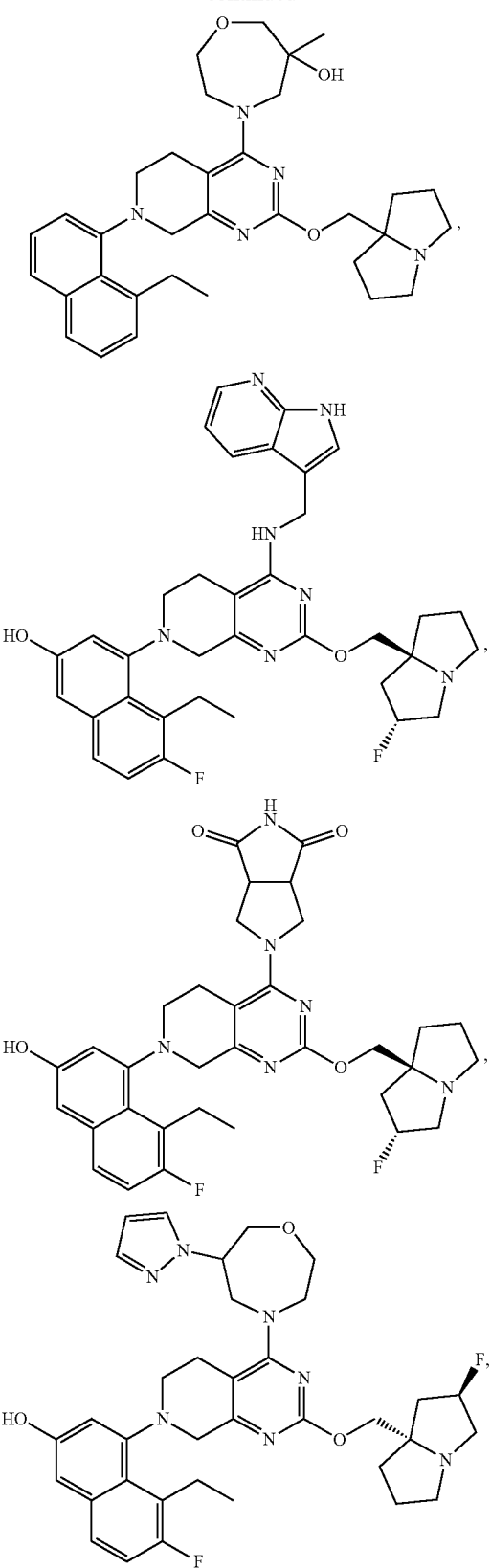
364
-continued
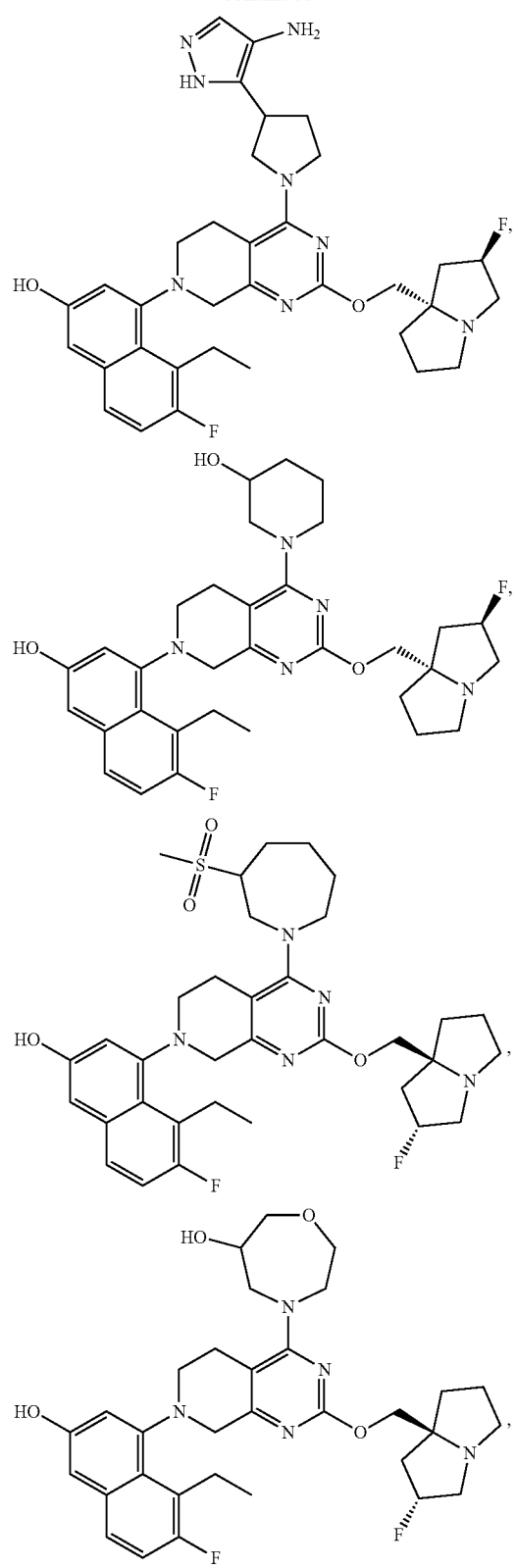

365
-continued
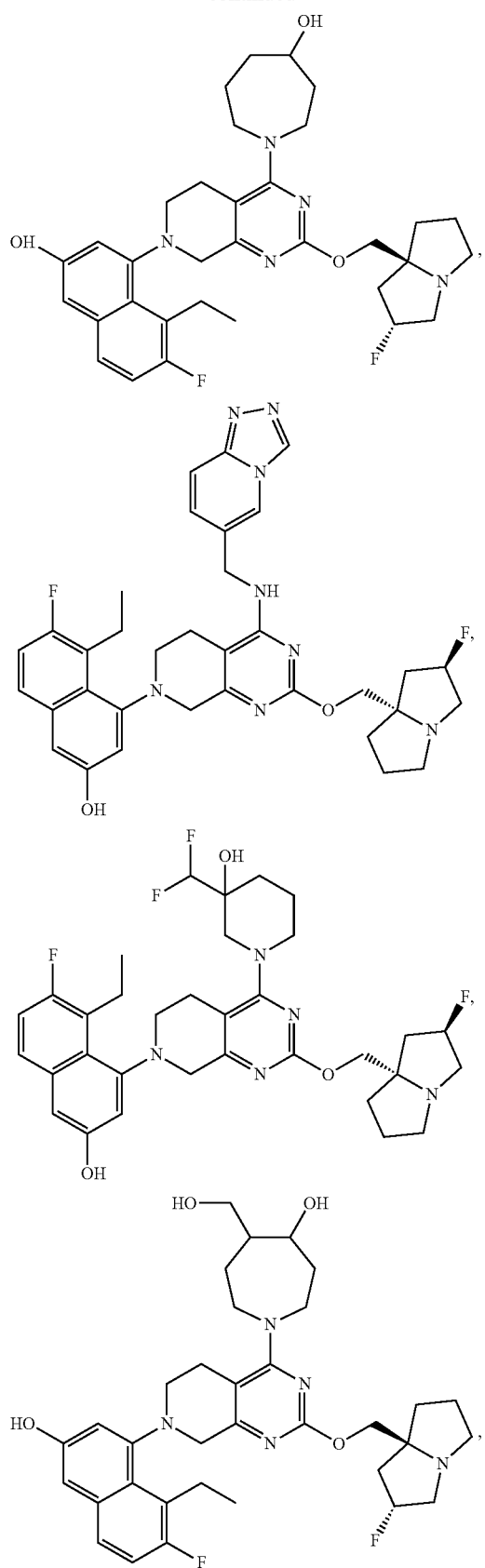
366
-continued
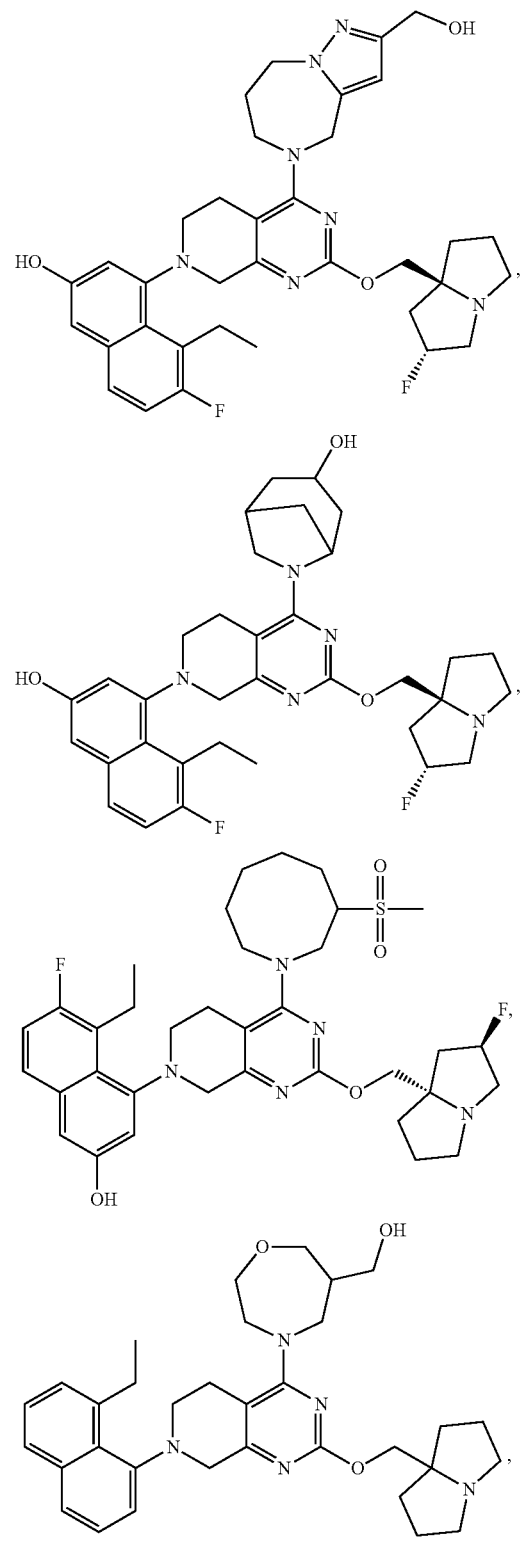

367
-continued
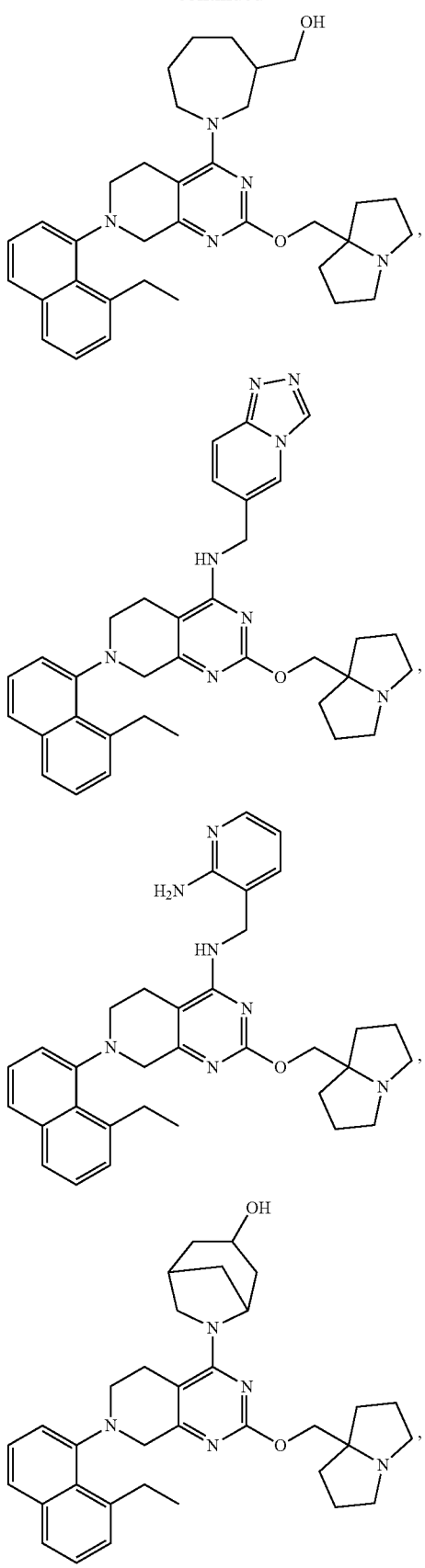
368
-continued
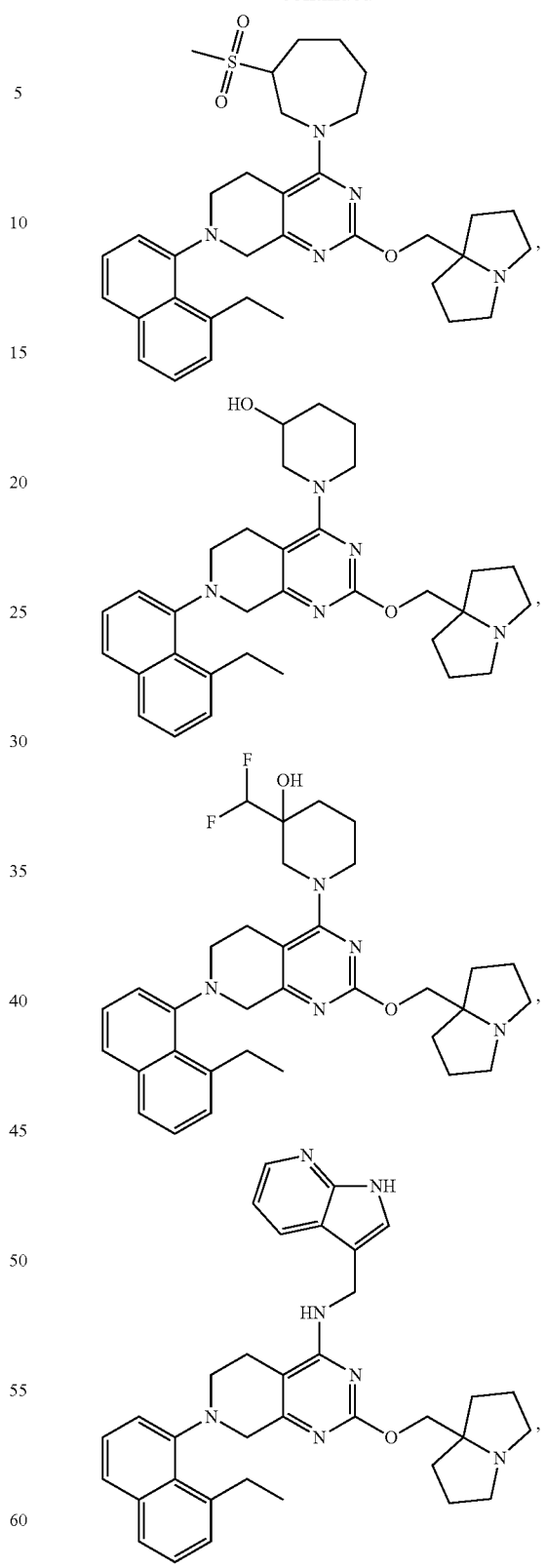

369 370
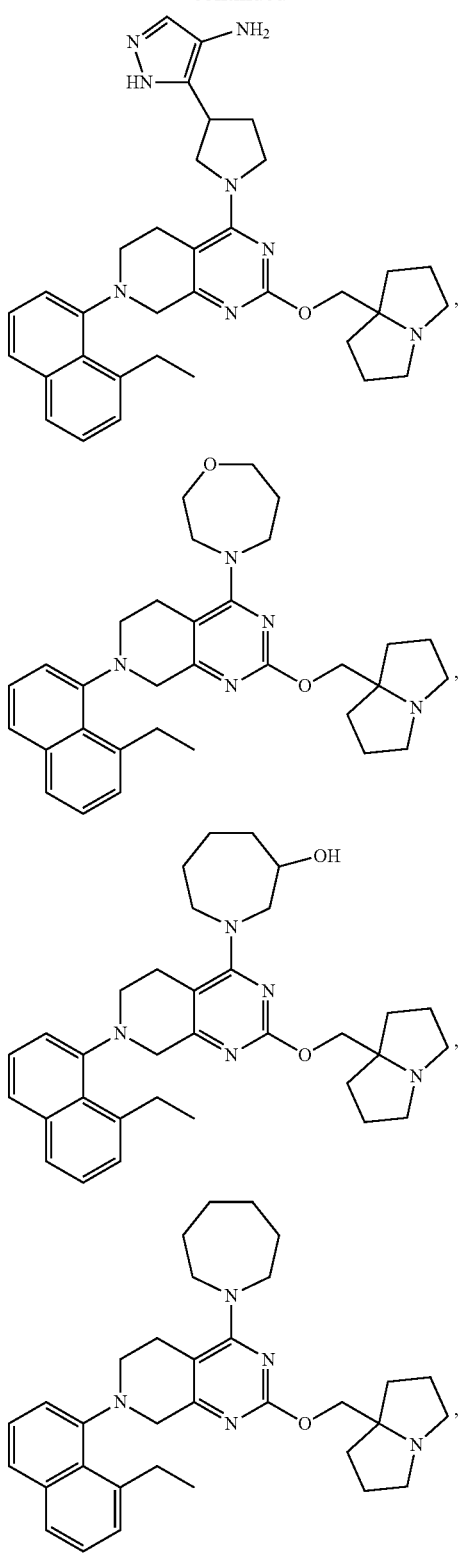
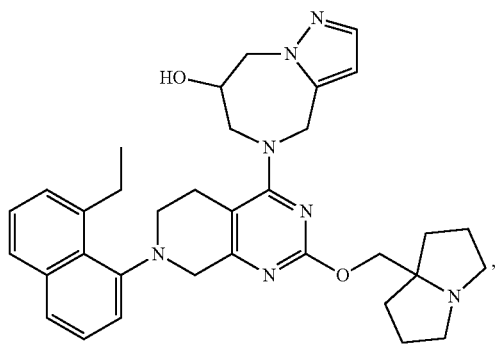
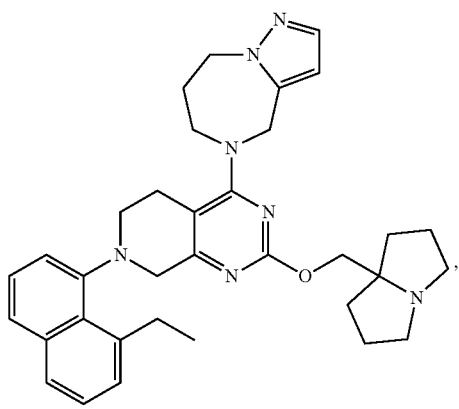
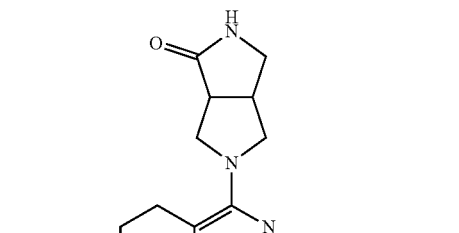
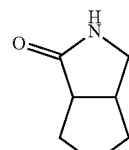
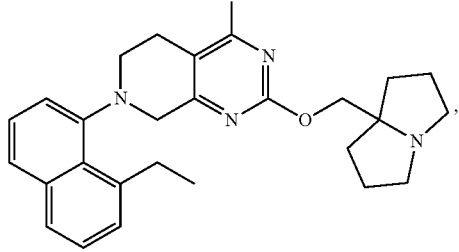
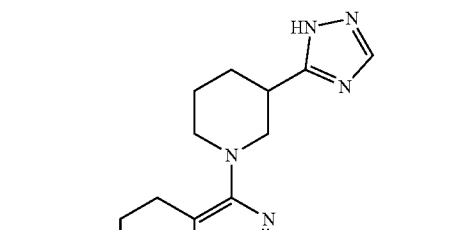
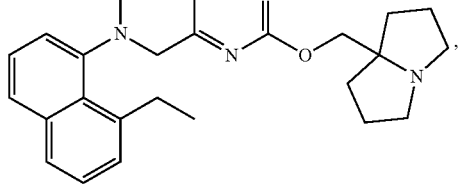

371
-continued
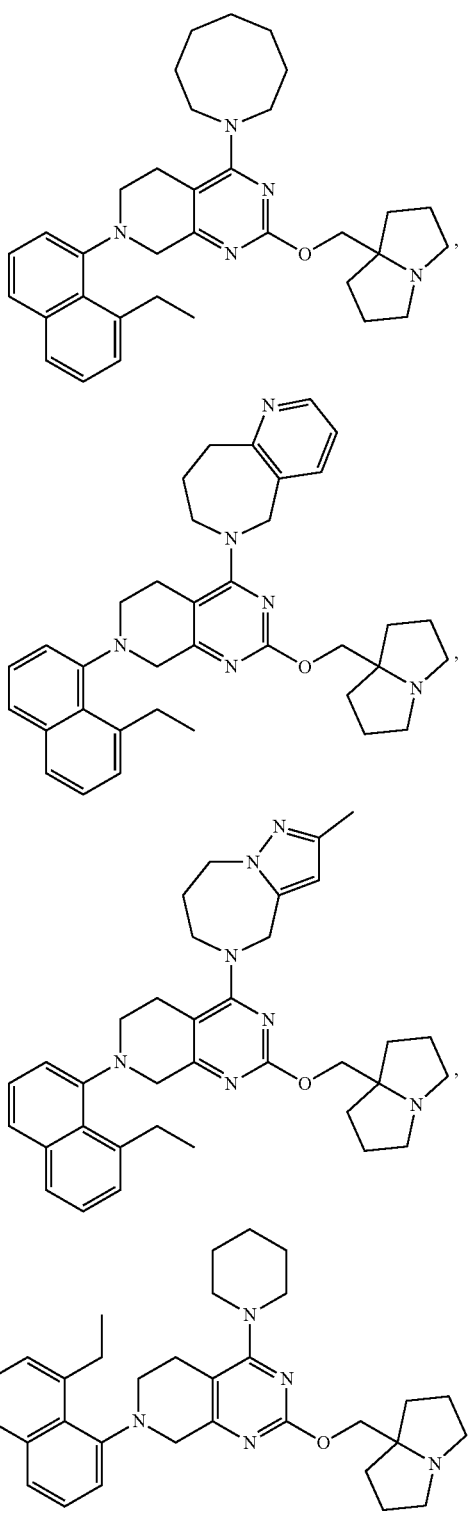
372
-continued
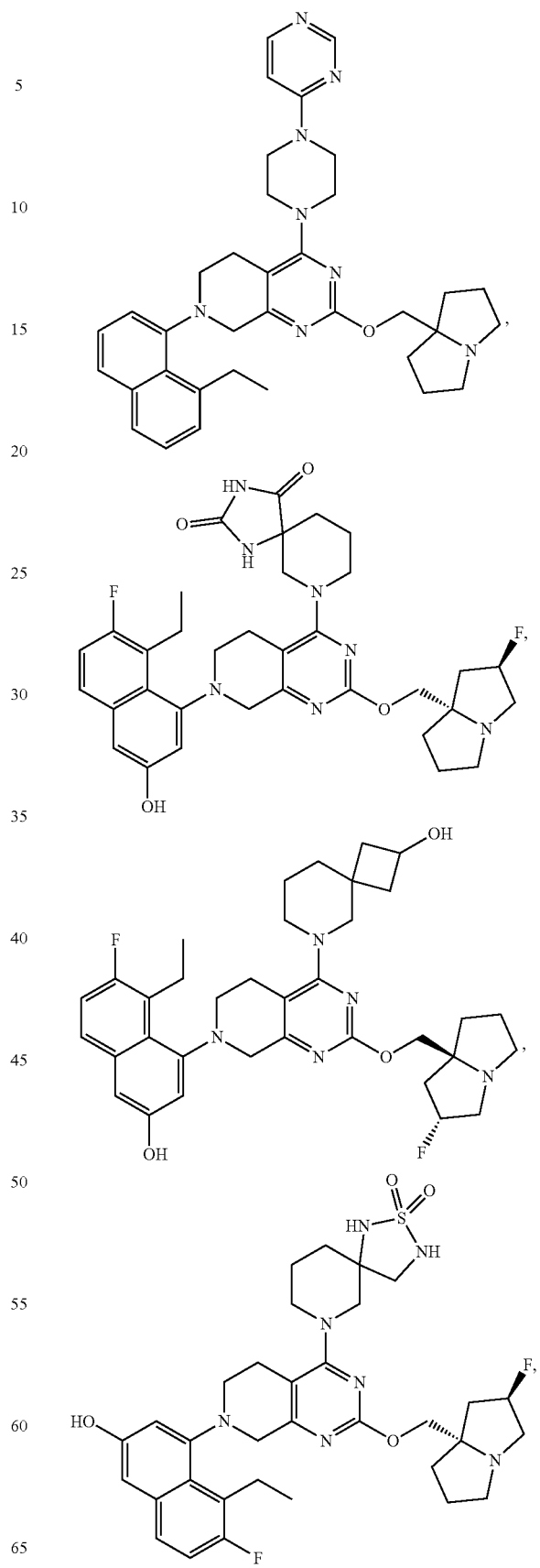

373
-continued
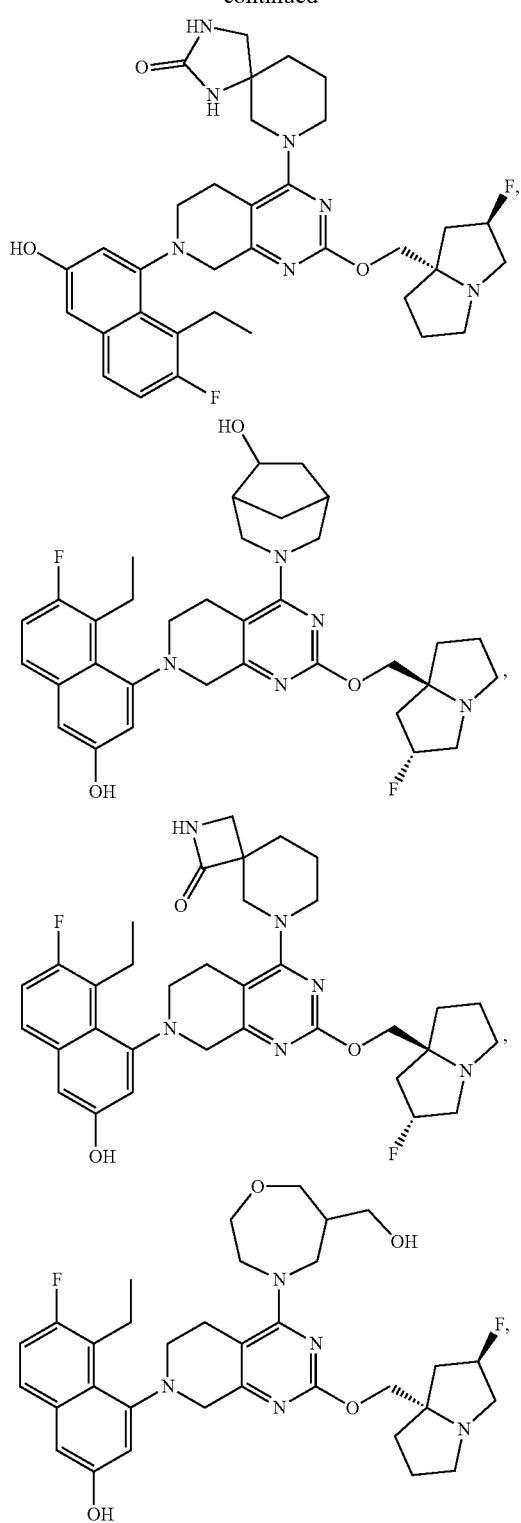
374
-continued
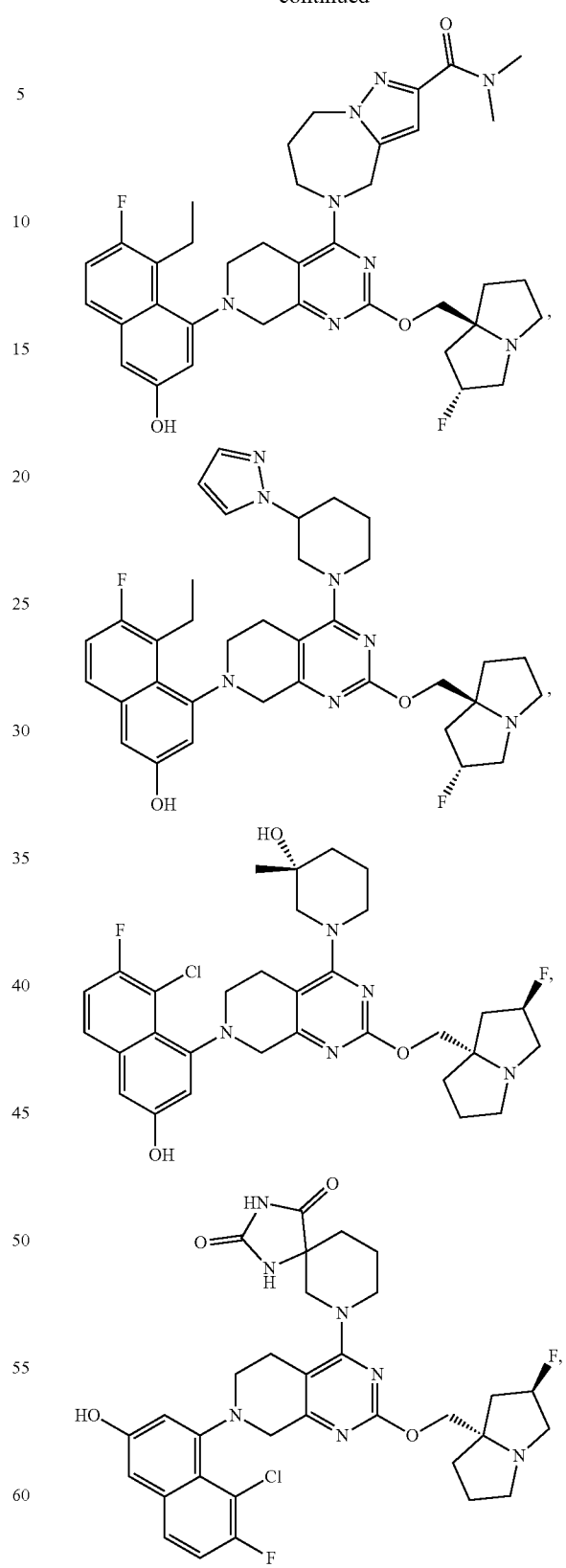

375
-continued
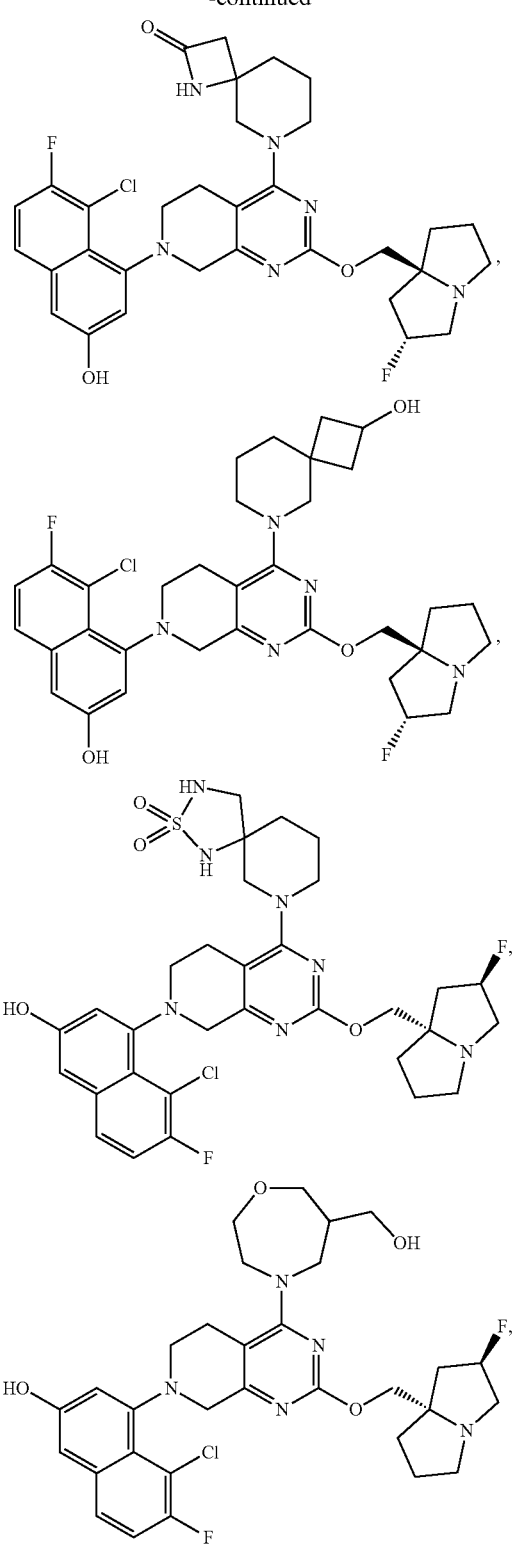
376
-continued
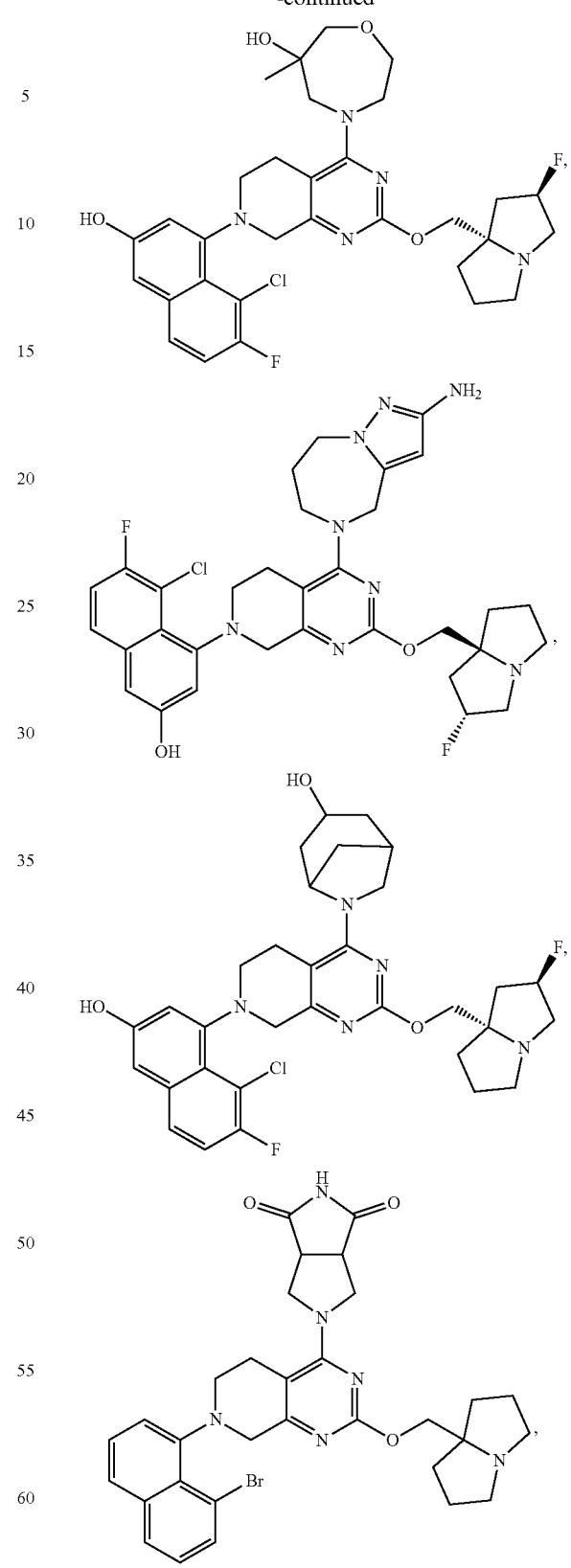

377
-continued
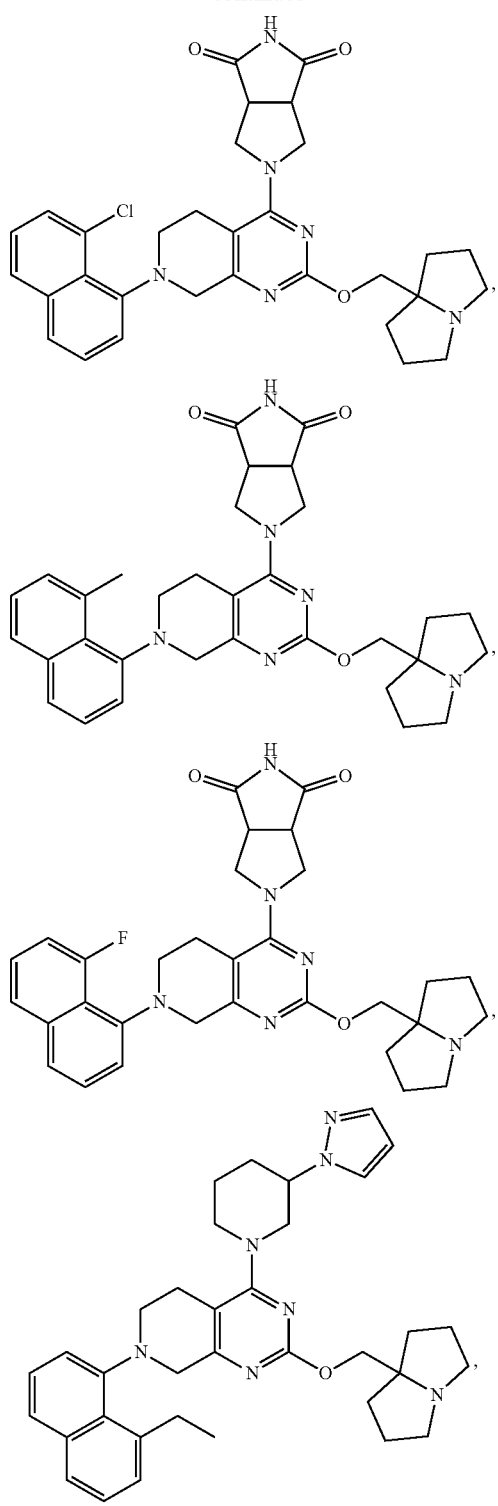
378
-continued
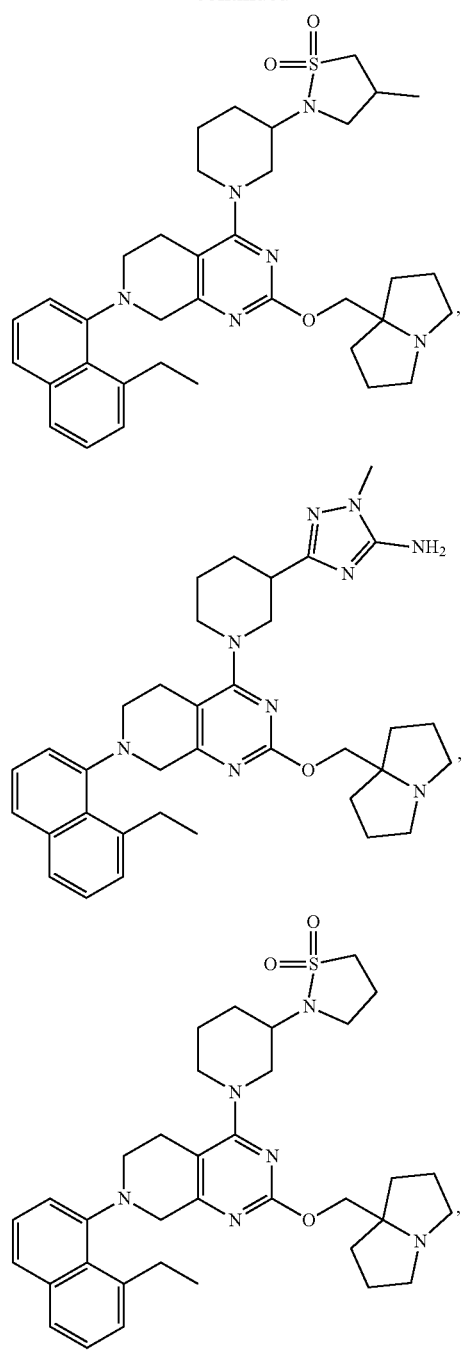

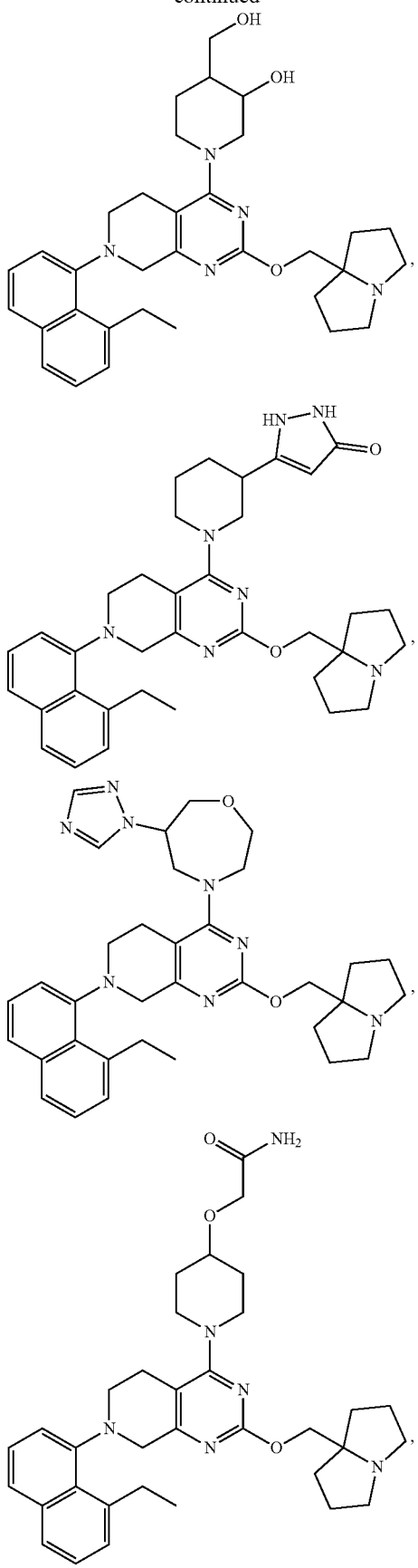
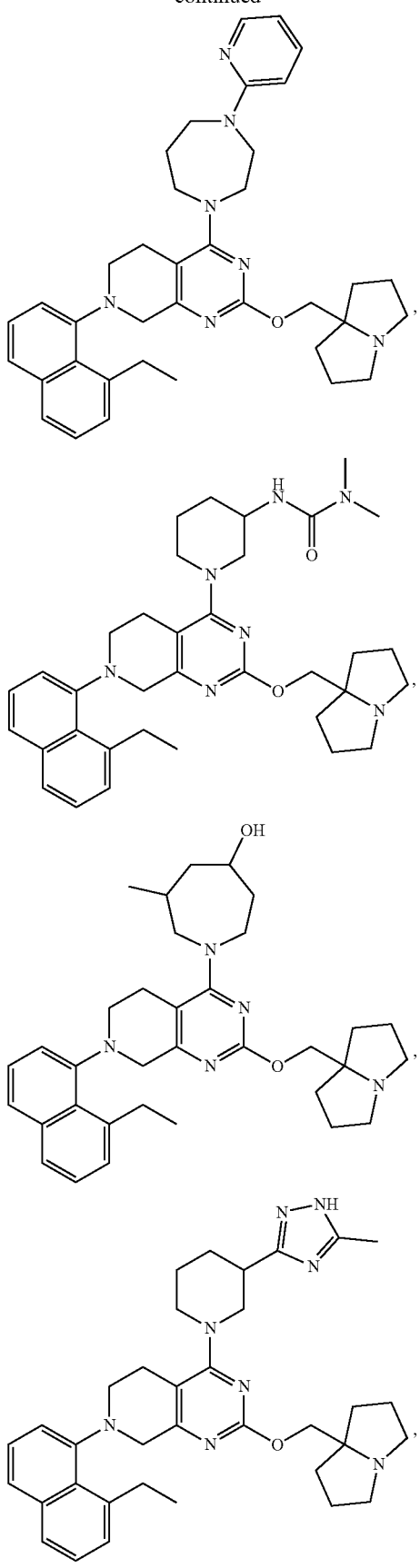

381
-continued
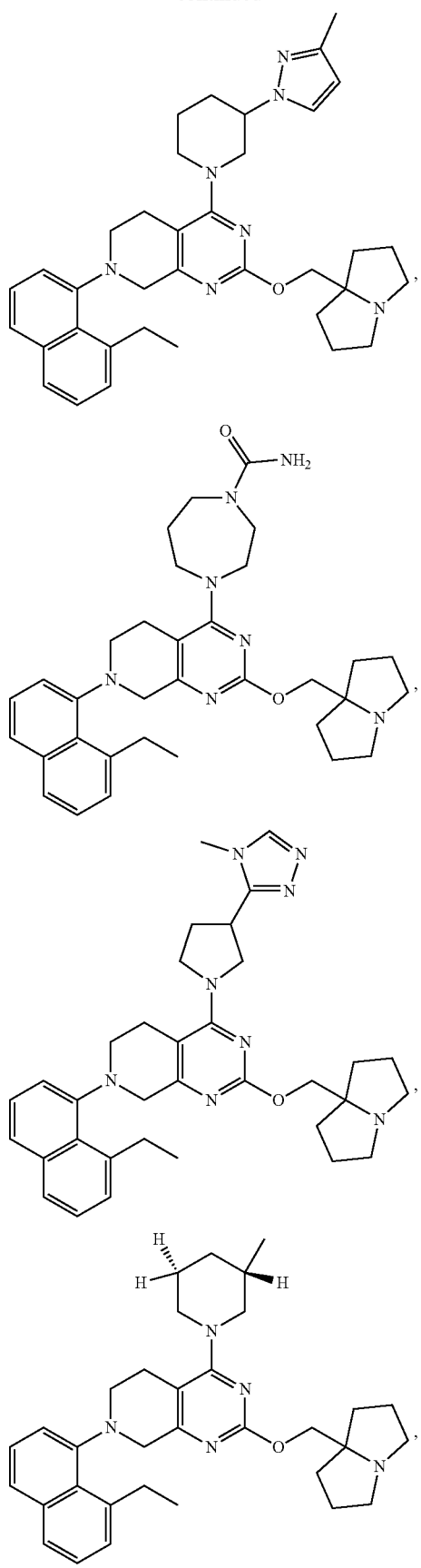
382
-continued
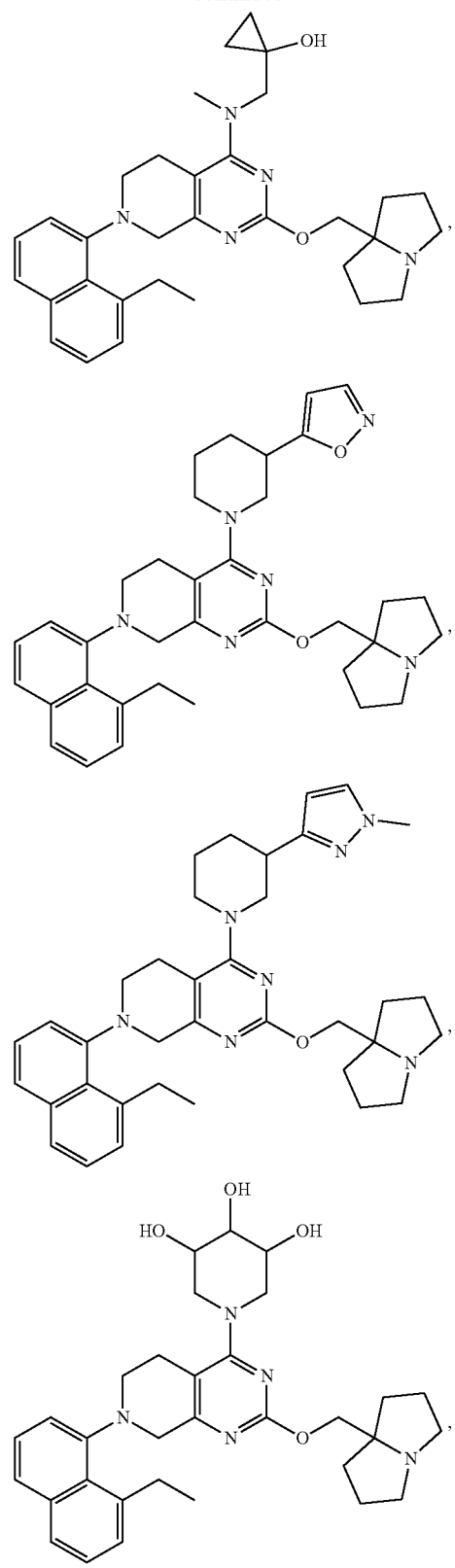

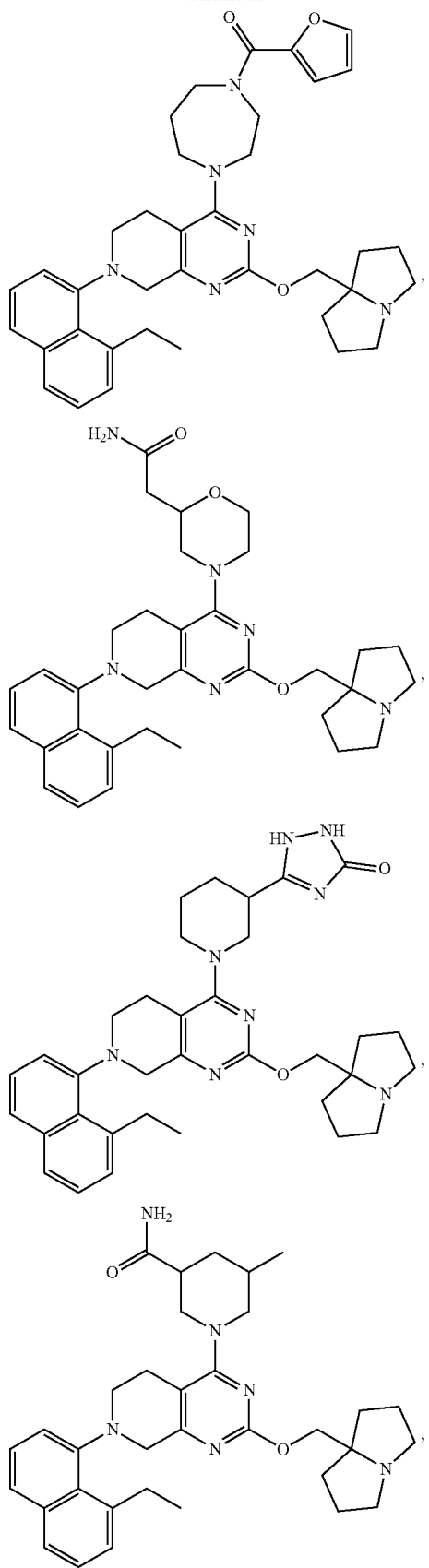

385
-continued
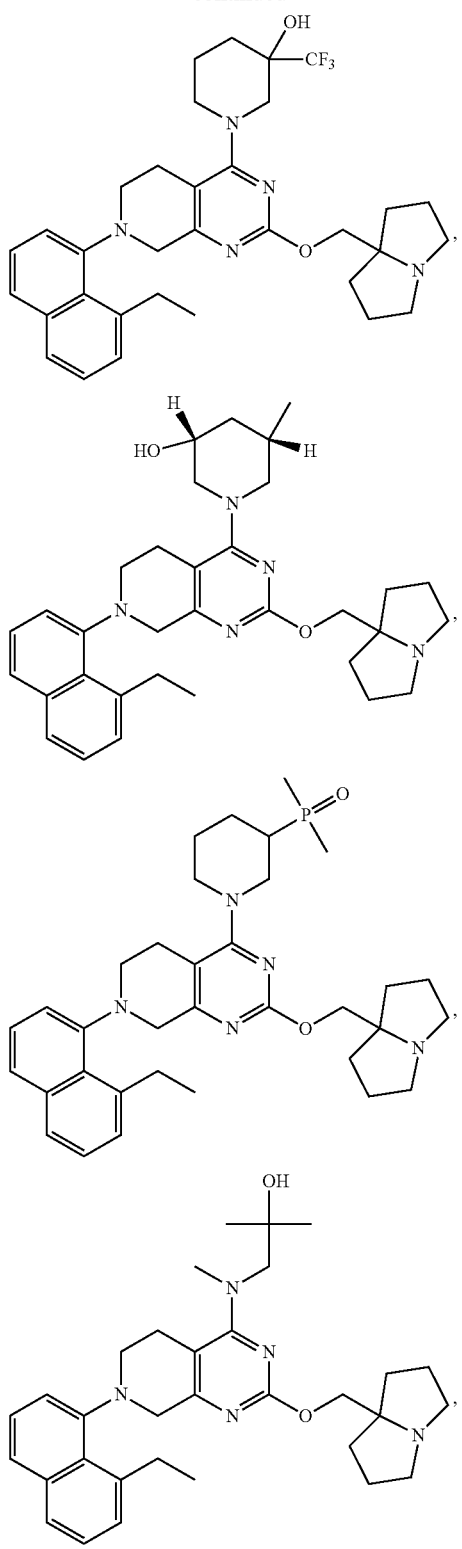
386
-continued
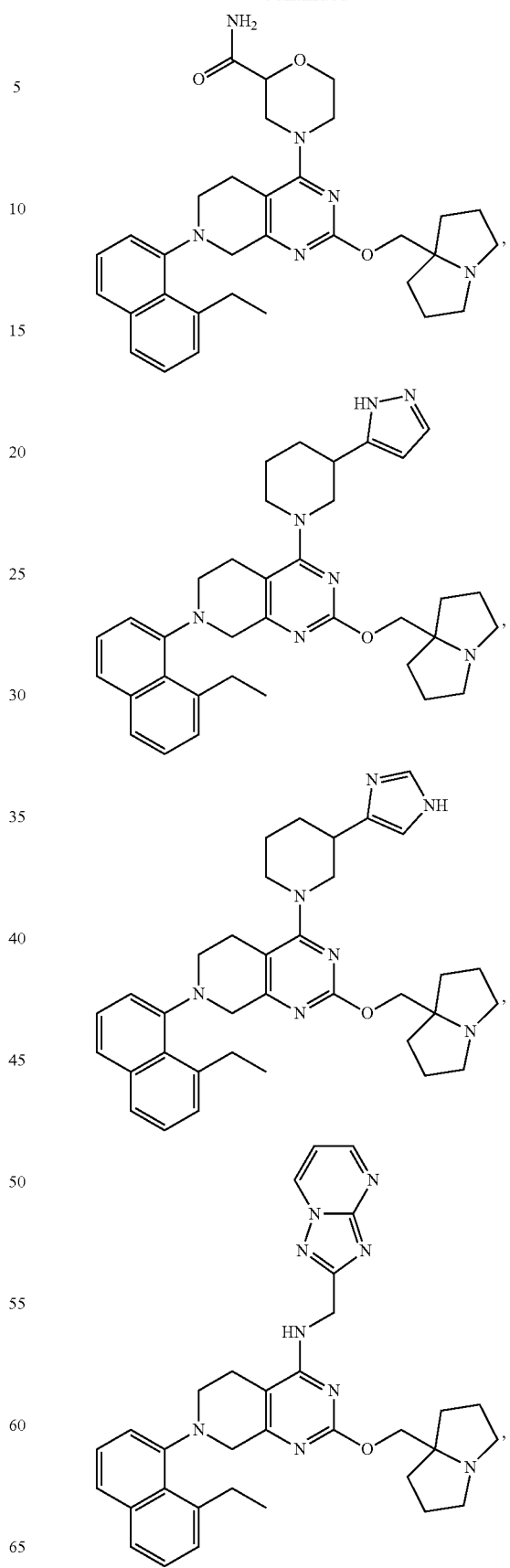

387
-continued
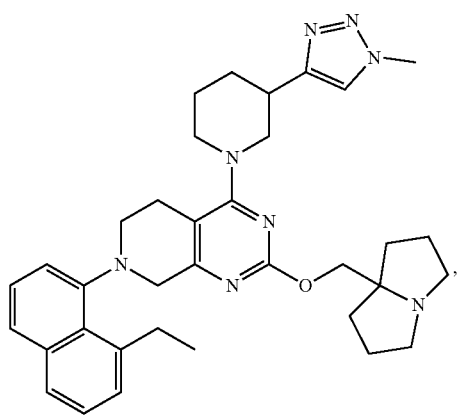
388
-continued
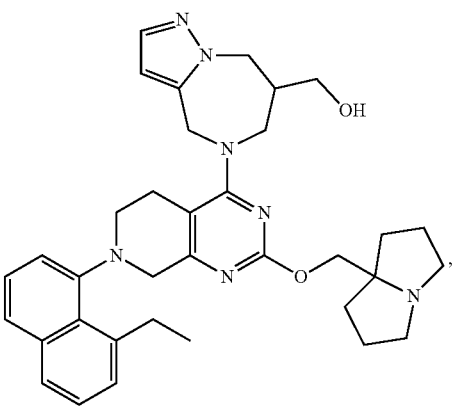
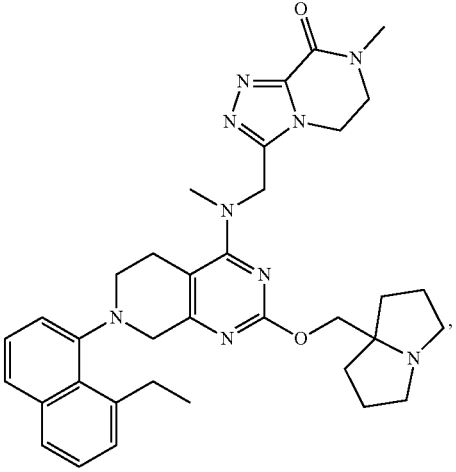
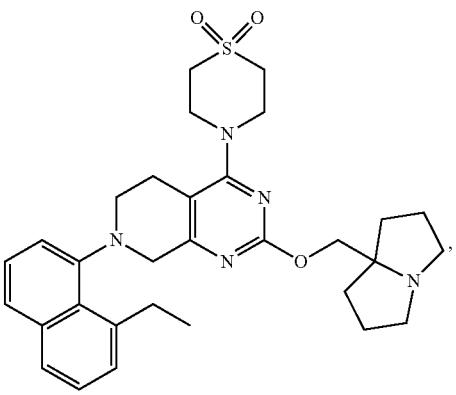
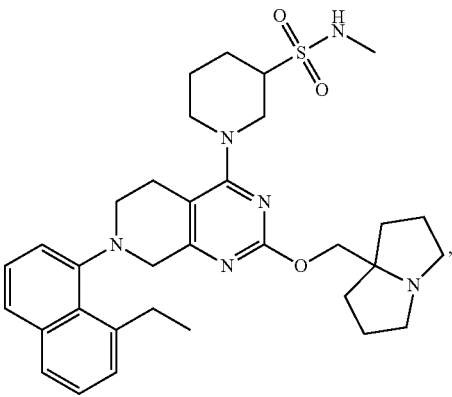

389
-continued
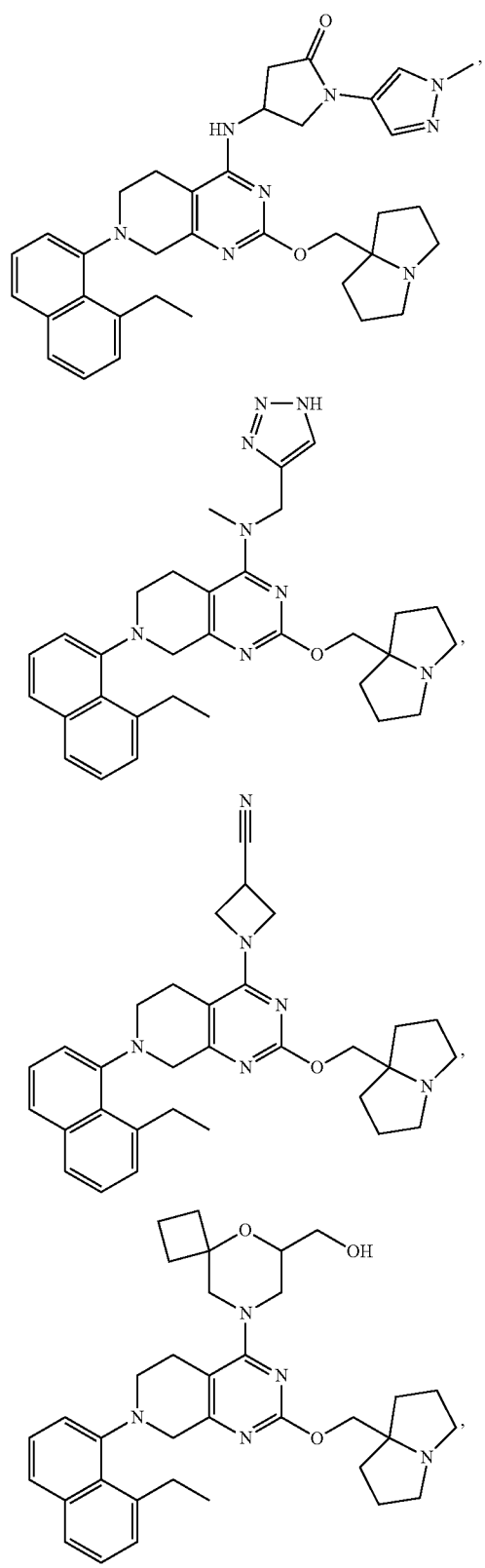
390
-continued
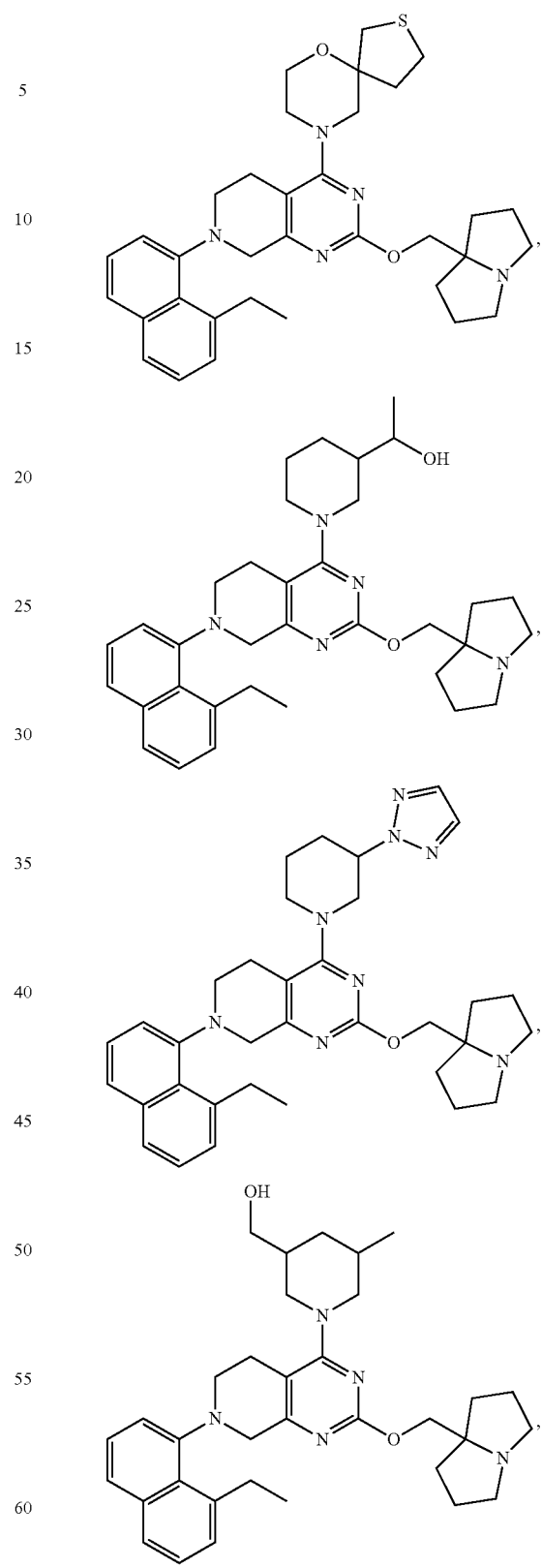

391
-continued
392
-continued
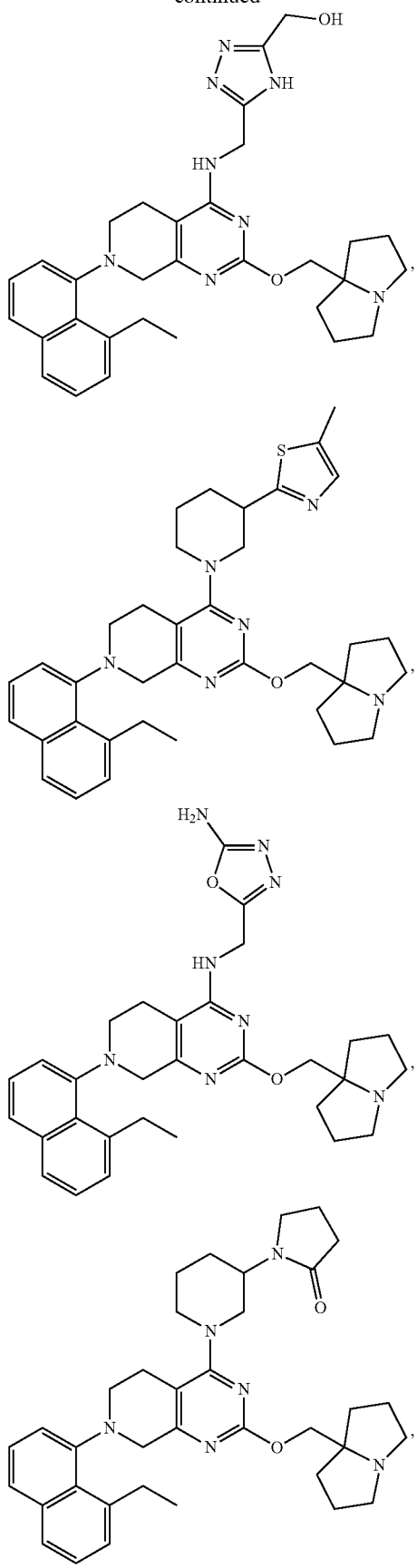
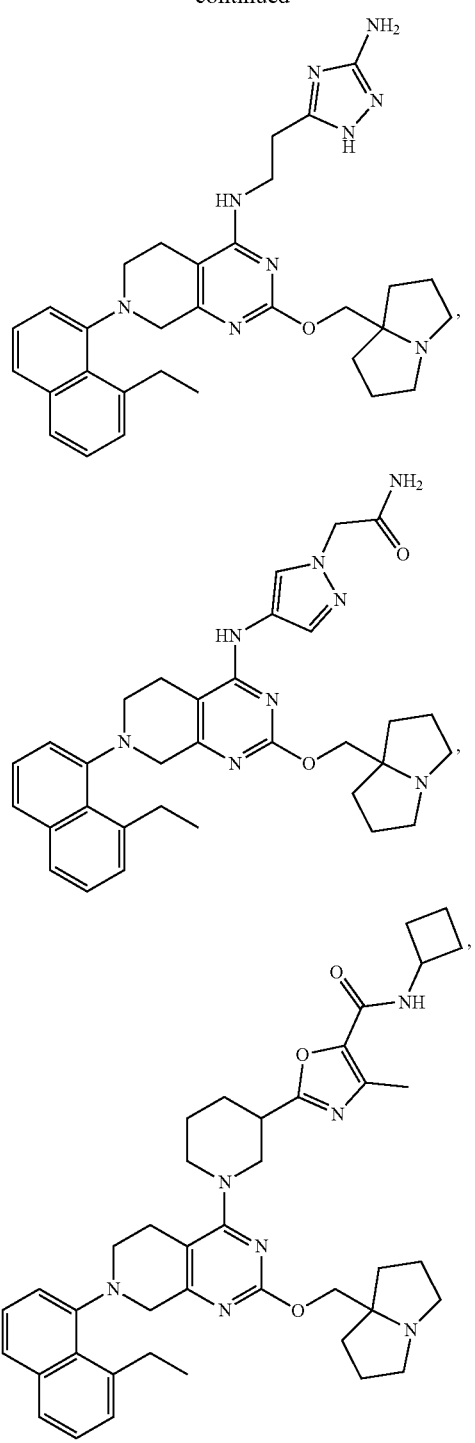

393
-continued
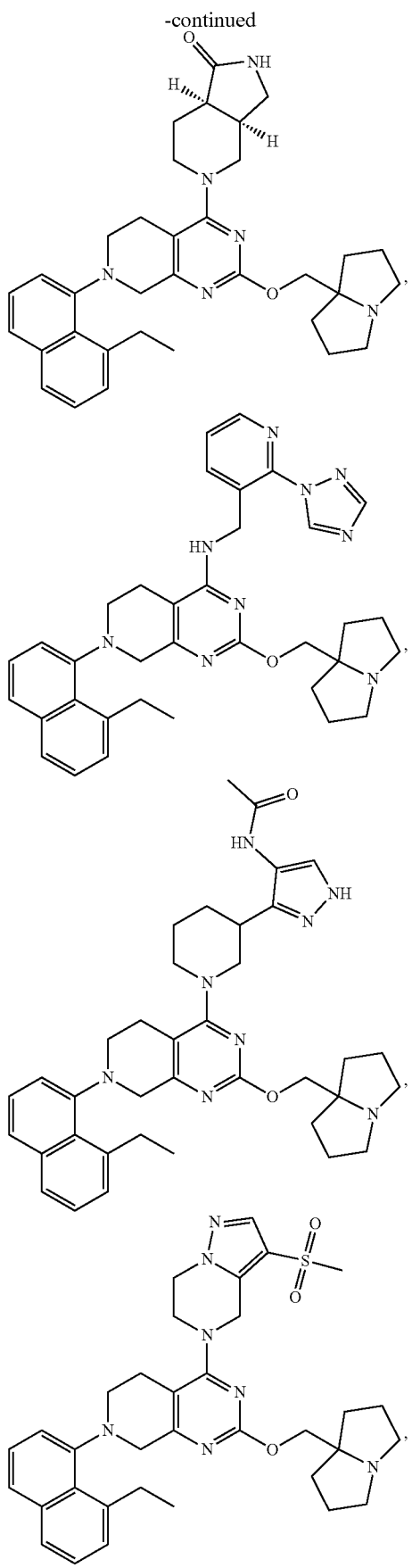
394
-continued
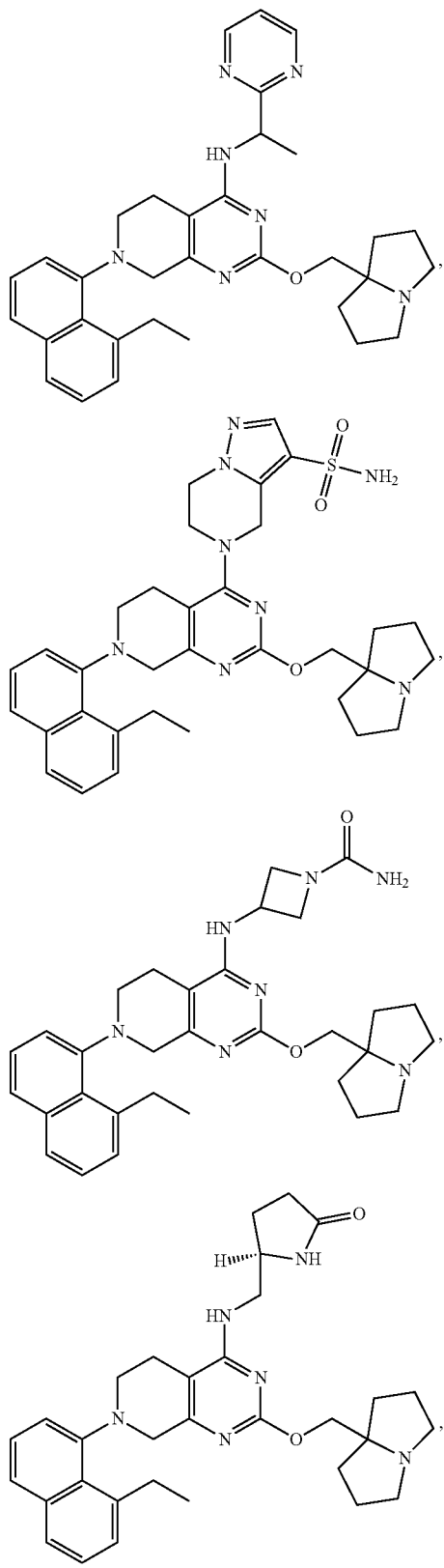

395
-continued
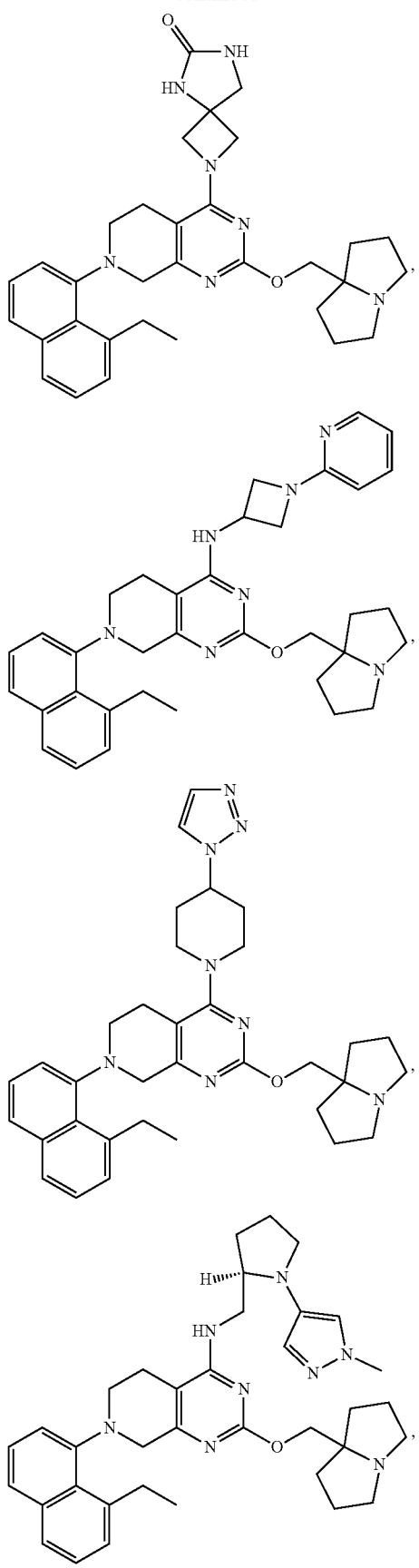
396
-continued
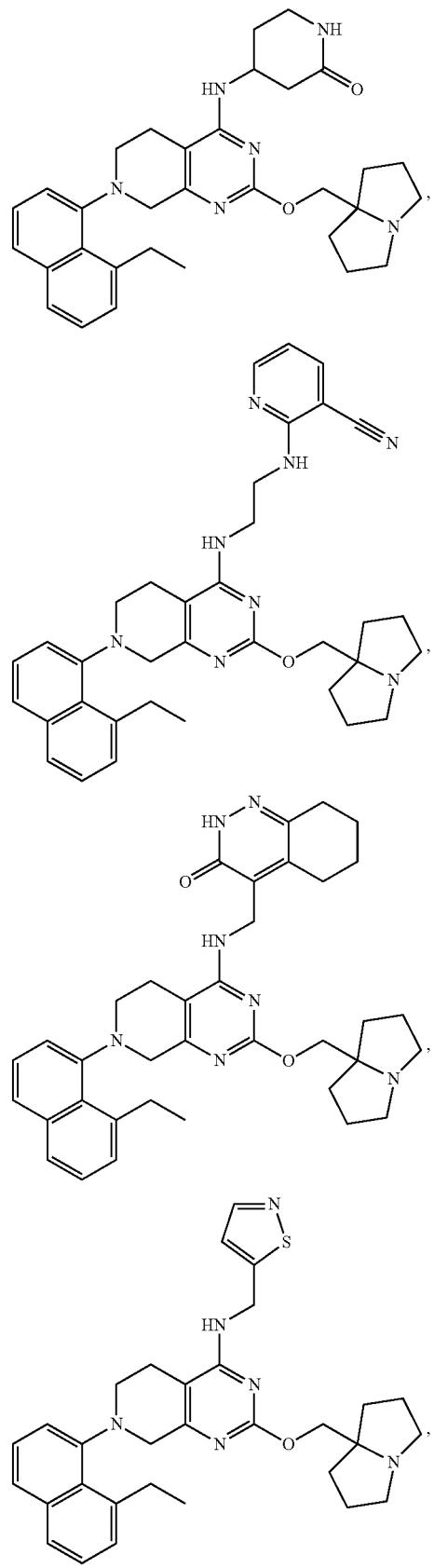

397
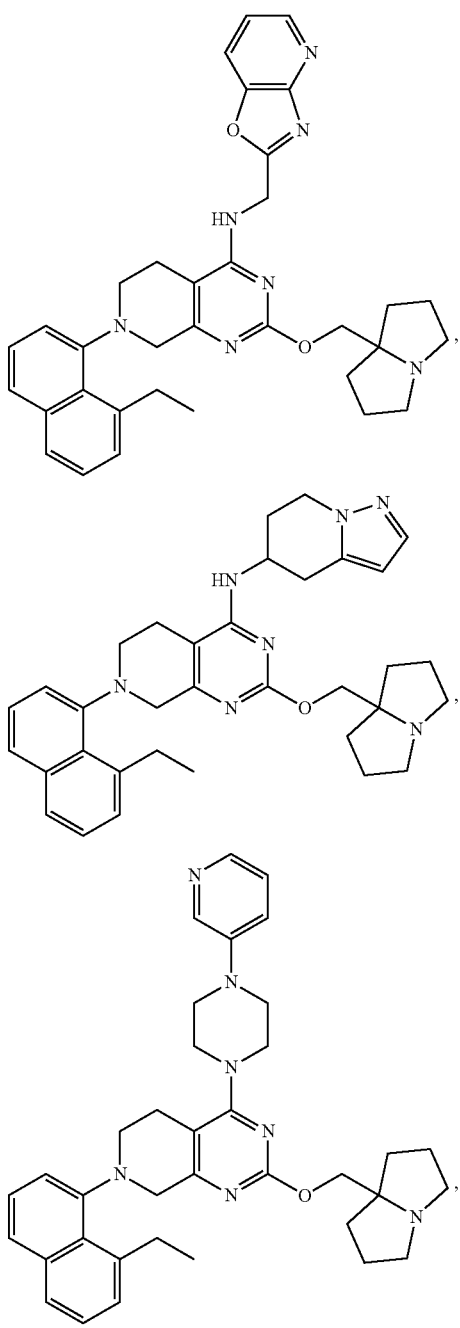
398
-continued
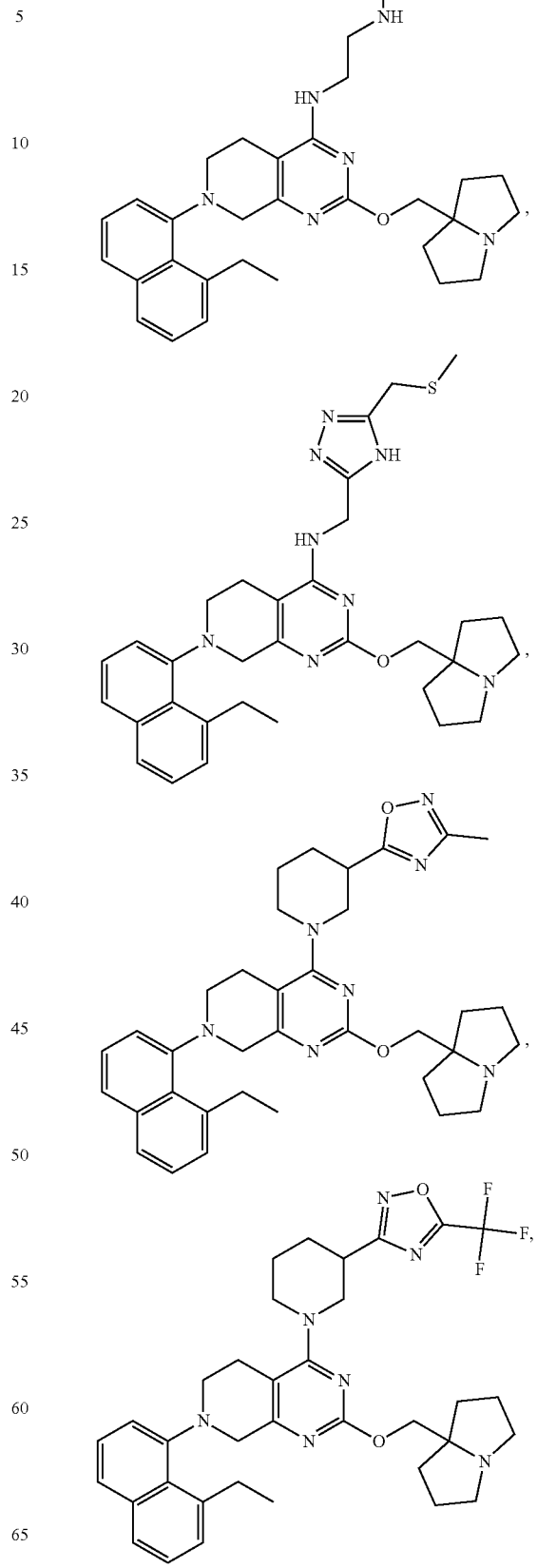

399
-continued

400
-continued

401
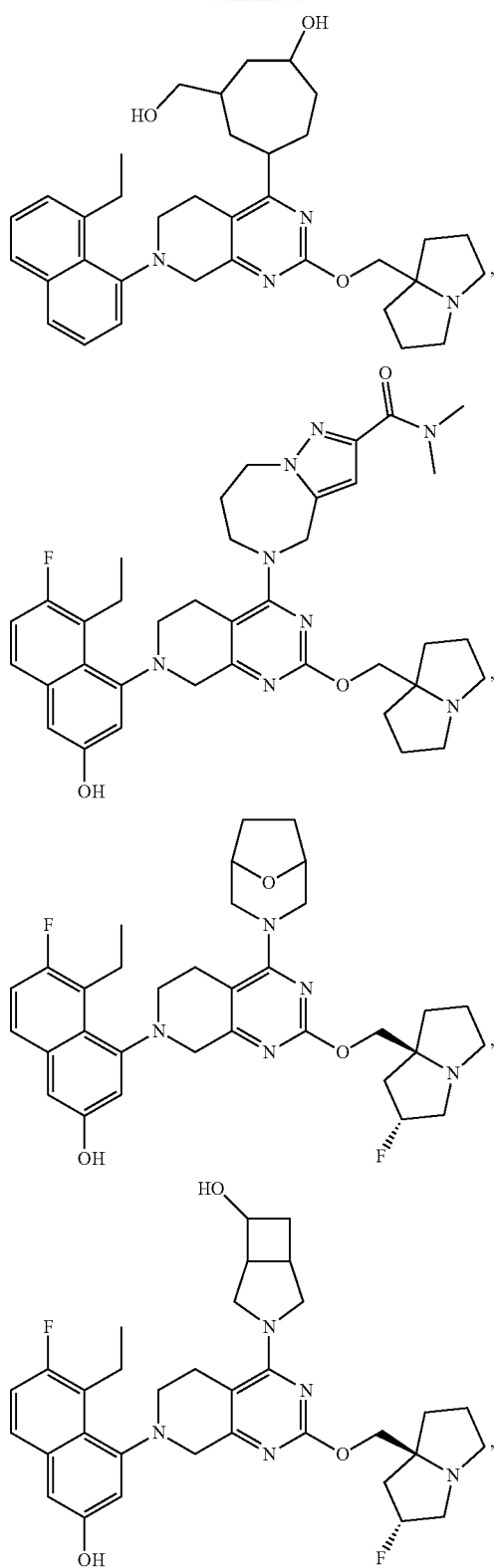
402
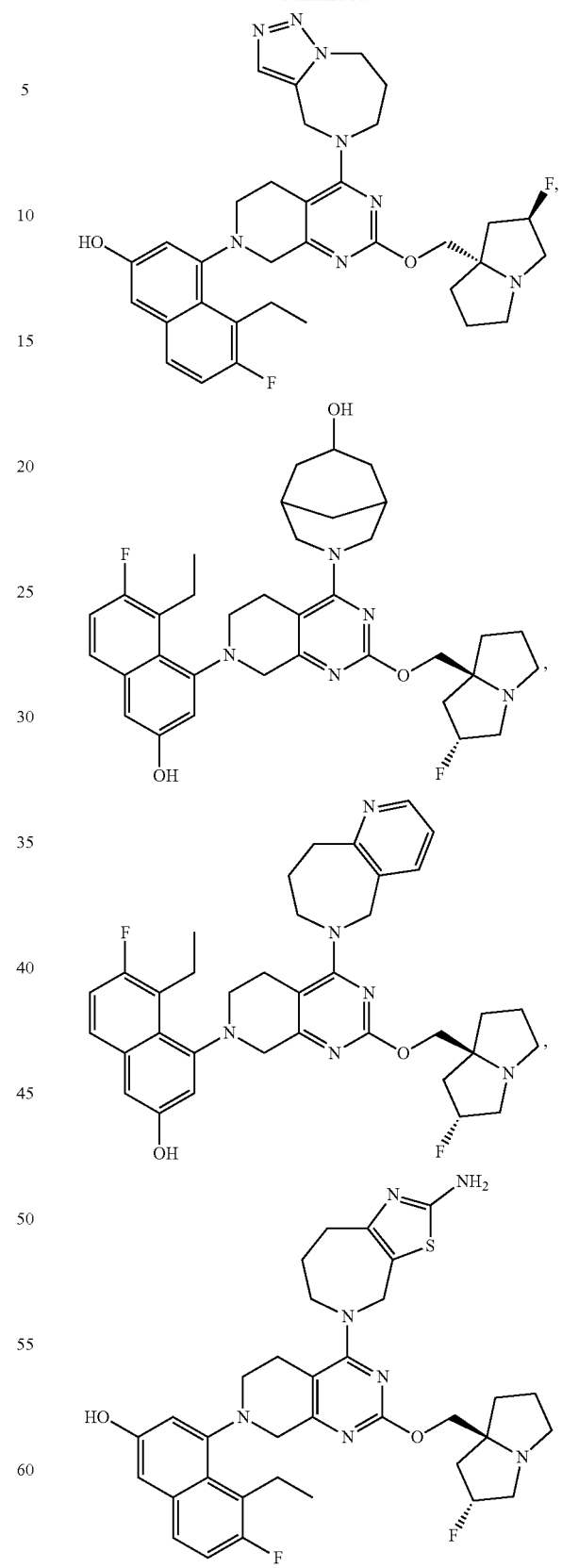

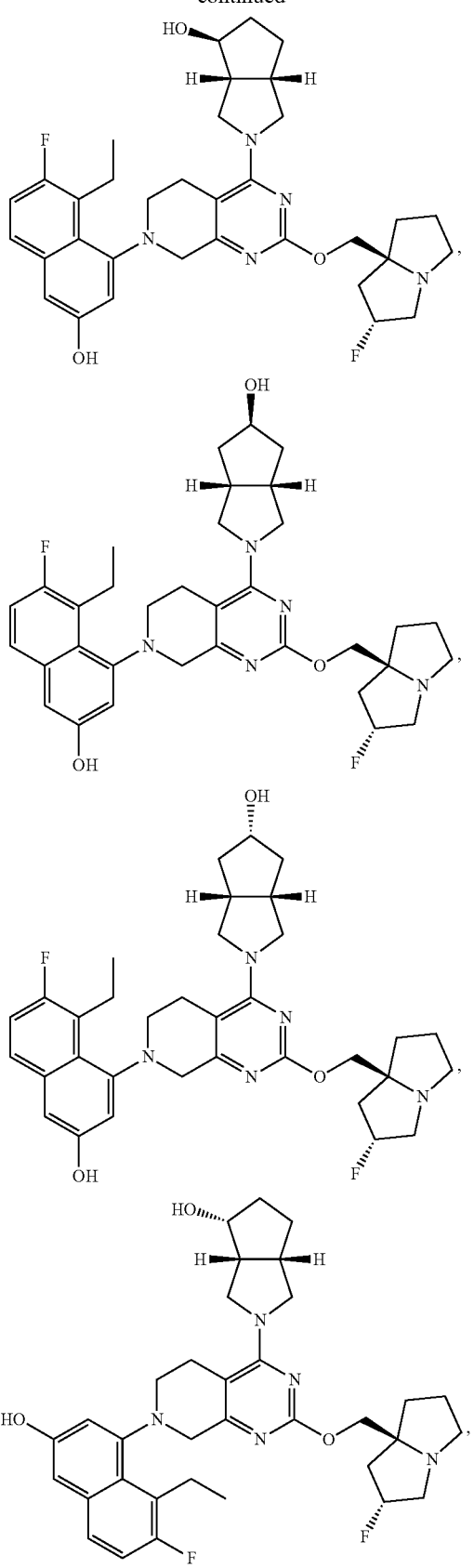
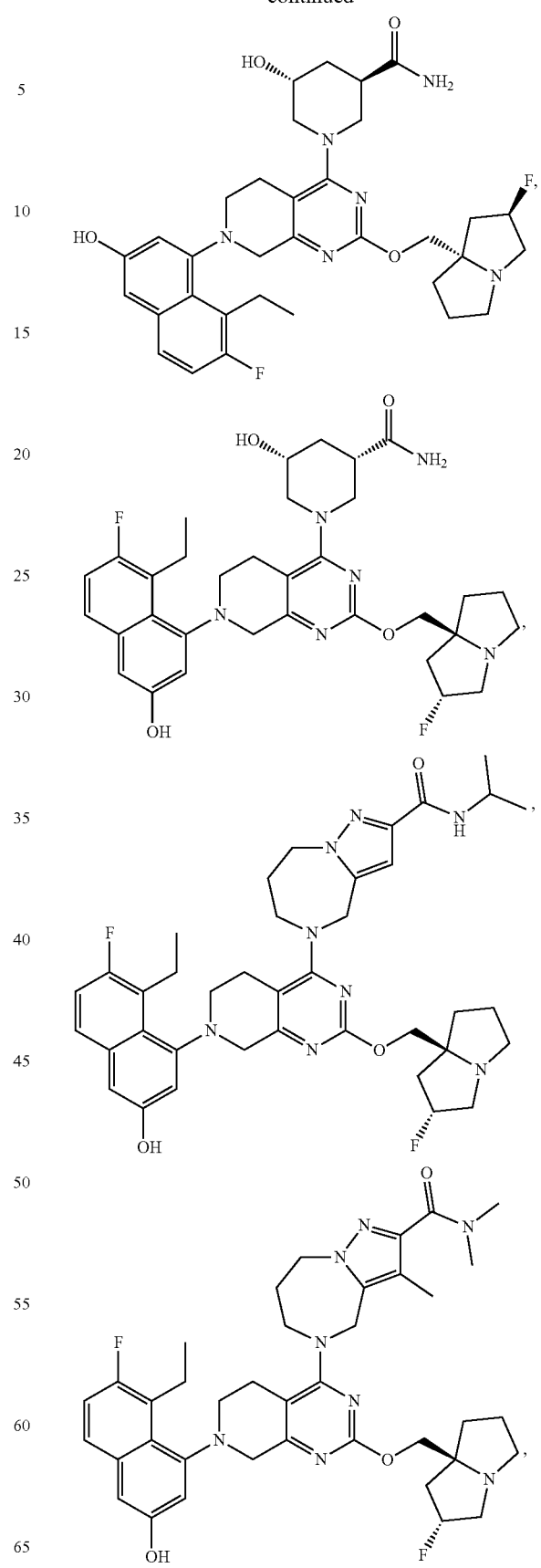

405
-continued
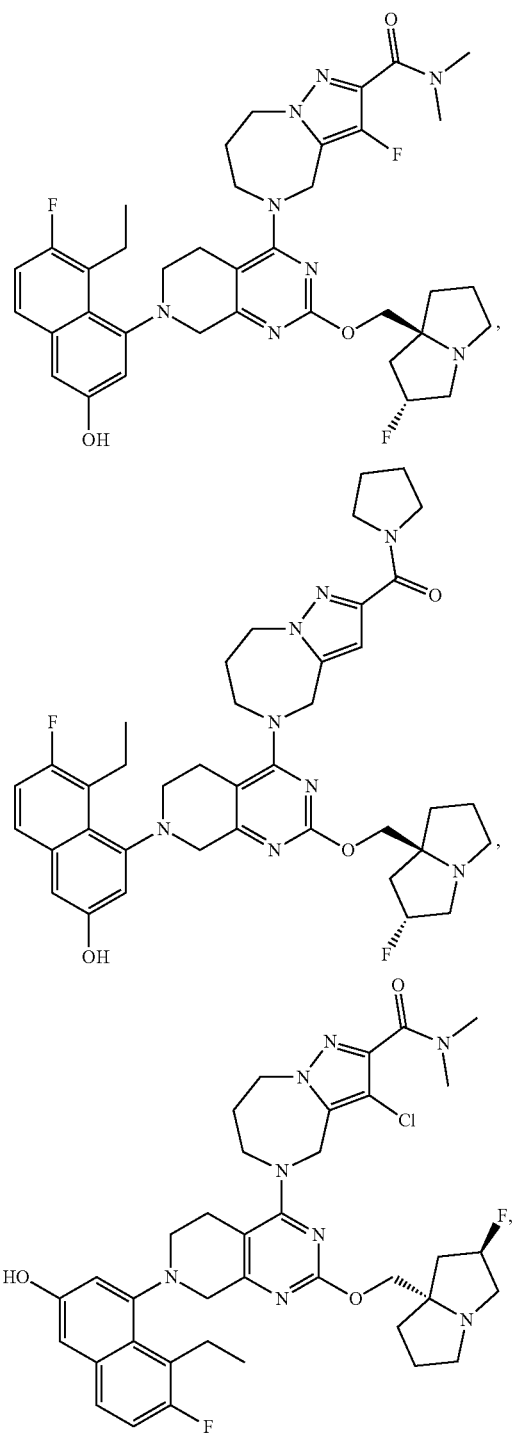
406
-continued
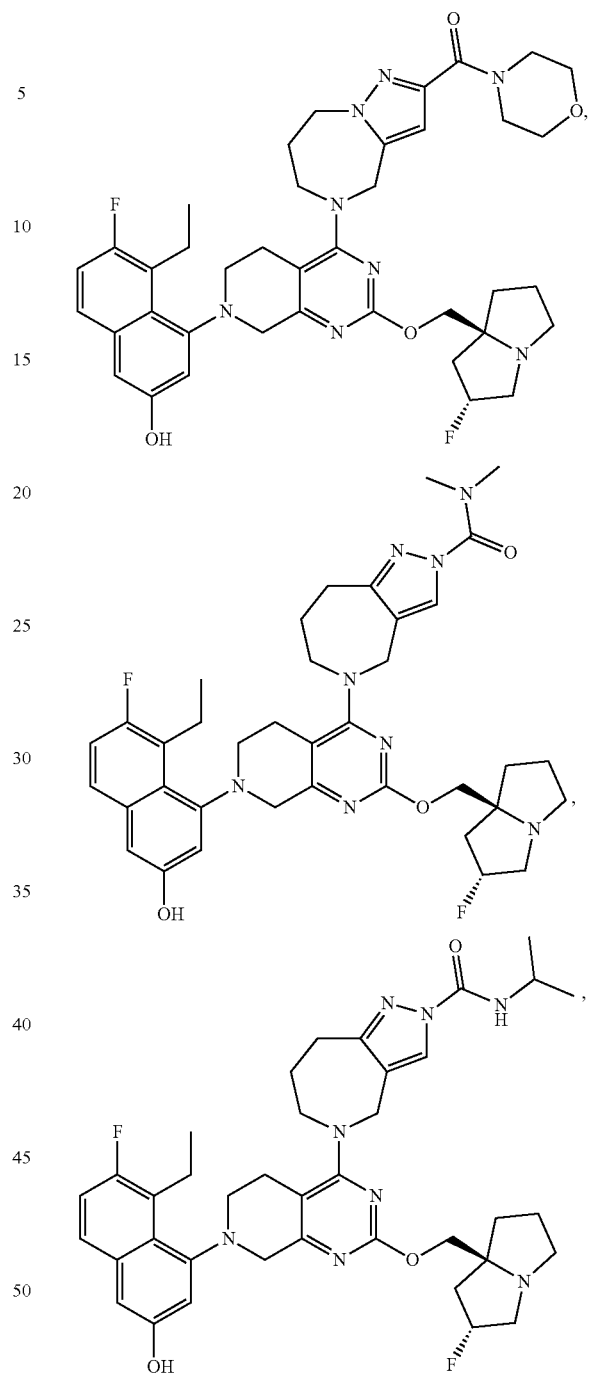

407
-continued
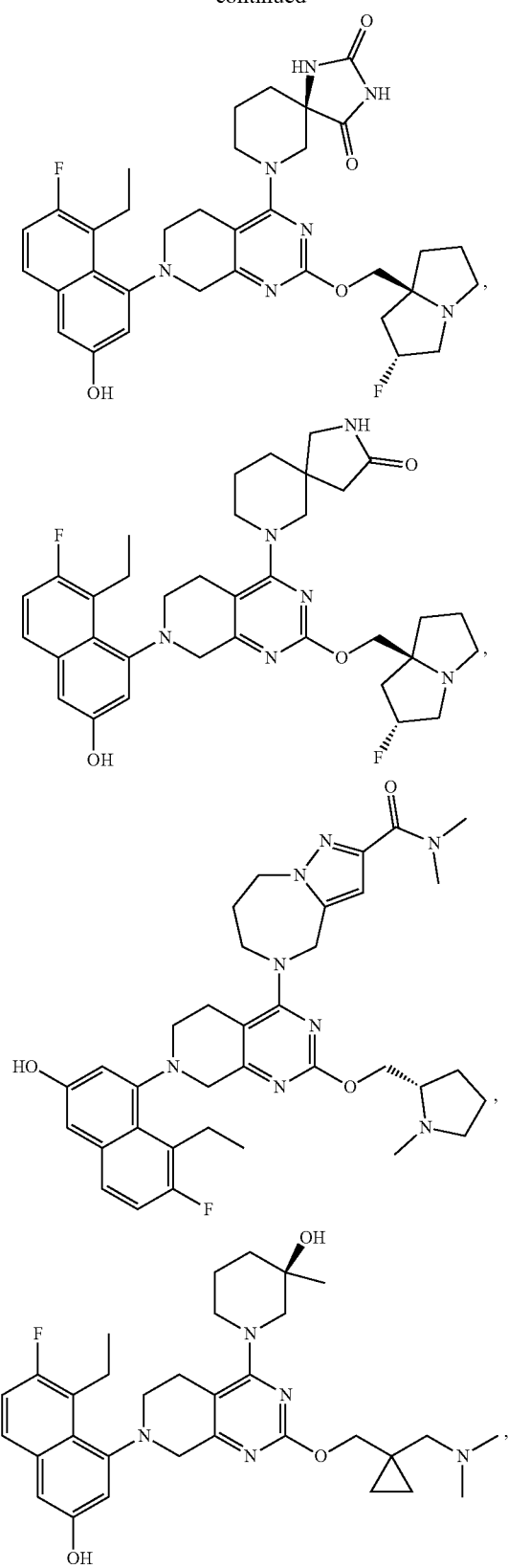
408
-continued
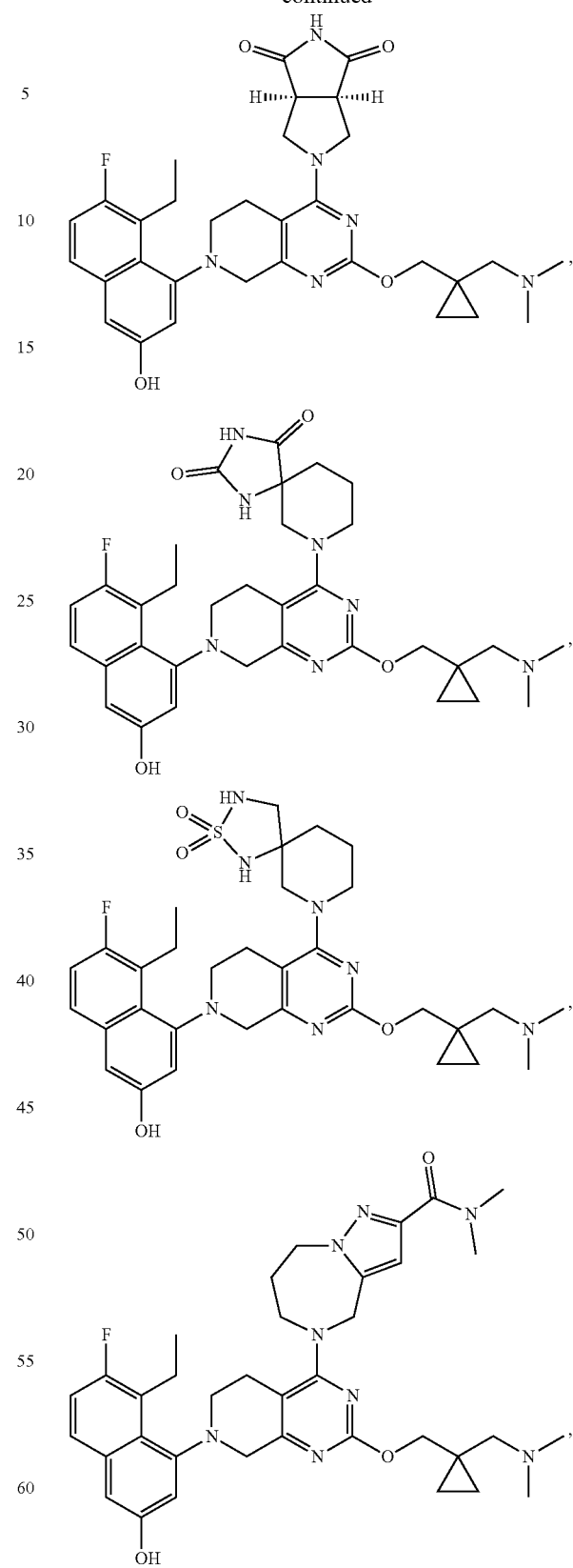

409
-continued
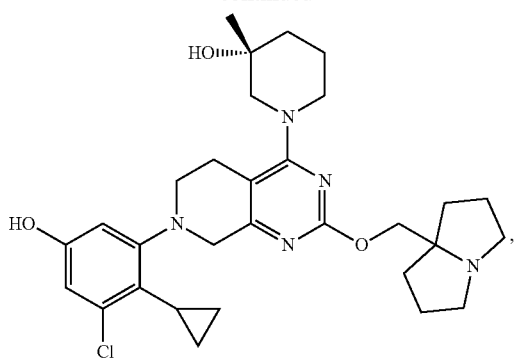
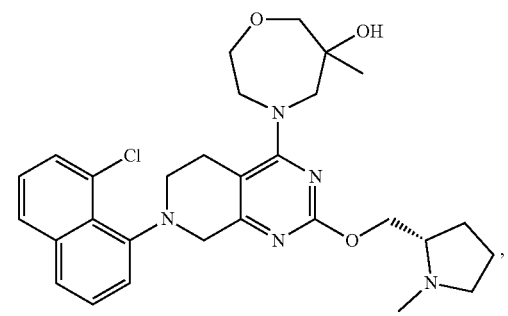
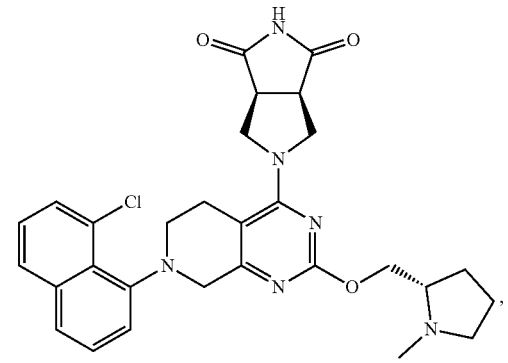
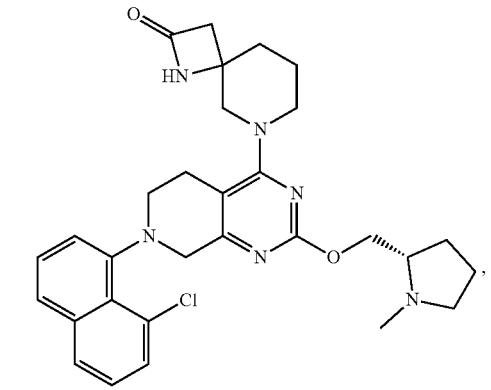
410
-continued
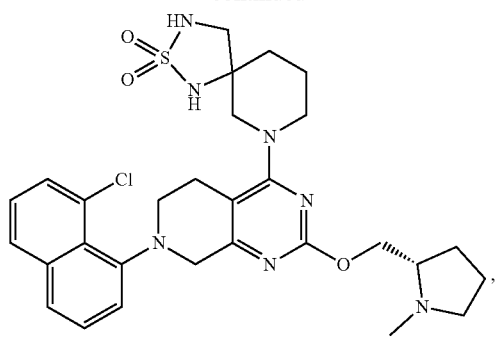
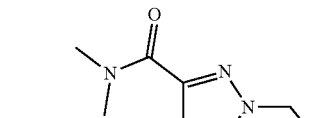
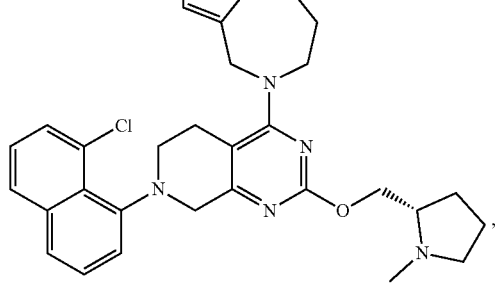
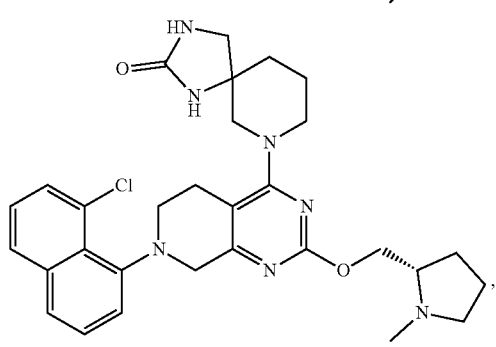

411
-continued
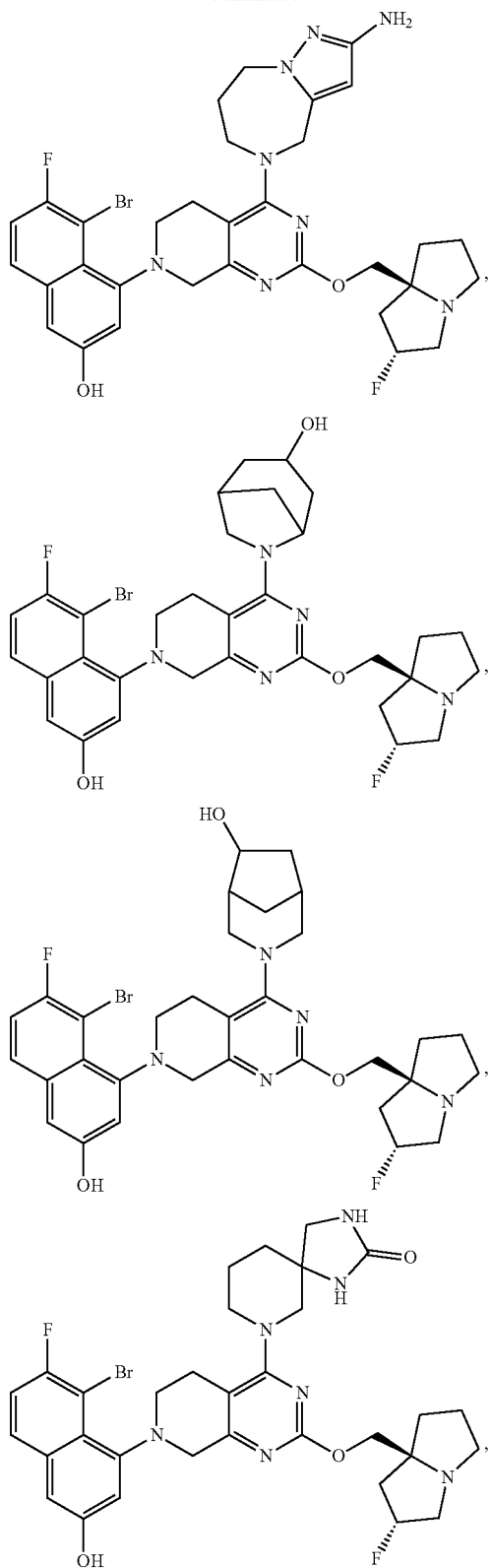
412
-continued
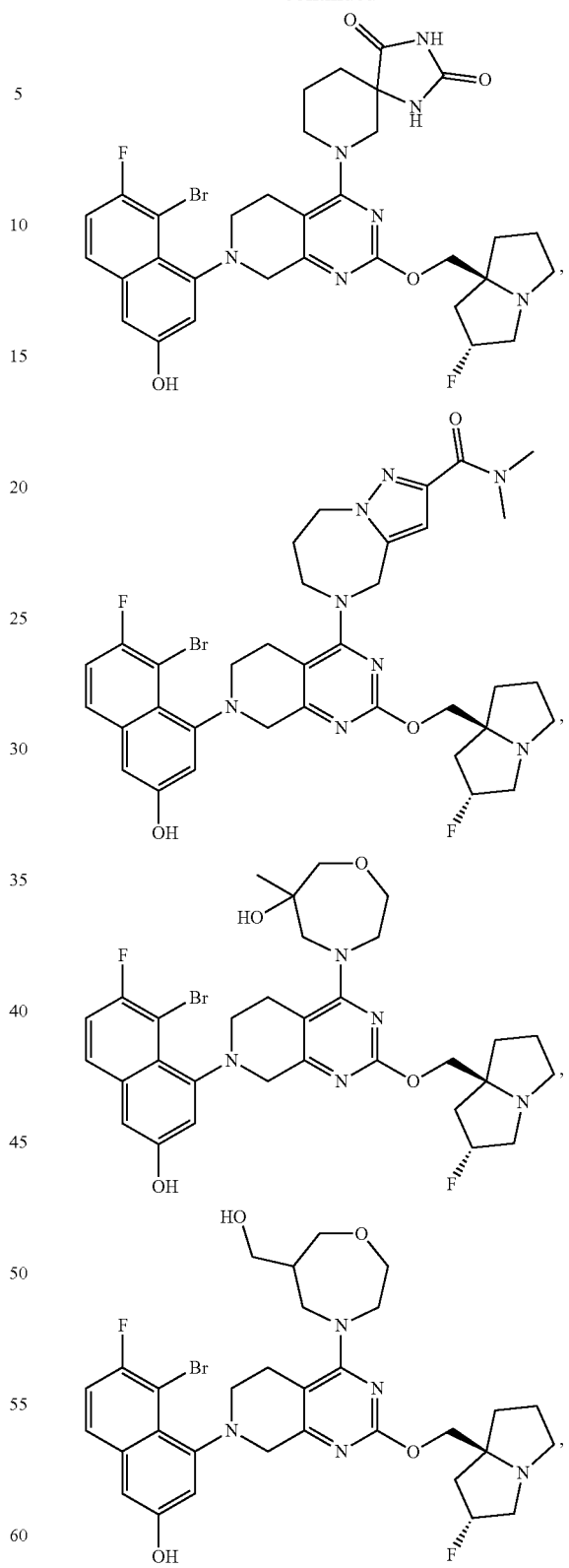

413
-continued
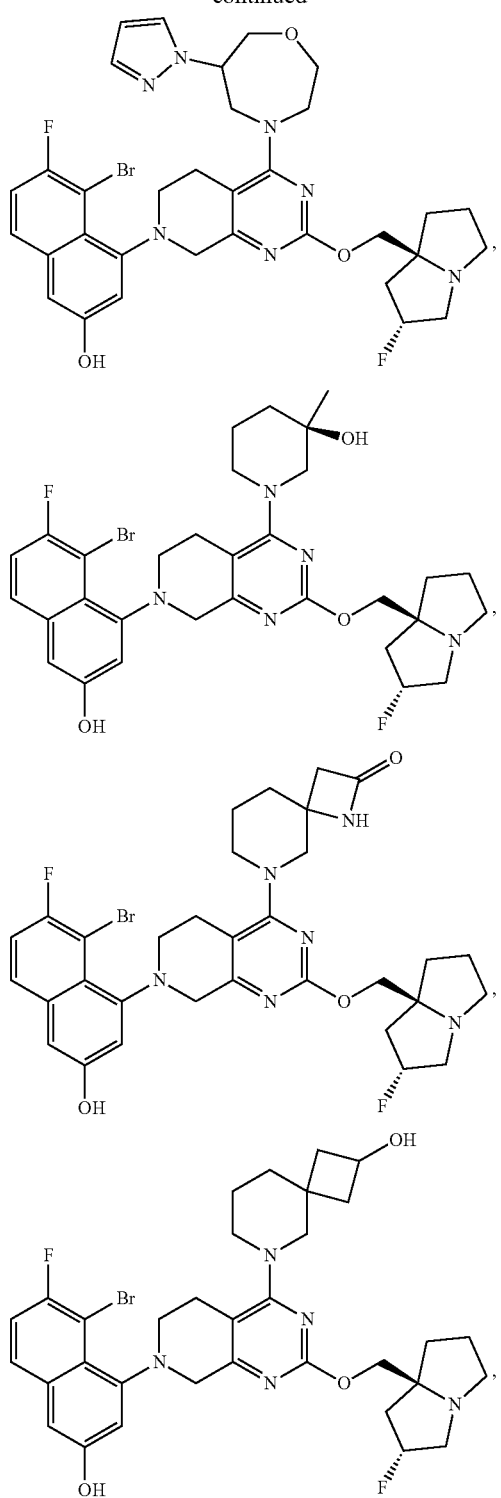
414
-continued
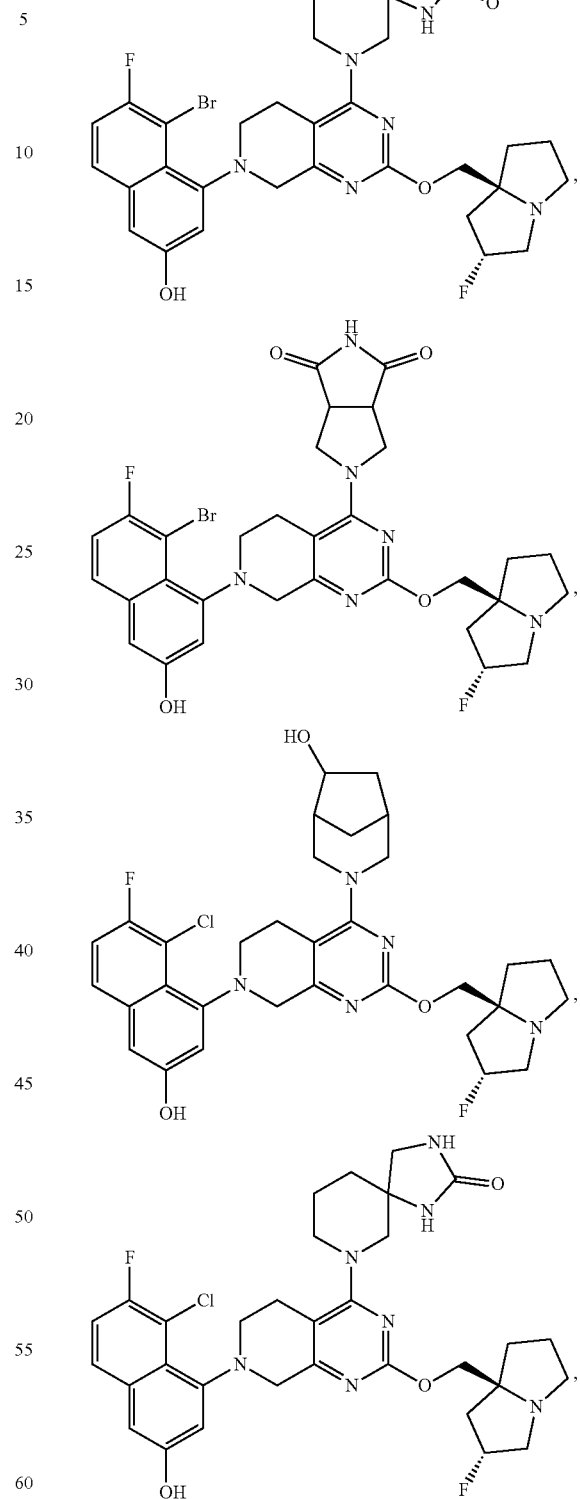

415

-continued

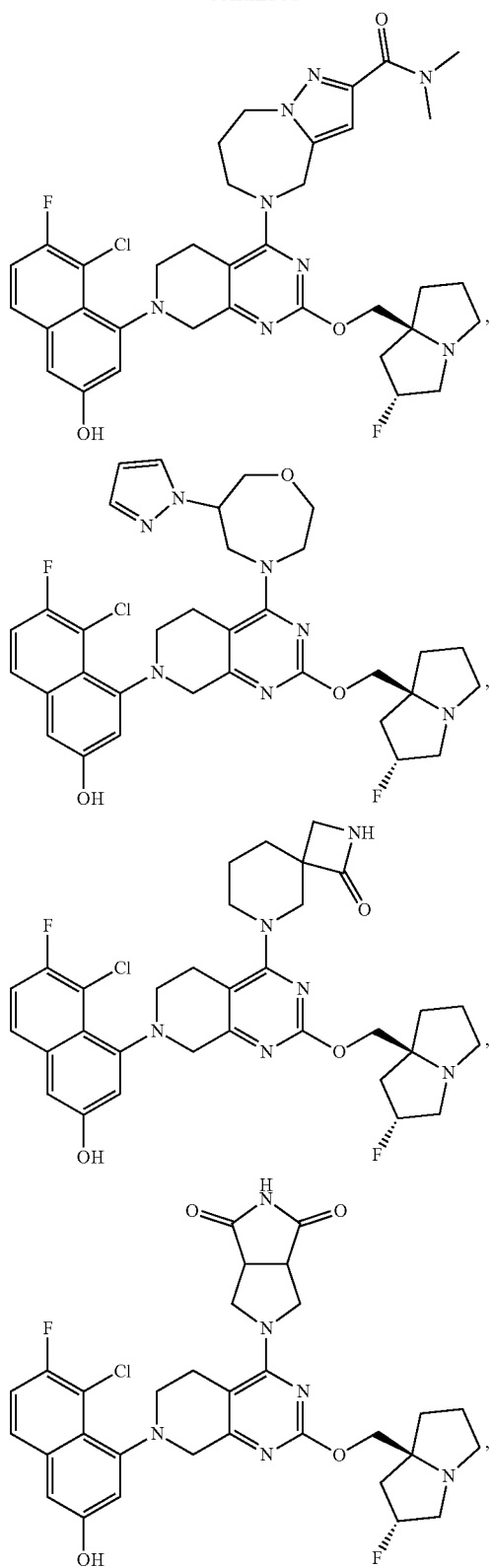

and a pharmaceutically acceptable salt thereof.

6. The method of claim 5, wherein the compound is

416

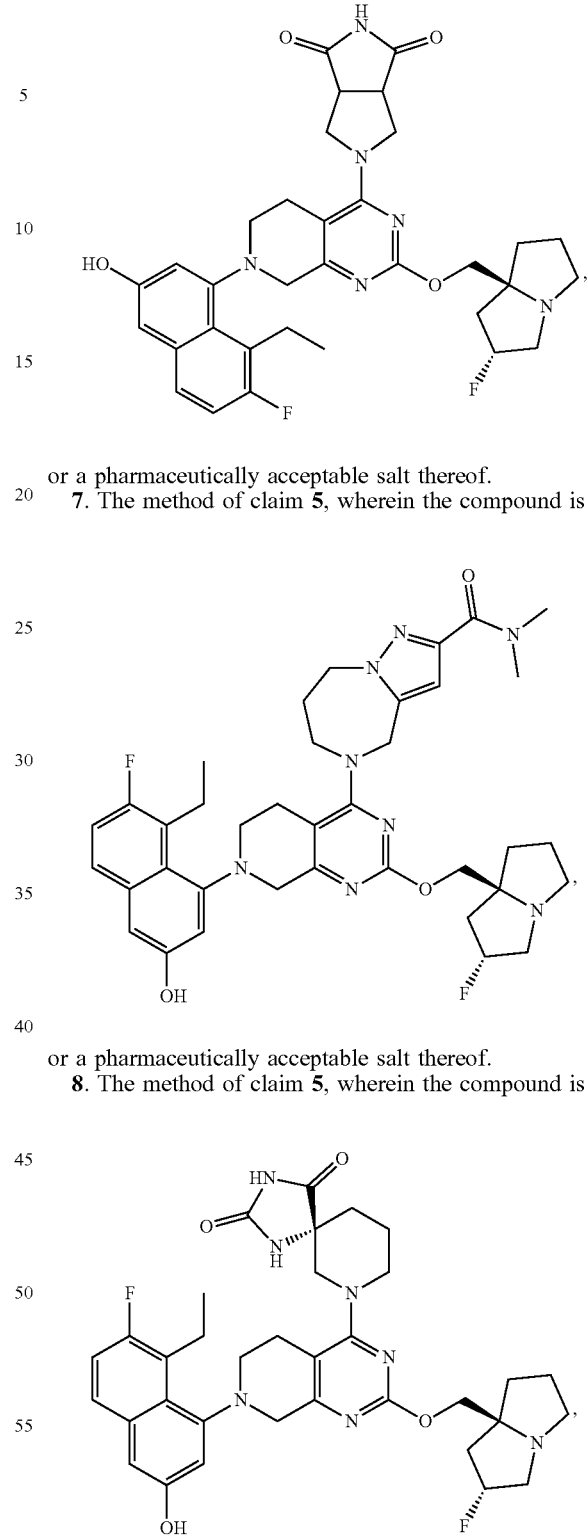

or a pharmaceutically acceptable salt thereof.

7. The method of claim 5, wherein the compound is or a pharmaceutically acceptable salt thereof.

8. The method of claim 5, wherein the compound is or a pharmaceutically acceptable salt thereof.

9. The method of claim 5, wherein the therapeutically effective amount of the compound is between about 0.01 to 100 mg/kg per day.

10. The method of claim 9, wherein the therapeutically effective amount of the compound is between about 0.1 to 50 mg/kg per day.

11. The method of claim 5, wherein the cancer is selected from the group consisting of cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial 'carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

12. The method of claim 11, wherein the cancer is a KRas G12A-associated cancer.

13. The method of claim 11, wherein the cancer is a KRas G12C-associated cancer.

14. The method of claim 11, wherein the cancer is a KRas G12D-associated cancer.

15. The method of claim 11, wherein the cancer is a KRas G12R-associated cancer.

16. The method of claim 11, wherein the cancer is a KRas G12S-associated cancer.

17. The method of claim 11, wherein the cancer is a KRas G12V-associated cancer.

18. The method of claim 11, wherein the cancer is a KRas G13D-associated cancer.

19. The method of claim 11, wherein the cancer is a KRas Q61H-associated cancer.

20. The method of claim 11, wherein the cancer is a wild type KRas-associated cancer.

21. The method of claim 11, wherein the cancer is associated with at least one of KRas wild type or KRas G12A, KRas G12C, KRas G12D, KRas G12R, KRas G12S, KRas G12V, KRas G13D or KRas Q61H.

22. The method of claim 11, wherein the cancer is non-small cell lung cancer, small cell lung cancer, colorectal cancer or pancreatic cancer.

23. A method for treating cancer in a patient in need thereof, the method comprising (a) determining that the cancer is associated with KRas wild type or a KRas G12A, KRas G12C, KRas G12D, KRas G12R, KRas G12S, KRas G12V, KRas G13D or KRas Q61H mutation; and (b) administering to the patient a therapeutically effective amount of a compound selected from:

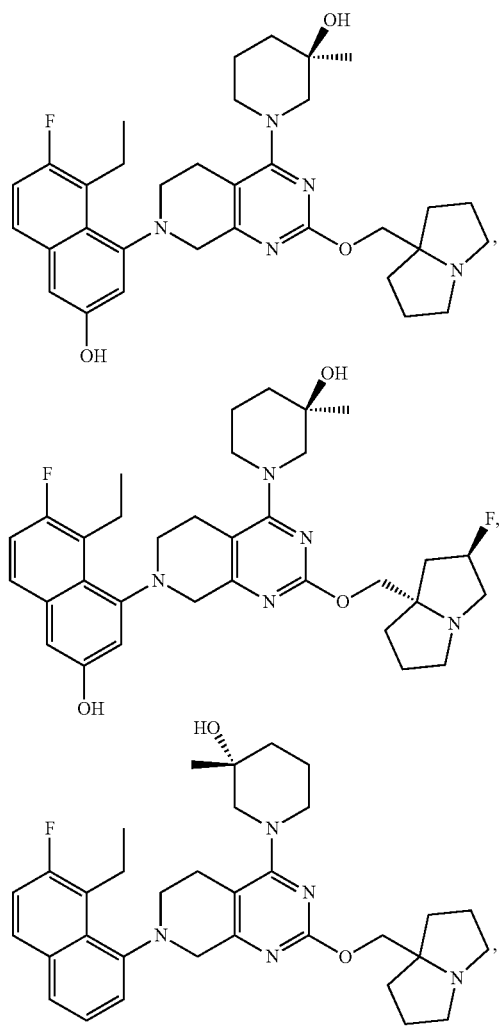

419
-continued
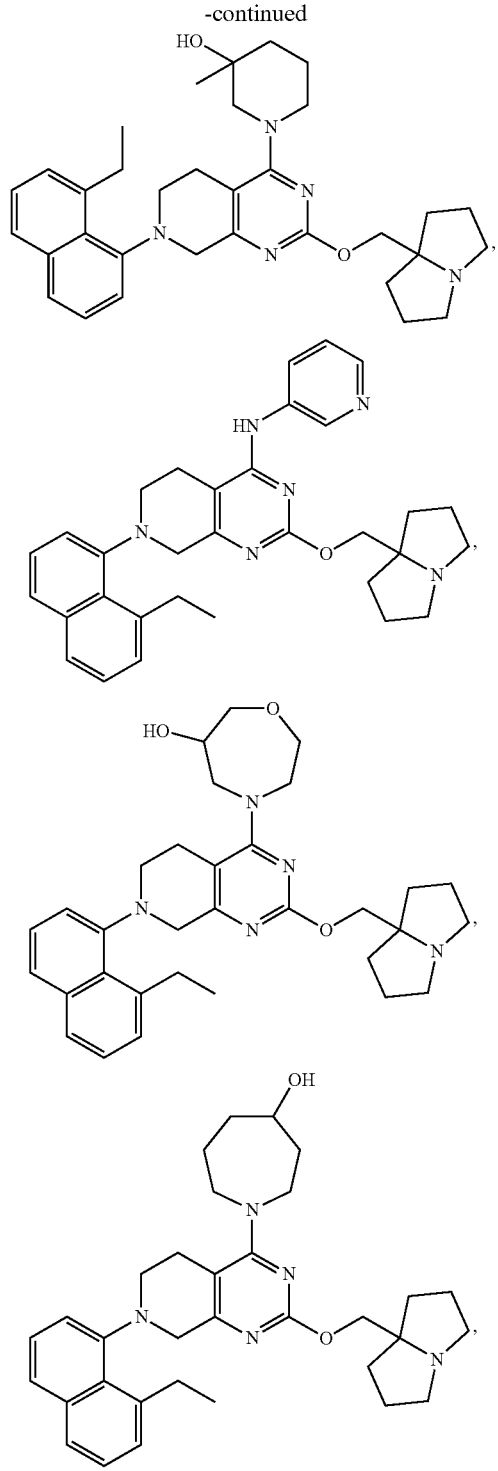
420
-continued
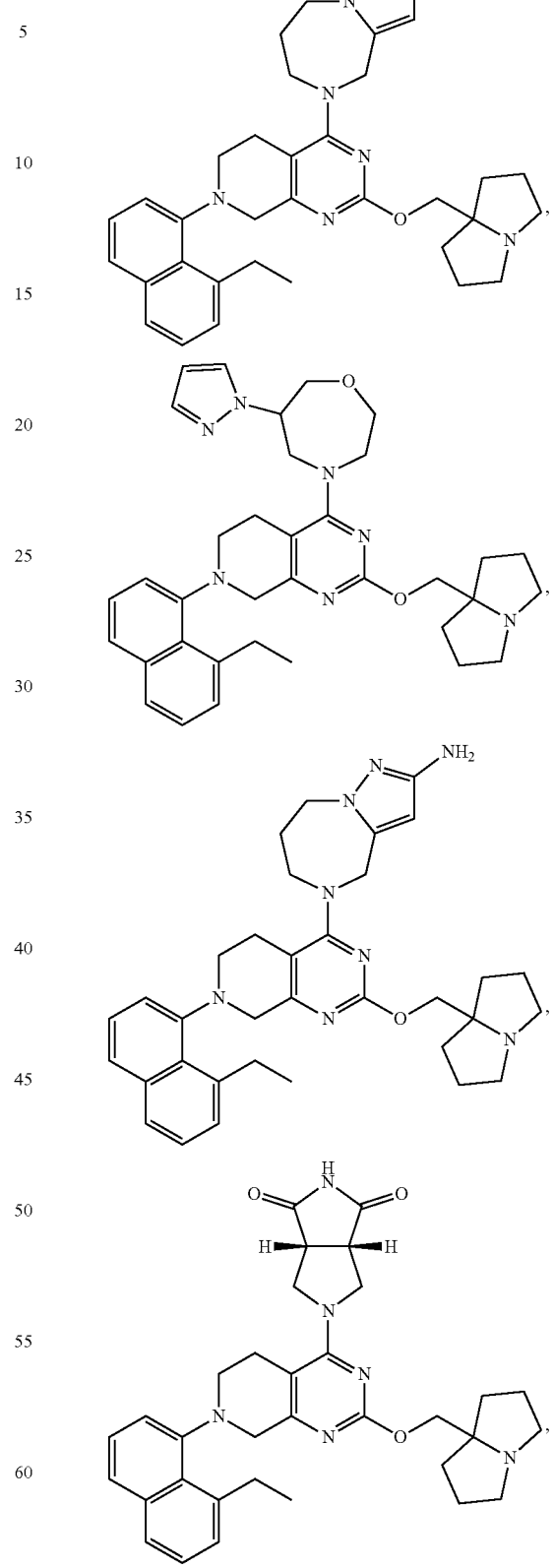

421
-continued
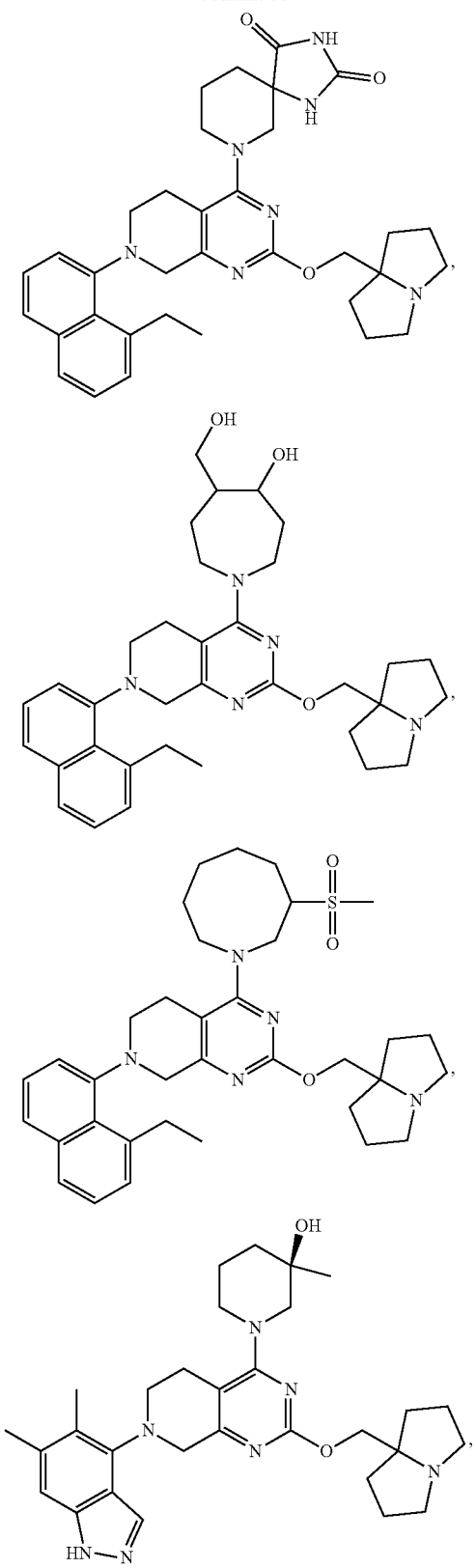
422
-continued
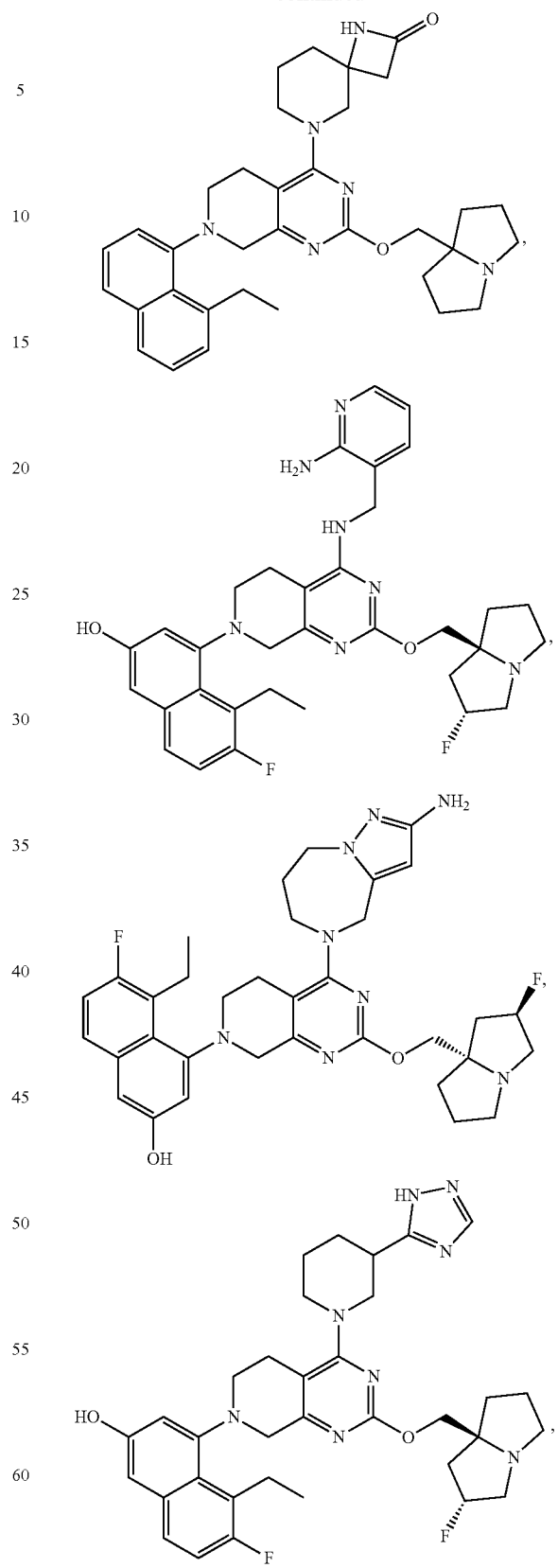

423
-continued
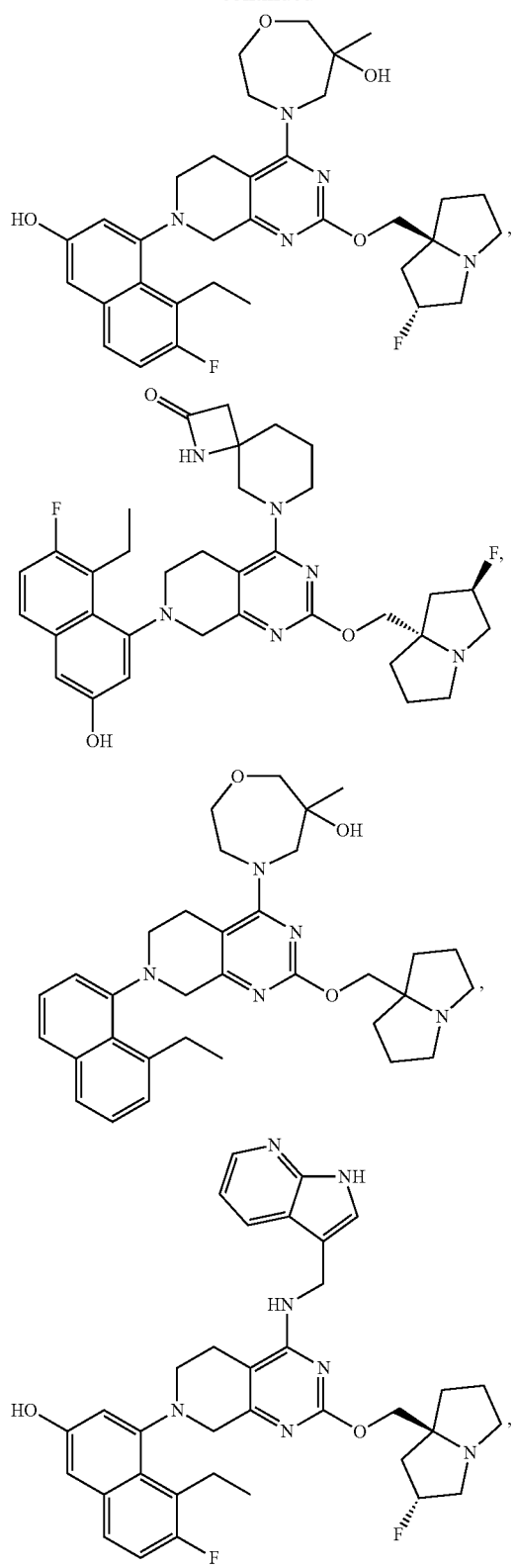
424
-continued
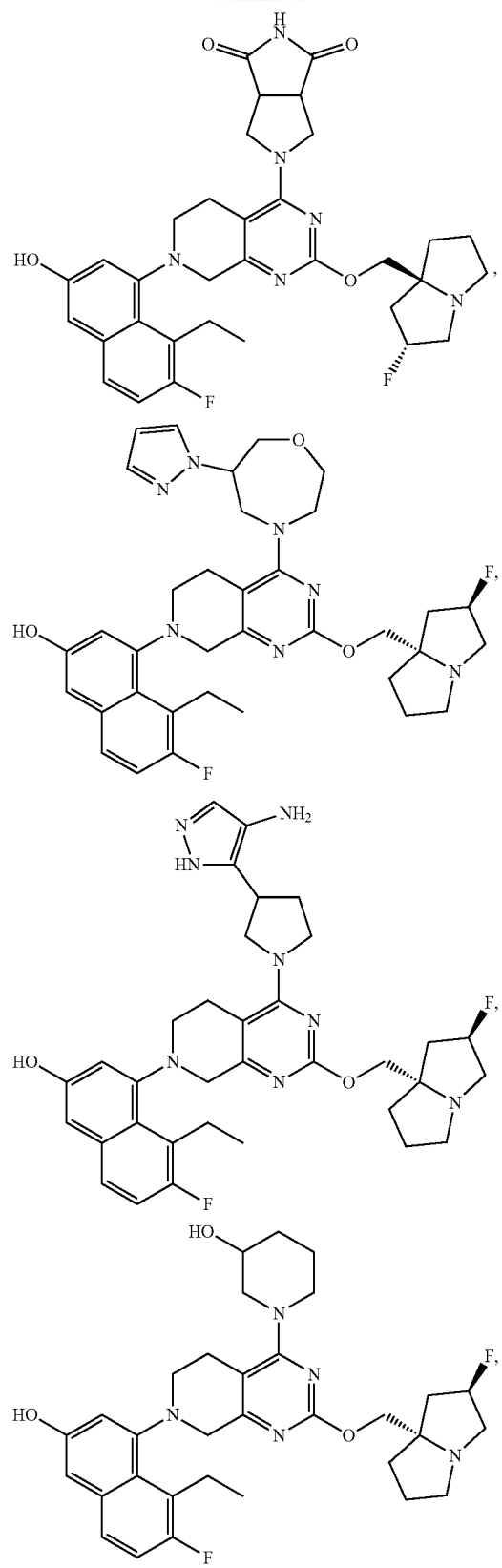

425
-continued
426
-continued
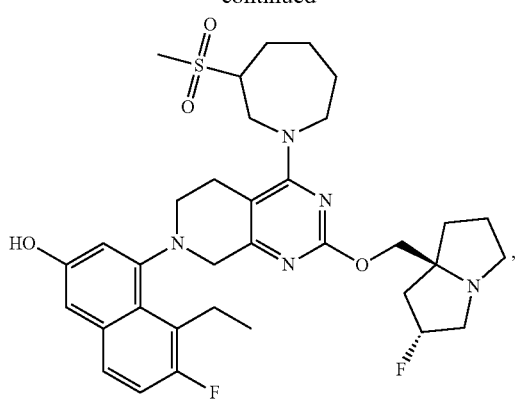
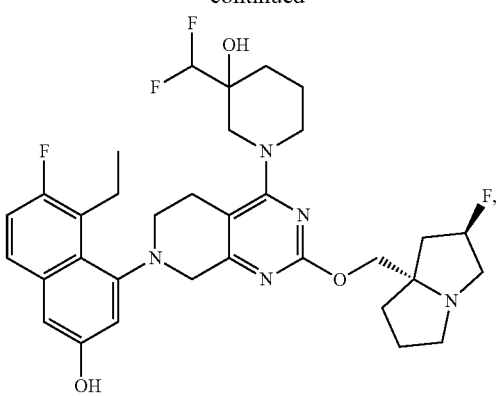
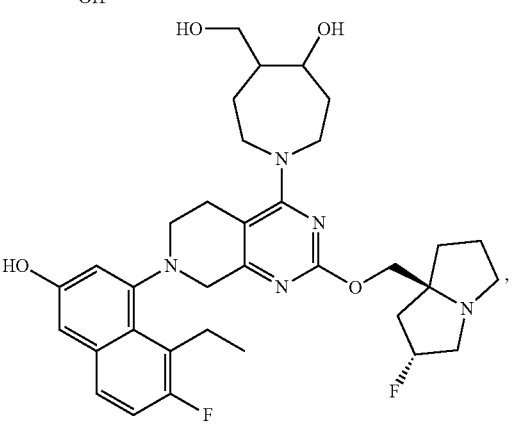
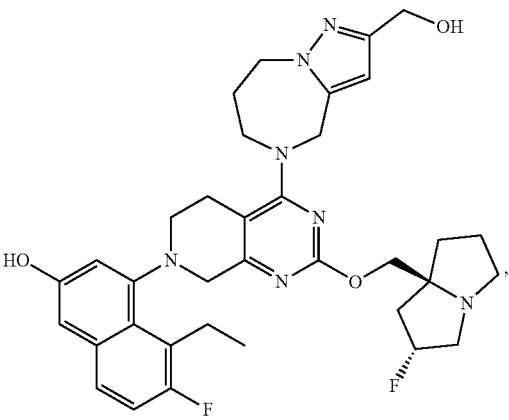
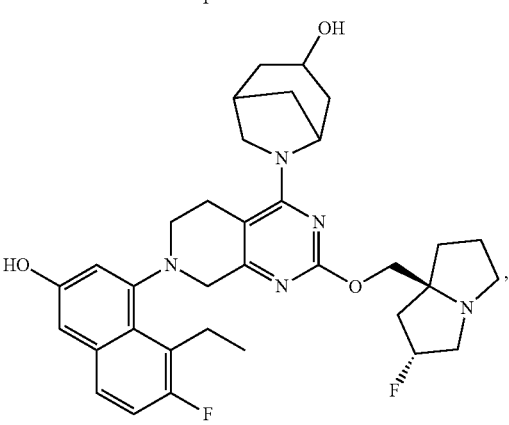

427
-continued
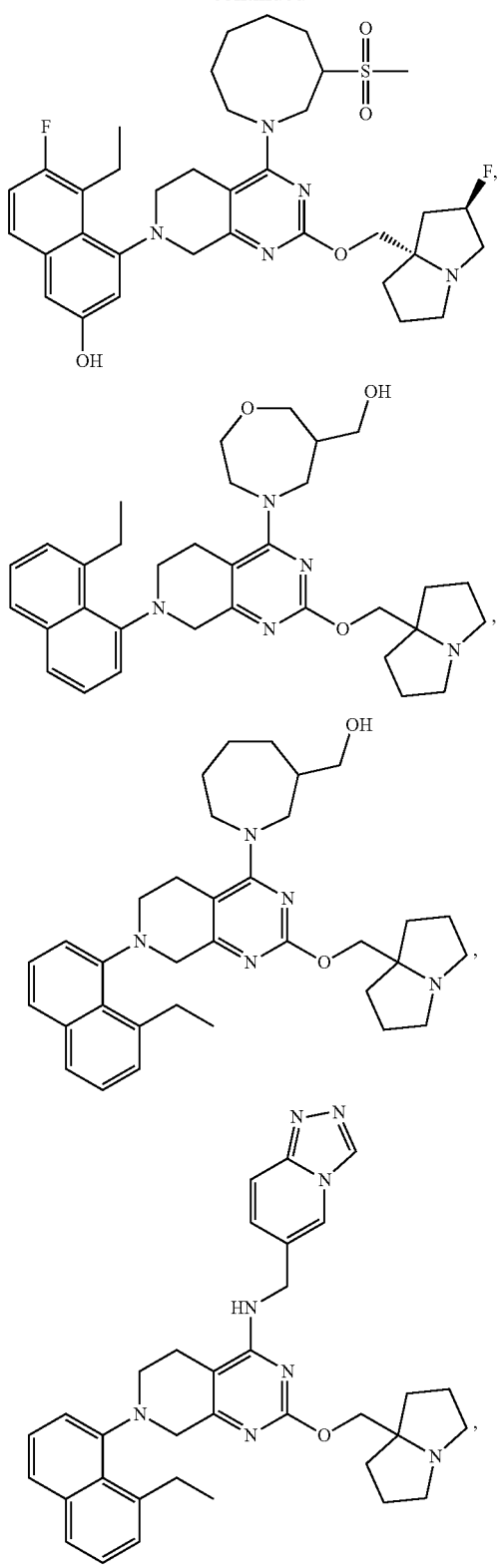
428
-continued
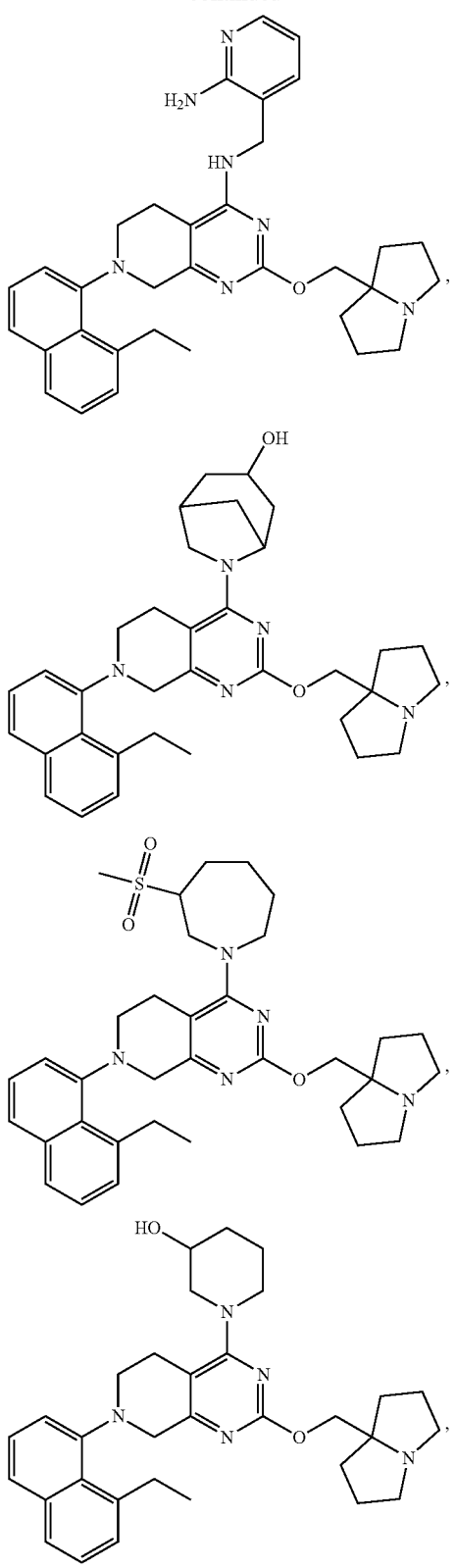

429
-continued
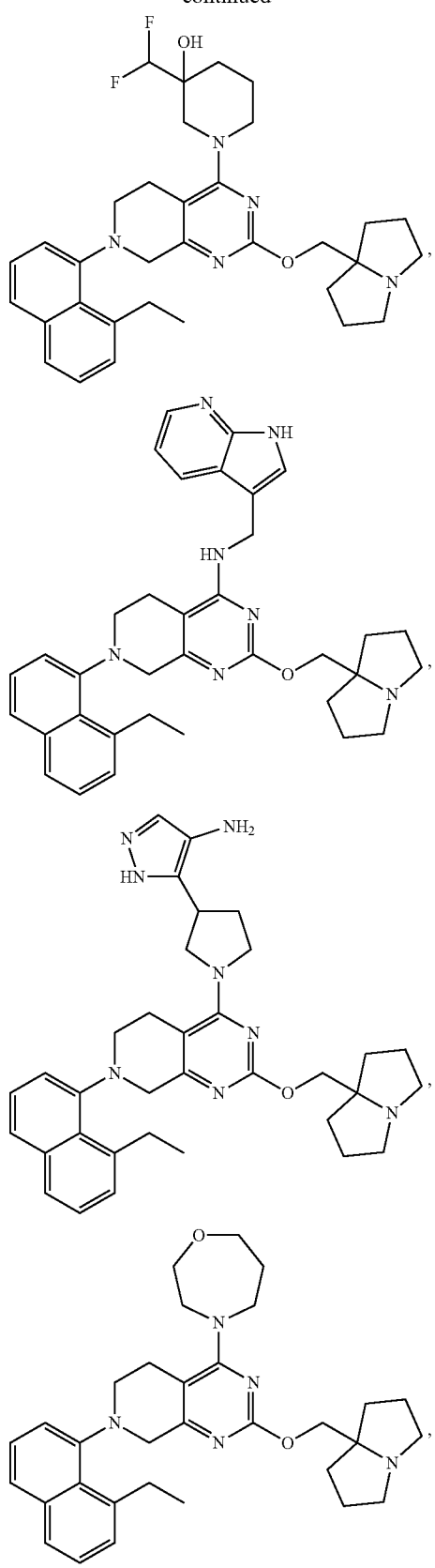
430
-continued
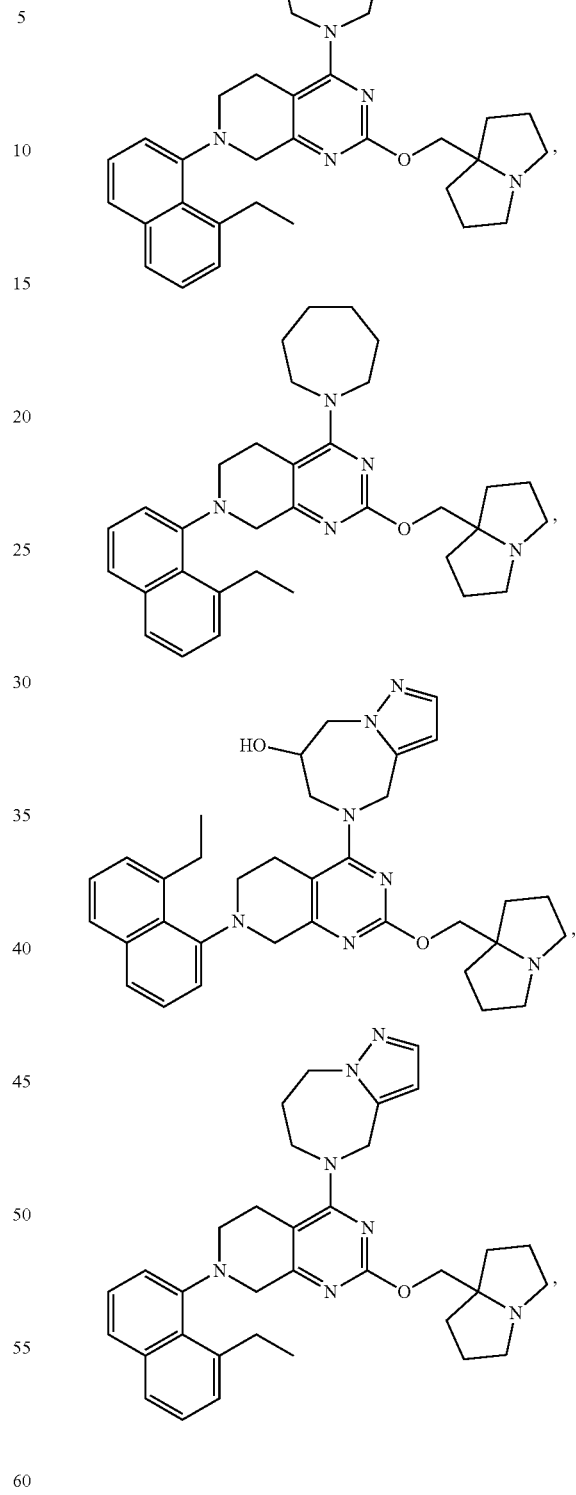

431
-continued
432
-continued
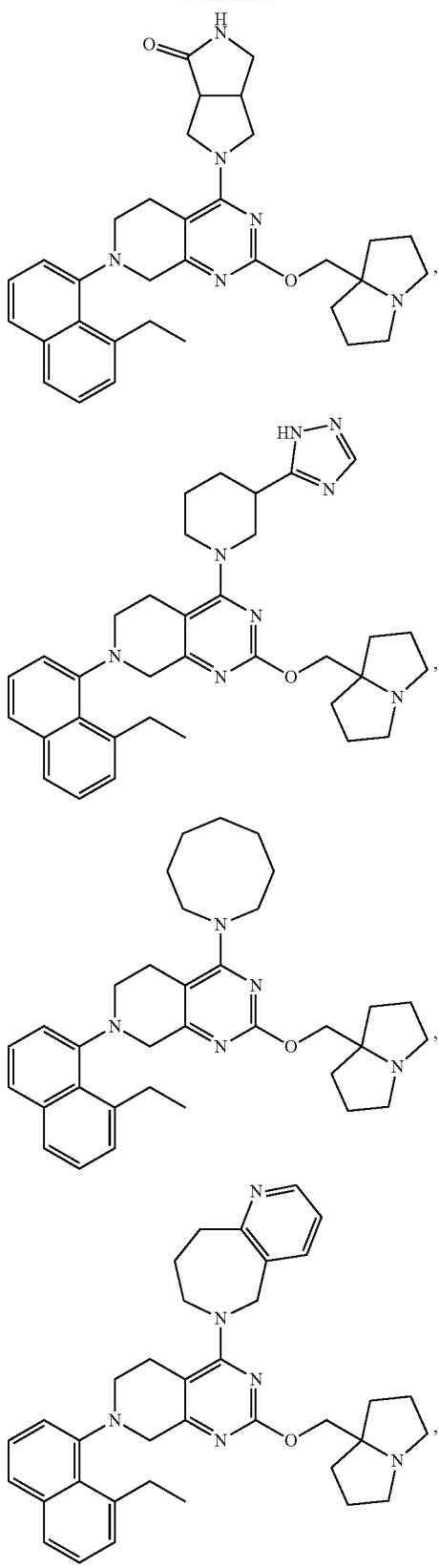
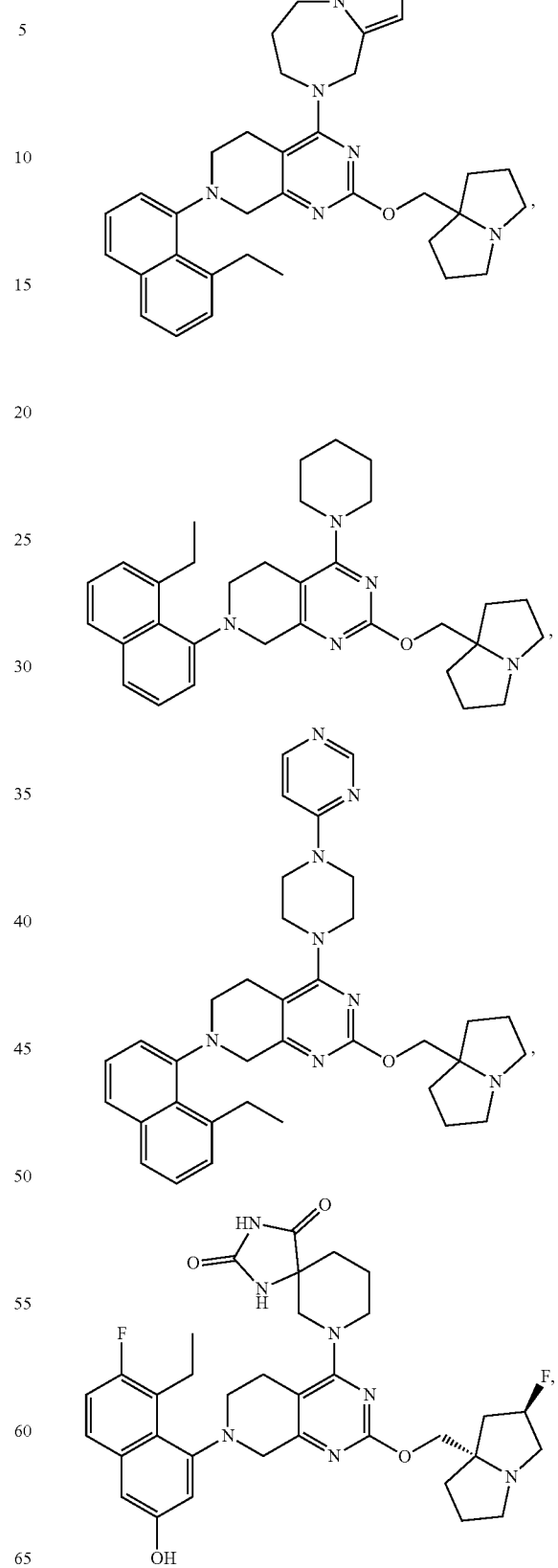

433
-continued
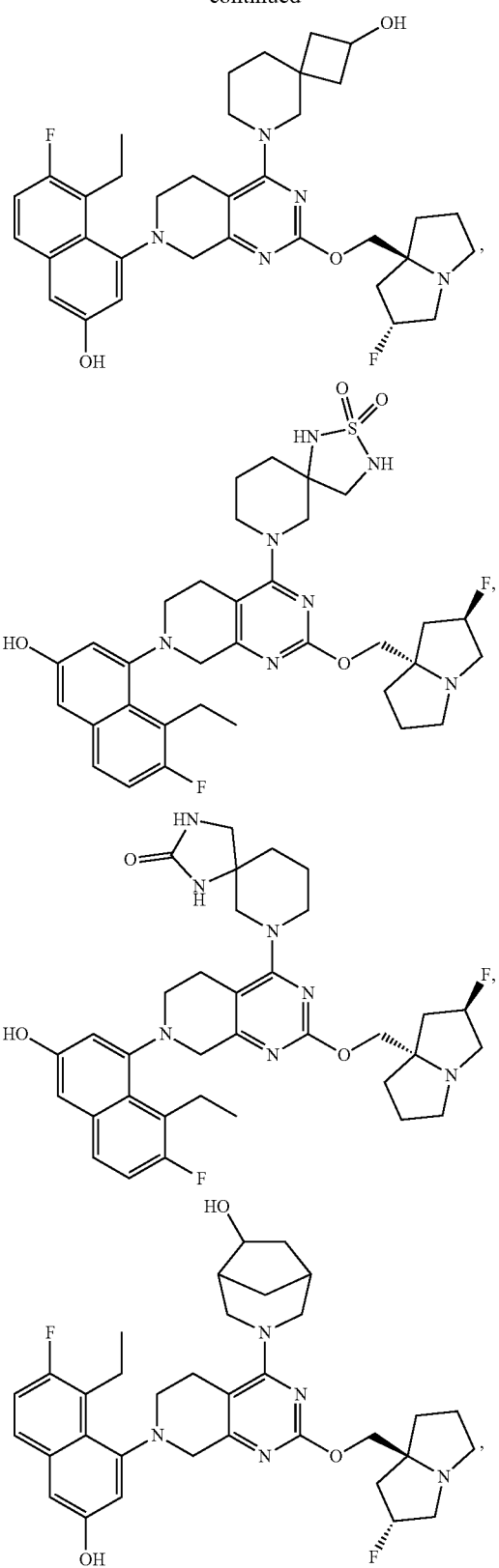
434
-continued
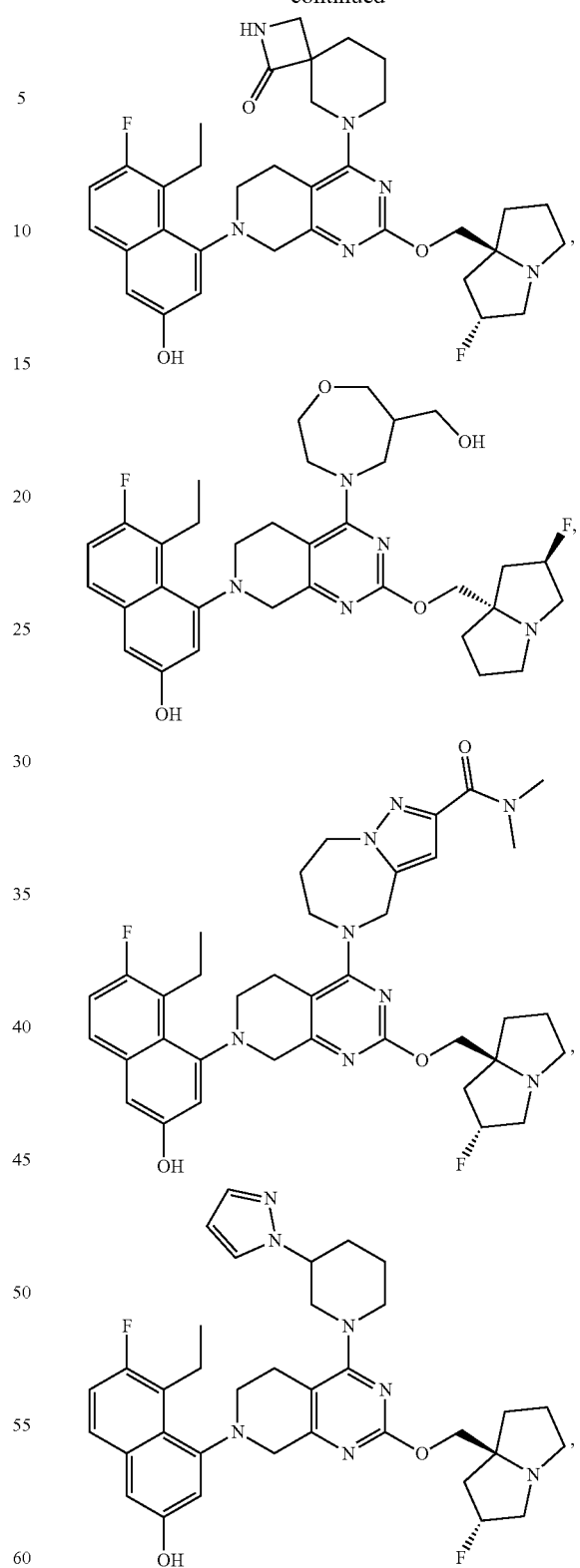

-continued
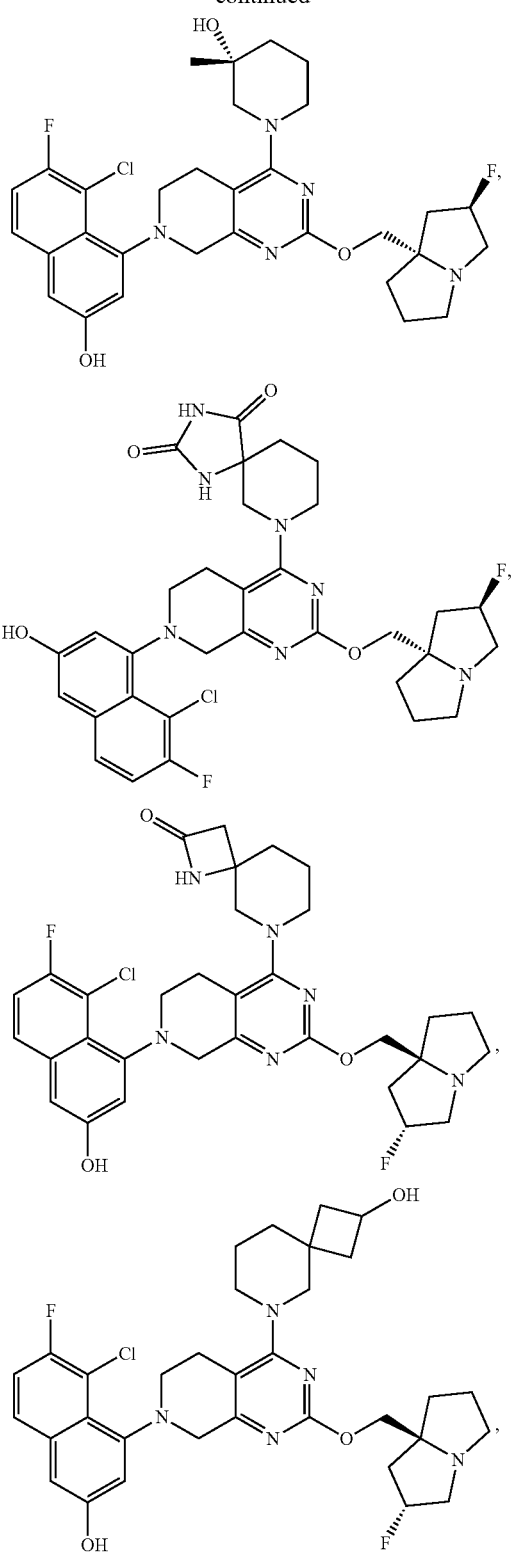
-continued
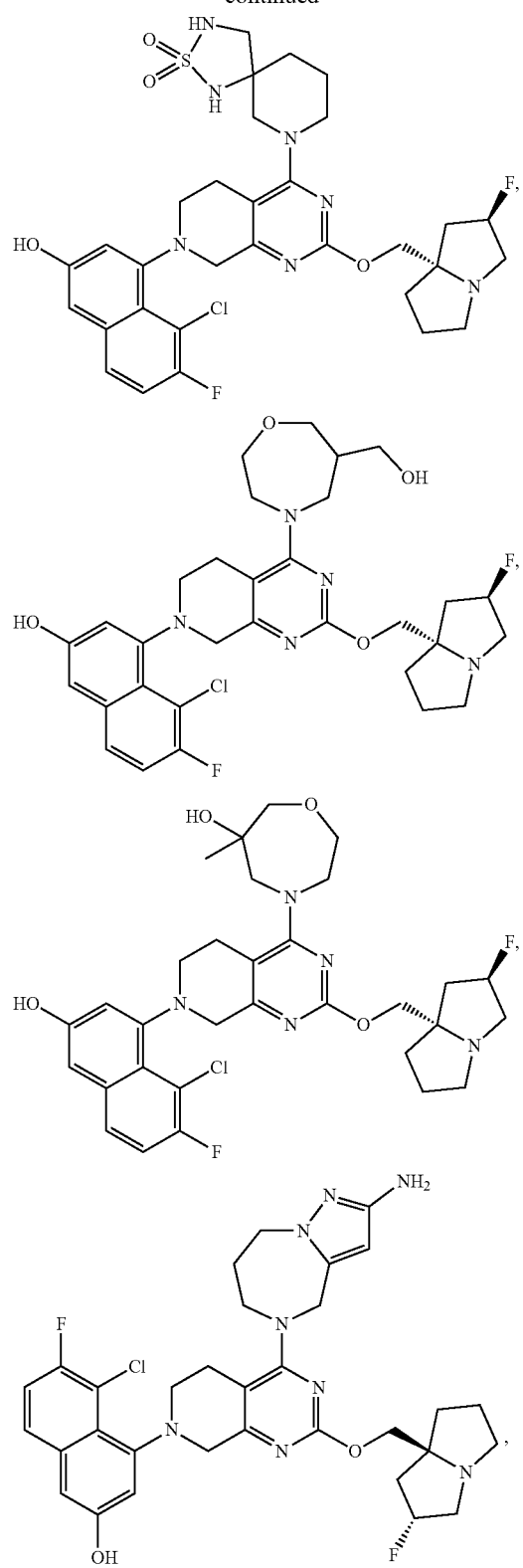

437
-continued
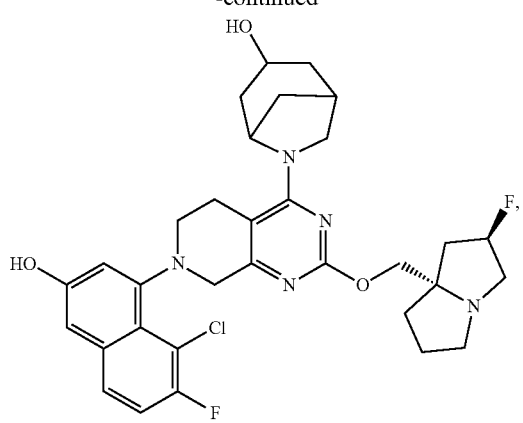
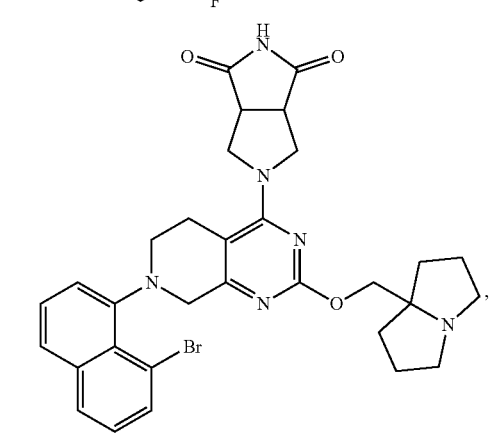
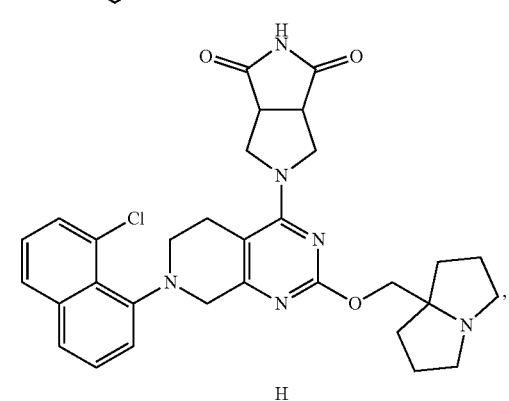
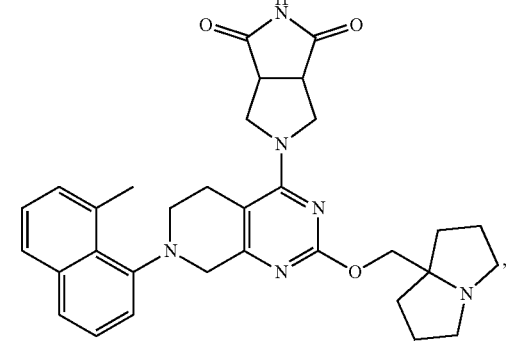
438
-continued
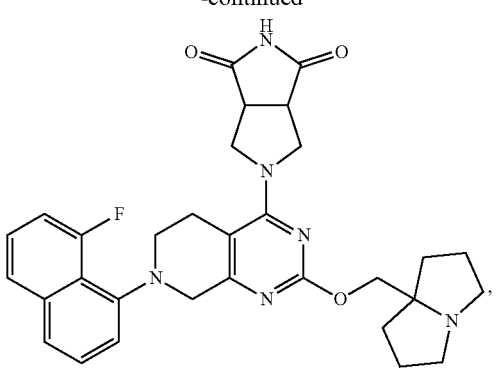
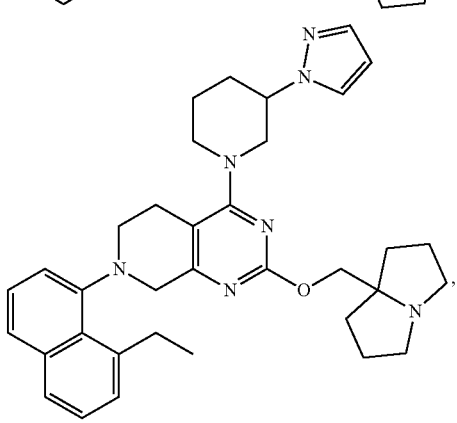
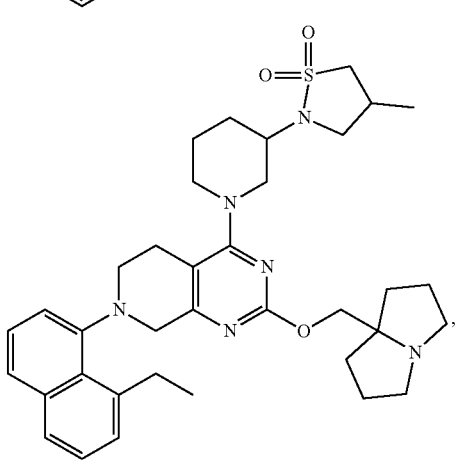
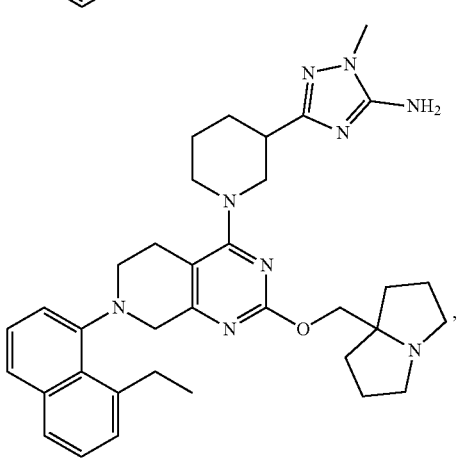

439
-continued
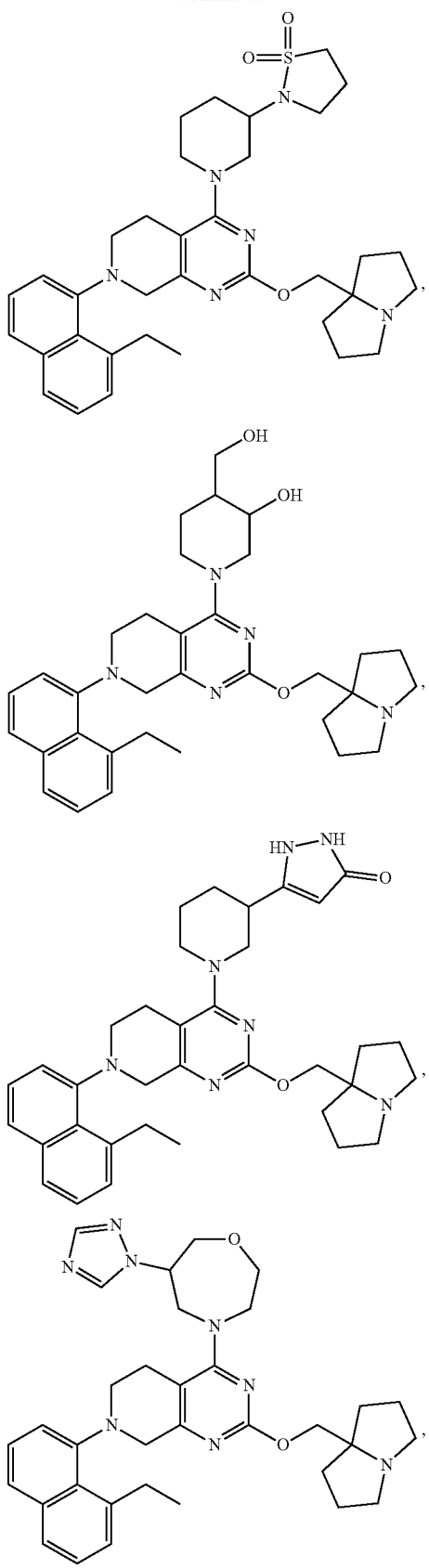
440
-continued
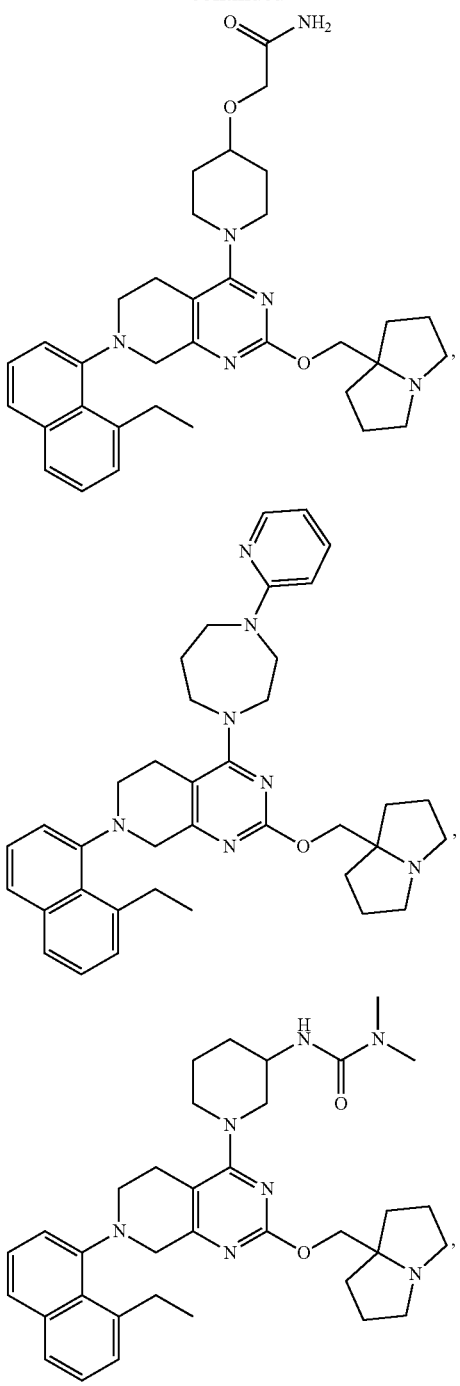

441
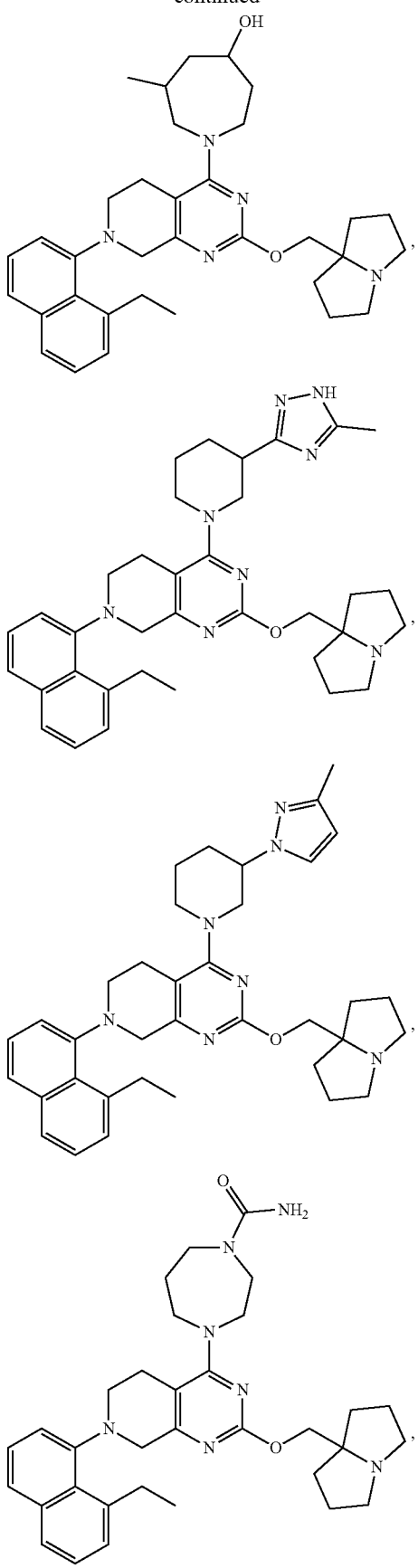
442
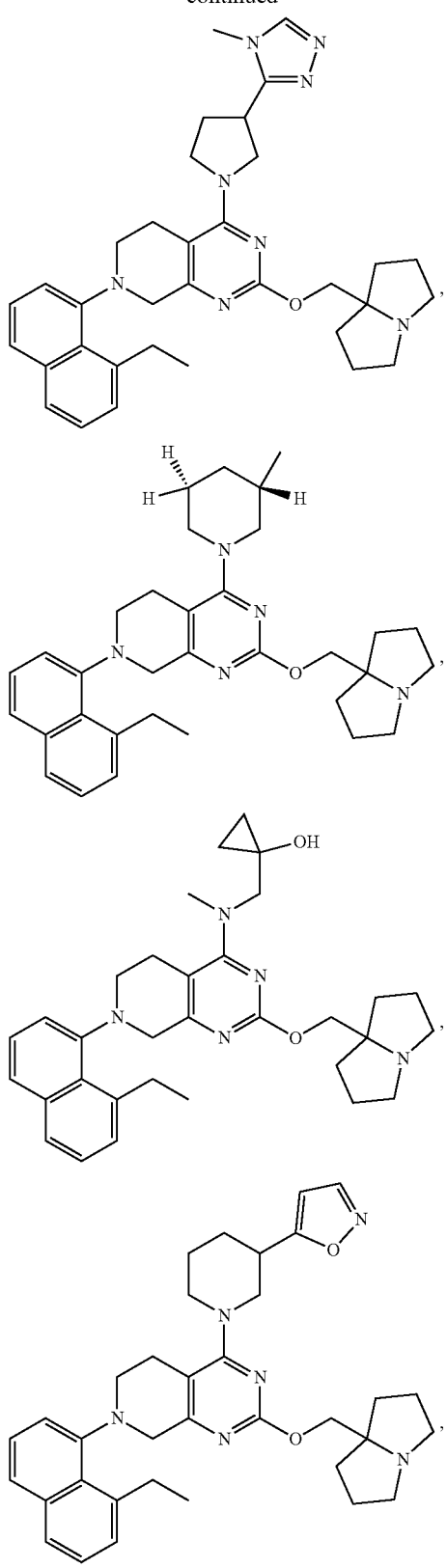

443
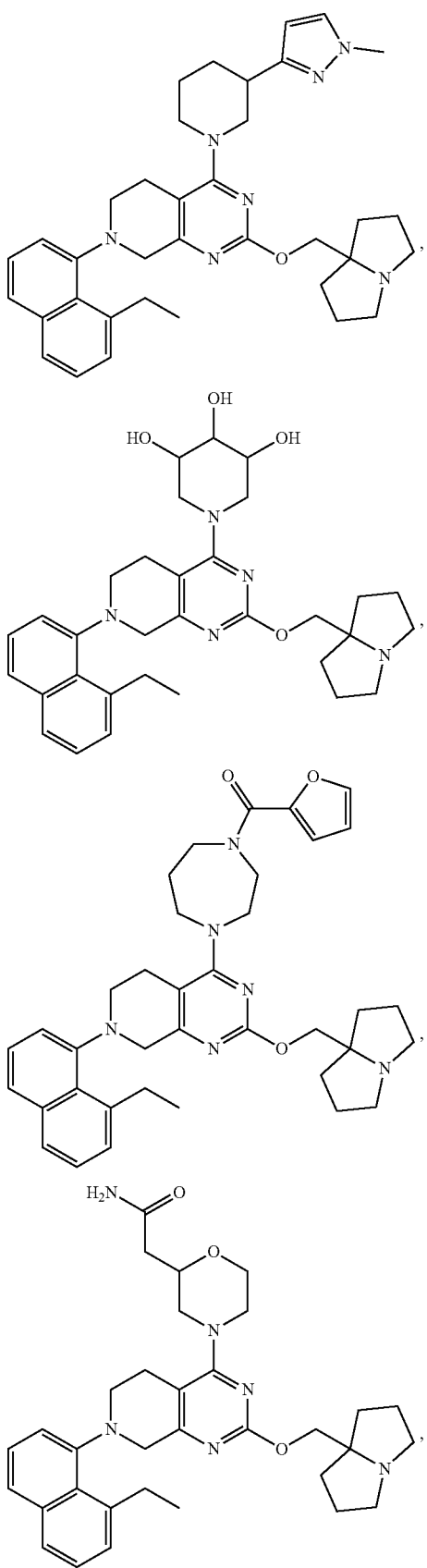
444
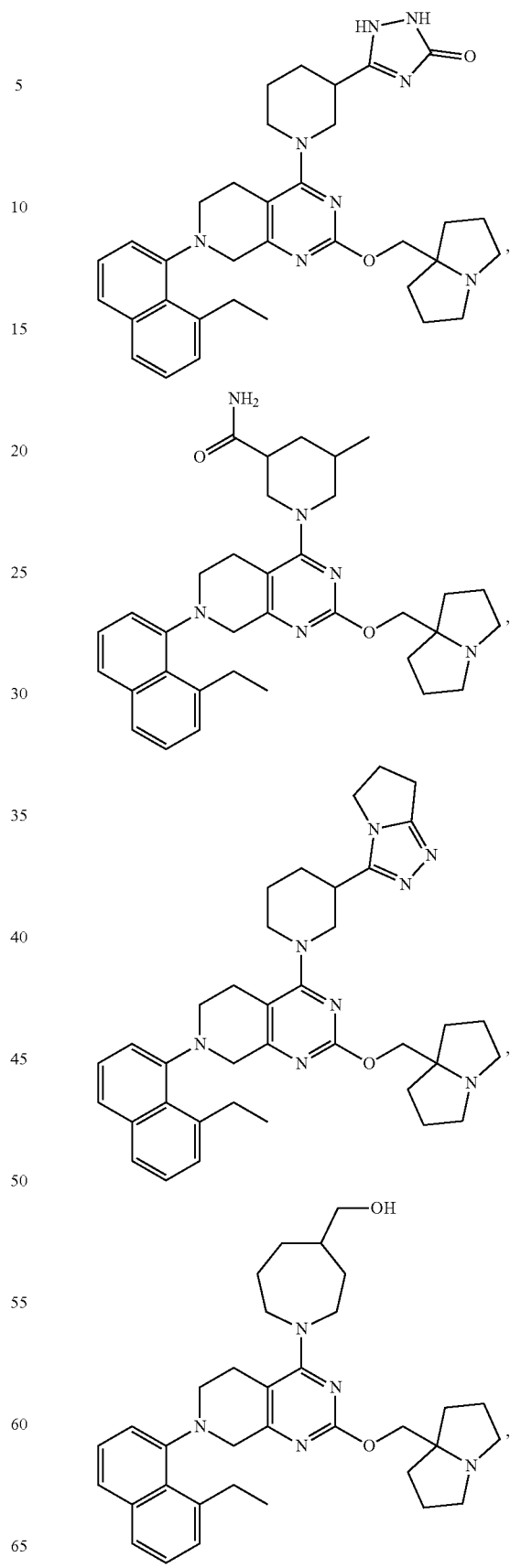

445
-continued
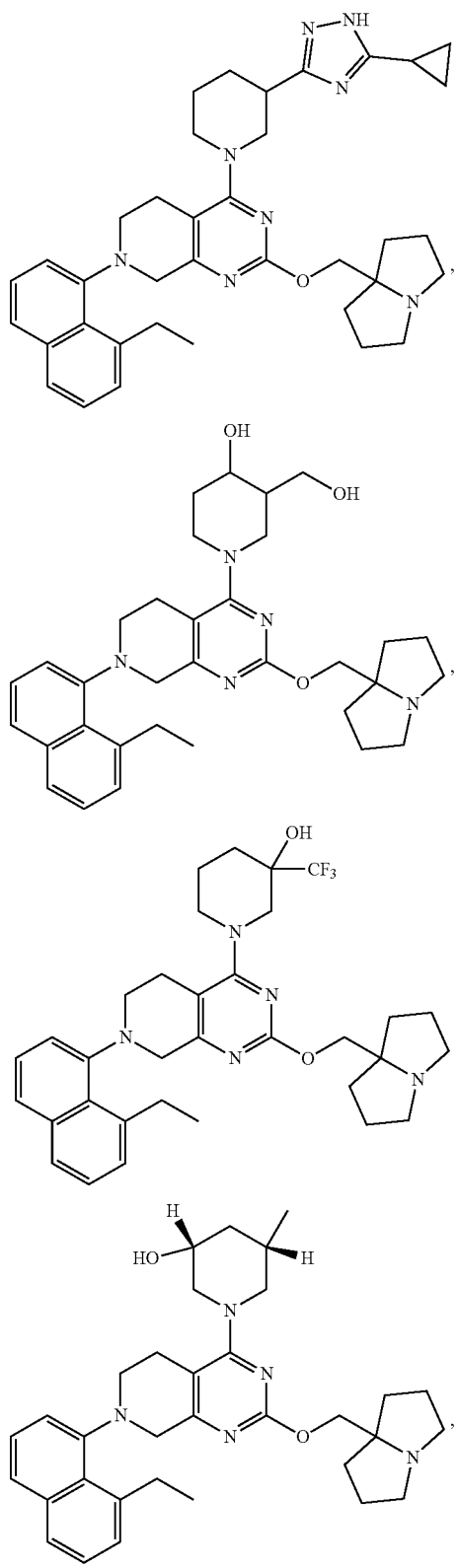
446
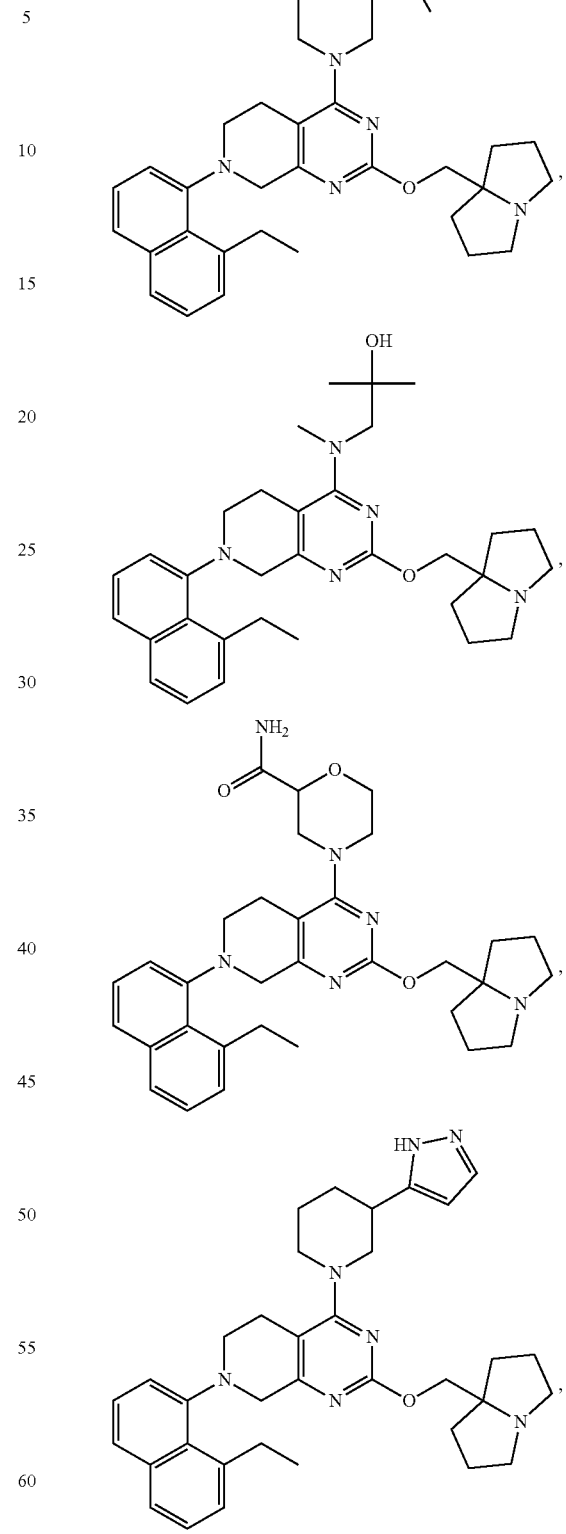

447
-continued
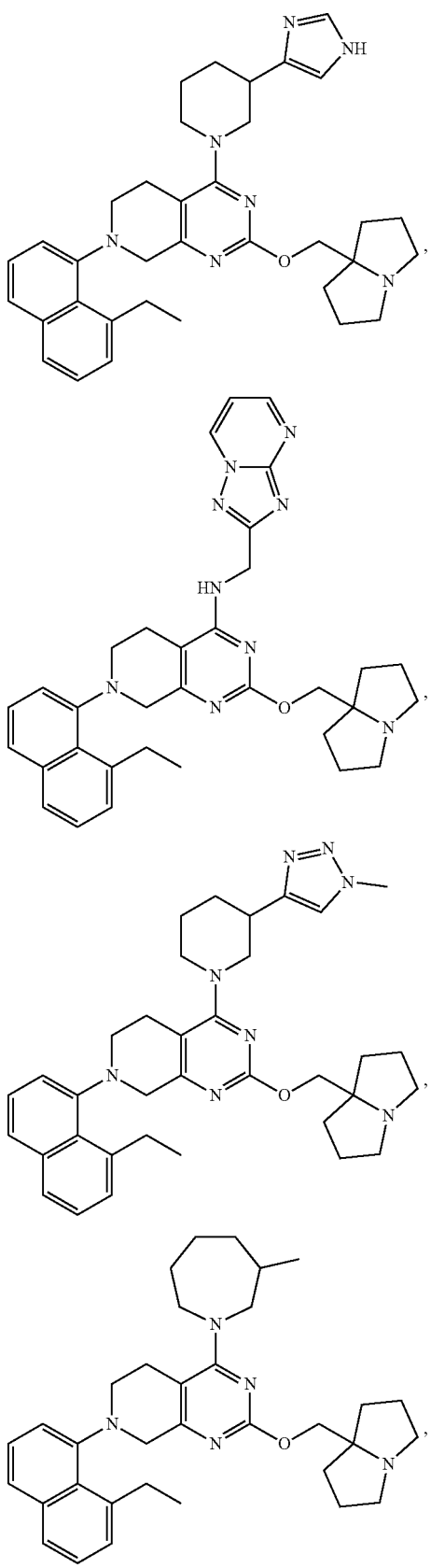
448
-continued
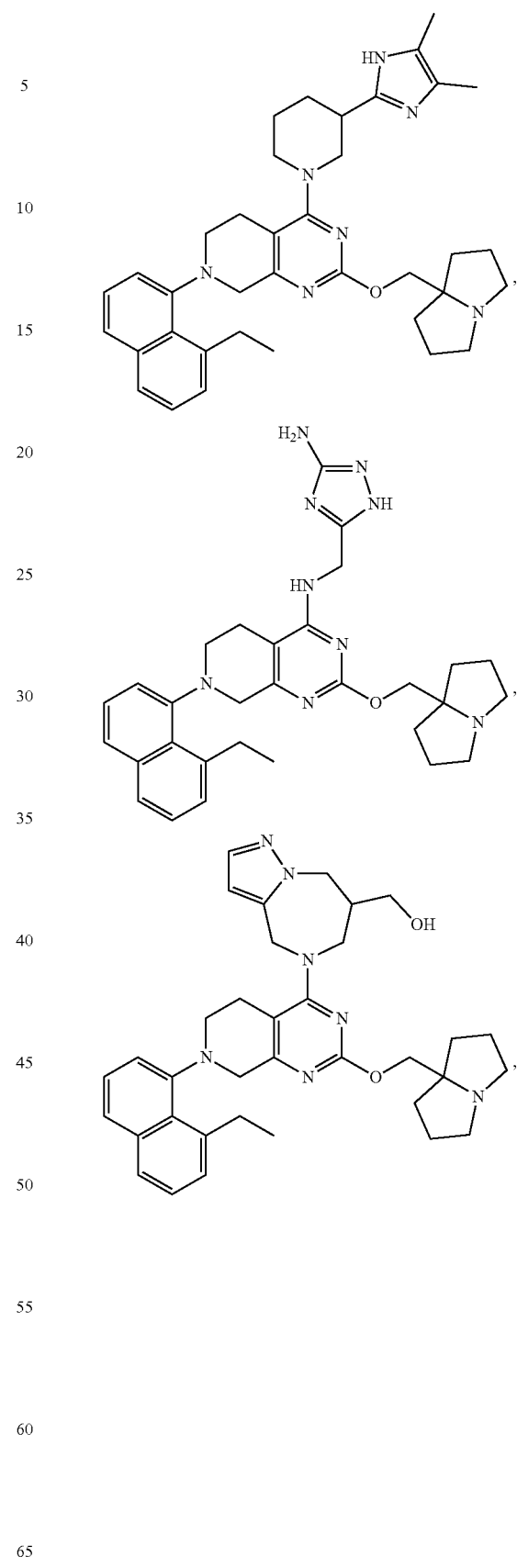

449
-continued
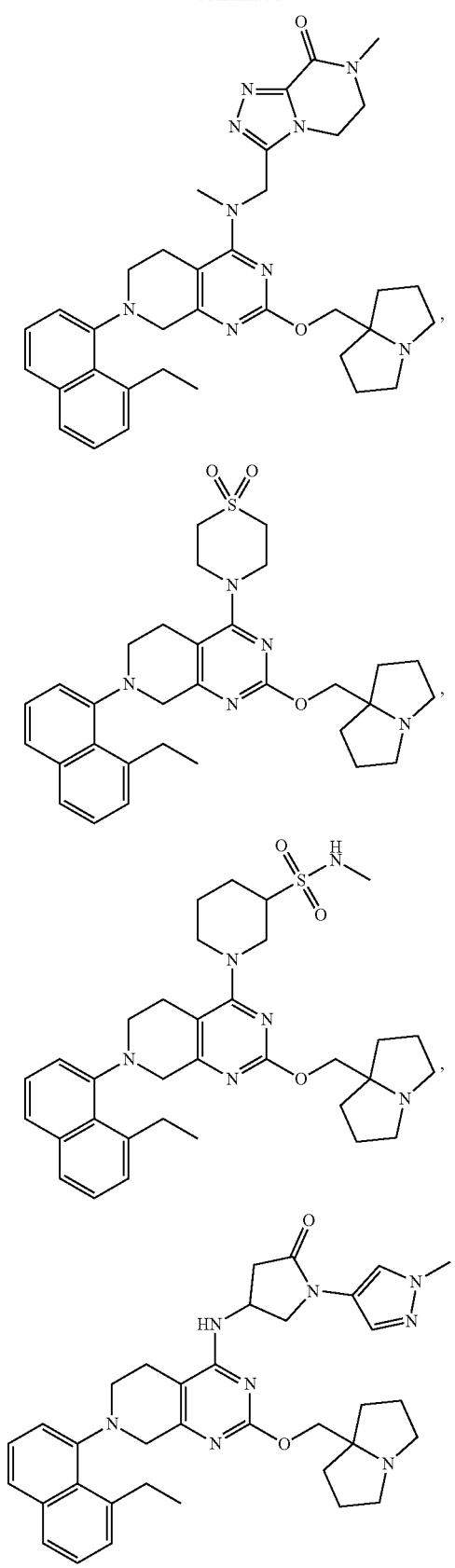
450
-continued
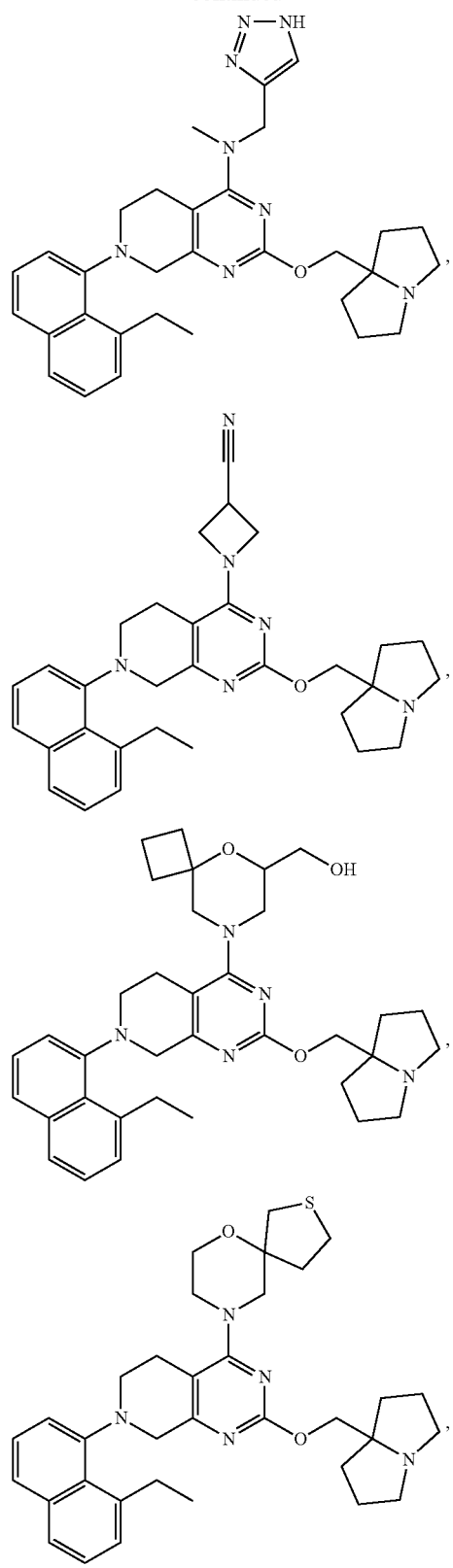

451
-continued
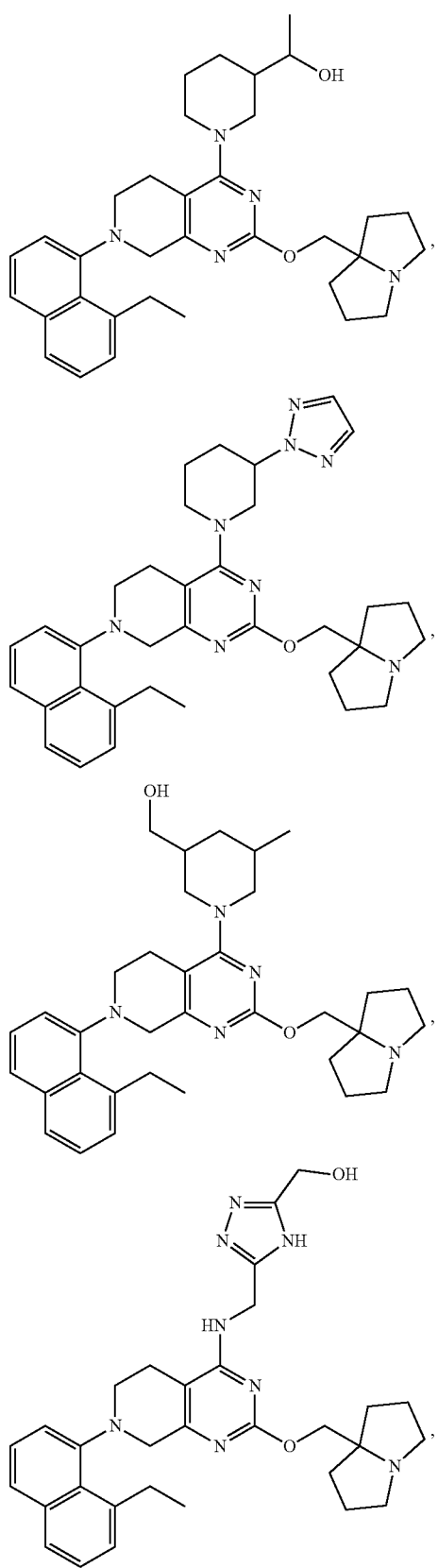
452
-continued
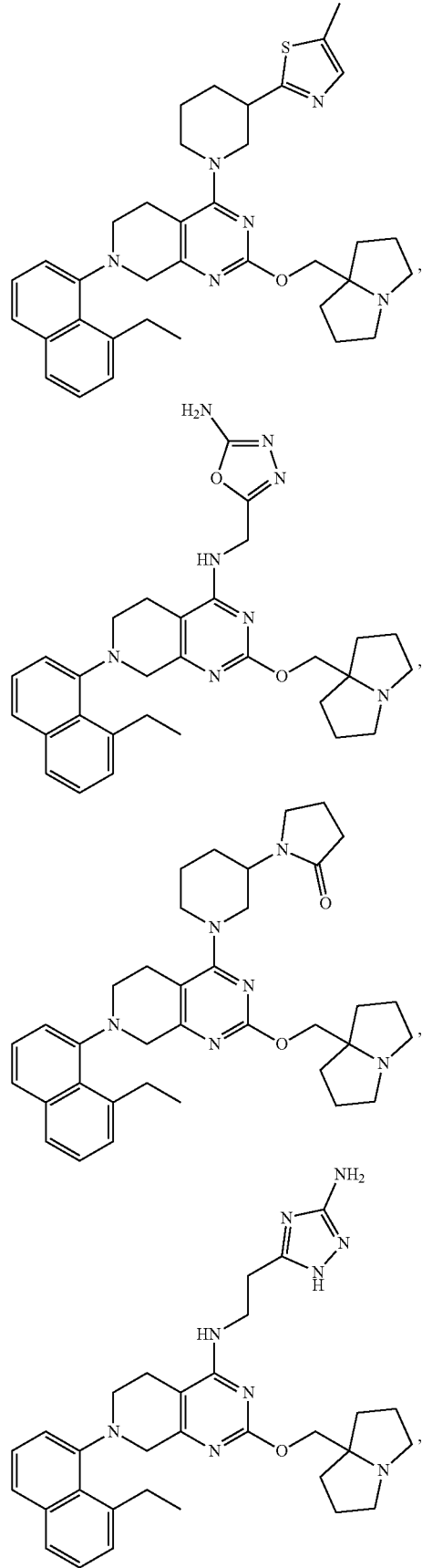

453
-continued
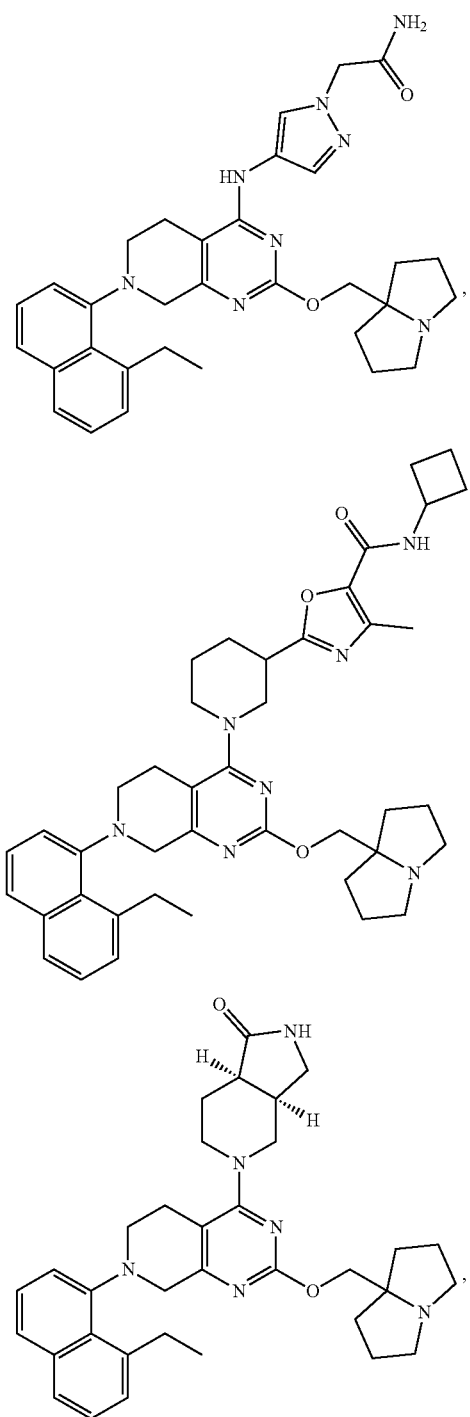
454
-continued
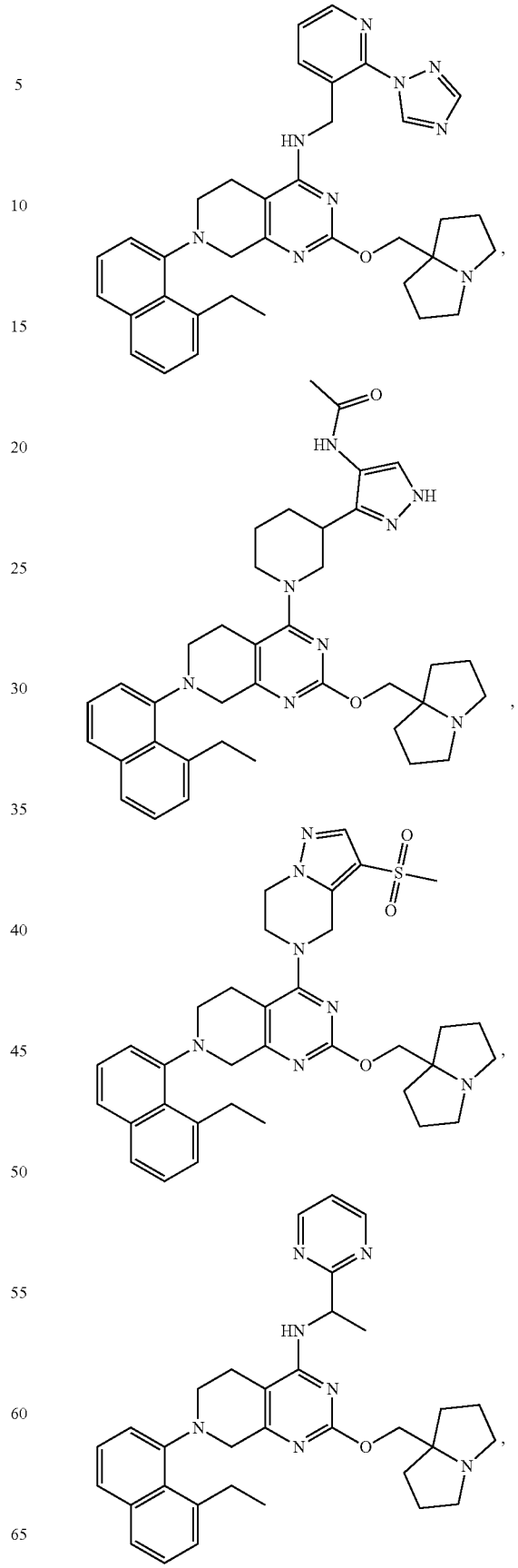

455
-continued
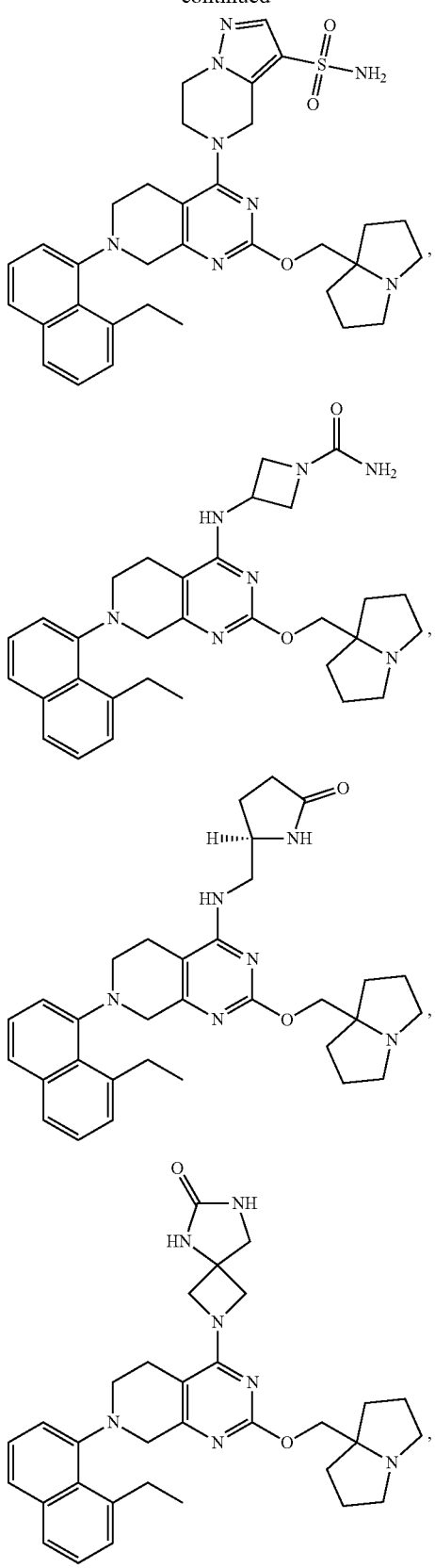
456
-continued
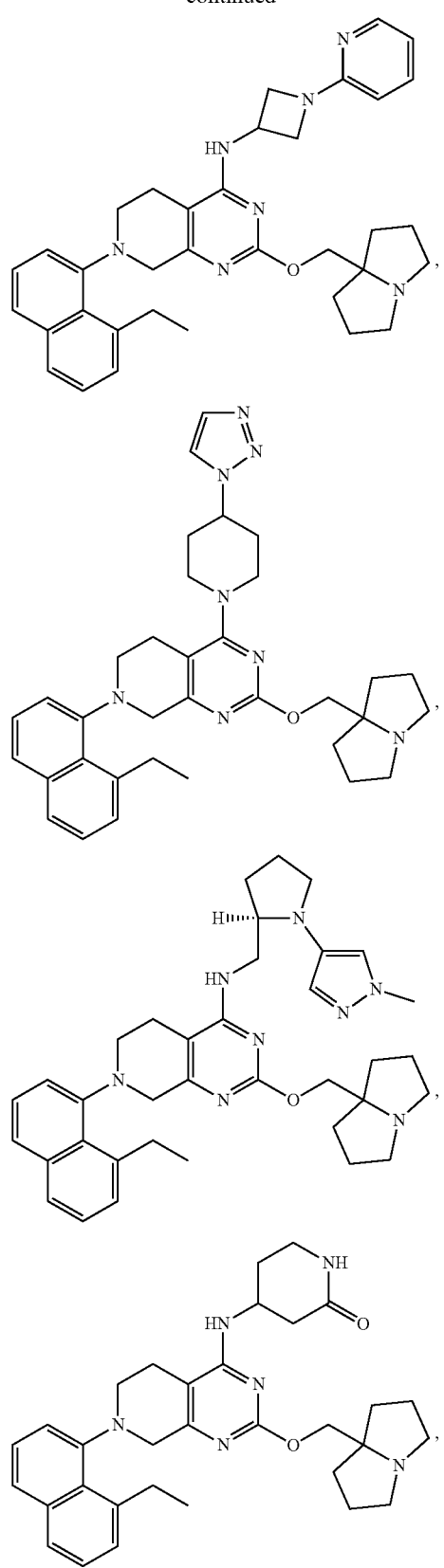

457
-continued
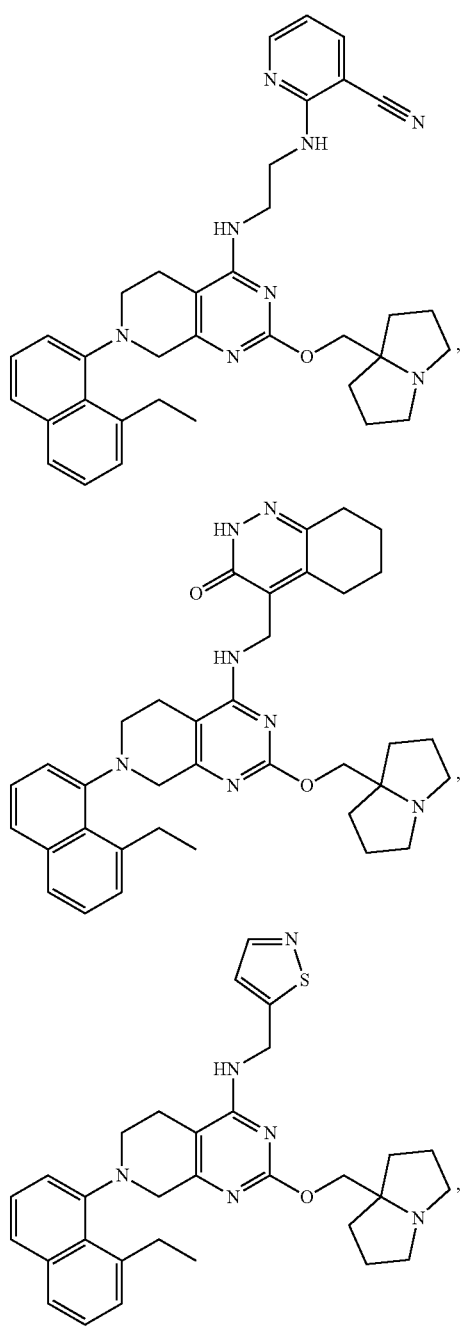
458
-continued
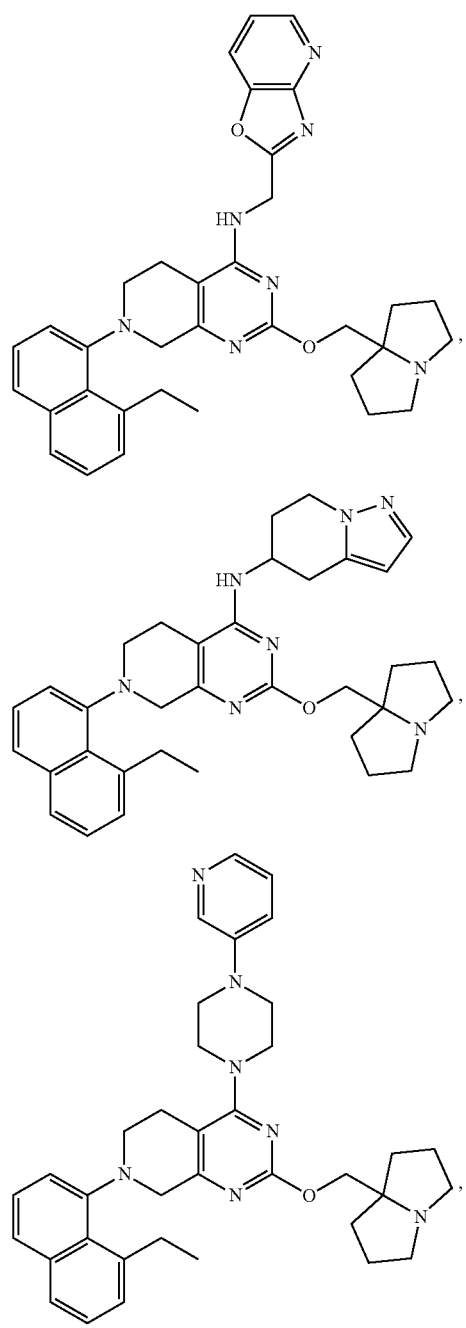

459
-continued
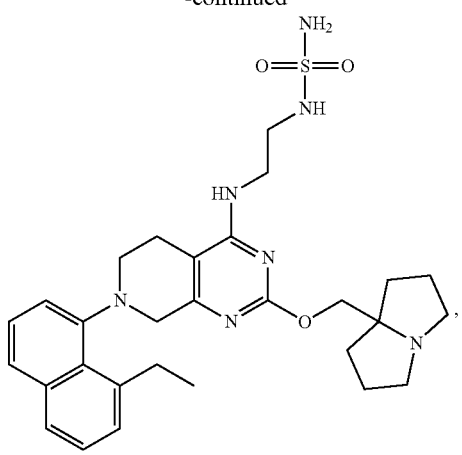
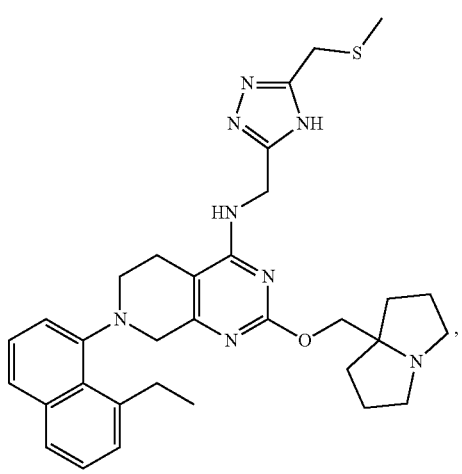
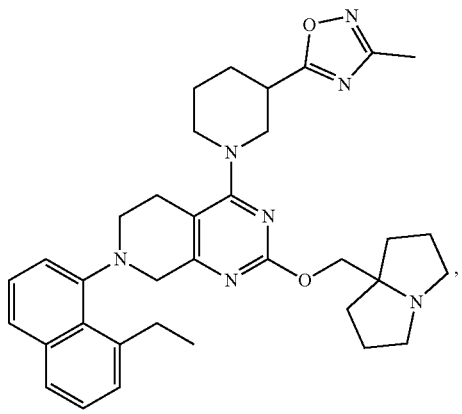
460
-continued
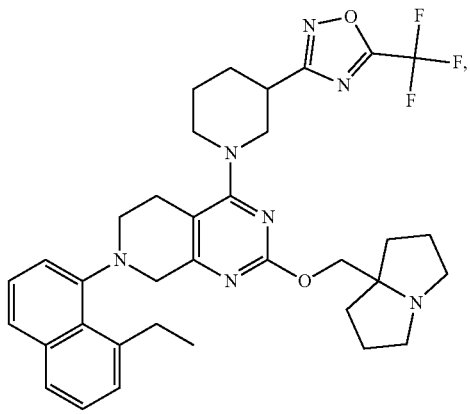
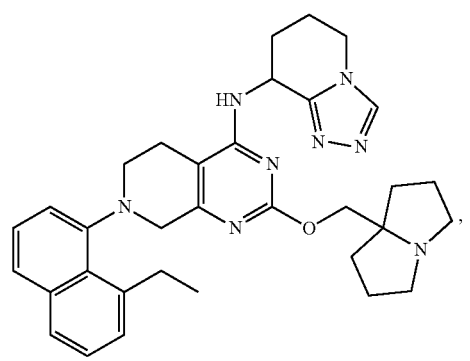
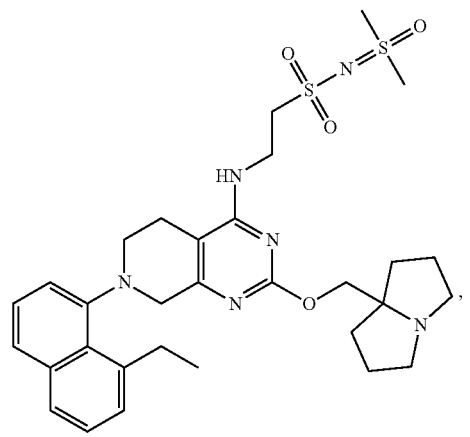 [SMILES: CCc1cccc2cccc(N3CCc4c(nc(OCC56CCCN5CCC6)nc4NCCS(=O)(=O)N=S(C)(C)=O)C3)c12]
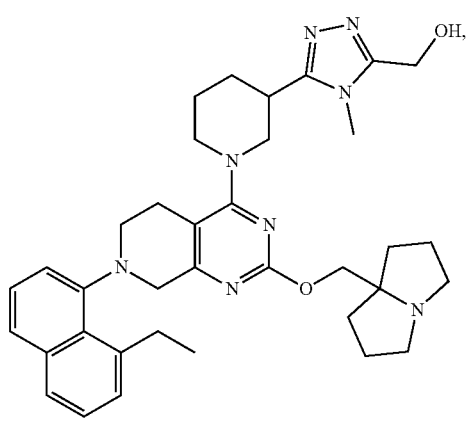

461
-continued
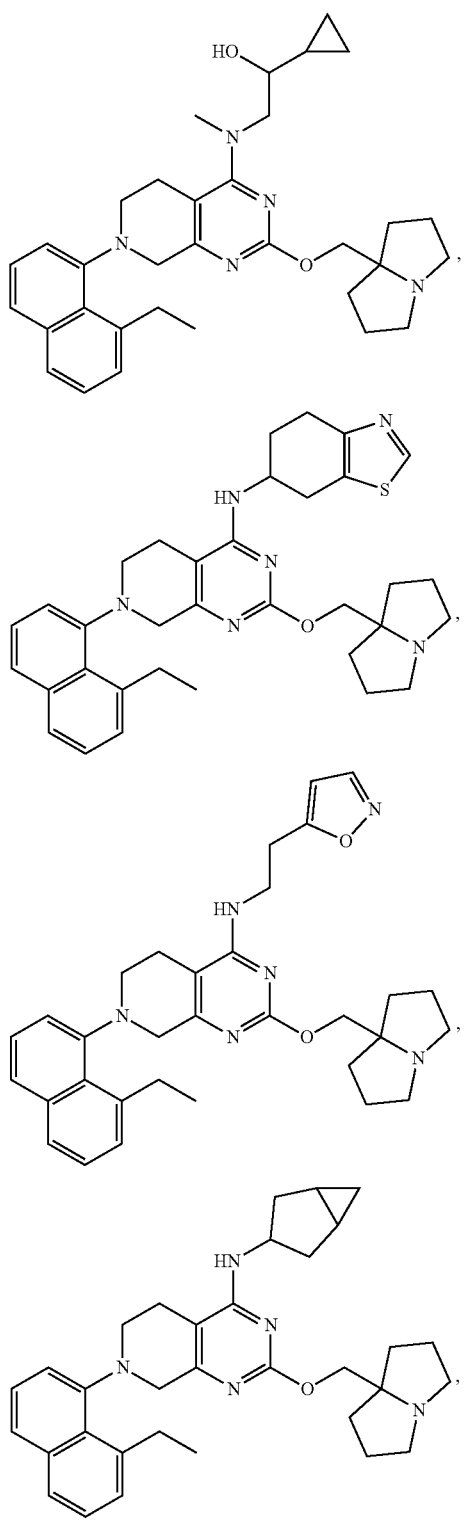
462
-continued
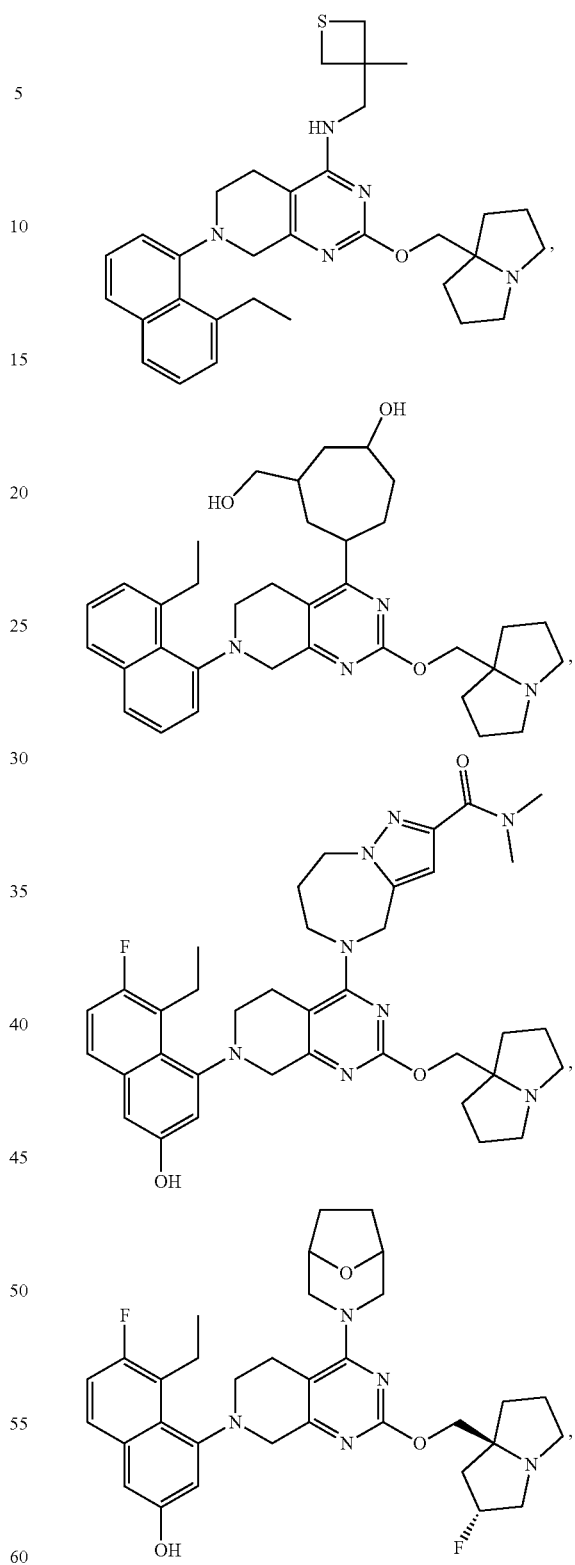

463
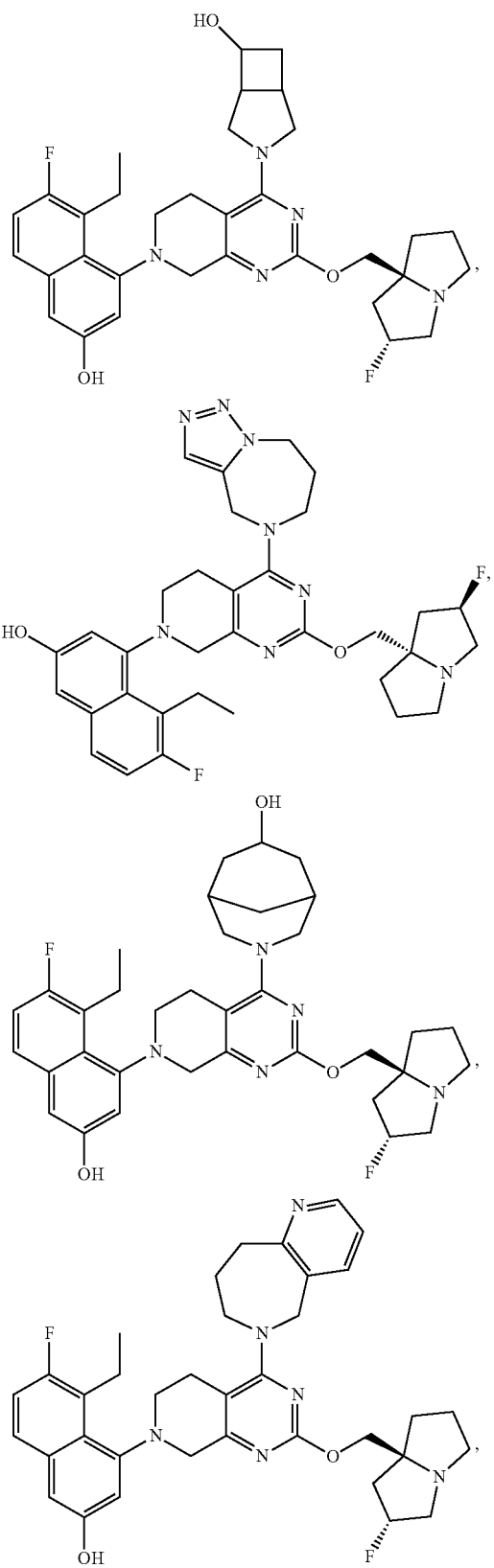
464
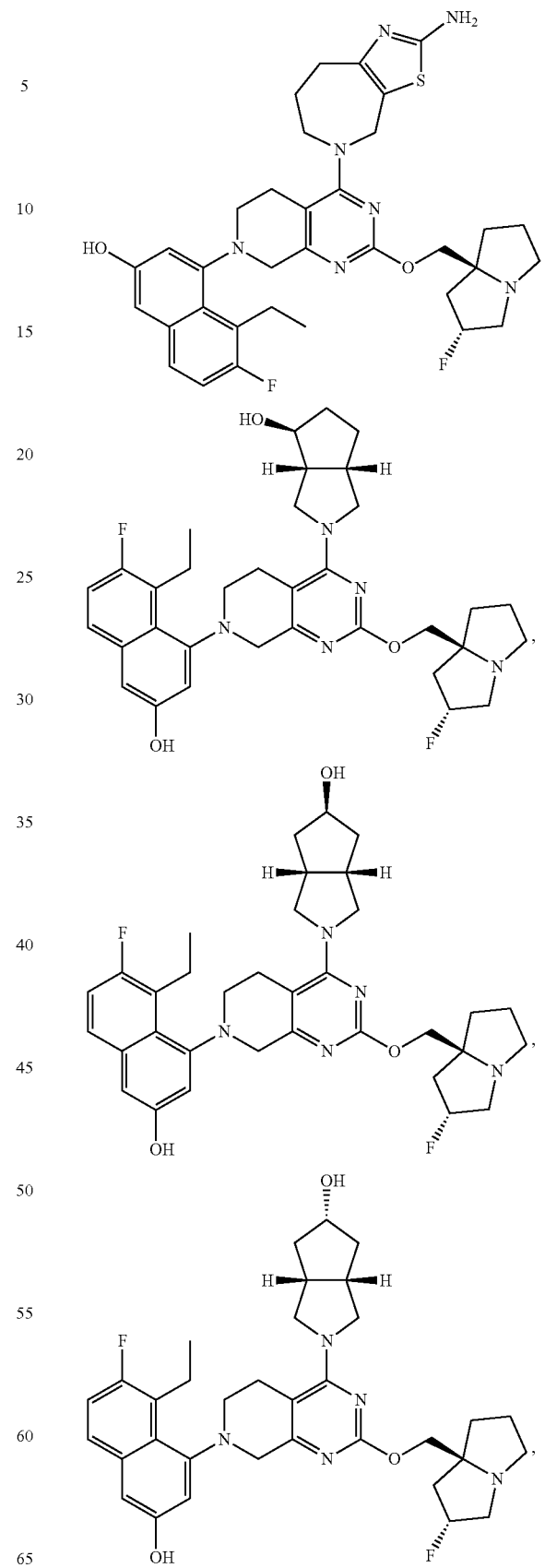

465
-continued
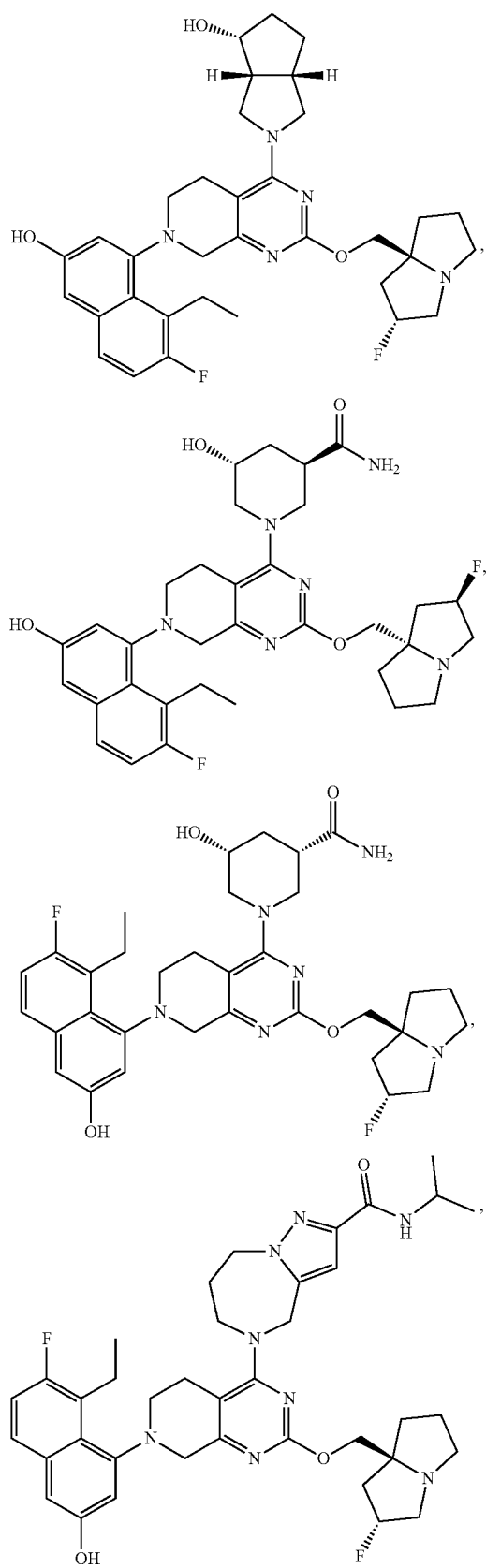
466
-continued
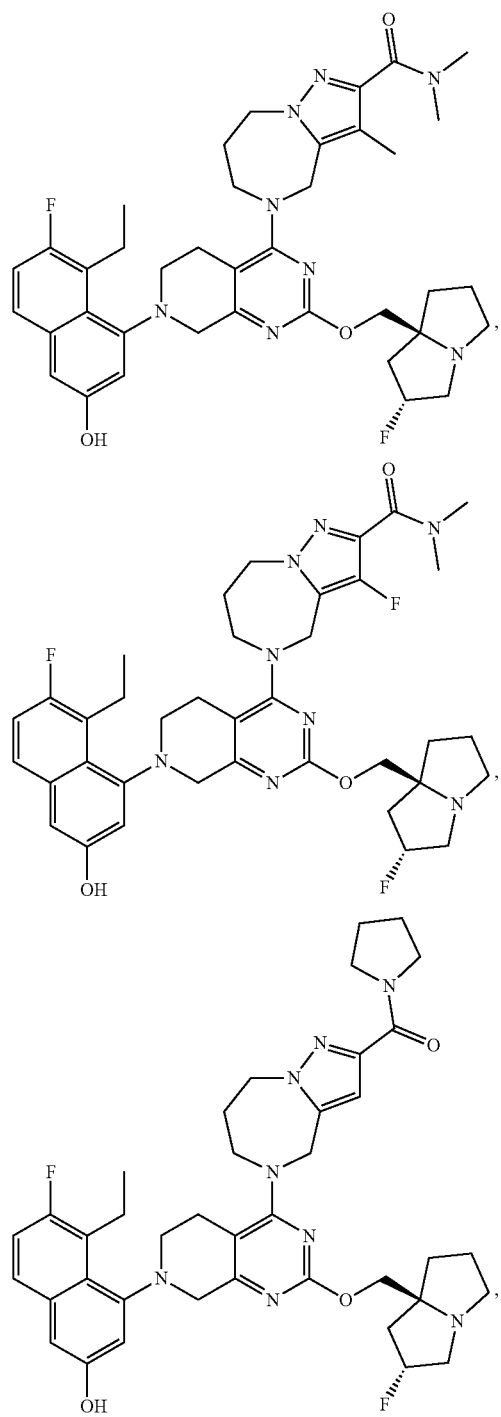

467
-continued
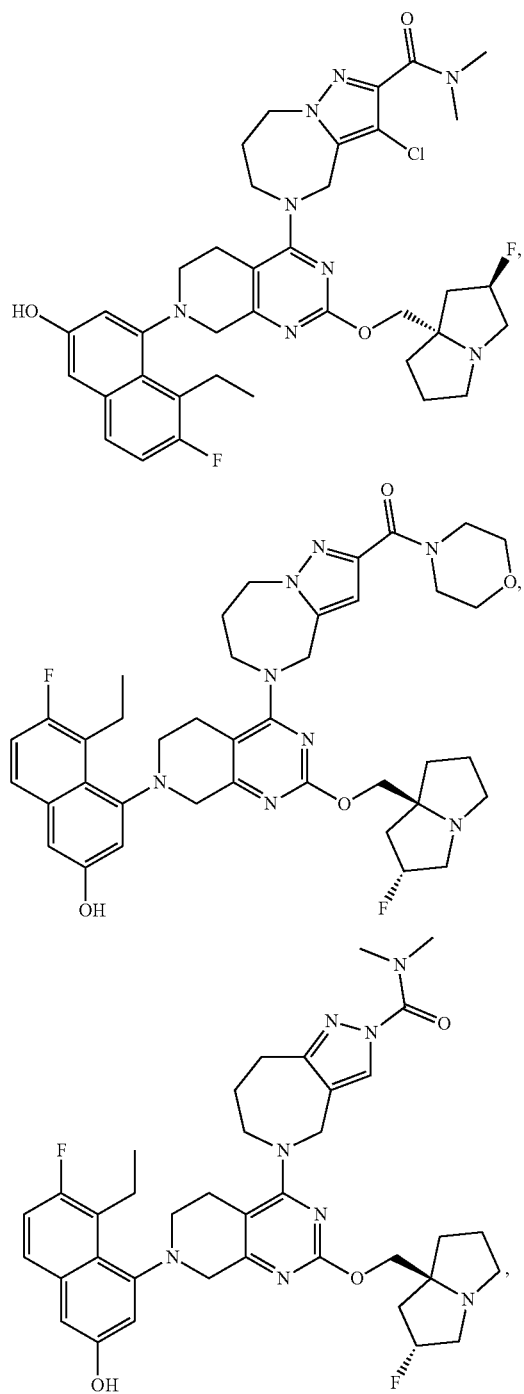
468
-continued
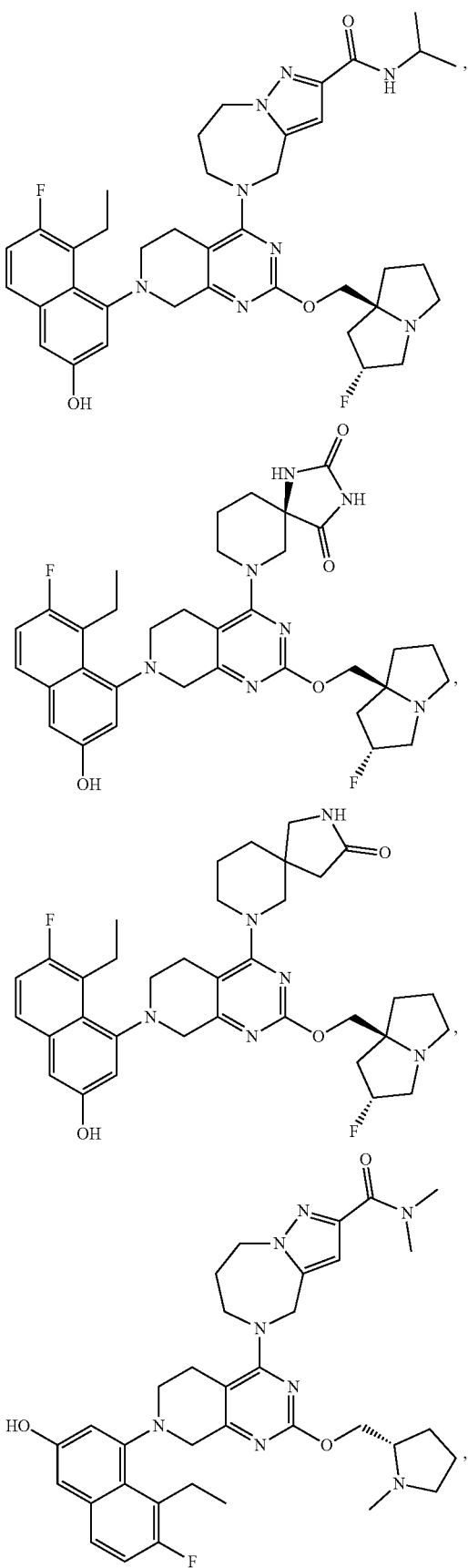

469
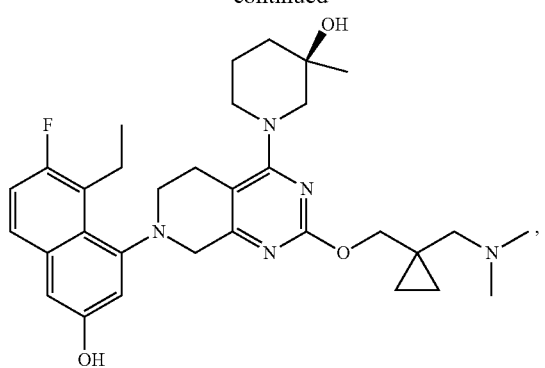
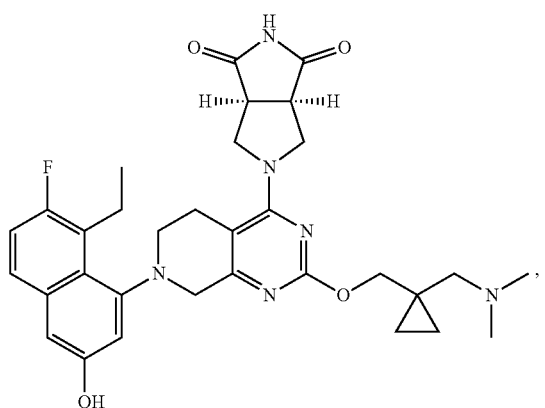
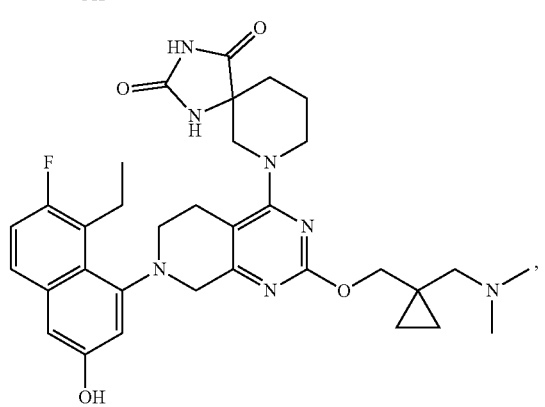
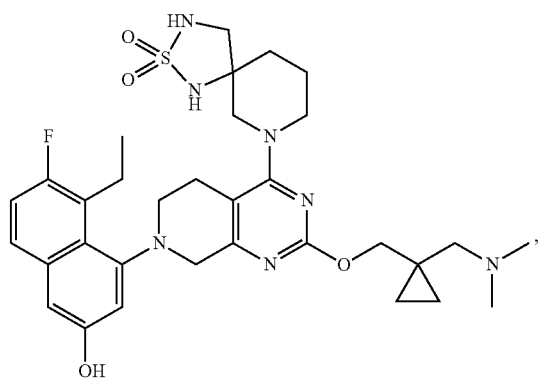
470
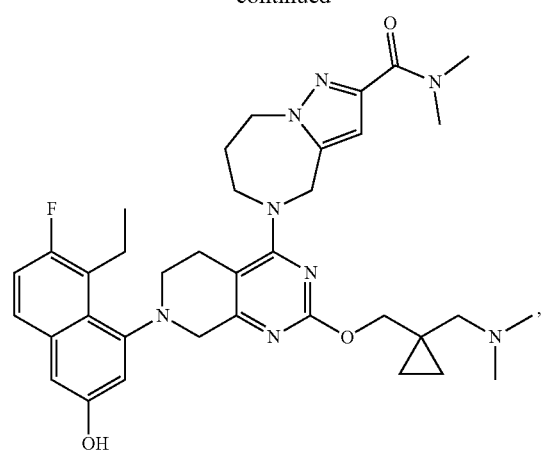
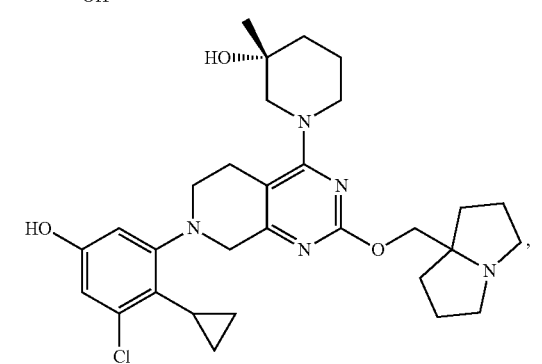
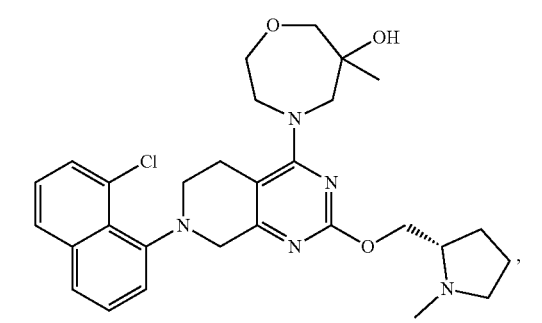
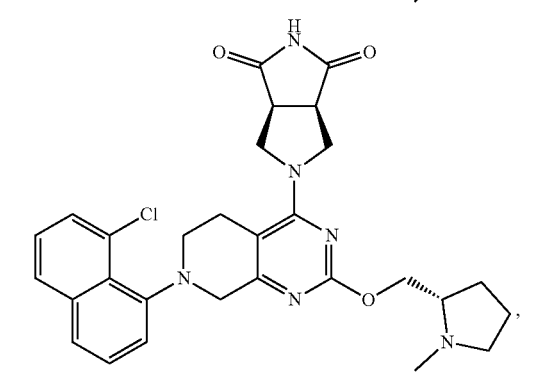

471
-continued
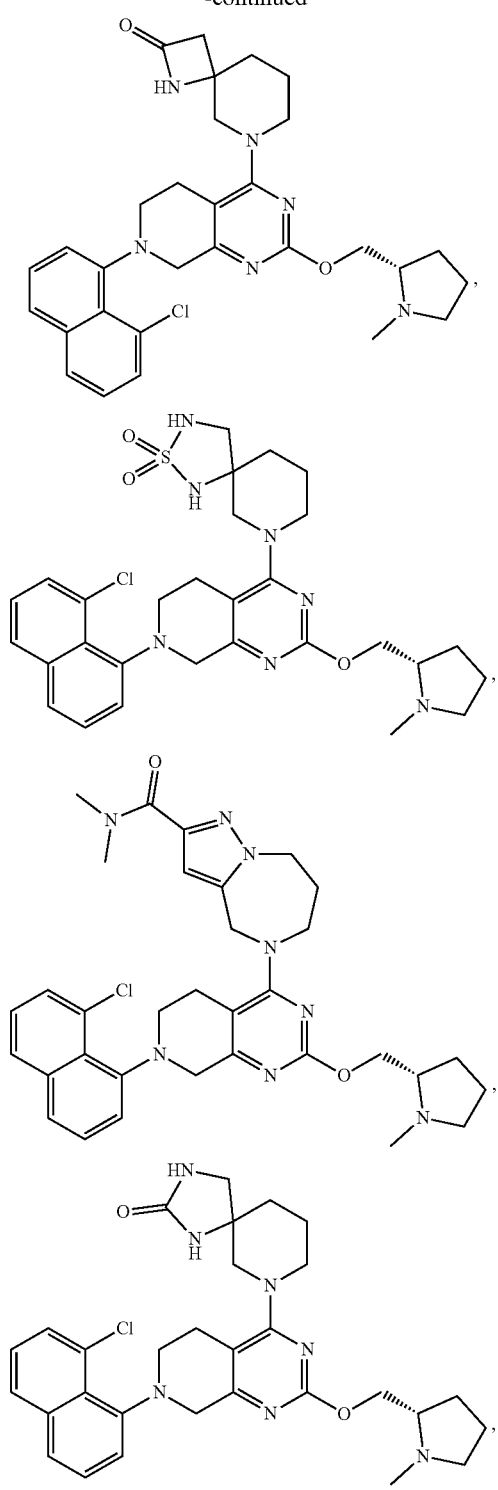
472
-continued
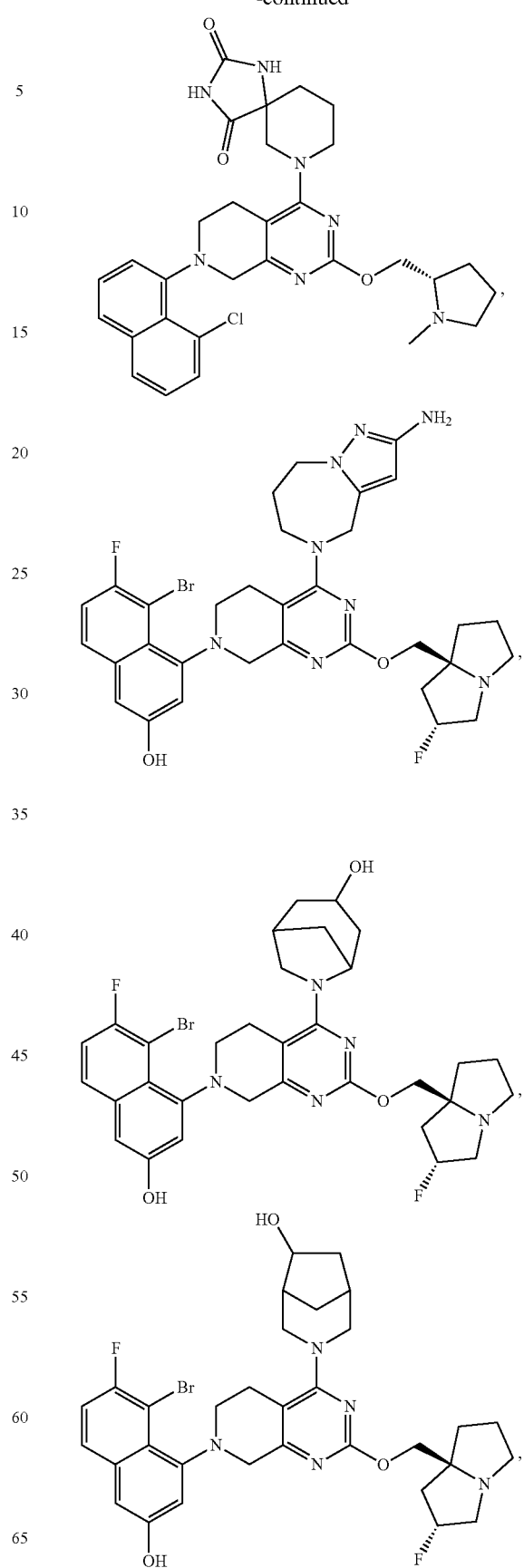

473
-continued
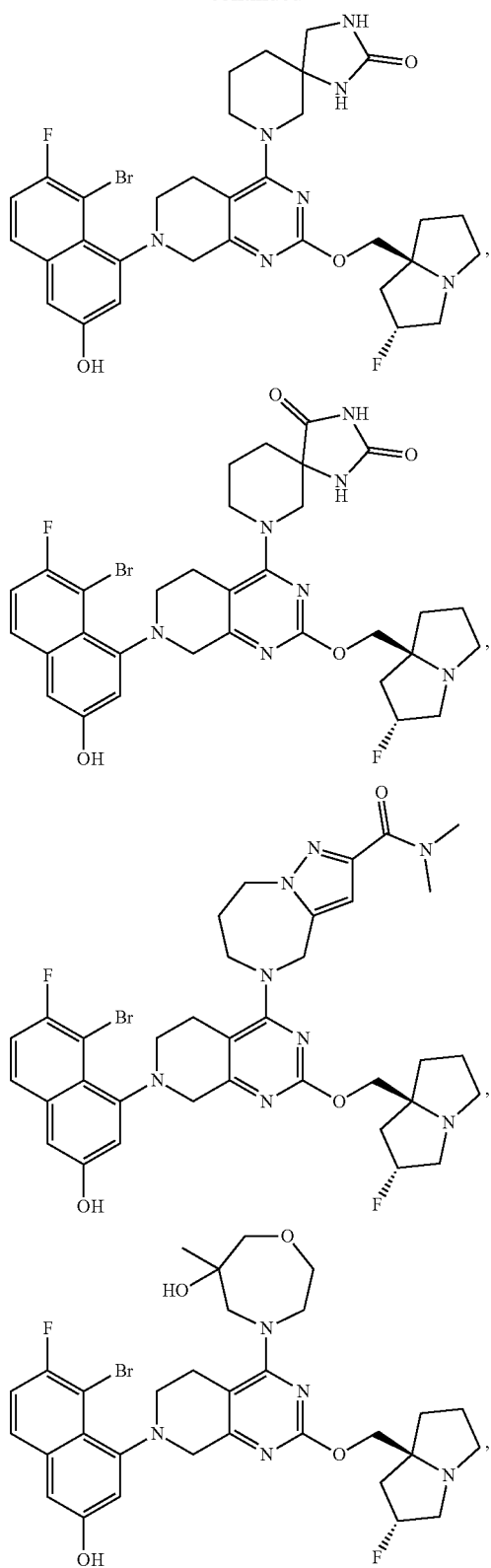
474
-continued
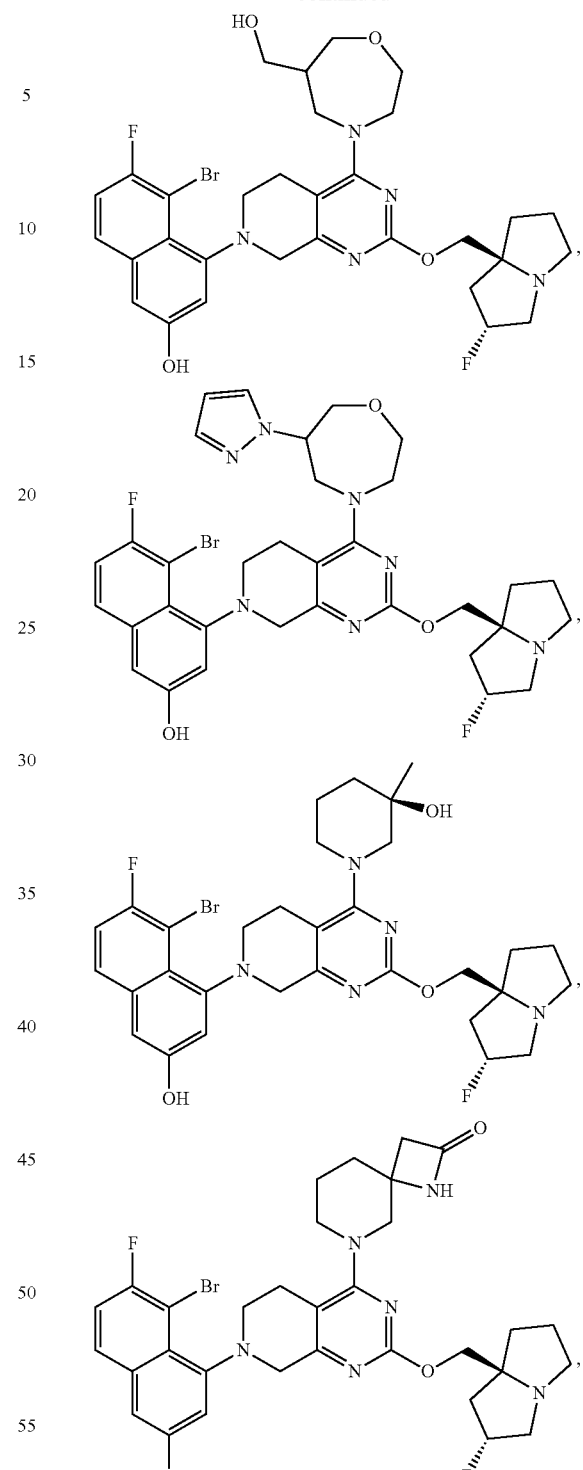

475
-continued
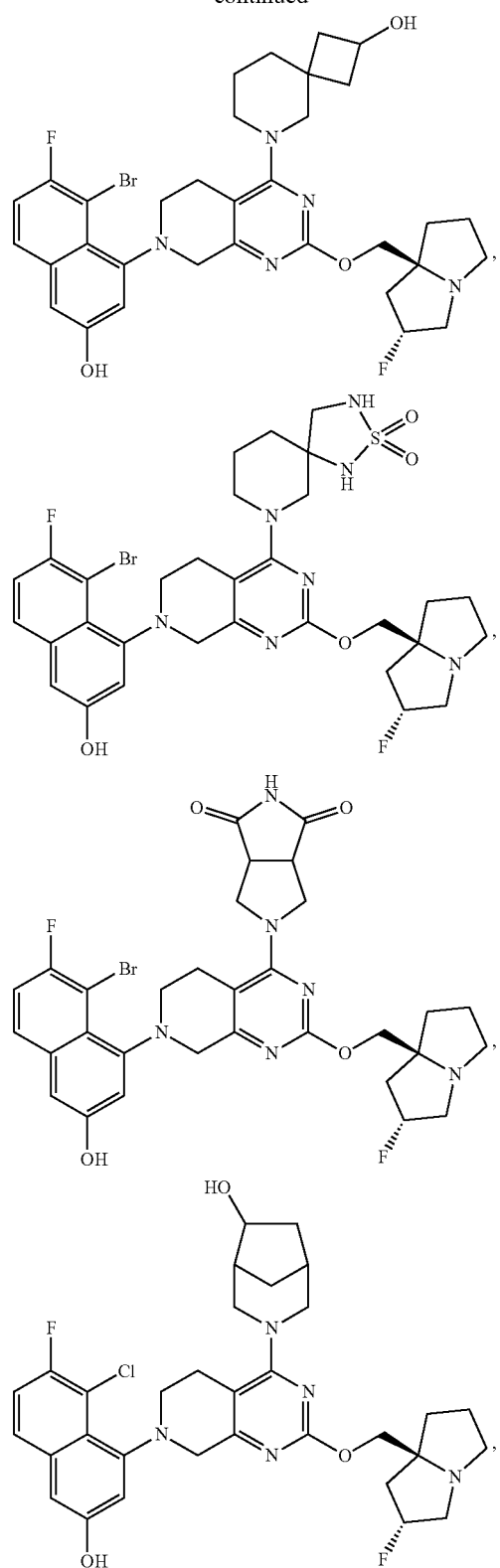
476
-continued
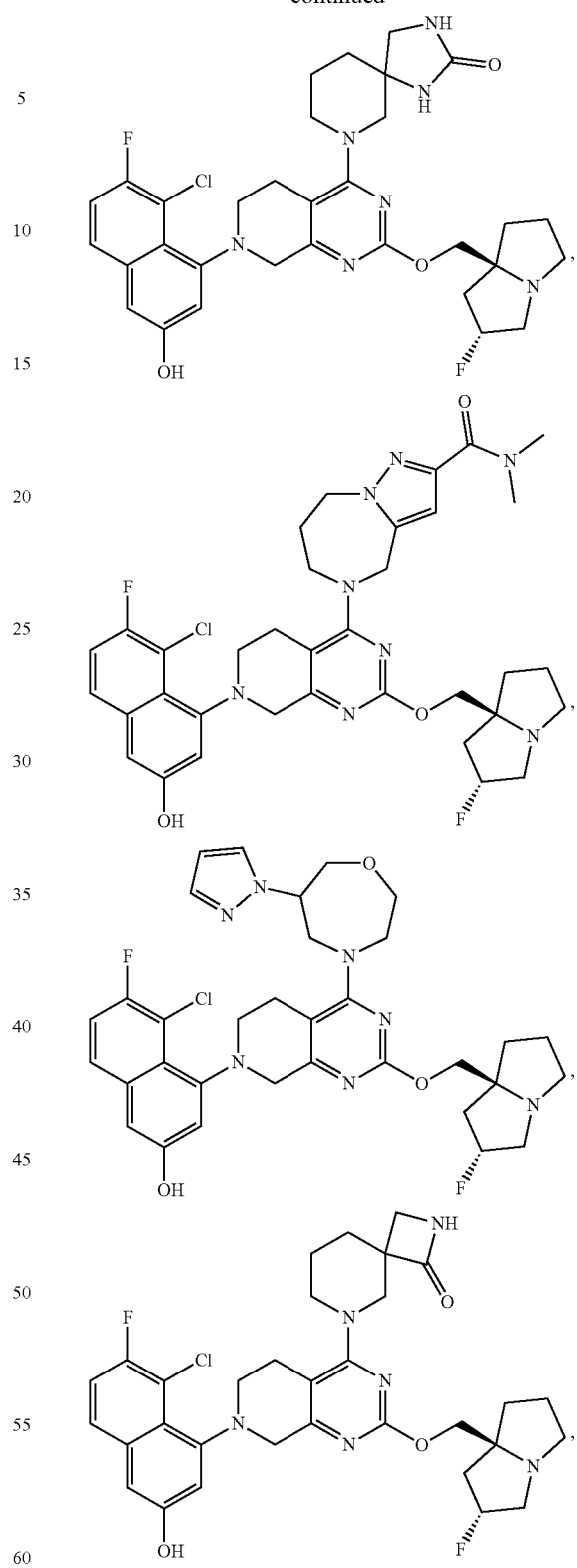

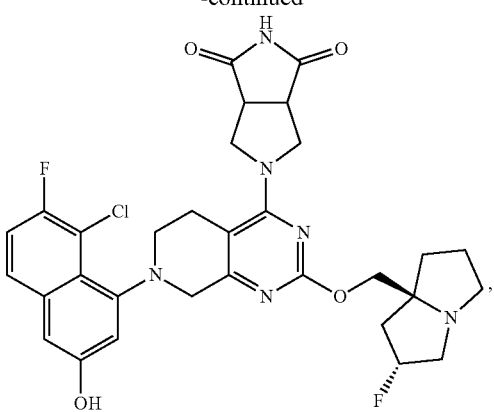

and a pharmaceutically acceptable salt thereof.

24. The method of claim 1, wherein the administering is done via a route selected from the group consisting of parenteral, intraperitoneal, intradermal, intracardiac, intraventricular, intracranial, intracerebrospinal, intrasynovial, intrathecal administration, intramuscular injection, intravitreous injection, intravenous injection, intra-arterial injection, oral, buccal, sublingual, transdermal, topical, intratracheal, intrarectal, subcutaneous, and topical administration.

25. The method of claim 24, wherein the administration route is oral.

26. The method of claim 24, wherein the administration is intravenous injection.

27. The method of claim 24, wherein the administration route is intramuscular injection.

28. The method of claim 24, wherein the administration route utilizes a delivery device.

29. The method of claim 24, wherein administration is done in a hospital setting.

* * * * *